United States Patent
Gokarn et al.

(10) Patent No.: US 8,076,120 B2
(45) Date of Patent: Dec. 13, 2011

(54) 3-HYDROXYPROPIONIC ACID AND OTHER ORGANIC COMPOUNDS

(75) Inventors: Ravi R. Gokarn, Minneapolis, MN (US); Olga V. Selifonova, Plymouth, MN (US); Holly Jean Jessen, Chanhassen, MN (US); Steven John Gort, Brooklyn Center, MN (US); Thorsten Selmer, Marburg (DE); Wolfgang Buckel, Marburg (DE)

(73) Assignee: Cargill, Incorporated, Wayzata, MN (US)

( * ) Notice: Subject to any disclaimer, the term of this patent is extended or adjusted under 35 U.S.C. 154(b) by 640 days.

(21) Appl. No.: 12/127,700

(22) Filed: May 27, 2008

(65) Prior Publication Data

US 2009/0053783 A1 Feb. 26, 2009

Related U.S. Application Data

(62) Division of application No. 11/539,856, filed on Oct. 9, 2006, now Pat. No. 7,393,676, which is a division of application No. 10/432,443, filed as application No. PCT/US01/43607 on Nov. 20, 2001, now Pat. No. 7,186,541.

(60) Provisional application No. 60/252,123, filed on Nov. 20, 2000, provisional application No. 60/285,478, filed on Apr. 20, 2001, provisional application No. 60/306,727, filed on Jul. 20, 2001, provisional application No. 60/317,845, filed on Sep. 7, 2001.

(51) Int. Cl.
*C12N 1/20* (2006.01)

(52) U.S. Cl. ...................... 435/252.3; 435/183; 435/232

(58) Field of Classification Search .................. 435/69.1, 435/141, 183, 232, 252.3
See application file for complete search history.

(56) References Cited

U.S. PATENT DOCUMENTS

| 6,323,010 B1 | 11/2001 | Skraly et al. |
| 6,329,183 B1 * | 12/2001 | Skraly et al. ................ 435/135 |
| 6,852,517 B1 * | 2/2005 | Suthers et al. ............... 435/135 |

FOREIGN PATENT DOCUMENTS

| EP | 0 494 707 A1 | 7/1992 |
| GB | 2 142 340 A | 1/1985 |
| JP | 53-18794 | 2/1978 |
| JP | 54-112877 | 9/1979 |
| JP | 58-158189 | 9/1983 |
| JP | 2002-053524 | 2/2002 |
| WO | WO 00/08198 A1 | 1/2000 |
| WO | WO 01/16346 | 3/2001 |
| WO | WO 01/16346 A1 | 3/2001 |

OTHER PUBLICATIONS

Notification (with English-language translation) from Japanese Patent Office, mailed Nov. 2, 2010, for Japanese Patent Application No. 2003-580264, filed Mar. 25, 2003, 2 pp.
Accession No. 053163 (May 30, 2000).
GenBank Accession No. AC008805 "*Homo sapiens* chromosome 19 clone CTD-2085J24, complete sequence" Aug. 3, 1999.
Database UniProt, "enoyl-CoA hydratase echA12," XP002343849 retrieved from EBI Database Accession No. ECH12_MYCTU, May 2000.
Baldwin et al., "Lactate Metabolism by *Peptostreptococcus elsdenii*: Evidence for Lactyl Coenzyme A Dehydrase," *Biochim. Biophys. Acta* 97:202-213 (1965).
Tung and Wood, "Purification, New Assay, and Properties of Coenzyme A Transferase from *Peptostreptococcus elsdenii*," *J. Bacteriol.* 124:1462-1474 (1975).
Accession No. P11569 (Oct. 1, 1989).
Accession No. D70893 (May 28, 1999).

\* cited by examiner

*Primary Examiner* — Tekchand Saidha

(57) ABSTRACT

Methods and materials related to producing 3-HP as well as other organic compounds are disclosed. Specifically, isolated nucleic acids, polypeptides, host cells, and methods and materials for producing 3-HP and other organic compounds are disclosed.

11 Claims, 105 Drawing Sheets

Figure 6

ATGAGAAAAGTAGAAATCATTACAGCTGAACAAGCAGCTCAGCTCGTAAAAGACAACGAC
ACGATTACGTCTATCGGCTTTGTCAGCAGCGCCCATCCGGAAGCACTGACCAAAGCTTTG
GAAAAACGGTTCCTGGACACGAACACCCCGCAGAACTTGACCTACATCTATGCAGGCTCT
CAGGGCAAACGCGATGGCCGTGCCGCTGAACATCTGGCACACACAGGCCTTTTGAAACGC
GCCATCATCGGTCACTGGCAGACTGTACCGGCTATCGGTAAACTGGCTGTCGAAAACAAG
ATTGAAGCTTACAACTTCTCGCAGGGCACGTTGGTCCACTGGTTCCGCGCCTTGGCAGGT
CATAAGCTCGGCGTCTTCACCGACATCGGTCTGGAAACTTTCCTCGATCCCCGTCAGCTC
GGCGGCAAGCTCAATGACGTAACCAAAGAAGACCTCGTCAAACTGATCGAAGTCGATGGT
CATGAACAGCTTTTCTACCCGACCTTCCCGGTCAACGTAGCTTTCCTCCGCGGTACGTAT
GCTGATGAATCCGGCAATATCACCATGGACGAAGAAATCGGGCCTTTCGAAAGCACTTCC
GTAGCCCAGGCCGTTCACAACTGTGGCGGTAAAGTCGTCGTCCAGGTCAAAGACGTCGTC
GCTCACGGCAGCCTCGACCCGCGCATGGTCAAGATCCCTGGCATCTATGTCGACTACGTC
GTCGTAGCAGCTCCGGAAGACCATCAGCAGACGTATGACTGCGAATACGATCCGTCCCTC
AGCGGTGAACATCGTGCTCCTGAAGGCGCTACCGATGCAGCTCTCCCCATGAGCGCTAAG
AAAATCATCGGCCGCCGCGGCGCTTTGGAATTGACTGAAAACGCTGTCGTCAACCTCGGC
GTCGGTGCTCCGGAATACGTTGCTTCTGTTGCCGGTGAAGAAGGTATCGCCGATACCATT
ACCCTGACCGTCGAAGGTGGCGCCATCGGTGGCGTACCGCAGGGCGGTGCCCGCTTCGGT
TCGTCCCGCAATGCCGATGCCATCATCGACCACACCTATCAGTTCGACTTCTACGATGGC
GGCGGTCTGGACATCGCTTACCTCGGCCTGGCCAGTGCGATGGCTCGGGCAACATCAAC
GTCAGCAAGTTCGGTACTAACGTTGCCGGCTGCGGCGGTTTCCCCAACATTTCCCAGCAG
ACACCGAATGTTTACTTCTGCGGCACCTTCACGGCTGGCGGCTTGAAAATCGCTGTCGAA
GACGGCAAAGTCAAGATCCTCCAGGAAGGCAAAGCCAAGAAGTTCATCAAAGCTGTCGAC
CAGATCACTTTCAACGGTTCCTATGCAGCCCGCAACGGCAAACACGTTCTCTACATCACA
GAACGCTGCGTATTTGAACTGACCAAAGAAGGCTTGAAACTCATCGAAGTCGCACCGGGC
ATCGATATTGAAAAGATATCCTCGCTCACATGGACTTCAAGCCGATCATTGATAATCCG
AAACTCATGGATGCCCGCCTCTTCCAGGACGGTCCCATGGGACTGAAAAAATAA     (SEQ
ID NO:1)

Figure 7

MRKVEIITAEQAAQLVKDNDTITSIGFVSSAHPEALTKALEKRFLDTNTPQNLTYIYAGS
QGKRDGRAAEHLAHTGLLKRAIIGHWQTVPAIGKLAVENKIEAYNFSQGTLVHWFRALAG
HKLGVFTDIGLETFLDPRQLGGKLNDVTKEDLVKLIEVDGHEQLFYPTFPVNVAFLRGTY
ADESGNITMDEEIGPFESTSVAQAVHNCGGKVVVQVKDVVAHGSLDPRMVKIPGIYVDYV
VVAAPEDHQQTYDCEYDPSLSGEHRAPEGATDAALPMSAKKIIGRRGALELTENAVVNLG
VGAPEYVASVAGEEGIADTITLTVEGGAIGGVPQGGARFGSSRNADAIIDHTYQFDFYDG
GGLDIAYLGLAQCDGSGNINVSKFGTNVAGCGGFPNISQQTPNVYFCGTFTAGGLKIAVE
DGKVKILQEGKAKKFIKAVDQITFNGSYAARNGKHVLYITERCVFELTKEGLKLIEVAPG
IDIEKDILAHMDFKPIIDNPKLMDARLFQDGPMGLKK    (SEQ ID NO:2)

```
SEQ ID NO:1     1  atgagaaaagtagaaatcattacagctgaacaagcagctc--agctcgta
SEQ ID NO:3     1  ---------gtgccggtcctgtcggcacaggaagcggtga--attatatt
SEQ ID NO:4     1  atgccgattctctcaaaaatatgggcggctccagcagctggaatcttgag
SEQ ID NO:5     1  -------------------------atgaa----------------tgca SEQ ID NO:1    49  aaagacaacgacacgattacgtctatcggctttgtcagcagcgcccatcc
SEQ ID NO:3    40  cccgacgaagcaacactttgtgtgttaggcgctg---gcggcggtattct
SEQ ID NO:4    51  aaaaactccgagaaatgctcatcaaatgaggctaatctcaatga-catcc
SEQ ID NO:5    10  aaaga---------atta------atcg----------------------

SEQ ID NO:1    99  ggaagcactgaccaaagctttggaaaaacggttcctg-------------
SEQ ID NO:3    87  ggaag------ccaccacgtt--aattactgctcttgctgataaatataa
SEQ ID NO:4   100  tcgatgaaagcaaaagtctttt-----aactctgc---------------
SEQ ID NO:5    23  --------------------------------------------------

SEQ ID NO:1   136  ---gacacgaacacccgcagaacttgacctacatctatgcag-gctctc
SEQ ID NO:3   129  acagactcaaacaccacgt--aatttatcgattattagtccaa-cagggc
SEQ ID NO:4   129  -------cgaagaagccgtgaaggatattccagat-aatgcaaagctttt
SEQ ID NO:5    23  --------------ctcgccgaatt-------------------------

SEQ ID NO:1   182  agggcaaacgcgatggccgtgccgctgaacatctggcacacacaggcctt
SEQ ID NO:3   176  ttggcgatcgcgccgaccgtggtattagtcctctggcgcaagaaggtctg
SEQ ID NO:4   171  a---------gttggc--ggcttcggactatgcgg-aatcccagaaaat
SEQ ID NO:5    34  ---------gcgatgg----------------------------------

SEQ ID NO:1   232  ttgaaacgcgccatcatcggtcactggcagactgtaccggc-tatcggta
SEQ ID NO:3   226  gtgaaatgggcattatgtggtcactgg-ggacaatcgccgcgtatttctg
SEQ ID NO:4   208  ctcatccaagctatca-caaaaactggtcaa----------aaaggtc
SEQ ID NO:5    41  --------------------aattacatgatgga---ga-tattgtta SEQ ID NO:1   281  aactggctgtcgaaaacaagattgaagcttacaacttctcgcagggcacg
SEQ ID NO:3   275  aactcgcagaacaaaataaaattattgcttataactacccacaaggtgta
SEQ ID NO:4   245  ttacatgtgtatcaaacaatgcgggagttgataatt-------ggggac-
SEQ ID NO:5    65  atctcggt-----------attg--gtttac---------caacacagg SEQ ID NO:1   331  ttggtccactggttccgcgccttggcaggtcataagctcggcgtcttcac
SEQ ID NO:3   325  cttacacaaaccttacgcgccgccgcagcccaccagcctggtattattag
SEQ ID NO:4   287  ttggcttgctccttc--aaactcgacaaatc--aagaaaatgatctcatc
SEQ ID NO:5    92  ttgt-----taattatttacctgataatgtcaata----------ttac SEQ ID NO:1   381  cgacatcggtct----ggaaa---ctttcctcgatccccgtcagctcggc
SEQ ID NO:3   375  tgatattggcat----cggga---catttgtcgatccacgccagcaaggc
SEQ ID NO:4   333  gtacgtcggtgaaaacggaga---atttgctcga----caatatcttagc
SEQ ID NO:5   126  --acttcaatca----gaaaatggctttcttggtttaactgca-------

SEQ ID NO:1   424  ggcaagctcaatgacgtaacca------aagaagacctcgtcaaactgat
SEQ ID NO:3   418  ggcaaactgaatgaagtcacta------aagaagacctgattaaactggt
SEQ ID NO:4   376  ggagagctcgagttggaattcacaccacaaggaacactcgccgaacgaat
SEQ ID NO:5   163  ---------tttgac----cca------gaaaatgctaattcaaact---

SEQ ID NO:1   468  cgaagtcgatggtca---tgaacagcttttctacccgacc----------
SEQ ID NO:3   462  cgagtttgataacaa---agaatatctctattacaaagcg----------
SEQ ID NO:4   426  tcgtgcagctggtgccggtgttcccgcattctacac-accaacaggatac
SEQ ID NO:5   191  --tagtaaatgctgg---tggtcagcctt---------------------
```

Figure 8A

```
SEQ ID NO:1    505  --ttcccgg--tcaacgtagctttcctccgcggtacgtatgctga---tg
SEQ ID NO:3    499  --attgcgc--cagatattgccttcattcgcgctaccacctgcga---ca
SEQ ID NO:4    475  ggtacccagattcaagaaggaggtgctccga-ttaagtacagtaaaactg
SEQ ID NO:5    215  ----------------------------gtggaa------ttaa---aa SEQ ID NO:1    548  aatccggcaatatc-accatggacg--------aagaaatcgggccttc
SEQ ID NO:3    542  gtgaaggctacgcc-actttgaag--------atgaggtgatgtatctc
SEQ ID NO:4    524  aaaaaggaaagattgaagttgcaagtaaagcgaaagaaacacgacaattc
SEQ ID NO:5    227  aaggcggctcta------------------------------ctttt SEQ ID NO:1    589  ga---aagcacttccgta---gcccaggccgttcac--aactgtggcggt
SEQ ID NO:3    583  ga-------cgcattggttattgcccaggcggtgcac--aataacggcggt
SEQ ID NO:4    574  aatggaattaattatgtaatggaagaggctatttggggagattttgcatt
SEQ ID NO:5    244  ga---tagtgctt-----------------t--ttctttcgcttt SEQ ID NO:1    631  aaagtcgtcgtccaggtcaaagacgtcgtcgc-----tcacggcagcctc
SEQ ID NO:3    625  attgtgatgatgcaggtgcagaaaatggttaa-----gaaagccacgctg
SEQ ID NO:4    624  gatcaaggcgtggagagcagatac-tcttggaaatattcaattcagacat
SEQ ID NO:5    267  aa--------------------------------------------ttc SEQ ID NO:1    676  gacccgcgcatggtcaagatccctg--------gcatctatgtcgactac
SEQ ID NO:3    670  catcctaaatctgtccgtattccgg--------g---ttatctggtggat
SEQ ID NO:4    673  gctgctggaaatttcaataatccaatgtgcaaagcctctaaatgcac--c
SEQ ID NO:5    272  gtggcggtcatgtt---gatgcctg--------tatactaagtggact--

SEQ ID NO:1    718  gtcgtcgtagcagctccggaagaccatcagcag--acgtatgactgcgaa
SEQ ID NO:3    709  attgtggtggtcgatccg---gatcaaacccaa--ctgtatggcggtgca
SEQ ID NO:4    721  atcgtcgaagtag---aggaaatcgtcgaaccgggagtaattgctccaaa
SEQ ID NO:5    309  ----------------------------------------------

SEQ ID NO:1    766  t--------acgatccgtccctcagcggtgaacatcgtgctcctg-aaggc
SEQ ID NO:3    754  c--------cggttaaccgctttatttctggtgacttcacccttg-atgac
SEQ ID NO:4    768  cgatgtgcacattccatcaatctattgtcatcgtctagttttgggaaaga
SEQ ID NO:5    309  -----------------------------------------tg-aagtt SEQ ID NO:1    808  gctac-------cgatgcagc----------tctccccatgagcgctaaga
SEQ ID NO:3    796  agtac-------caaacttag---------cctgccccctaaac-caacgt
SEQ ID NO:4    818  actacaaaaaaccaatcgaacggccaatgttcgcacacgaaggaccaata
SEQ ID NO:5    316  gatca-------agaagcaaa----------tctcgc-------------

SEQ ID NO:1    842  aaatcatcggc-cgccgcggcgctttggaattgactgaaaacgctgtcgt
SEQ ID NO:3    829  aaattagttgcgcggcgcgcattattcgaaatgcgtaaaggcgcggtggg
SEQ ID NO:4    868  aaaccatctac-atcggc--tgctggaaaatcgagagaaatcattg-cag
SEQ ID NO:5    336  -----------------------------taactgga----------

SEQ ID NO:1    891  caacctcggcgtcggtgctcc-----ggaat--acgttgcttctgttgcc
SEQ ID NO:3    879  gaatgtcggcgtcggtattgc-----tgacg--gcattggcctggtcgcc
SEQ ID NO:4    914  cacgtgcagcttggagttcacagatggaatgtacgccaatttgggtatc
SEQ ID NO:5    344  -------------------------------------------tggtgcc SEQ ID NO:1    934  gg--tgaagaaggtatcgccga------tacca-------ttaccctgac
SEQ ID NO:3    922  cg--agaagaaggttgtgctga------tgact-------ttattctgac
SEQ ID NO:4    964  gggattccgactttggcgccaaattatataccaaatggatttactgttca
SEQ ID NO:5    351  tg--gcaaaatggta---------------------------------

SEQ ID NO:1    969  cgtcgaaggtg------gcgccatcggtggcgt-accgcagggcggtgcc
SEQ ID NO:3    957  ggtagaaacag------gtccgattggcggaattacttcacaggggatcg
SEQ ID NO:4   1014  tttgcaaagtgagaatggtattattggagtggg-accata------tcca
SEQ ID NO:5    364  -----------------------------------------------
```

Figure 8B

```
SEQ ID NO:1   1012  cgcttcggttcgtcccgca-atgccgatgccatca----tcgaccacacc
SEQ ID NO:3   1001  c-ctttggcgcgaacgtga-atacccgtgccattc----tggatatgacg
SEQ ID NO:4   1057  agaaaag----gaacagaagacgccgatctcattaatgctggaaaagagc
SEQ ID NO:5    364  --------------ccagga-atg--------------------------

SEQ ID NO:1   1057  tatcagttcgacttctacgatggcggc----------ggtctggacatcg
SEQ ID NO:3   1045  tcccagtttgattttatcacggtggc----------ggtctggatgttt
SEQ ID NO:4   1103  ---caattactcttct-caaaggagcttcaattgttggttctgatgaatc
SEQ ID NO:5    373  ----------------------ggcgga----------gcaatggacttag SEQ ID NO:1   1097  cttacctcggcctgg-----cccagtgcgatg-------gctcgggcaac
SEQ ID NO:3   1085  gttatttgagttttg-----ctgaagtcgacc-------agcacggtaac
SEQ ID NO:4   1149  attcgcaatgattcgtggttctcatatggatattactgtgctcggtgcac
SEQ ID NO:5    392  -----------------------------tg-------actggtgcaa- SEQ ID NO:1   1135  atcaacgtcagca-agttcggtactaacgttgccggctgcggcggtttcc
SEQ ID NO:3   1123  gtcggcgtgcata-aattcaatggtaaaatcatgggcaccggtggattta
SEQ ID NO:4   1199  ttca--gtgctcacagtttgg----agatttagcgaattggatgattccg
SEQ ID NO:5    404  --------------------------------------------------

SEQ ID NO:1   1184  ccaacatt--tcccagcagacaccgaatgtttacttctgcggcacct-tc
SEQ ID NO:3   1172  ttgatatcagtgccacttcgaagaaaatcatt--ttctgcggcacat-ta
SEQ ID NO:4   1243  ggaaaatt-------ggtga-aaggaatgggcggtgcaatggatcttgtc
SEQ ID NO:5    404  -------------------aaaaagtgattatt-----ggca------

SEQ ID NO:1   1231  acggctggcggcttgaaaatcgctgtcgaagacggcaaagtcaagatcct
SEQ ID NO:3   1219  actgcgggcagtttaaaaacagaaattaccgacggcaaattaaatatcgt
SEQ ID NO:4   1285  tctgctcccgg------agcccgtgt-gatcgttgtaatggagcatgtat
SEQ ID NO:5    422  -----------tggaacattg-----------tgccaagtcaggttcct SEQ ID NO:1   1281  ccaggaaggcaaagccaagaagttcatcaaagctgtcgaccagatcactt
SEQ ID NO:3   1269  ccaggaaggacgggtgaagaaatttattcgggaactaccggaaattactt
SEQ ID NO:4   1328  cgaagaacggagagccaaaaatt---------------ctagagcactg
SEQ ID NO:5    449  caaaaattctaaag---aaatgtacattaccgct------cacagcaagt SEQ ID NO:1   1331  tcaacgg-----ttcctatgcagc---ccgcaacggcaaaacgttctct
SEQ ID NO:3   1319  tcagcggaaaaatcgctctcgagc---gagggctgg-----atgttcgtt
SEQ ID NO:4   1362  cgaac-------ttcctctga--c---cggcaaagg--agtaatttcccg
SEQ ID NO:5    490  aaaaaag-----ttgccatggtggttaccgaattggca-----gtattta SEQ ID NO:1   1373  a--catcacagaacgctgcgtatttgaactgacca--aagaa-ggcttga
SEQ ID NO:3   1361  a--tatcactgagcgcgcagtattcacgctgaaag--aagac-ggcctgc
SEQ ID NO:4   1398  aatcattactgatatggcagtttcgacgtggacacaaagaacggattga
SEQ ID NO:5    530  a--cttcattgaaggcagattagttcta------a--aagaa----catgc SEQ ID NO:1   1418  aactcatcgaagtcgcaccgggcatcgatattgaaaaagatatcctcgct
SEQ ID NO:3   1406  atttaatcgaaatcgcccctggcgtcgatttacaaaaagatattctcgac
SEQ ID NO:4   1448  cattgatcgaagt--caggaaggatc-ttactgtagatgatat-------
SEQ ID NO:5    567  tcctcat-----------------gtggatttagaaaca---attaaagcc SEQ ID NO:1   1468  cacatggacttcaagccgat--cattgata---atccga--aactcatgg
SEQ ID NO:3   1456  aaaatggatttcaccccagt--gatttcgccagaactca--aactgatgg
SEQ ID NO:4   1488  --caagaaactca--ccg-----cttgcaa---attcga--aatttccga
SEQ ID NO:5    598  aaaacag------aagccgatttcattgtt-----gccgatgatttcaaag SEQ ID NO:1   1511  atgcccgcctcttccaggacggtcccatggga------ctgaaaaaa---
SEQ ID NO:3   1502  acgaaagattatttatcgatgcggcgatgggttttgtcctgcctgaagcg
SEQ ID NO:4   1524  aaatctgaagccaatgggacaggctcctcttta------atcaaggataa-
SEQ ID NO:5    638  aaatgcaaatcagccag---------aaagga------cttgaattatga
```

Figure 8C

```
SEQ ID NO:1    1552 --------taa
SEQ ID NO:3    1552 gctcattaa
SEQ ID NO:4    1567 ----------
SEQ ID NO:5     673 ----------
```

Figure 8D

```
SEQ ID NO:2    1 ------------------------mrkveiit----------aeqaaqlv
SEQ ID NO:6    1 ------------------------mpvls------------aqeavnyi
SEQ ID NO:7    1 mpilskiwaapaagilrktprnahqmrlismtssmkakvfnsaeeavkdi
SEQ ID NO:8    1 ------------------------mnakeli----------arriamel SEQ ID NO:2   17 kdndtitsigfvssahpealt--kalekrfldtntpqnltyiyagsqgkr
SEQ ID NO:6   14 pdeatlcvlg-agggileattlitaladkykqtqtprnlsiisptglgdr
SEQ ID NO:7   51 pdnakllvggfglcgipenli--qai------tktgqkgltcvsnnagv-
SEQ ID NO:8   16 hdgd-ivnlg----------------------------------------

SEQ ID NO:2   65 dgraaehlahtgllkraiighwqtvpaigklavenkieaynfsqgtlvhw
SEQ ID NO:6   63 adrgisplaqeglvkwalcghwgqsepriselaeqnkiiaynypqgvltqt
SEQ ID NO:7   92 dnwglglllqtrqikkmissyvgengefarqylsgeleleftpqgtlaer
SEQ ID NO:8   25 --------------------------------------------------

SEQ ID NO:2  115 fralaghklgvftdigletfldprqlggklndvtkedlvkliev------
SEQ ID NO:6  113 lraaaahqpgiisdigigtfvdprqqggklnevtkedlliklvef-----
SEQ ID NO:7  142 iraagagvpafytptgygtqi---qeggapikysktekgk-ievaskake
SEQ ID NO:8   25 -------------igl----------------------------------

SEQ ID NO:2  159 ----dgheqlfyptfpvnvaflrgtyadesgnitmdeeigpfestsvaqa
SEQ ID NO:6  157 ----dnkeylyykaiapdiafirattcdsegyatfedevmyldalviaqa
SEQ ID NO:7  188 trqfnginyvmeeaiwgdfalikawradtlgniqfrhaagnfnnpmckas
SEQ ID NO:8   28 -----------ptqvvn-------ylpdnvnitlqsengflglta-----

SEQ ID NO:2  205 vhncggkvvvqvkdvvahgsldprmvkipgiyvdyvvvaapedhqqtydc
SEQ ID NO:6  203 vhnnggivmmqvqkmvkkatlhpksvripgylvd-ivvvdpdqtqlygga
SEQ ID NO:7  238 --kc---tiveveeivepgviapndvhipsiychrlvlg------knykk
SEQ ID NO:8   55 --------------------------------------------------

SEQ ID NO:2  255 eydpslsgehrapegatdaalpmsakkiigrrgaleltenavvnlgvg--
SEQ ID NO:6  252 pvnrfisgdftl-ddstklslplnqrklvarralfemrkgavgnvgvg--
SEQ ID NO:7  277 pierpmfahegpikpstsaa--gksreiiaaraaleftdgmyanlgigip
SEQ ID NO:8   55 -fdp-----------------------------enansnl-vn--

SEQ ID NO:2  303 --apeyvasvageegiadtitltveggaig--gvpqggarfgssrnad--
SEQ ID NO:6  299 --iadgiglvareegcadddfiltvatgpig--gitsqgiafganvntr--
SEQ ID NO:7  325 tlapnyipn-------gftvhlqsengiigvgpyprkgtedadlinagke
SEQ ID NO:8   67 --a--------------------gggpc--gikkggstf---------

SEQ ID NO:2  347 --------aiidhtyqfdfydgggldiaylglaqcdgsgni-nvskfgtn
SEQ ID NO:6  343 --------aildmtsqfdfyhgggldvcylsfaevdqhgnv-gvhkfngk
SEQ ID NO:7  368 pitllkgasivgsdesfamirgshmditvlgalcsqfgdlanwmipgkl
SEQ ID NO:8   82 -----------dsafsfalirgghvdacvlgglevdqeanlanwmvpgkm SEQ ID NO:2  388 vagcggfpnisqqtpnvyfcgtftagglkiav------edgkvkilqegk
SEQ ID NO:6  384 imgtggfidisatskkiifcgtltagslktei------tdgklnivqegr
SEQ ID NO:7  418 vkgmggamdl-----------vsapgarvivmehvskngepkilehce
SEQ ID NO:8  121 vpgmggamdlvtgakkvii-------gmehca------ksgsskilk---

SEQ ID NO:2  432 akkfikavdqitfngsyaarngkhvl--yitercvfel-tkeglklieva
SEQ ID NO:6  428 vkkfirelpeitfsgkialergldvr--yiteravftl-kedglhllieia
SEQ ID NO:7  456 -----------------lpltgkgvisriitdmavfdvdtknglitlievr
SEQ ID NO:8  155 -----kctlplt--------askkvam--vvtelavfnf-iegrlvlkeha
```

Figure 9A

SEQ ID NO:2   479 pgidiekdi--lahmdfkpiidnp-klmdarlfqdgpmglkk-----
SEQ ID NO:6   475 pgvdlqkdi--ldkmdftpvispelklmderlfidaamgfvlpeaah
SEQ ID NO:7   489 kdltvd-dikkltackfe-isenl-kpmgqaplnqg-----------
SEQ ID NO:8   190 phvdle-ti--kakteadfivad-----dfkemqisqkglel-----

```
GTGAAAACTGTGTATACTCTCGGAATCGACGTTGGTTCTTCTTCTTCCAAGGCAGTCATC
CTGGAAGATGGCAAGAAGATCGTCGCCCATGCCGTCGTTGAAATCGGCACCGGTTCGACC
GGTCCGGAACGCGTCCTGGACGAAGTCTTCAAAGATACCAACTTAAAAATTGAAGACATG
GCGAACATCATCGCCACAGGCTATGGCCGTTTCAATGTCGACTGCGCCAAAGGCGAAGTC
AGCGAAATCACGTGCCATGCCAAAGGGGCCCTCTTTGAATGCCCCGGTACGACGACCATC
CTCGATATCGGCGGTCAGGACGTCAAGTCCATCAAATTGAATGGCCAGGGCCTGGTCATG
CAGTTTGCCATGAACGACAAATGCGCCGCTGGTACGGGCCGTTTCCTCGACGTCATGTCG
AAGGTACTGGAAATCCCCATGTCTGAAATGGGGACTGGTACTTCAAATCGAAGCATCCC
GCTGCCGTCAGCAGTACCTGCACGGTTTTTGCTGAATCGGAAGTCATTTCCCTTCTTTCC
AAGAATGTCCCGAAAGAAGATATCGTAGCCGGTGTCCATCAGTCCATCGCCGCCAAAGCC
TGCGCTCTCGTGCGCCGCGTCGGTGTCGGTGAAGACCTGACCATGACCGGCGGTGGCTCC
CGCGATCCGGCGTCGTCGATGCCGTATCGAAAGAATTAGGTATTCCTGTCAGAGTCGCT
CTGCATCCCCAAGCGGTGGGTGCTCTCGGAGCTGCTTTGATTGCTTATGATAAAATCAAG
AAATAA (SEQ ID NO:9)
```

Figure 11

VKTVYTLGIDVGSSSSKAVILEDGKKIVAHAVVEIGTGSTGPERVLDEVFKDTNLKIEDM
ANIIATGYGRFNVDCAKGEVSEITCHAKGALFECPGTTTILDIGGQDVKSIKLNGQGLVM
QFAMNDKCAAGTGRFLDVMSKVLEIPMSEMGDWYFKSKHPAAVSSTCTVFAESEVISLLS
KNVPKEDIVAGVHQSIAAKACALVRRVGVGEDLTMTGGGSRDPGVVDAVSKELGIPVRVA
LHPQAVGALGAALIAYDKIKK   (SEQ ID NO:10)

```
SEQ ID NO:9     1 gtgaaaactgtgtatactctcggaatcgacgttggttcttcttcttccaa
SEQ ID NO:11    1 ---atgagtatctataccttgggaatcgatgttggatctactgcatccaa
SEQ ID NO:12    1 gtggcagtggcatattcgattggcattgattccggctcaaccgccaccaa
SEQ ID NO:13    1 ------------atgattttagggatagatgttggatctacaacaacgaa SEQ ID NO:9    51 ggcagtcatcctggaagatggcaagaagatcgtcgc-ccatgccgtcgtt
SEQ ID NO:11   48 gtgcattatcctgaaagatggaaaagaaatcgtggc-gaaatccctggta
SEQ ID NO:12   51 agggatcttactggcagacggcgtgatta----cgcgccgtttcctcgtt
SEQ ID NO:13   39 gatggttctaatggaagatagc---aagataatttg-gtataagatagag SEQ ID NO:9   100 gaaatcggcaccggttcgaccggtccggaacgcgtcctggacgaagtctt
SEQ ID NO:11   97 gccgtggggaccggaacttccggtcccgcacggtctatttcggaagtcct
SEQ ID NO:12   97 ccaa----cccccttcgcccgg-caacagcaattact----gaagcctg
SEQ ID NO:13   85 gatattgg-agttgtta-----ttgaggaagatatttattaaaaatggt SEQ ID NO:9   150 caaagatacc-aacttaaaaattgaagacatggcgaacatcatcgc-cac
SEQ ID NO:11  147 ggaaaatgcc-cacatgaaaaaagaagacatggcctttaccctggc-tac
SEQ ID NO:12  138 ggaa-actct-gcgcgaagggttagagacaacgccgtttctgacgctcac
SEQ ID NO:13  129 taaggagattgaacaaaaatatccaatagat----aaaatcgttgc-aac SEQ ID NO:9   198 aggctatggccgtttcaatgtcg---------actgcgccaaaggcgaag
SEQ ID NO:11  195 cggctacggacg---caat-tcgctggaaggcattgccgacaagcaga--
SEQ ID NO:12  186 cggctacgggcggcaactggtgg---------attttgccgataaacagg
SEQ ID NO:13  174 tggatatggaaggcataaggtta---------gttttgcagataagatag SEQ ID NO:9   239 tcagcgaaatcacgtgccatgccaaaggggcc---ctctttgaatgcccc
SEQ ID NO:11  239 tgagcgaactgagctgccatgccatgggcgcc---agctttatctggccc
SEQ ID NO:12  227 taacgaaatctcctgtcacgggctgggcgca---cggtttcttgcgcca
SEQ ID NO:13  215 ttccagaagtta-ttgcattgggaaaaggagctaactatttctttaacga SEQ ID NO:9   286 ggtacgacga--ccatcctcgatatcggcggtcaggacgtcaa-gtccat
SEQ ID NO:11  286 --aacgtccataccgtcatcgatatcggcgggcaggatgtgaa-ggtcat
SEQ ID NO:12  274 gcaacgcgcg--cggtaatcgacatcggtggtcaggacagcaaagtgatt
SEQ ID NO:13  264 ggcagatgga----gttatagacattggagggcaagatacaaa-ggtctt SEQ ID NO:9   333 caaattga--atggccagggcctggtcatgcagtttgcc-atgaacgaca
SEQ ID NO:11  333 ccatgtgg--aaaacgggaccatgacca---atttccag-atgaatgata
SEQ ID NO:12  322 cagcttgatgatgacggtaacctg----tgcgatttcctgatgaatgaca
SEQ ID NO:13  309 aaagattg--ataaaaacggaaaagttgttgattttatc-ctatcagata SEQ ID NO:9   380 aatgcgccgctggtacgggccgtttcctcgacgtcatgtcgaaggtactg
SEQ ID NO:11  377 aatgcgctgccggactggccgtttcctggatgttatggccaatatcctg
SEQ ID NO:12  368 aatgcgcggcgggcaccgggcgtttcctggaggtgatctcgcgcacgctt
SEQ ID NO:13  356 aatgtgccgctggaactggaaaattcttaga---------aaaggcatta SEQ ID NO:9   430 gaaatccccatgtct-ga--aatgggggactggtactt-caaatcgaagc
SEQ ID NO:11  427 gaagtgaaggtttcc-ga--cctggctgagctgggagc-caaatccacca
SEQ ID NO:12  418 ggca--ccagcgtcgagc--aactcgacagcattaccg-aaaat---gtc
SEQ ID NO:13  397 gatattttaaaaatt-gataaaaatgagataaataaatacaaatcagata SEQ ID NO:9   476 atcccgct-gccgtcagcagtacctgcacggttttgctgaatcggaagt
SEQ ID NO:11  473 aacgggtg-gctatcagctccacctgtactgtgtttgcagaaagtgaagt
SEQ ID NO:12  460 acgccgcacgccatcacgagtatgtgcacagtgtttgctgaatcagaagc
SEQ ID NO:13  446 atatcgct-aaaatatcttcaatgtgtgctgtctttgctgaaagtgagat
```

Figure 12A

```
SEQ ID NO:9    525 catttcccttctttccaagaatgtcccgaaagaa--gatatcgtagccgg
SEQ ID NO:11   522 catcagccagctgtccaa--aggaaccgacaagatcgacatcattgccgg
SEQ ID NO:12   510 gatcagcctgcgctcagcgggcgtcgcgccagaa--gcgattctcgcagg
SEQ ID NO:13   495 aataagcttactatcaaaaaaagttccaaaggaa--ggcattttaatggg SEQ ID NO:9    573 tgtccatcagtccatcgccgccaaagcctgcgctctcgtgc-gccgcgtc
SEQ ID NO:11   570 gatccatcgttctgtagccagccgggtcattggtcttgcca-atcgggtg
SEQ ID NO:12   558 agtgattaacgcgat-ggcgcggaggagtgc-caatttcat-tgctcgtc
SEQ ID NO:13   543 cgtctatgagagtat------aataaatagggttatcccaatgaccaata SEQ ID NO:9    622 ggtgtcgg--tgaagacctgaccatgaccggcggtggctcccgcgat--c
SEQ ID NO:11   619 gggattgt--gaaagacgtggtcatgaccggcggtgtagcccagaac--t
SEQ ID NO:12   605 tctc-ctg--tgaagcgccgattctgtttactggtggcgttagtcattgc
SEQ ID NO:13   587 ggcttaaaattcaaaacatagtgtttagtggaggagttgctaaaaat--a SEQ ID NO:9    668 ccggcgtcgtcgatgccgtatcgaaagaat------taggtattcctgtc
SEQ ID NO:11   665 atggcgtgagaggagccct------ggaag------aaggccttggcgtg
SEQ ID NO:12   652 cagaagt-----ttgcccggatgctggaatctcacctgcgaatgccggta
SEQ ID NO:13   635 aggttttggttgagatgtttgagaaaaaat------tgaataaaaaacta SEQ ID NO:9    712 agagtcgctctgcatccccaagcggtg------ggtgctctcggagctgc
SEQ ID NO:11   703 gaaatcaagacgtctcccctggctcagtacaacggtgccctgggtgccgc
SEQ ID NO:12   697 aatacccatcctgatgcgcaatttgct------ggcgcaattggcgcggc
SEQ ID NO:13   679 ctaattccaaaagaaccacagattgtt------tgctgtgttggagctat SEQ ID NO:9    756 tttgattgctta-----tgataaaatcaagaaa-taa
SEQ ID NO:11   753 tctgtatgcgta-----t-aaaaaagcagccaaataa
SEQ ID NO:12   741 ggtaattggtcaacgagtgaggacacgccgatga---
SEQ ID NO:13   723 attggtt-------------taa--------------
```

```
SEQ ID NO:10    1 vktvytlgldvgsssskaviledgkkivahavveigtgstgpervldevf
SEQ ID NO:14    1 ms-iytlgidvgstaskciilkdgkeivakslvavgtgtsgparsisevl
SEQ ID NO:15    1 mavaysigidsgstatkgilladg-vitrrflvpt---pfrpataiteaw
SEQ ID NO:16    1 ----milgidvgstttkmvlmeds-kliwykiedigv--vieedillkmv SEQ ID NO:10   51 kdtnlkiedmaniiatgygrfnvd-cakgevseitchakgalfecpgttt
SEQ ID NO:14   50 enahmkkedmaftlatgygrnslegiadkqmselschamgasfiwpnvht
SEQ ID NO:15   47 etlreglettpfltltgygrqlvd-fadkqvteischglgarflapatra
SEQ ID NO:16   44 keieqkyp-idkivatgygrhkvs-fadkivpevialgkganyffneadg SEQ ID NO:10  100 ildiggqdvksiklngqglvmqfamndkcaagtgrfldvmskvleipmse
SEQ ID NO:14  100 vidiggqdvkvihve-ngtmtnfqmndkcaagtgrfldvmanilevkvsd
SEQ ID NO:15   96 vidiggqdskviqldddgnlcdflmndkcaagtgrflevisrtlgtsveq
SEQ ID NO:16   92 vidiggqdtkvlkidkngkvvdfilsdkcaagtgkflekaldilkidkne SEQ ID NO:10  150 mgdwyfkskhpaavsstctvfaeseviallsknvpkedivagvhqsiaak
SEQ ID NO:14  149 laelgakstkrvaisstctvfaesevisqlskgtdkidiiagihrsvasr
SEQ ID NO:15  146 l-dsitenvtphaitsmctvfaeseaislrsagvapeailagvinamarr
SEQ ID NO:16  142 ink--yksdniakissmcavfaeseiiallskkvpkegilmgvyesiinr SEQ ID NO:10  200 acalvrrvgvgedltmtgggsrdpgvvdavskelgipvrvalhpqavgal
SEQ ID NO:14  199 viglanrvgivkdvvmtggvaqnygvrgaleeglgveiktsplaqyngal
SEQ ID NO:15  195 sanfiarlsceapilftggvehcqkfarmleshlrmpvnthpdaqfagai
SEQ ID NO:16  190 vipmtnrlki-qnivfsggvaknkvlvemfekklnkkllipkepqivccv SEQ ID NO:10  250 gaaliaydkikk--
SEQ ID NO:14  249 gaalyaykkaak--
SEQ ID NO:15  245 gaavig-qrvrtrr
SEQ ID NO:16  239 gailv---------
```

Figure 14

```
ATGAGTGAAGAAAAAACAGTAGATATTGAAAGCATGAGCTCCAAGGAAGCCCTTGGTTAC
TTCTTGCCGAAAGTCGATGAAGACGCACGTAAAGCGAAAAAAGAAGGCCGCCTCGTTTGC
TGGTCCGCTTCTGTCGCTCCTCCGGAATTCTGCACGGCTATGGACATCGCCATCGTCTAT
CCGGAAACTCACGCAGCTGGTATCGGTGCCCGTCACGGTGCTCCGGCCATGCTCGAAGTT
GCTGAAAACAAAGGTTACAACCAGGACATCTGTTCCTACTGCCGCGTCAACATGGGCTAC
ATGGAACTCCTCAAACAGCAGGCTCTGACAGGCGAAACGCCGGAAGTCCTCAAAAACTCC
CCGGCTTCTCCGATTCCCCTTCCGGATGTTGTCCTCACTTGCAACAACATCTGCAATACC
TTGCTCAAATGGTATGAAAACTTGGCTAAAGAATTGAACGTACCTCTCATCAACATCGAC
GTACCGTTCAACCATGAATTCCCTGTTACGAAACACGCTAAACAGTACATCGTCGGCGAA
TTCAAACATGCTATCAAACAGCTCGAAGACCTTTGCGGCCGTCCCTTCGACTATGACAAA
TTCTTCGAAGTACAGAAACAGACACAGCGCTCCATCGCTGCCTGGAACAAAATCGCTACG
TACTTCCAGTACAAACCGTCGCCGCTCAACGGCTTCGACCTCTTCAACTACATGGGCCTC
GCCGTTGCTGCCCGCTCCTTGAACTACTCGGAAATCACGTTCAACAAATTCCTCAAAGAA
TTGGACGAAAAAGTAGCTAATAAGAAATGGGCTTTCGGTGAAAACGAAAAATCCCGTGTT
ACTTGGGAAGGTATCGCTGTCTGGATCGCTCTCGGCCACACCTTCAAAGAACTCAAAGGT
CAGGGCGCTCTCATGACTGGTTCCGCTTATCCTGGCATGTGGGACGTTTCCTACGAACCG
GGCGACCTCGAATCCATGGCAGAAGCTTATTCCCGTACATACATCAACTGCTGCCTCGAA
CAGCGCGGTGCTGTTCTTGAAAAAGTTGTCCGCGATGGCAAATGCGACGGCTTGATCATG
CACCAGAACCGTTCCTGCAAGAACATGAGCCTCCTCAACAACGAAGGCGGCCAGCGCATC
CAGAAGAACCTCGGCGTACCGTACGTCATCTTCGACGGCGACCAGACCGATGCTCGTAAC
TTCTCGGAAGCACAGTTCGATACCCGCGTAGAAGCTTTGGCAGAAATGATGGCAGACAAA
AAAGCCAATGAAGGAGGAAACCACTAA    (SEQ ID NO:17)
```

Figure 15

MSEEKTVDIESMSSKEALGYFLPKVDEDARKAKKEGRLVCWSASVAPPEFCTAMDIAIVY
PETHAAGIGARHGAPAMLEVAENKGYNQDICSYCRVNMGYMELLKQQALTGETPEVLKNS
PASPIPLPDVVLTCNNICNTLLKWYENLAKELNVPLINIDVPFNHEFPVTKHAKQYIVGE
FKHAIKQLEDLCGRPFDYDKFFEVQKQTQRSIAAWNKIATYFQYKPSPLNGFDLFNYMGL
AVAARSLNYSEITFNKFLKELDEKVANKKWAFGENEKSRVTWEGIAVWIALGHTFKELKG
QGALMTGSAYPGMWDVSYEPGDLESMAEAYSRTYINCCLEQRGAVLEKVVRDGKCDGLIM
HQNRSCKNMSLLNNEGGQRIQKNLGVPYVIFDGDQTDARNFSEAQFDTRVEALAEMMADK
KANEGGNH (SEQ ID NO:18)

```
SEQ ID NO:17    1 atgagtgaagaaaaaacagtagatattgaaagcatgagctccaaggaagc
SEQ ID NO:19    1 atg------ccaaagacagta---------agccctggcgttcagg----
SEQ ID NO:20    1 ----atgatgaaattaaag--gcaattgaaaagttga--tgcaa------
SEQ ID NO:21    1 ------------atgtcacttgtcaccga-----------tcta--cccgc SEQ ID NO:17   51 cctt---ggttacttcttgccgaaa--gtcgatgaagacgca-------c
SEQ ID NO:19   32 -cat---tgagagatgtagttgaaaaggtttacagagaactg-------c
SEQ ID NO:20   37 ----------aaatt-----cgcca--gtagaaaagaacagc-------t
SEQ ID NO:21   27 cattttcgatcagttct--ctgaag--ctcgccagacaggctttctcacc SEQ ID NO:17   89 gta-aagcgaaaa-aagaaggccgcctcgttt-gctggtccgcttctgtc
SEQ ID NO:19   71 ggg-aaccgaaag-aaagaggagaaaaagtag-gctggtcctcttc--ca
SEQ ID NO:20   63 atataagcaaaagaagaaggtagaaaagtttt---ttggaatgttctgtg
SEQ ID NO:21   73 gtc-atggatctc-aaggag--cgcggcattccgctggt--------tggc SEQ ID NO:17  136 gctcctccggaattctgcacggctatggacatcgccatcgtc--tatccg
SEQ ID NO:19  116 agttccctgcgaactggctgaatcttttcggctgcatgttgggtatccg
SEQ ID NO:20  110 cct--------atgttcca-----atagaaat---aat--tt--tagcag
SEQ ID NO:21  112 act----------tactgcacctttatg----ccgcaagag-----atccc SEQ ID NO:17  184 gaaactca--cgcagctggtatcggtgcc---cgtcacggtg--------
SEQ ID NO:19  166 gaaaacca--ggctgctggtatcgctgccaaccgtgacggcgaagtgatg
SEQ ID NO:20  140 caaatgcaatcccagttggtttgtgtgga---ggtaaaaat---------
SEQ ID NO:21  144 ga-----t--ggcagc------cggtgcg---gtt----gtg--------

SEQ ID NO:17  221 --------------------------------------ctccggccatgc
SEQ ID NO:19  214 tgccaggctgcagaagatatcggttatgacaacgatatctgcggctatgc
SEQ ID NO:20  178 ----------------------------------------------gacacaa
SEQ ID NO:21  166 ----------------------------------------gtttcgctctgt SEQ ID NO:17  233 tcgaagt-t-----------gctg---------------------aaaa--
SEQ ID NO:19  264 ccgtatt-tccctggcttatgctgccggggttccggggtgccaacaaaatg
SEQ ID NO:20  185 tcccaat-a-----------gcag---------------------a-----
SEQ ID NO:21  178 tccacctct----------gatg---------------------aaac--

SEQ ID NO:17  249 --caaaggttacaaccaggacatctgttcctactgccgcgtcaacatg--
SEQ ID NO:19  313 gacaaagatggcaactatgtcatcaacccccacagcggcaaacagatgaa
SEQ ID NO:20  198 ---ggaggat-ttgccaagaaacctatgcc--------cattaata----
SEQ ID NO:21  195 --ca---ttgaagaagcggagaaagat------ctgccgcg-caacct---

SEQ ID NO:17  295 ----------ggctacatggaactc--ctcaaacagcag-----------
SEQ ID NO:19  363 agatgccaatggcaaaaaggtattcgacgcagatggcaaaccgtaatcg
SEQ ID NO:20  232 ------------------aaatc--atccta----tg-----------
SEQ ID NO:21  231 -----------ctgcccg---ctg--attaaa-agca------------

SEQ ID NO:17  322 --------------------------------------------------
SEQ ID NO:19  413 atcccaagaccctgaaacccttggccaccaccgacaacatctatgaaatc
SEQ ID NO:20  245 --------------------------------------------------
SEQ ID NO:21  251 --------------------------------------------------

SEQ ID NO:17  322 ---gctctgac---aggcgaaa-----------cgccggaa-gtcctcaa
SEQ ID NO:19  463 gctgctctgccggaaggggaagaaaagacccgccgccagaatgccctgca
SEQ ID NO:20  245 ---gttttaa-------------------------gaa-ggca--aa
SEQ ID NO:21  251 ---gctacggc---ttcggcaa----------aaccg---------at
```

Figure 16A

```
SEQ ID NO:17   354 aaactccccggcttctccgattcccttccggatgttgtcctcacttgca
SEQ ID NO:19   513 caaatatcgtcagatgaccatgcccatgccggacttcgtgctgtgctgca
SEQ ID NO:20   261 aacctgccc--ttactttgaagcatct----gatatagttat-tggagaa
SEQ ID NO:21   274 aaatgcccctacttct-------actttcggatctggtggtc---ggtg SEQ ID NO:17   404 acaacatctgca-------ataccttgctcaaatggtatgaaaacttgg-
SEQ ID NO:19   563 acaacatctgca-------actgcatgaccaaatggtatgaagacattg-
SEQ ID NO:20   304 actacctgtgaaggaaagaagaagatgtttgagttgatggagagattggt
SEQ ID NO:21   314 aaaccacctgcg-------acggcaaaagaaaatgtatgaatacatgg- SEQ ID NO:17   446 -ctaaagaattgaac---gtacctctca----tcaacatcgacgtac--c
SEQ ID NO:19   605 -cccgtcggcacaac---attcctttga----tcatgatcgacgttc--c
SEQ ID NO:20   354 gccaatgcatataat---gcacctcccacacatgaaagatgaagatt--c
SEQ ID NO:21   356 -c---ggagtttaagcctgttcatgtga----tgca-attgcccaacagc SEQ ID NO:17   486 gttca--accatgaattc---cctg--tta-cgaa----ac--acgctaa
SEQ ID NO:19   645 ttaca--ac---gaattcgaccatg--tcaacgaa----gccaacgtgaa
SEQ ID NO:20   399 tttga--a------aatct---ggat--taa-agaagttgaa--aagctaa
SEQ ID NO:21   397 gttaaggacgatgcctcg---cgtgcgtta-tgga----a----------

SEQ ID NO:17   522 acagtacatcgtcg-----gcgaattcaaacatgctatca----aacagc
SEQ ID NO:19   684 a---tacatccggt-----cccagctggatacggccatcc----gtcaaa
SEQ ID NO:20   434 --aagaattggttgagaaagagactggaaataaaataacagaggaaaagt
SEQ ID NO:21   429 --agccgagatgct-----gcgcttgcaa----------a----aaacgg SEQ ID NO:17   563 tcgaagacctttgcggccgtcccttcgactatgacaaattcttcgaagta
SEQ ID NO:19   722 tggaagaaatcaccggcaagaagttcgatgaagacaaattc------gaa
SEQ ID NO:20   482 taaaaga--------------------------gacagttgat--aaagta
SEQ ID NO:21   458 tagaagaacgttttgggcacgagattagcgaagatgctctgcgcgatgcc SEQ ID NO:17   613 cagaaacagacacagcgctc-catcg--ctgcc------tggaacaaaat
SEQ ID NO:19   766 cag-tgctgccagaacgc-c-aaccgtactgccaaagcatggctgaaggt
SEQ ID NO:20   505 aataaagttagggag-----------------t------tgttttataaa
SEQ ID NO:21   508 attacgctgaaaaaccgcgaacgtcg--cgcac------tgg---ctaat SEQ ID NO:17   654 cgctacgtacttc--c---agtacaaaccgtcgccgctcaacggcttcgac
SEQ ID NO:19   813 ttgcgactacctg--c--agtacaaaccggctccgttcaacgggttcgac
SEQ ID NO:20   532 ctctatgaattga--ggaagaataaaccagctccaattaagggtttagat
SEQ ID NO:21   547 ttttatcatcttgggc--agttaaatcctccggcgcttagcggcagcgac SEQ ID NO:17   700 ctcttcaactacatgggcctcgccg-ttgctgcccgctccttgaactact
SEQ ID NO:19   859 ctgttcaaccatatggctgacgtgg-ttaccgcccgtggccgtgtggaag
SEQ ID NO:20   580 gttttaaaattattccagtttgcctatttattggatattgatgacacaat
SEQ ID NO:21   595 attctga---aagtggtttacggcg-caaccttccggttcgataaagagg SEQ ID NO:17   749 cggaaatcacgttcaacaaattcctcaaagaattggacgaaaaagtagc-
SEQ ID NO:19   908 ctgctgaagctttcgaactgctggccaaggaactggaacagcatgt----
SEQ ID NO:20   630 agggatt----ttagaggatttaattgaggagttagaggagagagtt---
SEQ ID NO:21   641 cg------------------ttgatcaatgaactggatgcaatgaccgcc SEQ ID NO:17   798 -----taataagaaatgggctttcggtgaa------aacgaaaaatccg
SEQ ID NO:19   954 -------gaaggaaggcaccaccaccgctcccttcaaagaacagcatcg
SEQ ID NO:20   673 -----aaaaaaggagaaggttatgaaggaa------agagaa--------
SEQ ID NO:21   673 cgcgttcgtcagcagtgggaagaag--gcc------agcgactggacccg SEQ ID NO:17   837 tgttacttgggaaggta-tcgctgtctggatcgctctcggccacacc---
SEQ ID NO:19   996 tatcatgttcgaaggga-tcccctgctgg--ccgaaactgccgaacc---
SEQ ID NO:20   704 -------ttttaataac-tggctgtc-caatggttgctggaaacaataag
SEQ ID NO:21   715 cgt--ccgcgcattttaatcaccggctg---cccgattggcggcgc----
```

Figure 16B

```
SEQ ID NO:17    883  ----t--tcaaagaactca--aaggtcagggcgctctcatgactggttcc
SEQ ID NO:19   1040  ----tgttcaaaccgctga--aagccaacggcctgaacatcaccggcgtt
SEQ ID NO:20    745  attgt--tgaaattattgaggaagtt---ggaggagtagttgttggtgaa
SEQ ID NO:21    756  ------------agcaga--aaaagtggtgcgcgcgattgaagagaatg SEQ ID NO:17    925  gcttat---cctggcatgtgggacgtttcctacgaacc--------ggg-
SEQ ID NO:19   1084  gtatatgctcctgctttcgggttcgtgtacaacaacct--------gga-
SEQ ID NO:20    790  g--aaa---gctgcactggaacaagattctttgaaaactttgttgaggg-
SEQ ID NO:21    791  gc---g---gctgggttgtcggttatgaaaactgcacc--------gggg SEQ ID NO:17    963  ------cga---cctcg-aatccatggcagaa----gcttattcccgtac
SEQ ID NO:19   1125  ------cga---attgg---tcaaagcctact----gcaaagccccgaac
SEQ ID NO:20    834  ------ctatagcgtag-aggacattgcaaaa----agata----cttta
SEQ ID NO:21    827  cgaaagcga---ccgagcaatgcgtggcagaaacgggcgatgtctacgac SEQ ID NO:17    999  atac------atcaactgctgcct----------cgaacagcgcggtgct
SEQ ID NO:19   1159  -tcc------gtca------gcat----------cgaacagggtgttgcc
SEQ ID NO:20    869  aaat------cccatgtgcttgtagatttaaaaacgatgagagagttgaa
SEQ ID NO:21    874  gcgctggcggataaatatctggc-----------gattggctgctcct SEQ ID NO:17   1033  gttcttgaaaaagttgtccgcgatggcaaatgcgacggc-ttgatcatgc
SEQ ID NO:19   1186  tggcgtgaaggcctgatccgcgacaacaaggttgacggc-gtactggttc
SEQ ID NO:20    913  aatataaagagattggttaaagagttggacgtcgatggagttgtttat--
SEQ ID NO:21    911  gtgtttcgccgaacgatcagcgcctgaaaatgc-tcagc-cagatggtgg SEQ ID NO:17   1082  accagaacc-gttcctgcaagaacatgagcctcctcaacaacgaaggcg-
SEQ ID NO:19   1235  actacaacc-ggtcctgcaaaccctggagcggctacatgcctgaaatgc-
SEQ ID NO:20    961  ----tacac-tttgcagtattgccat----acatttaacatagagggagc
SEQ ID NO:21    959  aggaatatcaggtcgatggcgtagttga-----tgtgattttgcaggcgt SEQ ID NO:17   1130  ---gccagcgcatc-cagaagaacctc--ggcgtaccgtacgtcatcttc
SEQ ID NO:19   1283  ---agcgtcgtttc-accaaagacatg--ggtatcccactgctggattc
SEQ ID NO:20   1002  taaggtagaggagg-cattaaaagaggagggcattccaattataagaatt
SEQ ID NO:21   1004  ---gccatacctacgcggtggaatcgc--tggcgattaaacgtcatgtgc SEQ ID NO:17   1174  gacggcgaccagaccgatgctcgtaacttctcggaagca-----------
SEQ ID NO:19   1327  gacggtgaccaggctgacccgagaaacttcaacgcggct-----------
SEQ ID NO:20   1051  gaaactgactattctga-------aagtgatag--agag-----------
SEQ ID NO:21   1049  gccagc-agcacaacattccttatatcgctattgaaacagactactccac SEQ ID NO:17   1213  -------------cagttcgatacccgcgtagaagctttggcagaaatga
SEQ ID NO:19   1366  -------------cagtatgagacccgtgttcagggcttggtcgaagcca
SEQ ID NO:20   1081  -------------cagttaaaaacaaggttggaggcatttattgagatga
SEQ ID NO:21   1098  ctcggatgtcgggcagctcagtacccgtgtcgcggcctttattgagatgc SEQ ID NO:17   1250  tggcagacaaaaaagccaatgaaggaggaaaccactaa
SEQ ID NO:19   1403  tggaag-caaatgatgaaaagaagg-ggaaataa----
SEQ ID NO:20   1118  t------------------ttaa---------------
SEQ ID NO:21   1148  tgtaa---------------------------------
```

```
SEQ ID NO:18    1 --mseektvdiesmsskealgyflpkvdedarkakkegrlvcwsasvapp
SEQ ID NO:22    1 ----mpktvs----pgvqalrdvvekvyrelrepkergekvgwssskfpc
SEQ ID NO:23    1 --mmklka--ieklmqkfa------srkeqlykqkeegrkvfgm------
SEQ ID NO:24    1 mslvtdlpaifdqfsearqtg-fltvmdlkergiplvg------------

SEQ ID NO:18   49 efctamdiaivypethaag---igarhgapamlevaenkgynqdicsycr
SEQ ID NO:22   43 elaesfrlhvgypenqaag---iaanrdgevmcqaaedigydndicgyar
SEQ ID NO:23   35 -fcayvpieiila-anaip---vglcggkndtipiae-edlprnlcplik
SEQ ID NO:24   38 tyctfmpqei----pmaagavvvslcstsdetieeae-kdlprnlcplik SEQ ID NO:18   96 vnmgym--------------------------------------------
SEQ ID NO:22   90 islayaagfrgankmdkdgnyvinphsgkqmkdangkkvfdadgkpvidp
SEQ ID NO:23   79 ssygf---------------------------------------------
SEQ ID NO:24   83 ssygf---------------------------------------------

SEQ ID NO:18  102 ellkqqaltgetpev--------------lknspaspiplpdvvltcnn
SEQ ID NO:22  140 ktlkpfattdniyeiaalpegsektrrqnalhkyrqmtmpmpdfvjccnn
SEQ ID NO:23   84 -----------------------------kkaktcpyfeasdiviget
SEQ ID NO:24   88 ------gktdkcpyf----------------y---------fsdlvvg-et SEQ ID NO:18  137 icntllkwyenlakelnvplinidvpfnhefpvtkhakqyivgefkhaik
SEQ ID NO:22  190 icncmtkwyediarrhniplimidvpynefdhvneanvkyirsqldtair
SEQ ID NO:23  103 tcegkkkmfelm--erlvpmhimhlphmkd----edslkiwikeveklke
SEQ ID NO:24  107 tcdgkkkmyeymaefkpvhvmqlpnsvkdd-----asralwkaemlrlqk SEQ ID NO:18  187 qledlcgrpfdydkffe---vqkqtqrsiaawnkiatyfqykpsplngfd
SEQ ID NO:22  240 qmeeitgkkfdedkfeq---ccqnanrtakawlkvcdylqykpapfngfd
SEQ ID NO:23  147 lveketgnkiteeklke---tvdkvnkvrelfyklyelrknkpapikgld
SEQ ID NO:24  152 tveerfgheisedalrdaialknrerralanfyhlg---qlnppalsgsd SEQ ID NO:18  234 ---lfnymglavaarslnyseitfnkflkeldekvan--kkwafge--n-
SEQ ID NO:22  287 ---lfnhmadvvtargrveaaeafellakeleqhvke--gtttapf--k-
SEQ ID NO:23  194 vlklfqfaylldiddtigile-----dlieeleerv----kk---ge--gy
SEQ ID NO:24  199 ---ilk----vvygatfrfdk---ealineldamtarvrqqweegqrld- SEQ ID NO:18  276 eksrvtwegiavwialghtfkelkgqgalmtg----say---pgmwdvsy
SEQ ID NO:22  329 eqhrimfegipcwpklpnlfkplkanglnitg----vvy---apafgfvy
SEQ ID NO:23  231 egkrilitgcpmvagnnkiveliesvggvvvg----eesctgtrffenfv
SEQ ID NO:24  238 prprilitgcpiggaaekvvraieenggwvvgyenctga---kateqcva SEQ ID NO:18  319 epgdl-esmaeaysrtyinccl--eqrgavlekvvrdgkcdglimhqnrs
SEQ ID NO:22  372 --nnl-delvkayckapnsvsi--eqgvawreglirdnkvdgvlvhynrs
SEQ ID NO:23  277 egysv-ediakryfkipcacrfknderveniklvkeldvdgvvyytlqy
SEQ ID NO:24  285 etgdvydaladkylaigcscvspndqrlkmlsqmveeyqvdgvvdvilqa SEQ ID NO:18  366 cknmsllnnegg--qriqknlgvpyvifdgdqtdarnfseaqfdtrveal
SEQ ID NO:22  417 ckpwsgympemq--rrftkdmgiptagfdgdqadprnfnaaqyetrvqgl
SEQ ID NO:23  326 cht---fniegakveealkeegipiirietdyses---dreqlktrleaf
SEQ ID NO:24  335 chtyaveslaik--rhvrqqhnipyiai---etdystsdvgqlstrvaaf SEQ ID NO:18  414 aemmadkkaneggnh
SEQ ID NO:22  465 veameandekkgk--
SEQ ID NO:23  370 iemi-----------
SEQ ID NO:24  380 ieml-----------
```

Figure 18

```
ATGAGTCAGATCGACGAACTTATCAGCAAATTACAGGAAGTATCCAACCATCCCCAGAAG
ACGGTTTTGAATTATAAAAAACAGGGTAAAGGCCTCGTAGGCATGATGCCCTACTACGCT
CCGGAAGAAATCGTATATGCTGCAGGCTACCTCCCGGTAGGCATGTTCGGTTCCCAGAAC
CCGCAGATCTCCGCAGCTCGTACGTACCTTCCTCCGTTCGCTTGCTCCTTGATGCAGGCT
GACATGGAACTCCAGCTCAACGGCACCTATGACTGCCTCGACGCTGTTATCTTCTCCGTT
CCTTGCGACACTCTCCGCTGCATGAGCCAGAAATGGCACGGCAAAGCTCCGGTCATCGTC
TTCACACAGCCGCAGAACCGTAAGATCCGCCCGGCTGTCGATTTCCTCAAAGCTGAATAC
GAACATGTCCGTACGGAATTGGGACGTATCCTCAACGTAAAAATCTCCGACCTGGCTATC
CAGGAAGCTATCAAAGTATATAACGAAACCGTCAGGTTATGCGTGAATTCTGCGACGTA
GCTGCTCAGTACCCGCAGATCTTCACTCCGATAAAACGTCATGACGTCATCAAAGCCCGC
TGGTTCATGGACAAAGCTGAACACACCGCTTTGGTCCGCGAACTCATCGACGCTGTCAAG
AAAGAACCGGTACAGCCGTGGAATGGCAAAAAAGTCATCCTCTCCGGTATCATGGCAGAA
CCGGATGAATTCCTCGATATCTTCAGCGAATTCAACATCGCTGTCGTCGCTGACGACCTC
GCTCAGGAATCCCGCCAGTTCCGTACAGACGTACCGTCCGGCATCGATCCCCTCGAACAG
CTCGCTCAGCAGTGGCAGGACTTCGATGGCTGCCCGCTCGCTTTGAACGAAGACAAACCG
CGTGGCCAGATGCTCATCGACATGACTAAGAAATACAATGCTGACGCCGTCGTCATCTGC
ATGATGCGTTTCTGCGATCCTGAAGAATTCGACTATCCGATTTACAAACCGGAATTTGAA
GCTGCTGGCGTTCGTTACACGGTCCTCGACCTCGACATCGAATCTCCGTCCCTCGAACAG
CTCCGCACCCGTATCCAGGCTTTCTCGGAAATCCTCTAA    (SEQ ID NO:25)
```

Figure 19

MSQIDELISKLQEVSNHPQKTVLNYKKQGKGLVGMMPYYAPEEIVYAAGYLPVGMFGSQN
PQISAARTYLPPFACSLMQADMELQLNGTYDCLDAVIFSVPCDTLRCMSQKWHGKAPVIV
FTQPQNRKIRPAVDFLKAEYEHVRTELGRILNVKISDLAIQEAIKVYNENRQVMREFCDV
AAQYPQIFTPIKRHDVIKARWFMDKAEHTALVRELIDAVKKEPVQPWNGKKVILSGIMAE
PDEFLDIFSEFNIAVVADDLAQESRQFRTDVPSGIDPLEQLAQQWQDFDGCPLALNEDKP
RGQMLIDMTKKYNADAVVICMMRFCDPEEFDYPIYKPEFEAAGVRYTVLDLDIESPSLEQ
LRTRIQAFSEIL   (SEQ ID NO:26)

```
SEQ ID NO:25    1 atgagtcagatcgacgaacttatcagcaaattacaggaagtatccaacca
SEQ ID NO:27    1 atggct---atcagtgcacttattgaagagttccaaaaagtat-ctgcca
SEQ ID NO:28    1 ----------atgatgaaattaaaggcaattgaaaagttgatgcaaaaat
SEQ ID NO:29    1 atgtcacttgtcaccgatctacccgccatttcgatcagttctctgaagc SEQ ID NO:25   51 tccccagaag---------ac-------ggttttg---aattataaaaaa
SEQ ID NO:27   47 gccc--gaag---------ac-------catgctggccaaatataaagcc
SEQ ID NO:28   41 tgccagtag---------aaaagaacagctatat---aagcaaaaagaa
SEQ ID NO:29   51 tgccagacaggctttctcac-------cgtcatg---gatctcaaggag SEQ ID NO:25   82 cagggtaaaggcctcgtaggca--tgatgccctactacgctccggaagaa
SEQ ID NO:27   79 cagggcaaaaaagccatcggct--gcctgccgtactatgttccggaagaa
SEQ ID NO:28   79 gaaggtagaaaagtttttggaa--tgttctgtgcctatgttccaatagaa
SEQ ID NO:29   91 cgcggcattccgctggttggcacttactgcacctttatgc--cgcaagag SEQ ID NO:25  130 atcgtatatgctgcaggctacctcccggtaggcatgt---tcggttccca
SEQ ID NO:27  127 ctggtctatgctgcaggcatggttcccatgggtgtat---ggggctgcaa
SEQ ID NO:28  127 ataattttagcagcaaatgcaatcccagttggtttgt---gtggaggtaa
SEQ ID NO:29  139 atcccgatggcagccgg------tgcggttgtggtttcgctctgttccac SEQ ID NO:25  177 -------gaacccgcag-atctccgcagctcgtacgtaccttcctccgtt
SEQ ID NO:27  174 -------tggcaaacaggaagtccgttccaaggaa-tactgtgcttcctt
SEQ ID NO:28  174 -------aaatgacaca-atcccaatagcagaggaggatttgccaagaaa
SEQ ID NO:29  183 ctctgatgaaacc-----attgaagagcggagaaagatctgccgcgcaa SEQ ID NO:25  219 cgcttgctccttgatgcaggctgacatggaactccagctcaacggca---
SEQ ID NO:27  216 ctactgcaccattgcccagcagtctctggaaatgctgctggacggga---
SEQ ID NO:28  216 cctatgcccattaataaaatcatcctatggttttaag----aaggca---
SEQ ID NO:29  228 cctctgccgctga-------ttaaaagcagctacggct--tcggcaaaa SEQ ID NO:25  266 cctatgactgcctcgacgctgttatcttctcc----gttcct-tgcg---
SEQ ID NO:27  263 ccctggatgggttggacgggatcatca-ctcc----ggtactgtgtg---
SEQ ID NO:28  259 --aaaacctgcccttactttg-aagcatctgatatagttatt-ggag---
SEQ ID NO:29  269 ccgataaatgcccctac----ttctactttc----ggatct-ggtggtc SEQ ID NO:25  308 ----acactctccgctgcatgagccagaaat-------gg--------c-
SEQ ID NO:27  305 ----atacccctgcgtcccatgagccagaacttcaaagtgg--------cc
SEQ ID NO:28  302 ----aaact-----------acctgtgaa-------gg--------a-
SEQ ID NO:29  310 ggtgaaaccacctgcgacggcaaaaagaaaa-------tgtatgaatac- SEQ ID NO:25  338 ----acggcaaagct----ccggtcatcg-tcttcacacagccgcagaac
SEQ ID NO:27  343 atgaaagacaagatg----ccggttatt-tcctggctcatcccccaggtc
SEQ ID NO:28  319 ----aagaagaagat----gtttgagttgatggagagattggtgccaatg
SEQ ID NO:29  352 ----atggcggagtttaagcctgttcatg-tgatgcaattgcccaacagc SEQ ID NO:25  379 cgtaaga-tccgcccggc-----------tgtcgatttcctcaaag-ct
SEQ ID NO:27  388 cgtcagaatgccgccggc-----------aagc-agttcacctatg-at
SEQ ID NO:28  361 catataa-tgcacctcccacacatgaagatgaagattctttgaaaatct
SEQ ID NO:29  397 gttaagg-acgatgcctc----------gcgtgcgttatggaaag-cc SEQ ID NO:25  415 gaat--acgaacatgtc---cgt-------acgg--aattgg----gacg
SEQ ID NO:27  424 gcct--acagcgaagt-----ga-------aaggccatctgg----aaga
SEQ ID NO:28  410 ggattaaagaagttgaaaagcta-------aaag--aattggttgagaaa
SEQ ID NO:29  433 ga------gatgctgcg---cttgcaaaaaacgg--tagaag----aacg
```

Figure 20A

```
SEQ ID NO:25   447 tatcctcaacgtaaaa--atctccgacctggctatccaggaagctatcaa
SEQ ID NO:27   456 aatctgcggccatgaa--atcaccaatgatgccatcctggatgccatcaa
SEQ ID NO:28   451 gagactggaaataaaataacagaggaaaagttaaaagagacagttgataa
SEQ ID NO:29   468 ttttgggcacg---ag--attagcgaagatgctctgcgcgatgccattgc SEQ ID NO:25   495 agtatataacgaaaaccgtcaggttatgcgtgaattct---------gcg
SEQ ID NO:27   504 agtgtacaacaagagccgtgctgcccgccgcgaattct---------gca
SEQ ID NO:28   501 agtaaataaagtta---gggagttgtttttataaactct---------atg
SEQ ID NO:29   513 gctgaaaaaccgcgaacgtcgcgcactggctaattttttatcatcttgggc SEQ ID NO:25   536 acgtagctgctcag-----tacccgcagatcttcactccgataaa--acg
SEQ ID NO:27   545 aactggc--caacg-----aacatcctgatctgatcccggcttccgtacg
SEQ ID NO:28   539 a-attgaggaagaa-----taaac-cag-------ctccaattaa--ggg
SEQ ID NO:29   563 agttaaatcctccggcgcttagcggcag--cgacattctgaaagt--ggt SEQ ID NO:25   579 tcatgacgtcatc--------------aaag----cccgctgg-----ttca
SEQ ID NO:27   588 ggccaccgtactg--------------cgtg----ccgcttac-----ttca
SEQ ID NO:28   573 tttagatgttta---------------aaattattccagtttgcctatttat
SEQ ID NO:29   609 ttacggcgcaaccttccggttcgataaag----aggcgttg-----atca SEQ ID NO:25   608 tggacaaagctgaacacaccgctttggtccgcgaactcatcgacgctgtc
SEQ ID NO:27   617 tgctgaaggatgaatacaccgaaaagctggaagaactgaacaagg-----
SEQ ID NO:28   611 tggatattgatgacacaataggggatttagagggatttaattgaggagtta
SEQ ID NO:29   650 atgaactggatgcaatgaccgc------ccgcg--ttcgtcagcagtggg SEQ ID NO:25   658 aagaa-------ag--aaccggtacagccgtggaat-----ggcaaaaaa
SEQ ID NO:27   662 aactg-------gc--agctgctcctgccggcaagttcgacggccacaaa
SEQ ID NO:28   661 gaggagagagttaa--aaaaggagaaggttatgaa------ggaaagaga
SEQ ID NO:29   692 aagaa-------ggccagcgactggaccccgcgtccg-----cgcatttta SEQ ID NO:25   694 gtcatcctctccggt------atcatggcagaaccggatgaattcct---
SEQ ID NO:27   703 gtggttgtttccggc------atcatctacaacacgcccggcatcct---
SEQ ID NO:28   703 attttaataactggctgtccaatggttgctggaaacaataagattgt---
SEQ ID NO:29   730 atcaccggctgcccg------attggcggcgcagcagaaaaagtggtgcg SEQ ID NO:25   735 cgatatcttcagcgaatt-caacatcgctgtcgtcgctgacgacctc-gc
SEQ ID NO:27   744 gaaagccatggatgacaa-caaactggccattgctgctgatgactgc-gc
SEQ ID NO:28   750 tgaaattattgaggaagt-tggaggagtagttgttggtgaagaaagctgc
SEQ ID NO:29   774 cgcgat-tgaagagaatggcggctgggttgtcggttatgaaaactgc-ac SEQ ID NO:25   783 tcagga-atcccgccagttccgtacagacgtaccgtccggcatcgatccc
SEQ ID NO:27   792 ttatga-aagccgcagctttgccgtggatgctccggaagatctgga---c
SEQ ID NO:28   799 actgga-a------caagattctttgaaaactttgttgagg--gctatagc
SEQ ID NO:29   822 cggggcgaaagcgaccgagcaatgc-gtggcagaaacggg---cgatgtc SEQ ID NO:25   832 ctcgaacagctcgctcag------cagtgg------caggacttcgat-g
SEQ ID NO:27   838 aacggactgcatgctctggctgtacagttctccaaacagaagaacgat-g
SEQ ID NO:28   841 gtagaggacattgcaaa------------------aaga-tacttt-a
SEQ ID NO:29   868 tacgacgcgctggcggat-------aaatat------ctgg----cgattg SEQ ID NO:25   869 ----gctgcccgctcgctttgaa----cgaagacaaaccgcg-tggccag
SEQ ID NO:27   887 ttctgctgtacgatcc---tgaatttgccaagaatacccgttctgaacac
SEQ ID NO:28   869 ----aaatcccatgtgcttgta------gatttaaaaacgat-gagagag
SEQ ID NO:29   902 ----gctgctc-ctgtgtttcgc----cga--acgatcagcg-cctgaaa SEQ ID NO:25   910 atgctcatcgaca-----tgactaagaaatacaatgctgacgccgtcgtc
SEQ ID NO:27   934 gttggca---atc-----tggtaaaagaaagcggcgcagaaggactgatc
SEQ ID NO:28   908 ttgaaaatataaagagattggttaaagagttggacgtcgatggagttgtt
SEQ ID NO:29   940 atgctcagccaga-----tggtggaggaatatcaggtcgatggcgtagtt
```

Figure 20B

```
SEQ ID NO:25    955  atctgcatgatgcgtttctgcgatcctgaagaattcgactatc---cgat
SEQ ID NO:27    976  gtgttcatgatgcagttctgcgatccggaagaaatggaatatc---ctga
SEQ ID NO:28    958  tattacactttgcagtattgccatacatttaacatagagggag---ctaa
SEQ ID NO:29    985  gatgtgattttgcaggcgtgccatacctacgcggtggaatcgctggcgat SEQ ID NO:25   1002  ttacaaaccggaatttgaagctgctgg----cgttcgttacacggtcctc
SEQ ID NO:27   1023  tctgaagaaggctctggatgcccacca----cattcctcatgtgaagatt
SEQ ID NO:28   1005  ggtagaggaggcattaaaagaggaggg----cattc------caattata
SEQ ID NO:29   1035  t----aaacgtcatgtgcgccagcagcacaacattccttatatcgctatt SEQ ID NO:25   1048  gacctcgacatcgaatctccgtccctcgaa------cagctccgcacccg
SEQ ID NO:27   1069  ggtgtggaccagatgacccgggactttggt------caggcccagaccgc
SEQ ID NO:28   1045  agaattgaaactgactattctgaaagtgatagagagcagttaaaaacaag
SEQ ID NO:29   1081  gaaacagactactccacctcggatgtcggg------cagctcagtacccg SEQ ID NO:25   1092  tatccaggctttctcggaaatcctctaa
SEQ ID NO:27   1113  tctggaagctttcgcagaaagcctgtaa
SEQ ID NO:28   1095  gttggaggcatttattgagatgatttaa
SEQ ID NO:29   1125  tgtcgcggcctttattgagatgctgtaa
```

```
SEQ ID NO:26    1  msqidelisklqevsnhpqk---tvlnykkqgkglvgmmpyyapeeivya
SEQ ID NO:30    1  -maisalieefqkvsaspkt---mlakykaqgkkaigclpyyvpeelvya
SEQ ID NO:31    1  mmkl-kaieklmqkfasrke---qlykqkeegrkvfgmfcayvpieiila
SEQ ID NO:32    1  mslvtdlpaifdqfsearqtgfltvmdlkergiplvgtyctfmpqeipma SEQ ID NO:26   48  agylpvgmfgsqnpqisaartylppfacslmqadmelqlngt---ydc--
SEQ ID NO:30   47  agmvpmgvwgcngkqevrskeycasfyctiaqqslemlldgt---ldg--
SEQ ID NO:31   47  ansipvglcggkndtipiaeedlprnlcpliksaygfkkaktcpyfea--
SEQ ID NO:32   51  agavvvslcstsdetieeaekdlprnlcplikss--ygfgkt----dkcpy SEQ ID NO:26   93  ---ldavifsvpcdtlrcmsqkwh----gkapvivftqpqnrkirpavdf
SEQ ID NO:30   92  ---ldgiitpvlcdtlrpmsqnfkvamkdkmpviflahpqvrqnaagkqf
SEQ ID NO:31   95  ---sdivigettcegkkkmfelme----rlvpmhimhlp-hmkdedslki
SEQ ID NO:32   96  fyfsdlvvgettcdgkkkmyeyma----efkpvhvmqlpnsvkddasral SEQ ID NO:26  136  lkaeyehvrtelgrilnvkisdlaiqeaikvynenrqvmrefcdvaaqyp
SEQ ID NO:30  139  tydaysevkghleeicgheitndaildaikvynksraarrefcklanehp
SEQ ID NO:31  137  wikeveklkelveketgnkiteeklketvdkvnkvrelfyklyslrknkp
SEQ ID NO:32  142  wkaemlrlqktveerfgheisedalrdaialknrerralanfyhlgqlnp SEQ ID NO:26  186  qiftpikrhdvik----arwf---mdkaehtalvrelidavkk--epvqp
SEQ ID NO:30  189  dlipasvratvlr----aayf---mlkdeytekleelnkelaa--apagk
SEQ ID NO:31  187  ---apikgldvlk----lfqfaylldiddtigiledlieeleervkkgeg
SEQ ID NO:32  192  ---palsgsdilkvvygatfr---fdk---ealinel-damta--rvrqq SEQ ID NO:26  227  wn-gkk------vilsg--imaepdefldifsefniavvaddlaqesrqf
SEQ ID NO:30  230  fd-ghk------vvvsg--iiyntpgilkamddnklaiaaddcayesrsf
SEQ ID NO:31  230  ye-gkr------ilitgcpmvagnnkiveiieevggvvvgeesctgtrff
SEQ ID NO:32  230  weegqrldprprilitgcpiggaaekvvraieenggwvvgyenctgakat SEQ ID NO:26  268  rtdvpsgidp-leqlaqqwqdfdgcplalned---kprgqmlidmtkkyn
SEQ ID NO:30  271  avdapedldnglhalavqfskqkndvllydpefakntrsehvgnlvkesg
SEQ ID NO:31  273  enfv-egys--vediakryfkip-cacrfknd---e-rvenikrlvkeld
SEQ ID NO:32  280  eqcvastgdv-ydaladkylai-gcscvspnd---q-rlkmlsqmveeyq SEQ ID NO:26  314  adavvicmmrfcdpeefdypiykpef-eaagvrytvldldiespsleqlr
SEQ ID NO:30  321  aeglivfmmqfcdpeemeypdlkkal-dahhiphvkigvdqmtrdfgqaq
SEQ ID NO:31  315  vdgvvyytlqychtfniegakveeal-keegipiirietdysesdreqlk
SEQ ID NO:32  324  vdgvvdvilqachtyaveslaikrhvrqqhnipyiaietdystsdvgqls SEQ ID NO:26  363  triqafseil
SEQ ID NO:30  370  taleafaesl
SEQ ID NO:31  364  trleafieml
SEQ ID NO:32  374  trvaafieml
```

```
   1 CGACGGCCCG GGCTGGTATC ATTCTAGTCA GTAATTCACC TTTGGAAAAT TTTCACAAAG
  61 GCAGTACGAC AGAAGCGTCG ATACATTCCA TTTAGCAGGA GGAAGTTACG GTAATGAGAA
 121 AAGTAGAAAT CATTACAGCT GAACAAGCAG CTCAGCTCGT AAAAGACAAC GACACGATTA
 181 CGTCTATCGG CTTTGTCAGC AGCGCCCATC CGGAAGCACT GACCAAAGCT TTGGAAAAAC
 241 GGTTCCTGGA CACGAACACC CCGCAGAACT TGACCTACAT CTATGCAGGC TCTCAGGGCA
 301 AACGCGATGG CCGTGCCGCT GAACATCTGG CACACACAGG CCTTTTGAAA CGCGCCATCA
 361 TCGGTCACTG GCAGACTGTA CCGGCTATCG GTAAACTGGC TGTCGAAAAC AAGATTGAAG
 421 CTTACAACTT CTCGCAGGGC ACGTTGGTCC ACTGGTTCCG CGCCTTGGCA GGTCATAAGC
 481 TCGGCGTCTT CACCGACATC GGTCTGGAAA CTTTCCTCGA TCCCCGTCAG CTCGGCGGCA
 541 AGCTCAATGA CGTAACCAAA GAAGACCTCG TCAAACTGAT CGAAGTCGAT GGTCATGAAC
 601 AGCTTTTCTA CCCGACCTTC CCGGTCAACG TAGCTTTCCT CCGCGGTACG TATGCTGATG
 661 AATCCGGCAA TATCACCATG GACGAAGAAA TCGGGCCTTT CGAAAGCACT TCCGTAGCCC
 721 AGGCCGTTCA CAACTGTGGC GGTAAAGTCG TCGTCCAGGT CAAAGACGTC GTCGCTCACG
 781 GCAGCCTCGA CCCGCGCATG GTCAAGATCC CTGGCATCTA TGTCGACTAC GTCGTCGTAG
 841 CAGCTCCGGA AGACCATCAG CAGACGTATG ACTGCGAATA CGATCCGTCC CTCAGCGGTG
 901 AACATCGTGC TCCTGAAGGC GCTACCGATG CAGCTCTCCC CATGAGCGCT AAGAAAATCA
 961 TCGGCCGCCG CGGCGCTTTG GAATTGACTG AAAACGCTGT CGTCAACCTC GGCGTCGGTG
1021 CTCCGGAATA CGTTGCTTCT GTTGCCGGTG AAGAAGGTAT CGCCGATACC ATTACCCTGA
1081 CCGTCGAAGG TGGCGCCATC GGTGGCGTAC CGCAGGGCGG TGCCCGCTTC GGTTCGTCCC
1141 GCAATGCCGA TGCCATCATC GACCACACCT ATCAGTTCGA CTTCTACGAT GGCGGCGGTC
1201 TGGACATCGC TTACCTCGGC CTGGCCCAGT GCGATGGCTC GGGCAACATC AACGTCAGCA
1261 AGTTCGGTAC TAACGTTGCC GGCTGCGGCG GTTTCCCCAA CATTTCCAG CAGACACCGA
1321 ATGTTTACTT CTGCGGCACC TTCACGGCTG GCGGCTTGAA AATCGCTGTC GAAGACGGCA
1381 AAGTCAAGAT CCTCCAGGAA GGCAAAGCCA GAAGTTCAT CAAAGCTGTC GACCAGATCA
1441 CTTTCAACGG TTCCTATGCA GCCCGCAACG GCAAACACGT TCTCTACATC ACAGAACGCT
1501 GCGTATTTGA ACTGACCAAA GAAGGCTTGA AACTCATCGA AGTCGCACCG GGCATCGATA
1561 TTGAAAAAGA TATCCTCGCT CACATGGACT TCAAGCCGAT CATTGATAAT CCGAAACTCA
1621 TGGATGCCCG CCTCTTCCAG GACGGTCCCA TGGGACTGAA AAAATAAATC TCTGCTGTAA
1681 AGGAGACTTT ACTATGAAAC CAATGAGACT ACATCACGTA GGCATTGTCC TGCCGACCTT
1741 AGAAAAAGCC CATGAATTCA TGCAGAATAA TGGACTTGAA ATCGACTATG CCGGCTATGT
1801 CGATGCTTAC CAGGCTGATC TCATTTTCAC TAAGTTTGGT GAATTTGCCA GCCCGATTGA
1861 AATGATTATC CCGCACTCCG GTGTGCTTAC CCAATTCAAT GGTGGCCGCG GCGGCATTGC
1921 CCACATCGCC TTCGAAGTGG ACGATGTCGA AGCTGTCCGC CAGGAAATGG AAGCAGATTG
1981 TCCGGGATGC ATGTTAGAAA AGAAAGCTGT CCAGGGTACG GACGACATTA TCGTCAACTT
2041 CCGCCGCCCG ACAACCAACC AGGGTATCCT CGTTGAATAT GTTCAGACGA CAGCACCTAT
2101 CACCGGCCGC GGCGAAAATC CTTTCGTTAA GAATCTCGGC CCGGAAAAAG GGAAGCTCAA
2161 CGAAACATGG CATCCCATGC GCCTGCACCA TATCGGCATC GTCTTGCCGA CCTTGGAAAA
2221 GGCCCATGAA TTCATCAAGA CCAATGGTCT GGAAGTGGAT TATTCCGGTT TCGTCGACGC
2281 CTACCATGCG GATCTCATTT TCACTAAAAA AGGTGAAAAC AGTACGCCTA TCGAATTCAT
2341 TATTCCCGT GAAGGGGTCC TCAAAGATTT CAATCATGGC AGGGGAGGTA TCGCTCATAT
2401 CGCCTTTGAA GTGGATGATG TCGAAAAGGT ACGTCAGATT ATGGAAAGCC AGAAGCCTGG
2461 TTGCATGCTC GAAAAGAAAG CCGTCCGGGG AACGGACGAT ATCATCGTCA ACTTCCGCCG
2521 TCCCAGCACG GACGCCGGCA TCCTCGTCGA ATATGTCCAG ACCGTAGCTC CCATCAATCG
2581 CAGCAATCCC AACCCTTTTA ATGATTGATT TTTTATAAAG AAAGGTGAAA ACTGTGTATA
2641 CTCTCGGAAT CGACGTTGGT TCTTCTTCTT CCAAGGCAGT CATCCTGGAA GATGGCAAGA
2701 AGATCGTCGC CCATGCCGTC GTTGAAATCG GCACCGGTTC GACCGGTCCG GAACGCGTCC
2761 TGGACGAAGT CTTCAAAGAT ACCAACTTAA AAATTGAAGA CATGGCGAAC ATCATCGCCA
2821 CAGGCTATGG CCGTTTCAAT GTCGACGCG CCAAAGGCGA AGTCAGCGAA ATCACGTGCC
2881 ATGCCAAAGG GGCCCTGCTTT GAATGCCCCG GTACGACGAC CATCCTCGAT ATCGGCGGTC
2941 AGGACGTCAA GTCCATCAAA TTGAATGGCC AGGGCCTGGT CATGCAGTTT GCCATGAACG
3001 ACAAATGCGC CGCTGGTACG GGCCGTTTCC TCGACGTCAT GTCGAAGGTA CTGGAAATCC
3061 CCATGTCTGA AATGGGGGAC TGGTACTTCA AATCGAAGCA TCCCGCTGCC GTCAGCAGTA
3121 CCTGCACGGT TTTTGCTGAA TCGAAGTCA TTTCCCTTCT TTCCAAGAAT GTCCCGAAAG
3181 AAGATATCGT AGCCGGTGTC CATCAGTCCA TCGCCGCCAA AGCCTGCGCT CTCGTGCGCC
3241 GCGTCGGTGT CGGTGAAGAC CTGACCATGA CCGGCGGTGG CTCCCGCGAT CCCGGCGTCG
3301 TCGATGCCGT ATCGAAAGAA TTAGGTATTC CTGTCAGAGT CGCTCTGCAT CCCCAAGCGG
3361 TGGGTGCTCT CGGAGCTGCT TTGATTGCTT ATGATAAAAT CAAGAAATAA GTCAAAGGAG
```

Figure 22A

```
3421  AGAACAAAAT CATGAGTGAA GAAAAAACAG TAGATATTGA AAGCATGAGC TCCAAGGAAG
3481  CCCTTGGTTA CTTCTTGCCG AAAGTCGATG AAGACGCACG TAAAGCGAAA AAAGAAGGCC
3541  GCCTCGTTTG CTGGTCCGCT TCTGTCGCTC CTCCGGAATT CTGCACGGCT ATGGACATCG
3601  CCATCGTCTA TCCGGAAACT CACGCAGCTG GTATCGGTGC CCGTCACGGT GCTCCGGCCA
3661  TGCTCGAAGT TGCTGAAAAC AAAGGTTACA ACCAGGACAT CTGTTCCTAC TGCCGCGTCA
3721  ACATGGGCTA CATGGAACTC CTCAAACAGC AGGCTCTGAC AGGCGAAACG CCGGAAGTCC
3781  TCAAAAACTC CCCGGCTTCT CCGATTCCCC TTCCGGATGT TGTCCTCACT TGCAACAACA
3841  TCTGCAATAC CTTGCTCAAA TGGTATGAAA ACTTGGCTAA AGAATTGAAC GTACCTCTCA
3901  TCAACATCGA CGTACCGTTC AACCATGAAT TCCCTGTTAC GAAACACGCT AAACAGTACA
3961  TCGTCGGCGA ATTCAAACAT GCTATCAAAC AGCTCGAAGA CCTTTGCGGC CGTCCCTTCG
4021  ACTATGACAA ATTCTTCGAA GTACAGAAAC AGACACAGCG CTCCATCGCT GCCTGGAACA
4081  AAATCGCTAC GTACTTCCAG TACAAACCGT CGCCGCTCAA CGGCTTCGAC CTCTTCAACT
4141  ACATGGGCCT CGCCGTTGCT GCCCGCTCCT TGAACTACTC GGAAATCACG TTCAACAAAT
4201  TCCTCAAAGA ATTGGACGAA AAAGTAGCTA ATAAGAAATG GGCTTTCGGT GAAAACGAAA
4261  AATCCCGTGT TACTTGGGAA GGTATCGCTG TCTGGATCGC TCTCGGCCAC ACCTTCAAAG
4321  AACTCAAAGG TCAGGGCGCT CTCATGACTG GTTCCGCTTA TCCTGGCATG TGGGACGTTT
4381  CCTACGAACC GGGCGACCTC GAATCCATGG CAGAAGCTTA TTCCCGTACA TACATCAACT
4441  GCTGCCTCGA ACAGCGCGGT GCTGTTCTTG AAAAAGTTGT CCGCGATGGC AAATGCGACG
4501  GCTTGATCAT GCACCAGAAC CGTTCCTGCA GAACATGAG CCTCCTCAAC AACGAAGGCG
4561  GCCAGCGCAT CCAGAAGAAC CTCGGCGTAC CGTACGTCAT CTTCGACGGC GACCAGACCG
4621  ATGCTCGTAA CTTCTCGGAA GCACAGTTCG ATACCCGCGT AGAAGCTTTG GCAGAAATGA
4681  TGGCAGACAA AAAAGCCAAT GAAGGAGGAA ACCACTAATG AGTCAGATCG ACGAACTTAT
4741  CAGCAAATTA CAGGAAGTAT CCAACCATCC CCAGAAGACG GTTTTGAATT ATAAAAAACA
4801  GGGTAAAGGC CTCGTAGGCA TGATGCCCTA CTACGCTCCG GAAGAAATCG TATATGCTGC
4861  AGGCTACCTC CCGGTAGGCA TGTTCGGTTC CCAGAACCCG CAGATCTCCG CAGCTCGTAC
4921  GTACCTTCCT CCGTTCGCTT GCTCCTTGAT GCAGGCTGAC ATGGAACTCC AGCTCAACGG
4981  CACCTATGAC TGCCTCGACG CTGTTATCTT CTCCGTTCCT TGCGACACTC TCCGCTGCAT
5041  GAGCCAGAAA TGGCACGGCA AGCTCCGGT CATCGTCTTC ACACAGCCGC AGAACCGTAA
5101  GATCCGCCCG GCTGTCGATT TCCTCAAAGC TGAATACGAA CATGTCCGTA CGGAATTGGG
5161  ACGTATCCTC AACGTAAAAA TCTCCGACCT GGCTATCCAG GAAGCTATCA AGTATATAA
5221  CGAAAACCGT CAGGTTATGC GTGAATTCTG CGACGTAGCT GCTCAGTACC GCAGATCTT
5281  CACTCCGATA AAACGTCATG ACGTCATCAA AGCCCGCTGG TTCATGGACA AAGCTGAACA
5341  CACCGCTTTG GTCCGCGAAC TCATCGACGC TGTCAAGAAA GAACCGGTAC AGCCGTGGAA
5401  TGGCAAAAAA GTCATCCTCT CCGGTATCAT GGCAGAACCG GATGAATTCC TCGATATCTT
5461  CAGCGAATTC AACATCGCTG TCGTCGCTGA CGACCTCGCT CAGGAATCCC GCCAGTTCCG
5521  TACAGACGTA CCGTCCGGCA TCGATCCCCT CGAACAGCTC GCTCAGCAGT GGCAGGACTT
5581  CGATGGCTGC CCGCTCGCTT TGAACGAAGA CAAACCGCGT GGCCAGATGC TCATCGACAT
5641  GACTAAGAAA TACAATGCTG ACGCCGTCGT CATCTGCATG ATGCGTTTCT GCGATCCTGA
5701  AGAATTCGAC TATCCGATTT ACAAACCGGA ATTTGAAGCT GCTGGCGTTC GTTACACGGT
5761  CCTCGACCTC GACATCGAAT CTCCGTCCCT CGAACAGCTC CGCACCCGTA TCCAGGCTTT
5821  CTCGGAAATC CTCTAAGAAT CGCCTGAATC ATCAAACATC TGGGCGGGAC TCCGAAAGGT
5881  GCCTGCTACA TGATACATTG CCTGTTTTCA GGCAGACAGA TTTGCAGCTT GCGGCCCCCA
5941  TTGTACGGGC TGCAAGCTGT CAATGATGCT TTAAAGACGG CTCTGCCGTT TTTAAATAAA
6001  AACATAAAAC CATATATAAT CTATTAGGAG GAAACTCAAT CATGGAATTC AAACTTTCTG
6061  AATTACAGCA AGATATCGCA AATCTCGCAA AAGATTTCGC AGAAAAAAAA TTAGCTCCCA
6121  CTGTCAAAGA GCGTGACGAA AAAGAAGTTT TCGATCGTGC TATCCTTGAC GAAGTGGGTA
6181  CTCTCGGCCT TCTCGGTATT CCCTGGGAAG AAGAAACGG CGGCGTAGGC GCTGACTTCC
6241  TCAGCCTCGC AGTTGCTTGC GAAGAAGTAG CTAAAGTTAC CAGCCCGGGC CGTCG    (SEQ
ID NO:33)
```

ATGAAACCAATGAGACTACATCACGTAGGCATTGTCCTGCCGACCTTAGAAAAAGCCCAT
GAATTCATGCAGAATAATGGACTTGAAATCGACTATGCCGGCTATGTCGATGCTTACCAG
GCTGATCTCATTTTCACTAAGTTTGGTGAATTTGCCAGCCCGATTGAAATGATTATCCCG
CACTCCGGTGTGCTTACCCAATTCAATGGTGGCCGCGGCGGCATTGCCCACATCGCCTTC
GAAGTGGACGATGTCGAAGCTGTCCGCCAGGAAATGGAAGCAGATTGTCCGGGATGCATG
TTAGAAAAGAAAGCTGTCCAGGGTACGGACGACATTATCGTCAACTTCCGCCGCCCGACA
ACCAACCAGGGTATCCTCGTTGAATATGTTCAGACGACAGCACCTATCACCGGCCGCGGC
GAAAATCCTTTCGTTAAGAATCTCGGCCCGGAAAAAGGGAAGCTCAACGAAACATGGCAT
CCCATGCGCCTGCACCATATCGGCATCGTCTTGCCGACCTTGGAAAAGGCCCATGAATTC
ATCAAGACCAATGGTCTGGAAGTGGATTATTCCGGTTTCGTCGACGCCTACCATGCGGAT
CTCATTTTCACTAAAAAAGGTGAAAACAGTACGCCTATCGAATTCATTATTCCCCGTGAA
GGGGTCCTCAAAGATTTCAATCATGGCAGGGGAGGTATCGCTCATATCGCCTTTGAAGTG
GATGATGTCGAAAAGGTACGTCAGATTATGGAAAGCCAGAAGCCTGGTTGCATGCTCGAA
AAGAAAGCCGTCCGGGGAACGGACGATATCATCGTCAACTTCCGCCGTCCCAGCACGGAC
GCCGGCATCCTCGTCGAATATGTCCAGACCGTAGCTCCCATCAATCGCAGCAATCCCAAC
CCTTTTAATGATTGA  (SEQ ID NO:34)

Figure 24

MKPMRLHHVGIVLPTLEKAHEFMQNNGLEIDYAGYVDAYQADLIFTKFGEFASPIEMIIP
HSGVLTQFNGGRGGIAHIAFEVDDVEAVRQEMEADCPGCMLEKKAVQGTDDIIVNFRRPT
TNQGILVEYVQTTAPITGRGENPFVKNLGPEKGKLNETWHPMRLHHIGIVLPTLEKAHEF
IKTNGLEVDYSGFVDAYHADLIFTKKGENSTPIEFIIPREGVLKDFNHGRGGIAHIAFEV
DDVEKVRQIMESQKPGCMLEKKAVRGTDDIIVNFRRPSTDAGILVEYVQTVAPINRSNPN
PFND    (SEQ ID NO:35)

Figure 25

ATGGAATTCAAACTTTCTGAATTACAGCAAGATATCGCAAATCTCGCAAAAGATTTCGCA
GAAAAAAAATTAGCTCCCACTGTCAAAGAGCGTGACGAAAAAGAAGTTTTCGATCGTGCT
ATCCTTGACGAAGTGGGTACTCTCGGCCTTCTCGGTATTCCCTGGGAAGAAGAAAACGGC
GGCGTAGGCGCTGACTTCCTCAGCCTCGCAGTTGCTTGCGAAGAAGTAGCTAAAGTTACC
AGCCCGGGCCGTCG   (SEQ ID NO: 36)

Figure 26

MEFKLSELQQDIANLAKDFAEKKLAPTVKERDEKEVFDRAILDEVGTLGLLGIPWEEENG
GVGADFLSLAVACEEVAKVTSPGR    (SEQ ID NO:37)

```
   1  GTGAGCACAC ACTTGATAGC TGATGCCGTC AATGATCAGT TGTTCGTCTA TAGCAGGCTG
  61  AAAGGACATG GGTTTGGTCA CAGTCTGAGC AGTTGCAGGC AGTCAAACAC GTTCGTAACT
 121  ACGCTGTAGA TGATATAAGC AGTATACCAT CTTGCTACGC TCTCGTTGAT CAGGTTGAAT
 181  GCTTTGAGGA AGGTCAGGCG AATAGCCATG CCTCTTGTTT CCAGAACATG GCATGGGAT
 241  GGATCGACGG TACCCTGTCG GATGCATGCT ATGCGTGGCA TTCATATCAT CAACCAGAAT
 301  TTGATCTTGA ACTACACAGC AATTCTGCGC GTTATGCAAG TGTCTTCGGT CAGATGGTGA
 361  ACAATTCTCA ATTGTTGAGG TCTTGACGAA TTGCGTTATA CACTGTAGGC TATAGTATGC
 421  ACCCCTTGTT ATCTATATCA CAACCGGTCT ATTAGCATTT GCGTCAAGGA GGATGGTCGA
 481  TGATCGACAC TGCGCCCCTT GCCCCACCAC GGGCGCCCCG CTCTAATCCG ATTCGGGATC
 541  GAGTTGATTG GGAAGCTCAG CGCGCTGCTG CGCTGGCAGA TCCCGGTGCC TTTCATGGCG
 601  CGATTGCCCG GACAGTTATC CACTGGTACG ACCCACAACA CCATTGCTGG ATTCGCTTCA
 661  ACGAGTCTAG TCAGCGTTGG GAAGGGCTGG ATGCCGCTAC CGGTGCCCCT GTAACGGTAG
 721  ACTATCCCGC CGATTATCAG CCCTGGCAAC AGGCGTTTGA TGATAGTGAA GCGCCGTTTT
 781  ACCGCTGGTT TAGTGGTGGG TTGACAAATG CCTGCTTTAA TGAAGTAGAC CGGCATGTCA
 841  TGATGGGCTA TGGCGACGAG GTGGCCTACT ACTTTGAAGG TGACCGCTGG GATAACTCGC
 901  TCAACAATGG TCGTGGTGGT CCGGTTGTCC AGGAGACAAT CACGCGGCGG CGCCTGTTGG
 961  TGGAGGTGGT GAAGGCTGCG CAGGTGTTGC GTGATCTGGG CCTGAAGAAG GGTGATCGGA
1021  TTGCTCTGAA TATGCCGAAT ATTATGCCGC AGATTTATTA TACGGAAGCG GCAAAACGAC
1081  TGGGTATTCT GTACACGCCG GTCTTCGGTG GCTTCTCGGA CAAGACTCTT TCCGACCGTA
1141  TTCACAATGC CGGTGCACGA GTGGTGATTA CCTCTGATGG TGCCGTACCGC AACGCGCAGG
1201  TGGTGCCCTA CAAAGAAGCG TATACCGATC AGGCGCTCGA TAAGTATATT CCGGTTGAGA
1261  CGGCGCAGGC GATTGTTGCG CAGACCCTGG CCACCTTGCC CCTGACTGAG TCGCAGCGCC
1321  AGACGATCAT CACCGAAGTG GAGGCCGCAC TGGCCGGTGA GATTACGGTT GAGCGCTCGG
1381  ACGTGATGCG TGGGGTTGGT TCTGCCCTCG CAAAGCTCCG CGATCTTGAT GCAAGCGTGC
1441  AGGCAAAGGT GCGTACAGTA CTGGCGCAGG CGCTGGTCGA GTCGCCGCCG CGGGTTGAAG
1501  CTGTGGTGGT TGTGCGTCAT ACCGGTCAGG AGATTTTGTG GAACGAGGGG CGAGATCGCT
1561  GGAGTCACGA CTTGCTGGAT GCTGCGCTGG CGAAGATTCT GGCCAATGCG CGTGCTGCCG
1621  GCTTTGATGT GCACAGTGAG AATGATCTGC TCAATCTCCC CGATGACCAG CTTATCCGTG
1681  CGCTCTACGC CAGTATTCCC TGTGAACCGG TTGATGCTGA ATATCCGATG TTTATCATTT
1741  ACACATCGGG TAGCACCGGT AAGCCCAAGG GTGTGATCCA CGTTCACGGC GGTTATGTCG
1801  CCGGTGTGGT GCACACCTTG CGGGTCAGTT TTGACGCCGA GCCGGGTGAT ACGATATATG
1861  TGATCGCCGA TCCGGGCTGG ATCACCGGTC AGAGCTATAT GCTCACAGCC ACAATGGCCG
1921  GTCGGCTGAC CGGGGTGATT GCCGAGGGAT CACCGCTCTT CCCCTCAGCC GGGCGTTATG
1981  CCAGCATCAT CGAGCGCTAT GGGGTGCAGA TCTTTAAGGC GGGTGTGACC TTCCTCAAGA
2041  CAGTGATGTC CAATCCGCAG AATGTTGAAG ATGTGCGACT CTATGATATG CACTCGCTGC
2101  GGGTTGCAAC CTTCTGCGCC GAGCCGGTCA GTCCGGCGGT GCAGCAGTTT GGTATGCAGA
2161  TCATGACCCC GCAGTATATC AATTCGTACT GGGCGACCGA GCACGGTGGA ATTGTCTGGA
2221  CGCATTTCTA CGGTAATCAG GACTTCCCGC TTCGTCCCGA TGCCCATACC TATCCCTTGC
2281  CCTGGGTGAT GGGTGATGTC TGGGTGGCCG AAACTGATGA GAGCGGGACG ACGCGCTATC
2341  GGGTCGCTGA TTTCGATGAG AAGGGCGAGA TTGTGATTCA CGCCCCGTAT CCCTACCTGA
2401  CCCGCACACT CTGGGGTGAT GTGCCCGGTT TCGAGGCGTA CCTGCGCGGT GAGATTCCGC
2461  TGCGGGCCTG GAAGGGTGAT GCCGAGCGTT TCGTCAAGAC CTACTGGCGA CGTGGGCCAA
2521  ACGGTGAATG GGGCTATATC CAGGGTGATT TTGCCATCAA GTACCCCGAT GGTAGCTTCA
2581  CGCTCCACGG ACGCCCTGAC GATGTGATCA ATGTGTCGGG CCACCGTATG GGCACCGAGG
2641  AGATTGAGGG TGCCATTTTG CGTGACCGCC AGATCACGCC CGACTCGCCC GTCGGTAATT
2701  GTATTGTGGT CGGTGCGCCG CACCGTGAGA AGGGTCTGAC CCCGGTTGCC TTCATTCAAC
2761  CTGCGCCTGG CCGTCATCTG ACCGGCGCCG ACCGGCGCCG TCTCGATGAG CTGGTGCGTA
2821  CCGAGAAGGG GGCGGTCAGT GTCCCAGAGG ATTACATCGA GGTCAGTGCC TTTCCCGAAA
2881  CCCGCAGCGG GAAGTATATG CGGCGCTTTT TGCGCAATAT GATGCTCGAT GAACCACTGG
2941  GTGATACGAC GACGTTGCGC AATCCTGAAG TGCTCGAAGA GATTGCAGCC AAGATCGCTG
3001  AGTGGAAACG CCGTCAGCGT ATGGCCGAAG AGCAGCAGAT CATCGAACGC TATCGCTACT
3061  TCCGGATCGA GTATCACCCA CCAACGGCCA GTGCGGGTAA ACTCGCGGTA GTGACGGTGA
3121  CAAATCCGCC GGTGAACGCA CTGAATGAGC GTGCGCTCGA TGAGTTGAAC ACAATTGTTG
3181  ACCACCTGGC CCGTCGTCAG GATGTTGCCG CAATTGTCTT CACCGGACAG GGCGCCAGGA
3241  GTTTTGTCGC CGGCGCTGAT ATTCGCCAGT TGCTCGAAGA GATTCATACG GTTGAAGAGG
3301  CAATGGCCCT GCCGAATAAC GCCCATCTTG CTTTCCGCAA GATTGAGCGT ATGAATAAGC
3361  CGTGTATCGC GGCGATCAAC GGTGTGGCGC TCGGTGGTGG TCTGGAATTC GCCATGGCCT
```

Figure 27A

```
3421  GCCATTACCG GGTTGCCGAT GTCTATGCCG AATTCGGTCA GCCAGAGATT AATCTGCGCT
3481  TGCTACCTGG TTATGGTGGC ACGCAGCGCT TGCCGCGCCT GTTGTACAAG CGCAACAACG
3541  GCACCGGTCT GCTCCGAGCG CTGGAGATGA TTCTGGGTGG GCGTAGCGTA CCGGCTGATG
3601  AGGCGCTGAA GCTGGGTCTG ATCGATGCCA TTGCTACCGG CGATCAGGAC TCACTGTCGC
3661  TGGCATGCGC GTTAGCCCGT GCCGCAATCG GCGCCGATGG TCAGTTGATC GAGTCGGCTG
3721  CGGTGACCCA GGCTTTCCGC CATCGCCACG AGCAGCTTGA CGAGTGGCGC AAACCAGACC
3781  CGCGCTTTGC CGATGACGAA CTGCGCTCGA TTATCGCCCA TCCACGTATC GAGCGGATTA
3841  TCCGGCAGGC CCATACCGTT GGGCGCGATG CGGCAGTGCA TCGGGCACTG GATGCAATCC
3901  GCTATGGCAT TATCCACGGC TTCGAGGCCG GTCTGGAGCA CGAGGCGAAG CTCTTTGCCG
3961  AGGCAGTGGT TGACCCGAAC GGTGGCAAGC GTGGTATTCG CGAGTTCCTC GACCGCCAGA
4021  GTGCGCCGTT GCCAACCCGC CGACCATTGA TTACACCTGA ACAGGAGCAA CTCTTGCGCG
4081  ATCAGAAAGA ACTGTTGCCG GTTGGTTCAC CCTTCTTCCC CGGTGTTGAC CGGATTCCGA
4141  AGTGGCAGTA CGCGCAGGCG GTTATTCGTG ATCCGGACAC CGGTGCGGCG GCTCACGGCG
4201  ATCCCATCGT GGCTGAAAAG CAGATTATTG TGCCGGTGGA ACGCCCCGC GCCAATCAGG
4261  CGCTGATCTA TGTTCTGGCC TCGAGGTGA ACTTCAACGA TATCTGGGCG ATTACCGGTA
4321  TTCCGGTGTC ACGGTTTGAT GAGCACGACC GCGACTGGCA CGTTACCGGT TCAGGTGGCA
4381  TCGGCCTGAT CGTTGCGCTG GGTGAAGAGG CGCGACGCGA AGGCCGGCTG AAGGTGGGTG
4441  ATCTGGTGGC GATCTACTCC GGGCAGTCGG ATCTGCTCTC ACCGCTGATG GGCCTTGATC
4501  CGATGGCCGC CGATTTCGTC ATCCAGGGGA ACGACACGCC AGATGGATCG CATCAGCAAT
4561  TTATGCTGGC CCAGGCCCCG CAGTGTCTGC CCATCCCAAC CGATATGTCT ATCGAGGCAG
4621  CCGGCAGCTA CATCCTCAAT CTCGGTACGA TCTATCGCGC CCTCTTTACG ACGTTGCAAA
4681  TCAAGGCCGG ACGCACCATC TTTATCGAGG GTGCGGCGAC CGGTACCGGT CTGGACGCAG
4741  CGCGCTCGGC GGCCCGGAAT GGTCTGCGCG TAATTGGAAT GGTCAGTTCG TCGTCACGTG
4801  CGTCTACGCT GCTGGCTGCG GGTGCCCACG GTGCGATTAA CCGTAAAGAC CCGGAGGTTG
4861  CCGATTGTTT CACGCGCGTG CCCGAAGATC CATCAGCCTG GGCAGCCTGG GAAGCCGCCG
4921  GTCAGCCGTT GCTGGCGATG TTCCGGGCGC AGAACGACGG GCGACTGGCC GATTATGTGG
4981  TCTCGCACGC GGGCGAGACG GCCTTCCCGC GCAGTTTCCA GCTTCTCGGC GAGCCACGCG
5041  ATGGTCACAT TCCGACGCTC ACATTCTACG GTGCCACCAG TGGCTACCAC TTCACCTTCC
5101  TGGGTAAGCC AGGGTCAGCT TCGCCGACCG AGATGCTGCG GCGGGCCAAT CTCCGCGCCG
5161  GTGAGGCGGT GTTGATCTAC TACGGGGTTG GGAGCGATGA CCTGGTAGAT ACCGGCGGTC
5221  TGGAGGCTAT CGAGGCGGCG CGGCAAATGG GAGCGCGGAT CGTCGTCGTT ACCGTCAGCG
5281  ATGCGCAACG CGAGTTTGTC CTCTCGTTGG GCTTCGGGGC TGCCCTACGT GGTGTCGTCA
5341  GCCTGGCGGA ACTCAAACGG CGCTTCGGCG ATGAGTTTGA GTGGCCGCGC ACGATGCCGC
5401  CGTTGCCGAA CGCCCGCCAG GACCCGCAGG GTCTGAAAGA GGCTGTCCGC CGCTTCAACG
5461  ATCTGGTCTT CAAGCCGCTA GGAAGCGCGG TCGGTGTCTT CTTGCGGAGT GCCGACAATC
5521  CGCGTGGCTA CCCCGATCTG ATCATCGAGC GGGCTGCCCA CGATGCACTG GCGGTGAGCG
5581  CGATGCTGAT CAAGCCCTTC ACCGGACGGA TTGTCTACTT CGAGGACATT GGTGGCGGC
5641  GTTACTCCTT CTTCGCACCG CAAATCTGGG TGCGCCAGCG CCGCATCTAC ATGCCGACGG
5701  CACAGATCTT TGGTACGCAC CTCTCAAATG CGTATGAAAT TCTGCGTCTG AATGATGAGA
5761  TCAGCGCCGG TCTGCTGACG ATTACCGAGC CGGCAGTGGT GCCGTGGGAT GAACTACCCG
5821  AAGCACATCA GGCGATGTGG GAAAATCGCC ACACGGCGGC CACTTATGTG GTGAATCATG
5881  CCTTACCACG TCTCGGCCTA AAGAACAGGG ACGAGCTGTA CGAGGCGTGG ACGGCCGGCG
5941  AGCGGTAGCG CGGATGGGTA TTGAACAGGT AACGGACGGA AGATCGAACC TTCCGTCCGT
6001  TATCTTTTGG CCGTCGAAGC GTGCTGAGCC GATTATCGTT GCCGTGGTTG TCCCGATGGG
6061  CAGACGCGCT CGAACCAGAT GATACCACCG ACGGCTATCG TCACCAAACC GGCGAAGACC
6121  AGGTAAGCCT CTGAAGGACG C (SEQ ID NO:38)
```

```
   1  MIDTAPLAPP RAPRSNPIRD RVDWEAQRAA ALADPGAFHG AIARTVIHWY DPQHHCWIRF
  61  NESSQRWEGL DAATGAPVTV DYPADYQPWQ QAFDDSEAPF YRWFSGGLTN ACFNEVDRHV
 121  MMGYGDEVAY YFEGDRWDNS LNNGRGGPVV QETITRRRLL VEVVKAAQVL RDLGLKKGDR
 181  IALNMPNIMP QIYYTEAAKR LGILYTPVFG GFSDKTLSDR IHNAGARVVI TSDGAYRNAQ
 241  VVPYKEAYTD QALDKYIPVE TAQAIVAQTL ATLPLTESQR QTIITEVEAA LAGEITVERS
 301  DVMRGVGSAL AKLRDLDASV QAKVRTVLAQ ALVESPPRVE AVVVVRHTGQ EILWNEGRDR
 361  WSHDLLDAAL AKILANARAA GFDVHSENDL LNLPDDQLIR ALYASIPCEP VDAEYPMFII
 421  YTSGSTGKPK GVIHVHGGYV AGVVHTLRVS FDAEPGDTIY VIADPGWITG QSYMLTATMA
 481  GRLTGVIAEG SPLFPSAGRY ASIIERYGVQ IFKAGVTFLK TVMSNPQNVE DVRLYDMHSL
 541  RVATFCAEPV SPAVQQFGMQ IMTPQYINSY WATEHGGIVW THFYGNQDFP LRPDAHTYPL
 601  PWVMGDVWVA ETDESGTTRY RVADFDEKGE IVITAPYPYL TRTLWGDVPG FEAYLRGEIP
 661  LRAWKGDAER FVKTYWRRGP NGEWGYIQGD FAIKYPDGSF TLHGRPDDVI NVSGHRMGTE
 721  EIEGAILRDR QITPDSPVGN CIVVGAPHRE KGLTPVAFIQ PAPGRHLTGA DRRRLDELVR
 781  TEKGAVSVPE DYIEVSAFPE TRSGKYMRRF LRNMMLDEPL GDTTTLRNPE VLEEIAAKIA
 841  EWKRRQRMAE EQQIIERYRY FRIEYHPPTA SAGKLAVVTV TNPPVNALNE RALDELNTIV
 901  DHLARRQDVA AIVFTGQGAR SFVAGADIRQ LLEEIHTVEE AMALPNNAHL AFRKIERMNK
 961  PCIAAINGVA LGGGLEFAMA CHYRVADVYA EFGQPEINLR LLPGYGGTQR LPRLLYKRNN
1021  GTGLLRALEM ILGGRSVPAD EALKLGLIDA IATGDQDSLS LACALARAAI GADGQLIESA
1081  AVTQAFRHRH EQLDEWRKPD PRFADDELRS IIAHPRIERI IRQAHTVGRD AAVHRALDAI
1141  RYGIIHGFEA GLEHEAKLFA EAVVDPNGGK RGIREFLDRQ SAPLPTRRPL ITPEQEQLLR
1201  DQKELLPVGS PFFPGVDRIP KWQYAQAVIR DPDTGAAAHG DPIVAEKQII VPVERPRANQ
1261  ALIYVLASEV NFNDIWAITG IPVSRFDEHD RDWHVTGSGG IGLIVALGEE ARREGRLKVG
1321  DLVAIYSGQS DLLSPLMGLD PMAADFVIQG NDTPDGSHQQ FMLAQAPQCL PIPTDMSIEA
1381  AGSYILNLGT IYRALFTTLQ IKAGRTIFIE GAATGTGLDA ARSAARNGLR VIGMVSSSSR
1441  ASTLLAAGAH GAINRKDPEV ADCFTRVPED PSAWAAWEAA GQPLLAMFRA QNDGRLADYV
1501  VSHAGETAFP RSFQLLGEPR DGHIPTLTFY GATSGYHFTF LGKPGSASPT EMLRRANLRA
1561  GEAVLIYYGV GSDDLVDTGG LEAIEAARQM GARIVVVTVS DAQREFVLSL GFGAALRGVV
1621  SLAELKRRFG DEFEWPRTMP PLPNARQDPQ GLKEAVRRFN DLVFKPLGSA VGVFLRSADN
1681  PRGYPDLIIE RAAHDALAVS AMLIKPFTGR IVYFEDIGGR RYSFFAPQIW VRQRRIYMPT
1741  AQIFGTHLSN AYEILRLNDE ISAGLLTITE PAVVPWDELP EAHQAMWENR HTAATYVVNH
1801  ALPRLGLKNR DELYEAWTAG ER (SEQ ID NO:39)
```

Figure 29

ATGAGTGAAGAGTCTCTGGTTCTCAGCACAATTGAAGGCCCCATCGCCATCCTCACCCTC
AATCGCCCCCAGGCCCTCAATGCGCTCAGTCCGGCCTTGATTGATGACCTCATTCGCCAT
TTAGAAGCCTGCGATGCCGATGACACAATCCGCGTGATCATTATCACCGGCGCCGGACGG
GCATTTGCTGCCGGCGCTGATATCAAAGCGATGGCCAATGCCACGCCTATTGATATGCTC
ACCAGTGGCATGATTGCGCGCTGGGCACGCATCGCCGCGGTGCGCAAACCGGTGATTGCT
GCCGTGAATGGGTATGCGCTCGGTGGTGGTTGTGAATTGGCAATGATGTGCGACATCATC
ATCGCCAGTGAAAACGCGCAGTTCGGACAACCGGAAATCAATCTGGGCATCATTCCCGGT
GCTGGTGGCACCCAACGGCTGACCCGCGCCCTTGGCCCGTATCGCGCAATGGAATTGATC
CTGACCGGCGCGACCATCAGTGCTCAGGAAGCTCTCGCCCACGGCCTGGTGTGCCGGGTC
TGCCCGCCTGAAAGCCTGCTCGATGAAGCCCGTCGGATCGCGCAAACCATTGCCACCAAA
TCACCACTGGCTGTACAGTTGGCGAAAGAGGCAGTCCGTATGGCCGCCGAAACCACTGTG
CGCGAGGGGTTGGCTATCGAGCTGCGTAACTTCTATCTGCTGTTTGCCAGTGCTGACCAA
AAAGAGGGGATGCAGGCATTTATCGAGAAACGCGCTCCCAACTTCAGTGGTCGTTGA
(SEQ ID NO:40)

Figure 30

MSEESLVLSTIEGPIAILTLNRPQALNALSPALIDDLIRHLEACDADDTIRVIIITGAGR
AFAAGADIKAMANATPIDMLTSGMIARWARIAAVRKPVIAAVNGYALGGGCELAMMCDII
IASENAQFGQPEINLGIIPGAGGTQRLTRALGPYRAMELILTGATISAQEALAHGLVCRV
CPPESLLDEARRIAQTIATKSPLAVQLAKEAVRMAAETTVREGLAIELRNFYLLFASADQ
KEGMQAFIEKRAPNFSGR      (SEQ ID NO:41)

Figure 31

GGCGTAATCCGACCGGCAGGTTAGGGTCTTCTACTGGGGTCAAGGCGCGTCTCCTTTTGG
TGGCGCGAGCAACCCGGCTTTTCCTGGCTTCAATGTACCATAGAGCGGTTACTTCGTGCA
ACGGGCGTGGTACAATCGAGAGCAACCTTTCGCAAAAGCTATCCAATCCTGCACACGTGC
ATCTGTTACAGGGTATTATTGTCGGCAAACGACAGTCCTGTCGTTTATGTACAAGGAGAT
CAACGTATGAGTGAAGAGTCTCTGGTTCTCAGCACAATTGAAGGCCCCATCGCCATCCTC
ACCCTCAATCGCCCCAGGCCCTCAATGCGCTCAGTCCGGCCTTGATTGATGACCTCATT
CGCCATTTAGAAGCCTGCGATGCCGATGACACAATCCGCGTGATCATTATCACCGGCGCC
GGACGGGCATTTGCTGCCGGCGCTGATATCAAAGCGATGGCCAATGCCACGCCTATTGAT
ATGCTCACCAGTGGCATGATTGCGCGCTGGGCACGCATCGCCGCGGTGCGCAAACCGGTG
ATTGCTGCCGTGAATGGGTATGCGCTCGGTGGTGGTTGTGAATTGGCAATGATGTGCGAC
ATCATCATCGCCAGTGAAAACGCGCAGTTCGGACAACCGGAAATCAATCTGGGCATCATT
CCCGGTGCTGGTGGCACCCAACGGCTGACCCGCGCCCTTGGCCCGTATCGCGCAATGGAA
TTGATCCTGACCGGCGCGACCATCAGTGCTCAGGAAGCTCTCGCCCACGGCCTGGTGTGC
CGGGTCTGCCCGCCTGAAAGCCTGCTCGATGAAGCCCGTCGGATCGCGCAAACCATTGCC
ACCAAATCACCACTGGCTGTACAGTTGGCGAAAGAGGCAGTCCGTATGGCCGCCGAAACC
ACTGTGCGCGAGGGGTTGGCTATCGAGCTGCGTAACTTCTATCTGCTGTTTGCCAGTGCT
GACCAAAAAGAGGGGATGCAGGCATTTATCGAGAAACGCGCTCCCAACTTCAGTGGTCGT
TGATCACGCGCAGAACATGGCAGCAGGGGCAATACCTGCACGTACTGCCTCCTGCCGCCA
TACTACCAGATGATCGAGCAGTAAAGGGTAAATACTCTATCAATCTGGCCAGATAAGCGG
TTGGGTAACAACGCAATGCTCCAAAGGAGACGATCATGGACATACACGAGCGATTGCGAT
CTCTCGAACGCGAAAATGCT    (SEQ ID NO:42)

```
SEQ ID NO:40      1 --------atgagtga----------agagt------------------
SEQ ID NO:43      1 ---------atgacgta----------cgaaa-----------------
SEQ ID NO:44      1 atggccgccctgcgtgt----------cctgctgtcctgcgccgcggcc
SEQ ID NO:45      1 atggcggccctgcgtgctctgctgcccagagc-----------------

SEQ ID NO:40     14 ----------ct--------ctg---------gttctc-agcacaattgaa
SEQ ID NO:43     14 ----------cc--------atc---------ctggtcgagcgc----gat
SEQ ID NO:44     41 cgctgaggccc---------ccg---------gttcgc-tgtcccgcctgg
SEQ ID NO:45     33 ----------ctgcaactcgctgttgtccccagttcgc-tgcccagaattc SEQ ID NO:40     37 ggccccatcgcc--------------------atcctcacc--------
SEQ ID NO:43     34 cagcgagttggc--------------------attatcacg--------
SEQ ID NO:44     73 cgtcccttcgcctcgggtgctaactttgagtacatcatcgcagaaaaaag
SEQ ID NO:45     73 cggcgcttcgcctcgggtgctaactttcagtacatcatcacg-------

SEQ ID NO:40     58 --------------------------------c----------------
SEQ ID NO:43     55 --------------------------------c----------------
SEQ ID NO:44    123 agggaagaataacaccgtgggggttgatccaac----------------
SEQ ID NO:45    115 --------------------------------gaaaagaaaggaaagaata SEQ ID NO:40     59 --------------------tcaatcgccccaggccctcaatgcgctc
SEQ ID NO:43     56 --------------------tgaaccgtcccaggcactgaacgcgctc
SEQ ID NO:44    155 --------------------tgaaccgccccaaggccctcaatgcactt
SEQ ID NO:45    134 gcagcgtggggctgatccagttgaaccgtcccaaagcactcaatgcactt SEQ ID NO:40     88 agtccggccttgattgatgacctcattc--gccatttagaagcctgcgat
SEQ ID NO:43     85 a--acagccagg--tgatgaacgaggtc--acca--gcgctgcaaccgaa
SEQ ID NO:44    184 tgcgatgcctgattgacgagctcaaccaggccctgaaga--tcttcgag
SEQ ID NO:45    184 tgcaatggactgattgaggagctcaacc--aagcactggagacctttgag SEQ ID NO:40    136 ---gccgatgacaca---atccgcgtgatcattatcaccggcgccggacg
SEQ ID NO:43    127 ctggacgatgacccggacattggggcgatcatcatcaccggttcggccaa
SEQ ID NO:44    232 ---gaggacccggcc---gttgggggcattgtcctcaccggcggggataa
SEQ ID NO:45    232 ---gaagatcccgct---gtgggcgccattgtgctcactggtggggagaa SEQ ID NO:40    180 ggcatttgctgccggcgctgatatcaaagcgatggccaa-------tgcc
SEQ ID NO:43    177 agcgtttgccgccggagccgacatcaaagaaatggccga-------cctg
SEQ ID NO:44    276 ggcctttgcagctggagctgatatcaaggaaatgcagaacctgagtttcc
SEQ ID NO:45    276 ggcctttgcagccggagctgacatcaaggaaatgcagaa-------ccgg SEQ ID NO:40    223 acgcctattgatatgctcaccagtggcatgattgcgcgc---tgggcacg
SEQ ID NO:43    220 acgttcgccgacgcgttcaccgccgacttcttcgccacc---tggggcaa
SEQ ID NO:44    326 aggactgtt-------actccagcaagttcttgaagcac---tggggcca
SEQ ID NO:45    319 acatttcagga-ctgttactca--ggcaagttcctgagccactgggacca SEQ ID NO:40    270 catcgccgggtgcgcaaaccggtgattgctgccgtgaatgggtatgcgc
SEQ ID NO:43    267 gctggccgccgtgcgcaccccgacgatcgccgcggtggcgggatacgcgc
SEQ ID NO:44    366 cctcacccaggtcaagaagccagtcatcgctgctgtcaatggctatccgt
SEQ ID NO:45    366 tatcacccggatcaagaaaccggtcatcgcggctgtcaatggctatgctc SEQ ID NO:40    320 tcggtggtggttgtgaattggcaatgatgtgcgacatcatcatcgccagt
SEQ ID NO:43    317 tcggcggtggctgcgagctggcgatgatgtgcgacgtgctgatcgccgcc
SEQ ID NO:44    416 ttggcggggggctgtgagcttgccatgatgtgtgatatcatctatgccggt
SEQ ID NO:45    416 ttggtggggctgtgaacttgccatgatgtgcgatatcatctatgctggt
```

Figure 32A

```
SEQ ID NO:40   370  gaaaacgcgcagttcggacaaccggaaatcaatctgggcatcattcccgg
SEQ ID NO:43   367  gacaccgcgaagttcggacagcccgagataaagctgggcgtgctgccagg
SEQ ID NO:44   466  gagaaggcccagtttgcacagccggagatcttaataggaaccatcccagg
SEQ ID NO:45   466  gagaaagcccagtttggacagccagaaatcctcctggggaccatcccagg SEQ ID NO:40   420  tgctggtggcacccaacggctgacccgcgcccttggcccgtatcgcgcaa
SEQ ID NO:43   417  catgggcggctcccagcggctgacccgggctatcggcaaggctaaggcga
SEQ ID NO:44   516  tgcaggcggcacccagagactcacccgtgctgttgggaagtcgctggagc
SEQ ID NO:45   516  tgcaggggcactcagagactcacccgagcagtcggcaaatcactagcaa SEQ ID NO:40   470  tggaattgatcctgaccggcgcgaccatcagtgctcaggaagctctcgcc
SEQ ID NO:43   467  tggacctcatcctgaccgggcgcaccatggacgccgccgaggc-cgagcg
SEQ ID NO:44   566  tggagatggtcctcaccggtgacgcgatctcagcccaggacgc-caagca
SEQ ID NO:45   566  tggagatggtcctcactggtgaccgaatttcagcacaggatgc-caagca SEQ ID NO:40   520  ca-c-ggcctggtgtgccgggtctgcccgcctgaaagcctgctcgatgaa
SEQ ID NO:43   516  cagc-ggtctggtttcacgggtggtgccggccgacgacttgctgaccgaa
SEQ ID NO:44   615  ag-caggtcttgtcagcaagatttgtcctgttgagacactggtggaagaa
SEQ ID NO:45   615  ag-caggtcttgtaagcaagatttttcccgttgaaacactggttgaagag SEQ ID NO:40   568  gcccgtcggatcgcgcaaaccattgccaccaaatcaccactggctgtaca
SEQ ID NO:43   565  gccagggccactgccacgaccatttcgcagatgtcggcctcggcggcccg
SEQ ID NO:44   664  gccatccagtgtgcagaaaaaattgccagcaattctaaaattgtagtagc
SEQ ID NO:45   664  gccatccaatgtgcagaaaagatcgccaacaattccaagatcatagtagc SEQ ID NO:40   618  gttggcgaaagaggcagtccgtatggccgccgaaaccactgtgcgcgagg
SEQ ID NO:43   615  gatggccaaggaggccgtcaacgggctttcgaatccagtttgtccgagg
SEQ ID NO:44   714  gatggccaaagaatcagtgaatgcagcttttgaaatgacattaacagaag
SEQ ID NO:45   714  catggcgaaagaatctgtgaatgcagcctttgaaatgacgttaacagaag SEQ ID NO:40   668  ggttggctatcgagctgcgtaacttctatctgctgtttgccagtgctgac
SEQ ID NO:43   665  ggctgctctacgaacgccggcttttccattcggctttcgcgaccgaagac
SEQ ID NO:44   764  gaagtaagttggagaagaaactcttttattcaacctttgccactgatgac
SEQ ID NO:45   764  gaaataagctggagaagaagctcttctattccaccttt-ccactgatgac SEQ ID NO:40   718  caaaaagagggatgcaggcatttatcgagaaacgcgctcccaacttcag
SEQ ID NO:43   715  caatccgaaggtatggcagcgttcatcgagaaacgcgctccccagttcac
SEQ ID NO:44   814  cggaaagaagggatgaccgcgtttgtggaaaagagaaaggccaacttcaa
SEQ ID NO:45   814  cggagagaagggatgtctgcctttgtggagaaaaggaaggccaacttcaa SEQ ID NO:40   768  tggtcgttga
SEQ ID NO:43   765  ccaccgatga
SEQ ID NO:44   864  agaccagtga
SEQ ID NO:45   864  agaccactga
```

```
SEQ ID NO:41    1 -mseeslv--------lstiegp-----------------------------
SEQ ID NO:46    1 -mtyetil--------ver-dqr-----------------------------
SEQ ID NO:47    1 -maalrvl--------lscargplrppvrcpawrpfasganfeyiiaekrg
SEQ ID NO:48    1 maalrallpracnsllspvrcpefrrfasganfqyiitekkgknss----

SEQ ID NO:41   15 ----iailtlnrpqalnalspaliddlirhleacdaddtirviiitgagr
SEQ ID NO:46   14 ----vgiitlnrpqalnalnsqvmnevtsaateldddpdigaiiitgsak
SEQ ID NO:47   43 knntvgliqlnrpkalnalcdglidelnqalkifeedpavgaivltggdk
SEQ ID NO:48   47 ----vgliqlnrpkalnalcnglieelnqaletfeedpavgaivltggek SEQ ID NO:41   61 afaagadikamanatpidmltsgmiarwariaavrkpviaavngyalggg
SEQ ID NO:46   60 afaagadikemadltfadaftadffatwgxlaavrtptiaavagyalgqg
SEQ ID NO:47   93 afaagadikemqnlsfqdcysskflkhwdhltqvkkpviaavngyafggg
SEQ ID NO:48   93 afaagadikemqnrtfqdcysgkflshwdhitrikkpviaavngyalggg SEQ ID NO:41  111 celammcdiiiasenaqfgqpeinlgiipgaggtqrltralgpyrameli
SEQ ID NO:46  110 celammcdvliaadtakfgqpeiklgvlpgmggsqrltraigkakamdli
SEQ ID NO:47  143 celammcdiiyagekaqfaqpeiligtipgaggtqrltravgkslamemv
SEQ ID NO:48  143 celammcdiiyagekaqfgqpeillgtipgaggtqrltravgkslamemv SEQ ID NO:41  161 ltgatisaqealahglvcrvcppeslldearriaqtiatksplavqlake
SEQ ID NO:46  160 ltgrtmdaaeaersglvsrvvpaddllteraratattisqmsasaarmake
SEQ ID NO:47  193 ltgdrisaqdakqaglvsklcpvetlveeaiqcaekiasnskivvamake
SEQ ID NO:48  193 ltgdrisaqdakqaglvskifpvetlveeaiqcaekiannskiivamake SEQ ID NO:41  211 avrmaaettvreglaielrnfyllfasadqkegmqafiekrapnfsgr
SEQ ID NO:46  210 avnrafesslseglllyerrlfhsafatedqsegmaafiekrapqfthr
SEQ ID NO:47  243 svnaafemtltegsklekklfystfatddrkegmtafvekrkanfkdq
SEQ ID NO:48  243 svnaafemtltegnklekklfystfatddrregmsafvekrkanfkdh
```

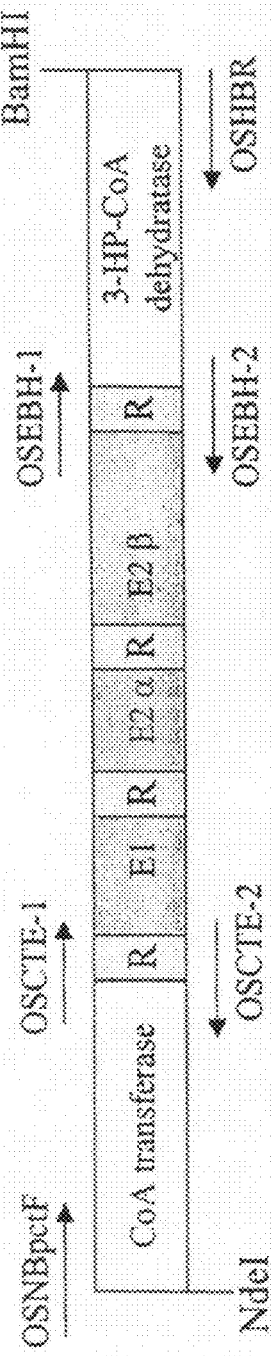

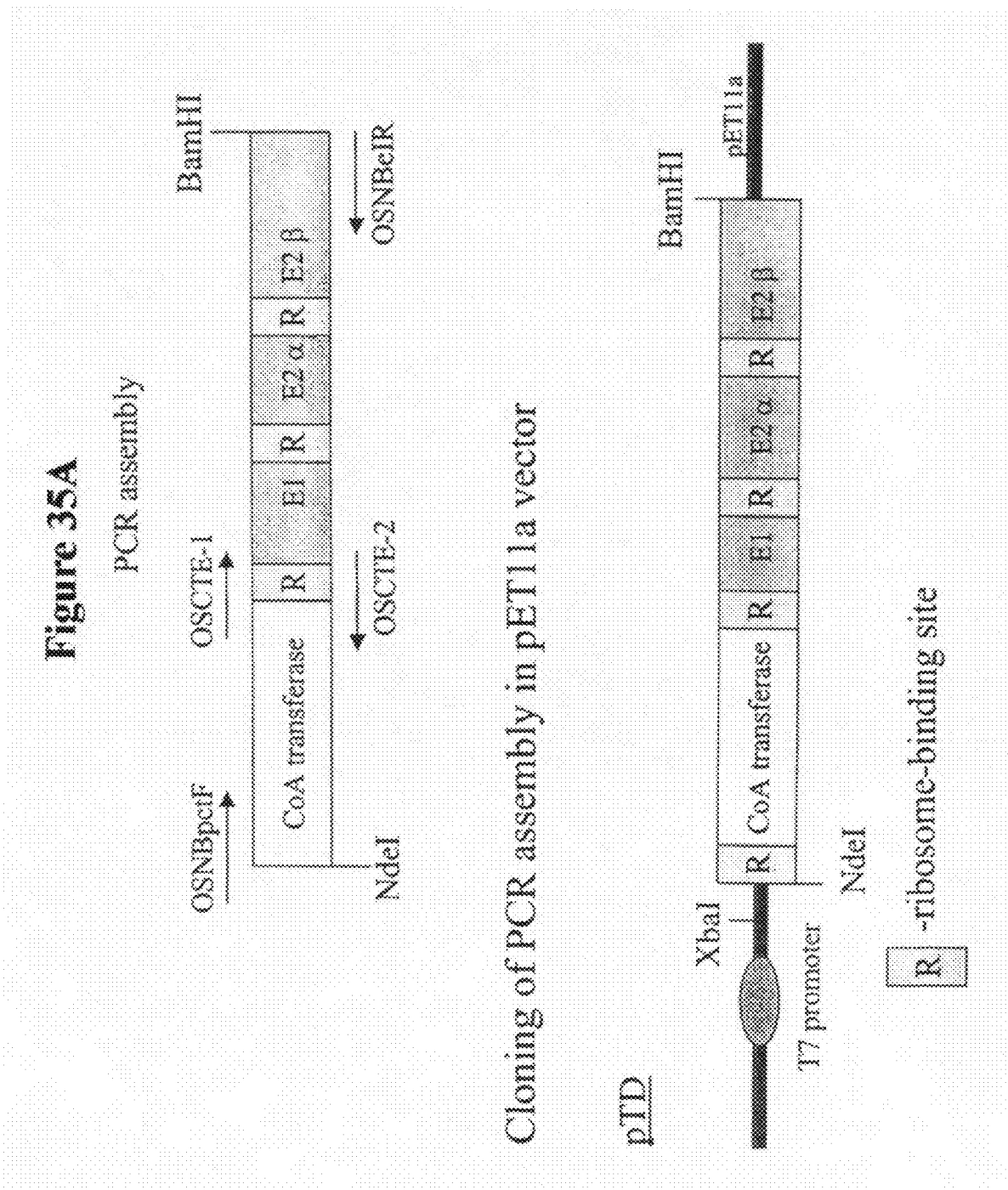

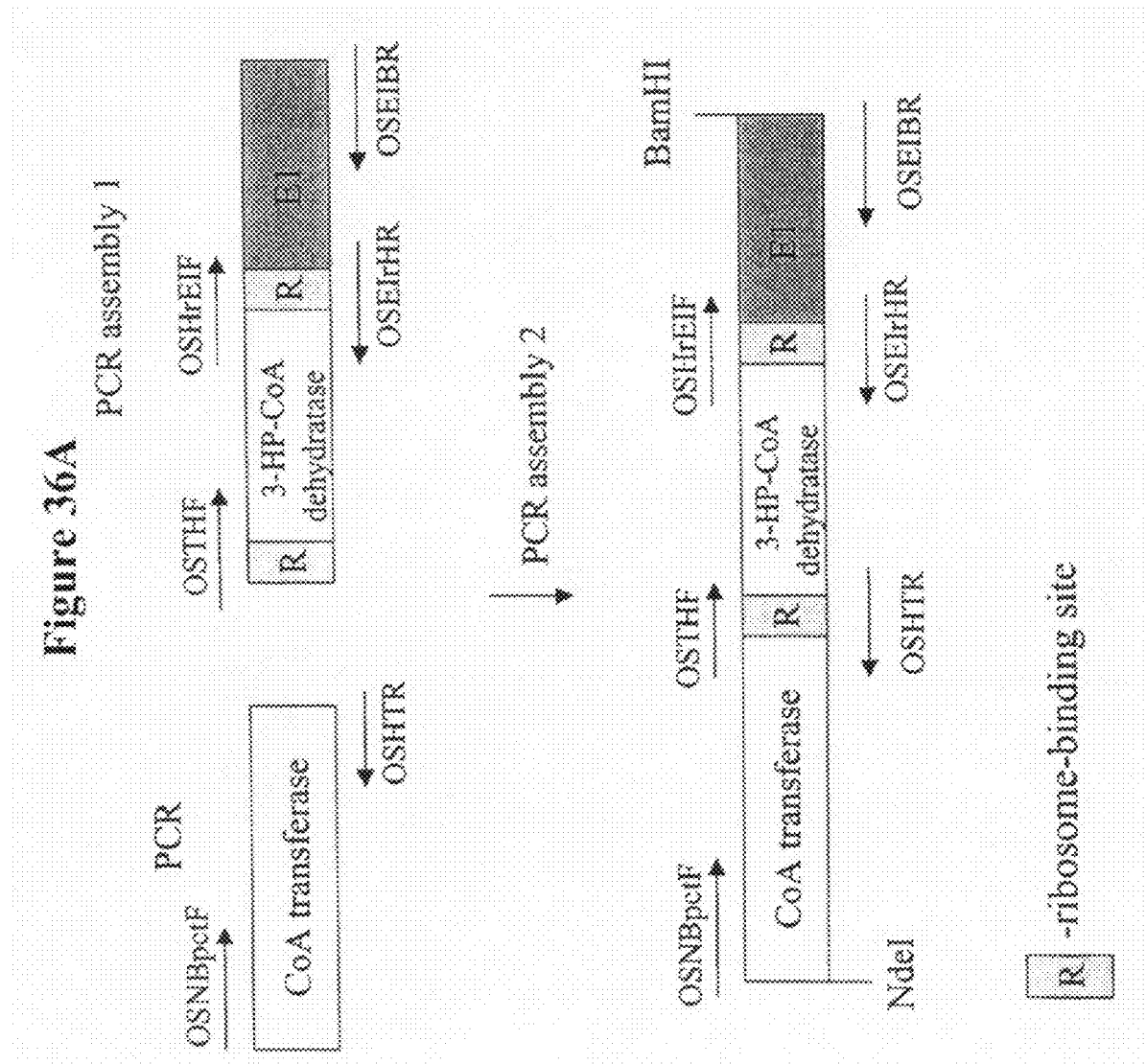

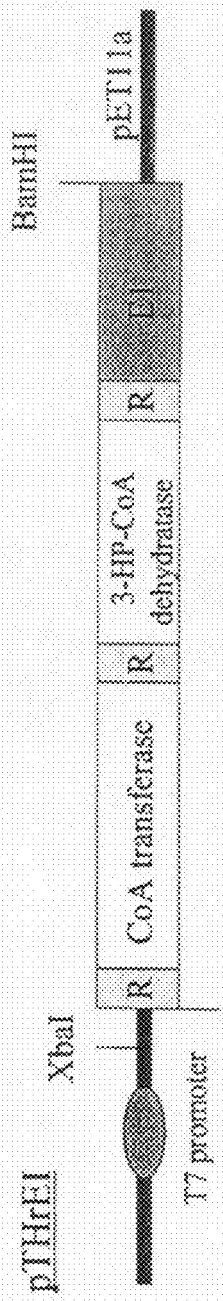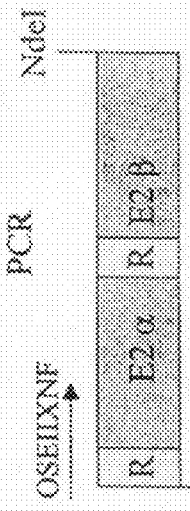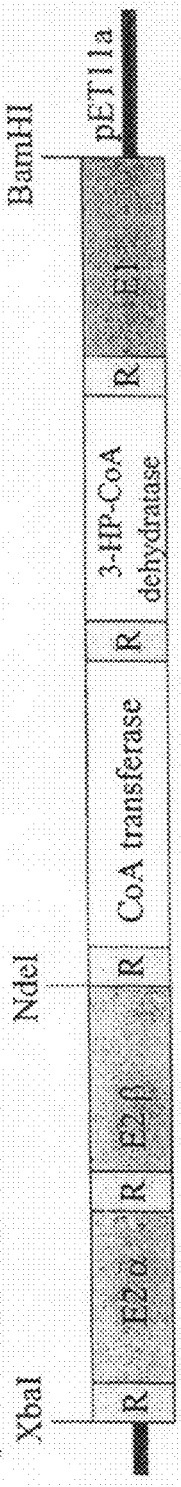
Figure 36B

```
ATGATCGACACTGCGCCCCTTGCCCCACCACGGGCGCCCCGCTCTAATCCGATTCGGGAT
CGAGTTGATTGGGAAGCTCAGCGCGCTGCTGCGCTGGCAGATCCCGGTGCCTTTCATGGC
GCGATTGCCCGGACAGTTATCCACTGGTACGACCCACAACACCATTGCTGGATTCGCTTC
AACGAGTCTAGTCAGCGTTGGGAAGGGCTGGATGCCGCTACCGGTGCCCCTGTAACGGTA
GACTATCCGCCGATTATCAGCCCTGGCAACAGGCGTTTGATGATAGTGAAGCGCCGTTT
TACCGCTGGTTTAGTGGTGGGTTGACAAATGCCTGCTTTAATGAAGTAGACCGGCATGTC
ATGATGGGCTATGGCGACGAGGTGGCCTACTACTTTGAAGGTGACCGCTGGGATAACTCG
CTCAACAATGGTCGTGGTGGTCCGGTTGTCCAGGAGACAATCACGCGGCGGCGCCTGTTG
GTGGAGGTGGTGAAGGCTGCGCAGGTGTTGCGTGATCTGGGCCTGAAGAAGGGTGATCGG
ATTGCTCTGAATATGCCGAATATTATGCCGCAGATTTATTATACGGAAGCGGCAAAACGA
CTGGGTATTCTGTACACGCCGGTCTTCGGTGGCTTCTCGGACAAGACTCTTTCCGACCGT
ATTCACAATGCCGGTGCACGAGTGGTGATTACCTCTGATGGTGCGTACCGCAACGCGCAG
GTGGTGCCCTACAAAGAAGCGTATACCGATCAGGCGCTCGATAAGTATATTCCGGTTGAG
ACGGCGCAGGCGATTGTTGCGCAGACCCTGGCCACCTTGCCCCTGACTGAGTCGCAGCGC
CAGACGATCATCACCGAAGTGGAGGCCGCACTGGCCGGTGAGATTACGGTTGAGCGCTCG
GACGTGATGCGTGGGGTTGGTTCTGCCCTCGCAAAGCTCCGCGATCTTGATGCAAGCGTG
CAGGCAAAGGTGCGTACAGTACTGGCGCAGGCGCTGGTCGAGTCGCCGCCGCGGGTTGAA
GCTGTGGTGGTTGTGCGTCATACCGGTCAGGAGATTTTGTGGAACGAGGGGCGAGATCGC
TGGAGTCACGACTTGCTGGATGCTGCGCTGGCGAAGATTCTGGCCAATGCGCGTGCTGCC
GGCTTTGATGTGCACAGTGAGAATGATCTGCTCAATCTCCCCGATGACCAGCTTATCCGT
GCGCTCTACGCCAGTATTCCCTGTGAACCGGTTGATGCTGAATATCCGATGTTTATCATT
TACACATCGGGTAGCACCGGTAAGCCCAAGGGTGTGATCCACGTTCACGGCGGTTATGTC
GCCGGTGTGGTGCACACCTTGCGGGTCAGTTTTGACGCCGAGCCGGGTGATACGATATAT
GTGATCGCCGATCCGGGCTGGATCACCGGTCAGAGCTATATGCTCACAGCCACAATGGCC
GGTCGGCTGACCGGGGTGATTGCCGAGGGATCACCGCTCTTCCCCTCAGCCGGGCGTTAT
GCCAGCATCATCGAGCGCTATGGGGTGCAGATCTTTAAGGCGGGTGTGACCTTCCTCAAG
ACAGTGATGTCCAATCCGCAGAATGTTGAAGATGTGCGACTCTATGATATGCACTCGCTG
CGGGTTGCAACCTTCTGCGCCGAGCCGGTCAGTCCGGCGGTGCAGCAGTTTGGTATGCAG
ATCATGACCCCGCAGTATATCAATTCGTACTGGGCGACCGAGCACGGTGGAATTGTCTGG
ACGCATTTCTACGGTAATCAGGACTTCCCGCTTCGTCCCGATGCCCATACCTATCCCTTG
CCCTGGGTGATGGGTGATGTCTGGGTGGCCGAAACTGATGAGAGCGGGACGACGCGCTAT
CGGGTCGCTGATTTCGATGAGAAGGGCGAGATTGTGATTACCGCCCCGTATCCCTACCTG
ACCCGCACACTCTGGGGTGATGTGCCCGGTTTCGAGGCGTACCTGCGCGGTGAGATTCCG
CTGCGGGCCTGGAAGGGTGATGCCGAGCGTTTCGTCAAGACCTACTGGCGACGTGGGCCA
AACGGTGAATGGGGCTATATCCAGGGTGATTTTGCCATCAAGTACCCCGATGGTAGCTTC
ACGCTCCACGGACGCCCTGACGATGTGATCAATGTGTCGGGCCACCGTATGGGCACCGAG
GAGATTGAGGGTGCCATTTTGCGTGACCGCCAGATCACGCCCGACTCGCCCGTCGGTAAT
TGTATTGTGGTCGGTGCGCCGCACCGTGAGAAGGGTCTGACCCCGGTTGCCTTCATTCAA
CCTGCGCCTGGCCGTCATCTGACCGGCGCCGACCGGCGCCGTCTCGATGAGCTGGTGCGT
ACCGAGAAGGGGCGGTCAGTGTCCCAGAGGATTACATCGAGGTCAGTGCCTTTCCCGAA
ACCCGCAGCGGGAAGTATATGCGGCGCTTTTGCGCAATATGATGCTCGATGAACCACTG
GGTGATACGACGACGTTGCGCAATCCTGAAGTGCTCAAGAGATTGCAGCCAAGATCGCT
GAGTGGAAACGCCGTCAGCGTATGGCCGAAGAGCAGCAGATCATCGAACGCTATCGCTAC
TTCCGGATCGAGTATCACCCACCAACGGCCAGTGCGGGTAAACTCGCGGTAGTGACGGTG
ACAAATCCGCCGGTGAACGCACTGAATGAGCGTGCGCTCGATGAGTTGAACACAATTGTT
GACCACCTGGCCCGTCGTCAGGATGTTGCCGCAATTGTCTTCACCGGACAGGGCGCCAGG
AGTTTTGTCGCCGGCGCTGATATTCGCCAGTTGCTCAAGAGATTCATACGGTTGAAGAG
GCAATGGCCCTGCCGAATAACGCCCATCTTGCTTTCCGCAAGATTGAGCGTATGAATAAG
```

Figure 39A

```
CCGTGTATCGCGGCGATCAACGGTGTGGCGCTCGGTGGTGGTCTGGAATTCGCCATGGCC
TGCCATTACCGGGTTGCCGATGTCTATGCCGAATTCGGTCAGCCAGAGATTAATCTGCGC
TTGCTACCTGGTTATGGTGGCACGCAGCGCTTGCCGCGCCTGTTGTACAAGCGCAACAAC
GGCACCGGTCTGCTCCGAGCGCTGGAGATGATTCTGGGTGGGCGTAGCGTACCGGCTGAT
GAGGCGCTGAAGCTGGGTCTGATCGATGCCATTGCTACCGGCGATCAGGACTCACTGTCG
CTGGCATGCGCGTTAGCCCGTGCCGCAATCGGCGCCGATGGTCAGTTGATCGAGTCGGCT
GCGGTGACCCAGGCTTTCCGCCATCGCCACGAGCAGCTTGACGAGTGGCGCAAACCAGAC
CCGCGCTTTGCCGATGACGAACTGCGCTCGATTATCGCCCATCCACGTATCGAGCGGATT
ATCCGGCAGGCCCATACCGTTGGGCGCGATGCGGCAGTGCATCGGGCACTGGATGCAATC
CGCTATGGCATTATCCACGGCTTCGAGGCCGGTCTGGAGCACGAGGCGAAGCTCTTTGCC
GAGGCAGTGGTTGACCCGAACGGTGGCAAGCGTGGTATTCGCGAGTTCCTCGACCGCCAG
AGTGCGCCGTTGCCAACCCGCCGACCATTGATTACACCTGAACAGGAGCAACTCTTGCGC
GATCAGAAAGAACTGTTGCCGGTTGGTTCACCCTTCTTCCCCGGTGTTGACCGGATTCCG
AAGTGGCAGTACGCGCAGGCGGTTATTCGTGATCCGGACACCGGTGCGGCGGCTCACGGC
GATCCCATCGTGGCTGAAAAGCAGATTATTGTGCCGGTGGAACGCCCCGCGCCAATCAG
GCGCTGATCTATGTTCTGGCCTCGGAGGTGAACTTCAACGATATCTGGGCGATTACCGGT
ATTCCGGTGTCACGGTTTGATGAGCACGACCGCGACTGGCACGTTACCGGTTCAGGTGGC
ATCGGCCTGATCGTTGCGCTGGGTGAAGAGGCGCGACGCGAAGGCCGGCTGAAGGTGGGT
GATCTGGTGGCGATCTACTCCGGGCAGTCGGATCTGCTCTCACCGCTGATGGGCCTTGAT
CCGATGGCCGCCGATTTCGTCATCCAGGGGAACGACACGCCAGATGGATCGCATCAGCAA
TTTATGCTGGCCCAGGCCCCGCAGTGTCTGCCCATCCCAACCGATATGTCTATCGAGGCA
GCCGGCAGCTACATCCTCAATCTCGGTACGATCTATCGCGCCCTCTTTACGACGTTGCAA
ATCAAGGCCGGACGCACCATCTTTATCGAGGGTGCGGCGACCGGTACCGGTCTGGACGCA
GCGCGCTCGGCGGCCCGGAATGGTCTGCGCGTAATTGGAATGGTCAGTTCGTCGTCACGT
GCGTCTACGCTGCTGGCTGCGGGTGCCCACGGTGCGATTAACCGTAAAGACCCGGAGGTT
GCCGATTGTTTCACGCGCGTGCCCGAAGATCCATCAGCCTGGGCAGCCTGGGAAGCCGCC
GGTCAGCCGTTGCTGGCGATGTTCCGGGCGCAGAACGACGGGCGACTGGCCGATTATGTG
GTCTCGCACGCGGGCGAGACGGCCTTCCCGCGCAGTTTCCAGCTTCTCGGCGAGCCACGC
GATGGTCACATTCCGACGCTCACATTCTACGGTGCCACCAGTGGCTACCACTTCACCTTC
CTGGGTAAGCCAGGGTCAGCTTCGCCGACCGAGATGCTGCGGCGGGCCAATCTCCGCGCC
GGTGAGGCGGTGTTGATCTACTACGGGGTTGGGAGCGATGACCTGGTAGATACCGGCGGT
CTGGAGGCTATCGAGGCGGCGCGGCAAATGGGAGCGCGGATCGTCGTCGTTACCGTCAGC
GATGCGCAACGCGAGTTTGTCCTCTCGTTGGGCTTCGGGGCTGCCCTACGTGGTGTCGTC
AGCCTGGCGGAACTCAAACGGCGCTTCGGCGATGAGTTTGAGTGGCCGCGCACGATGCCG
CCGTTGCCGAACGCCCGCCAGGACCCGCAGGGTCTGAAAGAGGCTGTCCGCCGCTTCAAC
GATCTGGTCTTCAAGCCGCTAGGAAGCGCGGTCGGTGTCTTCTTGCGGAGTGCCGACAAT
CCGCGTGGCTACCCCGATCTGATCATCGAGCGGGCTGCCCACGATGCACTGGCGGTGAGC
GCGATGCTGATCAAGCCCTTCACCGGACGGATTGTCTACTTCGAGGACATTGGTGGGCGG
CGTTACTCCTTCTTCGCACCGCAAATCTGGGTGCGCCAGCGCCGCATCTACATGCCGACG
GCACAGATCTTTGGTACGCACCTCTCAAATGCGTATGAAATTCTGCGTCTGAATGATGAG
ATCAGCGCCGGTCTGCTGACGATTACCGAGCCGGCAGTGGTGCCGTGGGATGAACTACCC
GAAGCACATCAGGCGATGTGGGAAAATCGCCACACGGCGGCCACTTATGTGGTGAATCAT
GCCTTACCACGTCTCGGCCTAAAGAACAGGGACGAGCTGTACGAGGCGTGGACGGCCGGC
GAGCGGTAG      (SEQ ID NO:129)
```

Figure 39B

```
SEQ ID NO:39    1  ------------------------midtaplappraprsnpirdrvdwe
SEQ ID NO:130   1  mglpeervrsgsgsrgqeeagaggrarswsp--ppevsrsahvpslqryr
SEQ ID NO:131   1  -------------------------mslelkekeselpfdeqiind
                                            PL PP    RS P SEQ ID NO:39   26  aqrasaladpgafhgaiartvihwydpqhhcwirfnessqrwegldaatg
SEQ ID NO:130  49  elhrrsveeprefwgdiake-fywktpcpgpflryn--------------
SEQ ID NO:131  22  kwrs------------kytpidayfkfhrqtvenlesf--wesv-----
                    R         P    FG IA T I WY P H    R NES    WE SEQ ID NO:39   76  apvtvdypadyqpwqqafddseap-fyrwfsggltnacfnevdrhvm-mg
SEQ ID NO:130  84  ----------------fdvtkgkifiewmkgattnicynvldrnvhekk
SEQ ID NO:131  52  -akelew---fkpwdkvldasnpp-fykwfvggrlnlsylavdrhvk-tw
                          PW     FD S   P  FY WF GG TN C N VDRHV SEQ ID NO:39  124  ygdevayyfegdrwdnslnngrggpvvqetitrrrllvevvkaaqglr-d
SEQ ID NO:130 117  lgdkvafywegne----------pgettqityhqllvqvcqfsnvlr-k
SEQ ID NO:131  96  rknklaiewegepvden-----gyptdrrkltyydlyrevnrvaymlkqn
                    GD VA Y EG  D          G P       IT   LLVEV   A VLR SEQ ID NO:39  173  lglkkgdrialnmpnimpqiyyte-aakrlgilytpvfggfsdktlsdri
SEQ ID NO:130 155  qgiqkgdrvaiympmipelvvaml-acarigalhsivfagfsseslceri
SEQ ID NO:131 141  fgvkkgdkitlylp-mvpelpitmlaawrigaitsvvfsgfsadalaeri
                    G KKGDRIAL MP I P     T   AA R G L   VF GFS   L  RI SEQ ID NO:39  222  hnagarvvitsdgayrnaqvvpykeaytdqal----dkyipvetaqaiva
SEQ ID NO:130 204  ldsscsllittdafyrgeklvnlkel-adealqkcqekgfpvrc--civv
SEQ ID NO:131 190  ndsqsrivitadgfwrrgrvvrlkev------------------------
                    R VIT DG YR   VV  KE    D AL    K  PV        IV SEQ ID NO:39  268  qtlatlplteeqrqtiiteveaalageitversdvmrgvgssalaklrdld
SEQ ID NO:130 251  khlgrael-------------------------gmgdsts------
SEQ ID NO:131 216  --------------------vdaal---------------------
                        L   L              V AAL              ; G SEQ ID NO:39  318  asvqakvrtvlaqalvespprveavvvvrhtg-qeilwnegrdrwshdll
SEQ ID NO:130 266  -----------qsppikrscpdv-----qiswnqgidlwwhelm
SEQ ID NO:131 221  -----------ekatgvesvivlprlglkdvpmtegrdywwnklm
                                  ESPP  VE V VV  G    I WNEGRD W H L SEQ ID NO:39  367  daalakilanaraagfdvhsendllnlpddqliralyasipcep--vdae
SEQ ID NO:130 294  qea----------------------gde----------cepewcdae
SEQ ID NO:131 255  q-----------------------gippn-------ayiepep--vese
                    A                        P D          A I CEP  VDAE SEQ ID NO:39  415  ypmfiiytsgstgkpkgvihvhggyvagvvhtlrvsfdaepgdtiyviad
SEQ ID NO:130 309  dplfilytsgstgkpkgvvhtvggymlyvattfkyvfdfhaedvfwctad
SEQ ID NO:131 272  hpsfilytsgttgkpkgivhdtggwavhvyatmkwvfdirdddifwctad
                    P FI YTSGSTGKPKGV H  GGY   V  T    FD  D        AD SEQ ID NO:39  465  pgwitgqsymltatmagrltgviaegsplfpsagryasiierygvqifka
SEQ ID NO:130 359  igwitghsyvtygplangatsvlfegiptypdvnrlwsivdkykvtkfyt
SEQ ID NO:131 322  igwvtghsyvvlgpllmgateviyegapdypqpdrwwsiierygvtifyt
                    GWITG SY      A   T VI EG P  P    R  SIIERYGV IF
```

Figure 40A

```
SEQ ID NO:39    515  gvtflktvmsnpqnveavrlyamnslrvatrcaepvspavqqrgmqimtp
SEQ ID NO:130   409  aptairllmkfgd--epvtkhsraslqvlgtvgepinpeawlwyhrvvga
SEQ ID NO:131   372  sptairmfmryge--evprkhdlstlriihsvgepinpeawrwayrvlgn
                        T    M       E VR D  SLRV      EP  P SEQ ID NO:39    565  q---yi---nsywatehggivwthfygnqdfplrpdahtyplpwvmgdvw
SEQ ID NO:130   457  qrcpiv---dtfwqtetgghmltplpgat--pmkpgsatfp----ffgva
SEQ ID NO:131   420  e---kvafgstwwmtetggivishapglylvpmkpgtngpplpgfevdv-
                      Q            W TE GGIV TH G     P P    T PLP    DV SEQ ID NO:39    609  vaetdesgttryrvadfdekgeivitapypyltrtlwgdvpgfeaylrge
SEQ ID NO:130   498  pailnesg----eelegeaegylvfkqpwpgimrtvy-------------
SEQ ID NO:131   466  ---vdengnp----appgvkgylvikkpwpgmlhgiw-------------
                        A  DESG     A    KG VI    P P   RT W SEQ ID NO:39    659  iplrawkgdaerfvktywrrgpngewgyiqgdfaikypdgsftlhgrpdd
SEQ ID NO:130   531  --------gnherfettyfkkfpg---yyvtgdgcqrdqdgyywitgridd
SEQ ID NO:131   496  --------gdperyiktywsrfpg---mfyagdyaikdkdgyiwvlgrade
                             GD ERF KTYW R P      Y  GD AIK  DG    GR DD SEQ ID NO:39    709  vinvsghrmgteeiegailrdrqitpdspvgncivvgaphrekgltpvaf
SEQ ID NO:130   571  mlnvsghllstaevesalve------heavaeaavvghphpvkgeclycf
SEQ ID NO:131   536  vikvaghrlgtyelesali------shpavaesavvgvpdaikgevpiaf
                     VINVSGHR GT E E A              V   VVG PH  KG  P AF SEQ ID NO:39    759  iqpapgrhltgadrrrldelvrtekgavsvpedyie-vsafpetrsgkym
SEQ ID NO:130   615  vtlcdghtfspklteelkkqirekigpiatp-dyiqnapglpktrsgkim
SEQ ID NO:131   580  vvlkqgvapsdelrkelrehvrrtigpiaepaqiff-vtklpktrsgkim
                            G      R  L E VR    G    P DYI  V   P TRSGK M SEQ ID NO:39    808  rrflrnmml-deplgdtttlrnpevleeiaakiaewkrrqrmaeeqqiie
SEQ ID NO:130   664  rrvlrkiaqndhdlgdmstvadpsvi------------------------
SEQ ID NO:131   629  rrllkavat-gaplgdvtt---------------------
                     RR LR        D PLGD TT    P V SEQ ID NO:39    857  ryryfrieyhpptasagklavvtvtnppvnalneraldelntivdhlarr
SEQ ID NO:130   690  --------------------------------------------------
SEQ ID NO:131   647  --------------------------------------------------

SEQ ID NO:39    907  qdvaaivftgqgarsfvagadirqlleeihtveeamalpnnahlafrkie
SEQ ID NO:130   690  --------------------------------------------shl------
SEQ ID NO:131   647  ---------------------ledetsveeak-----------------
                                            LE        VEEA       HL SEQ ID NO:39    957  rmnkpciaaingvalggglefamachyrvadvyaefgqpeinlrllpgyg
SEQ ID NO:130   693  --------------------------------------------------
SEQ ID NO:131   658  --------------------------------------------------

SEQ ID NO:39   1007  gtqrlprllykrnngtgllralemilggrsvpadealklglidaiatgdq
SEQ ID NO:130   693  ---------------------------------------------
SEQ ID NO:131   658  --------------------raye---------------------
                                           RA E SEQ ID NO:39   1057  dslslacalaraaigadgqliesaavtqafrhrheqldewrkpdprfadd
SEQ ID NO:130   693  --------------------------------fshr--------------
SEQ ID NO:131   662  --------------------------------------------------
                                                    F HR
```

Figure 40B

```
SEQ ID NO:39   1107  elrsiiahprieriirqahtvgrdaavhraldairygiihgfeaglehea
SEQ ID NO:130   697  -------------------------------------------------
SEQ ID NO:131   662  -------------------------------------------------

SEQ ID NO:39   1157  klfaeavvdpnggkrgirefldrqsaplptrrplitpeqeqllrdqkell
SEQ ID NO:130   697  -------------------------------------------------
SEQ ID NO:131   662  -------------------------------------------------

SEQ ID NO:39   1207  pvgspffpgvdripkwqyaqavirdpdtgaaahgdpivaekqiivpverp
SEQ ID NO:130   697  -------------------------------------------------
SEQ ID NO:131   662  -------------------------------------------------

SEQ ID NO:39   1257  ranqaliyvlasevnfndiwaitgipvsrfdehdrdwhvtgsggigliva
SEQ ID NO:130   697  -------------------------------------------------
SEQ ID NO:131   662  -------------------------------------------------

SEQ ID NO:39   1307  lgeearregrlkvgdlvaiysgqsdllsplmgldpmaadfviqgndtpdg
SEQ ID NO:130   697  -------------------------------------------------
SEQ ID NO:131   662  -------------------------------------------------

SEQ ID NO:39   1357  shqqfmlaqapqclpiptdmsieaagsyilnlgtiyralfttlqikagrt
SEQ ID NO:130   697  -------------cl-----------------------tiq--------
SEQ ID NO:131   662  ------------------------------------------eika---
                                  CL                          T QIKA SEQ ID NO:39   1407  ifiegaatgtgldaarsaarnglrvigmvsssrastllaagahgainrk
SEQ ID NO:130   702  ------------------------------------------------
SEQ ID NO:131   666  ------------------------------------------------

SEQ ID NO:39   1457  dpevadcftrvpedpsawaaweaagqpllamfraqndgrladyvvshage
SEQ ID NO:130   702  -------------------------------------------------
SEQ ID NO:131   666  -------------------------------------------------

SEQ ID NO:39   1507  tafprsfqllgeprdghiptltfygatsgyhftflgkpgsasptemlrra
SEQ ID NO:130   702  -------------------------------------------------
SEQ ID NO:131   666  -------------------------------------------------

SEQ ID NO:39   1557  nlrageavliyygvgsddlvdtggleaieaarqmgarivvvtvsdaqref
SEQ ID NO:130   702  -------------------------------------------------
SEQ ID NO:131   666  -------------------------------------------------

SEQ ID NO:39   1607  vlslgfgaalrgvvslaelkrrfgdefewprtmpplpnarqdpqglkeav
SEQ ID NO:130   702  -------------------------------------------------
SEQ ID NO:131   666  ------------------------------emart--------------
                                                    E   RT SEQ ID NO:39   1657  rrfndlvfkplgsavgvflrsadnprgypdliieraahdalavsamlikp
SEQ ID NO:130   702  -------------------------------------------------
SEQ ID NO:131   671  -------------------------------------------------
```

Figure 40C

```
SEQ ID NO:39    1707  ftgrivyfediggrrysffapqiwvrqrriymptaqifgthlsnayeilr
SEQ ID NO:130    702  --------------------------------------------------
SEQ ID NO:131    671  --------------------------------------------------

SEQ ID NO:39    1757  lndeisaglltitepavvpwdelpeahqamwenrhtaatyvvnhalprlg
SEQ ID NO:130    702  --------------------------------------------------
SEQ ID NO:131    671  --------------------------------------------------

SEQ ID NO:39    1807  lknrdelyeawtager
SEQ ID NO:130    702  ----------------
SEQ ID NO:131    671  ----------------
```

Figure 40D

```
SEQ ID NO:39    1  midtaplappraprsnpirdrvdweaqraaaladpgafhgaiartvihwy
SEQ ID NO:132   1  --------------------------------------------------
SEQ ID NO:133   1  --------------------------------------------------

SEQ ID NO:39   51  dpqhhcwirfnessqrwegldaatgapvtvdypadyqpwqqafddseapf
SEQ ID NO:132   1  --------------------------------------------------
SEQ ID NO:133   1  ---------------md---------------------------------
                                  D SEQ ID NO:39  101  yrwfsggltnacfnevdrhvmmgygdevayyfegdrwdnslnngrggpvv
SEQ ID NO:132   1  ------------------------------------melnn---------
SEQ ID NO:133   3  -------------fnnv---------------------------------
                                FN V                            LNN SEQ ID NO:39  151  qetitrrrllvevvkaaqvlrdlglkkgdrialnmpnimpqiyyteaakr
SEQ ID NO:132   6  --------------------------------------------------
SEQ ID NO:133   7  ------------------llnkddgial----------------------
                                     L K D IAL SEQ ID NO:39  201  lgilytpvfggfsdktlsdrihnagarvvitsdgayrnaqvvpykeaytd
SEQ ID NO:132   6  --------------------------------------------------
SEQ ID NO:133  17  --------------------------------------------------

SEQ ID NO:39  251  qaldkyipvetaqaivaqtlatlpltesqrqtiiteveaalageitvers
SEQ ID NO:132   6  ------------------------------------vileke--------
SEQ ID NO:133  17  --------------------------------------------------
                                                       I E E SEQ ID NO:39  301  dvmrgvgsalaklrdldasvqakvrtvlaqalvespprveavvvvrhtgq
SEQ ID NO:132  12  --------------------------------------------------
SEQ ID NO:133  17  --------------------------------------------------

SEQ ID NO:39  351  eilwnegrdrwshdlldaalakilanaraagfdvhsendllnlpddqlir
SEQ ID NO:132  12  --------------------------------------------------
SEQ ID NO:133  17  --------------------iiin--------------------------
                                       I N SEQ ID NO:39  401  alyasipcepvdaeypmfiiytsgstgkpkgvihvhggyvagvvhtlrvs
SEQ ID NO:132  12  --------------------------------------------------
SEQ ID NO:133  21  --------------------------------------------------

SEQ ID NO:39  451  fdaepgdtiyviadpgwitgqsymltatmagrltgviaegsplfpsagry
SEQ ID NO:132  12  --------------------------------------------------
SEQ ID NO:133  21  --------------------------------------------------

SEQ ID NO:39  501  asiierygvqifkagvtflktvmsnpqnvedvrlydmhslrvatfcaepv
SEQ ID NO:132  12  --------------------------------------------------
SEQ ID NO:133  21  --------------------------------------------------
```

Figure 41A

```
SEQ ID NO:39    551  spavqqfgmqimtpqyinsywatehggivwthfygnqdfplrpdahtypl
SEQ ID NO:132    12  -------------------------------------------------
SEQ ID NO:133    21  ---------------------------------------------rpka----
                                                                  RP A SEQ ID NO:39    601  pwvmgdvwvaetdesgttryrvadfdekgeivitapypyltrtlwgdvpg
SEQ ID NO:132    12  -------------------------------------------------
SEQ ID NO:133    25  -------------------------------------------------

SEQ ID NO:39    651  feaylrgeiplrawkgdaerfvktywrrgpngewgyiqgdfaikypdgsf
SEQ ID NO:132    12  -------------------------------------------------
SEQ ID NO:133    25  -------------------------------------------------

SEQ ID NO:39    701  tlhgrpddvinvsghrmgteeiegailrdrqitpdspvgncivvgaphre
SEQ ID NO:132    12  -------------------------------------------------
SEQ ID NO:133    25  -------------------------------------------------

SEQ ID NO:39    751  kgltpvafiqpapgrhltgadrrrldelvrtekgavsvpedyievsafpe
SEQ ID NO:132    12  -------------------------------------------------
SEQ ID NO:133    25. -------------------------------------------------

SEQ ID NO:39    801  trsgkymrrflrnmmldeplgdtttlrnpevleeiaakiaewkrrqrmae
SEQ ID NO:132    12  -------------------------------------------------
SEQ ID NO:133    25  -------------------------------------------------

SEQ ID NO:39    851  eqqiieryryfrieyhpptasagklavvtvtnpp-vnalneraldelnti
SEQ ID NO:132    12  ----------------------gkvavvtinrpkalnalnsdtlkemdyv
SEQ ID NO:133    25  -------------------------lnalnyetlkeldsv
                                              GK AVVT   P   NALN   L EL SEQ ID NO:39    900  vdhlarrqdvaaivftgqgarsfvagadirqlleeihtve-eamalpnna
SEQ ID NO:132    40  igeiendsevlaviltgagekefvagadisem-kemntiegrkfgilgnk
SEQ ID NO:133    40  ldivendkeikvliitgsgektfvagadiaemsn--mtpl-eakkfslyg
                        D    V A  TG G SFVAGADI   E  T E EA      N SEQ ID NO:39    949  hlafrkiermnkpciaaingvalgggglefamachyrvadvyaefgqpein
SEQ ID NO:132    89  --vfrrlellekpviaavngfalgggceiamscdiriassnarfgqpevg
SEQ ID NO:133    87  qkvfrkiemlskpviaavngfalgggcelsmacdiriasknakfgqpevg
                         FRKIE   KP IAA NG ALGGG E AMAC   R A    A FGQPE SEQ ID NO:39    999  lrllpgyggtqrlprllykrnngtgllralemilggrsvpadealklgli
SEQ ID NO:132   137  lgitpgfggtqrlsrlv-------gmgmakqliftaqnikadealriglv
SEQ ID NO:133   137  lgiipgfsgtqrlprli-------gtskakeliftgdminsdeaykigli
                      L   PG GGTQRLPRL        G  A E I G      ADEALK GLI SEQ ID NO:39   1049  daiatgdqdslslacalaraaigadgqliesaavtqafrhrheqldewrk
SEQ ID NO:132   180  n-------------------------------------------------
SEQ ID NO:133   180  skvv----------------------------------------------

SEQ ID NO:39   1099  pdprfaddelrsiiahpriereiirqahtvgrdaavhraldairygiihgf
SEQ ID NO:132   181  -------------------------------------------------
SEQ ID NO:133   184  --------elsdli------------------------------------
                             EL   I
```

Figure 41B

```
SEQ ID NO:39    1149 eagleheaklfaeavvdpnggkrgirefldrqsaplptrrplitpeqeql
SEQ ID NO:132    181 --------------kvveps-----------------------------el
SEQ ID NO:133    190 -----eeakklak-------------------------------------
                      EAK   A   VV P                                   L SEQ ID NO:39    1199 lrdqkellpvgspffpgvdripkwqyaqavirdpdtgaaahgdpivaekq
SEQ ID NO:132    189 mntakei-------------------------------------------
SEQ ID NO:133    198 -------------------------------------------kmmsksq
                      KE                                                Q SEQ ID NO:39    1249 iivpverpranqaliyvlasevnfndiwaitgipvsrfdehdrdwhvtgs
SEQ ID NO:132    196 ---------ank----------------ivsnapva--------------
SEQ ID NO:133    205 i-------------------------------------------------
                     I        AN                 PV SEQ ID NO:39    1299 ggiglivalgeearregrlkvgdlvaiysgqsdllsplmgldpmaadfvi
SEQ ID NO:132    207 ------vklskqainrgm--------------------------------
SEQ ID NO:133    206 -----aislakeainkg---------------------------------
                      V L  EA    G SEQ ID NO:39    1349 qgndtpdgshqqfmlaqapqclpiptdmsieaagsyilnlgtiyralftt
SEQ ID NO:132    219 --------------------qc-didtalafesea---------fgecfst
SEQ ID NO:133    218 ------------------------metdld--------------------
                                         QC  I TD    E               F T SEQ ID NO:39    1399 lqikagrtifiegaatgtgldaarsaarnglrvigmvsassrastllaag
SEQ ID NO:132    240 edqkdamtafie--------------------------------------
SEQ ID NO:133    224 --------------tgntieaekfsl------------------------
                      K   T FIE    TG   A SEQ ID NO:39    1449 ahgainrkdpevadcftrvpedpsawaaweaagqpllamfraqndgrlad
SEQ ID NO:132    252 --------------------------------------------------
SEQ ID NO:133    236 -----------cft------------------------------------
                                CFT SEQ ID NO:39    1499 yvvshagetafprsfqllgeprdghiptltfygatsgyhftflgkpgsas
SEQ ID NO:132    252 --------------------------------------------------
SEQ ID NO:133    239 --------------------------------------------------

SEQ ID NO:39    1549 ptemlrranlrageavliyygvgsddlvdtggleaieaarqmgarivvvt
SEQ ID NO:132    252 --------------------------------------------------
SEQ ID NO:133    239 --------------------------------------------------

SEQ ID NO:39    1599 vsdaqrefvlslgfgaalrgvvslaelkrrfgdefewprtmpplpnarqd
SEQ ID NO:132    252 ----------------------------krk-------------------
SEQ ID NO:133    239 -tddqke-----------gmiafse-kr----------------------
                      D Q E              G       E KR SEQ ID NO:39    1649 pqglkeavrrfndlvfkplgsavgvflrsadnprgypdliieraahdala
SEQ ID NO:132    255 -------------------------------------ie-----------
SEQ ID NO:133    254 --------------------------------------------------
                                                           IE SEQ ID NO:39    1699 vsamlikpftgrivyfediggrrysffapqiwvrqrriymptaqifgthl
SEQ ID NO:132    257 --------------------------------------------------
SEQ ID NO:133    254 -----------------------apk---------------fgk-----
                                            AP                FG
```

Figure 41C

```
SEQ ID NO:39    1749 snayeilrlndeisaglltitepavvpwdelpeahqamwenrhtaatyvv
SEQ ID NO:132    257 --------------------------------------------------
SEQ ID NO:133    260 --------------------------------------------------

SEQ ID NO:39    1799 nhalprlglknrdelyeawtager
SEQ ID NO:132    257 -------gfknr------------
SEQ ID NO:133    260 ------------------------
                            G KNR
```

Figure 41D

```
SEQ ID NO:39    1  midtaplapprapraprsnpirdrvdweaqraaaladpgafhgaiartvihwy
SEQ ID NO:134   1  ----------------------------------------------------
SEQ ID NO:135   1  ----------------------------------------------------

SEQ ID NO:39   51  dpqhhcwirfnessqrwegldaatgapvtvdypadyqpwqqafddseapf
SEQ ID NO:134   1  -------------------maasaap------------------------
SEQ ID NO:135   1  --------------------------------------------------
                                      AA  AP SEQ ID NO:39  101  yrwfsggltnacfnevdrhvmmgygdevayyfegdrwdnslnngrggpvv
SEQ ID NO:134   8  --------------------------------------------------
SEQ ID NO:135   1  --------------------------------------------------

SEQ ID NO:39  151  qetitrrrllvevvkaaqvlrdlglkkgdrialnmpnimpqiyyteaakr
SEQ ID NO:134   8  --------------------------------------------------
SEQ ID NO:135   1  --------------------------------------------------

SEQ ID NO:39  201  lgilytpvfggfsdktlsdrihnagarvvitsdgayrnaqvvpykeaytd
SEQ ID NO:134   8  ----------------------------------------------awtg
SEQ ID NO:135   1  --------------------------------------------------
                                                                  A T SEQ ID NO:39  251  qaldkyipvetaqaivaqtlatlpltesqrqtiiteveaalageitvers
SEQ ID NO:134  12  q--------------------------------------------taeak
SEQ ID NO:135   1  -------------mtiqtlettalkd------------------------
                   Q            QTL T   L                       T E SEQ ID NO:39  301  dvmrgvgsalaklrdldasvqakvrtvlaqaivesppprveavvvrhtgq
SEQ ID NO:134  18  d-------------------------------------------------
SEQ ID NO:135  14  --------------------------------------------------
                   D SEQ ID NO:39  351  eilwnegrdrwshdlldaalakilanaraagfdvhsendllnlpddqlir
SEQ ID NO:134  19  --------------------------------------------------
SEQ ID NO:135  14  --------------------------------------------------

SEQ ID NO:39  401  alyasipcepvdaeypmfiiytsgstgkpkgvihvhggyvagvvhtlrvs
SEQ ID NO:134  19  --------------------------------------------------
SEQ ID NO:135  14  --------------------------------------------------

SEQ ID NO:39  451  fdaepgdtiyviadpgwitgqsymltatmagrltgviaegsplfpsagry
SEQ ID NO:134  19  --------------------------------------------------
SEQ ID NO:135  14  --------------------------------------------------

SEQ ID NO:39  501  asiierygvqifkagvtflktvmsnpqnvedvrlydmhslrvatfcaepv
SEQ ID NO:134  19  ------------------------------------lyel---------
SEQ ID NO:135  14  ------------------------------------lyei---------
                                                       LY
```

Figure 42A

```
SEQ ID NO:39    551 spavqqfgmqimtpqyinsywatehggivwthfygnqdfplrpdahtypl
SEQ ID NO:134    23 --------------------------------------------------
SEQ ID NO:135    18 --------------------------------------------------

SEQ ID NO:39    601 pwvmgdvwvaetdesgttryrvadfdekgeivitapypyltrtlwgdvpg
SEQ ID NO:134    23 --------------------------------------------------
SEQ ID NO:135    18 --------------------------------------------------

SEQ ID NO:39    651 feaylrgeiplrawkgdaerfvktywrrgpngewgyiqgdfaikypdgsf
SEQ ID NO:134    23 ------geip----------------------------------------
SEQ ID NO:135    18 ------geip----------------------------------------
                          GEIP SEQ ID NO:39    701 tlhgrpddvinvsghrmgteeiegailrdrqitpdspvgncivvgaphre
SEQ ID NO:134    27 --------------------------------------------------
SEQ ID NO:135    22 --------------------------------------------------

SEQ ID NO:39    751 kgltpvafiqpapgrhltgadrrrldelvrtekgavsvpedyievsafpe
SEQ ID NO:134    27 --------------------------------------------------
SEQ ID NO:135    22 ------------pafhv--------------------------------pk
                                P H                                    P SEQ ID NO:39    801 trsgkymrrflrnmmldeplgdtttlrnpevleeiaakiaewkrrqrmae
SEQ ID NO:134    27 --------------------plg------------hvpakmyawairr----
SEQ ID NO:135    29 t-----------------------------------myawsirk----
                    T                   PLG            AK   W R SEQ ID NO:39    851 eqqiieryryfrieyhpptasagklavvtvtnppvnalneraldelntiv
SEQ ID NO:134    43 -----erh------------------------------------------
SEQ ID NO:135    38 --------------------------------------------------
                         ER SEQ ID NO:39    901 dhlarrqdvaaivftgqgarsfvagadirqlleeihtveeamalpnnahl
SEQ ID NO:134    46 --------------------------------------------------
SEQ ID NO:135    38 --------------------------------------------------

SEQ ID NO:39    951 afrkiermnkpciaaingvalggglefamachyrvadvyaefgqpeinlr
SEQ ID NO:134    46 -------------------------------------------gppe----
SEQ ID NO:135    38 -----erhgkp---------------------------------------
                         ER  KP                                G PE SEQ ID NO:39   1001 llpgyggtqrlprllykrnngtgllralemilggrsvpadealklglida
SEQ ID NO:134    50 --------------------------------------------------
SEQ ID NO:135    44 --------------------------------------------------

SEQ ID NO:39   1051 iatgdqdslslacalaraaigadgqliesaavtqafrhrheqldewrkpd
SEQ ID NO:134    50 --------------------------------------------------
SEQ ID NO:135    44 ---------------------------tqamq------------------
                                               TQA SEQ ID NO:39   1101 prfaddelrsiiahprieriirqahtvgrdaavhraldairygiihgfea
SEQ ID NO:134    50 -----------qsh------------------------------------
SEQ ID NO:135    49 --------------------------------------------------
                            Q H
```

Figure 42B

SEQ ID NO:39   1151 gleheaklfaeavvdpnggkrgirefldrqsaplptrrplitpeqeqllr
SEQ ID NO:134    53 --------------------------------------------------
SEQ ID NO:135    49 --------------------------------------------------

SEQ ID NO:39   1201 dqkellpvgspffpgvdripkwqyaqavirdpdtgaaahgdpivaekqii
SEQ ID NO:134    53 -qlevlpv------------wei--------------gd-----------
SEQ ID NO:135    49 --------------vevvptweige-------------------------
                     Q E LPV       V   P W                 GD SEQ ID NO:39   1251 vpverpranqaliyvlasevnfndiwaitgipvsrfdehdrdwhvtgsgg
SEQ ID NO:134    65 ---------devlvyvmaagvnyngvwaglgepispfdvhkgeyhiagsda
SEQ ID NO:135    60 ---------devlvlvmaagvnyngvwaalgepispldghkqpfhiagsda
                              L YV A  VN N WA GP S FD H      H  GS SEQ ID NO:39   1301 iglivalgeearregrlkvgdlvaiysgqsdllsp-lmgldpm-aadfv-
SEQ ID NO:134   107 sgivwkvgakvk---rwkvgdevivhcnqddgddeecnggdpm-faptqr
SEQ ID NO:135   102 sgivwkvgakvk---rwklgdevvihcnqddgddeecnggdpmfsssqr-
                      G         G    R KVGD V I  Q D       G DPM SEQ ID NO:39   1348 iqgndtpdgshqqfmlaqapqclpiptdmsieaagsyilnlgtiyralf-
SEQ ID NO:134   153 iwgyetgdgsfaqfcrvqsrqlmarpkhltweeascytltlatayrmlfg
SEQ ID NO:135   148 iwgyetgdgsfaqfcrvqsrqllprpkhltweesacytltlatayrmlfg
                      I G TPDGS QF  Q  Q LP P    E A   Y L L T YR LF SEQ ID NO:39   1397 -ttlqikagrtifiegaatgtgldaarsaarnglrvigmvsssrastll
SEQ ID NO:134   203 haphtvrpgqnvliwgasgglgvfgvqlcaasganaiavisdeskrdyvm
SEQ ID NO:135   198 hkphelkpgqnvlvwgasgglgvfatqlaavaganaigvvssedkrefvl
                           K G    I GA  GG  A    AA G   IG VSS S    L SEQ ID NO:39   1446 aagahgainrkdpevadcftrvpedpsawaaweaagqpllamfraqndgr
SEQ ID NO:134   253 slgakgvinrkd---fdc---w----------------------------
SEQ ID NO:135   248 smgakavlnrge---fncwgqlpk--------------------------
                         GA G INRKD    DC    P SEQ ID NO:39   1496 ladyvvshagetafprsfqllgeprdghiptltfygatsgyhftflgkpg
SEQ ID NO:134   269 --------------------------gqlptv------------------
SEQ ID NO:135   269 -------------------------------vngpef-------------
                                              G PT         G F SEQ ID NO:39   1546 sasptemlrranlrageavliyygvgsddlvdtggleaieaarqmgariv
SEQ ID NO:134   275 --------------------------------------------------
SEQ ID NO:135   275 --------------------------------------------------

SEQ ID NO:39   1596 vvtvsdaqrefvlslgfgaalrgvvslaelkrrfgdefewprtmpplpna
SEQ ID NO:134   275 ------------------------------------------------ns
SEQ ID NO:135   275 ----ndymke-------------------srkfgkai-wqit--------
                        D E                    R FG     W  T     N SEQ ID NO:39   1646 rqdpqglkeavrrfndlvfkplgsavgvflrsadnprgypdliieraahd
SEQ ID NO:134   277 peyntwlkea-rkfgkaiwditgkgndv------------divfehpgea
SEQ ID NO:135   293 -----gnkdv------------------------------dmvfehpgeq
                        GLKEA R F            G   V              D E SEQ ID NO:39   1696 alavsamlikpftgrivyfediggrrysffapqiwvrqrriymptaqifg
SEQ ID NO:134   314 tfpvstlvakr-ggmivfcagttgfnitfdaryvwmrqkriq-------g
SEQ ID NO:135   308 tfpvsvflvkr-ggmvvicagttgfnltmdarflwmrqkrvq-------g
                        VS  L K   G IV      G    FA  W RQ RI        G

Figure 42C

```
SEQ ID NO:39    1746  thlsnayeilrlndeisaglltitepavvpwdelpeahqamwenrhtaat
SEQ ID NO:134    356  shfahlkqasaanqfvmdrrvdpcmsevfpwdkipaahtkmwknqhppgn
SEQ ID NO:135    350  shfanlmqasaanqlvidrrvdpclsevfpwdqipaahekmlanqhlpgn
                       H  N          N              V PWD  P AH  MW N H SEQ ID NO:39    1796  yvvnhalprlglknrdelyeawtager
SEQ ID NO:134    406  mavlvnstraglrtvedvieagplkam
SEQ ID NO:135    400  mavlvcaqrpglrtfeevqelsgap--
                         V    R GL   E  EA A
```

Figure 42D

```
ATGGCGACGGGGGAGTCCATGAGCGGAACAGGACGACTGGCAGGAAAGATTGCGTTAATT
ACCGGTGGCGCCGGCAATATCGGCAGTGAATTGACACGTCGCTTTCTCGCAGAGGGAGCG
ACGGTCATTATTAGTGGACGGAATCGGGCGAAGTTGACCGCACTGGCCGAACGGATGCAG
GCAGAGGCAGGAGTGCCGGCAAAGCGCATCGATCTCGAAGTCATGGATGGGAGTGATCCG
GTCGCGGTACGTGCCGGTATCGAAGCGATTGTGGCCCGTCACGGCCAGATCGACATTCTG
GTCAACAATGCAGGAAGTGCCGGTGCCCAGCGTCGTCTGGCCGAGATTCCACTCACTGAA
GCTGAATTAGGCCCTGGCGCCGAAGAGACGCTTCATGCCAGCATCGCCAATTTACTTGGT
ATGGGATGGCATCTGATGCGTATTGCGGCACCTCATATGCCGGTAGGAAGTGCGGTCATC
AATGTCTCGACCATCTTTTCACGGGCTGAGTACTACGGGCGGATTCCGTATGTCACCCCT
AAAGCTGCTCTTAATGCTCTATCTCAACTTGCTGCGCGTGAGTTAGGTGCACGTGGCATC
CGCGTTAATACGATCTTTCCCGGCCCGATTGAAAGTGATCGCATCCGTACAGTGTTCCAG
CGTATGGATCAGCTCAAGGGGCGGCCCGAAGGCGACACAGCGCACCATTTTTTGAACACC
ATGCGATTGTGTCGTGCCAACGACCAGGGCGCGCTTGAACGTCGGTTCCCCTCCGTCGGT
GATGTGGCAGACGCCGCTGTCTTTCTGGCCAGTGCCGAATCCGCCGCTCTCTCCGGTGAG
ACGATTGAGGTTACGCACGGAATGGAGTTGCCGGCCTGCAGTGAGACCAGCCTGCTGGCC
CGTACTGATCTGCGCACGATTGATGCCAGTGGCCGCACGACGCTCATCTGCGCCGGCGAC
CAGATTGAAGAGGTGATGGCGCTCACCGGTATGTTGCGTACCTGTGGGAGTGAAGTGATC
ATCGGCTTCCGTTCGGCTGCGGCGCTGGCCCAGTTCGAGCAGGCAGTCAATGAGAGTCGG
CGGCTGGCCGGCGCAGACTTTACGCCTCCCATTGCCTTGCCACTCGATCCACGCGATCCG
GCAACAATTGACGCTGTCTTCGATTGGGCCGGCGAGAATACCGGCGGGATTCATGCAGCG
GTGATTCTGCCTGCTACCAGTCACGAACCGGCACCGTGCGTGATTGAGGTTGATGATGAG
CGGGTGCTGAATTTTCTGGCCGATGAAATCACCGGGACAATTGTGATTGCCAGTCGCCTG
GCCCGTTACTGGCAGTCGCAACGGCTTACCCCCGGCGCACGTGCGCGTGGGCCGCGTGTC
ATTTTTCTCTCGAACGGTGCCGATCAAAATGGGAATGTTTACGGACGCATTCAAAGTGCC
GCTATCGGTCAGCTCATTCGTGTGTGGCGTCACGAGGCTGAACTTGACTATCAGCGTGCC
AGCGCCGCCGGTGATCATGTGCTGCCGCCGGTATGGGCCAATCAGATTGTGCGCTTCGCT
AACCGCAGCCTTGAAGGGTTAGAATTTGCCTGTGCCTGGACAGCTCAATTGCTCCATAGT
CAACGCCATATCAATGAGATTACCCTCAACATCCCTGCCAACATTAGCGCCACCACCGGC
GCACGCAGTGCATCGGTCGGATGGGCGGAAAGCCTGATCGGGTTGCATTTGGGGAAAGTT
GCCTTGATTACCGGTGGCAGCGCCGGTATTGGTGGGCAGATCGGGCGCCTCCTGGCTTTG
AGTGGCGCGCGCGTGATGCTGGCAGCCCGTGATCGGCATAAGCTCGAACAGATGCAGGCG
ATGATCCAATCTGAGCTGGCTGAGGTGGGGTATACCGATGTCGAAGATCGCGTCCACATT
GCACCGGGCTGCGATGTGAGTAGCGAAGCGCAGCTTGCGGATCTTGTTGAACGTACCCTG
TCAGCTTTTGGCACCGTCGATTATCTGATCAACAACGCCGGGATCGCCGGTGTCGAAGAG
ATGGTTATCGATATGCCAGTTGAGGGATGGCGCCATACCCTCTTCGCCAATCTGATCAGC
AACTACTCGTTGATGCGCAAACTGGCGCCGTTGATGAAAAAACAGGGTAGCGGTTACATC
CTTAACGTCTCATCATACTTTGGCGGTGAAAAAGATGCGGCCATTCCCTACCCCAACCGT
GCCGATTACGCCGTCTCGAAGGCTGGTCAGCGGGCAATGGCCGAAGTCTTTGCGCGCTTC
CTTGGCCCGGAGATACAGATCAATGCCATTGCGCCGGGTCCGGTCGAAGGTGATCGCTTG
CGCGGTACCGGTGAACGTCCCGGCCTCTTTGCCCGTCGGGCGCGGCTGATTTTGGAGAAC
AAGCGGCTGAATGAGCTTCACGCTGCTCTTATCGCGGCTGCGCGCACCGATGAGCGATCT
ATGCACGAACTGGTTGAACTGCTCTTACCCAATGATGTGGCCGCACTAGAGCAGAATCCC
GCAGCACCTACCGCGTTGCGTGAACTGGCACGACGTTTTCGCAGCGAAGGCGATCCGGCG
GCATCATCAAGCAGTGCGCTGCTGAACCGTTCAATTGCCGCTAAATTGCTGGCTCGTTTG
CATAATGGTGGCTATGTGTTGCCTGCCGACATCTTTGCAAACCTGCCAAACCCGCCCGAT
CCCTTCTTCACCCGAGCCCAGATTGATCGCGAGGCTCGCAAGGTTCGTGACGGCATCATG
GGGATGCTCTACCTGCAACGGATGCCGACTGAGTTTGATGTCGCAATGGCCACCGTCTAT
TACCTTGCCGACCGCAATGTCAGTGGTGAGACATTCCACCCATCAGGTGGTTTGCGTTAC
```

Figure 49A

```
GAACGCACCCCTACCGGTGGCGAACTCTTCGGCTTGCCCTCACCGGAACGGCTGGCGGAG
CTGGTCGGAAGCACGGTCTATCTGATAGGTGAACATCTGACTGAACACCTTAACCTGCTT
GCCCGTGCGTACCTCGAACGTTACGGGGCACGTCAGGTAGTGATGATTGTTGAGACAGAA
ACCGGGGCAGAGACAATGCGTCGCTTGCTCCACGATCACGTCGAGGCTGGTCGGCTGATG
ACTATTGTGGCCGGTGATCAGATCGAAGCCGCTATCGACCAGGCTATCACTCGCTACGGT
CGCCCAGGGCCGGTCGTCTGTACCCCCTTCCGGCCACTGCCGACGGTACCACTGGTCGGG
CGTAAAGACAGTGACTGGAGCACAGTGTTGAGTGAGGCTGAATTTGCCGAGTTGTGCGAA
CACCAGCTCACCCACCATTTCCGGGTAGCGCGCAAGATTGCCCTGAGTGATGGTGCCAGT
CTCGCGCTGGTCACTCCCGAAACTACGGCTACCTCAACTACCGAGCAATTTGCTCTGGCT
AACTTCATCAAAACGACCCTTCACGCTTTTACGGCTACGATTGGTGTCGAGAGCGAAAGA
ACTGCTCAGCGCATTCTGATCAATCAAGTCGATCTGACCCGGCGTGCGCGTGCCGAAGAG
CCGCGTGATCCGCACGAGCGTCAACAAGAACTGGAACGTTTTATCGAGGCAGTCTTGCTG
GTCACTGCACCACTCCCGCCTGAAGCCGATACCCGTTACGCCGGGCGGATTCATCGCGGA
CGGGCGATTACCGTGTAA (SEQ ID NO:140)
```

MATGESMSGTGRLAGKIALITGGAGNIGSELTRRFLAEGATVIISGRNRAKLTALAERMQ
AEAGVPAKRIDLEVMDGSDPVAVRAGIEAIVARHGQIDILVNNAGSAGAQRRLAEIPLTE
AELGPGAEETLHASIANLLGMGWHLMRIAAPHMPVGSAVINVSTIFSRAEYYGRIPYVTP
KAALNALSQLAARELGARGIRVNTIFPGPIESDRIRTVFQRMDQLKGRPEGDTARHFLNT
MRLCRANDQGALERRFPSVGDVADAAVFLASAESAALSGETIEVTHGMELPACSETSLLA
RTDLRTIDASGRTTLICAGDQIEEVMALTGMLRTCGSEVIIGFRSAAALAQFEQAVNESR
RLAGADFTPPIALPLDPRDPATIDAVFDWAGENTGGIHAAVILPATSHEPAPCVIEVDDE
RVLNFLADEITGTIVIASRLARYWQSQRLTPGARARGPRVIFLSNGADQNGNVYGRIQSA
AIGQLIRVWRHEAELDYQRASAAGDHVLPPVWANQIVRFANRSLEGLEFACAWTAQLLHS
QRHINEITLNIPANISATTGARSASVGWAESLIGLHLGKVALITGGSAGIGGQIGRLLAL
SGARVMLAARDRHKLEQMQAMIQSELAEVGYTDVEDRVHIAPGCDVSSEAQLADLVERTL
SAFGTVDYLINNAGIAGVEEMVIDMPVEGWRHTLFANLISNYSLMRKLAPLMKKQGSGYI
LNVSSYFGGEKDAAIPYPNRADYAVSKAGQRAMAEVFARFLGPEIQINAIAPGPVEGDRL
RGTGERPGLFARRARLILENKRLNELHAALIAAARTDERSMHELVELLLPNDVAALEQNP
AAPTALRELARRFRSEGDPAASSSSALLNRSIAAKLLARLHNGGYVLPADIFANLPNPPD
PFFTRAQIDREARKVRDGIMGMLYLQRMPTEFDVAMATVYYLADRNVSGETFHPSGGLRY
ERTPTGGELFGLPSPERLAELVGSTVYLIGEHLTEHLNLLARAYLERYGARQVVMIVETE
TGAETMRRLLHDHVEAGRLMTIVAGDQIEAAIDQAITRYGRPGPVVCTPFRPLPTVPLVG
RKDSDWSTVLSEAEFAELCEHQLTHHFRVARKIXLSDGASLALVTPETTATSTTEQFALA
NFIKTTLHAFTATIGVESERTAQRILINQVDLTRRARAREPRDPHERQQELERFIEAVLL
VTAPLPPEADTRYAGRIHRGRAITV  (SEQ ID NO:141)

Figure 51
TCTTTCTGGCCAGTGCCGAATCCGCCGCTCTCTCCGGTGAGACGATTGAGGTTACGCACG
GAATGGAGTTGCCGGCCTGCAGTGAGACCAGCCTGCTGGCCCGTACTGATCTGCGCACGA
TTGATGCCAGTGGCCGCACGACGCTCATCTGCGCCGGCGACCAGATTGAAGAGGTGATGG
CGCTCACCGGTATGTTGCGTACCTGTGGGAGTGAAGTGATCATCGGCTTCCGTTCGGCTG
CGGCGCTGGCCCAGTTCGAGCAGGCAGTCAATGAGAGTCGGCGGCTGGCCGGCGCAGACT
TTACGCCTCCCATTGCCTTGCCACTCGATCCACGCG (SEQ ID NO:142)

| | | |
|---|---|---|
| SEQ ID NO:141 | 1 | matgesmsgtgrlagkialitggagnigseltrrflaegatvlisgrnra |
| SEQ ID NO:143 | 1 | ----------mfankvvlvtggssgigaatveafvkegasvafvgrnqa |
| SEQ ID NO:144 | 1 | ---------mrlegkvclitgaasgigkattllfaqegatviagdiske |
| SEQ ID NO:145 | 1 | ------------------------------------------------ |
| SEQ ID NO:146 | 1 | ----------------------------mekf---------------- |
| SEQ ID NO:147 | 1 | ---------mrllhkrtlvtggsdgiglaiaeaflsegadvlivgrdaa |
| SEQ ID NO:141 | 51 | kltalaermqa--e-agvpakridlevmdgsdpvavragieaivarhgqi |
| SEQ ID NO:143 | 40 | klkevesrcqq--hganilaikadv-----skdeeakiivqqtvdkfgkl |
| SEQ ID NO:144 | 41 | nldslvk--ea--e--glp---------------------------gkv |
| SEQ ID NO:145 | 1 | ------------------------------------------------ |
| SEQ ID NO:146 | 5 | ------------------------------------------------ |
| SEQ ID NO:147 | 41 | kleaarqklaalgq-aga-----vetssadlatslgvatvveqvketgrpl |
| SEQ ID NO:141 | 98 | dilvnnagsagaqrrlaeipltesaelgpgaeetihasianllgmgwhlmr |
| SEQ ID NO:143 | 83 | dvlvnnagil----rfasv--leptliqtfdetmntnlrpvv----lits |
| SEQ ID NO:144 | 57 | d----------------------------------------------- |
| SEQ ID NO:145 | 1 | ------------------------------------------------ |
| SEQ ID NO:146 | 5 | ------------------------------------------------ |
| SEQ ID NO:147 | 86 | dipinnagvadl------vpfesv-----seaqfqhsfalnvaaaffltq |
| SEQ ID NO:141 | 148 | iaaphm-pvgsavinvstifsr-aeyygrip--yvtpkaalnaisqiaar |
| SEQ ID NO:143 | 123 | laiphliatkgsivnvssilstivripgims--ysvskaamdhftklaal |
| SEQ ID NO:144 | 58 | --------------------p--yv-----lnv--------------- |
| SEQ ID NO:145 | 1 | ------------------------------------------------ |
| SEQ ID NO:146 | 5 | ---php-p---------------------------------------- |
| SEQ ID NO:147 | 125 | gllphf-gagasiinissyfar-kmipkrpssvyslskgalnsltrslaf |
| SEQ ID NO:141 | 194 | elgargirvntifpgpiesdrirtvfqrmdqlkgrpegdtahhflntmrl |
| SEQ ID NO:143 | 171 | elapsgvrvnsvnpgpv------------------------------- |
| SEQ ID NO:144 | 64 | --------------tdr------------------------------- |
| SEQ ID NO:145 | 1 | ------------------------mnpmdrqtegqepqh--------- |
| SEQ ID NO:146 | 9 | ------------------------------------------------ |
| SEQ ID NO:147 | 173 | elgprgirvnaiapgtvdt----------------------------- |
| SEQ ID NO:141 | 244 | crandqgalerrfpsvgdvadaavflasaesaalsgetievthgmalpac |
| SEQ ID NO:143 | 188 | -------------ltdia------------------------------ |
| SEQ ID NO:144 | 67 | ------------------------------------------------ |
| SEQ ID NO:145 | 16 | ------------------------------------------------ |
| SEQ ID NO:146 | 9 | -------fpr-------------------------------------- |
| SEQ ID NO:147 | 192 | -----amrr--------------------------------------- |
| SEQ ID NO:141 | 294 | setsllartdlrtidasgrttllicagdqieevmaltgmlrtcgseviigf |
| SEQ ID NO:143 | 193 | ------------------------------------------------ |
| SEQ ID NO:144 | 67 | ---------------------dqikev-------------------- |
| SEQ ID NO:145 | 16 | ------------------------------------------------ |
| SEQ ID NO:146 | 12 | -----------------qtqem------------------------- |
| SEQ ID NO:147 | 196 | -----------ktvd-------------------------------- |
| SEQ ID NO:141 | 344 | rsaaalaqfeqavnesrrlagadftppialpldprdpatidavfdwagen |
| SEQ ID NO:143 | 193 | --------------------agsgfspdll------------------ed |
| SEQ ID NO:144 | 73 | ------------------------------------------------ |
| SEQ ID NO:145 | 16 | --------------qdrqpgieskmnp--------------------- |
| SEQ ID NO:146 | 17 | -----------------------------pgttdrm----------- |
| SEQ ID NO:147 | 200 | ------------------------------------------------ |

Figure 52A

```
SEQ ID NO:141  394  tggihaavilpatshepapcvievddervlnfladeitgtiviasrlary
SEQ ID NO:143  205  tg-----------ahtp---------------------------------
SEQ ID NO:144   73  --------------------------------------------------
SEQ ID NO:145   29  --------lp----------------------------------------
SEQ ID NO:146   24  ----------------qplp------------------------------
SEQ ID NO:147  200  --------------------------------------------------

SEQ ID NO:141  444  wqsqrltpgarargprviflsngadqngnvygriqsaaigqlirvwrhea
SEQ ID NO:143  211  --------------------------------------------------
SEQ ID NO:144   73  --------------------------------------------------
SEQ ID NO:145   31  --------------------lsededyrgs--gklk--------------
SEQ ID NO:146   28  ----------------------------------------------dhg
SEQ ID NO:147  200  --------------------------------------------------

SEQ ID NO:141  494  eldyqrasaagdhvlppvwanqivrfanraleglefacawtaqllhsqrh
SEQ ID NO:143  211  --------------------------------------------------
SEQ ID NO:144   73  --------------------------------------------------
SEQ ID NO:145   45  --------------------------------------------------
SEQ ID NO:146   31  ensyqgsgrlkd--------------------------------------
SEQ ID NO:147  200  --------------------------------------------------

SEQ ID NO:141  544  ineitlnipanisattgarsasvgwaesliglhlgkvalitggsagiggq
SEQ ID NO:143  211  ------------------------------------lgkaa---------
SEQ ID NO:144   73  --------------------------------------------------
SEQ ID NO:145   45  -------------------------------gkvalitggdsgigra
SEQ ID NO:146   43  -------------------------------kralitggdsgigra
SEQ ID NO:147  200  -------nlpa---------------------------------------

SEQ ID NO:141  594  igrllalsgarvmlaardrhk-leqmqamiqselaevgytdvedrvhiap
SEQ ID NO:143  216  ----------------------qse-------------------------
SEQ ID NO:144   73  --------------------------------------------------
SEQ ID NO:145   61  aaiafakegadisilyldehsdaeetrkrieke---------nvrcllip
SEQ ID NO:146   58  vaiayaregadvlisylsehd-----damatkalve----eagrkavlaa
SEQ ID NO:147  204  --------------------------------------------------

SEQ ID NO:141  643  gcdvsseaqladlvertlsafgtvdylinnagiagveemvidmpvegwrh
SEQ ID NO:143  219  --------eiadmi------------------------------------
SEQ ID NO:144   73  -------------vekvvqkygridvlvnnagitr-dallvrmkeedwda
SEQ ID NO:145  102  g-dvgdenhceqavqqtvdhfgkldilvnnaaeqhpqdsilnisteqlek
SEQ ID NO:146   99  g-diqssdhcrrivetavrelggidilvnnaahqatfkniedisdeewel
SEQ ID NO:147  204  ----eakaelkayvers---------------------------------

SEQ ID NO:141  693  tlfanlisnyslmrklaplmkkqgsgyilnvssyfggekdaaipypnrad
SEQ ID NO:143  225  --------------------------------------------------
SEQ ID NO:144  109  vinvnlkgvfnvtqmvpymikqrngsivnvssvvg-----iygnpgqtn
SEQ ID NO:145  151  tfrtnifsmfhmtkkalphl--qegcaiinttsitayegdtal-----id
SEQ ID NO:146  148  tfrvnmhamfyltkaavphmkk-gsa-iintasi-----nadvpnpilla
SEQ ID NO:147  217  --------------------------------------------------

SEQ ID NO:141  743  yavskagqramaevfarfl-gpe-iqinaiapgpvegdrlrgtgerpglf
SEQ ID NO:143  225  --------------------------------------------------
SEQ ID NO:144  154  yaaskagvigmtktwakelagrn-irvnavapgfie--------------
SEQ ID NO:145  194  ysstkgaivsftrsmaksl-adkgirvnavapgpi---------------
SEQ ID NO:146  191  yattkgaihnfsaglaqml-aergirvnvvapgpi---------------
SEQ ID NO:147  217  yplgrigr------------------------------------------
```

Figure 52B

```
SEQ ID NO:141   791  arrarlilenkrlnelhaaliaaartdersmhelvelllpndvaaleqnp
SEQ ID NO:143   225  --------------------------------------------------
SEQ ID NO:144   189  --------------------------------------------------
SEQ ID NO:145   228  -----------------------------------------------wtp
SEQ ID NO:146   225  ----------------------------wtplipstmpedtva-dfgk
SEQ ID NO:147   225  ---------------------------------pddlagm----

SEQ ID NO:141   841  aaptalrelarrfrsegdpaassssallnrsiaakllarlhnggyvlpad
SEQ ID NO:143   225  --------------------------------------------------
SEQ ID NO:144   189  --------------------------------------------------
SEQ ID NO:145   231  lipatfpe------------------------------------------
SEQ ID NO:146   244  qvp---------mkrpgqpvelasa------------------yvmlad
SEQ ID NO:147   232  --------------------------------------------------

SEQ ID NO:141   891  ifanlpnppdpfftraqidrearkvrdgimgmlylqrmptefdvamatvy
SEQ ID NO:143   225  ------------------------------------------------vy
SEQ ID NO:144   189  --------------------------------------------------
SEQ ID NO:145   239  ----------------------ekvkq-----------------------
SEQ ID NO:146   266  pmssy---------------------------------------------
SEQ ID NO:147   232  ------------------------------------------------av SEQ ID NO:141   941  yladrnvsgetfhpsgglryertptggelfglpsperlaelvgstvylig
SEQ ID NO:143   227  lasdk-----------------------------aksvtgscyi--
SEQ ID NO:144   189  ------------------------------tpmteklpekareta----
SEQ ID NO:145   244  ----------------------------hgldtp---------------
SEQ ID NO:146   271  ------vsgatiavtgg---------------------------------
SEQ ID NO:147   234  yla----sdeaawtsggi--------------------------------

SEQ ID NO:141   991  ehltehlnllaraylerygarqvvmivetetgaetmrrllhdhveagrlm
SEQ ID NO:143   242  --------------------------------------------------
SEQ ID NO:144   204  ---------lsriplgrfgkpe--------------------evaqvi
SEQ ID NO:145   250  --------------------------------------------------
SEQ ID NO:146   282  --------------------------------------------------
SEQ ID NO:147   248  --------------------------------------------------

SEQ ID NO:141  1041  tivagdqieaaidqaitrygrpqpvvctpfrplptvplvgrkdsdwstvl
SEQ ID NO:143   242  --------------------------------------------------
SEQ ID NO:144   223  lflasdessyvtgqvi---gidgglvi-----------------------
SEQ ID NO:145   250  -----------------mgrpgqpv-------------------------
SEQ ID NO:146   282  ------------------------------kpfl----------------
SEQ ID NO:147   248  --------favdggyt----------------------------------

SEQ ID NO:141  1091  seaefaelcehqlthhfrvarkialsdgaslalvtpettatstteqfala
SEQ ID NO:143   242  ----------------------mdnglalq--------------------
SEQ ID NO:144   247  --------------------------------------------------
SEQ ID NO:145   258  ----------eha---------------gayvllasdes-----------
SEQ ID NO:146   286  --------------------------------------------------
SEQ ID NO:147   256  --------------------------------------------------

SEQ ID NO:141  1141  nfikttlhaftatigvesertaqrililnqvdltrraraeeprdpherqqe
SEQ ID NO:143   250  --------------------------------------------------
SEQ ID NO:144   247  --------------------------------------------------
SEQ ID NO:145   272  -----------------symtgqtlhvn----------------------
SEQ ID NO:146   286  --------------------------------------------------
SEQ ID NO:147   256  --------------------------------------------------
```

Figure 52C

```
SEQ ID NO:141   1191  lerfieavllvtaplppeadtryagrihrgraitv
SEQ ID NO:143    250  -----------------------------------
SEQ ID NO:144    247  -----------------------------------
SEQ ID NO:145    283  -----------------------------ggrfist
SEQ ID NO:146    286  -----------------------------------
SEQ ID NO:147    256  ----------------------ag-----------
```

Figure 52D

```
SEQ ID NO:140    1 atggcgacgggggagtccatgagcggaacaggacgactggcaggaaagat
SEQ ID NO:148    1 ------------------atga-----------gacttctgcacaagcg
SEQ ID NO:149    1 ------------------atg-------------ttcgcaaataaagt
SEQ ID NO:150    1 --------------------------atgaggcttgaagggaaag--
SEQ ID NO:151    1 ---------------------------------------atggaaa---
SEQ ID NO:152    1 --------------------------------------------------

SEQ ID NO:140   51 tgcgt-taattaccggtggcgccggcaatatcggcagtgaattgacacgt
SEQ ID NO:148   21 cacgc-tggtgaccggcggctc----------------------------
SEQ ID NO:149   18 ggtac-tagtaacaggtggtagctccggtatcggc---------------
SEQ ID NO:150   20 tgtgtctgatcacagg----ggctgcaagcgggatagggaaa-gccacca
SEQ ID NO:151    8 ----------------------aatttccgca----------ccct
SEQ ID NO:152    1 --------------------------------------------------

SEQ ID NO:140  100 cgctt--tctcgcagagggagcgacggtcattattagtggacggaatcgg
SEQ ID NO:148   42 -------------------------------------ggacggtatcgg
SEQ ID NO:149   52 ------------------gcagctactgt---------------------
SEQ ID NO:150   65 cgcttcttttcgcacaggaag-------------------------ga
SEQ ID NO:151   22 ccctt--tc-----------------------------------------
SEQ ID NO:152    1 --------------------------------------------------

SEQ ID NO:140  148 gcgaagttgaccgcactggccgaacggatgcaggcagaggcaggagtgcc
SEQ ID NO:148   54 cc--------tggcaatcgccgaggcgttcctgagcgagg----------
SEQ ID NO:149   63 -----------------------ggaagcattc-----------------
SEQ ID NO:150   88 gctacggtgatcg--ctggc------gat---------------------
SEQ ID NO:151   29 --------------------------------------------------
SEQ ID NO:152    1 ------gtgaacccaatgg----acaga--caaacagaaggacaag----

SEQ ID NO:140  198 ggcaaagcgcatcgatctcgaagtcatggatgggagtgatccggtcgcgg
SEQ ID NO:148   86 ------gcgc--------cgatgtcct----------------------
SEQ ID NO:149   73 ----------------------gttaaggaagg-----------------
SEQ ID NO:150  109 ------------atctcga-------------------------------
SEQ ID NO:151   29 --------------------------------------------------
SEQ ID NO:152   35 ----aaccgcagc---------------------------atcagg-----

SEQ ID NO:140  248 tacgtgccggtatcgaagcgattgtggcccgtcacggccagatcgacatt
SEQ ID NO:148   99 -------------------gatcgtcggccgtgacgcc------------
SEQ ID NO:149   84 --------cgcttctgtagccttcgtg----------------------
SEQ ID NO:150  116 ---------------------------------aagaaaatctcgactct
SEQ ID NO:151   29 -----------------------------cccgcca-----------
SEQ ID NO:152   50 ---------------------------------acagacagccgggcatt SEQ ID NO:140  298 ctggtcaacaatgcaggaagtgccggtgcccagcgtcgtctggccgagat
SEQ ID NO:148  118 ---------------------------------------gcc-------
SEQ ID NO:149  103 ----------------ggaagaaaccaagccaag----------------
SEQ ID NO:150  133 cttgtgaaagaggcagaagg------------------------------
SEQ ID NO:151   36 --------aacccaggaaatgcc---------------------------
SEQ ID NO:152   67 g-agtcaaaaatgaa------tccgctgcc--------------------

SEQ ID NO:140  348 tccactcactgaagctgaattaggccctggcgccgaagagacgcttcatg
SEQ ID NO:148  121 ----------aagct---------------cgaagccgcg-----g
SEQ ID NO:149  121 --------cttaag--gaagtag------------agccgc----tg
SEQ ID NO:150  153 --------------------------------------------------
SEQ ID NO:151   51 --------------------------------------------------
SEQ ID NO:152   90 --------------------------------------------------
```

Figure 53A

```
SEQ ID NO:140   398  ccagcatcgccaatttacttggtatgggatggcatctgatgcgtattgcg
SEQ ID NO:148   138  ccagaagc---------------------------------tggcg
SEQ ID NO:149   144  ccagcagc--------------------------------------
SEQ ID NO:150   153  ----------------actt--------------------------
SEQ ID NO:151    51  --------------------------------------------cg
SEQ ID NO:152    90  ------------------------gctgtcagaggacgaggattatc SEQ ID NO:140   448  gcacctcatatgccggtaggaagtgcggtcatcaatgtctcgaccatctt
SEQ ID NO:148   151  gc----------------------------------tcttggcca----
SEQ ID NO:149   152  -------------------------------atggagccaacatc--
SEQ ID NO:150   157  ----------ccgg--ggaag-------------------------
SEQ ID NO:151    53  gcac------------------------------------------
SEQ ID NO:152   113  g-------------aggaa---------------------------

SEQ ID NO:140   498  ttcacgggctgagtactacgggcggattccgtatgtcacccctaaagctg
SEQ ID NO:148   162  -----------------ggc--------------------------
SEQ ID NO:149   166  --------ctggctatcaaag--------cagatgtctcc---aaag---
SEQ ID NO:150   166  ----------------------------------------------
SEQ ID NO:151    57  -------------tac--cgatcggatgc---------------agccg
SEQ ID NO:152   119  -------------------gcgg---------------aaaactg SEQ ID NO:140   548  ctcttaatgctctatctcaacttgctgcgcgtgagttaggtgcacgtggc
SEQ ID NO:148   165  ---------------------------cggcgc--------ggtggagacgtc
SEQ ID NO:149   194  --------------------------------------acgagga
SEQ ID NO:150   166  ----------------------------------------------
SEQ ID NO:151    76  c------tgcccgat--------------------------cacgggg-
SEQ ID NO:152   130  aaaggaa----------aagttg-----------------------

SEQ ID NO:140   598  atccgcgttaatacgatctttccggcccgattgaaagtgatcgcatccg
SEQ ID NO:148   183  gtccgc-------cgatcttgcc-----------------------
SEQ ID NO:149   201  agc------------------------gaaaatcatcgta----
SEQ ID NO:150   166  ------gttgatccctacgtt---------ttgaacgtgaccg------
SEQ ID NO:151    92  --------aaaac--------------------------tcct
SEQ ID NO:152   143  ------------cgatcattactgg---------------------

SEQ ID NO:140   648  tacagtgttccagcgtatggatcagctcaaggggcggcccgaaggcgaca
SEQ ID NO:148   199  ----------------------------------------------
SEQ ID NO:149   217  ----------------------------------------------
SEQ ID NO:150   194  -acag------------ggatcagataaag---------gaag------
SEQ ID NO:151   101  accagggttcc--------------------ggacgcctgaag------
SEQ ID NO:152   156  --------------------------------------aggcgaca SEQ ID NO:140   698  cagcgcaccatttttgaacaccatgcgattgtgtcgtgccaacgaccag
SEQ ID NO:148   199  ---------------------------------------accag
SEQ ID NO:149   217  ---------------------------------------caacaa----
SEQ ID NO:150   215  ------------ttgtggaaaa-----------agtcgttcaaa-----ag
SEQ ID NO:151   124  ----------------------------------------gacaag
SEQ ID NO:152   164  ----------------------------------------------

SEQ ID NO:140   748  ggcgcgcttgaacgtcggttcccctccgtcggtgatgtggcagacgccgc
SEQ ID NO:148   204  -------------------cct------------------------
SEQ ID NO:149   223  ---------------------------------------------ac
SEQ ID NO:150   238  tacg---------gtcgaatc---------gatgt-----------
SEQ ID NO:151   130  agagc-----------catcatcaccggcgggga-----cagcggcatc
SEQ ID NO:152   164  ----------------------------------------------
```

Figure 53B

```
SEQ ID NO:140   798  tgtctttctggccagtgccgaatccgccgctctctccggtgagacgattg
SEQ ID NO:148   207  -----------cggtgtcgcaaccgtcg-tcgagcaggtgaaa------
SEQ ID NO:149   225  tgtc-----gacaagttc---------------------gggaagcttg
SEQ ID NO:150   255  ------------------------------------tctggtga-------
SEQ ID NO:151   163  gg-----cagggccgtggcga-----------tcgcc-------------
SEQ ID NO:152   164  --------------------------------------------------

SEQ ID NO:140   848  aggttacgcacggaatggagttgccggcctgcagtgagaccagcctgctg
SEQ ID NO:148   238  -----------------------------------gagaccggcc-----
SEQ ID NO:149   248  atgt----------------------------------------------
SEQ ID NO:150   263  --------------------------------------------------
SEQ ID NO:151   184  ----tatgcgcgcgagggag-----------------------------c
SEQ ID NO:152   164  --------gcggaat---------------agggagagc-----------

SEQ ID NO:140   898  gcccgtactgatctgcgcacgattgatgccagtggccgcacgacgctcat
SEQ ID NO:148   248  -----------------------------ggccgctcgacattcct
SEQ ID NO:149   252  --------------------gcttgtt------------aacaacgc----
SEQ ID NO:150   263  ---------------------------------------acaacgc----
SEQ ID NO:151   201  ggacgtccttatcagc-------------------------------tat
SEQ ID NO:152   180  --------------------------------------------------

SEQ ID NO:140   948  ctgcgccggcgaccagattgaagaggtgatggcgctcaccggtatgttgc
SEQ ID NO:148   265  .at---------caacaatg---------------ccggt--------
SEQ ID NO:149   267  --------------------------------------------------
SEQ ID NO:150   270  --------------------------------------------------
SEQ ID NO:151   220  ctgag-------cgagcatgacgacgcgatggccaccaaggct-------
SEQ ID NO:152   180  --------------------------------------------------

SEQ ID NO:140   998  gtacctgtgggagtgaagtgatcatcggcttccgttcggctgcggcgctg
SEQ ID NO:148   280  --------------------------------------gtcgccgacctc
SEQ ID NO:149   267  --------tgggatt-------------ctacggttcg------------
SEQ ID NO:150   270  ---------gggaat-----------------------------------
SEQ ID NO:151   256  ----ctggtggag-gaag--------------------------------
SEQ ID NO:152   180  --------------------------------------------------

SEQ ID NO:140  1048  gcccagttcgagcaggcagtcaatgagagtcggcggctggccggcgcaga
SEQ ID NO:148   292  gtgccgttcga-----------gagcgtcagcg------aggcgca--
SEQ ID NO:149   284  ---------------------cgagtgt----------tctggagcga
SEQ ID NO:150   276  --------------------------------------------------
SEQ ID NO:151   269  ---caggtcgc-aaggccgt------------gcttgccgccggcga
SEQ ID NO:152   180  -----------agcag----------------------------------

SEQ ID NO:140  1098  ctttacgcctcccattgccttgccactcgatccacgcgatccggcaacaa
SEQ ID NO:148   321  --------------------------------gttccagcactcc
SEQ ID NO:149   302  cttta-------------------ataca----------aactt
SEQ ID NO:150   276  -----------------------------------------aacaa
SEQ ID NO:151   300  c-----------------------------atccagtcg-tccg---acca
SEQ ID NO:152   185  ----------ctattgcctt------------------------------

SEQ ID NO:140  1148  ttgacgctg--tcttcgattgggccggcgagaataccggcgggattcatg
SEQ ID NO:148   334  ttcgcgctc--------aatgtggcgg---------cggcg--------
SEQ ID NO:149   317  ttga----------------------------------------------
SEQ ID NO:150   281  gggatgc-----------------------------------gcttcttg
SEQ ID NO:151   318  ttgccgcaggatcgtcgaaacggccgttcgggaactcggcggcat-----
SEQ ID NO:152   195  --------------------------------------------------
```

Figure 53C

```
SEQ ID NO:140   1196  cagcggtgattctgcctgctaccagtcacgaaccggcaccgtgcgtgatt
SEQ ID NO:148    358  ---------ttcttcct-----------------cacc-----------
SEQ ID NO:149    321  ------tgaaact------------------------------------
SEQ ID NO:150    296  -------------------------------------------------
SEQ ID NO:151    363  -------------------------------------------------
SEQ ID NO:152    195  ---------------tgcta-----------------------------

SEQ ID NO:140   1246  gaggttgatgatgagcgggtgctgaatttctggccgatgaaatcaccgg
SEQ ID NO:148    370  ---------caggggctgctgccgcattt--------------------
SEQ ID NO:149    328  ------------atgaac-----------------acgaatttac--g
SEQ ID NO:150    296  --------------tgag-----------------gatgaaa-------
SEQ ID NO:151    363  ------------------------------------------------c
SEQ ID NO:152    200  -------------aagagggggctga-----------------------

SEQ ID NO:140   1296  gacaattgtgattgccagtcgcctggcccgttactggcagtcgcaacgg
SEQ ID NO:148    390  -------------------------------------------------
SEQ ID NO:149    345  tccagttgtcctcatcactagcctg------------------------
SEQ ID NO:150    307  -------------------------------------------------
SEQ ID NO:151    364  gaca---------------------------------------------
SEQ ID NO:152    213  -------------------------------------------------

SEQ ID NO:140   1346  ttaccccggcgcacgtgcgcgtgggccgcgtgtcatttttctctcgaac
SEQ ID NO:148    390  -------cggcgc-----------------------------------c
SEQ ID NO:149    370  -------------------------------------------------
SEQ ID NO:150    307  -------------------------------------------------
SEQ ID NO:151    368  -----------------------------------ttctcgtcaac
SEQ ID NO:152    213  ----------------------------tatctccattctat---ac SEQ ID NO:140   1396  ggtgccgatcaaaatgggaatgtttacggacgcattcaaagtgccgctat
SEQ ID NO:148    397  ggtgc------------------------------------------at
SEQ ID NO:149    370  ------------------------------------------gctat
SEQ ID NO:150    307  ------gaagaagactgggatg---------------------------
SEQ ID NO:151    379  aatgc--------------------------------------------
SEQ ID NO:152    229  ttagacgagca-------------ttcggacgca---------------

SEQ ID NO:140   1446  cggtcagctcattcgtgtgtggcgtcacgaggctgaacttgactatcagc
SEQ ID NO:148    404  cgatca-------------------------------------------
SEQ ID NO:149    375  ccctcatttgatt--------gctacaaaagggag--------------
SEQ ID NO:150    323  cggt------------------------------------aataaac
SEQ ID NO:151    384  -------------------------------------------------
SEQ ID NO:152    250  --------------------------------gagg-----------aaac SEQ ID NO:140   1496  gtgccagcgccgccggtgatcatgtgctgccgccggtatgggccaatcag
SEQ ID NO:148    410  -------------------------------------------------
SEQ ID NO:149    402  -------------------------------------------------
SEQ ID NO:150    334  gtg--------------------------------------aatc--
SEQ ID NO:151    384  -----------------------------------------agcccatcag
SEQ ID NO:152    258  acgcaaacg--------gatc------------------gaaaggag SEQ ID NO:140   1546  attgtgcgcttcgctaaccgcagccttgaagggttagaatttgcctgtgc
SEQ ID NO:148    410  -------------------------------------------------
SEQ ID NO:149    402  -------------------------------------------------
SEQ ID NO:150    341  -----------------------tgaagggt------------------
SEQ ID NO:151    394  ------------------gcgaccttcaag-------------------
SEQ ID NO:152    280  aatgtccgctgc----------------------------ctgcttatcc
```

Figure 53D

```
SEQ ID NO:140  1596  ctggacagctcaattgctccatagtcaacgccatatcaatgagattaccc
SEQ ID NO:148   410  --------------------------------------------------
SEQ ID NO:149   402  ------------------catagttaacg---tatccagtata------
SEQ ID NO:150   349  -----------------gttttcaacg----------------------
SEQ ID NO:151   406  --------------------------------------------------
SEQ ID NO:152   302  cggga---------------------------------------------

SEQ ID NO:140  1646  tcaacatccctgccaacattagcgccaccaccggcgcacgcagtgcatcg
SEQ ID NO:148   410  tcaacatctcttcctattt-------------cgcccgca---------
SEQ ID NO:149   424  ---------ctgtctacaatag----------------------------
SEQ ID NO:150   359  --------------------------------------------------
SEQ ID NO:151   406  --aacatc---gaagacatcagcgac------------------------
SEQ ID NO:152   307  --------------------------------------------------

SEQ ID NO:140  1696  gtcggatgggcggaaagcctgatcgggttgcatttggggaaagttgcctt
SEQ ID NO:148   437  --------------------------------------------------
SEQ ID NO:149   437  --------------------------------------------------
SEQ ID NO:150   359  --------------------------------------------------
SEQ ID NO:151   427  ---------------------------------gagga------------
SEQ ID NO:152   307  ----gatg-------------------------ttgggga----------

SEQ ID NO:140  1746  gattaccggtggcagcgccggtattggtgggcagatcgggcgcctcctgg
SEQ ID NO:148   437  --------------------------------------------------
SEQ ID NO:149   437  --------------------------------------------------
SEQ ID NO:150   359  --------------------------------------------------
SEQ ID NO:151   432  -------------------------------gtggg--------------
SEQ ID NO:152   318  --------------------------------------------------

SEQ ID NO:140  1796  ctttgagtggcgcgcgcgtgatgctggcagcccgtgatcggcataagctc
SEQ ID NO:148   437  --------------------------------------------------
SEQ ID NO:149   437  ---------------------------------------------taa----
SEQ ID NO:150   359  --------------------------------------------------
SEQ ID NO:151   437  ------------------agctgacattccg----------------c
SEQ ID NO:152   318  --------------------------------------------------

SEQ ID NO:140  1846  gaacagatgcaggcgatgatccaatctgagctggctgaggtggggtatac
SEQ ID NO:148   437  -------------agatgatcc----------------------------
SEQ ID NO:149   440  -------------------------------------------gaatac
SEQ ID NO:150   359  -----------------------------------tgactcagatgg------
SEQ ID NO:151   451  gtcaacatgcacgccatgttc-----------------------tac
SEQ ID NO:152   318  ------------cga-gaaccattgtgaacaagctg-------------

SEQ ID NO:140  1896  cgatgtcgaagatcgcgtccacattgcaccgggctgcgatgtgagtagcg
SEQ ID NO:148   446  -------------------------------------------------cg
SEQ ID NO:149   446  c-------------------------------------------------
SEQ ID NO:150   371  --------------------------------------------------
SEQ ID NO:151   475  c--tgaccaag-------------gcagcgg-------------------
SEQ ID NO:152   341  ------------------------tgca----------------------

SEQ ID NO:140  1946  aagcgcagcttgcggatcttgttgaacgtaccctgtcagcttttggcacc
SEQ ID NO:148   448  aagcg----------------------------gccatc------cagc
SEQ ID NO:149   447  --------------------------------------------------
SEQ ID NO:150   371  --------------------------------------------------
SEQ ID NO:151   491  ----------tgccgcacatgaagaa----------------gggcagc
SEQ ID NO:152   345  ----gcaaacagtggacc-------------------attttggtaaa
```

Figure 53E

```
SEQ ID NO:140   1996  gtcgattatctga-tcaacaacgccgggatcgccggtgtcgaagagatgg
SEQ ID NO:148    463  gtctactccctgt-ccaagggcgc--------------------------
SEQ ID NO:149    447  --------------------------------------------------
SEQ ID NO:150    371  --------------------------------------------------
SEQ ID NO:151    514  g--------cga-tcatcaacaccg-------------------------
SEQ ID NO:152    370  ctcgat-atcttagtgaacaacgcc-------------------------

SEQ ID NO:140   2045  ttatcgatatgccagttgagggatggcgccatacctcttcgccaatctg
SEQ ID NO:148    486  -----------gttga---------------------------------
SEQ ID NO:149    447  -------------------agggattatgtcatacagt------------
SEQ ID NO:150    371  -------------------------------------------------
SEQ ID NO:151    530  ---------cttcca--------------tcaatgccgacgttcccaatccg
SEQ ID NO:152    395  ----------------------------------------------ctg SEQ ID NO:140   2095  atcagcaactactcgttgatgcgcaaactggcgccgttgatgaaaaaaca
SEQ ID NO:148    491  ----------actcgttga-------------------------------
SEQ ID NO:149    466  --------------------------------------------------
SEQ ID NO:150    371  ------------------------------tggtgccctacatgatcaaaca
SEQ ID NO:151    559  atc-----ctactcgcctatgcg-------------------accacca
SEQ ID NO:152    398  aacagcatc------------------------------------ccca SEQ ID NO:140   2145  gggtagcggttacatccttaacgtctcatcatactttggcggtgaaaaag
SEQ ID NO:148    500  --------------------------------------------------
SEQ ID NO:149    466  --------------------------------------------------
SEQ ID NO:150    393  gaggaacggttcgatcgtgaacgtctcctctgtcgttgg---------aat
SEQ ID NO:151    584  agggcgcg-----atc--------------cacaatttt-----------
SEQ ID NO:152    411  ggacag------cattctcaatatttcaaca-------------------

SEQ ID NO:140   2195  atgcggccattccctaccccaaccgtgccgattacgccgtctcgaaggct
SEQ ID NO:148    500  ---------------------------------------ccagatcgct
SEQ ID NO:149    466  ---------------------------------------gtgtcaaaggct
SEQ ID NO:150    435  atacgggaat-------cctggtcagacgaattacgcggcgtcgaaggcg
SEQ ID NO:151    603  ----------------------cagcgccg--------gtctcg------
SEQ ID NO:152    436  --------------------------------------------------

SEQ ID NO:140   2245  ggtcagcgggcaatggccgaagtctttgcgcgcttccttggcccg---ga
SEQ ID NO:148    510  ggccttcgag----------------------ctcggcccgcgcgg
SEQ ID NO:149    478  g-------------------------------------------------
SEQ ID NO:150    478  ggagtcataggaatgacc-aagacgt------------------------
SEQ ID NO:151    617  ----cgcagatgctggccgaa---------------------cgcg---g-
SEQ ID NO:152    436  gaacagctggaa------aaaacctttcgc-------------------

SEQ ID NO:140   2292  gatacagatcaatgccattgcgccgggtccggtcgaaggtgatcgcttgc
SEQ ID NO:148    534  catccgcgtcaacgccatcgcgcccggcacggtcga--------------
SEQ ID NO:149    479  --------------------------------------------------
SEQ ID NO:150    503  ----------------------------gggcgaaggaactcgct----
SEQ ID NO:151    639  gataagagtgaatgtcgtggcccgggcccgatc----------------
SEQ ID NO:152    460  -acaaatatttttccat--------------------------------

SEQ ID NO:140   2342  gcggtaccggtgaacgtcccagcctctttgcccgtcgggcgcggctgatt
SEQ ID NO:148    570  --------------------------------------------------
SEQ ID NO:149    479  --------------------------------------------------
SEQ ID NO:150    520  --------------------------------------------------
SEQ ID NO:151    673  ---------------------------------------tggacgccgctg---
SEQ ID NO:152    477  --------------------------------------------------
```

Figure 53F

```
SEQ ID NO:140   2392 ttggagaacaagcggctgaatgagcttcacgctgctcttatcgcggctgc
SEQ ID NO:148    570 --------------------------------------------------
SEQ ID NO:149    479 --------------------------------------------------
SEQ ID NO:150    520 ------------ggaagaaacatcagggtgaac--------gctgt----
SEQ ID NO:151    685 ------------------atcccctccaccatgc----------------
SEQ ID NO:152    477 ------------------gtttca--------------------------

SEQ ID NO:140   2442 gcgcaccgatgagcgatctatgcacgaactggttgaactgctcttaccca
SEQ ID NO:148    570 --------------------------------------------------
SEQ ID NO:149    479 ------ctatg---gatcacttcacaaaat--------------------
SEQ ID NO:150    546 g-gcacc------------------------------------cgga---
SEQ ID NO:151    701 -----ccgagga--------------------------------------
SEQ ID NO:152    483 -----------------tatg-acgaa-----------------------

SEQ ID NO:140   2492 atgatgtggccgcactagagcagaatcccgcagcacctaccgcgttgcgt
SEQ ID NO:148    570 ------------------------------------cacc----------
SEQ ID NO:149    500 -------tggcagcgttggagctg---------gctccttctggcgtgcga
SEQ ID NO:150    556 ttcat--------------agaaacccccatgac----------------
SEQ ID NO:151    708 -----------------------------------taccg----------
SEQ ID NO:152    492 ----------------------------------gaaagctttgcct---

SEQ ID NO:140   2542 gaactggcacgacgttttcgcagcgaaggcgatccggcggcatcatcaag
SEQ ID NO:148    574 -------------------------gccatgcggcg-------caag---
SEQ ID NO:149    535 g-------------------------------------------------
SEQ ID NO:150    576 ----------------------cgaaaaacttccag-------aaaaag-
SEQ ID NO:151    713 --------tcgccgatttcg------------------------------
SEQ ID NO:152    505 cacctg---------------------------------------caag- SEQ ID NO:140   2592 cagtgcgctgctgaaccgttcaattgccgctaaattgctggctcgtttgc
SEQ ID NO:148    589 ----------accgt-----------------------------------
SEQ ID NO:149    536 ---------tgaac---tcagt----------------------------
SEQ ID NO:150    596 c------------ccgtgaaacggcc------------------------
SEQ ID NO:151    725 --------------------------------------------------gc
SEQ ID NO:152    515 agggggtg-----------------tgccatta-----------------

SEQ ID NO:140   2642 ataatggtggctatgtgttgcctgccgacatctttgcaaacctgccaaac
SEQ ID NO:148    594 -----------------------------cgac--------aacctgcc----
SEQ ID NO:149    546 ---------------------------------------caaccctg------
SEQ ID NO:150    610 -----------------------------------ctttccaga---------
SEQ ID NO:151    727 aaacaggtgcctatg-----------------------------------
SEQ ID NO:152    530 ttaat-----------------acgacat---------------------

SEQ ID NO:140   2692 ccgcccgatcccttcttcacccgagcccagattgatcgcgaggctcgcaa
SEQ ID NO:148    606 --------------------------------------------------
SEQ ID NO:149    554 ------gaccagttct----------------------------------
SEQ ID NO:150    619 ------atacc----------------------------gctgggaa
SEQ ID NO:151    742 ------------------------------------------------aa
SEQ ID NO:152    542 -----cgattaccgctt---------------------------------

SEQ ID NO:140   2742 ggttcgtgacggcatcatggggatgctctacctgcaacggatgccgactg
SEQ ID NO:148    606 ----------------------------------------ggccga---
SEQ ID NO:149    564 -------------------------------tac----------------
SEQ ID NO:150    632 ggtttgggaagccagaagagg-----------------------------
SEQ ID NO:151    744 g-------------------------------------------------
SEQ ID NO:152    554 -----------------atgaaggggat-----------acgg-------
```

Figure 53G

```
SEQ ID NO:140  2792  agtttgatgtcgcaatggccaccgtctattaccttgccgaccgcaatgtc
SEQ ID NO:148   612  ----------------ggcca-----------aggccgaactgaaggcc
SEQ ID NO:149   567  ----tgatatcgc-------------------------------------
SEQ ID NO:150   653  -------tggcgca------------------------------------
SEQ ID NO:151   745  -----------------------------------------cgaccg------
SEQ ID NO:152   569  -------------------cgttaattgattattccagcacaaag--

SEQ ID NO:140  2842  agtggtgagaca-ttccacccatcaggtggtttgcgttacgaacgcaccc
SEQ ID NO:148   634  tatg-----------------------------tcgaacgcagc-
SEQ ID NO:149   576  --------------------------------------------------
SEQ ID NO:150   660  ---ggttatactcttcctcgcatcggacgagtcgagttacg---------
SEQ ID NO:151   751  --------------------------------------------------
SEQ ID NO:152   595  ---ggtgcga--------------------ttgtttcctttacg--------

SEQ ID NO:140  2891  ctaccggtggcgaactcttcggcttgccctcaccggaacggctggcggag
SEQ ID NO:148   649  ---------------tatccgctgggccgcatcgg-ccgtccggacgac
SEQ ID NO:149   576  -----------------------------------------------ag
SEQ ID NO:150   698  --------------------------------tcaccggacagg---------
SEQ ID NO:151   751  ---------------------ggccagccc--------------gtggaa
SEQ ID NO:152   616  cgttccatggcgaagtc----gcttgc----------------------

SEQ ID NO:140  2941  ctggtcggaagcacggtctatctgataggtgaacatctgactgaacacct
SEQ ID NO:148   682  ctcgccggcatggcggtttatct---------------------------
SEQ ID NO:149   578  ctggt-----------------------tctggct---------
SEQ ID NO:150   710  ----------------------tgatag---------------------
SEQ ID NO:151   766  ctcg------cctcggcctatgtcat-----------------------
SEQ ID NO:152   639  ---------------------agataaa---------------------

SEQ ID NO:140  2991  taacctgcttgcccgtgcgtacctcgaacgttacggggcacgtcaggtag
SEQ ID NO:148   705  --------------------------------------------------
SEQ ID NO:149   590  --------------------------------------------------
SEQ ID NO:150   716  --------------------------------------------------
SEQ ID NO:151   786  --------------------------------------------------
SEQ ID NO:152   646  ---------------------------------------ggca---------

SEQ ID NO:140  3041  tgatgattgttgagacagaaaccggggcagagacaatgcgtcgcttgctc
SEQ ID NO:148   705  --------------------------------------------------
SEQ ID NO:149   590  ---------------------------------------------tttctc
SEQ ID NO:150   716  --------------------------------------------------
SEQ ID NO:151   786  --------------------------------------------------
SEQ ID NO:152   650  --------------------------tcagagtgaatgcg-----------

SEQ ID NO:140  3091  cacgatcacgtcgaggctggtcggctgatgactattgtggccggtgatca
SEQ ID NO:148   705  --------------------------------------------------
SEQ ID NO:149   596  c-----------------------------------------tgatct
SEQ ID NO:150   716  --------------------------------------------------
SEQ ID NO:151   786  -------------gctgg------------------------------
SEQ ID NO:152   664  -------------------------------gtggcgcccggt-----

SEQ ID NO:140  3141  gatcgaagccgctatcgaccaggctatcactcgctacggtcgcccagggc
SEQ ID NO:148   705  ---------agccagcgacgaggc--------------------------
SEQ ID NO:149   603  gcttgaag-------------------------------------
SEQ ID NO:150   716  --------------------------------------------------
SEQ ID NO:151   791  ---cggatccgatgtcga---------------gctac-------------
SEQ ID NO:152   676  --------ccgatttggacaccgct-------------------------
```

Figure 53H

```
SEQ ID NO:140   3191  cggtcgtctgtaccccttccggccactgccgacggtaccactggtcggg
SEQ ID NO:148    720  -------------------------------------------------
SEQ ID NO:149    611  -------------------------------------------------
SEQ ID NO:150    716  -------------------------------------------------
SEQ ID NO:151    811  -------------------------------------------------
SEQ ID NO:152    693  -------------tattccgg-------cgacattccctgagg-----

SEQ ID NO:140   3241  cgtaaagacagtgactggagcacagtgttgagtgaggctgaatttgccga
SEQ ID NO:148    720  -----------ggcctgga-------------------------cga
SEQ ID NO:149    611  -----atacaggg----------------------------------
SEQ ID NO:150    716  -----------------------------------gaat-------
SEQ ID NO:151    811  ---------gtgtcaggcgca--------------------------
SEQ ID NO:152    716  -----aaaaagtga-aacagcac------------ggcttggataccca SEQ ID NO:140   3291  gttgtgcgaacaccagctcacccaccatttccgggtagcgcgcaagattg
SEQ ID NO:148    731  gcggtgggatc------------------------------tttg
SEQ ID NO:149    619  -----------gctcatacaccgt-----------------------
SEQ ID NO:150    720  -------------------------------------------------
SEQ ID NO:151    823  ------------------------------------------acgattg
SEQ ID NO:152    748  ---atgggaagaccgggacagcc-----------ggttgagc--------

SEQ ID NO:140   3341  ccctgagtgatggtgc-cagtctcgcgctggtcactcccgaaactacggc
SEQ ID NO:148    746  ccgtg---gatggt-----------------------------------
SEQ ID NO:149    632  ---tggggaaagctgcgcagtct--------------------------
SEQ ID NO:150    720  --------agatgg-----------------------------------
SEQ ID NO:151    830  ccgtga-------------------------------------------
SEQ ID NO:152    776  -------atgcaggcgc-ctatgtfctgctggcgtctgacgaa--------

SEQ ID NO:140   3390  tacctcaactaccgagcaatttgctctggctaacttcatcaaaacgaccc
SEQ ID NO:148    757  -------------------------------------------------
SEQ ID NO:149    652  -----------gaggagattgct---------------------------
SEQ ID NO:150    726  -------------------------------------------------
SEQ ID NO:151    836  -------------------------------------------------
SEQ ID NO:152    811  ----------------------tcttccta--------------------

SEQ ID NO:140   3440  ttcacgcttttacggctacgattggtgtcgagagcgaaagaactgctcag
SEQ ID NO:148    757  -----------ggcta---------------------------------
SEQ ID NO:149    664  -----------gatatgatt-----------------------------
SEQ ID NO:150    726  -------------------------------------------------
SEQ ID NO:151    836  -------------------------------------------------
SEQ ID NO:152    819  ---------------tatga-------------------------cag SEQ ID NO:140   3490  cgcattctgatcaatcaagtcgatctgacccggcgtgcgcgtgccgaaga
SEQ ID NO:148    762  -------------------------------------------------
SEQ ID NO:149    673  -----------gtgtatctg--------gctagtgataaagc
SEQ ID NO:150    726  ---------------------------------------------gg
SEQ ID NO:151    836  -------------------------------------------------
SEQ ID NO:152    827  ggca----gaccattcatgt--------------------gaatg SEQ ID NO:140   3540  gccgcgtgatccgcacgagcgtcaacaagaactggaacgttttatcgagg
SEQ ID NO:148    762  -------------------------------------------------
SEQ ID NO:149    696  taagagtgtt-------------------acggggtcctgttat-----
SEQ ID NO:150    728  gcctcgtgat---------------------------------------
SEQ ID NO:151    836  -------------------------------------------------
SEQ ID NO:152    848  gcggc--------------------------cgttttat-----
```

Figure 53I

```
SEQ ID NO:140   3590 cagtcttgctggtcactgcaccactcccgcctgaagccgatacccgttac
SEQ ID NO:148    762 --------------------------------------------------
SEQ ID NO:149    721 -----atcatggacaatg---gactcgcgc--------------------
SEQ ID NO:150    738 -------------------------------ctga---------------
SEQ ID NO:151    836 -----------------------------ccggcggcaagcc--------
SEQ ID NO:152    861 --------------------------------------------------

SEQ ID NO:140   3640 gccgggcggattcatcgcggacgggcgattaccgtgtaa
SEQ ID NO:148    762 -------------cacggccggatga-------------
SEQ ID NO:149    743 ----------tgca--------------------gtaa
SEQ ID NO:150    742 ---------------------------------------
SEQ ID NO:151    849 ------------------------------tttcctttga-
SEQ ID NO:152    861 ----------ttcaac------------------gtaa
```

```
  1   MVGKKVVHHL  MMSAKDAHYT  GNLVNGARIV  NQWGDVGTEL
 41   MVYVDGDISL  FLGYKDIEFT  APVYVGDFME  YHGWIEKVGN
 81   QSYTCKFEAW  KVATMVDITN  PQDTRATACE  PPVLCGRATG
121   SLFIAKKDQR  GPQESSFKER  KHPGE    (SEQ ID NO:160)
```

Figure 57

```
  1   MVGKKVVHHL MMSAKDAHYT GNLVNGARIV NQWGDVGTEL
 41   MVYVDGDISL FLGYKDIEFT APVYVGDFME YHGWIEKVGN
 81   QSYTCKFEAW KVAKMVDITN PQDTRATACE PPVLCGTATG
121   SLFIAKDNQR GPQESSFKDA KHPQ (SEQ ID NO:161)
```

Figure 58

```
  1  ATGGTAGGTA AAAAGGTTGT ACATCATTTA ATGATGAGCG
 41  CAAAAGATGC TCACTATACT GGAAACTTAG TAAACGGCGC
 81  TAGAATTGTG AATCAGTGGG GCGACGTTGG TACAGAATTA
121  ATGGTTTATG TTGATGGTGA CATAAGCTTA TTCTTGGGCT
161  ACAAAGATAT CGAATTCACA GCTCCTGTAT ATGTTGGTGA
201  CTTTATGGAA TACCACGGCT GGATTGAAAA AGTTGGTAAC
241  CAGTCCTATA CATGTAAATT TGAAGCATGG AAAGTTGCAA
281  CAATGGTTGA TATCACAAAT CCTCAGGATA CACGCGCAAC
321  AGCTTGTGAG CCTCCGGTAT TGTGCGGAAG AGCAACGGGT
361  AGTTTGTTCA TCGCAAAAAA AGATCAGAGA GGCCCTCAGG
401  AATCCTCTTT TAAAGAGAGA AAGCACCCCG GTGAATGA
(SEQ ID NO:162)
```

Figure 59

```
  1  ATGGTAGGTA AAAAGGTTGT ACATCATTTA ATGATGAGCG
 41  CAAAAGATGC TCACTATACT GGAAACTTAG TAAACGGCGC
 81  TAGAATTGTG AATCAGTGGG GCGACGTAGG TACAGAATTA
121  ATGGTTTATG TTGATGGTGA CATCAGCTTA TTCTTGGGCT
161  ACAAAGATAT CGAATTCACA GCTCCTGTAT ATGTTGGTGA
201  TTTTATGGAA TACCACGGCT GGATTGAAAA AGTTGGCAAC
241  CAGTCCTATA CATGTAAATT TGAAGCATGG AAAGTAGCAA
281  AGATGGTTGA TATCACAAAT CCACAGGATA CACGTGCAAC
321  AGCTTGTGAA CCTCCGGTAC TTTGTGGTAC TGCAACAGGC
361  AGCCTTTTCA TCGCAAAGGA TAATCAGAGA GGTCCTCAGG
401  AATCTTCCTT CAAGGATGCA AAGCACCCTC AATAA
(SEQ ID NO:163)
```

3-HYDROXYPROPIONIC ACID AND OTHER ORGANIC COMPOUNDS

CROSS REFERENCE TO RELATED APPLICATIONS

This is a divisional of U.S. application Ser. No. 11/539,856 filed Oct. 9, 2006, now U.S. Pat. No. 7,393,676, which is a divisional of U.S. application Ser. No. 10/432,443 filed Oct. 20, 2003 now U.S. Pat. No. 7,186,541, which is the National Stage of International Application No. PCT/US01/43607, filed Nov. 20, 2001, which in turn claims the benefit of U.S. Provisional Application Nos. 60/252,123 filed Nov. 20, 2000, 60/285,478 filed Apr. 20, 2001, 60/306,727 filed Jul. 20, 2001, and 60/317,845 filed Sep. 7, 2001, all herein incorporated by reference.

FIELD OF THE INVENTION

The invention relates to enzymes and methods that can be used to produce organic acids and related products.

BACKGROUND

Organic chemicals such as organic acids, esters, and polyols can be used to synthesize plastic materials and other products. To meet the increasing demand for organic chemicals, more efficient and cost effective production methods are being developed which utilize raw materials based on carbohydrates rather than hydrocarbons. For example, certain bacteria have been used to produce large quantities of lactic acid used in the production of polylactic acid.

3-hydroxypropionic acid (3-HP) is an organic acid. Although several chemical synthesis routes have been described to produce 3-HP, only one biocatalytic route has been heretofore previously disclosed (WO 01/16346 to Suthers, et al.). 3-HP has utility for specialty synthesis and can be converted to commercially important intermediates by known art in the chemical industry, e.g., acrylic acid by dehydration, malonic acid by oxidation, esters by esterification reactions with alcohols, and reduction to 1,3 propanediol.

SUMMARY

The invention relates to methods and materials involved in producing 3-hydroxypropionic acid and other organic compounds (e.g., 1,3-propanediol, acrylic acid, polymerized acrylate, esters of acrylate, polymerized 3-HP, esters of 3-HP, and malonic acid and its esters). Specifically, the invention provides nucleic acid molecules, polypeptides, host cells, and methods that can be used to produce 3-HP and other organic compounds such as 1,3-propanediol, acrylic acid, polymerized acrylate, esters of acrylate, polymerized 3-HP, esters of 3-HP, and malonic acid and its esters. 3-HP has potential to be both biologically and commercially important. For example, the nutritional industry can use 3-HP as a food, feed additive or preservative, while the derivatives mentioned above can be produced from 3-HP. The nucleic acid molecules described herein can be used to engineer host cells with the ability to produce 3-HP as well as other organic compounds such as 1,3-propanediol, acrylic acid, polymerized acrylate, esters of acrylate, polymerized 3-HP, and esters of 3-HP. The polypeptides described herein can be used in cell-free systems to make 3-HP as well as other organic compounds such as 1,3-propanediol, acrylic acid, polymerized acrylate, esters of acrylate, polymerized 3-HP, and esters of 3-HP. The host cells described herein can be used in culture systems to produce large quantities of 3-HP as well as other organic compounds such as 1,3-propanediol, acrylic acid, polymerized acrylate, esters of acrylate, polymerized 3-HP, and esters of 3-HP.

One aspect of the invention provides cells that have lactyl-CoA dehydratase activity and 3-hydroxypropionyl-CoA dehydratase activity, and methods of making products such as those described herein by culturing at least one of the cells that have lactyl-CoA dehydratase activity and 3-hydroxypropionyl-CoA dehydratase activity. In some embodiments, the cell can also contain an exogenous nucleic acid molecule that encodes one or more of the following polypeptides: a polypeptide having E1 activator activity; an E2 α polypeptide that is a subunit of an enzyme having lactyl-CoA dehydratase activity; an E2 β polypeptide that is a subunit of an enzyme having lactyl-CoA dehydratase activity; and a polypeptide having 3-hydroxypropionyl-CoA dehydratase activity. Additionally, the cell can have CoA transferase activity, CoA synthetase activity, poly hydroxyacid synthase activity, 3-hydroxypropionyl-CoA hydrolase activity, 3-hydroxyisobutryl-CoA hydrolase activity, and/or lipase activity. Moreover, the cell can contain at least one exogenous nucleic acid molecule that expresses one or more polypeptides that have CoA transferase activity, 3-hydroxypropionyl-CoA hydrolase activity, 3-hydroxyisobutryl-CoA hydrolase activity, CoA synthetase activity, poly hydroxyacid synthase activity, and/or lipase activity.

In another embodiment of the invention, the cell that has lactyl-CoA dehydratase activity and 3-hydroxypropionyl-CoA dehydratase activity produces a product, for example, 3-HP, polymerized 3-HP, and/or an ester of 3-HP, such as methyl hydroxypropionate, ethyl hydroxypropionate, propyl hydroxypropionate, and/or butyl hydroxypropionate. Accordingly, the invention also provides methods of producing one or more of these products. These methods involve culturing the cell that has lactyl-CoA dehydratase activity and 3-hydroxypropionyl-CoA dehydratase activity under conditions that allow the product to be produced. These cells also can have CoA synthetase activity and/or poly hydroxyacid synthase activity.

Another aspect of the invention provides cells that have CoA synthetase activity, lactyl-CoA dehydratase activity, and poly hydroxyacid synthase activity. In some embodiments, these cells also can contain an exogenous nucleic acid molecule that encodes one or more of the following polypeptides: a polypeptide having E1 activator activity; an E2 α polypeptide that is a subunit of an enzyme having lactyl-CoA dehydratase activity; an E2 β polypeptide that is a subunit of an enzyme having lactyl-CoA dehydratase activity; a polypeptide having CoA synthetase activity; and a polypeptide having poly hydroxyacid synthase activity.

In another embodiment of the invention, the cell that has CoA synthetase activity, lactyl-CoA dehydratase activity, and poly hydroxyacid synthase activity can produce a product, for example, polymerized acrylate.

Another aspect of the invention provides a cell comprising CoA transferase activity, lactyl-CoA dehydratase activity, and lipase activity. In some embodiments, the cell also can contain an exogenous nucleic acid molecule that encodes one or more of the following polypeptides: a polypeptide having CoA transferase activity; a polypeptide having E1 activator activity; an E2 α polypeptide that is a subunit of an enzyme having lactyl-CoA dehydratase activity; an E2 β polypeptide that is a subunit of an enzyme having lactyl-CoA dehydratase activity; and a polypeptide having lipase activity. This cell can be used, among other things, to produce products such as esters of acrylate (e.g., methyl acrylate, ethyl acrylate, propyl acrylate, and butyl acrylate).

In some embodiments, 1,3 propanediol can be created from either 3-HP-CoA or 3-HP via the use of polypeptides having enzymatic activity. These polypeptides can be used either in vitro or in vivo. When converting 3-HP-CoA to 1,3 propanediol, polypeptides having oxidoreductase activity or reductase activity (e.g., enzymes from the 1.1.1.- class of enzymes) can be used. Alternatively, when creating 1,3 propanediol from 3-HP, a combination of (1) a polypeptide having aldehyde dehydrogenase activity (e.g., an enzyme from the 1.1.1.34 class) and (2) a polypeptide having alcohol dehydrogenase activity (e.g., an enzyme from the 1.1.1.32 class) can be used.

In some embodiments of the invention, products are produced in vitro (outside of a cell). In other embodiments of the invention, products are produced using a combination of in vitro and in vivo (within a cell) methods. In yet other embodiments of the invention, products are produced in vivo. For methods involving in vivo steps, the cells can be isolated cultured cells or whole organisms such as transgenic plants, non-human mammals, or single-celled organisms such as yeast and bacteria (e.g., *Lactobacillus, Lactococcus, Bacillus*, and *Escherichia* cells). Hereinafter such cells are referred to as production cells. Products produced by these production cells can be organic products such as 3-HP and/or the nucleic acid molecules and polypeptides described herein.

Another aspect of the invention provides polypeptides having an amino acid sequence that (1) is set forth in SEQ ID NO:2, 10, 18, 26, 35, 37, 39, 41, 141, 160, or 161, (2) is at least 10 contiguous amino acid residues of a sequence set forth in SEQ ID NO:2, 10, 18, 26, 35, 37, 39, 41, 141, 160, or 161, (3) has at least 65 percent sequence identity with at least 10 contiguous amino acid residues of a sequence set forth in SEQ ID NO:2, 10, 18, 26, 35, 37, 39, 41, 141, 160, or 161, (4) is a sequence set forth in SEQ ID NO:2, 10, 18, 26, 35, 37, 39, 41, 141, 160, or 161 having conservative amino acid substitutions, or (5) has at least 65 percent sequence identity with a sequence set forth in SEQ ID NO:2, 10, 18, 26, 35, 37, 39, 41, 141, 160, or 161. Accordingly, the invention also provides nucleic acid sequences that encode any of the polypeptides described herein as well as specific binding agents that bind to any of the polypeptides described herein. Likewise, the invention provides transformed cells that contain any of the nucleic acid sequences that encode any of the polypeptides described herein. These cells can be used to produce nucleic acid molecules, polypeptides, and organic compounds. The polypeptides can be used to catalyze the formation of organic compounds or can be used as antigens to create specific binding agents.

In yet another embodiment, the invention provides isolated nucleic acid molecules that contain at least one of the following nucleic acid sequences: (1) a nucleic acid sequence as set forth in SEQ ID NO:1, 9, 17, 25, 33, 34, 36, 38, 40, 42, 129, 140, 142, 162, or 163; (2) a nucleic acid sequence having at least 10 consecutive nucleotides from a sequence set forth in SEQ ID NO:1, 9, 17, 25, 33, 34, 36, 38, 40, 42, 129, 140, 142, 162, or 163; (3) a nucleic acid sequences that hybridize under hybridization conditions (e.g., moderately or highly stringent hybridization conditions) to a sequence set forth in SEQ ID NO:1, 9, 17, 25, 33, 34, 36, 38, 40, 42, 129, 140, 142, 162, or 163; (4) a nucleic acid sequence having 65 percent sequence identity with at least 10 consecutive nucleotides from a sequence set forth in SEQ ID NO:1, 9, 17, 25, 33, 34, 36, 38, 40, 42, 129, 140, 142, 162, or 163; and (5) a nucleic acid sequence having at least 65 percent sequence identity with a sequence set forth in SEQ ID NO:1, 9, 17, 25, 33, 34, 36, 38, 40, 42, 129, 140, 142, 162, or 163. Accordingly, the invention also provides a production cell that contains at least one exogenous nucleic acid having any the nucleic acid sequences provided above. The production cell can be used to express polypeptides that have an enzymatic activity such as CoA transferase activity, lactyl-CoA dehydratase activity, CoA synthase activity, dehydratase activity, dehydrogenase activity, malonyl CoA reductase activity, β-alanine ammonia lyase activity, and/or 3-hydroxypropionyl-CoA dehydratase activity. Accordingly, the invention also provides methods of producing polypeptides encoded by the nucleic acid sequences described above.

The invention also provides several methods such as methods for making 3-HP from lactate, phosphoenolpyruvate (PEP), or pyruvate. In some embodiments, methods for making 3-HP from lactate, PEP, or pyruvate involve culturing a cell containing at least one exogenous nucleic acid under conditions that allow the cell to produce 3-HP. These methods can be practiced using the various types of production cells described herein. In some embodiments, the production cells can have one or more of the following activities: CoA transferase activity, 3-hydroxypropionyl-CoA hydrolase activity, 3-hydroxyisobutryl-CoA hydrolase activity, dehydratase activity, and/or malonyl CoA reductase activity.

In other embodiments, the methods involve making 3-HP wherein lactate is contacted with a first polypeptide having CoA transferase activity or CoA synthetase activity such that lactyl-CoA is formed, then contacting lactyl-CoA with a second polypeptide having lactyl-CoA dehydratase activity to form acrylyl-CoA, then contacting acrylyl-CoA with a third polypeptide having 3-hydroxypropionyl-CoA dehydratase activity to form 3-hydroxypropionic acid-CoA, and then contacting 3-hydroxypropionic acid-CoA with the first polypeptide to form 3-HP or with a fourth polypeptide having 3-hydroxypropionyl-CoA hydrolase activity or 3-hydroxyisobutryl-CoA hydrolase activity to form 3-HP.

Another aspect of the invention provides methods for making polymerized 3-HP. These methods involve making 3-hydroxypropionic acid-CoA as described above, and then contacting the 3-hydroxypropionic acid-CoA with a polypeptide having poly hydroxyacid synthase activity to form polymerized 3-HP.

In yet another embodiment of the invention, methods for making an ester of 3-HP are provided. These methods involve making 3-HP as described above, and then additionally contacting 3-HP with a fifth polypeptide having lipase activity to form an ester.

The invention also provides methods for making polymerized acrylate. These methods involve culturing a cell that has both CoA synthetase activity, lactyl-CoA dehydratase activity, and poly hydroxyacid synthase activity such that polymerized acrylate is made. Accordingly, the invention also provides methods of making polymerized acrylate wherein lactate is contacted with a first polypeptide having CoA synthetase activity to form lactyl-CoA, then contacting lactyl-CoA with a second polypeptide having lactyl-CoA dehydratase activity to form acrylyl-CoA, and then contacting acrylyl-CoA with a third polypeptide having poly hydroxyacid synthase activity to form polymerized acrylate.

The invention also provides methods of making an ester of acrylate. These methods involve culturing a cell that has CoA transferase activity, lipase activity, and lactyl-CoA dehydratase activity under conditions that allow the cell to produce an ester.

In another embodiment, the invention provides methods for making an ester of acrylate, wherein acrylyl-CoA is formed as described above, and then acrylyl-CoA is contacted with a polypeptide having CoA transferase activity to form acrylate, and acrylate is contacted with a polypeptide having lipase activity to form the ester.

The invention also provides methods for making 3-HP. These methods involve culturing a cell containing at least one exogenous nucleic acid that encodes at least one polypeptide such that 3-HP is produced from acetyl-CoA or malonyl-CoA.

Alternative embodiments provide methods of making 3-HP, wherein acetyl-CoA is contacted with a first polypeptide having acetyl-CoA carboxylase activity to form malonyl-CoA, and malonyl-CoA is contacted with a second polypeptide having malonyl-CoA reductase activity to form 3-HP.

In other embodiments, malonyl-CoA can be contacted with a polypeptide having malonyl-CoA reductase activity so that 3-HP can be made.

In another embodiment, the invention provides a method for making 3-HP that uses a β-alanine intermediate. This method can be performed by contacting β-alanine CoA with a first polypeptide having β-alanyl-CoA ammonia lyase activity (such as a polypeptide having the amino acid sequence set forth in SEQ ID NO: 160 or 161) to form acrylyl-CoA, contacting acrylyl-CoA with a second polypeptide having 3-HP-CoA dehydratase activity to form 3-HP-CoA, and contacting 3-HP-CoA with a third polypeptide having glutamate dehydrogenase activity to make 3-HP.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 6 is a listing of a nucleic acid sequence that encodes a polypeptide having CoA transferase activity (SEQ ID NO:1).
FIG. 7 is a listing of an amino acid sequence of a polypeptide having CoA transferase activity (SEQ ID NO:2).
FIG. 8 is an alignment of the nucleic acid sequences set forth in SEQ ID NOs:1, 3, 4, and 5.
FIG. 9 is an alignment of the amino acid sequences set forth in SEQ ID NOs:2, 6, 7, and 8.
FIG. 10 is a listing of a nucleic acid sequence that encodes a polypeptide having E1 activator activity (SEQ ID NO:9).
FIG. 11 is a listing of an amino acid sequence of a polypeptide having E1 activator activity (SEQ ID NO:10).
FIG. 12 is an alignment of the nucleic acid sequences set forth in SEQ ID NOs:9, 11, 12, and 13.
FIG. 13 is an alignment of the amino acid sequences set forth in SEQ ID NOs:10, 14, 15, and 16.
FIG. 14 is a listing of a nucleic acid sequence that encodes an E2 α subunit of an enzyme having lactyl-CoA dehydratase activity (SEQ ID NO:17).
FIG. 15 is a listing of an amino acid sequence of an E2 α subunit of an enzyme having lactyl-CoA dehydratase activity (SEQ ID NO:18).
FIG. 16 is an alignment of the nucleic acid sequences set forth in SEQ ID NOs:17, 19, 20, and 21.
FIG. 17 is an alignment of the amino acid sequences set forth in SEQ ID NOs:18, 22, 23, and 24.
FIG. 18 is a listing of a nucleic acid sequence that encodes an E2 β subunit of an enzyme having lactyl-CoA dehydratase activity (SEQ ID NO:25). The "G" at position 443 can be an "A"; and the "A" at position 571 can be a "G".
FIG. 19 is a listing of an amino acid sequence of an E2 β subunit of an enzyme having lactyl-CoA dehydratase activity (SEQ ID NO:26).
FIG. 20 is an alignment of the nucleic acid sequences set forth in SEQ ID NOs:25, 27, 28, and 29.
FIG. 21 is an alignment of the amino acid sequences set forth in SEQ ID NOs:26, 30, 31, and 32.
FIG. 22 is a listing of a nucleic acid sequence of genomic DNA from *Megasphaera elsdenii* (SEQ ID NO:33).
FIG. 23 is a listing of a nucleic acid sequence that encodes a polypeptide from *Megasphaera elsdenii* (SEQ ID NO:34).
FIG. 24 is a listing of an amino acid sequence of a polypeptide from *Megasphaera elsdenii* (SEQ ID NO:35).
FIG. 25 is a listing of a nucleic acid sequence that encodes a polypeptide having enzymatic activity (SEQ ID NO:36).
FIG. 26 is a listing of an amino acid sequence of a polypeptide having enzymatic activity (SEQ ID NO:37).
FIG. 27 is a listing of a nucleic acid sequence that contains non-coding as well as coding sequence of a polypeptide having CoA synthase, dehydratase, and dehydrogenase activity (SEQ ID NO:38). The start site for the coding sequence is at position 480, a ribosome binding site is at position 466-473, and the stop codon is at position 5946.
FIG. 28 is a listing of an amino acid sequence from a polypeptide having CoA synthase, dehydratase, and dehydrogenase activity (SEQ ID NO:39).
FIG. 29 is a listing of a nucleic acid sequence that encodes a polypeptide having 3-hydroxypropionyl-CoA dehydratase activity (SEQ ID NO:40).
FIG. 30 is a listing of an amino acid sequence of a polypeptide having 3-hydroxypropionyl-CoA dehydratase activity (SEQ ID NO:41).
FIG. 31 is a listing of a nucleic acid sequence that contains non-coding as well as coding sequence of a polypeptide having 3-hydroxypropionyl-CoA dehydratase activity (SEQ ID NO:42).
FIG. 32 is an alignment of the nucleic acid sequences set forth in SEQ ID NOs:40, 43, 44, and 45.
FIG. 33 is an alignment of the amino acid sequences set forth in SEQ ID NOs:41, 46, 47, and 48.
FIG. 34 is a diagram of the construction of a synthetic operon (pTDH) that encodes for polypeptides having CoA transferase activity, lactyl-CoA dehydratase activity (E1, E2 α, and E2 β), and 3-hydroxypropionyl-CoA dehydratase activity (3-HP-CoA dehydratase).
FIGS. 36A and B is a diagram of the construction of a synthetic operon (pEIITHrEI) that encodes for polypeptides having CoA transferase activity, lactyl-CoA dehydratase activity (E1, E2 α, and E2 β), and 3-hydroxypropionyl-CoA dehydratase activity (3-HP-CoA dehydratase).

FIG. 39 is a listing of a nucleic acid sequence that encodes a polypeptide having CoA synthase, dehydratase, and dehydrogenase activity (SEQ ID NO:129).

FIG. 40 is an alignment of the amino acid sequences set forth in SEQ ID NOs:39, 130, and 131. The uppercase amino acid residues represent positions where that amino acid residue is present in two or more sequences.

FIG. 41 is an alignment of the amino acid sequences set forth in SEQ ID NOs:39, 132, and 133. The uppercase amino acid residues represent positions where that amino acid residue is present in two or more sequences.

FIG. 42 is an alignment of the amino acid sequences set forth in SEQ ID NOs: 39, 134, and 135. The uppercase amino acid residues represent positions where that amino acid residue is present in two or more sequences.

FIG. 49 is a listing of a nucleic acid sequence that encodes a polypeptide having malonyl-CoA reductase activity (SEQ ID NO: 140).

FIG. 50 is a listing of an amino acid sequence of a polypeptide having malonyl-CoA reductase activity (SEQ ID NO:141).

FIG. 51 is a listing of a nucleic acid sequence that encodes a portion of a polypeptide having malonyl-CoA reductase activity (SEQ ID NO:142).

FIG. 52 is an alignment of the amino acid sequences set forth in SEQ ID NOs: 141, 143, 144, 145, 146, and 147.

FIG. 53 is an alignment of the nucleic acid sequences set forth in SEQ ID NOs: 140, 148, 149, 150, 151, and 152.

FIG. 56 is a listing of an amino acid sequence of a polypeptide having β-alanyl-CoA ammonia lyase activity (SEQ ID NO:160).

FIG. 57 is a listing of an amino acid sequence of a polypeptide having β-alanyl-CoA ammonia lyase activity (SEQ ID NO:161).

FIG. 58 is a listing of a nucleic acid sequence that encodes a polypeptide having β-alanyl-CoA ammonia lyase activity (SEQ ID NO:162).

FIG. 59 is a listing of a nucleic acid sequence that can encode a polypeptide having β-alanyl-CoA ammonia lyase activity (SEQ ID NO:163).

DETAILED DESCRIPTION

I. Terms

Figure 1:
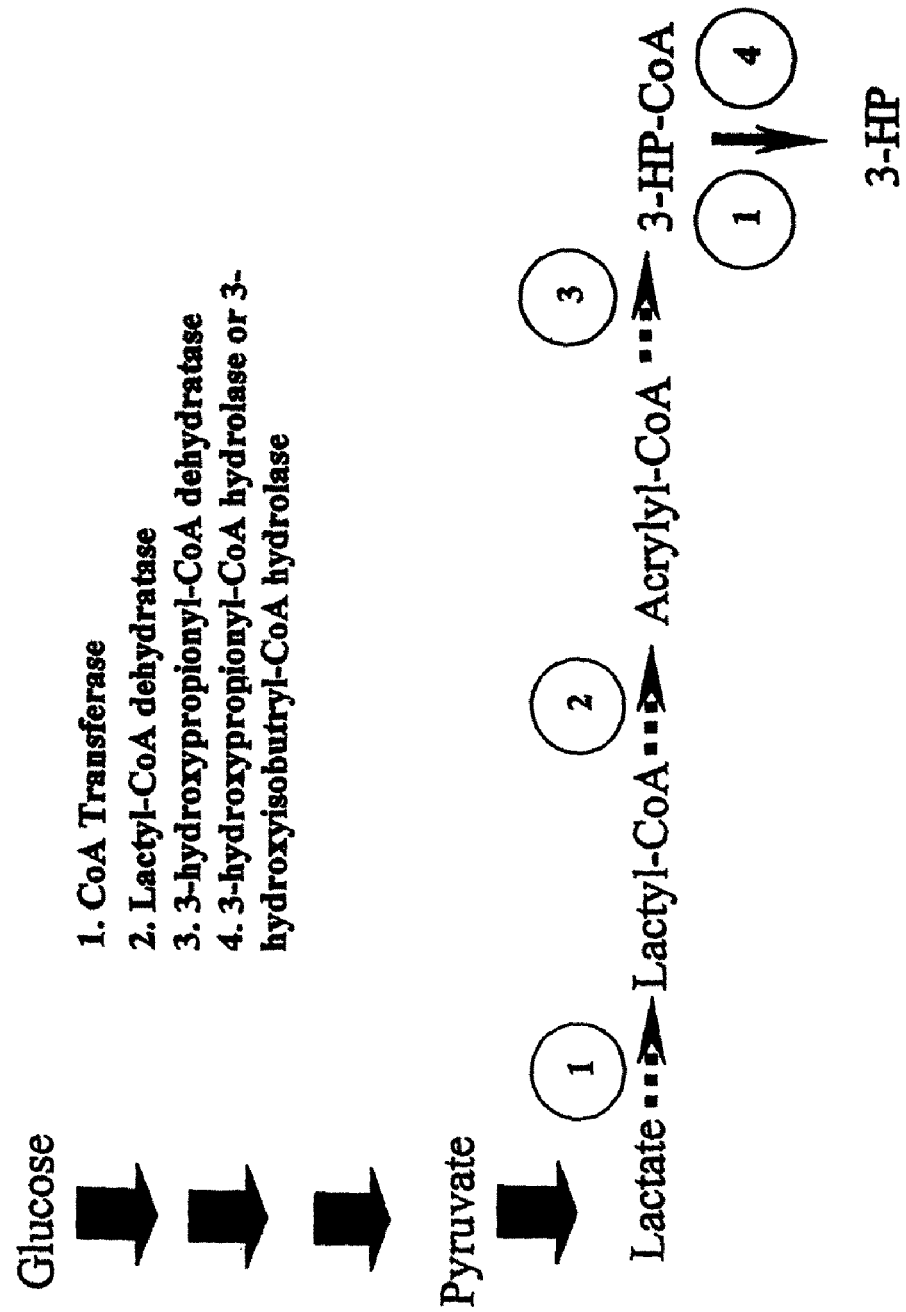
FIG. 1 is a diagram of a pathway for making 3-HP.

Nucleic acid: The term "nucleic acid" as used herein encompasses both RNA and DNA including, without limitation, cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

Isolated: The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

Exogenous: The term "exogenous" as used herein with reference to nucleic acid and a particular cell refers to any nucleic acid that does not originate from that particular cell as found in nature. Thus, non-naturally-occurring nucleic acid is considered to be exogenous to a cell once introduced into the cell. Nucleic acid that is naturally-occurring also can be exogenous to a particular cell. For example, an entire chromosome isolated from a cell of person X is an exogenous nucleic acid with respect to a cell of person Y once that chromosome is introduced into Y's cell.

Hybridization: The term "hybridization" as used herein refers to a method of testing for complementarity in the nucleotide sequence of two nucleic acid molecules, based on the ability of complementary single-stranded DNA and/or RNA to form a duplex molecule. Nucleic acid hybridization techniques can be used to obtain an isolated nucleic acid within the scope of the invention. Briefly, any nucleic acid having some homology to a sequence set forth in SEQ ID NO:1, 9, 17, 25, 33, 34, 36, 38, 40, 42, 129, 140, 142, 162, or 163 can be used as a probe to identify a similar nucleic acid by hybridization under conditions of moderate to high stringency. Once identified, the nucleic acid then can be purified, sequenced, and analyzed to determine whether it is within the scope of the invention as described herein.

Hybridization can be done by Southern or Northern analysis to identify a DNA or RNA sequence, respectively, that hybridizes to a probe. The probe can be labeled with a biotin, digoxygenin, an enzyme, or a radioisotope such as $^{32}$P. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39-7.52 of Sambrook et al., (1989) Molecular Cloning, second edition, Cold Spring Harbor Laboratory, Plainview, N.Y. Typically, a probe is at least about 20 nucleotides in length. For example, a probe corresponding to a 20 nucleotide sequence set forth in SEQ ID NO: 1, 9, 17, 25, 33, 34, 36, 38, 40, 42, 129, 140, or 142 can be used to identify an identical or similar nucleic acid. In addition, probes longer or shorter than 20 nucleotides can be used.

The invention also provides isolated nucleic acid sequences that are at least about 12 bases in length (e.g., at least about 13, 14, 15, 16, 17, 18, 19, 20, 25, 30, 40, 50, 60, 100, 250, 500, 750, 1000, 1500, 2000, 3000, 4000, or 5000 bases in length) and hybridize, under hybridization conditions, to the sense or antisense strand of a nucleic acid having the sequence set forth in SEQ ID NO:1, 9, 17, 25, 33, 34, 36, 38, 40, 42, 129, 140, 142, 162, or 163. The hybridization conditions can be moderately or highly stringent hybridization conditions.

For the purpose of this invention, moderately stringent hybridization conditions mean the hybridization is performed at about 42° C. in a hybridization solution containing 25 mM KPO$_4$ (pH 7.4), 5×SSC, 5×Denhart's solution, 50 µg/mL denatured, sonicated salmon sperm DNA, 50% formamide, 10% Dextran sulfate, and 1-15 ng/mL probe (about 5×10$^7$ cpm/µg), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM KPO$_4$ (pH 7.4), 5×SSC, 5×Denhart's solution, 50 µg/mL denatured, sonicated salmon sperm DNA, 50% formamide, 10% Dextran sulfate, and 1-15 ng/mL probe (about 5×10$^7$ cpm/µg), while the washes are performed at about 65° C. with a wash solution containing 0.2×SSC and 0.1% sodium dodecyl sulfate.

Purified: The term "purified" as used herein does not require absolute purity; rather, it is intended as a relative term. Thus, for example, a purified polypeptide or nucleic acid preparation can be one in which the subject polypeptide or nucleic acid, respectively, is at a higher concentration than the polypeptide or nucleic acid would be in its natural environment within an organism. For example, a polypeptide preparation can be considered purified if the polypeptide content in the preparation represents at least 50%, 60%, 70%, 80%, 85%, 90%, 92%, 95%, 98%, or 99% of the total protein content of the preparation.

Transformed: A "transformed" cell is a cell into which a nucleic acid molecule has been introduced by, for example, molecular biology techniques. As used herein, the term "transformation" encompasses all techniques by which a nucleic acid molecule might be introduced into such a cell including, without limitation, transfection with a viral vector, conjugation, transformation with a plasmid vector, and introduction of naked DNA by electroporation, lipofection, and particle gun acceleration.

Recombinant: A "recombinant" nucleic acid is one having (1) a sequence that is not naturally occurring in the organism in which it is expressed or (2) a sequence made by an artificial combination of two otherwise-separated, shorter sequences. This artificial combination is often accomplished by chemical synthesis or, more commonly, by the artificial manipulation of isolated segments of nucleic acids, e.g., by genetic engineering techniques. "Recombinant" is also used to describe nucleic acid molecules that have been artificially manipulated, but contain the same regulatory sequences and coding regions that are found in the organism from which the nucleic acid was isolated.

Specific binding agent: A "specific binding agent" is an agent that is capable of specifically binding to any of the polypeptide described herein, and can include polyclonal antibodies, monoclonal antibodies (including humanized monoclonal antibodies), and fragments of monoclonal antibodies such as Fab, F(ab')$_2$, and Fv fragments as well as any other agent capable of specifically binding to an epitope of such polypeptides.

Antibodies to the polypeptides provided herein (or fragments thereof) can be used to purify or identify such polypeptides. The amino acid and nucleic acid sequences provided herein allow for the production of specific antibody-based binding agents that recognize the polypeptides described herein.

Monoclonal or polyclonal antibodies can be produced to the polypeptides, portions of the polypeptides, or variants thereof. Optimally, antibodies raised against one or more epitopes on a polypeptide antigen will specifically detect that polypeptide. That is, antibodies raised against one particular polypeptide would recognize and bind that particular polypeptide, and would not substantially recognize or bind to other polypeptides. The determination that an antibody specifically binds to a particular polypeptide is made by any one of a number of standard immunoassay methods; for instance, Western blotting (See, e.g., Sambrook et al. (ed.), Molecular Cloning: A Laboratory Manual, 2nd ed., vol. 1-3, Cold Spring Harbor Laboratory Press, Cold Spring Harbor, N.Y., 1989).

To determine that a given antibody preparation (such as a preparation produced in a mouse against a polypeptide having the amino acid sequence set forth in SEQ ID NO: 2) specifically detects the appropriate polypeptide (e.g., a polypeptide having the amino acid sequence set forth in SEQ ID NO: 2) by Western blotting, total cellular protein can be extracted from cells and separated by SDS-polyacrylamide gel electrophoresis. The separated total cellular protein can then be transferred to a membrane (e.g., nitrocellulose), and the antibody preparation incubated with the membrane. After washing the membrane to remove non-specifically bound antibodies, the presence of specifically bound antibodies can be detected using an appropriate secondary antibody (e.g., an anti-mouse antibody) conjugated to an enzyme such as alkaline phosphatase since application of 5-bromo-4-chloro-3-indolyl phosphate/nitro blue tetrazolium results in the production of a densely blue-colored compound by immuno-localized alkaline phosphatase.

Substantially pure polypeptides suitable for use as an immunogen can be obtained from transfected cells, transformed cells, or wild-type cells. Polypeptide concentrations in the final preparation can be adjusted, for example, by concentration on an Amicon filter device, to the level of a few micrograms per milliliter. In addition, polypeptides ranging in size from full-length polypeptides to polypeptides having as few as nine amino acid residues can be utilized as immunogens. Such polypeptides can be produced in cell culture, can be chemically synthesized using standard methods, or can be obtained by cleaving large polypeptides into smaller polypeptides that can be purified. Polypeptides having as few as nine amino acid residues in length can be immunogenic when presented to an immune system in the context of a Major Histocompatibility Complex (MHC) molecule such as an MHC class I or MHC class II molecule. Accordingly, polypeptides having at least 9, 10, 11, 12, 13, 14, 15, 20, 25, 30, 35, 40, 45, 50, 55, 60, 70, 80, 90, 100, 150, 200, 250, 300, 350, 400, 450, 500, 550, 600, 650, 700, 750, 800, 900, 1000, 1050, 1100, 1150, 1200, 1250, 1300, 1350, or more consecutive amino acid residues of any amino acid sequence disclosed herein can be used as immunogens for producing antibodies.

Monoclonal antibodies to any of the polypeptides disclosed herein can be prepared from murine hybridomas according to the classic method of Kohler & Milstein (Nature 256:495 (1975)) or a derivative method thereof.

Polyclonal antiserum containing antibodies to the heterogeneous epitopes of any polypeptide disclosed herein can be prepared by immunizing suitable animals with the polypeptide (or fragment thereof), which can be unmodified or modified to enhance immunogenicity. An effective immunization protocol for rabbits can be found in Vaitukaitis et al. (*J. Clin. Endocrinol. Metab.* 33:988-991 (1971)).

Antibody fragments can be used in place of whole antibodies and can be readily expressed in prokaryotic host cells. Methods of making and using immunologically effective portions of monoclonal antibodies, also referred to as "antibody fragments," are well known and include those described in Better & Horowitz (*Methods Enzymol.* 178:476-496 (1989)), Glockshuber et al. (*Biochemistry* 29:1362-1367 (1990), U.S. Pat. No. 5,648,237 ("Expression of Functional Antibody Fragments"), U.S. Pat. No. 4,946,778 ("Single Polypeptide Chain Binding Molecules"), U.S. Pat. No. 5,455,030 ("Immunotherapy Using Single Chain Polypeptide Binding Molecules"), and references cited therein.

Operably linked: A first nucleic acid sequence is "operably linked" with a second nucleic acid sequence whenever the first nucleic acid sequence is placed in a functional relationship with the second nucleic acid sequence. For instance, a promoter is operably linked to a coding sequence if the promoter affects the transcription of the coding sequence. Generally, operably linked DNA sequences are contiguous and, where necessary to join two polypeptide-coding regions, in the same reading frame.

Probes and primers: Nucleic acid probes and primers can be prepared readily based on the amino acid sequences and nucleic acid sequences provided herein. A "probe" includes an isolated nucleic acid containing a detectable label or reporter molecule. Typical labels include radioactive isotopes, ligands, chemiluminescent agents, and enzymes. Methods for labeling and guidance in the choice of labels appropriate for various purposes are discussed in, for example, Sambrook et al. (ed.), Molecular Cloning: A Laboratory Manual 2nd ed., vol. 1-3, Cold Spring Harbor Laboratory Press, Cold Spring Harbor, N.Y., 1989, and Ausubel et al. (ed.) Current Protocols in Molecular Biology, Greene Publishing and Wiley-Interscience, New York (with periodic updates), 1987.

"Primers" are typically nucleic acid molecules having ten or more nucleotides (e.g., nucleic acid molecules having between about 10 nucleotides and about 100 nucleotides). A primer can be annealed to a complementary target nucleic acid strand by nucleic acid hybridization to form a hybrid between the primer and the target nucleic acid strand, and then extended along the target nucleic acid strand by, for example, a DNA polymerase enzyme. Primer pairs can be used for amplification of a nucleic acid sequence, for example, by the polymerase chain reaction (PCR) or other nucleic-acid amplification methods known in the art.

Methods for preparing and using probes and primers are described, for example, in references such as Sambrook et al. (ed.), Molecular Cloning: A Laboratory Manual, 2nd ed., vol. 1-3, Cold Spring Harbor Laboratory Press, Cold Spring Harbor, N.Y., 1989; Ausubel et al. (ed.), Current Protocols in Molecular Biology, Greene Publishing and Wiley-Interscience, New York (with periodic updates), 1987; and Innis et al., PCR Protocols: A Guide to Methods and Applications, Academic Press: San Diego, 1990. PCR primer pairs can be derived from a known sequence, for example, by using computer programs intended for that purpose such as Primer (Version 0.5, .COPYRGT. 1991, Whitehead Institute for Biomedical Research, Cambridge, Mass.). One of skill in the art will appreciate that the specificity of a particular probe or primer increases with the length, but that a probe or primer can range in size from a full-length sequence to sequences as short as five consecutive nucleotides. Thus, for example, a primer of 20 consecutive nucleotides can anneal to a target with a higher specificity than a corresponding primer of only 15 nucleotides. Thus, in order to obtain greater specificity, probes and primers can be selected that comprise, for example, 10, 20, 25, 30, 35, 40, 50, 60, 70, 80, 90, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 2000, 2050, 2100, 2150, 2200, 2250, 2300, 2350, 2400, 2450, 2500, 2550, 2600, 2650, 2700, 2750, 2800, 2850, 2900, 3000, 3050, 3100, 3150, 3200, 3250, 3300, 3350, 3400, 3450, 3500, 3550, 3600, 3650, 3700, 3750, 3800, 3850, 3900, 4000, 4050, 4100, 4150, 4200, 4250, 4300, 4350, 4400, 4450, 4500, 4550, 4600, 4650, 4700, 4750, 4800, 4850, 4900, 5000, 5050, 5100, 5150, 5200, 5250, 5300, 5350, 5400, 5450, or more consecutive nucleotides.

Percent sequence identity: The "percent sequence identity" between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (www.fr.com) or the United States government's National Center for Biotechnology Information web site (www.ncbi.nlm.nih.gov). Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output-.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, a nucleic acid sequence that has 1166 matches when aligned with the sequence set forth in SEQ ID NO:1 is 75.0 percent identical to the sequence set forth in SEQ ID NO:1 (i.e., 1166÷1554*100=75.0). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It is also noted that the length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

```
                      1                    20
Target Sequence:      AGGTCGTGTACTGTCAGTCA
                      | || |||  |||| ||||| |
Identified Sequence:  ACGTGGTGAACTGCCAGTGA
```

Conservative substitution: The term "conservative substitution" as used herein refers to any of the amino acid substitutions set forth in Table 1. Typically, conservative substitutions have little to no impact on the activity of a polypeptide. A polypeptide can be produced to contain one or more conservative substitutions by manipulating the nucleotide sequence that encodes that polypeptide using, for example, standard procedures such as site-directed mutagenesis or PCR.

TABLE 1

| Original Residue | Conservative Substitution(s) |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

II. Metabolic Pathways

The invention provides methods and materials related to producing 3-HP as well as other organic compounds (e.g., 1,3-propanediol, acrylic acid, polymerized acrylate, esters of acrylate, polymerized 3-HP, and esters of 3-HP). Specifically, the invention provides isolated nucleic acids, polypeptides, host cells, and methods and materials for producing 3-HP as well as other organic compounds such as 1,3-propanediol, acrylic acid, polymerized acrylate, esters of acrylate, polymerized 3-HP, and esters of 3-HP.

Accordingly, the invention provides several metabolic pathways that can be used to produce organic compounds from PEP (FIGS. 1-5, 43-44, 54, and 55). As depicted in FIG. 1, lactate can be converted into lactyl-CoA by a polypeptide having CoA transferase activity (EC 2.8.3.1); the resulting lactyl-CoA can be converted into acrylyl-CoA by a polypeptide (or multiple polypeptide complex such as an activated E2 α and E2 β complex) having lactyl-CoA dehydratase activity (EC 4.2.1.54); the resulting acrylyl-CoA can be converted into 3-hydroxypropionyl-CoA (3-HP-CoA) by a polypeptide having 3-hydroxypropionyl-CoA dehydratase activity (EC 4.2.1.-); and the resulting 3-HP-CoA can be converted into 3-HP by a polypeptide having CoA transferase activity, a polypeptide having 3-hydroxypropionyl-CoA hydrolase activity (EC 3.1.2.-), or a polypeptide having 3-hydroxyisobutryl-CoA hydrolase activity (EC 3.1.2.4).

Polypeptides having CoA transferase activity as well as nucleic acid encoding such polypeptides can be obtained from various species including, without limitation, Megas-

*phaera elsdenii, Clostridium propionicum, Clostridium kluyveri*, and *Escherichia coli*. For example, nucleic acid that encodes a polypeptide having CoA transferase activity can be obtained from *Megasphaera elsdenii* as described in Example 1 and can have a sequence as set forth in SEQ ID NO: 1. In addition, polypeptides having CoA transferase activity as well as nucleic acid encoding such polypeptides can be obtained as described herein. For example, the variations to SEQ ID NO: 1 provided herein can be used to encode a polypeptide having CoA transferase activity.

Polypeptides (or the polypeptides of a multiple polypeptide complex such as an activated E2 α and E2 β complex) having lactyl-CoA dehydratase activity as well as nucleic acid encoding such polypeptides can be obtained from various species including, without limitation, *Megasphaera elsdenii* and *Clostridium propionicum*. For example, nucleic acid encoding an E1 activator, an E2 α subunit, and an E2 β subunit that can form a multiple polypeptide complex having lactyl-CoA dehydratase activity can be obtained from *Megasphaera elsdenii* as described in Example 2. The nucleic acid encoding the E1 activator can contain a sequence as set forth in SEQ ID NO: 9; the nucleic acid encoding the E2 α subunit can contain a sequence as set forth in SEQ ID NO: 17; and the nucleic acid encoding the E2 β subunit can contain a sequence as set forth in SEQ ID NO: 25. In addition, polypeptides (or the polypeptides of a multiple polypeptide complex) having lactyl-CoA dehydratase activity as well as nucleic acid encoding such polypeptides can be obtained as described herein. For example, the variations to SEQ ID NO: 9, 17, and 25 provided herein can be used to encode the polypeptides of a multiple polypeptide complex having CoA transferase activity.

Polypeptides having 3-hydroxypropionyl-CoA dehydratase activity as well as nucleic acid encoding such polypeptides can be obtained from various species including, without limitation, *Chloroflexus aurantiacus, Candida rugosa, Rhodosprillium rubrum*, and *Rhodobacter capsulates*. For example, nucleic acid that encodes a polypeptide having 3-hydroxypropionyl-CoA dehydratase activity can be obtained from *Chloroflexus aurantiacus* as described in Example 3 and can have a sequence as set forth in SEQ ID NO: 40. In addition, polypeptides having 3-hydroxypropionyl-CoA dehydratase activity as well as nucleic acid encoding such polypeptides can be obtained as described herein. For example, the variations to SEQ ID NO: 40 provided herein can be used to encode a polypeptide having 3-hydroxypropionyl-CoA dehydratase activity.

Polypeptides having 3-hydroxypropionyl-CoA hydrolase activity as well as nucleic acid encoding such polypeptides can be obtained from various species including, without limitation, *Candida rugosa*. Polypeptides having 3-hydroxyisobutryl-CoA hydrolase activity as well as nucleic acid encoding such polypeptides can be obtained from various species including, without limitation, *Pseudomonas fluorescens, rattus*, and *homo sapiens*. For example, nucleic acid that encodes a polypeptide having 3-hydroxyisobutryl-CoA hydrolase activity can be obtained from *homo sapiens* and can have a sequence as set forth in GenBank® accession number U66669.

The term "polypeptide having enzymatic activity" as used herein refers to any polypeptide that catalyzes a chemical reaction of other substances without itself being destroyed or altered upon completion of the reaction. Typically, a polypeptide having enzymatic activity catalyzes the formation of one or more products from one or more substrates. Such polypeptides can have any type of enzymatic activity including, without limitation, the enzymatic activity or enzymatic activities associated with enzymes such as dehydratases/hydratases, 3-hydroxypropionyl-CoA dehydratases/hydratases, CoA transferases, lactyl-CoA dehydratases, 3-hydroxypropionyl-CoA hydrolases, 3-hydroxyisobutryl-CoA hydrolases, poly hydroxyacid synthases, CoA synthetases, malonyl-CoA reductases, β-alanine ammonia lyases, and lipases.

Figure 2:
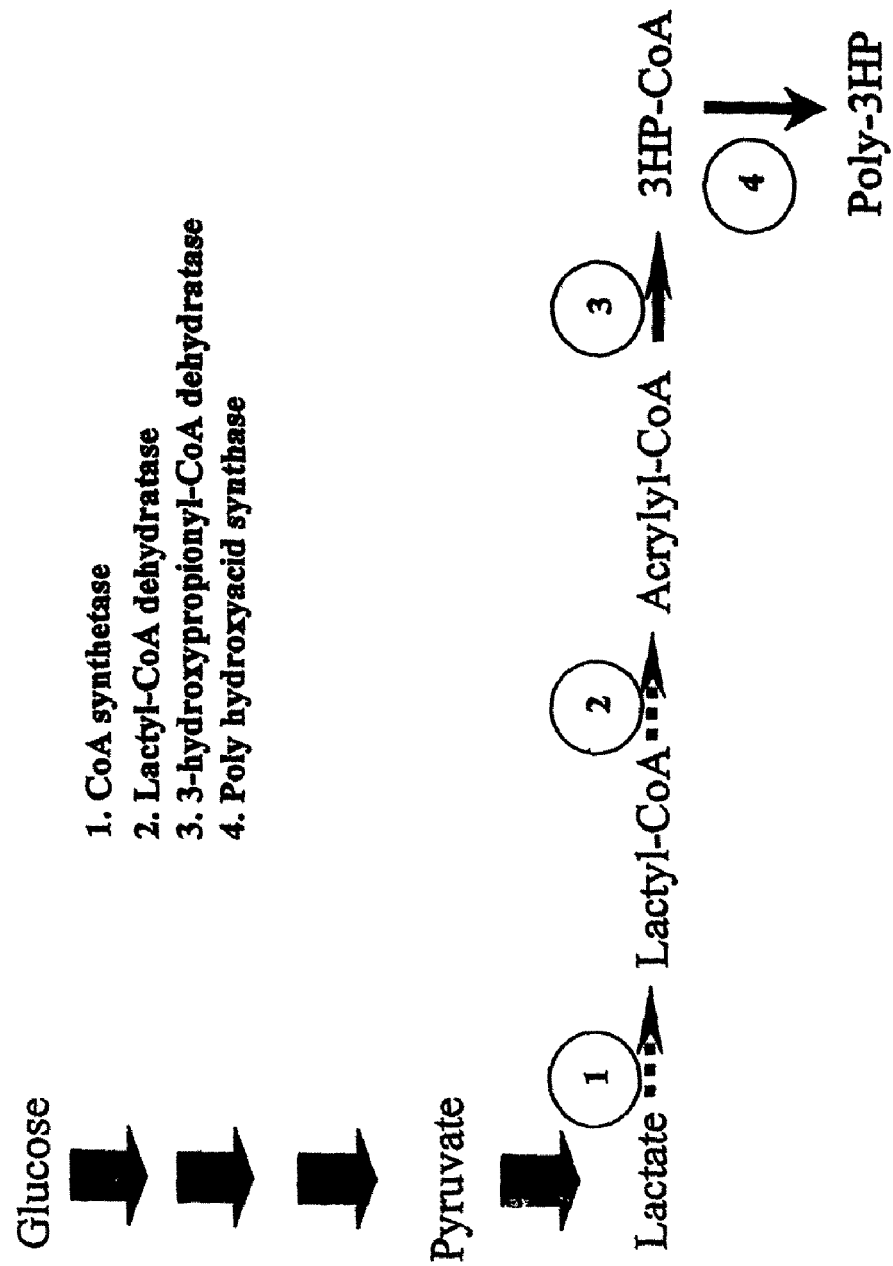
FIG. 2 is a diagram of a pathway for making polymerized 3-HP.

As depicted in FIG. 2, lactate can be converted into lactyl-CoA by a polypeptide having CoA synthetase activity (EC 6.2.1.-); the resulting lactyl-CoA can be converted into acrylyl-CoA by a polypeptide (or multiple polypeptide complex) having lactyl-CoA dehydratase activity; the resulting acrylyl-CoA can be converted into 3-HP-CoA by a polypeptide having 3-hydroxypropionyl-CoA dehydratase activity; and the resulting 3-HP-CoA can be converted into polymerized 3-HP by a polypeptide having poly hydroxyacid synthase activity (EC 2.3.1.-). Polypeptides having CoA synthetase activity as well as nucleic acid encoding such polypeptides can be obtained from various species including, without limitation, *Escherichia coli, Rhodobacter sphaeroides, Saccharomyces cervisiae*, and *Salmonella enterica*. For example, nucleic acid that encodes a polypeptide having CoA synthetase activity can be obtained from *Escherichia coli* and can have a sequence as set forth in GenBank® accession number U00006. Polypeptides (or multiple polypeptide complexes) having lactyl-CoA dehydratase activity as well as nucleic acid encoding such polypeptides can be obtained as provided herein. Polypeptides having 3-hydroxypropionyl-CoA dehydratase activity as well as nucleic acid encoding such polypeptides also can be obtained as provided herein. Polypeptides having poly hydroxyacid synthase activity as well as nucleic acid encoding such polypeptides can be obtained from various species including, without limitation, *Rhodobacter sphaeroides, Comamonas acidororans, Ralstonia eutropha*, and *Pseudomonas oleovorans*. For example, nucleic acid that encodes a polypeptide having poly hydroxyacid synthase activity can be obtained from *Rhodobacter sphaeroides* and can have a sequence as set forth in GenBank® accession number X97200.

Figure 3:
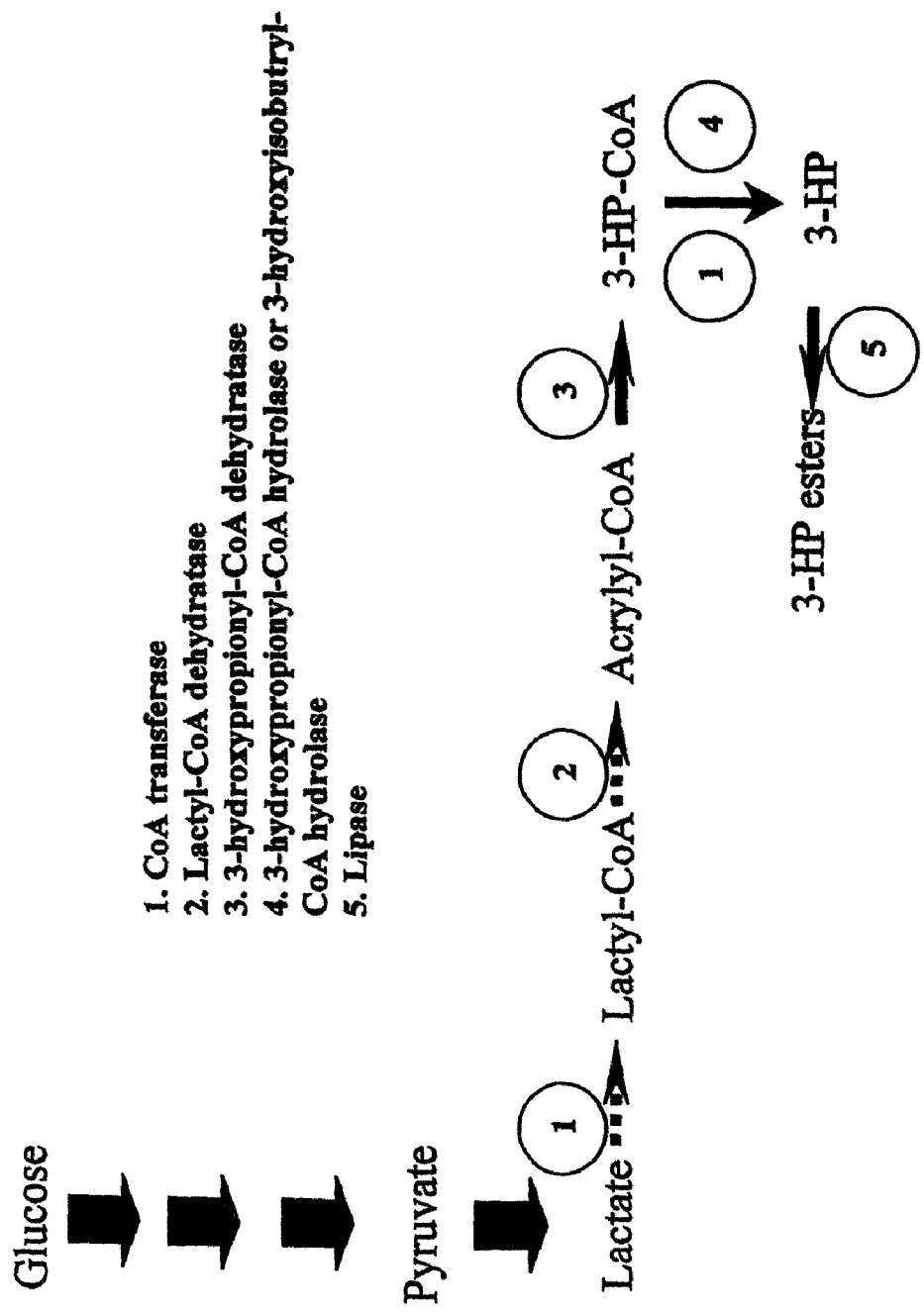
FIG. 3 is a diagram of a pathway for making esters of 3-HP.

As depicted in FIG. 3, lactate can be converted into lactyl-CoA by a polypeptide having CoA transferase activity; the resulting lactyl-CoA can be converted into acrylyl-CoA by a polypeptide (or multiple polypeptide complex) having lactyl-CoA dehydratase activity; the resulting acrylyl-CoA can be converted into 3-HP-CoA by a polypeptide having 3-hydroxypropionyl-CoA dehydratase activity; the resulting 3-HP-CoA can be converted into 3-HP by a polypeptide having CoA transferase activity, a polypeptide having 3-hydroxypropionyl-CoA hydrolase activity, or a polypeptide having 3-hydroxyisobutryl-CoA hydrolase activity; and the resulting 3-HP can be converted into an ester of 3-HP by a polypeptide having lipase activity (EC 3.1.1.-). Polypeptides having lipase activity as well as nucleic acid encoding such polypeptides can be obtained from various species including, without limitation, *Candida rugosa, Candida tropicalis*, and *Candida albicans*. For example, nucleic acid that encodes a polypeptide having lipase activity can be obtained from *Candida rugosa* and can have a sequence as set forth in GenBank® accession number A81171.

Figure 4:
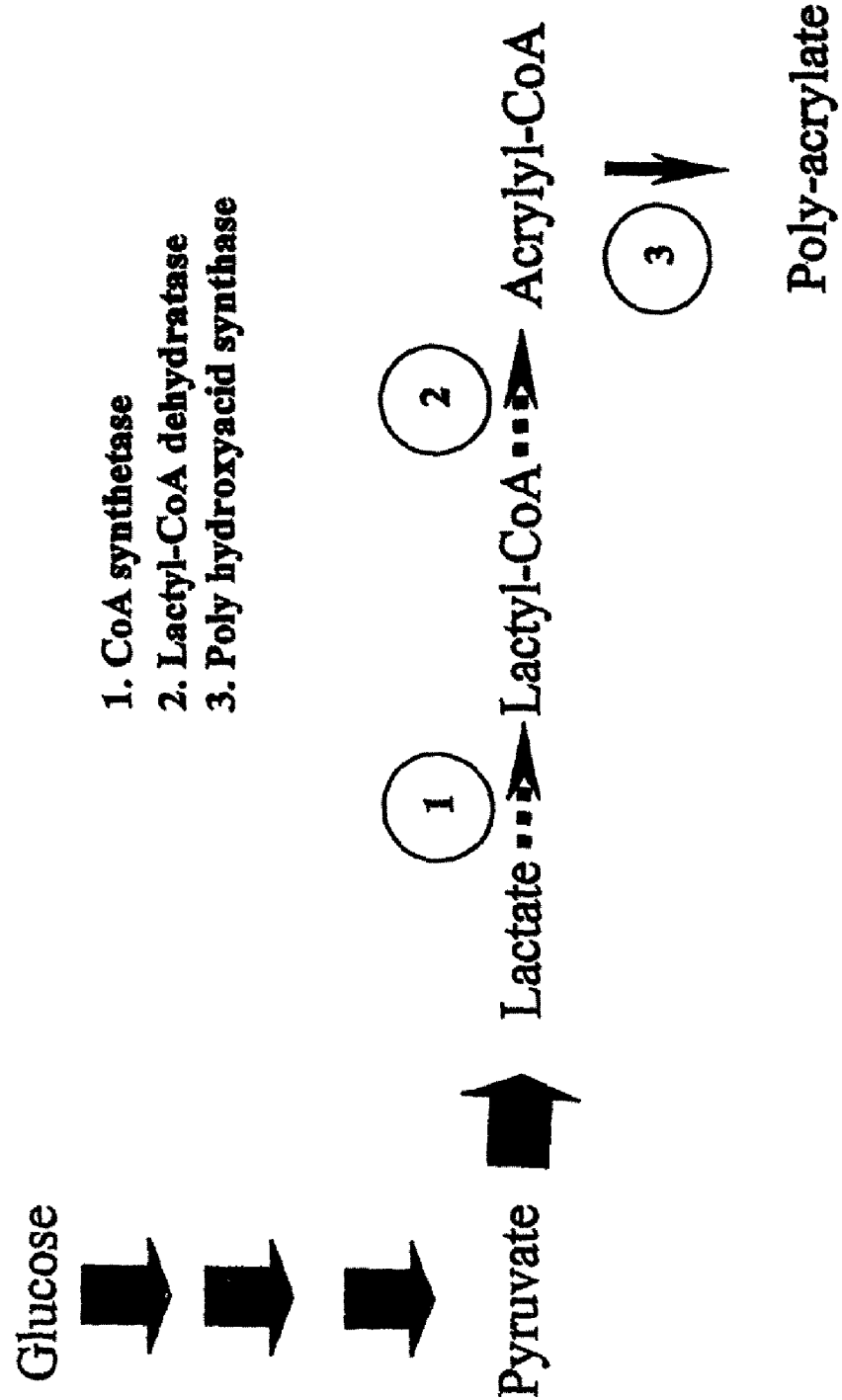
FIG. 4 is a diagram of a pathway for making polymerized acrylic acid.

As depicted in FIG. 4, lactate can be converted into lactyl-CoA by a polypeptide having CoA synthetase activity; the resulting lactyl-CoA can be converted into acrylyl-CoA by a polypeptide (or multiple polypeptide complex) having lactyl-CoA dehydratase activity; and the resulting acrylyl-CoA can be converted into polymerized acrylate by a polypeptide having poly hydroxyacid synthase activity.

Figure 5:
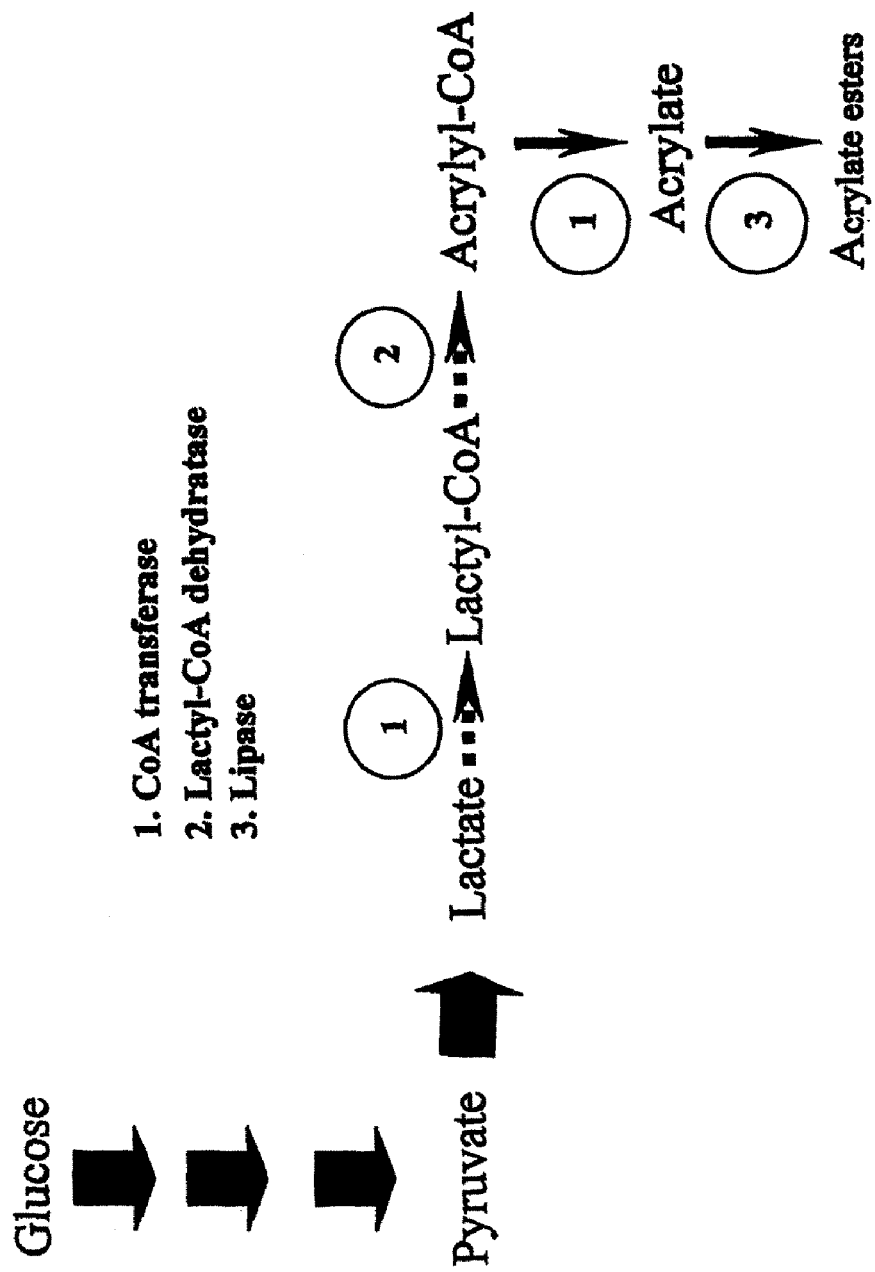
FIG. 5 is a diagram of a pathway for making esters of acrylate.

As depicted in FIG. 5, lactate can be converted into lactyl-CoA by a polypeptide having CoA transferase activity; the resulting lactyl-CoA can be converted into acrylyl-CoA by a polypeptide (or multiple polypeptide complex) having lactyl-CoA dehydratase activity; the resulting acrylyl-CoA can be converted into acrylate by a polypeptide having CoA transferase activity; and the resulting acrylate can be converted into an ester of acrylate by a polypeptide having lipase activity.

Figure 44:
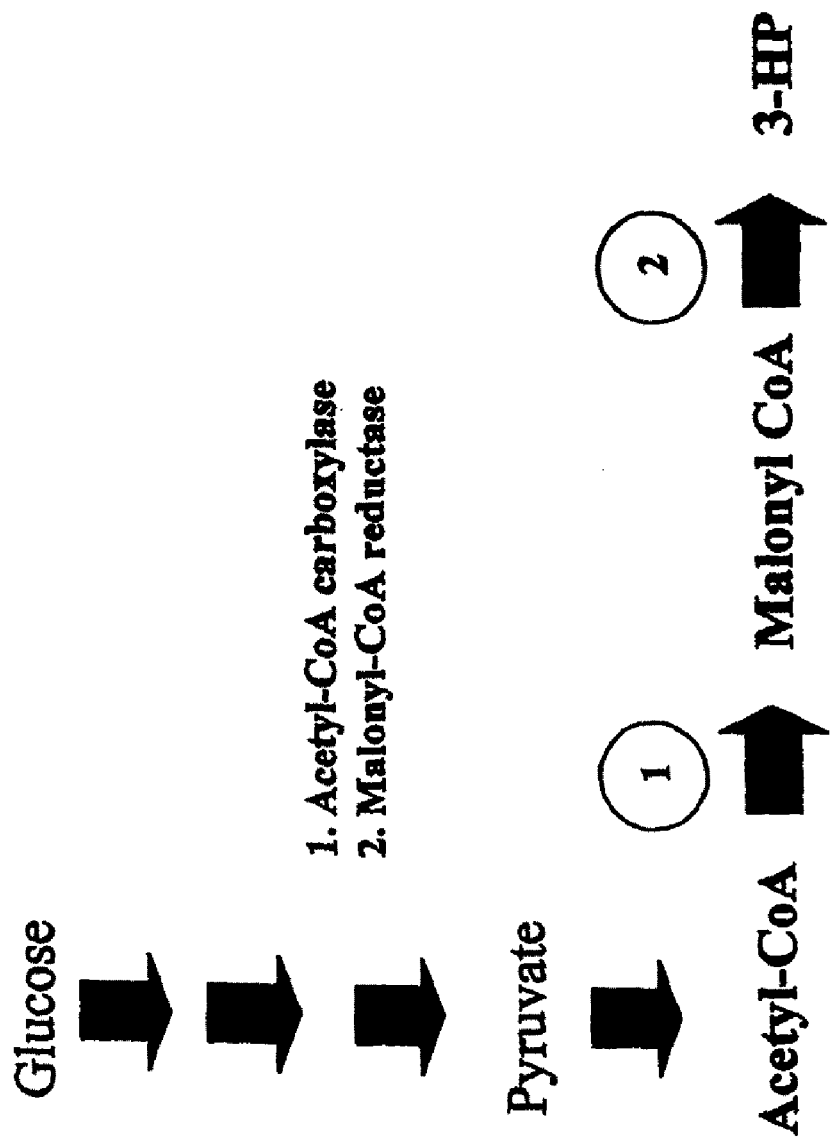
FIG. 44 is a diagram of a pathway for making 3-HP via acetyl-CoA and malonyl-CoA.

As depicted in FIG. 44, acetyl-CoA can be converted into malonyl-CoA by a polypeptide having acetyl-CoA carboxylase activity, and the resulting malonyl-CoA can be converted into 3-HP by a polypeptide having malonyl-CoA reductase activity. Polypeptides having acetyl-CoA carboxylase activity as well as nucleic acid encoding such polypeptides can be obtained from various species including, without limitation, *Escherichia coli* and *Chloroflexus aurantiacus*. For example, nucleic acid that encodes a polypeptide having acetyl-CoA carboxylase activity can be obtained from *Escherichia coli* and can have a sequence as set forth in GenBank® accession number M96394 or U18997. Polypeptides having malonyl-CoA reductase activity as well as nucleic acid encoding such polypeptides can be obtained from various species including, without limitation, *Chloroflexus aurantiacus, Sulfolobus metacillus*, and *Acidianus brierleyi*. For example, nucleic acid that encodes a polypeptide having malonyl-CoA reductase activity can be obtained as described herein and can have a sequence similar to the sequence set forth in SEQ ID NO: 140. In addition, polypeptides having malonyl-CoA reductase activity as well as nucleic acid encoding such polypeptides contains can be obtained as described herein. For example, the variations to SEQ ID NO: 140 provided herein can be used to encode a polypeptide having malonyl-CoA reductase activity.

Polypeptides having malonyl-CoA reductase activity can use NADPH as a co-factor. For example, the polypeptide having the amino acid sequence set forth in SEQ ID NO: 141 is a polypeptide having malonyl-CoA reductase activity that uses NADPH as a co-factor when converting malonyl-CoA into 3-HP. Likewise, polypeptides having malonyl-CoA reductase activity can use NADH as a co-factor. Such polypeptides can be obtained by converting a polypeptide that has malonyl-CoA reductase activity and uses NADPH as a cofactor into a polypeptide that has malonyl-CoA reductase activity and uses NADH as a cofactor. Any method can be used to convert a polypeptide that uses NADPH as a cofactor into a polypeptide that uses NADH as a cofactor such as those described by others (Eppink et al., *J. Mol. Biol.,* 292(1):87-96 (1999), Hall and Tomsett, *Microbiology,* 146(Pt 6):1399-406 (2000), and Dohr et al., *Proc. Natl. Acad. Sci.,* 98(1):81-86 (2001)). For example, mutagenesis can be used to convert the polypeptide encoded by the nucleic acid sequence set forth in SEQ ID NO: 140 into a polypeptide that, when converting malonyl-CoA into 3-HP, uses NADH as a co-factor instead of NADPH.

Figure 43:
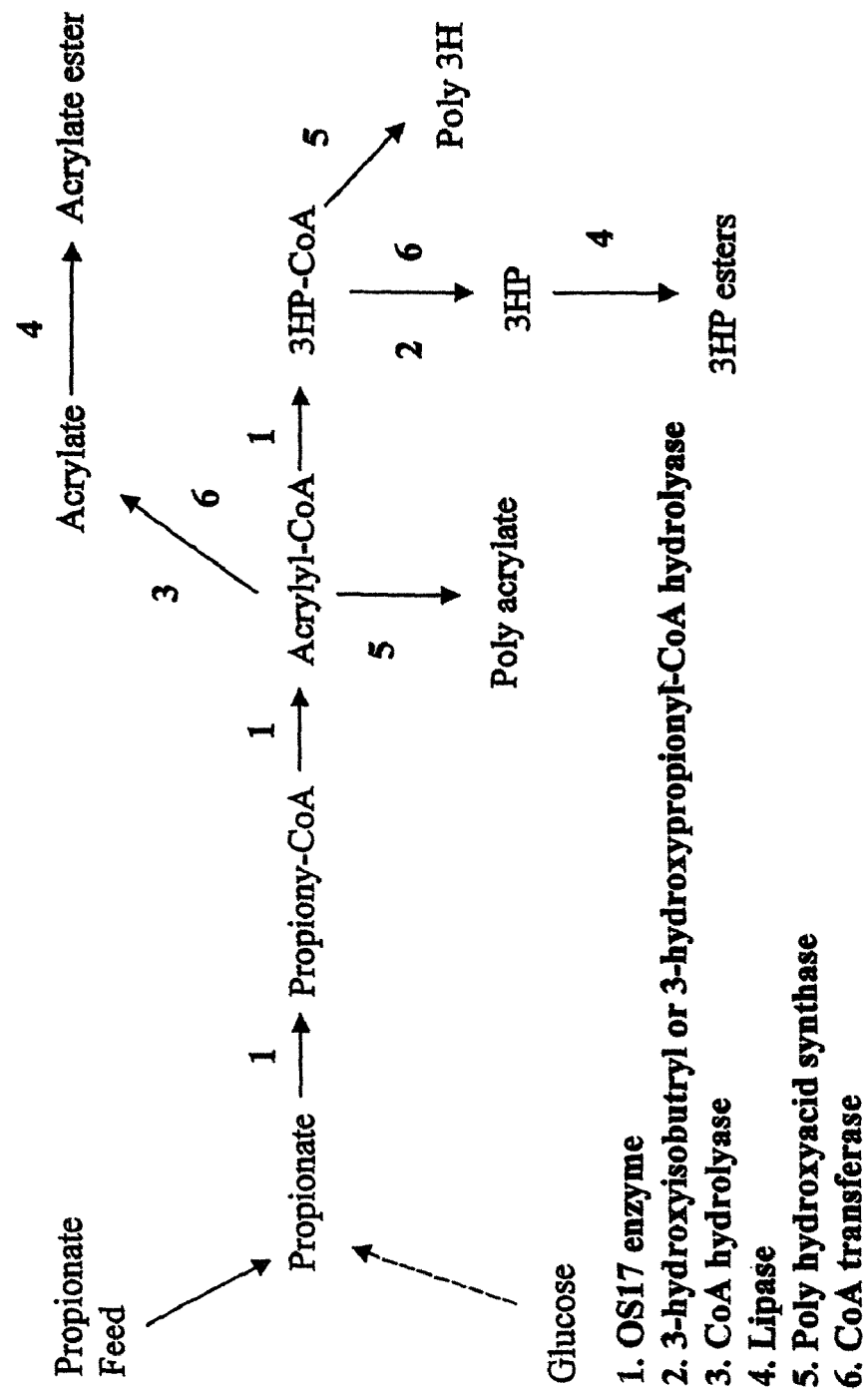
FIG. 43 is a diagram of several pathways for making organic compounds using the multifunctional OS17 enzyme.

As depicted in FIG. 43, propionate can be converted into propionyl-CoA by a polypeptide having CoA synthetase activity such as the polypeptide having the sequence set forth in SEQ ID NO: 39; the resulting propionyl-CoA can be converted into acrylyl-CoA by a polypeptide having dehydrogenase activity such as the polypeptide having the sequence set forth in SEQ ID NO: 39; and the resulting acrylyl-CoA can be converted into (1) acrylate by a polypeptide having CoA transferase activity or CoA hydrolase activity, (2) 3-HP-CoA by a polypeptide having 3-HP dehydratase activity (also referred to as acrylyl-CoA hydratase or simply hydratase) such as the polypeptide having the sequence set forth in SEQ ID NO:39, or (3) polymerized acrylate by a polypeptide having poly hydroxyacid synthase activity. The resulting acrylate can be converted into an ester of acrylate by a polypeptide having lipase activity. The resulting 3-HP-CoA can be converted into (1) 3-HP by a polypeptide having CoA transferase activity, a polypeptide having 3-hydroxypropionyl-CoA hydrolase activity (EC 3.1.2.-), or a polypeptide having 3-hydroxyisobutyryl-CoA hydrolase activity (EC 3.1.2.4), or (2) polymerized 3-HP by a polypeptide having poly hydroxyacid synthase activity (EC 2.3.1.-).

Figure 54:
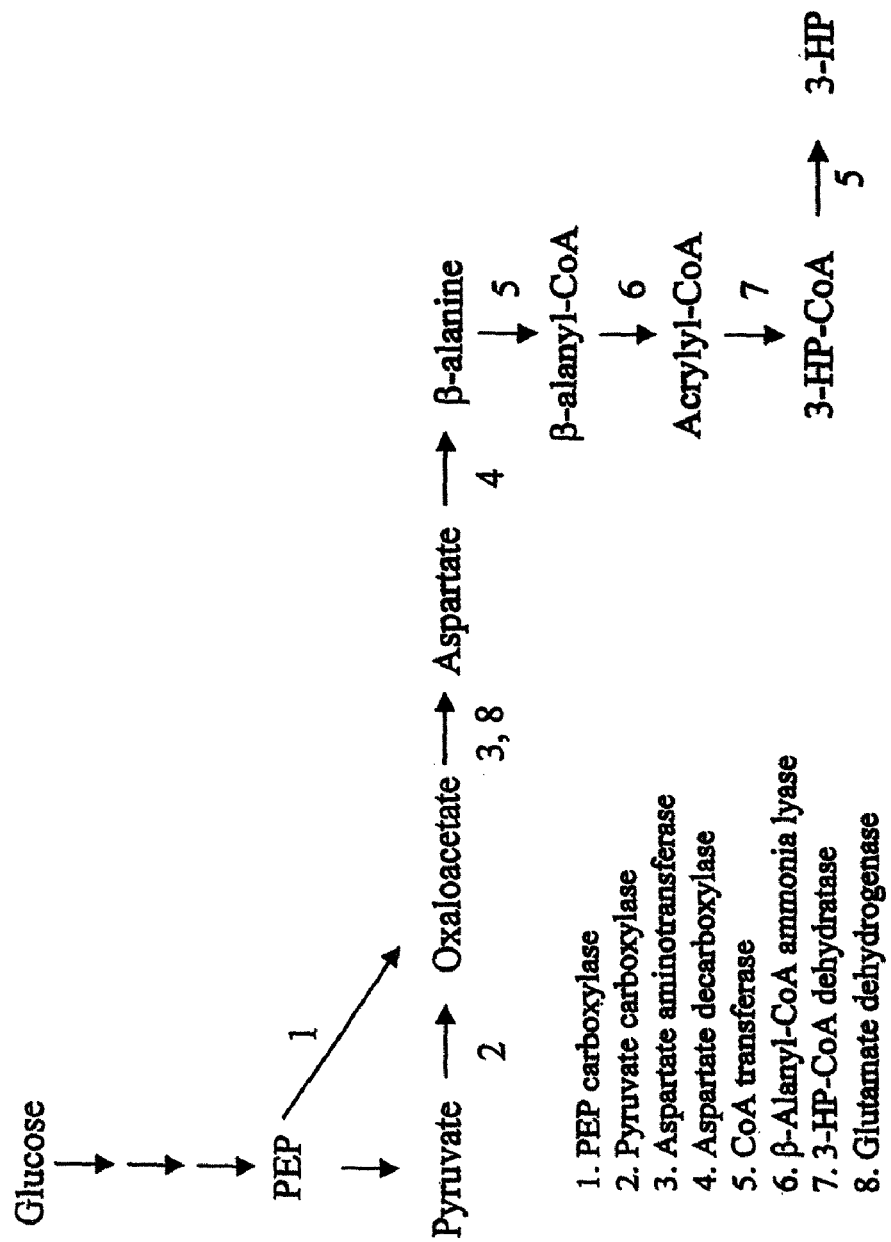
FIG. 54 is a diagram of a pathway for making 3-HP via a β-alanine intermediate.

As depicted in FIG. 54, PEP can be converted into β-alanine. β-alanine can be converted into β-alanyl-CoA through the use of a polypeptide having CoA transferase activity. β-alanyl-CoA can then be converted into acrylyl-CoA through the use of a polypeptide having β-alanyl-CoA ammonia lyase activity. Acrylyl-CoA can then be converted into 3-HP-CoA through the use of a polypeptide having 3-HP-CoA dehydratase activity, and a polypeptide having glutamate dehydrogenase activity can be used to convert 3-HP-CoA into 3-HP.

Figure 55:
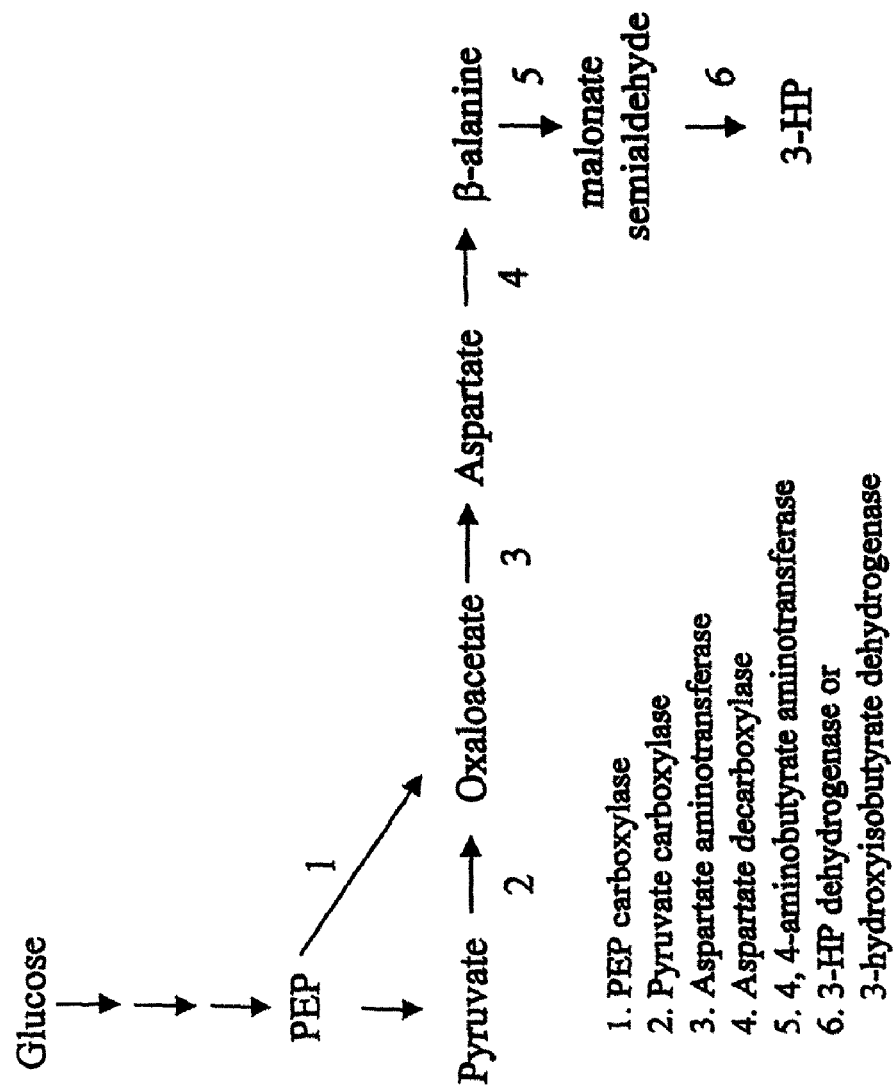
FIG. 55 is a diagram of a pathway for making 3-HP via a β-alanine intermediate.

As depicted in FIG. 55, 3-HP can be made from β-alanine by first contacting β-alanine with a polypeptide having 4,4-aminobutyrate aminotransferase activity to create malonate semialdehyde. The malonate semialdehyde can be converted into 3-HP with a polypeptide having 3-HP dehydrogenase activity or a polypeptide having 3-hydroxyisobutyrate dehydrogenase activity.

III. Nucleic Acid Molecules and Polypeptides

The invention provides isolated nucleic acid that contains the entire nucleic acid sequence set forth in SEQ ID NO:1, 9, 17, 25, 33, 34, 36, 38, 40, 42, 129, 140, 142, 162, or 163. In addition, the invention provides isolated nucleic acid that contains a portion of the nucleic acid sequence set forth in SEQ ID NO:1, 9, 17, 25, 33, 34, 36, 38, 40, 42, 129, 140, 142, 162, or 163. For example, the invention provides isolated nucleic acid that contains a 15 nucleotide sequence identical to any 15 nucleotide sequence set forth in SEQ ID NO:1, 9, 17, 25, 33, 34, 36, 38, 40, 42, 129, 140, 142, 162, or 163 including, without limitation, the sequence starting at nucleotide number 1 and ending at nucleotide number 15, the sequence starting at nucleotide number 2 and ending at nucleotide number 16, the sequence starting at nucleotide number 3 and ending at nucleotide number 17, and so forth. It will be appreciated that the invention also provides isolated nucleic acid that contains a nucleotide sequence that is greater than 15 nucleotides (e.g., 16, 17, 18, 19, 20, 21, 22, 23, 24, 25, 26, 27, 28, 29, 30, or more nucleotides) in length and identical to any portion of the sequence set forth in SEQ ID NO:1, 9, 17, 25, 33, 34, 36, 38, 40, 42, 129, 140, 142, 162, or 163. For example, the invention provides isolated nucleic acid that contains a 25 nucleotide sequence identical to any 25 nucleotide sequence set forth in SEQ ID NO:1, 9, 17, 25, 33, 34, 36, 38, 40, 42, 129, 140, 142, 162, or 163 including, without limitation, the sequence starting at nucleotide number 1 and ending at nucleotide number 25, the sequence starting at nucleotide number 2 and ending at nucleotide number 26, the sequence starting at nucleotide number 3 and ending at nucleotide number 27, and so forth. Additional examples include, without limitation, isolated nucleic acids that contain a nucleotide sequence that is 50 or more nucleotides (e.g., 100, 150, 200, 250, 300, or more nucleotides) in length and identical to any portion of the sequence set forth in SEQ ID NO:1, 9, 17, 25, 33, 34, 36, 38, 40, 42, 129, 140, 142, 162, or 163. Such isolated nucleic acids can include, without limitation, those isolated nucleic acids containing a nucleic acid sequence represented in a single line of sequence depicted in FIG. 6, 10, 14, 18, 22, 23, 25, 27, 29, 31, 39, 49, or 51 since each line of sequence depicted in these figures, with the possible exception of the last line, provides a nucleotide sequence containing at least 50 bases.

In addition, the invention provides isolated nucleic acid that contains a variation of the nucleic acid sequence set forth in SEQ ID NO:1, 9, 17, 25, 33, 34, 36, 38, 40, 42, 129, 140, 142, 162, or 163. For example, the invention provides isolated nucleic acid containing a nucleic acid sequence set forth in SEQ ID NO:1, 9, 17, 25, 33, 34, 36, 38, 40, 42, 129, 140, 142, 162, or 163 that contains a single insertion, a single deletion, a single substitution, multiple insertions, multiple deletions, multiple substitutions, or any combination thereof (e.g., single deletion together with multiple insertions). Such isolated nucleic acid molecules can share at least 60, 65, 70, 75, 80, 85, 90, 95, 97, 98, or 99 percent sequence identity with a sequence set forth in SEQ ID NO:1, 9, 17, 25, 33, 34, 36, 38, 40, 42, 129, 140, 142, 162, or 163.

The invention provides multiple examples of isolated nucleic acid that contains a variation of a nucleic acid sequence set forth in SEQ ID NO:1, 9, 17, 25, 33, 34, 36, 38, 40, 42, 129, 140, 142, 162, or 163. For example, FIG. 8 provides the sequence set forth in SEQ ID NO:1 aligned with three other nucleic acid sequences. Examples of variations of the sequence set forth in SEQ ID NO:1 include, without limitation, any variation of the sequence set forth in SEQ ID NO:1 provided in FIG. 8. Such variations are provided in FIG. 8 in that a comparison of the nucleotide (or lack thereof) at a particular position of the sequence set forth in SEQ ID NO:1 with the nucleotide (or lack thereof) at the same aligned position of any of the other three nucleic acid sequences depicted in FIG. 8 (i.e., SEQ ID NOs:3, 4, and 5) provides a list of specific changes for the sequence set forth in SEQ ID NO:1. For example, the "a" at position 49 of SEQ ID NO:1 can be substituted with an "c" as indicated in FIG. 8. As also indicated in FIG. 8, the "a" at position 590 of SEQ ID NO:1 can be substituted with a "atgg"; an "aaac" can be inserted before the "g" at position 393 of SEQ ID NO:1; or the "gaa" at position 736 of SEQ ID NO:1 can be deleted. It will be appreciated that the sequence set forth in SEQ ID NO:1 can contain any number of variations as well as any combination of types of variations. For example, the sequence set forth in SEQ ID NO:1 can contain one variation provided in FIG. 8 or more than one (e.g., 2, 3, 4, 5, 6, 7, 8, 9, 10, 15, 20, 25, 50, 100, or more) of the variations provided in FIG. 8. It is noted that the nucleic acid sequences provided by FIG. 8 can encode polypeptides having CoA transferase activity. The invention also provides isolated nucleic acid that contains a variant of a portion of the sequence set forth in SEQ ID NO:1 as depicted in FIG. 8 and described herein.

Likewise, FIG. 12 provides variations of SEQ ID NO:9 and portions thereof; FIG. 16 provides variations of SEQ ID NO:17 and portions thereof; FIG. 20 provides variations of SEQ ID NO:25 and portions thereof; FIG. 32 provides variations of SEQ ID NO:40 and portions thereof; and FIG. 53 provides variations of SEQ ID NO:140.

The invention provides isolated nucleic acid that contains a nucleic acid sequence that encodes the entire amino acid sequence set forth in SEQ ID NO:2, 10, 18, 26, 35, 37, 39, 41, 141, 160, or 161. In addition, the invention provides isolated nucleic acid that contains a nucleic acid sequence that encodes a portion of the amino acid sequence set forth in SEQ ID NO:2, 10, 18, 26, 35, 37, 39, 41, 141, 160, or 161. For example, the invention provides isolated nucleic acid that contains a nucleic acid sequence that encodes a 15 amino acid sequence identical to any 15 amino acid sequence set forth in SEQ ID NO:2, 10, 18, 26, 35, 37, 39, 41, 141, 160, or 161 including, without limitation, the sequence starting at amino acid residue number 1 and ending at amino acid residue number 15, the sequence starting at amino acid residue number 2 and ending at amino acid residue number 16, the sequence starting at amino acid residue number 3 and ending at amino acid residue number 17, and so forth. It will be appreciated that the invention also provides isolated nucleic acid that contains a nucleic acid sequence that encodes an amino acid sequence that is greater than 15 amino acid residues (e.g., 16, 17, 18, 19, 20, 21, 22, 23, 24, 25, 26, 27, 28, 29, 30, or more amino acid residues) in length and identical to any portion of the sequence set forth in SEQ ID NO:2, 10, 18, 26, 35, 37, 39, 41, 141, 160, or 161. For example, the invention provides isolated nucleic acid that contains a nucleic acid sequence that encodes a 25 amino acid sequence identical to any 25 amino acid sequence set forth in SEQ ID NO:2, 10, 18, 26, 35, 37, 39, 41, 141, 160, or 161 including, without limitation, the sequence starting at amino acid residue number 1 and ending at amino acid residue number 25, the sequence starting at amino acid residue number 2 and ending at amino acid residue number 26, the sequence starting at amino acid residue number 3 and ending at amino acid residue number 27, and so forth. Additional examples include, without limitation, isolated nucleic acids that contain a nucleic acid sequence that encodes an amino acid sequence that is 50 or more amino acid residues (e.g., 100, 150, 200, 250, 300, or more amino acid residues) in length and identical to any portion of the sequence set forth in SEQ ID NO:2, 10, 18, 26, 35, 37, 39, 41, 141, 160, or 161. Such isolated nucleic acids can include, without limitation, those isolated nucleic acids containing a nucleic acid sequence that encodes an amino acid sequence represented in a single line of sequence depicted in FIG. 7, 11, 15, 19, 24, 26, 28, 30, or 50 since each line of sequence depicted in these figures, with the possible exception of the last line, provides an amino acid sequence containing at least 50 residues.

In addition, the invention provides isolated nucleic acid that contains a nucleic acid sequence that encodes an amino acid sequence having a variation of the amino acid sequence set forth in SEQ ID NO:2, 10, 18, 26, 35, 37, 39, 41, 141, 160, or 161. For example, the invention provides isolated nucleic acid containing a nucleic acid sequence encoding an amino acid sequence set forth in SEQ ID NO:2, 10, 18, 26, 35, 37, 39, 41, 141, 160, or 161 that contains a single insertion, a single deletion, a single substitution, multiple insertions, multiple deletions, multiple substitutions, or any combination thereof (e.g., single deletion together with multiple insertions). Such isolated nucleic acid molecules can contain a nucleic acid sequence encoding an amino acid sequence that shares at least 60, 65, 70, 75, 80, 85, 90, 95, 97, 98, or 99 percent sequence identity with a sequence set forth in SEQ ID NO:2, 10, 18, 26, 35, 37, 39, 41, 141, 160, or 161.

The invention provides multiple examples of isolated nucleic acid containing a nucleic acid sequence encoding an amino acid sequence having a variation of an amino acid sequence set forth in SEQ ID NO:2, 10, 18, 26, 35, 37, 39, 41, 141, 160, or 161. For example, FIG. 9 provides the amino acid sequence set forth in SEQ ID NO:2 aligned with three other amino acid sequences. Examples of variations of the sequence set forth in SEQ ID NO:2 include, without limitation, any variation of the sequence set forth in SEQ ID NO:2 provided in FIG. 9. Such variations are provided in FIG. 9 in that a comparison of the amino acid residue (or lack thereof) at a particular position of the sequence set forth in SEQ ID NO:2 with the amino acid residue (or lack thereof) at the same aligned position of any of the other three amino acid sequences of FIG. 9 (i.e., SEQ ID NOs:6, 7, and 8) provides a list of specific changes for the sequence set forth in SEQ ID NO:2. For example, the "k" at position 17 of SEQ ID NO:2 can be substituted with a "p" or "h" as indicated in FIG. 9. As also indicated in FIG. 9, the "v" at position 125 of SEQ ID NO:2 can be substituted with an "i" or "f". It will be appreciated that the sequence set forth in SEQ ID NO:2 can contain any number of variations as well as any combination of types of variations. For example, the sequence set forth in SEQ ID NO:2 can contain one variation provided in FIG. 9 or more than one (e.g., 2, 3, 4, 5, 6, 7, 8, 9, 10, 15, 20, 25, 50, 100, or more) of the variations provided in FIG. 9. It is noted that the amino acid sequences provided in FIG. 9 can be polypeptides having CoA transferase activity.

The invention also provides isolated nucleic acid containing a nucleic acid sequence encoding an amino acid sequence that contains a variant of a portion of the sequence set forth in SEQ ID NO:2 as depicted in FIG. 9 and described herein.

Likewise, FIG. 13 provides variations of SEQ ID NO:10 and portions thereof; FIG. 17 provides variations of SEQ ID NO:18 and portions thereof; FIG. 21 provides variations of SEQ ID NO:26 and portions thereof; FIG. 33 provides variations of SEQ ID NO:41 and portions thereof; FIGS. 40, 41, and 42 provide variations of SEQ ID NO:39; and FIG. 52 provides variations of SEQ ID NO:141 and portions thereof.

It is noted that codon preferences and codon usage tables for a particular species can be used to engineer isolated nucleic acid molecules that take advantage of the codon usage preferences of that particular species. For example, the isolated nucleic acid provided herein can be designed to have codons that are preferentially used by a particular organism of interest.

The invention also provides isolated nucleic acid that is at least about 12 bases in length (e.g., at least about 13, 14, 15, 16, 17, 18, 19, 20, 25, 30, 40, 50, 60, 100, 250, 500, 750, 1000, 1500, 2000, 3000, 4000, or 5000 bases in length) and hybridizes, under hybridization conditions, to the sense or antisense strand of a nucleic acid having the sequence set forth in SEQ ID NO:1, 9, 17, 25, 33, 34, 36, 38, 40, 42, 129, 140, 142, 162, or 163. The hybridization conditions can be moderately or highly stringent hybridization conditions.

The invention provides polypeptides that contain the entire amino acid sequence set forth in SEQ ID NO:2, 10, 18, 26, 35, 37, 39, 41, 141, 160, or 161. In addition, the invention provides polypeptides that contain a portion of the amino acid sequence set forth in SEQ ID NO:2, 10, 18, 26, 35, 37, 39, 41, 141, 160, or 161. For example, the invention provides polypeptides that contain a 15 amino acid sequence identical to any 15 amino acid sequence set forth in SEQ ID NO:2, 10, 18, 26, 35, 37, 39, 41, 141, 160, or 161 including, without limitation, the sequence starting at amino acid residue number 1 and ending at amino acid residue number 15, the sequence starting at amino acid residue number 2 and ending at amino acid residue number 16, the sequence starting at amino acid residue number 3 and ending at amino acid residue number 17, and so forth. It will be appreciated that the invention also provides polypeptides that contain an amino acid sequence that is greater than 15 amino acid residues (e.g., 16, 17, 18, 19, 20, 21, 22, 23, 24, 25, 26, 27, 28, 29, 30, or more amino acid residues) in length and identical to any portion of the sequence set forth in SEQ ID NO:2, 10, 18, 26, 35, 37, 39, 41, 141, 160, or 161. For example, the invention provides polypeptides that contain a 25 amino acid sequence identical to any 25 amino acid sequence set forth in SEQ ID NO:2, 10, 18, 26, 35, 37, 39, 41, 141, 160, or 161 including, without limitation, the sequence starting at amino acid residue number 1 and ending at amino acid residue number 25, the sequence starting at amino acid residue number 2 and ending at amino acid residue number 26, the sequence starting at amino acid residue number 3 and ending at amino acid residue number 27, and so forth. Additional examples include, without limitation, polypeptides that contain an amino acid sequence that is 50 or more amino acid residues (e.g., 100, 150, 200, 250, 300, or more amino acid residues) in length and identical to any portion of the sequence set forth in SEQ ID NO:2, 10, 18, 26, 35, 37, 39, 41, 141, 160, or 161. Such polypeptides can include, without limitation, those polypeptides containing a amino acid sequence represented in a single line of sequence depicted in FIG. 7, 11, 15, 19, 24, 26, 28, 30, or 50 since each line of sequence depicted in these figures, with the possible exception of the last line, provides an amino acid sequence containing at least 50 residues.

In addition, the invention provides polypeptides that an amino acid sequence having a variation of the amino acid sequence set forth in SEQ ID NO:2, 10, 18, 26, 35, 37, 39, 41, 141, 160, or 161. For example, the invention provides polypeptides containing an amino acid sequence set forth in SEQ ID NO:2, 10, 18, 26, 35, 37, 39, 41, 141, 160, or 161 that contains a single insertion, a single deletion, a single substitution, multiple insertions, multiple deletions, multiple substitutions, or any combination thereof (e.g., single deletion together with multiple insertions). Such polypeptides can contain an amino acid sequence that shares at least 60, 65, 70, 75, 80, 85, 90, 95, 97, 98, or 99 percent sequence identity with a sequence set forth in SEQ ID NO:2, 10, 18, 26, 35, 37, 39, 41, 141, 160, or 161.

The invention provides multiple examples of polypeptides containing an amino acid sequence having a variation of an amino acid sequence set forth in SEQ ID NO:2, 10, 18, 26, 35, 37, 39, 41, 141, 160, or 161. For example, FIG. 9 provides the amino acid sequence set forth in SEQ ID NO:2 aligned with three other amino acid sequences. Examples of variations of the sequence set forth in SEQ ID NO:2 include, without limitation, any variation of the sequence set forth in SEQ ID NO:2 provided in FIG. 9. Such variations are provided in FIG. 9 in that a comparison of the amino acid residue (or lack thereof) at a particular position of the sequence set forth in SEQ ID NO:2 with the amino acid residue (or lack thereof) at the same aligned position of any of the other three amino acid sequences of FIG. 9 (i.e., SEQ ID NOs:6, 7, and 8) provides a list of specific changes for the sequence set forth in SEQ ID NO:2. For example, the "k" at position 17 of SEQ ID NO:2 can be substituted with a "p" or "h" as indicated in FIG. 9. As also indicated in FIG. 9, the "v" at position 125 of SEQ ID NO:2 can be substituted with an "i" or "f". It will be appreciated that the sequence set forth in SEQ ID NO:2 can contain any number of variations as well as any combination of types of variations. For example, the sequence set forth in SEQ ID NO:2 can contain one variation provided in FIG. 9 or more than one (e.g., 2, 3, 4, 5, 6, 7, 8, 9, 10, 15, 20, 25, 50, 100, or more) of the variations provided in FIG. 9. It is noted that the amino acid sequences provided in FIG. 9 can be polypeptides having CoA transferase activity.

The invention also provides polypeptides containing an amino acid sequence that contains a variant of a portion of the sequence set forth in SEQ ID NO:2 as depicted in FIG. 9 and described herein.

Likewise, FIG. 13 provides variations of SEQ ID NO:10 and portions thereof; FIG. 17 provides variations of SEQ ID NO:18 and portions thereof; FIG. 21 provides variations of SEQ ID NO:26 and portions thereof; FIG. 33 provides variations of SEQ ID NO:41 and portions thereof, FIGS. 40, 41, and 42 provide variations of SEQ ID NO:39; and FIG. 52 provides variations of SEQ ID NO:141 and portions thereof.

Polypeptides having a variant amino acid sequence can retain enzymatic activity. Such polypeptides can be produced by manipulating the nucleotide sequence encoding a polypeptide using standard procedures such as site-directed mutagenesis or PCR. One type of modification includes the substitution of one or more amino acid residues for amino acid residues having a similar biochemical property. For example, a polypeptide can have an amino acid sequence set forth in SEQ ID NO:2, 10, 18, 26, 35, 37, 39, 41, 141, 160, or 161 with one or more conservative substitutions.

More substantial changes can be obtained by selecting substitutions that are less conservative than those in Table 1, i.e., selecting residues that differ more significantly in their effect on maintaining: (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue, e.g., serine or threonine, is substituted for (or by) a hydrophobic residue, e.g., leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine. The effects of these amino acid substitutions (or other deletions or additions) can be assessed for polypeptides having enzymatic activity by analyzing the ability of the polypeptide to catalyze the conversion of the same substrate as the related native polypeptide to the same product as the related native polypeptide. Accordingly, polypeptides having 5, 10, 20, 30, 40, 50 or less conservative substitutions are provided by the invention.

Polypeptides and nucleic acid encoding polypeptide can be produced by standard DNA mutagenesis techniques, for example, M13 primer mutagenesis. Details of these techniques are provided in Sambrook et al. (ed.), Molecular Cloning: A Laboratory Manual 2nd ed., vol. 1-3, Cold Spring Harbor Laboratory Press, Cold Spring, Harbor, N.Y., 1989, Ch. 15. Nucleic acid molecules can contain changes of a coding region to fit the codon usage bias of the particular organism into which the molecule is to be introduced.

Alternatively, the coding region can be altered by taking advantage of the degeneracy of the genetic code to alter the coding sequence in such a way that, while the nucleic acid sequence is substantially altered, it nevertheless encodes a polypeptide having an amino acid sequence identical or substantially similar to the native amino acid sequence. For example, the ninth amino acid residue of the sequence set forth in SEQ ID NO: 2 is alanine, which is encoded in the open reading frame by the nucleotide codon triplet GCT. Because of the degeneracy of the genetic code, three other nucleotide codon triplets—GCA, GCC, and GCG—also code for alanine. Thus, the nucleic acid sequence of the open reading frame can be changed at this position to any of these three codons without affecting the amino acid sequence of the encoded polypeptide or the characteristics of the polypeptide. Based upon the degeneracy of the genetic code, nucleic acid variants can be derived from a nucleic acid sequence disclosed herein using a standard DNA mutagenesis techniques as described herein, or by synthesis of nucleic acid sequences. Thus, this invention also encompasses nucleic acid molecules that encode the same polypeptide but vary in nucleic acid sequence by virtue of the degeneracy of the genetic code.

IV. Methods of Making 3-HP and Other Organic Acids

Each step provided in the pathways depicted in FIGS. 1-5, 43-44, 54, and 55 can be performed within a cell (in vivo) or outside a cell (in vitro, e.g., in a container or column). Additionally, the organic acid products can be generated through a combination of in vivo synthesis and in vitro synthesis. Moreover, the in vitro synthesis step, or steps, can be via chemical reaction or enzymatic reaction.

For example, a microorganism provided herein can be used to perform the steps provided in FIG. 1, or an extract containing polypeptides having the indicated enzymatic activities can be used to perform the steps provided in FIG. 1. In addition, chemical treatments can be used to perform the conversions provided in FIGS. 1-5, 43-44, 54, and 55. For example, acrylyl-CoA can be converted into acrylate by hydrolysis. Other chemical treatments include, without limitation, trans esterification to convert acrylate into an acrylate ester.

Carbon sources suitable as starting points for bioconversion include carbohydrates and synthetic intermediates. Examples of carbohydrates which cells are capable of metabolizing to pyruvate include sugars such as dextrose, triglycerides, and fatty acids.

Additionally, intermediate chemical products can be starting points. For example, acetic acid and carbon dioxide can be introduced into a fermentation broth. Acetyl-CoA, malonyl-CoA, and 3-HP can be sequentially produced using a polypeptide having CoA synthase activity, a polypeptide having acetyl-CoA carboxylase activity, and a polypeptide having malonyl-CoA reductase activity. Other useful intermediate chemical starting points can include propionic acid, acrylic acid, lactic acid, pyruvic acid, and β-alanine.

A. Expression of Polypeptides

The polypeptides described herein can be produced individually in a host cell or in combination in a host cell. Moreover, the polypeptides having a particular enzymatic activity can be a polypeptide that is either naturally-occurring or non-naturally-occurring. A naturally-occurring polypeptide is any polypeptide having an amino acid sequence as found in nature, including wild-type and polymorphic polypeptides. Such naturally-occurring polypeptides can be obtained from any species including, without limitation, animal (e.g., mammalian), plant, fungal, and bacterial species. A non-naturally-occurring polypeptide is any polypeptide having an amino acid sequence that is not found in nature. Thus, a non-naturally-occurring polypeptide can be a mutated version of a naturally-occurring polypeptide, or an engineered polypeptide. For example, a non-naturally-occurring polypeptide having 3-hydroxypropionyl-CoA dehydratase activity can be a mutated version of a naturally-occurring polypeptide having 3-hydroxypropionyl-CoA dehydratase activity that retains at least some 3-hydroxypropionyl-CoA dehydratase activity. A polypeptide can be mutated by, for example, sequence additions, deletions, substitutions, or combinations thereof.

The invention provides genetically modified cells that can be used to perform one or more steps of the steps in the metabolic pathways described herein or the genetically modified cells can be used to produce the disclosed polypeptides for subsequent use in vitro. For example, an individual microorganism can contain exogenous nucleic acid such that each of the polypeptides necessary to perform the steps depicted in FIG. 1, 2, 3, 4, 5, 43, 44, 54, or 55 are expressed. It is important to note that such cells can contain any number of exogenous nucleic acid molecules. For example, a particular cell can contain six exogenous nucleic acid molecules with each one encoding one of the six polypeptides necessary to convert lactate into 3-HP as depicted in FIG. 1, or a particular cell can endogenously produce polypeptides necessary to convert lactate into acrylyl-CoA while containing exogenous nucleic acid that encodes polypeptides necessary to convert acrylyl-CoA into 3-HP.

In addition, a single exogenous nucleic acid molecule can encode one or more than one polypeptide. For example, a single exogenous nucleic acid molecule can contain sequences that encode three different polypeptides. Further, the cells described herein can contain a single copy, or multiple copies (e.g., about 5, 10, 20, 35, 50, 75, 100 or 150 copies), of a particular exogenous nucleic acid molecule. For example, a particular cell can contain about 50 copies of the constructs depicted in FIG. 34, 35, 36, 37, 38, or 45. Again, the cells described herein can contain more than one particular exogenous nucleic acid molecule. For example, a particular cell can contain about 50 copies of exogenous nucleic acid molecule X as well as about 75 copies of exogenous nucleic acid molecule Y.

In another embodiment, a cell within the scope of the invention can contain an exogenous nucleic acid molecule that encodes a polypeptide having 3-hydroxypropionyl-CoA dehydratase activity. Such cells can have any level of 3-hydroxypropionyl-CoA dehydratase activity. For example, a cell containing an exogenous nucleic acid molecule that encodes a polypeptide having 3-hydroxypropionyl-CoA dehydratase activity can have 3-hydroxypropionyl-CoA dehydratase activity with a specific activity greater than about 1 mg 3-HP-CoA formed per gram dry cell weight per hour (e.g., greater than about 10, 20, 30, 40, 50, 60, 70, 80, 90, 100, 125, 150, 200, 250, 300, 350, 400, 500, or more mg 3-HP-CoA formed per gram dry cell weight per hour). Alternatively, a cell can have 3-hydroxypropionyl-CoA dehydratase activity such that a cell extract from $1 \times 10^6$ cells has a specific activity greater than about 1 µg 3-HP-CoA formed per mg total protein per 10 minutes (e.g., greater than about 10, 20, 30, 40, 50, 60, 70, 80, 90, 100, 125, 150, 200, 250, 300, 350, 400, 500, or more µg 3-HP-CoA formed per mg total protein per 10 minutes).

A nucleic acid molecule encoding a polypeptide having enzymatic activity can be identified and obtained using any method such as those described herein. For example, nucleic acid molecules that encode a polypeptide having enzymatic activity can be identified and obtained using common molecular cloning or chemical nucleic acid synthesis procedures and techniques, including PCR. In addition, standard nucleic acid sequencing techniques and software programs that translate nucleic acid sequences into amino acid sequences based on the genetic code can be used to determine whether or not a particular nucleic acid has any sequence homology with known enzymatic polypeptides. Sequence alignment software such as MEGALIGN® (DNASTAR, Madison, Wis., 1997) can be used to compare various sequences. In addition, nucleic acid molecules encoding known enzymatic polypeptides can be mutated using common molecular cloning techniques (e.g., site-directed mutagenesis). Possible mutations include, without limitation, deletions, insertions, and base substitutions, as well as combinations of deletions, insertions, and base substitutions. Further, nucleic acid and amino acid databases (e.g., GenBank®) can be used to identify a nucleic acid sequence that encodes a polypeptide having enzymatic activity. Briefly, any amino acid sequence having some homology to a polypeptide having enzymatic activity, or any nucleic acid sequence having some homology to a sequence encoding a polypeptide having enzymatic activity can be used as a query to search GenBank®. The identified polypeptides then can be analyzed to determine whether or not they exhibit enzymatic activity.

In addition, nucleic acid hybridization techniques can be used to identify and obtain a nucleic acid molecule that encodes a polypeptide having enzymatic activity. Briefly, any nucleic acid molecule that encodes a known enzymatic polypeptide, or fragment thereof, can be used as a probe to identify a similar nucleic acid molecules by hybridization under conditions of moderate to high stringency. Such similar nucleic acid molecules then can be isolated, sequenced, and analyzed to determine whether the encoded polypeptide has enzymatic activity.

Expression cloning techniques also can be used to identify and obtain a nucleic acid molecule that encodes a polypeptide having enzymatic activity. For example, a substrate known to interact with a particular enzymatic polypeptide can be used to screen a phage display library containing that enzymatic polypeptide. Phage display libraries can be generated as described elsewhere (Burritt et al., *Anal. Biochem.* 238:1-13 (1990)), or can be obtained from commercial suppliers such as Novagen (Madison, Wis.).

Further, polypeptide sequencing techniques can be used to identify and obtain a nucleic acid molecule that encodes a polypeptide having enzymatic activity. For example, a purified polypeptide can be separated by gel electrophoresis, and its amino acid sequence determined by, for example, amino acid microsequencing techniques. Once determined, the amino acid sequence can be used to design degenerate oligonucleotide primers. Degenerate oligonucleotide primers can be used to obtain the nucleic acid encoding the polypeptide by PCR. Once obtained, the nucleic acid can be sequenced, cloned into an appropriate expression vector, and introduced into a microorganism.

Any method can be used to introduce an exogenous nucleic acid molecule into a cell. In fact, many methods for introducing nucleic acid into microorganisms such as bacteria and yeast are well known to those skilled in the art. For example, heat shock, lipofection, electroporation, conjugation, fusion of protoplasts, and biolistic delivery are common methods for introducing nucleic acid into bacteria and yeast cells. See, e.g., Ito et al., *J. Bacterol.* 153:163-168 (1983); Durrens et al., *Curr. Genet.* 18:7-12 (1990); and Becker and Guarente, *Methods in Enzymology* 194:182-187 (1991).

An exogenous nucleic acid molecule contained within a particular cell of the invention can be maintained within that cell in any form. For example, exogenous nucleic acid molecules can be integrated into the genome of the cell or maintained in an episomal state. In other words, a cell of the invention can be a stable or transient transformant. Again, a microorganism described herein can contain a single copy, or multiple copies (e.g., about 5, 10, 20, 35, 50, 75, 100 or 150 copies), of a particular exogenous nucleic acid molecule as described herein.

Methods for expressing an amino acid sequence from an exogenous nucleic acid molecule are well known to those skilled in the art. Such methods include, without limitation, constructing a nucleic acid such that a regulatory element promotes the expression of a nucleic acid sequence that encodes a polypeptide. Typically, regulatory elements are DNA sequences that regulate the expression of other DNA sequences at the level of transcription. Thus, regulatory elements include, without limitation, promoters, enhancers, and the like. Any type of promoter can be used to express an amino acid sequence from an exogenous nucleic acid molecule. Examples of promoters include, without limitation, constitutive promoters, tissue-specific promoters, and promoters responsive or unresponsive to a particular stimulus (e.g., light, oxygen, chemical concentration, and the like). Moreover, methods for expressing a polypeptide from an exogenous nucleic acid molecule in cells such as bacterial cells and yeast cells are well known to those skilled in the art. For example, nucleic acid constructs that are capable of expressing exogenous polypeptides within *E. coli* are well known. See, e.g., Sambrook et al., Molecular cloning: a laboratory manual, Cold Spring Harbour Laboratory Press, New York, USA, second edition (1989).

B. Production of Organic Acids and Related Products Via Host Cells

The nucleic acid and amino acid sequences provided herein can be used with cells to produce 3-HP and/or other organic compounds such as 1,3-propanediol, acrylic acid, polymerized acrylate, esters of acrylate, esters of 3-HP, and polymerized 3-HP. Such cells can be from any species including those listed within the taxonomy web pages at the National Institute of Health sponsored by the United States government (www.ncbi.nlm.nih.gov). The cells can be eukaryotic or prokaryotic. For example, genetically modified cells of the invention can be mammalian cells (e.g., human, murine, and bovine cells), plant cells (e.g., corn, wheat, rice, and soybean cells), fungal cells (e.g., *Aspergillus* and *Rhizopus* cells), yeast cells, or bacterial cells (e.g., *Lactobacillus, Lactococcus, Bacillus, Escherichia*, and *Clostridium* cells). A cell of the invention also can be a microorganism. The term "microorganism" as used herein refers to any microscopic organism including, without limitation, bacteria, algae, fungi, and protozoa. Thus, *E. coli, S. cerevisiae, Kluveromyces lactis, Candida blankii, Candida rugosa*, and *Pichia postoris* are considered microorganisms and can be used as described herein.

Typically, a cell of the invention is genetically modified such that a particular organic compound is produced. In one embodiment, the invention provides cells that make 3-HP from PEP. Examples biosynthetic pathways that may be used by cells to make 3-HP are shown in FIGS. 1-5, 43-44, 54, and 55.

Generally, cells that are genetically modified to synthesize a particular organic compound contain one or more exogenous nucleic acid molecules that encode polypeptides having specific enzymatic activities. For example, a microorganism can contain exogenous nucleic acid that encodes a polypeptide having 3-hydroxypropionyl-CoA dehydratase activity. In this case, acrylyl-CoA can be converted into 3-hydroxypropionic acid-CoA which can lead to the production of 3-HP. It is noted that a cell can be given an exogenous nucleic acid molecule that encodes a polypeptide having an enzymatic activity that catalyzes the production of a compound not normally produced by that cell. Alternatively, a cell can be given an exogenous nucleic acid molecule that encodes a polypeptide having an enzymatic activity that catalyzes the production of a compound that is normally produced by that cell. In this case, the genetically modified cell can produce more of the compound, or can produce the compound more efficiently, than a similar cell not having the genetic modification.

In one embodiment, the invention provides a cell containing an exogenous nucleic acid molecule that encodes a polypeptide having enzymatic activity that leads to the formation of 3-HP. It is noted that the produced 3-HP can be secreted from the cell, eliminating the need to disrupt cell membranes to retrieve the organic compound. Typically, the cell of the invention produces 3-HP with the concentration being at least about 100 mg per L (e.g., at least about 1 g/L, 5 g/L, 10 g/L, 25 g/L, 50 g/L, 75 g/L, 80 g/L, 90 g/L, 100 g/L, or 120 g/L). When determining the yield of an organic compound such as 3-HP for a particular cell, any method can be used. See, e.g., *Applied Environmental Microbiology* 59(12): 4261-4265 (1993). Typically, a cell within the scope of the invention such as a microorganism catabolizes a hexose carbon source such as glucose. A cell, however, can catabolize a variety of carbon sources such as pentose sugars (e.g., ribose, arabinose, xylose, and lyxose), fatty acids, acetate, or glycerols. In other words, a cell within the scope of the invention can utilize a variety of carbon sources.

As described herein, a cell within the scope of the invention can contain an exogenous nucleic acid molecule that encodes a polypeptide having enzymatic activity that leads to the formation of 3-HP or other organic compounds such as 1,3-propanediol, acrylic acid, poly-acrylate, acrylate-esters, 3-HP-esters, and poly-3-HP. Methods of identifying cells that contain exogenous nucleic acid are well known to those skilled in the art. Such methods include, without limitation, PCR and nucleic acid hybridization techniques such as Northern and Southern analysis (see hybridization described herein). In some cases, immunohisto-chemistry and biochemical techniques can be used to determine if a cell contains a particular nucleic acid by detecting the expression of the polypeptide encoded by that particular nucleic acid molecule. For example, an antibody having specificity for a polypeptide can be used to determine whether or not a particular cell contains nucleic acid encoding that polypeptide. Further, biochemical techniques can be used to determine if a cell contains a particular nucleic acid molecule encoding a polypeptide having enzymatic activity by detecting an organic product produced as a result of the expression of the polypeptide having enzymatic activity. For example, detection of 3-HP after introduction of exogenous nucleic acid that encodes a polypeptide having 3-hydroxypropionyl-CoA dehydratase activity into a cell that does not normally express such a polypeptide can indicate that that cell not only contains the introduced exogenous nucleic acid molecule but also expresses the encoded polypeptide from that introduced exogenous nucleic acid molecule. Methods for detecting specific enzymatic activities or the presence of particular organic products are well known to those skilled in the art. For example, the presence of an organic compound such as 3-HP can be determined as described elsewhere. See, Sullivan and Clarke, *J. Assoc. Offic. Agr. Chemists,* 38:514-518 (1955).

C. Cells with Reduced Polypeptide Activity

The invention also provides genetically modified cells having reduced polypeptide activity. The term "reduced" as used herein with respect to a cell and a particular polypeptide's activity refers to a lower level of activity than that measured in a comparable cell of the same species. For example, a particular microorganism lacking enzymatic activity X is considered to have reduced enzymatic activity X if a comparable microorganism has at least some enzymatic activity X. It is noted that a cell can have the activity of any type of polypeptide reduced including, without limitation, enzymes, transcription factors, transporters, receptors, signal molecules, and the like. For example, a cell can contain an exogenous nucleic acid molecule that disrupts a regulatory and/or coding sequence of a polypeptide having pyruvate decarboxylase activity or alcohol dehydrogenase activity. Disrupting pyruvate decarboxylase and/or alcohol dehydrogenase expression can lead to the accumulation of lactate as well as products produced from lactate such as 3-HP, 1,3-propanediol, acrylic acid, poly-acrylate, acrylate-esters, 3-HP-esters, and poly-3-HP. It is also noted that reduced polypeptide activities can be the result of lower polypeptide concentration, lower specific activity of a polypeptide, or combinations thereof. Many different methods can be used to make a cell having reduced polypeptide activity. For example, a cell can be engineered to have a disrupted regulatory sequence or polypeptide-encoding sequence using common mutagenesis or knock-out technology. See, e.g., Methods in Yeast Genetics (1997 edition), Adams, Gottschling, Kaiser, and Stems, Cold Spring Harbor Press (1998). Alternatively, antisense technology can be used to reduce the activity of a particular polypeptide. For example, a cell can be engineered to contain a cDNA that encodes an antisense molecule that prevents a polypeptide from being translated. The term "antisense molecule" as used herein encompasses any nucleic acid molecule or nucleic acid analog (e.g., peptide nucleic acids) that contains a sequence that corresponds to the coding strand of an endogenous polypeptide. An antisense molecule also can have flanking sequences (e.g., regulatory sequences). Thus, antisense molecules can be ribozymes or antisense oligonucleotides. A ribozyme can have any general structure including, without limitation, hairpin, hammerhead, or axhead structures, provided the molecule cleaves RNA. Further, gene silencing can be used to reduce the activity of a particular polypeptide.

A cell having reduced activity of a polypeptide can be identified using any method. For example, enzyme activity assays such as those described herein can be used to identify cells having a reduced enzyme activity.

A polypeptide having (1) the amino acid sequence set forth in SEQ ID NO:39 (the OS17 polypeptide) or (2) an amino acid sequence sharing at least about 60 percent sequence identity with the amino acid sequence set forth in SEQ ID NO:39 can have three functional domains: a domain having CoA-synthatase activity, a domain having 3-HP-CoA dehydratase activity, and a domain having CoA-reductase activity. Such polypeptides can be selectively modified by mutating and/or deleting domains such that one or two of the enzymatic activities are reduced. Reducing the dehydratase activity of the OS17 polypeptide can cause acrylyl-CoA to be created from propionyl-CoA. The acrylyl-CoA then can be contacted with a polypeptide having CoA hydrolase activity to produce acrylate from propionate (FIG. 43). Similarly, acrylyl-CoA can be created from 3-HP by using, for example, an OS17 polypeptide having reduced reductase activity.

D. Production of Organic Acids and Related Products Via In Vitro Techniques

In addition, purified polypeptides having enzymatic activity can be used alone or in combination with cells to produce 3-HP or other organic compounds such as 1,3-propanediol, acrylic acid, polymerized acrylate, esters of acrylate, esters of 3-HP, and polymerized 3-HP. For example, a preparation containing a substantially pure polypeptide having 3-hydroxypropionyl-CoA dehydratase activity can be used to catalyze the formation of 3-HP-CoA, a precursor to 3-HP. Further, cell-free extracts containing a polypeptide having enzymatic activity can be used alone or in combination with purified polypeptides and/or cells to produce 3-HP. For example, a cell-free extract containing a polypeptide having CoA transferase activity can be used to form lactyl-CoA, while a microorganism containing polypeptides have the enzymatic activities necessary to catalyze the reactions needed to form 3-HP from lactyl-CoA can be used to produce 3-HP. Any method can be used to produce a cell-free extract. For example, osmotic shock, sonication, and/or a repeated freeze-thaw cycle followed by filtration and/or centrifugation can be used to produce a cell-free extract from intact cells.

It is noted that a cell, purified polypeptide, and/or cell-free extract can be used to produce 3-HP that is, in turn, treated chemically to produce another compound. For example, a microorganism can be used to produce 3-HP, while a chemical process is used to modify 3-HP into a derivative such as polymerized 3-HP or an ester of 3-HP. Likewise, a chemical process can be used to produce a particular compound that is, in turn, converted into 3-HP or other organic compound (e.g., 1,3-propanediol, acrylic acid, polymerized acrylate, esters of acrylate, esters of 3-HP, and polymerized 3-HP) using a cell, substantially pure polypeptide, and/or cell-free extract described herein. For example, a chemical process can be used to produce acrylyl-CoA, while a microorganism can be used convert acrylyl-CoA into 3-HP.

E. Fermentation of Cells to Produce Organic Acids

Typically, 3-HP is produced by providing a production cell, such as a microorganism, and culturing the microorganism with culture medium such that 3-HP is produced. In general, the culture media and/or culture conditions can be such that the microorganisms grow to an adequate density and produce 3-HP efficiently. For large-scale production processes, any method can be used such as those described elsewhere (Manual of Industrial Microbiology and Biotechnology, $2^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing appropriate culture medium with, for example, a glucose carbon source is inoculated with a particular microorganism. After inoculation, the microorganisms are incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank. For example, the first tank can contain medium with xylose, while the second tank contains medium with glucose.

Once transferred, the microorganisms can be incubated to allow for the production of 3-HP. Once produced, any method can be used to isolate the 3-HP. For example, common separation techniques can be used to remove the biomass from the broth, and common isolation procedures (e.g., extraction, distillation, and ion-exchange procedures) can be used to obtain the 3-HP from the microorganism-free broth. In addition, 3-HP can be isolated while it is being produced, or it can be isolated from the broth after the product production phase has been terminated.

F. Products Created from the Disclosed Biosynthetic Routes

The organic compounds produced from any of the steps provided in FIGS. 1-5, 43-44, 54, and 55 can be chemically converted into other organic compounds. For example, 3-HP can be hydrogenated to form 1,3 propanediol, a valuable polyester monomer. Hydrogenating an organic acid such as 3-HP can be performed using any method such as those used to hydrogenate succinic acid and/or lactic acid. For example, 3-HP can be hydrogenated using a metal catalyst. In another example, 3-HP can be dehydrated to form acrylic acid. Any method can be used to perform a dehydration reaction. For example, 3-HP can be heated in the presence of a catalyst (e.g., a metal or mineral acid catalyst) to form acrylic acid. Propanediol also can be created using polypeptides having oxidoreductase activity (e.g., enzymes is the 1.1.1.- class of enzymes) in vitro or in vivo.

V. Overview of Methodology Used to Create Biosynthetic Pathways that Make 3-HP from PEP The invention provides methods of making 3-HP and related products from PEP via the use of biosynthetic pathways. Illustrative examples include methods involving the production of 3-HP via a lactate intermediate, a malonyl-CoA intermediate, and a 13-alanine intermediate.

A. Biosynthetic Pathway for Making 3-HP Through a Lactic Acid Intermediate

A biosynthetic pathway that allows for the production of 3-HP from PEP was constructed (FIG. 1). This pathway involved using several polypeptides that were cloned and expressed as described herein. *M. elsdenii* cells (ATCC 17753) were used as a source of genomic DNA. Primers were used to identify and clone a nucleic acid sequence encoding a polypeptide having CoA transferase activity (SEQ ID NO: 1). The polypeptide was subsequently tested for enzymatic activity and found to have CoA transferase activity.

Similarly, PCR primers were used to identify nucleic acid sequences from *M. elsdenii* genomic DNA that encoded an E1 activator, E2 α, and E2 β polypeptides (SEQ ID NOs: 9, 17, and 25, respectively). These polypeptides were subsequently shown to have lactyl-CoA dehydratase activity.

*Chloroflexus aurantiacus* cells (ATCC 29365) were used as a source of genomic DNA. Initial cloning lead to the identification of nucleic acid sequences: OS17 (SEQ ID NO: 129) and OS19 (SEQ ID NO: 40). Subsequence assays revealed that OS17 encodes a polypeptide having CoA synthase activity, dehydratase activity, and dehydrogenase activity (propionyl-CoA synthatase). Subsequence assays also revealed that OS19 encodes a polypeptide having 3-hydroxypropionyl-CoA dehydratase activity (also referred to as acrylyl-CoA hydratase activity).

Several operons were constructed for use in *E. coli*. These operons allow for the production of 3-HP in bacterial cells. Additional experiments allowed for the expression of these polypeptide is yeast, which can be used to produce 3-HP.

B. Biosynthetic Pathway for Making 3-HP Through a Malonyl-CoA Intermediate

Another pathway leading to the production of 3-HP from PEP was constructed. This pathway used a polypeptide having acetyl CoA carboxylase activity that was isolated from *E. coli* (Example 9), and a polypeptide having malonyl-CoA reductase activity that was isolated from *Chloroflexus aurantacius* (Example 10). The combination of these two polypeptides allows for the production of 3-HP from acetyl-CoA (FIG. 44).

Nucleic acid encoding a polypeptide having malonyl-CoA reductase activity (SEQ ID NO:140) was cloned, sequenced, and expressed. The polypeptide having malonyl-CoA reductase activity was then used to make 3-HP.

C. Biosynthetic Pathways for Making 3-HP Through a β-alanine Intermediate

In general, prokaryotes and eukaryotes metabolize glucose via the Embden-Meyerhof-Parnas pathway to PEP, a central metabolite in carbon metabolism. The PEP generated from glucose is either carboxylated to oxaloacetate or is converted to pyruvate. Carboxylation of PEP to oxaloacetate can be catalyzed by a polypeptide having PEP carboxylase activity, a polypeptide having PEP carboxykinase activity, or a polypeptide having PEP transcarboxylase activity. Pyruvate that is generated from PEP by a polypeptide having pyruvate kinase activity can also be converted to oxaloacetate by a polypeptide having pyruvate carboxylase activity.

Oxaloacetate generated either from PEP or pyruvate can act as a precursor for production of aspartic acid. This conversion can be carried out by a polypeptide having aspartate aminotransferase activity, which transfers an amino group from glutamate to oxaloacetate. Glutamate consumed in this reaction can be regenerated by the action of a polypeptide having glutamate dehydrogenase activity or by the action of a polypeptide having 4,4-aminobutyrate aminotransferase activity. The decarboxylation of aspartate to β-alanine is catalyzed by a polypeptide having aspartate decarboxylase activity. β-alanine produced through this biochemistry can be converted to 3-HP via two possible pathways. These pathways are provided in FIGS. 54 and 55.

The steps involved in the production of β-alanine can be the same for both pathways. These steps can be accomplished by endogenous polypeptides in the host cells which convert PEP to β-alanine, or these steps can be accomplished with recombinant DNA technology using known polypeptides such as polypeptides having PEP-carboxykinase activity (4.1.1.32), aspartate aminotransferase activity (2.6.1.1), and aspartate alpha-decarboxylase activity (4.1.1.11).

As depicted in FIG. 54, a polypeptide having CoA transferase activity (e.g., a polypeptide having a sequence set forth in SEQ ID NO:2) can be used to convert β-alanine to β-alanyl-CoA. β-alanyl-CoA can be converted to acrylyl-CoA via a polypeptide having β-alanyl-CoA ammonia lyase activity (e.g., a polypeptide having a sequence set forth in SEQ ID NO:160). Acrylyl-CoA can be converted to 3-HP-CoA using a polypeptide having 3-HP-CoA dehydratase activity (e.g., a polypeptide having a sequence set forth in SEQ ID NO:40). 3-HP-CoA can be converted into 3-HP via a polypeptide having CoA transferase activity (e.g., a polypeptide having a sequence set forth in SEQ ID NO:2).

As depicted in FIG. 55, a polypeptide having 4,4-aminobutyrate aminotransferase activity (2.6.1.19) can be used to convert β-alanine into malonate semialdehyde. The malonate semialdehyde can be converted into 3-HP using either a polypeptide having 3-hydroxypropionate dehydrogenase activity (1.1.1.159) or a polypeptide having 3-hydroxyisobutyrate dehydrogenase activity.

EXAMPLES

Example 1

Cloning Nucleic Acid Molecules that Encode a Polypeptide Having CoA Transferase Activity Genomic DNA was isolated from *Megasphaera elsdenii* cells (ATCC 17753) grown in 1053 Reinforced *Clostridium* media under anaerobic conditions at 37° C. in roll tubes for 12-14 hours. Once grown, the cells were pelleted, washed with 5 mL of a 10 mM Tris solution, and repelleted. The pellet was resuspended in 1 mL of Gentra Cell Suspension Solution to which 14.2 mg of lysozyme and 4 µL of 20 mg/mL proteinase K solution was added. The cell suspension was incubated at 37° C. for 30 minutes. The genomic DNA was than isolated using a Gentra Genomic DNA Isolation Kit following the provided protocol. The precipitated genomic DNA was spooled and air-dried for 10 minutes. The genomic DNA was suspended in 500 µL of a 10 mM Tris solution and stored at 4° C.

Two degenerate forward (CoAF1 and CoAF2) and three degenerate reverse (CoAR1, CoAR2, and CoAR3) PCR primers were designed based on conserved acetoacetyl CoA transferase and propionate CoA transferase sequences (CoAF1 5'-GAAWSCGGYSCNATYGGYGG-3', SEQ ID NO: 49; CoAF2 5'-TTYTGYGGYRSBTTYACBGCWGG-3', SEQ ID NO: 50; CoAR1 5'-CCWGCVGTRAAVSYRC-CRCARAA-3', SEQ ID NO: 51; CoAR2 5'-AARACDSM-RCGTTCVGTRATRTA-3', SEQ ID NO: 52; and CoAR3 5'-TCRAYRCCSGGWGCRAYTTC-3', SEQ ID NO: 53). The primers were used in all logical combinations in PCR using Taq polymerase (Roche Molecular Biochemicals, Indianapolis, Ind.) and 1 ng of genomic DNA per µL reaction mix. PCR was conducted using a touchdown PCR program with 4 cycles at an annealing temperature of 59° C., 4 cycles at 57° C., 4 cycles at 55° C., and 18 cycles at 52° C. Each cycle used an initial 30-second denaturing step at 94° C. and a 3 minute extension at 72° C. The program had an initial denaturing step for 2 minutes at 94° C. and a final extension step of 4 minutes at 72° C. Time allowed for annealing was 45 seconds. The amounts of PCR primer used in the reactions were increased 2-8 fold above typical PCR amounts depending on the amount of degeneracy in the 3' end of the primer. In addition, separate PCR reactions containing each individual primer were made to identify PCR products resulting from single degenerate primers. Each PCR product (25 µL) was separated by electrophoresis using a 1% TAE (Tris-acetate-EDTA) agarose gel.

The CoAF1-CoAR2, CoAF1-CoAR3, CoAF2-CoAR2, and CoAF2-CoAR3 combinations produced a band of 423, 474, 177, and 228 bp, respectively. These bands matched the sizes based on other CoA transferase sequences. No band was visible from the individual primer control reactions. The CoAF1-CoAR3 fragment (474 bp) was isolated and purified using a Qiagen Gel Extraction Kit (Qiagen Inc., Valencia, Calif.). Four µL of the purified band was ligated into pCRII vector and transformed into TOP10 *E. coli* cells by heat-shock using a TOPO cloning procedure (Invitrogen, Carlsbad, Calif.). Transformations were plated on LB media containing 100 µg/mL of ampicillin (Amp) and 50 µg/mL of 5-Bromo-4-Chloro-3-Indolyl-B-D-Galactopyranoside (X-gal). Single, white colonies were plated onto fresh media and screened in a PCR reaction using the CoAF1 and CoAR3 primers to confirm the presence of the insert.

Plasmid DNA obtained using a QiaPrep Spin Miniprep Kit (Qiagen, Inc) was quantified and used for DNA sequencing with M13R and M13F primers. Sequence analysis revealed that the CoAF1-CoAR3 fragment shared sequence similarity with acetoacetyl CoA transferase sequences.

Genome walking was performed to obtain the complete coding sequence. The following primers for genome walking in both upstream and downstream directions were designed using the portion of the 474 bp CoAF1-CoAR3 fragment sequence that was internal to the degenerate primers (COAGSP1F 5'-GAATGTTTACTTCTGCGGCACCT-TCAC-3', SEQ ID NO:54; COAGSP2F 5'-GACCAGAT-CACTTTCAACGGTTCCTATG-3', SEQ ID NO:55; COAGSP1R 5'-GCATAGGAACCGTTGAAAGT-GATCTGG-3', SEQ ID NO:56; and COAGSP2R 5'-GTTAG-TACCGAACTTGCTGACGTTGATG-3', SEQ ID NO:57). The COAGSP1F and COAGSP2F primers face downstream, while the COAGSP1R and COAGSP2R primers face upstream. In addition, the COAGSP2F and COAGSP2R primers are nested inside the COAGSP1F and COAGSP1R primers. Genome walking was performed using the Universal Genome Walking kit (ClonTech Laboratories, Inc., Palo Alto, Calif.) with the exception that additional libraries were generated with enzymes Nru I, Sca I, and Hinc II. First round PCR was conducted in a Perkin Elmer 2400 Thermocycler with 7 cycles of 2 seconds at 94° C. and 3 minutes at 72° C., and 36 cycles of 2 seconds at 94° C. and 3 minutes at 65° C. with a final extension at 65° C. for 4 minutes. Second round PCR used 5 cycles of 2 seconds at 94° C. and 3 minutes at 72° C., and 20 cycles of 2 seconds at 94° C. and 3 minutes at 65° C. with a final extension at 65° C. for 4 minutes. The first and second round product (20 µL) was separated by electrophoresis on a 1% TAE agarose gel. Amplification products were obtained with the Stu I library for the reverse direction. The second round product of 1.5 Kb from this library was gel purified, cloned, and sequenced. Sequence analysis revealed that the sequence derived from genome walking overlapped with the CoAF1-CoAR3 fragment and shared sequence similarity with other sequences such as acetoacetyl CoA transferase sequences (FIGS. 8-9).

Nucleic acid encoding the CoA transferase (propionyl-CoA transferase or pct) from *Megasphaera elsdenii* was PCR amplified from chromosomal DNA using following PCR program: 25 cycles of 95° C. for 30 seconds to denature, 50° C. for 30 seconds to anneal, and 72° C. for 3 minutes for extension (plus 2 seconds per cycle). The primers used were designated PCT-1.114 (5'-ATGAGAAAAGTAGAAATCAT-TAC-3'; SEQ ID NO:58) and PCT-2.2045 (5'-GGCGGAAGTTGACGATAATG-3'; SEQ ID NO:59). The resulting PCR product (about 2 kb as judged by agarose gel electrophoresis) was purified using a Qiagen PCR purification kit (Qiagen Inc., Valencia, Calif.). The purified product was ligated to pETBlue-1 using the Perfectly Blunt cloning Kit (Novagen, Madison, Wis.). The ligation reaction was transformed into NovaBlue chemically competent cells (Novagen, Madison, Wis.) that were spread on LB agar plates supplemented with 50 µg/mL carbenicillin, 40 µg/mL IPTG, and 40 µg/mL X-Gal. White colonies were isolated and screened for the presence of inserts by restriction mapping. Isolates with the correct restriction pattern were sequenced from each end using the primers pETBlueUP and pETBlue-DOWN (Novagen) to confirm the sequence at the ligation points.

The plasmid was transformed into Tuner (DE3) pLacI chemically competent cells (Novagen, Madison, Wis.), and expression from the construct tested. Briefly, a culture was grown overnight to saturation and diluted 1:20 the following morning in fresh LB medium with the appropriate antibiotics. The culture was grown at 37° C. with aeration to an $OD_{600}$ of about 0.6. The culture was induced with IPTG at a final concentration of 100 µM. The culture was incubated for an additional two hours at 37° C. with aeration. Aliquots were taken pre-induction and 2 hours post-induction for SDS-PAGE analysis. A band of the expected molecular weight (55,653 Daltons predicted from the sequence) was observed after IPTG treatment. This band was not observed in cells containing a plasmid lacking the nucleic acid encoding the transferase.

Cell free extracts were prepared to assess enzymatic activity. Briefly, the cells were harvested by centrifugation and disrupted by sonication. The sonicated cell suspension was centrifuged to remove cell debris, and the supernatant was used in the assays.

Transferase activity was measured in the following assay. The assay mixture used contained 100 mM potassium phosphate buffer (pH 7.0), 200 mM sodium acetate, 1 mM dithiobisnitrobenzoate (DTNB), 500 µM oxaloacetate, 25 µM CoA-ester substrate, and 3 µg/mL citrate synthase. If present, the CoA transferase transfers the CoA from the CoA ester to acetate to form acetyl-CoA. The added citrate synthase condenses oxaloacetate and acetyl-CoA to form citrate and free CoASH. The free CoASH complexes with DTNB, and the formation of this complex can be measured by a change in the optical density at 412 nm. The activity of the CoA transferase was measured using the following substrates: lactyl-CoA, propionyl-CoA, acrylyl-CoA, and 3-hydroxypropionyl-CoA. The units/mg of protein was calculated using the following formula:

$$(\Delta E/min * V_f * \text{dilution factor})/(V_S * 14.2) = \text{units/mL}$$

where $\Delta E/min$ is the change in absorbance per minute at 412 nm, $V_f$ is the final volume of the reaction, and $V_S$ is the volume of sample added. The total protein concentration of the cell free extract was about 1 mg/mL so the units/mL equals units/mg.

Cell free extracts from cells containing nucleic acid encoding the CoA transferase exhibited CoA transferase activity (Table 2). The observed CoA transferase activity was detected for the lactyl-CoA, propionyl-CoA, acrylyl-CoA, and 3-hydroxypropionyl-CoA substrates (Table 2). The highest CoA transferase activity was detected for lactyl-CoA and propionyl-CoA.

TABLE 2

| Substrate | Units/mg |
| --- | --- |
| Lactyl-CoA | 211 |
| Propionyl-CoA | 144 |
| Acrylyl-CoA | 118 |
| 3-Hydroxypropionyl-CoA | 110 |

The following assay was performed to test whether the CoA transferase activity can use the same CoA substrate donors as recipients. Specifically, CoA transferase activity was assessed using a Matrix-assisted Laser Desorption/Ionization Time of Flight Mass Spectrometry (MALDI-TOF MS) Voyager RP workstation (PerSeptive Biosystems). The following five reactions were analyzed:

1) acetate+lactyl-CoA→lactate+acetyl-CoA
2) acetate+propionyl-CoA→propionate+acetyl-CoA
3) lactate+acetyl-CoA→acetate+lactyl-CoA
4) lactate+acrylyl-CoA→acrylate+lactyl-CoA
5) 3-hydroxypropionate+lactyl-CoA→lactate+3-hydroxypropionyl-CoA MALDI-TOF MS was used to measure simultaneously the appearance of the product CoA ester and the disappearance of the donor CoA ester. The assay buffer contained 50 mM potassium phosphate (pH 7.0), 1 mM CoA ester, and 100 mM respective acid salt. Protein from a cell free extract prepared as described above was added to a final concentration of 0.005 mg/mL. A control reaction was prepared from a cell free extract prepared from cells lacking the construct containing the CoA transferase-encoding nucleic acid. For each reaction, the cell free extract was added last to start the reaction. Reactions were allowed to proceed at room temperature and were stopped by adding 1 volume 10% trifluoroacetic acid (TFA). The reaction mixtures were purified prior to MALDI-TOF MS analysis using Sep Pak Vac $C_{18}$ 50 mg columns (Waters, Inc.). The columns were conditioned with 1 mL methanol and equilibrated with two washes of 1 mL 0.1% TFA. Each sample was applied to the column, and the flow through was discarded. The column was washed twice with 1 mL 0.1% TFA. The sample was eluted in 200 µL 40% acetonitrile, 0.1% TFA. The acetonitrile was removed by centrifugation in vacuo. Samples were prepared for MALDI-TOF MS analysis by mixing 1:1 with 110 mM sinapinic acid in 0.1% TFA, 67% acetonitrile. The samples were allowed to air dry.

In reaction #1, the control sample exhibited a main peak at a molecular weight corresponding to lactyl-CoA (MW 841). There was a minor peak at the molecular weight corresponding to acetyl-CoA (MW 811). This minor peak was determined to be the left-over acetyl-CoA from the synthesis of lactyl-CoA. The reaction #1 sample containing the cell extract from cells transfected with the CoA transferase-encoding plasmid exhibited complete conversion of lactyl-CoA to acetyl-CoA. No peak was observed for lactyl-CoA. This result indicates that the CoA transferase activity can transfer CoA from lactyl-CoA to acetate to form acetyl-CoA.

In reaction #2, the control sample exhibited a dominant peak at a molecular weight corresponding to propionyl-CoA (MW 825). The reaction #2 sample containing the cell extract from cells transfected with the CoA transferase-encoding plasmid exhibited a dominant peak at a molecular weight corresponding to acetyl-CoA (MW 811). No peak was observed for propionyl-CoA. This result indicates that the CoA transferase activity can transfer CoA from propionyl-CoA to acetate to form acetyl-CoA.

In reaction #3, the control sample exhibited a dominant peak at a molecular weight corresponding to acetyl-CoA (MW 811). The reaction #3 sample containing the cell extract from cells transfected with the CoA transferase-encoding plasmid exhibited a peak corresponding to lactyl-CoA (MW 841). The peak corresponding to acetyl-CoA did not disappear. In fact, the ratio of the size of the two peaks was about 1:1. The observed appearance of the peak corresponding to lactyl-CoA demonstrates that the CoA transferase activity catalyzes reaction #3.

In reaction #4, the control sample exhibited a dominant peak at a molecular weight corresponding to acrylyl-CoA (MW 823). The reaction #4 sample containing the cell extract from cells transfected with the CoA transferase-encoding plasmid exhibited a dominant peak corresponding to lactyl-CoA (MW 841). This result demonstrates that the CoA transferase activity catalyzes reaction #4.

In reaction #5, deuterated lactyl-CoA was used to detect the transfer of CoA from lactate to 3-hydroxypropionate since lactic acid and 3-HP have the same molecular weight as do their respective CoA esters. Using deuterated lactyl-CoA allowed for the differentiation between lactyl-CoA and 3-hydroxypropionate using MALDI-TOF MS. The control sample exhibited a diffuse group of peaks at molecular weights ranging from MW 841 to 845 due to the varying amounts of hydrogen atoms that were replaced with deuterium atoms. In addition, a significant peak was observed at a molecular weight corresponding to acetyl-CoA (MW 811). This peak was determined to be the left-over acetyl-CoA from the synthesis of lactyl-CoA. The reaction #5 sample containing the cell extract from cells transfected with the CoA transferase-encoding plasmid exhibited a dominant peak at a molecular weight corresponding to 3-hydroxypropionyl-CoA (MW 841) as opposed to a group of peaks ranging from MW 841 to 845. This result demonstrates that the CoA transferase catalyzes reaction #5.

Example 2

Cloning Nucleic Acid Molecules that Encode a Multiple Polypeptide Complex Having Lactyl-CoA Dehydratase Activity The following methods were used to clone an E1 activator polypeptide. Briefly, four degenerate forward and five degenerate reverse PCR primers were designed based on conserved sequences of E1 activator protein homologs (E1F1 5'-GCWACBGGYTAYGGYCG-3', SEQ ID NO:60; E1F2 5'-GTYRTYGAYRTYGGYGGYCAGGA-3', SEQ ID NO:61; E1F3 5'-ATGAACGAYAARTGYGCWGCWGG-3', SEQ ID NO:62; E1F4 5'-TGYGCWGCWGGYACBGGY-CGYTT-3', SEQ ID NO:63; E1R15'-TCCTGRCCRC-CRAYRTCRAYRAC-3', SEQ ID NO:64; E1R25'-CCWGCWGCRCAYTTRTCGTTCAT-3', SEQ ID NO:65; E1R35'-AARCGRCCVGTRCCWGCWGCRCA-3', SEQ ID NO:66; E1R45'-GCTTCGSWTTCRACRATGSW-3', SEQ ID NO:67; and E1R55'-GSWRATRACTTCGCWT-TCWGCRAA-3', SEQ ID NO:68).

The primers were used in all logical combinations in PCR using Taq polymerase (Roche Molecular Biochemicals, Indianapolis, Ind.) and 1 ng of genomic DNA per μL reaction mix. PCR was conducted using a touchdown PCR program with 4 cycles at an annealing temperature of 60° C., 4 cycles at 58° C., 4 cycles at 56° C., and 18 cycles at 54° C. Each cycle used an initial 30-second denaturing step at 94° C. and a 3 minute extension step at 72° C. The program had an initial denaturing step for 2 minutes at 94° C. and a final extension step of 4 minutes at 72° C. Time allowed for annealing was 45 seconds. The amounts of PCR primer used in the reactions were increased 2-10 fold above typical PCR amounts depending on the amount of degeneracy in the 3' end of the primer. In addition, separate PCR reactions containing each individual primer were made to identify PCR product resulting from single degenerate primers. Each PCR product (25 μL) was separated by electrophoresis using a 1% TAE (Tris-acetate-EDTA) agarose gel.

The E1F2-E1R4, E1F2-E1R5, E1F3-E1R4, E1F3-E1R5, and E1F4-E1R4R2 combinations produced a band of 195, 207, 144, 156, and 144 bp, respectively. These bands matched the expected size based on E1 activator sequences from other species. No band was visible with individual primer control reactions. The E1F2-E1R5 fragment (207 bp) was isolated and purified using Qiagen Gel Extraction procedure (Qiagen Inc., Valencia, Calif.). The purified band (4 μL) was ligated into a pCRII vector that then was transformed into TOP10 *E. coli* cells by heat-shock using a TOPO cloning procedure (Invitrogen, Carlsbad, Calif.). Transformations were plated on LB media containing 100 μg/mL of ampicillin (Amp) and 50 μg/mL of 5-Bromo-4-Chloro-3-Indolyl-B-D-Galactopyranoside (X-gal). Single, white colonies were plated onto fresh media and screened in a PCR reaction using the E1F2 and E1R5 primers to confirm the presence of the insert. Plasmid DNA was obtained from multiple colonies using a QiaPrep Spin Miniprep Kit (Qiagen, Inc). Once obtained, the plasmid DNA was quantified and used for DNA sequencing with M13R and M13F primers. Sequence analysis revealed a nucleic acid sequence encoding a polypeptide and revealed that the E1F2-E1R5 fragment shared sequence similarity with E1 activator sequences (FIGS. 12-13).

Genome walking was performed to obtain the complete coding sequence of E2 α and β subunits. Briefly, four primers for performing genome walking in both upstream and downstream directions were designed using the portion of the 207 bp E1F2-E1R5 fragment sequence that was internal to the EIF2 and E1R5 degenerate primers (E1GSP1F 5'-ACGT-CATGTCGAAGGTACTGGAAATCC-3', SEQ ID NO:69; E1GSP2F 5'-GGGACTGGTACTTCAAATCGAAGCATC-3', SEQ ID NO:70; E1GSP1R 5'-TGACGGCAGCGGGAT-GCTTCGATTTGA-3', SEQ ID NO:71; and E1GSP2R 5'-TCAGACATGGGGATTTCCAGTACCTTC-3', SEQ ID NO:72). The E1GSP1F and E1GSP2F primers face downstream, while the E1GSP1R and E1GSP2R primers face upstream. In addition, the E1GSP2F and E1GSP2R primers are nested inside the E1GSP1F and E1GSP1R primers.

Genome walking was performed using the Universal Genome Walking Kit (ClonTech Laboratories, Inc., Palo Alto, Calif.) with the exception that additional libraries were generated with enzymes Nru I, Sca I, and Hinc II. First round PCR was performed in a Perkin Elmer 2400 Thermocycler with 7 cycles of 2 seconds at 94° C. and 3 minutes at 72° C., and 36 cycles of 2 seconds at 94° C. and 3 minutes at 65° C. with a final extension at 65° C. for 4 minutes. Second round PCR used 5 cycles of 2 seconds at 94° C. and 3 minutes at 72° C., and 20 cycles of 2 seconds at 94° C. and 3 minutes at 65° C. with a final extension at 65° C. for 4 minutes. The first and second round product (20 μL) was separated by electrophoresis using 1% TAE agarose gel. Amplification products were obtained with the Stu I library for both forward and reverse directions. The second round product of about 1.5 kb for forward direction and 3 kb fragment for reverse direction from the Stu I library were gel purified, cloned, and sequenced. Sequence analysis revealed that the sequence derived from genome walking overlapped with the E1F2-E1R5 fragment.

To obtain additional sequence, a second genome walk was performed using a first round primer (E1GSPF5 5'-CCGT-GTTACTTGGGAAGGTATCGCTGTCTG-3', SEQ ID NO:73) and a second round primer (E1GSPF6 5'-GCCAAT-GAAGGAGGAAA-CCACTAATGAGTC-3', SEQ ID NO:74). The genome walk was performed using the NruI, ScaI, and HincII libraries. In addition, ClonTech's Advantage-Genomic Polymerase was used for the PCR. First round PCR was performed in a Perkin Elmer 2400 Thermocycler with an initial denaturing step at 94° C. for 2 minutes, 7 cycles of 2 seconds at 94° C. and 3 minutes at 72° C., and 36 cycles of 2 seconds at 94° C. and 3 minutes at 65° C. with a final extension at 65° C. for 4 minutes. Second round PCR used 5 cycles of 2 seconds at 94° C. and 3 minutes at 72° C., and 20 cycles of 2 seconds at 94° C. and 3 minutes at 65° C. with a final extension at 65° C. for 4 minutes. The first and second round product (20 μL) was separated by electrophoresis on a 1% agarose gel. An about 1.5 kb amplification product was obtained from second round PCR of the HincII library. This band was gel purified, cloned, and sequenced. Sequence analysis revealed that it overlapped with the previously obtained genome walk fragment. In addition, sequence analysis revealed a nucleic acid sequence encoding an E2 α subunit that shares sequence similarities with other sequences (FIGS. 16-17). Further, sequence analysis revealed a nucleic acid sequence encoding an E2 β subunit that shares sequence similarities with other sequences (FIGS. 20-21).

Additional PCR and sequence analysis revealed the order of polypeptide encoding sequences within the region containing the lactyl-CoA dehydratase-encoding sequences. Specifically, the E1GSP1F and COAGSP1R primer pair and the COAGSP1F and E1GSP1R primer pair were used to amplify fragments that encode both the CoA transferase and E1 activator polypeptides. Briefly, *M. elsdenii* genome DNA (1 ng) was used as a template. The PCR was conducted in Perkin Elmer 2400 Thermocycler using Long Template Polymerase (Roche Molecular Biochemicals, Indianapolis, Ind.). The PCR program used was as follows: 94° C. for 2 minutes; 29 cycles of 94° C. for 30 seconds, 61° C. for 45 seconds, and 72° C. for 6 minutes; and a final extension of 72° C. for 10 minutes. Both PCR products (20 μL) were separated on a 1% agarose gel. An amplification product (about 1.5 kb) was obtained using the COAGSP1F and E1GSP1R primer pair. This product was gel purified, cloned, and sequenced (FIG. 22).

The organization of the *M. elsdenii* operon containing the lactyl-CoA dehydratase-encoding sequences was determined to containing the following polypeptide-encoding sequences in the following order: CoA transferase (FIG. 6), ORFX (FIG. 23), E1 activator protein of lactyl-CoA dehydratase (FIG. 10), E2 α subunit of lactyl-CoA dehydratase (FIG. 14), E2 β subunit of lactyl-CoA dehydratase (FIG. 18), and truncated CoA dehydrogenase (FIG. 25).

The lactyl-CoA dehydratase (lactyl-CoA dehydratase or lcd) from *M. elsdenii* was PCR amplified from chromosomal DNA using the following program: 94° C. for 2 minutes; 7 cycles of 94° C. for 30 seconds, 47° C. for 45 seconds, and 72° C. for 3 minutes; 25 cycles of 94° C. for 30 seconds, 54° C. for 45 seconds, and 72° C. for 3 minutes; and 72° C. for 7 minutes. One primer pair was used (OSNBE1F 5'-GGGAAT-TCCATATGAAAACTGTGTATACTCTC-3', SEQ ID NO:75 and OSNBE1R 5'-CGACGGATCCTTAGAG-GATTTCCGAGAAAGC-3', SEQ ID NO:76). The amplified product (about 3.2 kb) was separated on 1% agarose gel, cut from the gel, and purified with a Qiagen Gel Extraction kit (Qiagen, Valencia, Calif.). The purified product was digested with Nde I and BamHI restriction enzymes and ligated into pET11a vector (Novagen) digested with the same enzymes. The ligation reaction was transformed into NovaBlue chemically competent cells (Novagen) that then were spread on LB agar plates supplemented with 50 µg/mL carbenicillin. Isolated individual colonies were screened for the presence of inserts by restriction mapping. Isolates with the correct restriction pattern were sequenced from each end using Novagen primers (T7 promoter primer #69348-3 and T7 terminator primer #69337-3) to confirm the sequence at the ligation points.

A plasmid having the correct insert was transformed into Tuner (DE3) pLacI chemically competent cells (Novagen, Madison, Wis.). Expression from this construct was tested as follows. A culture was grown overnight to saturation and diluted 1:20 the following morning in fresh LB medium with the appropriate antibiotics. The culture was grown at 37° C. with aeration to an $OD_{600}$ of about 0.6. The culture was induced with IPTG at a final concentration of 100 µM. The culture was incubated for an additional two hours at 37° C. with aeration. Aliquots were taken pre-induction and 2 hours post-induction for SDS-PAGE analysis. Bands of the expected molecular weight (27,024 Daltons for the E1 subunit, 48,088 Daltons for the E2 α subunit, and 42,517 Daltons for the E2 β subunit—all predicted from the sequence) were observed. These bands were not observed in cells containing a plasmid lacking the nucleic acid encoding the three components of the lactyl-CoA dehydratase.

Cell free extracts were prepared by growing cells in a sealed serum bottle overnight at 37° C. Following overnight growth, the cultures were induced with 1 mM IPTG (added using anaerobic technique) and incubated an additional 2 hours at 37° C. The cells were harvested by centrifugation and disrupted by sonication under strict anaerobic conditions. The sonicated cell suspension was centrifuged to remove cell debris, and the supernatant was used in the assays. The buffer used for cell resuspension/sonication was 50 mM Tris-HCl (pH 7.5), 200 µM ATP, 7 mM $Mg(SO_4)$, 4 mM DTT, 1 mM dithionite, and 100 µM NADH.

Dehydratase activity was detected with MALDI-TOF MS. The assay was conducted in the same buffer as above with 1 mM lactyl-CoA or 1 mM acrylyl-CoA added and about 5 mg/mL cell free extract. Prior to MALDI-TOF MS analysis, samples were purified using Sep Pak Vac $C_{18}$ columns (Waters, Inc.) as described in Example 1. The following two reactions were analyzed:

1) acrylyl-CoA→lactyl-CoA
2) lactyl-CoA→acrylyl-CoA

In reaction #1, the control sample exhibited a peak at a molecular weight corresponding to acrylyl-CoA (MW 823). The reaction #1 sample containing the cell extract from cells transfected with the dehydratase-encoding plasmid exhibited a major peak at a molecular weight corresponding to lactyl-CoA (MW 841). This result indicates that the dehydratase activity can convert acrylyl-CoA into lactyl-CoA.

To detect dehydratase activity on lactyl-CoA, reaction #2 was carried out in 80% $D_2O$. The control sample exhibited a peak at a molecular weight corresponding to lactyl-CoA (MW 841). The reaction #2 sample containing the cell extract from cells transfected with the dehydratase-encoding plasmid revealed a lactyl-CoA peak shifted to a deuterated form. This result indicates that the dehydratase enzyme is active on lactyl-CoA. In addition, the results from both reactions indicate that the dehydratase enzyme can catalyze the lactyl-CoA←→acrylyl-CoA reaction in both directions.

Example 3

Cloning Nucleic Acid Molecules that Encode a Polypeptide Having 3-hydroxypropionyl CoA Dehydratase Activity Genomic DNA was isolated from *Chloroflexus aurantiacus* cells (ATCC 29365). Briefly, *C. aurantiacus* cells in 920 *Chloroflexus* medium were grown in 50 mL cultures (Falcon 2070 polypropylene tubes) using an Innova 4230 Incubator, Shaker (New Brunswick Scientific; Edison, N.J.) at 50° C. with interior lights. Once grown, the cells were pelleted, washed with 5 mL of a 10 mM Tris solution, and re-pelleted. Genomic DNA was isolated from the pelleted cells using a Gentra Genomic "Puregene" DNA isolation kit (Gentra Systems; Minneapolis, Minn.). Briefly, the pelleted cells were resuspended in 1 mL Gentra Cell Suspension Solution to which 14.2 mg of lysozyme and 4 µL of 20 mg/mL proteinase K solution was added. The cell suspension was incubated at 37° C. for 30 minutes. The precipitated genomic DNA was recovered by centrifugation at 3500×g for 25 minutes and air-dried for 10 minutes. The genomic DNA was suspended in 300 µL of a 10 mM Tris solution and stored at 4° C.

The genomic DNA was used as a template in PCR amplification reactions with primers designed based on conserved domains of crotonase homologs and a *Chloroflexus aurantiacus* codon usage table. Briefly, two degenerate forward (CRF1 and CRF2) and three degenerate reverse (CRR1, CRR2, and CRR3) PCR primers were designed (CRF1 5'-AAYCGBCCVAARGCNCTSAAYGC-3', SEQ ID NO:77; CRF2: 5'-TTYGTBGCNGGYGCNGAYAT-3', SEQ ID NO:78; CRR15'-ATRTCNGCRCCNGCVACRAA-3', SEQ ID NO:79; CRR25'-CCRCCRCCSAGNGCRWARC-CRTT-3', SEQ ID NO:80; and CRR35'-SSWNG-CRATVCGRATRTCRAC-3', SEQ ID NO:81).

These primers were used in all logical combinations in PCR using Taq polymerase (Roche Molecular Biochemicals; Indianapolis, Ind.) and 1 ng of the genomic DNA per µL reaction mix. The PCR was conducted using a touchdown PCR program with 4 cycles at an annealing temperature of 61° C., 4 cycles at 59° C., 4 cycles at 57° C., 4 cycles at 55° C., and 16 cycles at 52° C. Each cycle used an initial 30-second denaturing step at 94° C. and a 3-minute extension step at 72° C. The program also had an initial denaturing step for 2 minutes at 94° C. and a final extension step of 4 minutes at 72° C. The time allowed for annealing was 45 seconds. The amounts of PCR primer used in the reaction were increased 4-12 fold above typical PCR amounts depending on the amount of degeneracy in the 3' end of the primer. In addition, separate PCR reactions containing each individual primer were performed to identify amplification products resulting from single degenerate primers. Each PCR product (25 µL) was separated by gel electrophoresis using a 1% TAE (Tris-acetate-EDTA) agarose gel.

The CRF1-CRR1 and CRF2-CRR2 combinations produced a unique band of about 120 and about 150 bp, respectively. These bands matched the expected size based on crotonase genes from other species. No 120 bp or 150 bp band was observed from individual primer control reactions. Both fragments (i.e., the 120 bp and 150 bp bands) were isolated and purified using the Qiagen Gel Extraction kit (Qiagen Inc., Valencia, Calif.). Each purified fragment (4 µL) was ligated into pCRII vector that then was transformed into TOP10 E. coli cells by a heat-shock method using a TOPO cloning procedure (Invitrogen, Carlsbad, Calif.). Transformations were plated on LB media containing 100 µg/mL of ampicillin (Amp) and 50 µg/mL of 5-Bromo-4-Chloro-3-Indolyl-B-D-Galactopyranoside (X-gal). Single, white colonies were plated onto fresh media and screened in a PCR reaction using the CRF1 and CRR1 primers and the CRF2 and CRR2 primers to confirm the presence of the desired insert. Plasmid DNA was obtained from multiple colonies with the desired insert using a QiaPrep Spin Miniprep Kit (Qiagen, Inc.). Once obtained, the DNA was quantified and used for DNA sequencing with M13R and M13F primers. Sequence analysis revealed the presence of two different clones from the PCR product of about 150 bp. Each shared sequence similarity with crotonase and hydratase sequences. The two clones were designated OS17 (157 bp PCR product) and OS19 (151 bp PCR product).

Genome walking was performed to obtain the complete coding sequence of OS17. Briefly, primers for conducting genome walking in both upstream and downstream directions were designed using the portion of the 157 bp CRF2-CRR2 fragment sequence that was internal to the CRF2 and CRR2 degenerate primers (OS17F1 5'-CGCTG-ATATTCGC-CAGTTGCTCGAAG-3', SEQ ID NO:82; OS17F2 5'-CCCATCTTG-CTTTCCGCAAGATTGAGC-3', SEQ ID NO:83; OS17F3 5'-CAATGGCCCTGCCGA-ATAACGC-CCATCT-3', SEQ ID NO:84; OS17R15'-CTTCGAG-CAACTGGCGAA-TATCAGCG-3', SEQ ID NO:85; OS17R25'-GCTCAATCTTGCGGAAAGCAAG-ATGGG-3', SEQ ID NO:86; and OS17R35'-AGATGGGCGTTAT-TCGGCAGGGCC-ATTG-3', SEQ ID NO:87). The OS17F1, OS17F3, and OS17F2 primers face downstream, while the OS17R2, OS17R3, and OS17R1 primers face upstream.

Genome walking was conducted using the Universal Genome Walking kit (ClonTech Laboratories, Inc., Palo Alto, Calif.) with the exception that additional libraries were generated with enzymes Nru I, Fsp I, and Hinc II. The first round PCR was conducted in a Perkin Elmer 2400 Thermocycler with 7 cycles of 2 seconds at 94° C. and 3 minutes at 72° C., and 36 cycles of 2 seconds at 94° C. and 3 minutes at 66° C. with a final extension at 66° C. for 4 minutes. Second round PCR used 5 cycles of 2 seconds at 94° C. and 3 minutes at 72° C., and 20 cycles of 2 seconds at 94° C. and 3 minutes at 66° C. with a final extension at 66° C. for 4 minutes. The first and second round amplification product (5 µL) was separated by gel electrophoresis on a 1% TAE agarose gel. After the second round PCR, an amplification product of about 0.4 kb was obtained with the Fsp I library using the OS17R1 primer in the reverse direction, and an amplification product of about 0.6 kb was obtained with the Hinc II library using the OS17F2 primer in the forward direction. These PCR products were cloned and sequenced.

Sequence analysis revealed that the sequences derived from genome walking overlapped with the CRF2-CRR2 fragment and shared sequence similarity with crotonase and hydratase sequences.

A second genome walking was performed to obtain additional sequences. Six primers were designed for this second genome walk (OS17F4 5'-AAGCTGGGTCTGATCGATGC-CATTGCTACC-3', SEQ ID NO:88; OS17F5 5'-CTCGAT-TATCG-CCCATCCACGTATCGAG-3', SEQ ID NO:89; OS17F6 5'-TGGATGCAATCCG-CTATGGCATTATC-CACG-3', SEQ ID NO:90; OS17R45'-TCATTCAGTGCG-TTCACCGGCGGATTTGTC-3', SEQ ID NO:91; OS17R55'-TCGATCCGGAAGT-AGCGATAGCGTTC-GATG-3', SEQ ID NO:92; and OS17R6 5'-CTTGGCTG-CAAT-CTCTTCGAGCACTTCAGG-3', SEQ ID NO:93). The OS17F4, OS17F5, and OS17F6 primers faced downstream, while the OS17R4, OS17R5, and OS17R6 primers faced upstream.

The second genome walk was performed using the same methods described for the first genome walk. After the second round of walking, an amplification product of about 2.3 kb was obtained with a Hinc II library using the OS 17R5 primer in the reverse direction, and an amplification product of about 0.6 kb was obtained with a Pvu II library using the OS 17F5 primer in the forward direction. The PCR products were cloned and sequenced. Sequence analysis revealed that the sequences derived from the second genome walking overlapped with the sequence obtained during the first genome walking. In addition, the sequence analysis revealed a sequence with 3572 bp.

A BLAST search revealed that the polypeptide encoded by this sequence shares sequence similarity with polypeptides having three different activities. Specifically, the beginning of the OS17 encoded-polypeptide shares sequence similarity with CoA-synthesases, the middle region of the OS17 encoded-polypeptide shares sequence similarity with enoyl-CoA hydratases, and the end region of the OS17 encoded-polypeptide shares sequence similarity with CoA-reductases.

A third genome walk was performed using four primers (OS17UP-6 5'-CATCAGAGGTAATCACCACTCGTGCA-3', SEQ ID NO:94; OS17UP-7 5'-AAGTAGTAGGCCAC-CTCGTCGCCATA-3', SEQ ID NO:95; OS17DN-1 5'-GC-CAATCAGGCGCTGATCTATGTTCT-3', SEQ ID NO:96; and OS17DN-2 5'-CTGATCTATGTTCTGGCCTCG-GAGGT-3', SEQ ID NO:97). The OS17UP-6 and OS17UP-7 primers face upstream, while the OS17DN-1 and OS17DN-2 primers face downstream. The third genome walk yielded an amplification product of about 1.2 kb with a Nru I library using the OS17UP-7 primer in the reverse direction. In addition, amplification products of about 4 kb and about 1.1 kb were obtained with a Hinc II and Fsp I library, respectively, using the OS17DN-2 primer in the forward direction. Sequence analysis revealed a nucleic acid sequence encoding a polypeptide (FIGS. 27-28). The complete OS17 gene had 5466 nucleotides and encoded a 1822 amino acid polypeptide. The calculated molecular weight of the OS17 polypeptide from the sequence was 201,346 (pI=5.71).

A BLAST search analysis revealed that the product of the OS17 nucleic acid has three different activities based on sequence similarity to (1) CoA-synthesases at the beginning of the OS17 sequence, (2) 3-HP dehydratases in the middle of the OS17 sequence, and (3) CoA-reductases at the end of the OS17 sequence. Thus, the OS17 clone appeared to encode a single enzyme capable of catalyzing three distinct reactions leading to the direct conversion of 3-hydroxypropionate to propionyl CoA: 3-HP→3-HP-CoA→acrylyl-CoA→propionyl-CoA.

The OS17 gene from C. aurantiacus was PCR amplified from chromosomal DNA using the following conditions: 94° C. for 3 minutes; 25 cycles of 94° C. for 30 seconds to denature, 54° C. for 30 seconds to anneal, and 68° C. for 6 minutes for extension; followed by 68° C. for 10 minutes for final extension. Two primers were used (OS17F 5'-GGGAAT-TCCATATGATCGACACTGCG-3', SEQ ID NO:136; and OS17R 5'-CGAAGGATCCAACGATAATCGGCTCAG-CAC-3', SEQ ID NO:137). The resulting PCR product (~5.6 Kb) was purified using Qiagen PCR purification kit (Qiagen Inc., Valencia, Calif.). The purified product was digested with NdeI and BamHI restriction enzymes, heated at 80° C. for 20 minutes to inactivate the enzymes, purified using Qiagen PCR purification kit, and ligated into a pET11a vector (Novagen, Madison, Wis.) previously digested with NdeI and BamHI enzymes. The ligation reaction was transformed into NovaBlue chemically competent cells (Novagen, Madison, Wis.) that were spread on LB agar plates supplemented with 50 μg/mL carbenicillin. Individual transformants were screened by PCR amplification of the OS17 DNA with the OS17F and OS17R primers and conditions as described above directly from colonies cells. Clones that yielded the 5.6 Kb product were used for plasmid purification with Qiagen QiaPrep Spin Miniprep Kit (Qiagen, Inc). Resulting plasmids were transformed into E. coli BL21(DE3) cells, and OS17 polypeptide expression induced. The apparent molecular weight of the OS17 polypeptide according to SDS gel electrophoresis was about 190,000 Da.

To assay OS17 polypeptide function, a 100 mL culture of BL21-DE3/pET11a-OS17 cells was started using 1 mL of overnight grown culture as an inoculum. The culture was grown to an OD of 0.5-0.6 and was induced with 100 μM IPTG. After two and a half hours of induction, the cells were harvested by spinning at 8000 rpm in the floor centrifuge. The cells were washed with 10 mM Tris-HCl (pH 7.8) and passed twice through a French Press at a gauge pressure of 1000 psi. The cell debris was removed by centrifugation at 15,000 rpm. The activity of the OS17 polypeptide was measured spectrophotometrically, and the products formed during this enzymatic transformation were detected by LC/MS. The assay mix was as follows (J. Bacteriol., 181:1088-1098 (1999)):

| Reagent | Volume | Final Conc. |
|---|---|---|
| Tris-HCl (1000 mM, 7.8 pH) | 10 μL | 50 mM |
| MgCl$_2$ (100 mM) | 10 μL | 5 mM |
| ATP (30 mM) | 20 μL | 3 mM |
| KCl (100 mM) | 20 μL | 10 mM |
| CoASH (5 mM) | 20 μL | 0.5 mM |
| NAD(P)H | 20 μL | 0.5 mM |
| 3-hydroxypropionate | 2 μL | 1 mM |
| Protein extract (7 mg/mL) | 20 (40) μL | 140 μg |
| DI water | 78 (58) μL | |
| Total | 200 μL | |

The initial rate of reaction was measured by monitoring the disappearance of NAD(P)H at 340 nm. The activity of the OS17 polypeptide was measured using 3-HP as the substrate. The units/mL of total protein was calculated using the formula set forth in Example 1. The activity of the expressed OS17 polypeptide was calculated to be 0.061 U/mL of total protein. The reaction products were purified using a Sep Pak Vac column (Waters). The column was conditioned with 1 mL methanol and washed two times with 0.5 mL 0.1% TFA. The sample was then applied to the column, and the column was washed two more times with 0.5 mL 0.1% TFA. The sample was eluted with 200 μL of 40% acetonitrile, 0.1% TFA. The acetonitrile was removed from the sample by vacuum centrifugation. The reaction products were analyzed by LC/MS.

Analyses of thioesters namely propionyl CoA, acrylyl CoA, and 3 HP CoA from the above reaction were carried out using a Waters/Micromass ZQ LC/MS instrument which had a Waters 2690 liquid chromatograph with a Waters 996 Photo-Diode Array (PDA) placed in series between the chromatograph and the single quadropole mass spectrometer. LC separations were made using a 4.6×150 mm YMC ods-AQ (3 μm particles, 120 Å pores) reversed-phase chromatography column at room temperature. CoA esters were eluted in Buffer A (25 mM ammonium acetate, 0.5% acetic acid) with a linear gradient of buffer B (acetonitrile, 0.5% acetic acid). A flow rate of 0.25 mL/minute was used, and photodiode array UV absorbance was monitored from 200 to 400 nm. All parameters of the electrospray MS system were optimized and selected based on generation of protonated molecular ions ([M+H]$^+$) of the analytes of interest and production of characteristic fragment ions. The following instrumental parameters were used for ESI-MS detection of CoA and organic acid-CoA thioesters in the positive ion mode; Extractor: 1 V; RF lens: 0 V; Source temperature: 100° C.; Desolvation temperature: 300° C.; Desolvation gas: 500 L/hour; Cone gas: 40 L/hour; Low mass resolution: 13.0; High mass resolution: 14.5; Ion energy: 0.5; Multiplier: 650. Uncertainties for mass charge ratios (m/z) and molecular masses are ±0.01%.

The enzyme assay mix from strains expressing the OS17 polypeptide exhibited peaks for propionyl CoA, acrylyl CoA, and 3-HP CoA with the propionyl CoA peak being the dominant peak. These peaks where missing in the enzyme assay mix obtained from the control strain, which carried vector pET11a without an insert. These results indicate that the OS17 polypeptide has CoA synthetase activity, CoA hydratase activity, and dehydrogenase activity.

Genome walking also was performed to obtain the complete coding sequence of OS19. Briefly, primers for conducting genome walking in both upstream and downstream directions were designed using the portion of the 151 bp CRF2-CRR2 fragment sequence that was internal to the CRF2 and CRR2 degenerate primers (OS19F1 5'-GGCTGATAT-CAAAGCGATGGCCAATGC-3', SEQ ID NO:98; OS19F2 5'-CCAC-GCCTATTGATATGCTCACCAGTG-3', SEQ ID NO:99; OS19F3 5'-GCAAACCGG-TGATTGCTGCCGT-GAATGG-3', SEQ ID NO:100; OS19R1 5'-GCATTGGC-CAT-CGCTTTGATATCAGCC-3', SEQ ID NO:101; OS19R2 5'-CACTGGTGAGCATATC-AATAGGCGTGG-3', SEQ ID NO:102; and OS19R3 5'-CCATTCACGGCAG-CAA-TCACCGGTTTGC-3', SEQ ID NO:103). The OS19F1, OS19F2, and OS19F3 primers face downstream, while the OS19R1, OS19R2, and OS19R3 primers face upstream.

An amplification product of about 0.25 kb was obtained with the Fsp I library using the OS19R1 primer, while an amplification product of about 0.65 kb was obtained with the Pvu II library using the OS19R1 primer. In addition, an amplification product of about 0.4 kb was obtained with the Pvu II library using the OS19F3 primer. The PCR products were cloned and sequenced. Sequence analysis revealed that the sequences derived from genome walking overlapped with the CRF2-CRR2 fragment and shared sequence similarity with crotonase and hydratase sequences. The obtained sequences accounted for most of the coding sequence including the start codon.

A second genome walk was performed to obtain additional sequence using two primers (OS19F7 5'-TCATCATCGC-CAGTGAAAACGCGCAGTTCG-3', SEQ ID NO:104 and OS19F8 5'-GGATCGCGCAAACCATTGCCACCAAAT-CAC-3', SEQ ID NO:105). The OS19F7 and OS19F8 primers face downstream.

An amplification product (about 0.7 kb) obtained from the Pvu II library was cloned and sequenced. Sequence analysis revealed that the sequence derived from the second genome walk overlapped with the sequence obtained from the first genome walk and contained the stop codon. The full-length OS19 clone was found to share sequence similarity with other sequences such as crotonase and enoyl-CoA hydratase sequences (FIGS. 32-33).

The OS19 clone was found to encode a polypeptide having 3-hydroxypropionyl-CoA dehydratase activity also referred to as acrylyl-CoA hydratase activity. The nucleic acid encoding the OS19 dehydratase from C. aurantiacus was PCR amplified from chromosomal DNA using the following conditions: 94° C. for 3 minutes; 25 cycles of 94° C. for 30 seconds to denature, 56° C. for 30 seconds to anneal, and 68° C. for 1 minute for extension; and 68° C. for 5 minutes for final extension. Two primers were used (OSACH3 5'-ATGAGTGAAGAGTCTCTGGTTCTCAGC-3', SEQ ID NO:106 and OSACH2 5'-AGATCGCAATCGCTCGTGTATGTC-3', SEQ ID NO:107).

The resulting PCR product (about 1.2 kb) was separated by agarose gel electrophoresis and purified using Qiagen PCR purification kit (Qiagen Inc.; Valencia, Calif.). The purified product was ligated into pETBlue-1 using the Perfectly Blunt cloning Kit (Novagen; Madison, Wis.). The ligation reaction was transformed into NovaBlue chemically competent cells (Novagen, Madison, Wis.) that then were spread on LB agar plates supplemented with 50 µg/mL carbenicillin, 40 µg/mL IPTG, and 40 µg/mL X-Gal. White colonies were isolated and screened for the presence of inserts by restriction mapping. Isolates with the correct restriction pattern were sequenced from each end using the primer pETBlueUP and pETBlue-DOWN (Novagen) to confirm the sequence at the ligation points.

The plasmid containing the OS19 dehydratase-encoding sequence was transformed into Tuner (DE3) pLacI chemically competent cells (Novagen, Madison, Wis.), and expression from the construct tested. Briefly, a culture was grown overnight to saturation and diluted 1:20 the following morning in fresh LB medium with the appropriate antibiotics. The culture was grown at 37° C. and 250 rpm to an $OD_{600}$ of about 0.6. At this point, the culture was induced with IPTG at a final concentration of 1 mM. The culture was incubated for an additional two hours at 37° C. and 250 rpm. Aliquots were taken pre-induction and 2 hours post-induction for SDS-PAGE analysis. A band of the expected molecular weight (27,336 Daltons predicted from the sequence) was observed. This band was not observed in cells containing a plasmid lacking the nucleic acid encoding the hydratase.

Cell free extracts were prepared by growing cells as described above. The cells were harvested by centrifugation and disrupted by sonication. The sonicated cell suspension was centrifuged to remove cell debris, and the supernatant was used in the assays. The ability of the 3-hydroxypropionyl-CoA dehydratase to perform the following three reactions was measured using MALDI-TOF MS:

1) acrylyl-CoA→3-hydroxypropionyl-CoA
2) 3-hydroxypropionyl-CoA→acrylyl-CoA
3) crotonyl-CoA→3-hydroxybutyryl-CoA The assay mixture contained 50 mM Tris-HCl (pH 7.5), 1 mM CoA ester, and about 1 µg cell free extract. Reactions were allowed to proceed at room temperature and were stopped by adding 1 volume 10% trifluoroacetic acid (TFA). The reaction mixtures were purified prior to MALDI-TOF MS analysis using Sep Pak Vac $C_{18}$ 50 mg columns (Waters, Inc.). The columns were conditioned with 1 mL methanol and then equilibrated with two washes of 1 mL 0.1% TFA. The sample was applied to the column, and the flow through was discarded. The column was washed twice with 1 mL 0.1% TFA. The sample was eluted in 200 µL 40% acetonitrile, 0.1% TFA. The acetonitrile was removed by centrifugation in vacuo. Samples were prepared for MALDI-TOF MS analysis by mixing 1:1 with 110 mM sinapinic acid in 0.1% TFA, 67% acetonitrile. The samples were allowed to air dry.

The conversion of acrylyl-CoA into 3-hydroxypropionyl-CoA catalyzed by the 3-hydroxypropionyl-CoA dehydratase was detected using the MALDI-TOF MS technique. In reaction #1, the control sample exhibited a dominant peak at a molecular weight corresponding to acrylyl-CoA (MW 823). The reaction #1 sample containing the cell extract from cells transfected with the 3-hydroxypropionyl-CoA dehydratase-encoding plasmid exhibited a dominant peak corresponding to 3-hydroxypropionyl-CoA (MW 841). This result demonstrates that the 3-hydroxypropionyl-CoA dehydratase activity catalyzes reaction #1.

To detect the conversion of 3-hydroxypropionyl-CoA into acrylyl-CoA, reaction #2 was carried out in 80% $D_2O$. The reaction #2 sample containing the cell extract from cells transfected with the 3-hydroxypropionyl-CoA dehydratase-encoding plasmid revealed incorporation of deuterium in the 3-hydroxypropionyl-CoA molecule. This result indicates that the 3-hydroxypropionyl-CoA dehydratase enzyme catalyzes reaction #2. In addition, the results from both #1 and #2 reactions indicate that the 3-hydroxypropionyl-CoA dehydratase enzyme can catalyze the 3-hydroxypropinyl-CoA←→acrylyl-CoA reaction in both directions. It is noted that for both the #1 and #2 reactions, a peak was observed at MW 811, due to leftover acetyl-CoA from the synthesis of 3-hydroxypropionyl-CoA from 3-hydroxypropionate and acetyl-CoA.

The assays assessing conversion of crotonyl-CoA into 3-hydroxybutyryl-CoA also were carried out in 80% $D_2O$. In reaction #3, the control sample exhibited a dominant peak at a molecular weight corresponding to crotonyl-CoA (MW 837). This result indicated that the crotonyl-CoA was not converted into other products. The reaction #3 sample containing the cell extract from cells transfected with the 3-hydroxypropionyl-CoA dehydratase-encoding plasmid exhibited a diffuse group of peaks corresponding to deuterated 3-hydroxybutyryl-CoA (MW 855 to MW 857). This result demonstrates that the 3-hydroxypropionyl-CoA dehydratase activity catalyzes reaction #3.

A series of control reactions were performed to confirm the specificity of the 3-hydroxypropionyl-CoA dehydratase. Lactyl-CoA (1 mM) was added to the reaction mixture containing 100 mM Tris (pH 7.0) both in the presence and the absence of the 3-hydroxypropionyl-CoA dehydratase. In both cases, the dominant peak observed had a molecular weight corresponding to lactyl-CoA (MW 841). This result indicates that lactyl-CoA is not affected by the presence of 3-hydroxypropionyl-CoA dehydratase activity even in the presence of $D_2O$ meaning that the 3-hydroxypropionyl-CoA dehydratase enzyme does not attach a hydroxyl group at the alpha carbon position. The presence of 3-hydroxypropionyl-CoA in an 80% $D_2O$ reaction mixture resulted in a shift upon addition of the 3-hydroxypropionyl-CoA dehydratase activity. In the absence of 3-hydroxypropionyl-CoA dehydratase activity, a peak corresponding to 3-hydroxypropionyl-CoA was observed in addition to a peak of MW 811. The MW 811 peak was due to leftover acetyl-CoA from the synthesis of 3-hydroxypropionyl-CoA. In the presence of 3-hydroxypropionyl-CoA dehydratase activity, a peak corresponding to deuterated 3-hydroxypropionyl-CoA was observed (MW 842) due to exchange of a hydroxyl group during the conversion of 3-hydroxypropionyl-CoA to acrylyl-CoA and visa-versa. These control reactions demonstrate that the 3-hydroxypropionyl-CoA dehydratase enzyme is active on 3-hydroxypropionyl-CoA and not active on lactyl-CoA. In addition, these results demonstrate that the product of the acrylyl-CoA reaction is 3-hydroxypropionyl-CoA not lactyl-CoA.

Example 4

Construction of Operon #1

The following operon was constructed and can be used to produce 3-HP in *E. coli* (FIG. 34). Briefly, the operon was cloned into a pET-11a expression vector under the control of a T7 promoter (Novagen, Madison, Wis.). The pET-11a expression vector is a 5677 bp plasmid that uses the ATG sequence of an NdeI restriction site as a start codon for inserted downstream sequences.

Nucleic acid molecules encoding a CoA transferase and a lactyl-CoA dehydratase were amplified from *Megasphaera elsdenii* genomic DNA by PCR. Two primers were used to amplify the CoA transferase-encoding sequence (OSNBpctF 5'-GGGAATTCC-ATATGAGAAAAGTAGAAATCATTA-CAGCTG-3', SEQ ID NO:108 and OSCTE-2 5'-GAGAG-TATACACAGTTTTCACCTCCTTTACAGCAGAGAT-3', SEQ ID NO:109), and two primers were used to amplify the lactyl-CoA dehydratase-encoding sequence (OSCTE-1 5'-ATCTCTGCTGTAAAGGAGGTGAAAACT-GTGTATACT-CTC-3', SEQ ID NO:110 and OSEBH-2 5'-ACGTTGATCTCCTTGTACATTAGAG-GATTTCCGAGAAAGC-3', SEQ ID NO:111). A nucleic acid molecule encoding a 3-hydroxypropionyl-CoA dehydratase was amplified from *Chloroflexus aurantiacus* genomic DNA of by PCR using two primers (OSEBH-1 5'-GCTTTCTCGG-AAATCCTCTAATGTACAAGGAGAT-CAACGT-3', SEQ ID NO:112 and OSHBR 5'-CGACG-GATCCTCAACGACCACTGAAGTTGG-3', SEQ ID NO:113).

PCR was conducted in a Perkin Elmer 2400 Thermocycler using 100 ng of genomic DNA and a mix of rTth polymerase (Applied Biosystems; Foster City, Calif.) and Pfu Turbo polymerase (Stratagene; La Jolla, Calif.) in 8:1 ratio. The polymerase mix ensured higher fidelity of the PCR reaction. The following PCR conditions were used: initial denaturation step of 94° C. for 2 minutes; 20 cycles of 94° C. for 30 seconds, 54° C. for 30 seconds, and 68° C. for 2 minutes; and a final extension at 68° C. for 5 minutes. The obtained PCR products were gel purified using a Qiagen Gel Extraction Kit (Qiagen, Inc.; Valencia, Calif.).

The CoA transferase, lactyl-CoA dehydratase (E1, E2 α subunit, and E2 β subunit), and 3-hydroxypropionyl-CoA dehydratase PCR products were assembled using PCR. The OSCTE-1 and OSCTE-2 primers as well as the OSEBH-1 and OSEBH-2 primers were complementary to each other. Thus, the complementary DNA ends could anneal to each other during the PCR reaction extending the DNA in both direction. To ensure the efficiency of the assembly, two end primers (OSNBpctF and OSHBR) were added to the assembly PCR mixture, which contained 100 ng of each PCR product (i.e., the PCR products from the CoA-transferase, lactyl-CoA dehydratase, and 3-hydroxypropionyl-CoA dehydratase reactions) as well as the rTth polymerase/Pfu Turbo polymerase mix described above. The following PCR conditions were used to assemble the products: 94° C. for 1 minute; 25 cycles of 94° C. for 30 seconds, 55° C. for 30 seconds, and 68° C. for 6 minutes; and a final extension at 68° C. for 7 minutes. The assembled PCR product was gel purified and digested with restriction enzymes (NdeI and BamHI). The sites for these restriction enzymes were introduced into the assembled PCR product using the OSNBpctF (NdeI) and OSHBR (BamHI) primers. The digested PCR product was heated at 80° C. for 30 minutes to inactive the restriction enzymes and used directly for ligation into pET-11a vector.

The pET-11a vector was digested with NdeI and BamHI restriction enzymes, gel purified using a Qiagen Gel Extraction kit, treated with shrimp alkaline phosphatase (Roche Molecular Biochemicals; Indianapolis, Ind.) and used in a ligation reaction with the assembled PCR product. The ligation was performed at 16° C. overnight using T4 ligase (Roche Molecular Biochemicals; Indianapolis, Ind.). The resulting ligation reaction was transformed into NovaBlue chemically competent cells (Novagen; Madison, Wis.) using a heat-shock method. Once heat shocked, the cells were plated on LB plates supplemented with 50 μg/mL carbenicillin. The plasmid DNA was purified from individual colonies using a QiaPrep Spin Miniprep Kit (Qiagen Inc., Valencia, Calif.) and analyzed by digestion with NdeI and BamHI restriction enzymes.

Example 5

Construction of Operon #2

Figure 35B:
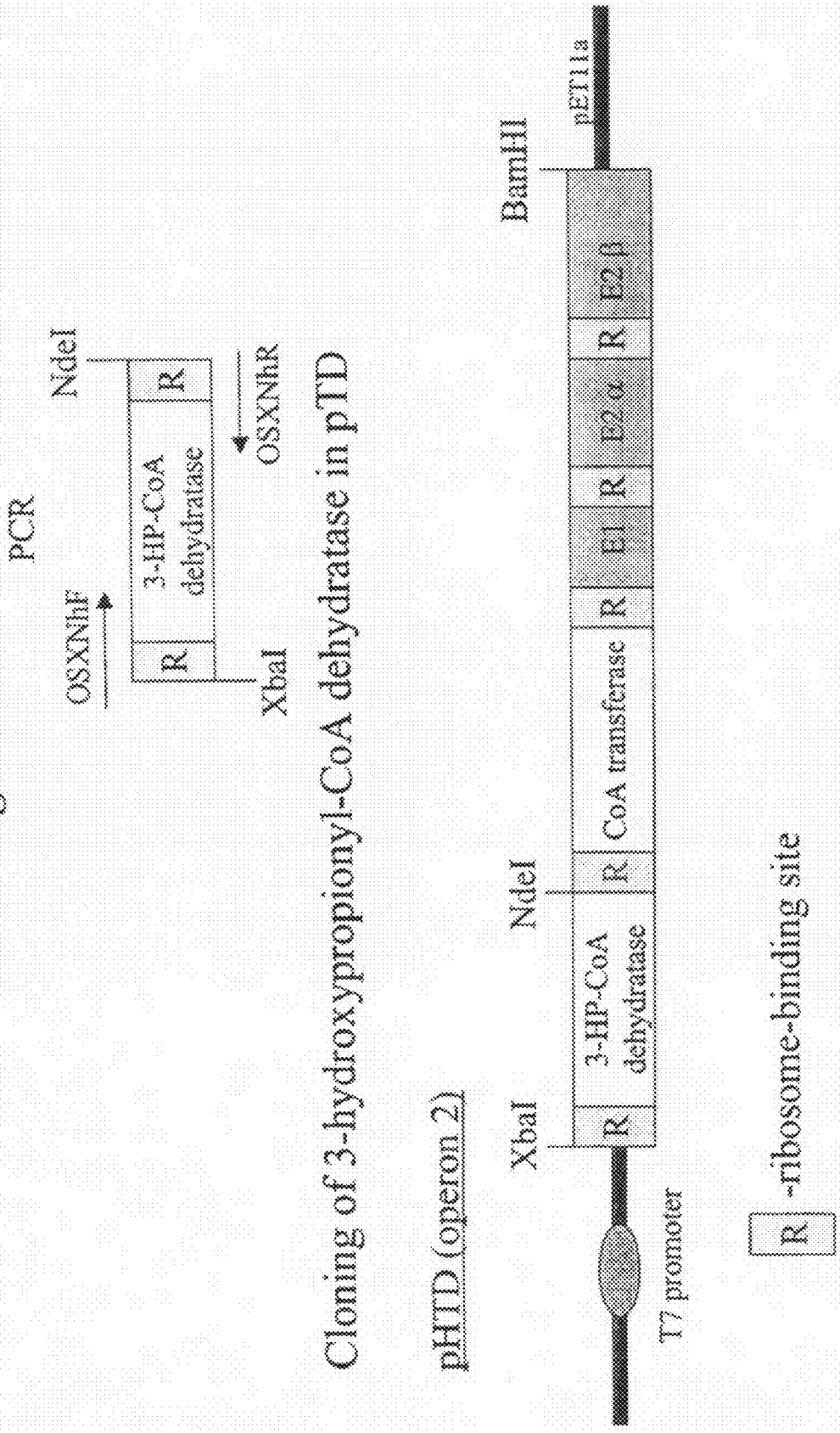
FIGS. 35A and B is a diagram of the construction of a synthetic operon (pHTD) that encodes for polypeptides having CoA transferase activity, lactyl-CoA dehydratase activity (E1, E2 α, and E2 β), and 3-hydroxypropionyl-CoA dehydratase activity (3-HP-CoA dehydratase).
Figure 37A:
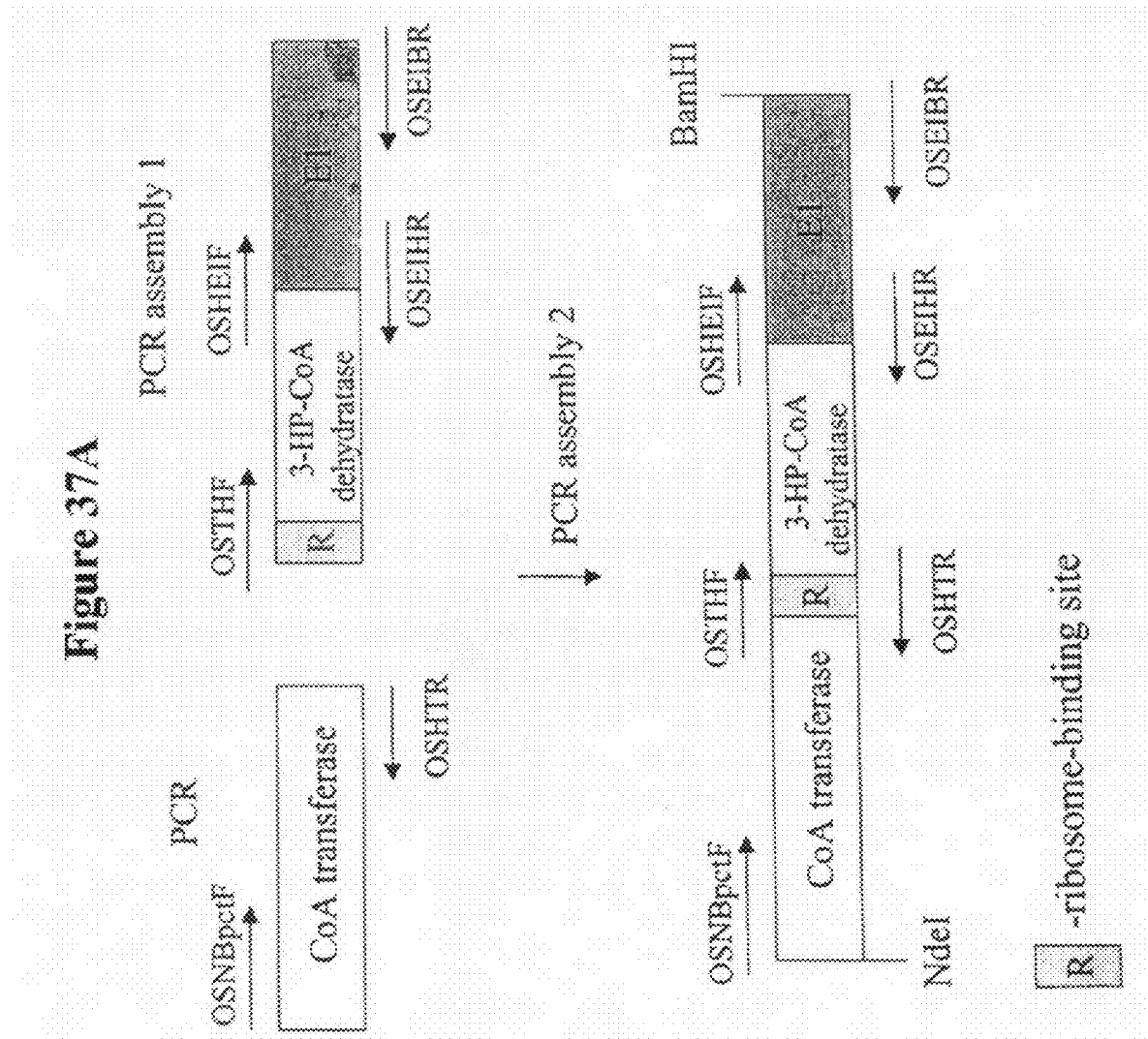
FIGS. 37A and B is a diagram of the construction of a synthetic operon (pEIITHEI) that encodes for polypeptides having CoA transferase activity, lactyl-CoA dehydratase activity (E1, E2 α, and E2 β), and 3-hydroxypropionyl-CoA dehydratase activity (3-HP-CoA dehydratase).
Figure 37B:
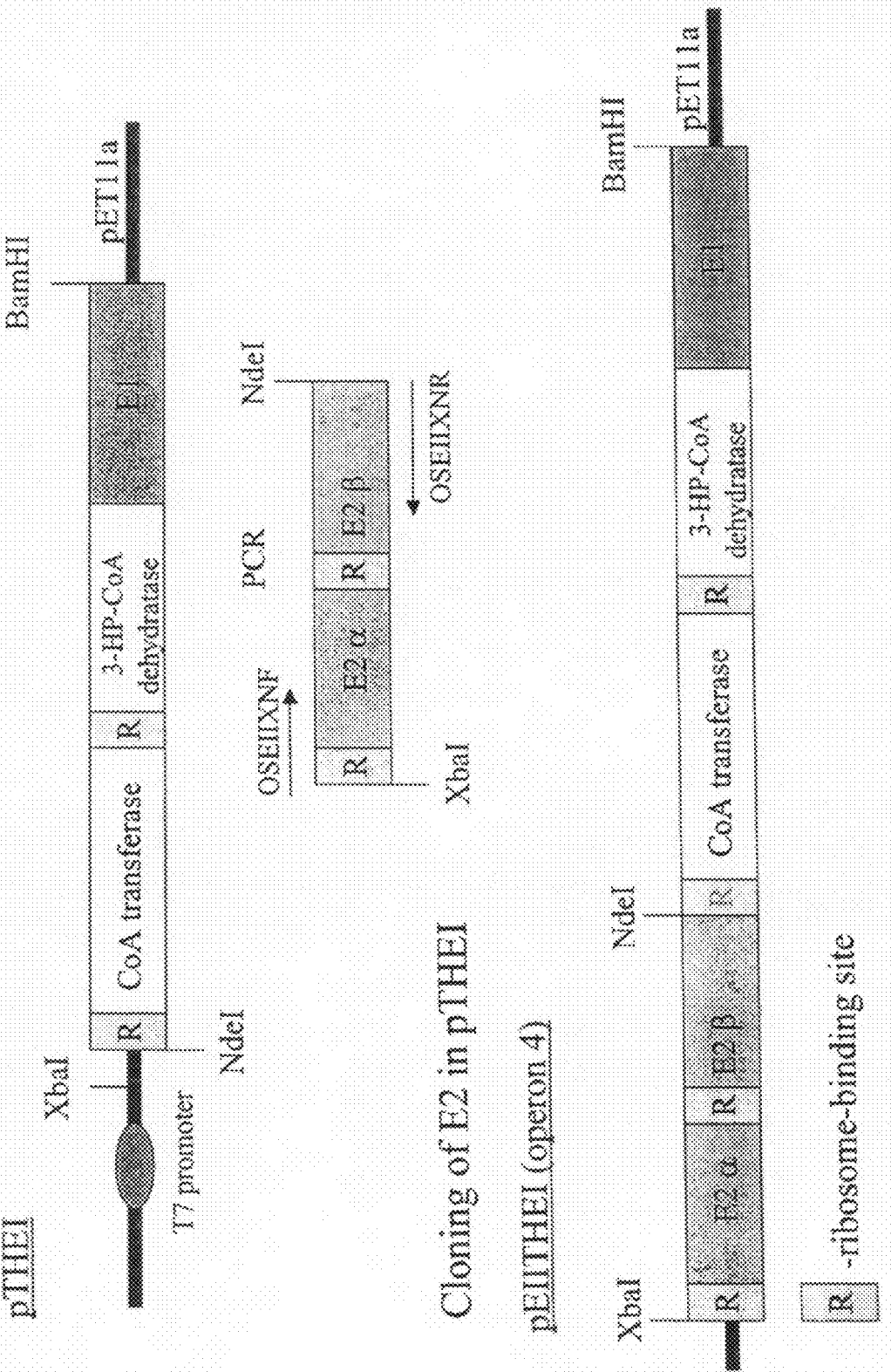

The following operon was constructed and can be used to produce 3-HP in *E. coli* (FIGS. 35A and B). Nucleic acid molecules encoding a CoA transferase and a lactyl-CoA dehydratase were amplified from *Megasphaera elsdenii* genomic DNA by PCR. Two primers were used to amplify the CoA transferase-encoding sequence (OSNBpctF and OSCTE-2), and two primers were used to amplify the lactyl-CoA dehydratase-encoding sequence (OSCTE-1 and OSNBelR 5'-CGACGGATCCTTAGAGGATTT-CCGAGAAAGC-3', SEQ ID NO:114). A nucleic acid molecule encoding a 3-hydroxypropionyl-CoA dehydratase was amplified from *Chloroflexus aurantiacus* genomic DNA of by PCR using two primers (OSXNHF 5'-GGTGTCT-AGAGA-CAGTCCTGTCGTTTATGTAGAAGGAG-3', SEQ ID NO:115 and OSXNhR 5'-GGGAATTCCATATGCGTAACT-TCCTCCTGCTATCAACGACCACTGAAGTTGG-3', SEQ ID NO:116).

PCR was conducted in a Perkin Elmer 2400 Thermocycler using 100 ng of genomic DNA and a mix of rTth polymerase (Applied Biosystems; Foster City, Calif.) and Pfu Turbo polymerase (Stratagene; La Jolla, Calif.) in 8:1 ratio. The polymerase mix ensured higher fidelity of the PCR reaction. The following PCR conditions were used: initial denaturation step of 94° C. for 2 minutes; 20 cycles of 94° C. for 30 seconds, 54° C. for 30 seconds, and 68° C. for 2 minutes; and a final extension at 68° C. for 5 minutes. The obtained PCR products were gel purified using a Qiagen Gel Extraction Kit (Qiagen, Inc.; Valencia, Calif.).

The CoA transferase and lactyl-CoA dehydratase (E1, E2 α subunit, and E2 β subunit) PCR products were assembled using PCR. The OSCTE-1 and OSCTE-2 primers were complementary to each other. Thus, the 22 nucleotides at the end of the CoA transferase sequence and the 22 nucleotides at the beginning of the lactyl-CoA dehydratase could anneal to each other during the PCR reaction extending the DNA in both direction. To ensure the efficiency of the assembly, two end primers (OSNBpctF and OSNBelR) were added to the assembly PCR mixture, which contained 100 ng of the CoA transferase PCR product, 100 ng of lactyl-CoA dehydratase PCR product, and the rTth polymerase/Pfu Turbo polymerase mix described above. The following PCR conditions were used to assemble the products: 94° C. for 1 minute; 20 cycles of 94° C. for 30 seconds, 54° C. for 30 seconds, and 68° C. for 5 minutes; and a final extension at 68° C. for 6 minutes.

The assembled PCR product was gel purified and digested with restriction enzymes (NdeI and BamHI). The sites for these restriction enzymes were introduced into the assembled PCR product using the OSNBpctF (NdeI) and OSNBeIR (BamHI) primers. The digested PCR product was heated at 80° C. for 30 minutes to inactive the restriction enzymes and used directly for ligation into a pET-11a vector.

The pET-11a vector was digested with NdeI and BamHI restriction enzymes, gel purified using a Qiagen Gel Extraction kit, treated with shrimp alkaline phosphatase (Roche Molecular Biochemicals; Indianapolis, Ind.) and used in a ligation reaction with the assembled PCR product. The ligation was performed at 16° C. overnight using T4 ligase (Roche Molecular Biochemicals; Indianapolis, Ind.). The resulting ligation reaction was transformed into NovaBlue chemically competent cells (Novagen; Madison, Wis.) using a heat-shock method. Once heat shocked, the cells were plated on LB plates supplemented with 50 µg/mL carbenicillin. The plasmid DNA was purified from individual colonies using a QiaPrep Spin Miniprep Kit (Qiagen Inc., Valencia, Calif.) and analyzed by digestion with NdeI and BamHI restriction enzymes. The digest revealed that the DNA fragment containing CoA transferase-encoding and lactyl-CoA dehydratase-encoding sequences was cloned into the pET-11a vector.

The plasmid carrying the CoA transferase-encoding and lactyl-CoA dehydratase-encoding sequences (pTD) was digested with XbaI and NdeI restriction enzymes, gel purified, and used for cloning the 3-hydroxypropionyl-CoA dehydratase-encoding product upstream of the CoA transferase-encoding sequence. Since this XbaI and NdeI digest eliminated a ribosome-binding site (RBS) from the pET-11a vector, a new homologous RBS was cloned into the plasmid together with the 3-hydroxypropionyl-CoA dehydratase-encoding product. Briefly, the 3-hydroxypropionyl-CoA dehydratase-encoding PCR product was digested with XbaI and NdeI restriction enzymes, heated at 65° C. for 30 minutes to inactivate the restriction enzymes, and ligated into pTD. The ligation mixture was transformed into chemically competent NovaBlue cells (Novagen) that then were plated on LB plates supplemented with 50 µg/mL carbenicillin.

Individual colonies were selected, and the plasmid DNA obtained using a Qiagen Spin Miniprep Kit. The obtained plasmids were digested with XbaI and NdeI restriction enzymes and analyzed by gel electrophoresis. pTD plasmids containing the inserted 3-hydroxypropionyl-CoA dehydratase-encoding PCR product were named pHTD. While expression of the lactyl-CoA hydratase, CoA transferase, and 3-hydroxypropionyl-CoA dehydratase sequences from pHTD was directed by a single T7 promoter, each coding sequence had an individual RBS upstream of their start codon.

To ensure the correct assembly and cloning of the lactyl-CoA hydratase, CoA transferase, and 3-hydroxypropionyl-CoA dehydratase sequences into one operon, both ends of the operon and all junctions between the coding sequences were sequenced. This DNA analysis revealed that the operon was assembled correctly.

The pHTD plasmid was transformed into BL21(DE3) cells to study the expression of the encoded sequences.

Example 6

Construction of Operons #3 and #4

Operon #3 (FIGS. 36A and B) and operon #4 (FIGS. 37A and B) each position the E1 activator at the end of the operon. Operon #3 contains a RBS between the 3-hydroxypropionyl-CoA dehydratase-encoding sequence and the E1 activator-encoding sequence. In operon #4, however, the stop codon of the 3-hydroxypropionyl-CoA dehydratase-encoding sequence is fused with the start codon of the E1 activator-encoding sequence as follows: TAGTG. The absence of the RBS in operon #4 can decrease the level of E1 activator expression.

To construct operon #3, nucleic acid molecules encoding a CoA transferase and a lactyl-CoA dehydratase were amplified from *Megasphaera elsdenii* genomic DNA by PCR. Two primers were used to amplify the CoA transferase-encoding sequence (OSNBpctF and OSHTR 5'-ACGTTGATCTCCT-TCTACATTATTTTTTCAGTCCCATG-3', SEQ ID NO:117), two primers were used to amplify the E2 α and β subunits of the lactyl-CoA dehydratase-encoding sequence (OSEIIXNF 5'-GGTGTCTAGAGTCAAAGGAGAGAA-CAAAATCATGAGTG-3', SEQ ID NO:118 and OSEIIXNR 5'-GGGAATTCCATATGCGTAACTTCCTCCT-GCTATTAGAGGATTTCCGAGAAAGC-3', SEQ ID NO:119), and two primers were used to amplify the E1 activator of the lactyl-CoA dehydratase-encoding sequence (OSHrEIF 5'-TCAGTGGTCGTTGATCACGCTATAAA-GAAAGGTGAAAACTGTGTATACTCTC-3', SEQ ID NO:120 and OSEIBR 5'-CGACGGATCCCTTCCTTG-GAGCTCATGCTTTC-3', SEQ ID NO:121). A nucleic acid molecule encoding a 3-hydroxypropionyl-CoA dehydratase was amplified from *Chloroflexus aurantiacus* genomic DNA of by PCR using two primers (OSTHF 5'-CATGGGACT-GAAAAAATAATGTAGAAGGAGATCAACGT-3', SEQ ID NO:122 and OSEIrHR 5'-GAGAGTATACA-CAGTTTTCACCTTTCTTTATAGCGTGAT-CAACGACCACTGA-3', SEQ ID NO:123).

PCR was conducted in a Perkin Elmer 2400 Thermocycler using 100 ng of genomic DNA and a mix of rTth polymerase (Applied Biosystems; Foster City, Calif.) and Pfu Turbo polymerase (Stratagene; La Jolla, Calif.) in 8:1 ratio. The polymerase mix ensured higher fidelity of the PCR reaction. The following PCR conditions were used: initial denaturation step of 94° C. for 2 minutes; 20 cycles of 94° C. for 30 seconds, 54° C. for 30 seconds, and 68° C. for 2 minutes; and a final extension at 68° C. for 5 minutes. The obtained PCR products were gel purified using a Qiagen Gel Extraction Kit (Qiagen, Inc.; Valencia, Calif.).

The 3-hydroxypropionyl-CoA dehydratase and E1 activator PCR products were assembled using PCR. The OSHrE1F and OSEIrHR primers were complementary to each other. Thus, the primers could anneal to each other during the PCR reaction extending the DNA in both direction. To ensure the efficiency of the assembly, two end primers (OSTHF and OSE1BR) were added to the assembly PCR mixture, which contained 100 ng of the 3-hydroxypropionyl-CoA dehydratase PCR product, 100 ng of E1 activator PCR product, and the rTth polymerase/Pfu Turbo polymerase mix described above. The following PCR conditions were used to assemble the products: 94° C. for 1 minute; 20 cycles of 94° C. for 30 seconds, 54° C. for 30 seconds, and 68° C. for 1.5 minutes; and a final extension at 68° C. for 5 minutes.

The assembled PCR product was gel purified and used in a second assembly PCR with gel purified the CoA transferase PCR product. The OSTHF and OSHTR primers were complementary to each other. Thus, the complementary DNA ends could anneal to each other during the PCR reaction extending the DNA in both direction. To ensure the efficiency of the assembly, two end primers (OSNBpctF and OSEIBR) were added to the second assembly PCR mixture, which contained 100 ng of the purified 3-hydroxypropionyl-CoA dehydratase/EI PCR assembly, 100 ng of the purified CoA transferase PCR product, and the polymerase mix described above. The following PCR conditions were used to assemble the products: 94° C. for 1 minute; 20 cycles of 94° C. for 30 seconds, 54° C. for 30 seconds, and 68° C. for 3 minutes; and a final extension at 68° C. for 5 minutes.

The assembled PCR product was gel purified and digested with NdeI and BamHI restriction enzymes. The sites for these restriction enzymes were introduced into the assembled PCR products with the OSNBpctF (NdeI) and OSEIBR (BamHI) primers. The digested PCR product was heated at 80° C. for 30 minutes to inactive the restriction enzymes and used directly for ligation into a pET11a vector.

The pET-11a vector was digested with NdeI and BamHI restriction enzymes, gel purified using a Qiagen Gel Extraction kit, treated with shrimp alkaline phosphatase (Roche Molecular Biochemicals; Indianapolis, Ind.) and used in a ligation reaction with the assembled PCR product. The ligation was performed at 16° C. overnight using T4 ligase (Roche Molecular Biochemicals; Indianapolis, Ind.). The resulting ligation reaction was transformed into NovaBlue chemically competent cells (Novagen; Madison, Wis.) using a heat-shock method. Once heat shocked, the cells were plated on LB plates supplemented with 50 µg/mL carbenicillin. The plasmid DNA was purified from individual colonies using a QiaPrep Spin Miniprep Kit (Qiagen Inc.; Valencia, Calif.). The resulting plasmids carrying the CoA transferase, 3-hydroxypropionyl-CoA dehydratase, and E1 activator sequences (pTHrEI) were digested with XbaI and NdeI, purified using gel electrophoresis and a Qiagen Gel Extraction kit, and used as a vector for cloning of the E2 α subunit/E2 β subunit PCR product.

The E2 α subunit/E2 β subunit PCR product was digested with the same enzymes and ligated into the pTHrEI vector. The ligation reaction was performed at 16° C. overnight using T4 ligase (Roche Molecular Biochemicals; Indianapolis, Ind.). The ligation mixture was transformed into chemically competent NovaBlue cells (Novagen) that then were plated on LB plates supplemented with 50 µg/mL carbenicillin. The plasmid DNA was purified from individual colonies using a QiaPrep Spin Miniprep Kit (Qiagen Inc., Valencia, Calif.) and digested with XbaI and NdeI restriction enzymes for gel electrophoresis analysis. The resulting plasmids carrying the constructed operon #3 (pEIITHrEI) were transformed into BL21 (DE3) cells to study the expression of the cloned sequences. Electrospray mass spectrometry assay confirmed that extracts from these cells have CoA transferase activity and 3-hydroxypropionyl-CoA dehydratase activity. Similar assays are used to confirm that extracts from these cells also have lactyl-CoA dehydratase activity.

To construct operon #4, nucleic acid molecules encoding a CoA transferase and a lactyl-CoA dehydratase were amplified from *Megasphaera elsdenii* genomic DNA by PCR. Two primers were used to amplify the CoA transferase-encoding sequence (OSNBpctF and OSHTR), two primers were used to amplify the E2 α and β subunits of the lactyl-CoA dehydratase-encoding sequence (OSEIIXNF and OSEIIXNR), and two primers were used to amplify the E1 activator of the lactyl-CoA dehydratase-encoding sequence (OSHEIF 5'-CCAACTTCAGTGGTCGTTAGTGAAAACT-GTGTATACTCTC-3', SEQ ID NO:124 and OSEIBR). A nucleic acid molecule encoding a 3-hydroxypropionyl-CoA dehydratase was amplified from *Chloroflexus aurantiacus* genomic DNA of by PCR using two primers (OSTHF and OSEIHR 5'-GAGAGTATACACAGTTTTCACTAACGAC-CACTGAAGTTGG-3', SEQ ID NO:125).

PCR was conducted in a Perkin Elmer 2400 Thermocycler using 100 ng of genomic DNA and a mix of rTth polymerase (Applied Biosystems; Foster City, Calif.) and Pfu Turbo polymerase (Stratagene; La Jolla, Calif.) in 8:1 ratio. The polymerase mix ensured higher fidelity of the PCR reaction. The following PCR conditions were used: initial denaturation step of 94° C. for 2 minutes; 20 cycles of 94° C. for 30 seconds, 54° C. for 30 seconds, and 68° C. for 2 minutes; and a final extension at 68° C. for 5 minutes. The obtained PCR products were gel purified using a Qiagen Gel Extraction Kit (Qiagen, Inc.; Valencia, Calif.).

The 3-hydroxypropionyl-CoA dehydratase and E1 activator PCR products were assembled using PCR. The OSHEIF and OSEIHR primers were complementary to each other. Thus, the primers could anneal to each other during the PCR reaction extending the DNA in both direction. To ensure the efficiency of the assembly, two end primers (OSTHF and OSE1BR) were added to the assembly PCR mixture, which contained 100 ng of the 3-hydroxypropionyl-CoA dehydratase PCR product, 100 ng of E1 activator PCR product, and the rTth polymerase/Pfu Turbo polymerase mix described above. The following PCR conditions were used to assemble the products: 94° C. for 1 minute; 20 cycles of 94° C. for 30 seconds, 54° C. for 30 seconds, and 68° C. for 1.5 minutes; and a final extension at 68° C. for 5 minutes.

The assembled PCR product was gel purified and used in a second assembly PCR with gel purified the CoA transferase PCR product. The OSTHF and OSHTR primers were complementary to each other. Thus, the complementary DNA ends could anneal to each other during the PCR reaction extending the DNA in both direction. To ensure the efficiency of the assembly, two end primers (OSNBpctF and OSEIBR) were added to the second assembly PCR mixture, which contained 100 ng of the purified 3-hydroxypropionyl-CoA dehydratase/EI PCR assembly, 100 ng of the purified CoA transferase PCR product, and the polymerase mix described above. The following PCR conditions were used to assemble the products: 94° C. for 1 minute; 20 cycles of 94° C. for 30 seconds, 54° C. for 30 seconds, and 68° C. for 3 minutes; and a final extension at 68° C. for 5 minutes.

The assembled PCR product was gel purified and digested with NdeI and BamHI restriction enzymes. The sites for these restriction enzymes were introduced into the assembled PCR products with the OSNBpctF (NdeI) and OSEIBR (BamHI) primers. The digested PCR product was heated at 80° C. for 30 minutes to inactive the restriction enzymes and used directly for ligation into a pET11a vector.

The pET-11a vector was digested with NdeI and BamHI restriction enzymes, gel purified using a Qiagen Gel Extraction kit, treated with shrimp alkaline phosphatase (Roche Molecular Biochemicals; Indianapolis, Ind.) and used in a ligation reaction with the assembled PCR product. The ligation was performed at 16° C. overnight using T4 ligase (Roche Molecular Biochemicals; Indianapolis, Ind.). The resulting ligation reaction was transformed into NovaBlue chemically competent cells (Novagen; Madison, Wis.) using a heat-shock method. Once shocked, the cells were plated on LB plates supplemented with 50 µg/mL carbenicillin. The plasmid DNA was purified from individual colonies using a QiaPrep Spin Miniprep Kit (Qiagen Inc., Valencia, Calif.). The resulting plasmids carrying the CoA transferase, 3-hydroxypropionyl-CoA dehydratase, and EI activator sequences (pTHE1) were digested with XbaI and NdeI, purified using gel electrophoresis and a Qiagen Gel Extraction kit, and used as a vector for cloning of the E2 α subunit/E2 β subunit PCR product.

The E2 α subunit/E2 β subunit PCR product was digested with the same enzymes and ligated into the pTHE1 vector. The ligation reaction was performed at 16° C. overnight using T4 ligase (Roche Molecular Biochemicals, Indianapolis, Ind.). The ligation mixture was transformed into chemically competent NovaBlue cells (Novagen) that then were plated on LB plates supplemented with 50 µg/mL carbenicillin. The plasmid DNA was purified from individual colonies using a QiaPrep Spin Miniprep Kit (Qiagen Inc., Valencia, Calif.) and digested with XbaI and NdeI restriction enzymes for gel electrophoresis analysis. The resulting plasmids carrying the constructed operon #4 (pEIITHEI) were transformed into BL21(DE3) cells to study the expression of the cloned sequences. Electrospray mass spectrometry assays confirmed that extracts from these cells have CoA transferase activity and 3-hydroxypropionyl-CoA dehydratase activity. Similar assays are used to confirm that extracts from these cells also have lactyl-CoA dehydratase activity.

E. coli plasmid pEIITHrEI carrying a synthetic 3-HP operon was digested with NruI, XbaI and BamHI restriction enzymes, XbaI-BamHI DNA fragment was gel purified with Quagen Gel Extraction Kit (Qiagen, Inc., Valencia Calif.) and used for further cloning into Bacillu vector pWH1520 (Mo-BiTec BmBH, Gottingen, Germany). Vector pWH1520 was digested with SpeI and BamHI restriction enzymes and gel purified with Qiagen Gel Extraction Kit. The XbaI-BamHI fragment carrying 3-HP operon was ligated into WH1520 vector at 16° C. overnight using T4 ligase. The ligation mixture was transformed into chemically competent TOP 10 cells and plated on LB plates supplemented with 50 µg/ml carbenicillin. One clone named B. megaterium (pBPO26) was used for assays of CoA-transferase and CoA-hydratase activities. The assays were performed as described above for E. Coli. The enzymatic activity was 5 U/mg and 13 U/mg respectively.

Example 7

Construction of a Two Plasmid System

Figure 38A:
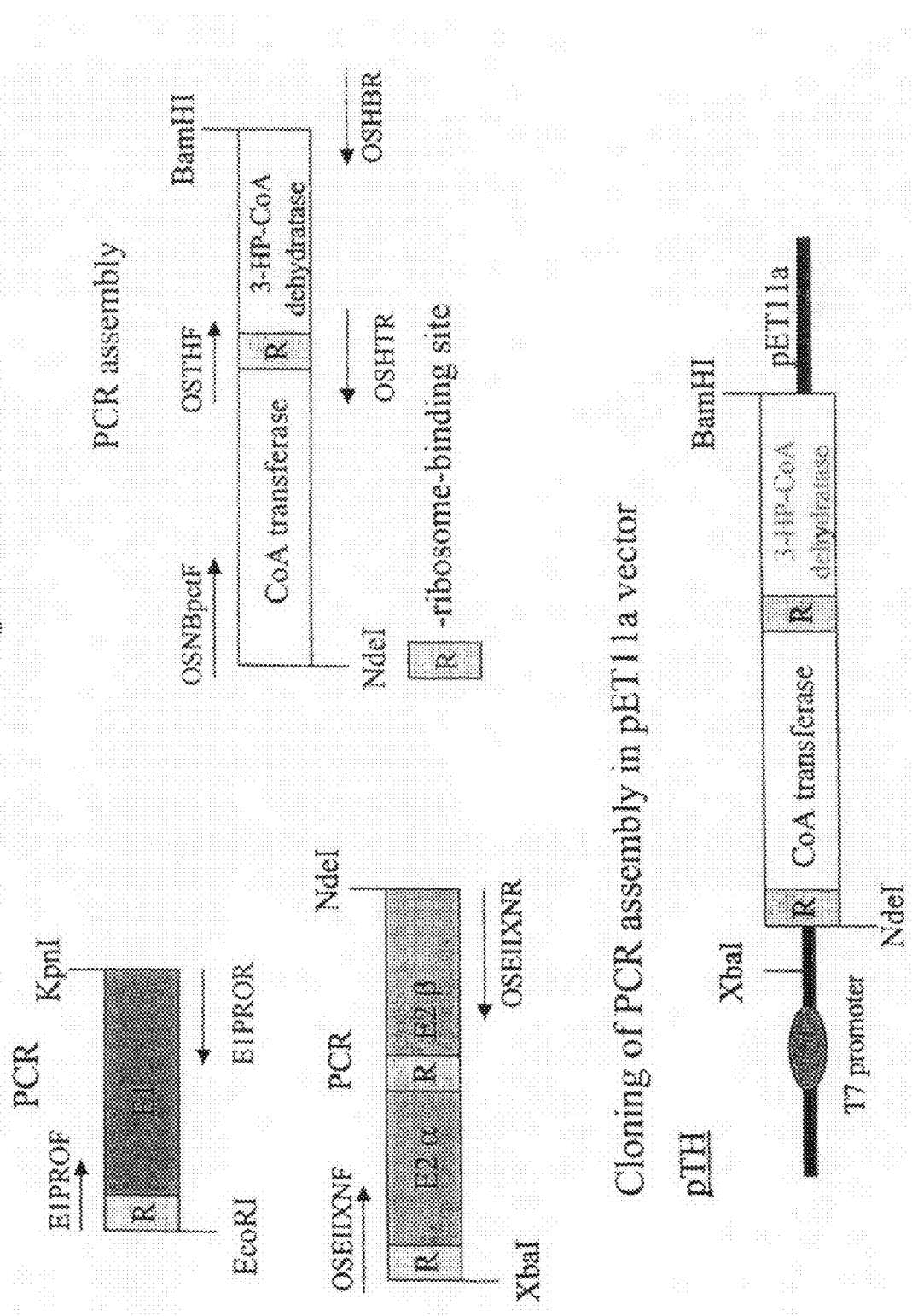
FIGS. 38A and B is a diagram of the construction of two plasmids, pEIITH and pPROEI. The pEIITH plasmid encodes polypeptides having CoA transferase activity, lactyl-CoA dehydratase activity (E2 α and E2 β), and 3-hydroxypropionyl-CoA dehydratase activity (3-HP-CoA dehydratase), and the pPROEI plasmid encodes a polypeptide having E1 activator activity.
Figure 38B:
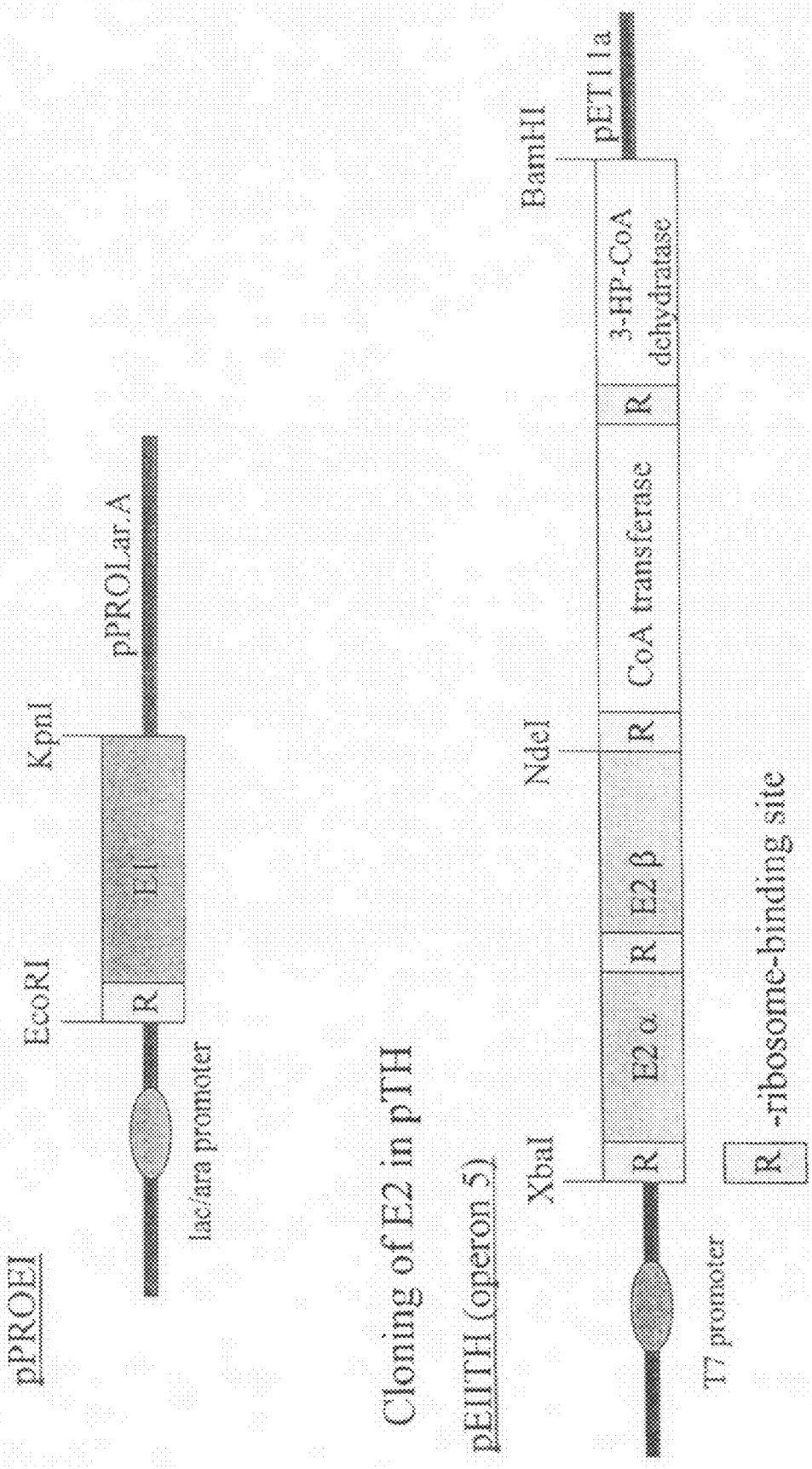

The following constructs were constructed and can be used to produce 3-HP in E. coli (FIGS. 38A and B). Nucleic acid molecules encoding a CoA transferase and a lactyl-CoA dehydratase were amplified from Megasphaera elsdenii genomic DNA by PCR. Two primers were used to amplify the CoA transferase-encoding sequence (OSNBpctF and OSHTR), two primers were used to amplify the E2 α and β subunits of the lactyl-CoA dehydratase-encoding sequence (OSEIIXNF and OSEIIXNR), and two primers were used to amplify the E1 activator of the lactyl-CoA dehydratase-encoding sequence (E1PROF 5'-GTCGCAGAATTCCCAT-CAATCGCAGCAATCCCAAC-3', SEQ ID NO:126 and E1PROR 5'-TAACATGGTACCGACAGAAGCGGAC-CAGCAAACGA-3', SEQ ID NO:127). A nucleic acid molecule encoding a 3-hydroxypropionyl-CoA dehydratase was amplified from Chloroflexus aurantiacus genomic DNA of by PCR using two primers (OSTHF and OSHBR 5'-CGACG-GATCCTCAACGACCA-CTGAAGTTGG-3', SEQ ID NO:128).

PCR was conducted in a Perkin Elmer 2400 Thermocycler using 100 ng of genomic DNA and a mix of rTth polymerase (Applied Biosystems; Foster City, Calif.) and Pfu Turbo polymerase (Stratagene; La Jolla, Calif.) in 8:1 ratio. The polymerase mix ensured higher fidelity of the PCR reaction. The following PCR conditions were used: initial denaturation step of 94° C. for 2 minutes; 20 cycles of 94° C. for 30 seconds, 54° C. for 30 seconds, and 68° C. for 2 minutes; and a final extension at 68° C. for 5 minutes. The obtained PCR products were gel purified using a Qiagen Gel Extraction Kit (Qiagen, Inc.; Valencia, Calif.).

The CoA transferase PCR product and the 3-hydroxypropionyl-CoA dehydratase PCR product were assembled using PCR. The OSTHF and OSHTR primers were complementary to each other. Thus, the complementary DNA ends could anneal to each other during the PCR reaction extending the DNA in both direction. To ensure the efficiency of the assembly, two end primers (OSNBpctF and OSHBR) were added to the assembly PCR mixture, which contained 100 ng of the purified CoA transferase PCR product, 100 ng of the purified 3-hydroxypropionyl-CoA dehydratase PCR product, and the polymerase mix described above. The following PCR conditions were used to assemble the products: 94° C. for 1 minute; 20 cycles of 94° C. for 30 seconds, 54° C. for 30 seconds, and 68° C. for 2.5 minutes; and a final extension at 68° C. for 5 minutes.

The assembled PCR product was gel purified and digested with NdeI and BamHI restriction enzymes. The sites for these restriction enzymes were introduced into the assembled PCR products with the OSNBpctF (NdeI) and OSHBR (BamHI) primers. The digested PCR product was heated at 80° C. for 30 minutes to inactive the restriction enzymes and used directly for ligation into a pET11a vector.

The pET-11a vector was digested with NdeI and BamHI restriction enzymes, gel purified using a Qiagen Gel Extraction kit, treated with shrimp alkaline phosphatase (Roche Molecular Biochemicals; Indianapolis, Ind.) and used in a ligation reaction with the assembled PCR product. The ligation was performed at 16° C. overnight using T4 ligase (Roche Molecular Biochemicals; Indianapolis, Ind.). The resulting ligation reaction was transformed into NovaBlue chemically competent cells (Novagen; Madison, Wis.) using a heat-shock method. Once shocked, the cells were plated on LB plates supplemented with 50 µg/mL carbenicillin. The plasmid DNA was purified from individual colonies using a QiaPrep Spin Miniprep Kit (Qiagen Inc.; Valencia, Calif.) and digested with NdeI and BamHI restriction enzymes for gel electrophoresis analysis. The resulting plasmids carrying the CoA transferase and 3-hydroxypropionyl-CoA dehydratase (pTH) were digested with XbaI and NdeI, purified using gel electrophoresis and a Qiagen Gel Extraction kit, and used as a vector for cloning of the E2 α subunit/E2 β subunit PCR product.

The E2 α subunit/E2 β subunit PCR product digested with the same enzymes was ligated into the pTH vector. The ligation reaction was performed at 16° C. overnight using T4 ligase (Roche Molecular Biochemicals; Indianapolis, Ind.). The ligation mixture was transformed into chemically competent NovaBlue cells (Novagen) that then were plated on LB plates supplemented with 50 µg/mL carbenicillin. The plasmid DNA was purified from individual colonies using a Qiaprep Spin Miniprep Kit (Qiagen Inc.; Valencia, Calif.) and digested with XbaI and NdeI restriction enzymes for gel electrophoresis analysis. The resulting plasmids carrying the E2 α and β subunits of the lactyl-CoA dehydratase, the CoA transferase, and the 3-hydroxypropionyl-CoA dehydratase (pEIITH) were transformed into BL21(DE3) cells to study the expression of the cloned sequences.

The gel purified E1 activator PCR product was digested with EcoRI and KpnI restriction enzymes, heated at 65° C. for 30 minutes, and ligated into a vector (pPROLar.A) that was digested with EcoRI and KpnI restriction enzymes, gel purified using Qiagen Gel Extraction kit, and treated with shrimp alkaline phosphatase (Roche Molecular Biochemicals; Indianapolis, Ind.). The ligation was performed at 16° C. overnight using T4 ligase (Roche Molecular Biochemicals; Indianapolis, Ind.). The resulting ligation reaction was transformed into DH10B electro-competent cells (Gibco Life Technologies; Gaithersburg, Md.) using electroporation. Once electroporated, the cells were plated on LB plates supplemented with 25 μg/mL kanamycin. The plasmid DNA was purified from individual colonies using a QiaPrep Spin Miniprep Kit (Qiagen Inc., Valencia, Calif.) and digested with EcoRI and KpnI restriction enzymes for gel electrophoresis analysis. The resulting plasmids carrying the E1 activator (pPROEI) are transformed into BL21 (DE3) cells to study the expression of the cloned sequence.

The pPROEI and pEIITH plasmids are compatible plasmids that can be used in the same bacterial host cell. In addition, the expression from the pPROEI and pEIITH plasmids can be induced at different levels using IPTG and arabinose, allowing for the fine-tuning of the expression of the cloned sequences.

Example 8

Production of 3-HP

3-HP was produced using recombinant *E. coli* in a small-scale batch fermentation reaction. The construction of strain ALS848 (also designated as TA3476 (*J. Bacteriol.*, 143: 1081-1085 (1980))) that carried inducible T7 RNA polymerase was performed using % DE3 lysogenization kit (Novagen, Madison, Wis.) according to the manufacture's instructions. The constructed strain was designated ALS484 (DE3). Strain ALS484(DE3) was transformed with pEIITHrEI plasmid using standard electroporation techniques. The transformants were selected on LB/carbenicillin (50 μg/mL) plates. A single colony was used to inoculate 4 mL culture in a 15 mL culture tube. Strain ALS484(DE3) strain carrying vector pET11a was used as a control. The cells were grown at 37° C. and 250 rpm in an Innova 4230 Incubator Shaker (New Brunswick Scientific, Edison, N.J.) for eight to nine hours. This culture (3 mL) was used to start an anaerobic fermentation. Two 100 mL anaerobic cultures of ALS(DE3)/pET11a and ALS(DE3)pEIITHrEI were grown in serum bottles using LB media supplemented with 0.4% glucose, 50 μg/mL carbenicillin, and 100 mM MOPS. The cultures were grown overnight at 37° C. without shaking. The overnight grown cultures were sub-cultured in serum bottles using fresh LB media supplemented with 0.4% glucose, 50 μg/mL carbenicillin, and 100 mM MOPS. The starting OD(600) of these cultures was adjusted to 0.3. These serum bottles were incubated at 37° C. without shaking. After one hour of incubation, the cultures were induced with 100 μM IPTG. A 3 mL sample was taken from each of the serum bottles at 30 minutes, 1 hour, 2 hours, 4 hours, 6 hours, 8 hours, and 24 hours. The samples were transferred into two properly labeled 2 mL microcentrifuge tubes, each containing 1.5 mL sample. The samples were spun down in a microcentrifuge centrifuge at 14000 g for 3 minutes. The supernatant was passed through a 0.45μ syringe filter, and the resulting filtrate was stored at −20° C. until further analysis. The formation of fermentation products, mainly lactate and 3-hydroxypropionate, was measured by detecting derivatized CoA esters of lactate and 3-HP using LC/MS.

The following methods were performed to convert lactate and 3-HP into their respective CoA esters. Briefly, the filtrates were mixed with CoA-reaction buffer (200 mM potassium phosphate buffer, 2 mM acetyl-CoA, and 0.1 mg/mL purified transferase) in 1:1 ratio. The reaction was allowed to proceed for 20 minutes at room temperature. The reaction was stopped by adding 1 volume of 10% TFA. The sample was purified using Sep Pak Vac columns (Waters). The column was conditioned with methanol and washed two times with 0.1% TFA. The sample was then applied to the column, and the column was washed two more times with 0.1% TFA. The sample was eluted with 40% acetonitrile, 0.1% TFA. The acetonitrile was removed from the sample by vacuum centrifugation. The samples were then analyzed by LC/MS.

Analysis of the standard CoA/CoA thioester mixtures and the CoA thioester mixtures derived from fermentation broths were carried out using a Waters/Micromass ZQ LC/MS instrument which had a Waters 2690 liquid chromatograph with a Waters 996 Photo-Diode Array (PDA) absorbance monitor placed in series between the chromatograph and the single quadrupole mass spectrometer. LC separations were made using a 4.6×150 mm YMC ODS-AQ (3 μm particles, 120 Å pores) reversed-phase chromatography column at room temperature. Two gradient elution systems were developed using different mobile phases for the separation of the CoA esters. These two systems are summarized in Table 3. Elution system 1 was developed to provide the most rapid and efficient separation of the five-component CoA/CoA thioester mixture (CoA, acetyl-CoA, lactyl-CoA, acrylyl-CoA, and propionyl-CoA), while elution system 2 was developed to provide baseline separation of the structurally isomeric esters lactyl-CoA and 3HP-CoA in addition to separation of the remaining esters listed above. In all cases, the flow rate was 0.250 mL/minute, and photodiode array UV absorbance was monitored from 200 nm to 400 nm. All parameters of the electrospray MS system were optimized and selected based on generation of protonated molecular ions ([M+H]$^+$) of the analytes of interest and production of characteristic fragment ions. The following instrumental parameters were used for ESI-MS detection of CoA and organic acid-CoA thioesters in the positive ion mode: Capillary: 4.0 V; Cone: 56 V; Extractor: 1 V; RF lens: 0 V; Source temperature: 100° C.; Desolvation temperature: 300° C.; Desolvation gas: 500 L/hour; Cone gas: 40 L/hour; Low mass resolution: 13.0; High mass resolution: 14.5; Ion energy: 0.5; Multiplier: 650. Uncertainties for reported mass/charge ratios (m/z) and molecular masses are ±0.01%. Table 3 provides a summary of gradient elution systems for the separation of organic acid-Coenzyme A thioesters.

TABLE 3

| System | Buffer A | Buffer B | Gradient | |
|---|---|---|---|---|
| | | | Time | Percent B |
| 1 | 25 mM ammonium acetate 0.5% acetic acid | ACN 0.5% acetic acid | 0 | 10 |
| | | | 40 | 40 |
| | | | 42 | 100 |
| | | | 47 | 100 |
| | | | 50 | 10 |
| 2 | 25 mM ammonium acetate 10 mM TEA 0.5% acetic acid | ACN 0.5% acetic acid | 0 | 10 |
| | | | 10 | 10 |
| | | | 45 | 60 |
| | | | 50 | 100 |
| | | | 53 | 100 |
| | | | 54 | 10 |

The following methods were used to separate the derivatized 3-hydroxypropionyl-CoA, which was formed from 3-HP, from 2-hydroxypropionyl-CoA (i.e., lactyl-CoA), which was formed from lactate. Because these structural isomers have identical masses and mass spectral fragmentation behavior, the separation and identification of these analytes in a mixture depends on their chromatographic separation. While elution system 1 provided excellent separation of the CoA thioesters tested (FIG. 46), it was unable to resolve 3-HP-CoA and lactyl-CoA. An alternative LC elution system was developed using ammonium acetate and triethylamine (system 2; Table 3).

Figure 47A:
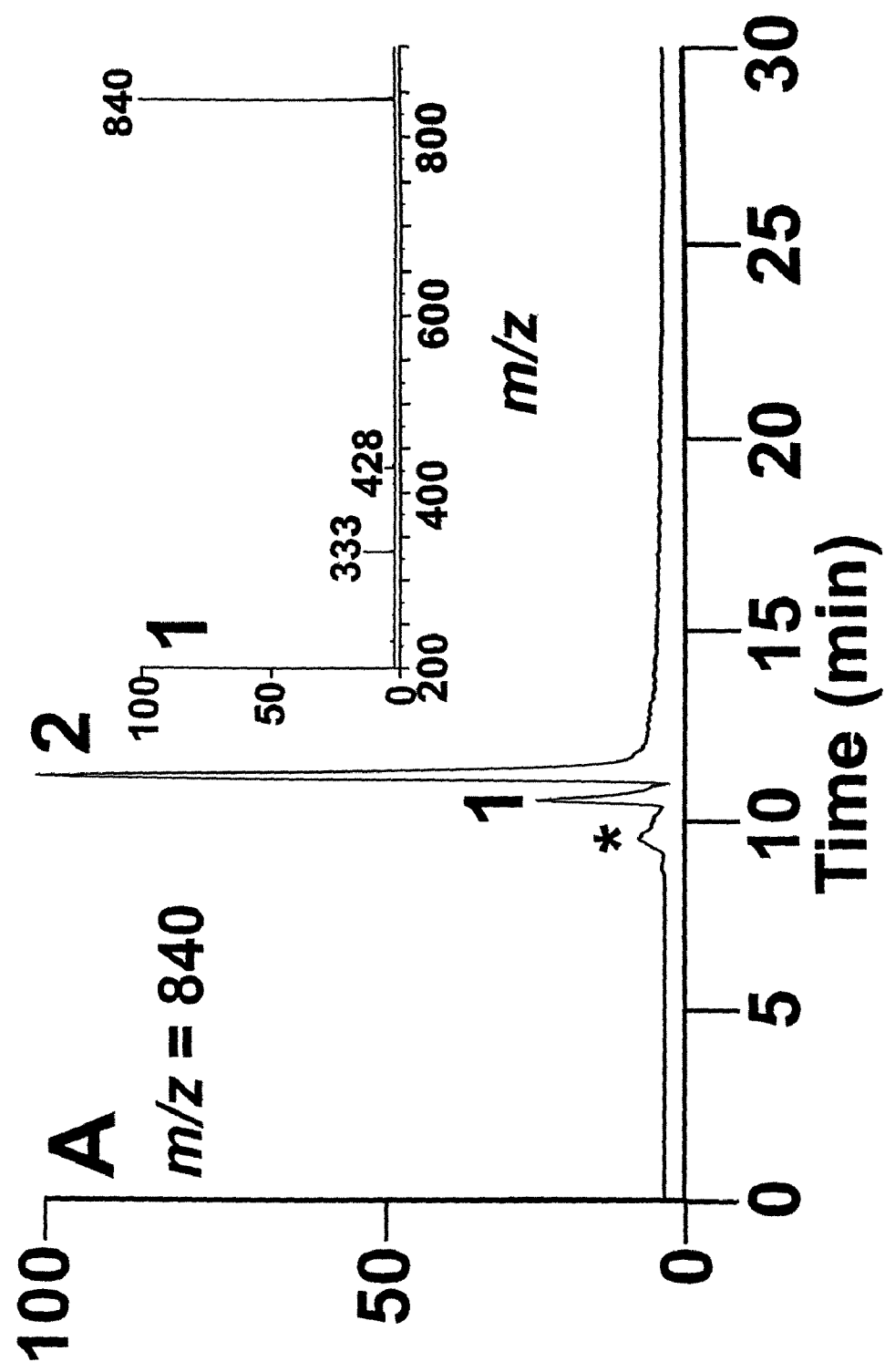
FIG. 47 contains ion chromatograms and mass spectrums. Panel A is a total ion chromatogram of a mixture of lactyl-CoA and 3-HP-CoA. The Panel A insert is the mass spectrum recorded under peak 1. Panel B is a total ion chromatogram of lactyl-CoA. The Panel B insert is the mass spectrum recorded under peak 2. In each panel, peak 1 is 3-HP-CoA, and peak 2 is lactyl-CoA. The peak labeled with an asterisk was confirmed not to be a CoA ester.
Figure 47B:
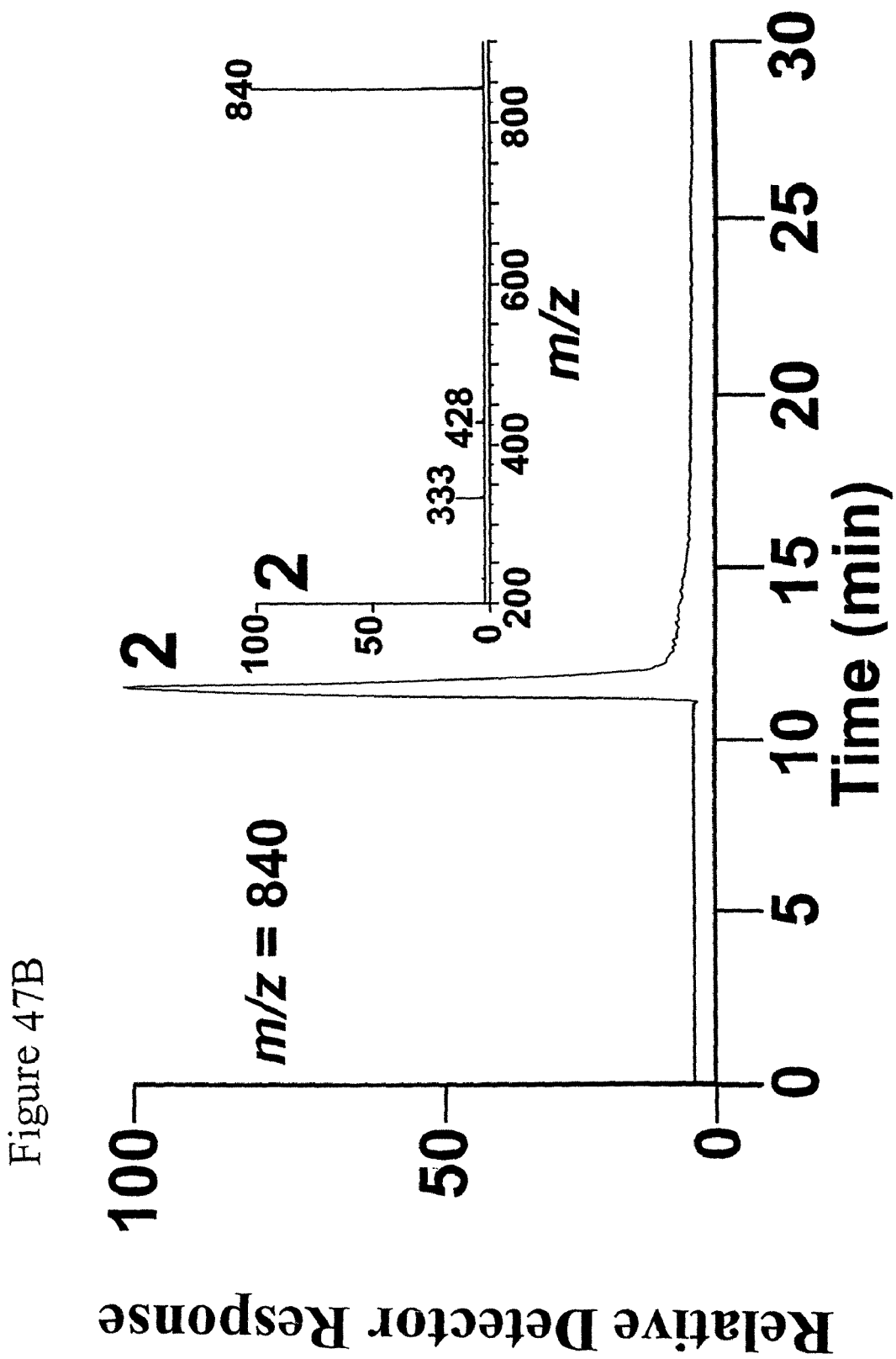

The ability of system 2 to separate 3-HP-CoA and lactyl-CoA was tested on a mixture of these two compounds. Comparing the results from a mixture of 3-HP-CoA and lactyl-CoA (FIG. 47, Panel A) to the results from lactyl-CoA only (FIG. 47, Panel B) revealed that system 2 can separate 3-HP-CoA and lactyl-CoA. The mass spectrum recorded under peak 1 (FIG. 47, Panel A insert) was used to identify peak 1 as being a hydroxypropionyl-CoA thioester when compared to FIG. 46, Panel C. In addition, comparison of Panels A and B of FIG. 47 as well as the mass spectra results corresponding to each peak revealed that peak 1 corresponds to 3-HP-CoA and peak 2 corresponds to lactyl-CoA.

Figure 48A:
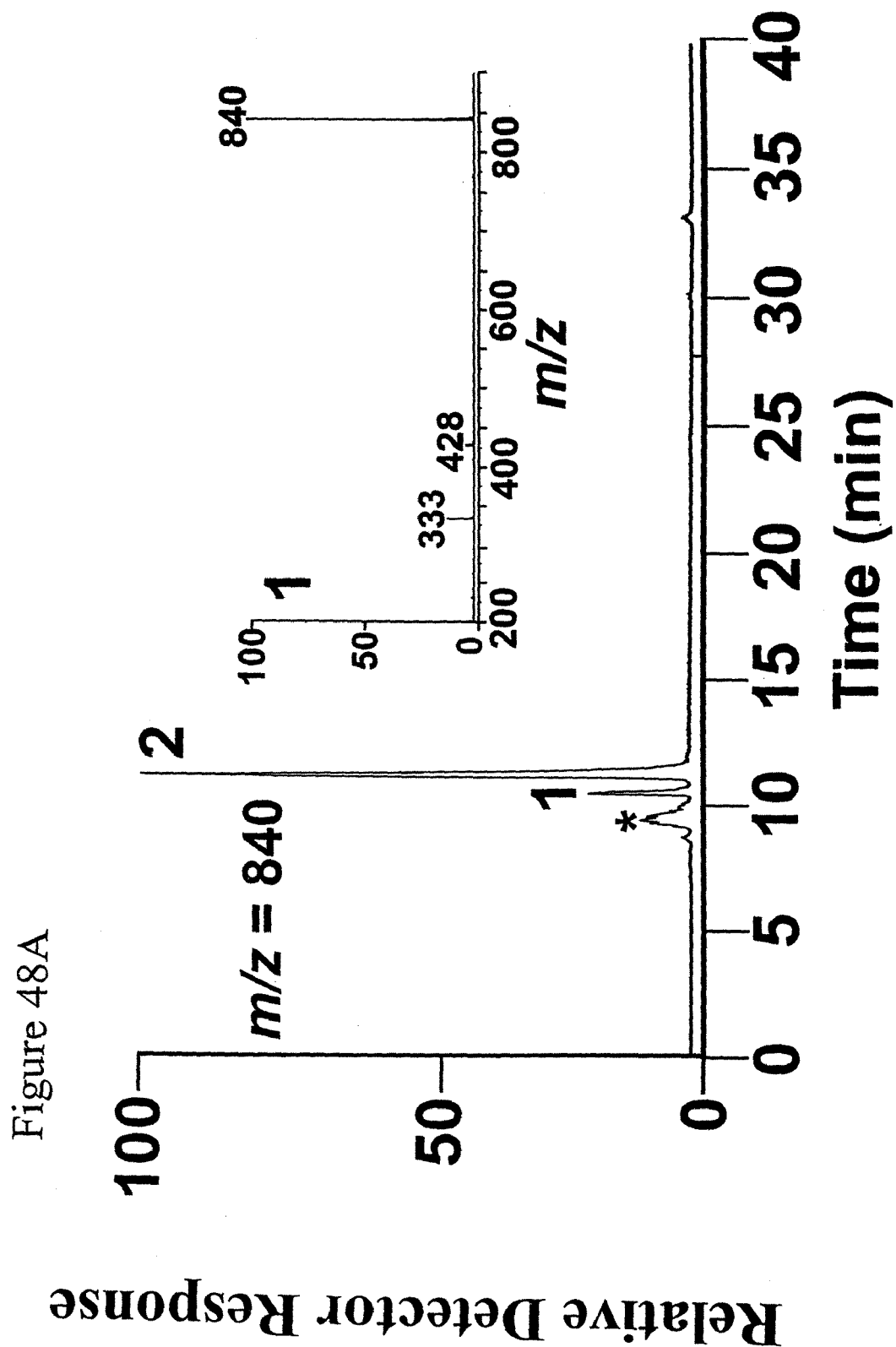
FIG. 48 contains ion chromatograms and mass spectrums. Panel A is a total ion chromatogram of CoA esters derived from a broth produced by *E. coli* transfected with pEIITHrEI. The Panel A insert is the mass spectrum recorded under peak 1. Panel B is a total ion chromatogram of CoA esters derived from a broth produced by control *E. coli* not transfected with pEIITHrEI. The Panel B insert is the mass spectrum recorded under peak 2. In each panel, peak 1 is 3-HP-CoA, and peak 2 is lactyl-CoA. The peaks labeled with an asterisk were confirmed not to be a CoA ester.
Figure 48B:
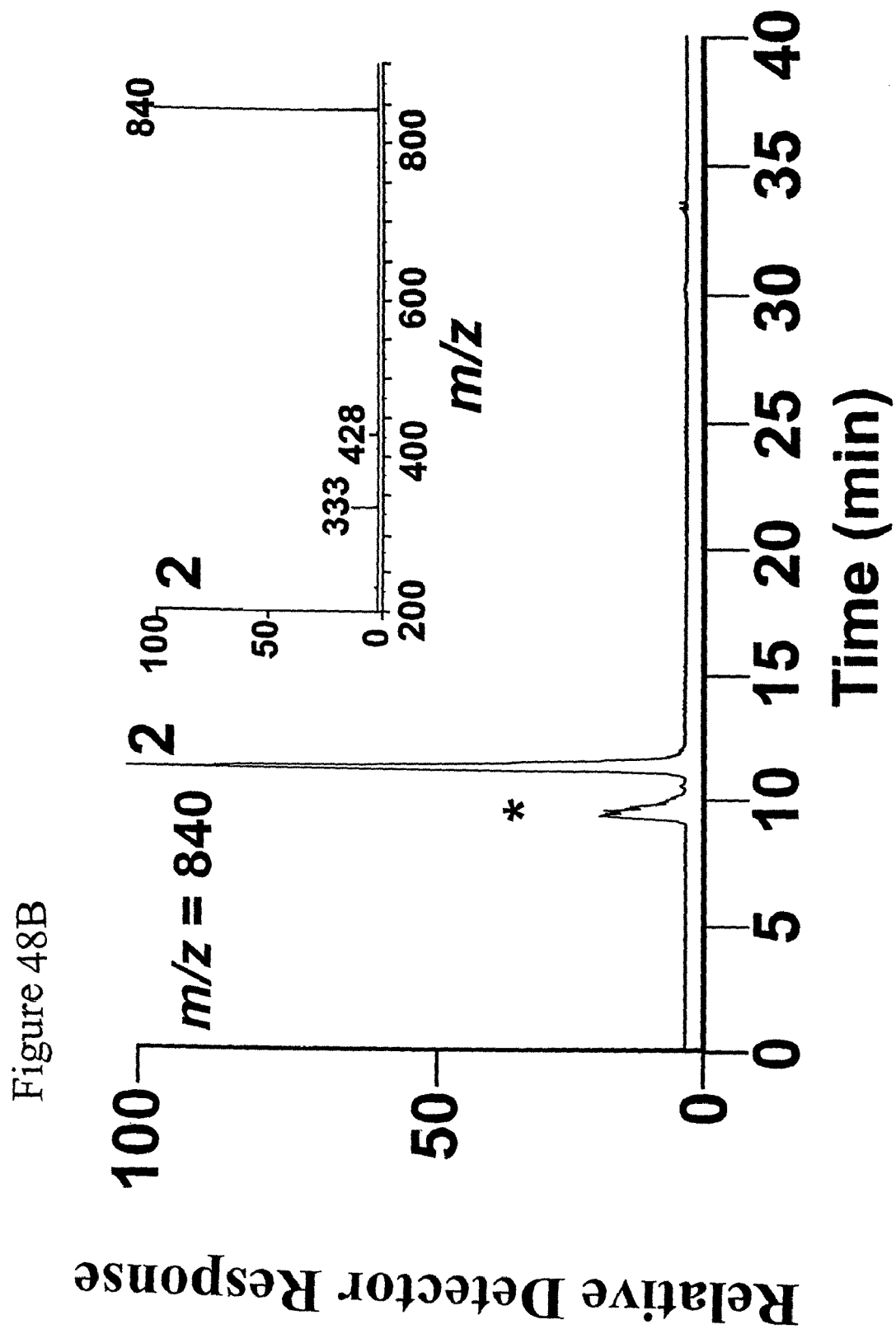

System 2 was used to confirm that *E. coli* transfected with pEIITHrEI produced 3-HP in that 3-HP-CoA was detected. Specifically, an ion chromatogram for m/z=840 in the analysis of a CoA transferase-treated fermentation broth aliquot collected from a culture of *E. coli* containing pEIITHrEI revealed the presence of 3-HP-CoA (FIG. 48, Panel A). The CoA transferase-treated fermentation broth aliquot collected from a culture of *E. coli* lacking pEIITHrEI did not exhibit the peak corresponding to 3-HP-CoA (FIG. 48, Panel B). Thus, these results indicate that the pEIITHrEI plasmid directs the expression of polypeptides having propionyl-CoA transferase activity, lactyl-CoA dehydratase activity, and acrylyl-CoA hydratase activity. These results also indicate that expression of these polypeptides leads to the formation of 3-HP.

Example 9

Cloning Nucleic Acid Molecules that Encode a Polypeptide Having Acetyl CoA Carboxylase Activity Polypeptides having acetyl-CoA carboxylase activity catalyze the first committed step of the fatty acid synthesis by carboxylation of acetyl-CoA to malonyl-CoA. Polypeptides having acetyl-CoA carboxylase activity are also responsible for providing malonyl-CoA for the biosynthesis of very-long-chain fatty acids required for proper cell function. Polypeptides having acetyl-CoA carboxylase activity can be biotin dependent enzymes in which the cofactor biotin is post-translationally attached to a specific lysine residue. The reaction catalyzed by such polypeptides consists of two discrete half reactions. In the first half reaction, biotin is carboxylated by biocarbonate in an ATP-dependent reaction to form carboxy-biotin. In the second half reaction, the carboxyl group is transferred to acetyl-CoA to form malonyl-CoA.

Prokaryotic and eukaryotic polypeptides having acetyl-CoA carboxylase activity exist. The prokaryotic polypeptide is a multi-subunit enzyme (four subunits), where each of the subunits is encoded by a different nucleic acid sequence. For example, in *E. coli*, the following genes encode for the four subunits of acetyl-CoA carboxylase:

accA: Acetyl-coenzyme a carboxylase carboxyl transferase subunit alpha (GenBank® accession number M96394)

accB: Biotin carboxyl carrier protein (GenBank® accession number U18997)

accC: Biotin carboxylase (GenBank® accession number U18997)

accD: Acetyl-coenzyme a carboxylase carboxyl transferase subunit beta (GenBank® accession number M68934)

The eukaryotic polypeptide is a high molecular weight multi-functional enzyme encoded by a single gene. For example, in *Saccharomyces cerevisiae*, the acetyl-CoA carboxylase can have the sequence set forth in GenBank® accession number M92156.

The prokaryotic type acetyl-CoA carboxylase from *E. coli* was overexpressed using T7 promoter vector pFN476 as described elsewhere (Davis et al. *J. Biol. Chem.*, 275:28593-28598 (2000)). The eukaryotic type acetyl-CoA carboxylase gene was amplified from *Saccharomyces cerevisiae* genomic DNA. Two primers were designed to amplify the acc1 gene from in *S. cerevisiae* (acc1F 5'-atagGCGGCCGC AGGAATGCTGTATGAGCGAAGAAAGCTTATT C-3', SEQ ID NO: 138 where the bold is homologous sequence, the italics is a Not I site, the underline is a RBS, and the lowercase is extra; and acc1R 5'-atgctcgcatCTCGAGTAGCTAAAT-TAAATTACATCAATAGTA-3', SEQ ID NO: 139 where the bold is homologous sequence, the italics is a Xho I site, and the lowercase is extra). The following PCR mix is used to amplify acc1 gene 10×pfu buffer (10 μL), dNTP (10 mM; 2 μL), cDNA (2 μL), acc1F (100 μM; 1 μL), acc1R (100 μM; 1 μL), pfu enzyme (2.5 units/μL; 2 μL), and DI water (82 μL). The following protocol was used to amplify the acc1 gene. After performing PCR, the PCR product was separated on a gel, and the band corresponding to acc1 nucleic acid (about 6.7 Kb) was gel isolated using Qiagen gel isolation kit. The PCR fragment is digested with Not I and Xho I (New England BioLab) restriction enzymes. The digested PCR fragment is then ligated to pET30a which was restricted with Not I and Xho I and dephosphorylated with SAP enzyme. The *E. coli* strain DH10B was transformed with 1 μL of the ligation mix, and the cells were recovered in 1 mL of SOC media. The transformed cells were selected on LB/kanamycin (50 μg/μL) plates. Eight single colonies are selected, and PCR was used to screen for the correct insert. The plasmid having correct insert was isolated using Qiagen Spin Mini prep kit.

To obtain a polypeptide having acetyl-CoA carboxylase activity, the plasmid pMSD8 or pET30a/acc1 overexpressing *E. coli* or *S. cerevisiae* acetyl-CoA carboxylase was transformed into Tuner pLacI chemically competent cells (Novagen, Madison, Wis.). The transformed cells were selected on LB/chloramphenicol (25 μg/mL) plus carbencillin (50 μg/mL) or kanamycin (50 μg/mL).

A crude extract of this strain can be prepared in the following manner. An overnight culture of Tuner pLacI with pMSD8 is subcultured into 200 mL (in one liter baffle culture flask) of fresh M9 media supplemented with 0.4% glucose, 1 μg/mL thiamine, 0.1% casamino acids, and 50 μg/mL carbencillin or 50 μg/mL kanamycin and 25 μg/mL chloramphenicol. The culture is grown at 37° C. in a shaker with 250 rpm agitation until it reaches an optical density at 600 nm of about 0.6. IPTG is then added to a final concentration of 100 μM. The culture is then incubated for an additional 3 hours with shaking speed of 250 rpm at 37° C. Cells are harvested by centrifugation at 8000×g and are washed one time with 0.85% NaCl. The cell pellet was resuspended in a minimal volume of 50 mM Tris-HCl (pH 8.0), 5 mM $MgCl_2$, 100 mM KCl, 2 mM DTT, and 5% glycerol. The cells are lysed by passing them two times through a French Pressure cell at 1000 psig pressure. The cell debris was removed by centrifugation for 20 minutes at 30,000×g.

The enzyme can be assayed using a method from Davis et al. (*J. Biol. Chem.*, 275:28593-28598 (2000)).

Example 10

Cloning a Nucleic Acid Molecule that Encodes a Polypeptide Having Malonyl-CoA Reductase Activity from *Chloroflexus auarantiacus*

A polypeptide having malonyl-CoA reductase activity was partially purified from *Chloroflexus auarantiacus* and used to obtained amino acid micro-sequencing results. The amino acid sequencing results were used to identify and clone the nucleic acid that encodes a polypeptide having malonyl-CoA reductase activity.

Biomass required for protein purification was grown in B. Braun BIOSTAT B fermenters (B. Braun Biotech International GmbH, Melsungen, Germany). A glass vessel fitted with a water jacket for heating was used to grow the required biomass. The glass vessel was connected to its own control unit. The liquid working volume was 4 L, and the fermenter was operated at 55° C. with 75 rpm of agitation. Carbon dioxide was occasionally bubbled through the headspace of the fermenter to maintain anaerobic conditions. The pH of the cultures was monitored using a standard pH probe and was maintained between 8.0 and 8.3. The inoculum for the fermenters was grown in two 250 mL bottles in an Innova 4230 Incubator, Shaker (New Brunswick Scientific, Edison, N.J.) at 55° C. with interior lights. The fermenters were illuminated by three 65 W plant light reflector lamps (General Electric, Cleveland, Ohio). Each lamp was placed approximately 50 cm away from the glass vessel. The media used for the inoculum and the fermenter culture was as follows per liter: 0.07 g EDTA, 1 mL micronutrient solution, 1 mL $FeCl_3$ solution, 0.06 g $CaSO_4.2H_2O$, 0.1 g $MgSO_4.7H_2O$, 0.008 g NaCl, 0.075 g KCl, 0.103 g $KNO_3$, 0.68 g $NaNO_3$, 0.111 g $Na_2HPO_4$, 0.2 g $NH_4Cl$, 1 g yeast extract, 2.5 g casamino acid, 0.5 g Glycyl-Glycine, and 900 mL DI water. The micronutrient solution contained the following per liter: 0.5 mL $H_2SO_4$ (conc.), 2.28 g $MnSO_4.7H_2O$, 0.5 g $ZnSO_4.7H_2O$, 0.5 g $H_3BO_3$, 0.025 g $CuSO_4.2H_2O$, 0.025 g $Na_2MoO_4.2H_2O$, and 0.045 g $CoCl_2.6H_2O$. The $FeCl_3$ solution contained 0.2905 g $FeCl_3$ per liter. After adjusting the pH of the media to 8.2 to 8.4, 0.75 g/L $Na_2S.9H_2O$ was added, the pH was readjusted to 8.2 to 8.4, and the media was filter-sterilized through a 0.22µ filter.

The fermenter was inoculated with 500 mL of grown culture. The fermentation was stopped, and the biomass was harvested after the cell density was about 0.5 to 0.6 units at 600 nm.

The cells were harvested by centrifugation at 5000×g (Beckman JLA 8.1000 rotor) at 4° C., washed with 1 volume of ice cold 0.85% NaCl, and centrifuged again. The cell pellet was resuspended in 30 mL of ice cold 100 mM Tris-HCl (pH 7.8) buffer that was supplemented with 2 mM DTT, 5 mM $MgCl_2$, 0.4 mM PEFABLOC (Roche Molecular Biochemicals, Indianapolis, Ind.), 1% streptomycin sulfate, and 2 tablets of Complete EDTA-free protease inhibitor cocktail (Roche Molecular Biochemicals, Indianapolis, Ind.). The cell suspension was lysed by passing the suspension, three times, through a 50 mL French Pressure Cell operated at 1600 psi (gauge reading). Cell debris was removed by centrifugation at 30,000×g (Beckman JA 25.50 rotor). The crude extract was filtered prior to chromotography using a 0.2 µm HT Tuffryn membrane syringe filter (Pall Corp., Ann Arbor, Mich.). The protein concentration of the crude extract was 29 mg/mL, which was determined using the BioRad Protein Assay according to the manufacturer's microassay protocol. Bovine gamma globulin was used for the standard curve determination. This assay was based on the Bradford dye-binding procedure (Bradford, *Anal. Biochem.*, 72:248 (1976)).

Before starting the protein purification, the following assay was used to determine the activity of malonyl-CoA reductase in the crude extract. A 50 µL aliquot of the cell extract (29 mg/mL) was added to 10 µL 1M Tris-HCl (final concentration in assay 100 mM), 10 µL 10 mM malonyl CoA (final concentration in assay 1 mM), 5.5 µL 5.5 mM NADPH (final concentration in assay 0.3 mM), and 24.5 µL DI water in a 96 well UV transparent plate (Corning, N.Y.). The enzyme activity was measured at 45° C. using SpectraMAX Plus 96 well plate reader (Molecular devices Sunnyvale, Calif.). The activity of malonyl-CoA reductase was monitored by measuring the disappearance of NADPH at 340 nm wavelength. The crude extract exhibited malonyl-CoA reductase activity.

The 5 mL (total 145 mg) protein cell extract was diluted with 20 mL buffer A (20 mM ethanolamine (pH 9.0), 5 mM $MgCl_2$, 2 mM DTT). The chromatographic protein purification was conducted using a BioLogic protein purification system (BioRad Hercules, Calif.). The 25 mL of cell suspension was loaded onto a UNO Q-6 ion-exchange column that had been equilibrated with buffer A at a rate of 1 mL/minute. After sample loading, the column was washed with 2.5 times column volume of buffer A at a rate of 2 mL/minute. The proteins were eluted with a linear gradient of NaCl in buffer A from 0-0.33 M in 25 Column volume. During the entire chromatographic separation, three mL fractions were collected. The collection tubes contained 50 µL of Tris-HCl (pH 6.5) so that the pH of the eluted sample dropped to about pH 7. Major chromatographic peaks were detected in the region that corresponded to fractions 18 to 21 and 23 to 30. A 200 µL sample was taken from these fractions and concentrated in a microcentrifuge at 4° C. using a Microcon YM-10 columns (Millipore Corp., Bedford, Mass.) as per manufacture's instructions. To each of the concentrated fraction, buffer A-Tris (100 mM Tris-HCl (pH 7.8), 5 mM $MgCl_2$, 2 mM DTT) was added to bring the total volume to 100 µL. Each of these fractions was tested for the malonyl-CoA reductase activity using the spectophotometric assay described above. The majority of specific malonyl CoA activity was found in fractions 18 to 21. These fractions were pooled together, and the pooled sample was desalted using PD-10 column (Amersham Pharmacia Piscataway, N.J.) as per manufacture's instructions.

The 10.5 mL of desalted protein extract was diluted with buffer A-Tris to a volume of 25 mL. This desalted diluted sample was applied to a 1 mL HiTrap Blue column (Amersham Pharmacia Piscataway, N.J.) which was equilibrated with buffer A-Tris. The sample was loaded at a rate of 0.1 mL/minute. Unbound proteins were washed with 2.5 CV buffer A-Tris. The protein was eluted with 100 Mm Tris (pH 7.8), 5 mM $MgCl_2$, 2 mM DTT, 2 mM NADPH, and 1 M NaCl. During this separation process, one mL fractions were collected. A 200 µL sample was drawn from fractions 49 to 54 and concentrated. Buffer A-Tris was added to each of the concentrated fractions to bring the total volume to 100 µL. Fractions were assayed for enzyme activity as described above. The highest specific activity was observed in fraction 51. The entire fraction 51 was concentrated as described above, and the concentrated sample was separated on an SDS-PAGE gel.

Electrophoresis was carried out using a Bio-Rad Protean II minigel system and pre-cast SDS-PAGE gels (4-15%), or a Protean II XI system and 16 cm×20 cm×1 mm SDS-PAGE gels (10%) cast as per the manufacturer's protocol. The gels were run according to the manufacturer's instructions with a running buffer of 25 mM Tris-HCl (pH 8.3), 192 mM glycine, and 0.1% SDS.

A gel thickness of 1 mm was used to run samples from fraction 51. Protein from fraction 51 was loaded onto 10% SDS-PAGE (3 lanes, each containing 75 µg of total protein). The gels were stained briefly with Coomassie blue (Bio-Rad, Hercules, Calif.) and then destained to a clear background with a 10% acetic acid and 20% methanol solution. The staining revealed a band of about 130 to 140 KDa.

The protein band of about 130-140 KDa was excised with no excess unstained gel present. An equal area gel without protein was excised as a negative control. The gel slices were placed in uncolored microcentrifuge tubes, prewashed with 50% acetonitrile in HPLC-grade water, washed twice with 50% acetonitrile, and shipped on dry ice to Harvard Microchemistry Sequencing Facility, Cambridge, Mass.

After in-situ enzymatic digestion of the polypeptide sample with trypsin, the resulting polypeptides were separated by micro-capillary reverse-phase HPLC. The HPLC was directly coupled to the nano-electrospray ionization source of a Finnigan LCQ quadrupole ion trap mass spectrometer (μLC/MS/MS). Individual sequence spectra (MS/MS) were acquired on-line at high sensitivity for the multiple polypeptides separated during the chromatographic run. The MS/MS spectra of the polypeptides were correlated with known sequences using the algorithm Sequest developed at the University of Washington (Eng et al., *J. Am. Soc. Mass Spectrom.*, 5:976 (1994)) and programs developed at Harvard (Chittum et al., *Biochemistry*, 37:10866 (1998)). The results were reviewed for consensus with known proteins and for manual confirmation of fidelity.

A similar purification procedure was used to obtain another sample (protein 1 sample) that was subjected to the same analysis that was used to evaluate the fraction 51 sample.

The polypeptide sequence results indicated that the polypeptides obtained from both the fraction 51 sample and the protein 1 sample had similarity to the six (764, 799, 859, 923, 1090, 1024) contigs sequenced from the *C. aurantiacus* genome and presented on the Joint Genome Institute's web site (http://www.jgi.doe.gov/). The 764 contig was the most prominent of the six with about 40 peptide sequences showing similarity. BLASTX analysis of each of these contigs on the GenBank web site (http://www.ncbi.nlm.nih.gov/BLAST/) indicated that the DNA sequence of the 764 contig (4201 bases) encoded for polypeptides that had a dehydrogenase/reductase type activity. Close inspection of the 764 contig, however, revealed that this contig did not have an appropriate ORF that would encode for a 130-140 KDa polypeptide.

BASLTX analysis also was conducted using the other five contigs. The results of this analysis were as follows. The 799 contig (3173 bases) appeared to encode polypeptides having phosphate and dehydrogenase type activities. The 859 contig (5865 bases) appeared to encode polypeptides having synthetase type activities. The 923 contig (5660 bases) appeared to encode polypeptides having elongation factor and synthetase type activities. The 1090 contig (15201 bases) appeared to encode polypeptides having dehydrogenase/reductase and cytochrome and sigma factor activities. The 1024 contig (12276 bases) appeared to encode polypeptides having dehydrogenase and decarboxylase and synthetase type activities. Thus, the 859 and 923 contigs were eliminated from any further analysis.

The results from the BLASTX analysis also revealed that the dehydrogenase found in the 1024 contig was most likely an inositol monophosphate dehydrogenase. Thus, the 1024 contig was eliminated as a possible candidate that might encode for a polypeptide having malonyl-CoA reductase activity. The 799 contig also was eliminated since this contig is part of the OS17 polypeptide described above.

This narrowed down the search to 2 contigs, the 764 and 1090 contigs. Since the contigs were identified using the same protein sample and the dehydrogenase activities found in these contigs gave very similar BLASTX results, it was hypothesized that they are part of the same polypeptide. Additional evidence supporting this hypothesis was obtained from the discovery that the 764 and 1090 contigs are adjacent to each other in the *C. aurantiacus* genome as revealed by an analysis of scaffold data provided by the Joint Genome Institute. Sequence similarity and assembly analysis, however, revealed no overlapping sequence between these two contigs, possibly due to the presence of gaps in the genome sequencing.

The polypeptide sequences that belonged to the 764 and 1090 contigs were mapped. Based on this analysis, an appropriate coding frame and potential start and stop codons were identified. The following PCR primers were designed to PCR amplify a fragment that encoded for a polypeptide having malonyl-CoA reductase activity: PRO140F 5'-ATGGC-GACGGGCGAGTCCATGAG-3', SEQ ID NO:153; PRO140R 5'-GGACACGAAGAACAGGGCGACAC-3', SEQ ID NO:154; and PRO140UP 5'-GAACTGTCTGGAG-TAAGGCTGTC-3', SEQ ID NO:155. The PRO140F primer was designed based on the sequence of the 1090 contig and corresponds to the start of the potential start codon. The twelfth base was change from G to C to avoid primer-dimer formation. This change does not change the amino acid that was encoded by the codon. The PRO140R primer was designed based on sequence of the 764 contig and corresponds to a region located about 1 kB downstream from the potential stop codon. The PRO140UPF primer was designed based on sequence of the 1090 contig and corresponds to a region located about 300 bases upstream of potential start codon.

Genomic *C. aurantiacus* DNA was obtained. Briefly, *C. aurantiacus* was grown in 50 mL cultures for 3 to 4 days. Cells were pelleted and washed with 5 mL of a 10 mM Tris solution. The genomic DNA was then isolated using the gram positive bacteria protocol provided with Gentra Genomic "Puregene" DNA isolation kit (Gentra Systems, Minneapolis, Minn.). The cell pellet was resuspended in 1 mL Gentra Cell Suspension Solution to which 14.2 mg of lysozyme and 4 μL of 20 mg/mL proteinase K solution was added. The cell suspension was incubated at 37° C. for 30 minutes. The precipitated genomic DNA was recovered by centrifugation at 3500 g for 25 minutes and air-dried for 10 minutes. The genomic DNA was suspended in an appropriate amount of a 10 mM Tris solution and stored at 4° C.

Two PCR reactions were set-up using *C. aurantiacus* genomic DNA as template as follows:

|  |  | PCR program |
|---|---|---|
| PCR Reaction #1 | | |
| 3.3 × rTH polymerase Buffer | 30 μL | 94° C. 2 minutes |
| Mg(OAC) (25 mM) | 4 μL | 29 cycles of: |
| dNTP Mix (10 mM) | 3 μL | 94° C. 30 seconds |
| PRO140F (100 μM) | 2 μL | 63° C. 45 seconds |
| PRO140R (100 μM) | 2 μL | 68° C. 4.5 minutes |
| Genomic DNA (100 ng/mL) | 1 μL | 68° C. 7 minutes |
| rTH polymerase (2 U/μL) | 2 μL | 4° C. Until further use |
| pfu polymerase (2.5 U/μL) | 0.25 μL | |
| DI water | 55.75 μL | |
| Total | 100 μL | |
| PCR Reaction #2 | | |
| 3.3 × rTH polymerase Buffer | 30 μL | 94° C. 2 minutes |
| Mg(OAC) (25 mM) | 4 μL | 29 cycles of: |
| dNTP Mix (10 mM) | 3 μL | 94° C. 30 seconds |
| PRO140UPF (100 μM) | 2 μL | 60° C. 45 seconds |
| PRO140R (100 μM) | 2 μL | 68° C. 4.5 minutes |
| Genomic DNA (100 ng/mL) | 1 μL | 68° C. 7 minutes |
| rTH polymerase (2 U/μL) | 2 μL | 4° C. Until further use |

| PCR program | | |
|---|---|---|
| pfu polymerase 2.5 U/μL | 0.25 μL | |
| DI water | 55.75 μL | |
| Total | 100 μL | |

The products from both PCR reactions were separated on a 0.8% TAE gel. Both PCR reactions produced a product of 4.7 to 5 Kb in size. This approximately matched the expected size of a nucleic acid molecule that could encode a polypeptide having malonyl-CoA reductase activity.

Both PCR products were sequenced using sequencing primers (1090Fseq 5'-GATTCCGTATGTCACCCCTA-3', SEQ ID NO:156; and 764Rseq 5'-CAGGCGACTGGCAAT-CACAA-3', SEQ ID NO:157). The sequence analysis revealed a gap between the 764 and 1090 contigs. The nucleic acid sequence between the sequences from the 764 and 1090 contigs was greater than 300 base pairs in length (FIG. 51). In addition, the sequence analysis revealed an ORF of 3678 bases that showed similarities to dehydrogenase/reductase type enzymes (FIG. 52). The amino acid sequence encoded by this ORF is 1225 amino acids in length (FIG. 50). Also, BLASTP analysis of the amino acid sequence encoded by this ORF revealed two short chain dehydrogenase domains (adh type). These results are consistent with a polypeptide having malonyl-CoA reductase activity since such an enzyme involves two reduction steps for the conversion of malonyl CoA to 3-HP. Further, the computed MW of the polypeptide was determined to be about 134 KDa.

PCR was conducted using the PRO140F/PRO140R primer pair, *C. aurantiacus* genomic DNA, and the protocol described above as PCR reaction #1. After the PCR was completed, 0.25 U of Taq polymerase (Roche Molecular Biochemicals, Indianapolis, Ind.) was added to the PCR mix, which was then incubated at 72° C. for 10 minutes. The PCR product was column purified using Qiagen PCR purification kit (Qiagen Inc., Valencia, Calif.). The purified PCR product was then TOPO cloned into expression vector pCRT7/CT as per manufacture's instructions (Invitrogen, Carlsbad, Calif.). TOP10 F' chemical competent cells were transformed with the TOPO ligation mix as per manufacture's instructions (Invitrogen, Carlsbad, Calif.). The cells were recovered for half an hour, and the transformants were selected on LB/ampicillin (100 μg/mL) plates. Twenty single colonies were selected, and the plasmid DNA was isolated using Qiagen spin Mini prep kit (Qiagen Inc., Valencia, Calif.).

Each of these twenty clones were tested for correct orientation and right insert size by PCR. Briefly, plasmid DNA was used as a template, and the following two primers were used in the PCR amplification: PCRT7 5'-GAGACCACAACG-GTTTCCCTCTA-3', SEQ ID NO:158; and PRO140R 5'-GGACACGAAGAACAGGGCGACAC-3', SEQ ID NO:159. The following PCR reaction mix and program was used:

| PCR Reaction | | PCR program |
|---|---|---|
| 3.3 X rTH polymerase Buffer | 7.5 μL | 94° C. 2 minutes |
| Mg(OAC) (25 mM) | 1 μL | 25 cycles of: |
| dNTP Mix (10 mM) | 0.5 μL | 94° C. 30 seconds |
| PCRT7 (100 μM) | 0.125 μL | 55° C. 45 seconds |
| PRO140R (100 μM) | 0.125 μL | 68° C. 4 minutes |
| Plasmid DNA | 0.5 μL | 68° C. 7 minutes |

| PCR Reaction | | PCR program |
|---|---|---|
| rTH polymerase (2 U/μL) | 0.5 μL | 4° C. Until further use |
| DI water | 14.75 μL | |
| Total | 25 μL | |

Out of twenty clone tested, only one clone exhibited the correct insert (Clone # P-10). Chemical competent cells of BL21(DE3)pLysS (Invitrogen, Carlsbad, Calif.) were transformed with 2 μL of the P-10 plasmid DNA as per the manufacture's instructions. The cells were recovered at 37° C. for 30 minutes and were plated on LB ampicillin (100 μg/mL) and chloramphenicol (25 μg/mL).

A 20 mL culture of BL21(DE3)pLysS/P-10 and a 20 mL control culture of BL21(DE3)pLysS was incubated overnight. Using the overnight cultures as an inoculum, two 100 mL BL21(DE3)pLysS/P-10 clone cultures and two control strain cultures (BL21(DE3)pLysS) were started. All the cultures were induced with IPTG when they reached an OD of about 0.5 at 600 nm. The control strain culture was induced with 10 μM IPTG or 100 μM IPTG, while one of the BL21 (DE3)pLysS/P-10 clone cultures was induced with 10 μM IPTG and the other with 100 μM IPTG. The cultures were grown for 2.5 hours after induction. Aliquots were taken from each of the culture flasks before and after 2.5 hours of induction and separated using 4-15% SDS-PAGE to analyze polypeptide expression. In the induced BL21(DE3)pLysS/P-10 samples, a band corresponding to a polypeptide having a molecular weight of about 135 KDa was observed. This band was absent in the control strain samples and in samples taken before IPTG induction.

To assess malonyl-CoA reductase activity, BL21(DE3) pLysS/P-10 and BL21(DE3)pLysS cells were cultured and then harvested by centrifugation at 8,000×g (Rotor JA 16.250, Beckman Coulter, Fullerton, Calif.). Once harvested, the cells were washed once with an equal volume of a 0.85% NaCl solution. The cell pellets were resuspended into 100 mM Tris-HCl buffer that was supplemented with 5 mM $Mg_2Cl$ and 2 mM DTT. The cells were disrupted by passing twice through a French Press Cell at 1,000 psi pressure (Gauge value). The cell debris was removed by centrifugation at 30,000×g (Rotor JA 25.50, Beckman Coulter, Fullerton, Calif.). The cell extract was maintained at 4° C. or on ice until further use.

Activity of malonyl-CoA reductase was measured at 37° C. for both the control cells and the IPTG-induced cells. The activity of malonyl-CoA reductase was monitored by observing the disappearance of added NADPH as described above. No activity was found in the cell extract of the control strain, while the cell extract from the IPTG-induced BL21(DE3) pLysS/P-10 cells displayed malonyl-CoA reductase activity with a specific activity calculated to be about 0.0942 μmole/minute/mg of total protein.

Malonyl-CoA reductase activity also was measured by analyzing 3-HP formation from malonyl CoA using the following reaction conducted at 37° C.:

| | Volume | Final conc. |
|---|---|---|
| Tris HCl (1 M) | 10 μL | 100 mM |
| Malonyl CoA (10 mM) | 40 μL | 4 mM |
| NADPH (10 mM) | 30 μL | 3 mM |
| Cell extract | 20 μL | |
| Total | 100 μL | |

The reaction was carried out at 37° C. for 30 minutes. In the control reaction, a cell extract from BL21(DE3)pLysS was added to a final concentration of 322 mg total protein. In the experimental reaction mix, a cell extract from BL21(DE3) pLysS/P-10 was added to a final concentration of 226 mg of total protein. The reaction mixtures were frozen at −20° C. until further analysis.

Chromatographic separation of the components in the reaction mixtures was performed using a HPX-87H (7.8×300 mm) organic acid HPLC column (BioRad Laboratories, Hercules, Calif.). The column was maintained at 60° C. Mobile phase composition was HPLC grade water pH to 2.5 using trifluoroacetic acid (TFA) and was delivered at a flow rate of 0.6 mL/minute.

Detection of 3-HP in the reaction samples was accomplished using a Waters/Micromass ZQ LC/MS instrument consisting of a Waters 2690 liquid chromatograph (Waters Corp., Milford, Mass.) with a Waters 996 Photo-diode Array (PDA) absorbance monitor placed in series between the chromatograph and the single quandrupole mass spectrometer. The ionization source was an Atmospheric Pressure Chemical Ionization (APCI) ionization source. All parameters of the APCI-MS system were optimized and selected based on the generation of the protonated molecular ion ([M+H])$^+$ of 3-HP. The following parameters were used to detect 3-HP in the positive ion mode: Corona: 10 µA; Cone: 20V; Extractor: 2V; RF lens: 0.2V; Source temperature: 100° C.; APCI Probe temperature: 300° C.; Desolvation gas: 500 L/hour; Cone gas: 50 L/hour; Low mass resolution: 15; High mass resolution: 15; Ion energy: 1.0; Multiplier: 650. Data was collected in Selected Ion Reporting (SIR) mode set at m/z=90.9.

Both the control reaction sample and the experimental reaction sample were probed for presence of 3-HP using the HPLC-mass spectroscopy technique. In the control samples, no 3-HP peak was observed, while the experimental sample exhibited a peak that matched the retention and the mass of 3-HP.

Example 11

Constructing Recombinant Cells that Produce 3-HP

Figure 45:
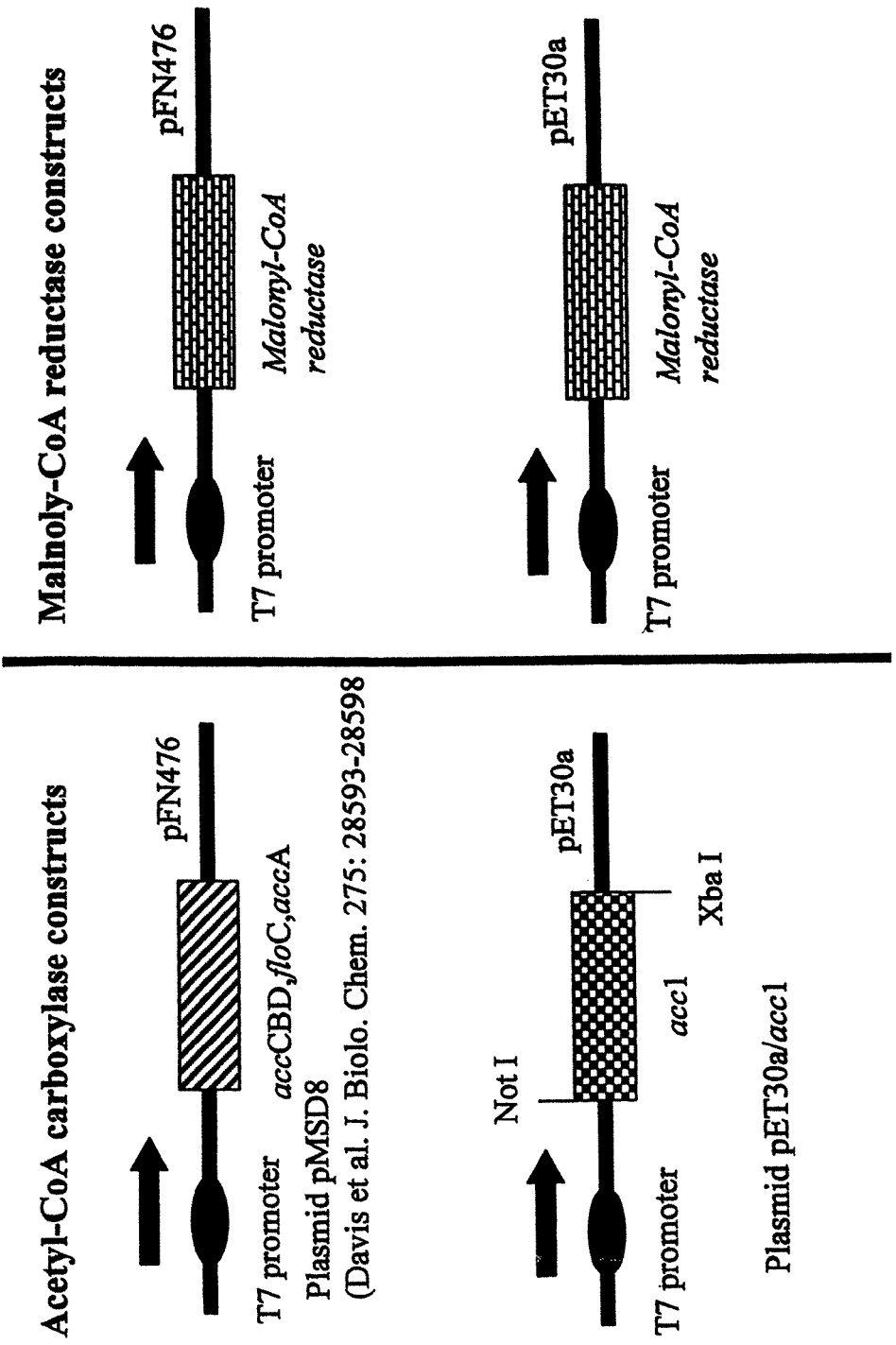
FIG. 45 is a diagram of pMSD8, pET30a/acc1, pFN476, and PET286 constructs.
Figure 46A:
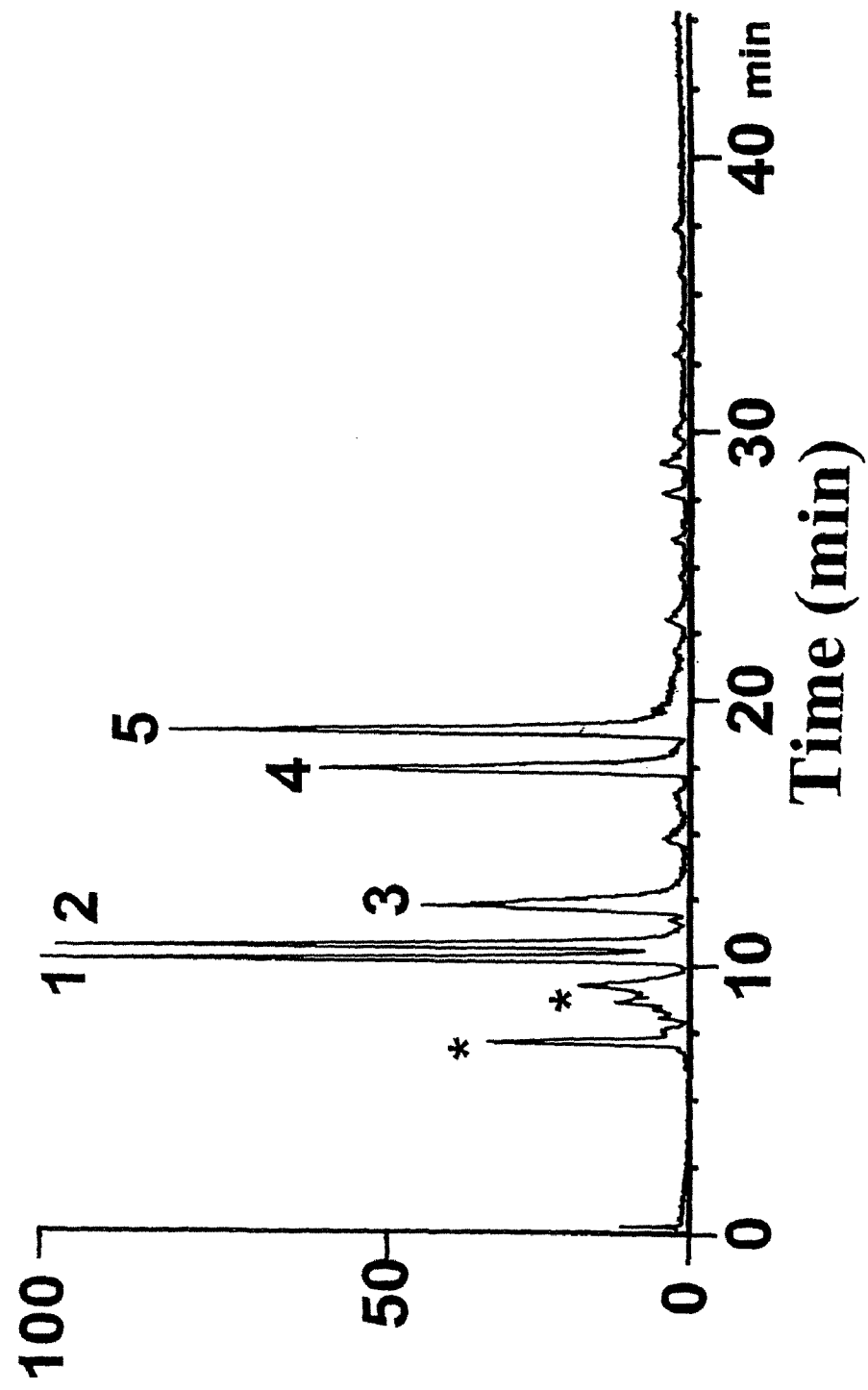
FIG. 46 contains a total ion chromatogram and five mass spectrums of Coenzyme A thioesters. Panel A is total ion chromatogram illustrating the separation of Coenzyme A and four CoA-organic thioesters: 1=Coenzyme A, 2=lactyl-CoA, 3=acetyl-CoA, 4=acrylyl-CoA, 5=propionyl-CoA. Panel B is a mass spectrum of Coenzyme A. Panel C is a mass spectrum of lactyl-CoA. Panel D is a mass spectrum of acetyl-CoA. Panel E is a mass spectrum of acrylyl-CoA. Panel F is a mass spectrum of propionyl-CoA.
Figure 46B:
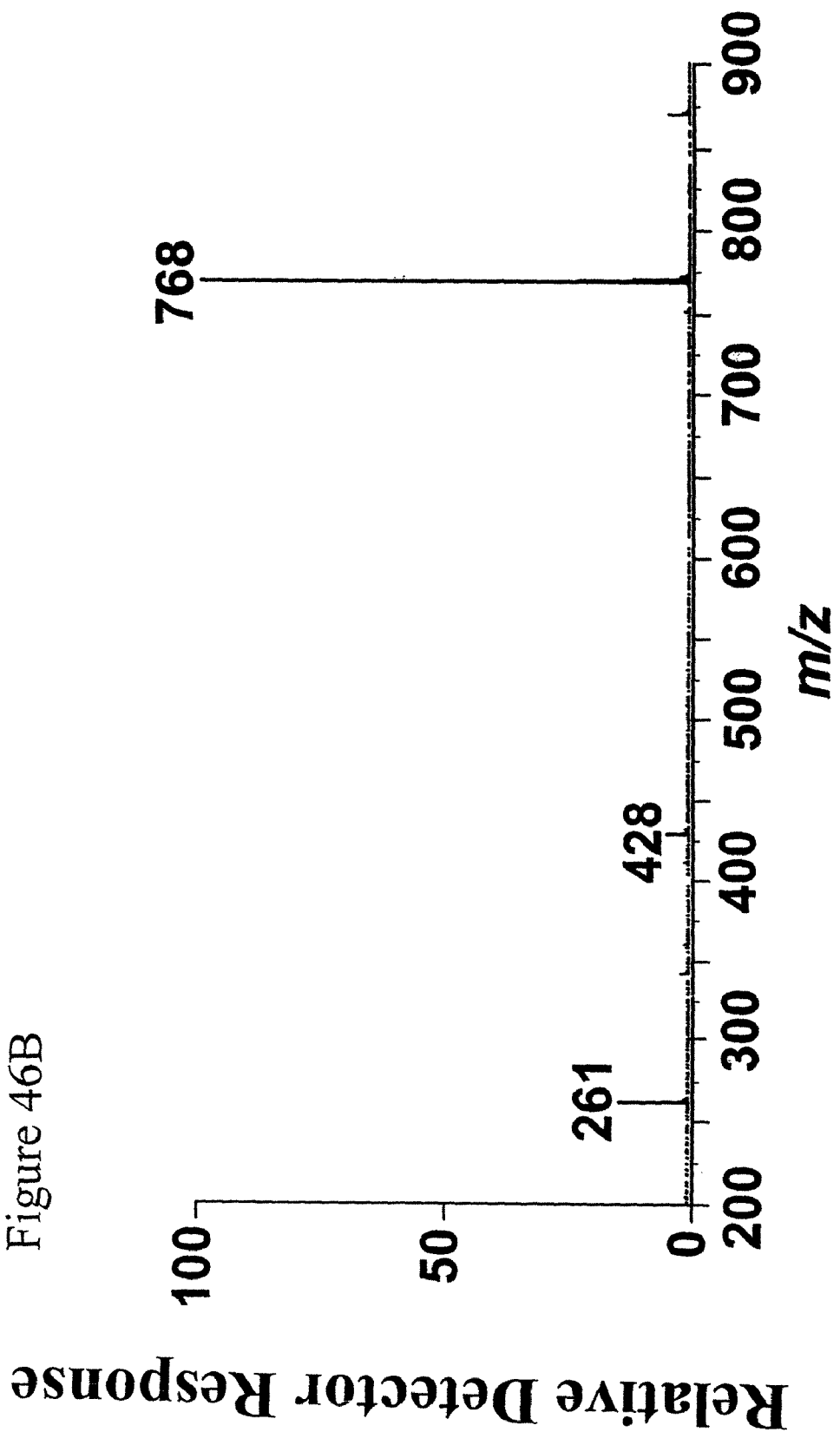
Figure 46C:
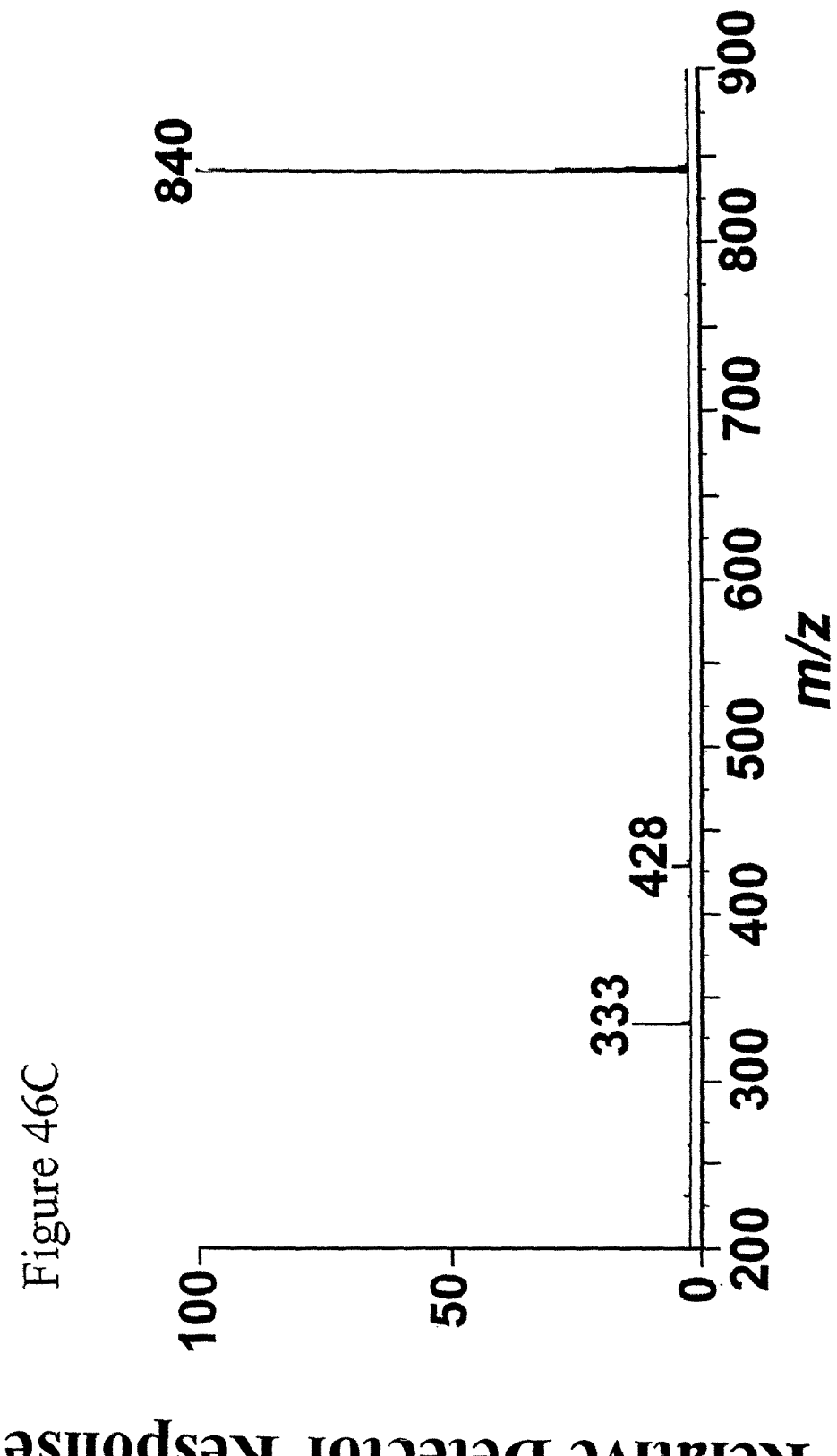
Figure 46D:
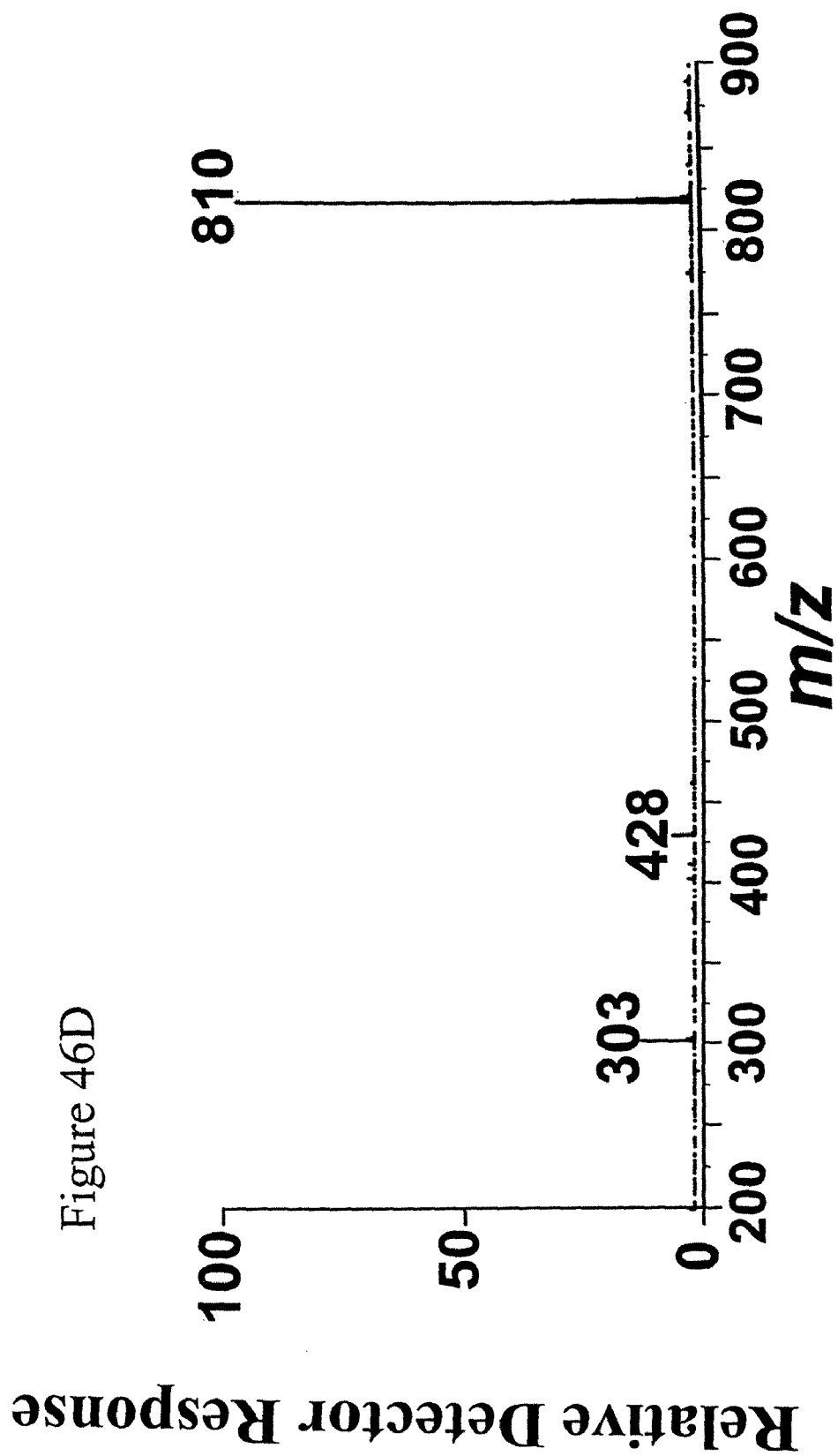
Figure 46E:
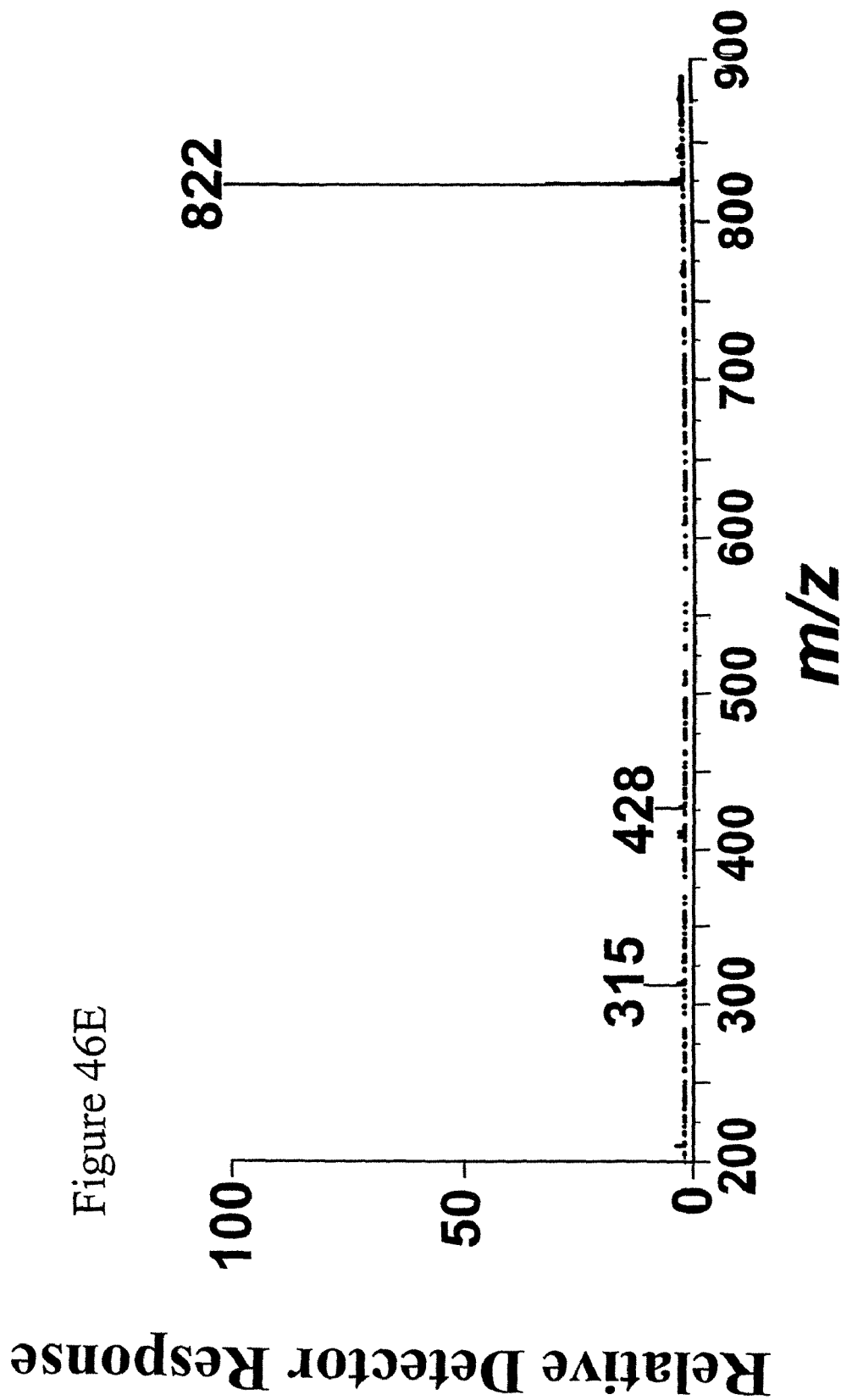
Figure 46F:
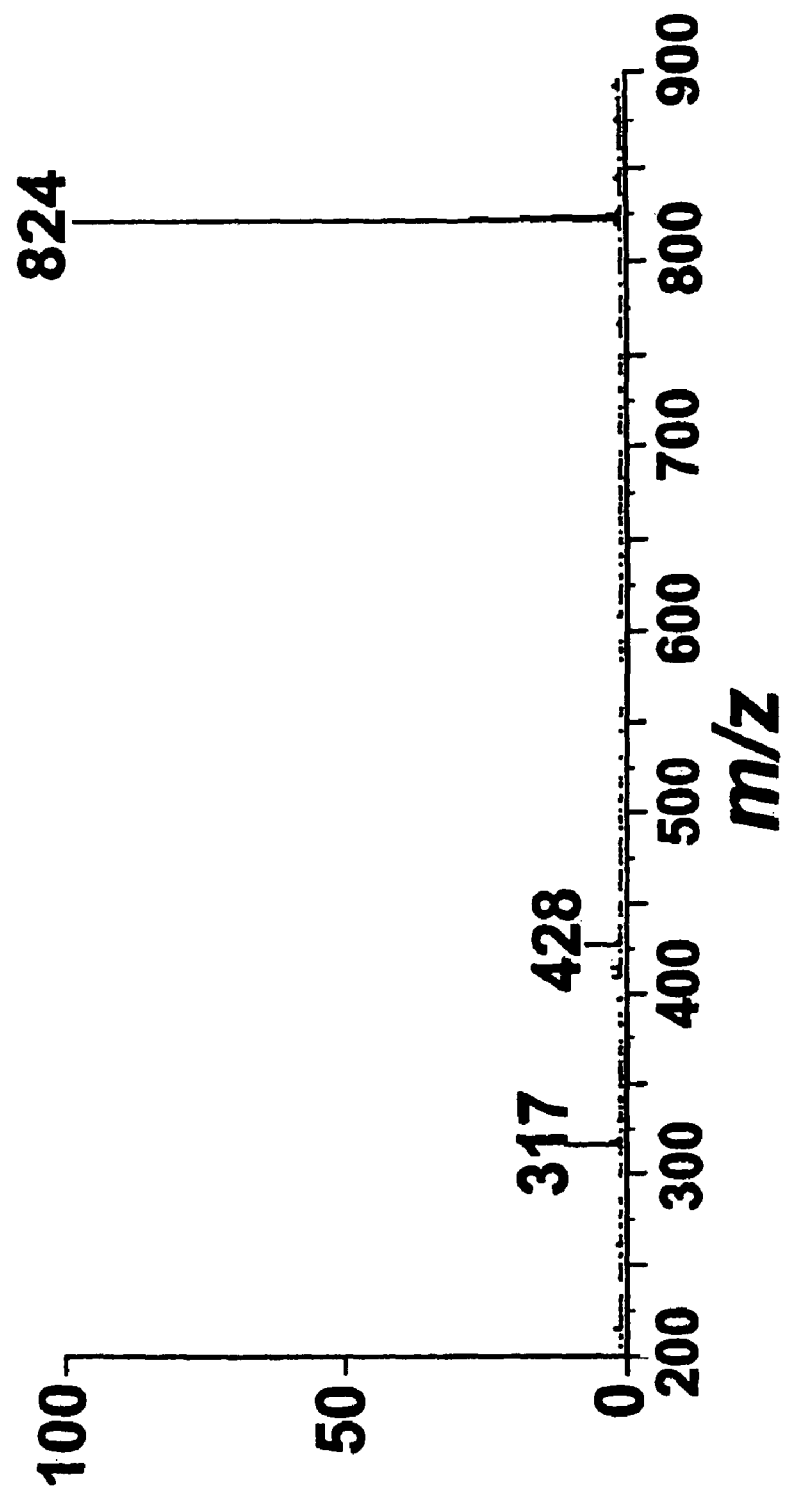

A pathway to make 3-hydroxypropionate directly from glucose via acetyl CoA is presented in FIG. 44. Most organisms such as *E. coli, Bacillus*, and yeast produce acetyl CoA from glucose via glycolysis and the action of pyruvate dehydrogenase. In order to divert the acetyl CoA generated from glucose, it is desirable to overexpress two genes, one encoding for acetyl CoA carboxylase and the other encoding malonyl-CoA reductase. As an example, these genes are expressed in *E. coli* through a T7 promoter using vectors pET30a and pFN476. The vector pET30a has a pBR ori and kanamycin resistance, while pFN476 has pSC101 ori and uses carbencillin resistance for selection. Because these two vectors have compatible ori and different markers they can be maintained in *E. coli* at the same time. Hence, the constructs used to engineer *E. coli* for direct production of 3-hydroxypropionate from glucose are pMSD8 (pFN476/accABCD) (Davis et al., *J. Biol. Chem.*, 275:28593-28598, 2000) and pET30a/malonyl-CoA reductase or pET30a/acc1 and pFN476/malonyl-CoA reductase. The constructs are depicted in FIG. 45.

To test the production of 3-hydroxypropionate from glucose, *E. coli* strain Tuner pLacI carrying plasmid pMSD8 (pFN476/accABCD) and pET30a/malonyl-CoA reductase or pET30a/acc1 and pFN476/malonyl-CoA reductase are grown in a B. Braun BIOSTAT B fermenter. A glass vessel fitted with a water jacket for heating is used to conduct this experiment. The fermenter working volume is 1.5 L and is operated at 37° C. The fermenter is continuously supplied with oxygen by bubbling sterile air through it at a rate of 1 vvm. The agitation is cascaded to the dissolve oxygen concentration which is maintained at 40% DO. The pH of the liquid media is maintained at 7 using 2 N NaOH. The *E. coli* strain is grown in M9 media supplemented with 1% glucose, 1 µg/mL thiamine, 0.1% casamino acids, 10 µg/mL biotin, 50 µg/mL carbencillin, 50 µg/mL kanamycin, and 25 µg/mL chloramphenicol. The expression of the genes is induced when the cell density reached 0.5 OD(600 nm) by adding 100 µM IPTG. After induction, samples of 2 mL volume are taken at 1, 2, 3, 4, and 8 hours. In addition, at 3 hours after induction, a 200 mL sample is taken to make a cell extract. The 2 mL samples are spun, and the supernatant is used to analyze products using LC/MS technique. The supernatant is stored at −20° C. until further analysis.

The extract is prepared by spinning the 200 mL of cell suspension at 8000 g and washing the cell pellet with of 50 mL of 50 mM Tris-HCl (pH 8.0), 5 mM MgCl$_2$, 100 mM KCl, 2 mM DTT, and 5% glycerol. The cell suspension is spun again at 8000 g, and the pellet is resuspended into 5 mL of 50 mM Tris-HCl (pH 8.0), 5 mM MgCl$_2$, 100 mM KCl, 2 mM DTT, and 5% glycerol. The cells are disrupted by passing twice through a French Press at 1000 pisg. The cell debris is removed by centrifugation for 20 minutes at 30,000 g. All the operations are conducted at 4° C. To demonstrated in vitro formation of 3-hydroxypropionate using this recombinant cell extract, the following reaction of 200 µL is conducted at 37° C. The reaction mix is as follows: Tris HCl (pH 8.0; 100 mM), ATP (1 mM), MgCl2 (5 mM), KCl (100 mM), DTT (5 mM), NaHCO$_3$ (40 mM), NADPH (0.5 mM), acetyl CoA (0.5 mM), and cell extract (0.2 mg). The reaction is stopped after 15 minutes by adding 1 volume of 10% trifluoroacetic acid (TFA). The products of this reaction are detected using an LC/MS technique.

The detection and analysis for the presence of 3-hydroxypropionate in the supernatant and the in vitro reaction mixture is carried out using a Waters/Micromass ZQ LC/MS instrument. This instrument consists of a Waters 2690 liquid chromatograph with a Waters 2410 refractive index detector placed in series between the chromatograph and the single quadropole mass spectrometer. LC separations are made using a Bio-Rad Aminex 87-H ion-exchange column at 45° C. Sugars, alcohol, and organic acid products are eluted with 0.015% TFA buffer. For elution, the buffer is passed at a flow rate of 0.6 mL/minute. For detection and quantification of 3-hydroxypropionate, a sample obtained from TCI, America (Portland, Oreg.) is used as a standard.

Example 12

Cloning of Propionyl-CoA Transferase, Lactyl-CoA Dehydratase (LDH), and a Hydratase (OS19) for Expression in *Saccharomyces cerevisiae*

The pESC Yeast Epitope Tagging Vector System (Stratagene, La Jolla, Calif.) was used in cloning the genes involved in 3-hydroxypropionic acid production via lactic acid. The pESC vectors each contain GAL1 and GAL10 promoters in opposing directions, allowing the expression of two genes from each vector. The GAL1 and GAL10 promoters are repressed by glucose and induced by galactose. Each of the four available pESC vectors has a different yeast-selectable marker (HIS3, TRP1, LEU2, URA3) so multiple plasmids can be maintained in a single strain. Each cloning region has a polylinker site for gene insertion, a transcription terminator, and an epitope coding sequence for C-terminal or N-terminal epitope tagging of expressed proteins. The pESC vectors also have a ColE1 origin of replication and an ampicillin resistance gene to allow replication and selection in *E. coli*. The following vector/promoter/nucleic acid combinations were constructed:

| Vector | Promoter | Polypeptide | Source of nucleic acid |
|---|---|---|---|
| pESC-Trp | GAL1 | OS19 hydratase | *Chloroflexus aurantiacus* |
| | GAL10 | E1 | *Megasphaera elsdenii* |
| pESC-Leu | GAL1 | E2α | *Megasphaera elsdenii* |
| | GAL10 | E2β | *Megasphaera elsdenii* |
| pESC-His | GAL1 | D-LDH | *Escherishia coli* |
| | GAL10 | PCT | *Megasphaera elsdenii* |

The primers used were as follows:

```
OS19APAF:
                                     (SEQ ID NO: 164)
5'-ATAGGGCCCAGGAGATCAAACCATGGGTGAAGAGTCT-CTGGTT
C-3'

OS19SALR:
                                     (SEQ ID NO: 165)
5'-CCTCTGCTACAGTCGACACAACGACCACTGAAGTTG-GGAG-3'

OS19KPNR:
                                     (SEQ ID NO: 166)
5'-AGTCTGCTATCGGTACCTCAACGACCACTGAAGTTG-GGAG-3'

E1NOTF:
                                     (SEQ ID NO: 167)
5'-ATAGCGGCCGCATAATGGATACTCTCGGAATCGACG-TTGG-3'

E1CLAR:
                                     (SEQ ID NO: 168)
5'-CCCCATCGATACATATTTCTTGATTTTATCATAAGCA-ATC-3'

EIIαAPAF:
                                     (SEQ ID NO: 169)
5'-CCAGGGCCCATAATGGGTGAAGAAAAAACAGTAGA-TATTG-3'

EIIαSALR:
                                     (SEQ ID NO: 170)
5'-GGTAGACTTGTCGACGTAGTGGTTTCCTCCTTCATT-GG-3'

EIIβNOTF:
                                     (SEQ ID NO: 171)
5'-ATAGCGGCCGCATAATGGGTCAGATCGACGAACTTA-TCAG-3'

EIIβSPER:
                                     (SEQ ID NO: 172)
5'-AGGTTCAACTAGTTCGTAGAGGATTTCCGAGAAAGC-CTG-3'

LDHAPAF:
                                     (SEQ ID NO: 173)
5'-CTAGGGCCCATAATGGAACTCGCCGTTTATAG-CAC-3'

LDHXHOR:
                                     (SEQ ID NO: 174)
5'-ACTTCTCGAGTTAAACCAGTTCGTTCGGGCA-GGT-3'

PCTSPEF:
                                     (SEQ ID NO: 175)
5'-GGGACTAGTATAATGGGAAAAGTAGAAATCAT-TACAG-3'

PCTPACR:
                                     (SEQ ID NO: 176)
5'-CGGCTTAATTAACAGCAGAGATTTATTTTTTCA-GTCC-3'
```

All restriction enzymes were obtained from New England Biolabs, Beverly, Mass. All plasmid DNA preparations were done using QIAprep Spin Miniprep Kits, and all gel purifications were done using QIAquick Gel Extraction Kits (Qiagen, Valencia, Calif.).

A. Construction of the pESC-Trp/OS19 Hydratase Vector

Two constructs in pESC-Trp were made for the OS19 nucleic acid from *C. aurantiacus*. One of these constructs utilized the Apa I and Sal I restriction sites of the GAL1 multiple cloning site and was designed to include the c-myc epitope. The second construct utilized the Apa I and Kpn I sites and thus did not include the c-myc epitope sequence.

Six μg of pESC-Trp vector DNA was digested with the restriction enzyme Apa I and the digest was purified using a QIAquick PCR Purification Column. Three μg of the Apa I-digested vector DNA was then digested with the restriction enzyme Kpn I, and 3 μg was digested with Sal I. The double-digested vector DNAs were separated on a 1% TAE-agarose gel, purified, dephosphorylated with shrimp alkaline phosphatase (Roche Biochemical Products, Indianapolis, Ind.), and purified with a QIAquick PCR Purification Column.

The nucleic acid encoding the *Chloroflexus aurantiacus* polypeptide having hydratase activity (OS19) was amplified from genomic DNA using the PCR primer pair OS19APAF and OS19SALR and the primer pair OS19APAF and OS19 KPNR. OS19APAF was designed to introduce an Apa I restriction site and a translation initiation site (ACCATGG) at the beginning of the amplified fragment. The OS19 KPNR primer was designed to introduce a Kpn I restriction site at the end of the amplified fragment and to contain the translational stop codon for the hydratase gene. OS19SALR introduces a Sal I site at the end of the amplified fragment and has an altered stop codon so that translation continues in-frame through the vector c-myc epitope. The PCR mix contained the following: 1× Expand PCR buffer, 100 ng *C. aurantiacus* genomic DNA, 0.2 μM of each primer, 0.2 mM each dNTP, and 5.25 units of Expand DNA Polymerase (Roche) in a final volume of 100 μL. The PCR reaction was performed in an MJ Research PTC100 under the following conditions: an initial denaturation at 94° C. for 1 minute; 8 cycles of 94° C. for 30 seconds, 57° C. for 1 minute, and 72° C. for 2.25 minutes; 24 cycles of 94° C. for 30 seconds, 62° C. for 1 minute, and 72° C. for 2.25 minutes; and a final extension for 7 minutes at 72° C. The amplification product was then separated by gel electrophoresis using a 1% TAE-agarose gel. A 0.8 Kb fragment was excised from the gel and purified for each primer pair. The purified fragments were digested with Kpn I or Sal I restriction enzyme, purified with a QIAquick PCR Purification Column, digested with Apa I restriction enzyme, purified again with a QIAquick PCR Purification Column, and quantified on a minigel.

50-60 ng of the digested PCR product containing the nucleic acid encoding the *C. aurantiacus* polypeptide having hydratase activity (OS19) and 50 ng of the prepared pESC-Trp vector were ligated using T4 DNA ligase at 16° C. for 16 hours. One μL of the ligation reaction was used to electroporate 40 μL of *E. coli* Electromax™ DH10B™ cells. The electroporated cells were plated onto LB plates containing 100 μg/mL of carbenicillin (LBC). Individual colonies were screened using colony PCR with the appropriate PCR primers. Individual colonies were suspended in about 25 μL of 10 mM Tris, and 2 μL of the suspension was plated on LBC media. The remnant suspension was heated for 10 minutes at 95° C. to break open the bacterial cells, and 2 μL of the heated cells was used in a 25 μL PCR reaction. The PCR mix contained the following: 1×Taq buffer, 0.2 μM each primer, 0.2 mM each dNTP, and 1 unit of Taq DNA polymerase per reaction. The PCR program used was the same as described above for amplification of the nucleic acid from genomic DNA.

Plasmid DNA was isolated from cultures of colonies having the desired insert and was sequenced to confirm the lack of nucleotide errors from PCR. A construct with a confirmed sequence was transformed into *S. cerevisiae* strain YPH500 using a Frozen-EZ Yeast Transformation II™ Kit (Zymo Research, Orange, Calif.). Transformation reactions were plated on SC-Trp media (see Stratagene pESC Vector Instruction Manual for media recipes). Individual yeast colonies were screened for the presence of the OS19 nucleic acid by colony PCR. Colonies were suspended in 20 µL of Y-Lysis Buffer (Zymo Research) containing 5 units of zymolase and heated at 37° C. for 10 minutes. Three µL of this suspension was then used in a 25 µL PCR reaction using the PCR reaction mixture and program described for the colony screen of the *E. coli* transformants. The pESC-Trp vector was also transformed into YPH500 for use as a hydratase assay control and transformants were screened by PCR using GAL1 and GAL10 primers.

B. Construction of the pESC-Trp/OS19/EI Hydratase Vector

Plasmid DNA of a pESC-Trp/OS19 construct (Apa I-Sal I sites) with confirmed sequence and positive assay results was used for insertion of the nucleic acid for the *M. elsdenii* E1 activator polypeptide downstream of the GAL10 promoter. Three µg of plasmid DNA was digested with the restriction enzyme Cla I, and the digest was purified using a QIAquick PCR Purification Column. The vector DNA was then digested with the restriction enzyme Not I, and the digest was inactivated by heating to 65° C. for 20 minutes. The double-digested vector DNA was dephosphorylated with shrimp alkaline phosphatase (Roche), separated on a 1% TAE-agarose gel, and gel purified.

The nucleic acid encoding the *M. elsdenii* E1 activator polypeptide was amplified from genomic DNA using the PCR primer pair EINOTF and EICLAR. EINOTF was designed to introduce a Not I restriction site and a translation initiation site at the beginning of the amplified fragment. The EICLAR primer was designed to introduce a Cla I restriction site at the end of the amplified fragment and to contain an altered translational stop codon to allow in-frame translation of the FLAG epitope. The PCR mix contained the following: 1×Expand PCR buffer, 100 ng *M. elsdenii* genomic DNA, 0.2 µM of each primer, 0.2 mM each dNTP, and 5.25 units of Expand DNA Polymerase in a final volume of 100 µL. The PCR reaction was performed in an MJ Research PTC100 under the following conditions: an initial denaturation at 94° C. for 1 minute; 8 cycles of 94° C. for 30 seconds, 55° C. for 45 seconds, and 72° C. for 3 minutes; 24 cycles of 94° C. for 30 seconds, 62° C. for 45 seconds, and 72° C. for 3 minutes; and a final extension for 7 minutes at 72° C. The amplification product was then separated by gel electrophoresis using a 1% TAE-agarose gel, and a 0.8 Kb fragment was excised and purified. The purified fragment was digested with Cla I restriction enzyme, purified with a QIAquick PCR Purification Column, digested with Not I restriction enzyme, purified again with a QIAquick PCR Purification Column, and quantified on a minigel.

60 ng of the digested PCR product containing the nucleic acid for the *M. elsdenii* E1 activator polypeptide and 70 ng of the prepared pESC-Trp/OS19 hydratase vector were ligated using T4 DNA ligase at 16° C. for 16 hours. One µL of the ligation reaction was used to electroporate 40 µL of *E. coli* Electromax™ DH10B™ cells. The electroporated cells were plated onto LBC media. Individual colonies were screened using colony PCR with the EINOTF and EICLAR primers.

Individual colonies were suspended in about 25 µL of 10 mM Tris, and 2 µL of the suspension was plated on LBC media. The remnant suspension was heated for 10 minutes at 95° C. to break open the bacterial cells, and 2 µL of the heated cells used in a 25 µL PCR reaction. The PCR mix contained the following: 1×Taq buffer, 0.2 µM each primer, 0.2 mM each dNTP, and 1 unit of Taq DNA polymerase per reaction. The PCR program used was the same as described above for amplification of the gene from genomic DNA. Plasmid DNA was isolated from cultures of colonies having the desired insert and was sequenced to confirm the lack of nucleotide errors from PCR.

C. Construction of the pESC-Leu/EIIα/EIIβ Vector

Three µg of DNA of the vector pESC-Leu was digested with the restriction enzyme Apa I, and the digest was purified using a QIAquick PCR Purification Column. The vector DNA was then digested with the restriction enzyme Sal I, and the digest was inactivated by heating to 65° C. for 20 minutes. The double-digested vector DNA was dephosphorylated with shrimp alkaline phosphatase (Roche), separated on a 1% TAE-agarose gel, and gel purified.

The nucleic acid encoding the *M. elsdenii* E2α polypeptide was amplified from genomic DNA using the PCR primer pair EIIαAPAF and EIIαSALR. EIIαAPAF was designed to introduce an Apa I restriction site and a translation initiation site at the beginning of the amplified fragment. The EIIαSALR primer was designed to introduce a Sal I restriction site at the end of the amplified fragment and to contain an altered translational stop codon to allow in-frame translation of the c-myc epitope. The PCR mix contained the following: 1×Expand PCR buffer, 100 ng *M. elsdenii* genomic DNA, 0.2 µM of each primer, 0.2 mM each dNTP, and 5.25 units of Expand DNA Polymerase in a final volume of 100 µL. The PCR reaction was performed in an MJ Research PTC100 under the following conditions: an initial denaturation at 94° C. for 1 minute; 8 cycles of 94° C. for 30 seconds, 55° C. for 1 minute, and 72° C. for 3 minutes; 24 cycles of 94° C. for 30 seconds, 62° C. for 1 minute, and 72° C. for 3 minutes; and a final extension for 7 minutes at 72° C. The amplification product was then separated by gel electrophoresis using a 1% TAE-agarose gel, and a 1.3 Kb fragment was excised and purified. The purified fragment was digested with Apa I restriction enzyme, purified with a QIAquick PCR Purification Column, digested with Sal I restriction enzyme, purified again with a QIAquick PCR Purification Column, and quantified on a minigel.

80 ng of the digested PCR product containing the nucleic acid encoding the *M. elsdenii* E2α polypeptide and 80 ng of the prepared pESC-Leu vector were ligated using T4 DNA ligase at 16° C. for 16 hours. One µL of the ligation reaction was used to electroporate 40 µL of *E. coli* Electromax™ DH10B™ cells. The electroporated cells were plated onto LBC media. Individual colonies were screened using colony PCR with the EIIαAPAF and EIIαSALR primers. Individual colonies were suspended in about 25 µl of 10 mM Tris, and 2 µL of the suspension was plated on LBC media. The remnant suspension was heated for 10 minutes at 95° C. to break open the bacterial cells, and 2 µL of the heated cells used in a 25 µL PCR reaction. The PCR mix contained the following: 1×Taq buffer, 0.2 µM each primer, 0.2 mM each dNTP, and 1 unit of Taq DNA polymerase per reaction. The PCR program used was the same as described above for amplification of the gene from genomic DNA. Plasmid DNA was isolated from cultures of colonies having the desired insert and was sequenced to confirm the lack of nucleotide errors from PCR.

Plasmid DNA of a pESC-Leu/EIIα vector with confirmed sequence was used for insertion of the nucleic acid encoding the *M. elsdenii* E2β polypeptide. Three µg of plasmid DNA was digested with the restriction enzyme Spe I, and the digest was purified using a QIAquick PCR Purification Column. The vector DNA was then digested with the restriction enzyme Not I and gel purified from a 1% TAE-agarose gel. The double-digested vector DNA was then dephosphorylated with shrimp alkaline phosphatase (Roche) and purified with a QIAquick PCR Purification Column.

The nucleic acid encoding the *M. elsdenii* E2β polypeptide was amplified from genomic DNA using the PCR primer pair EIIβNOTF and EIIβSPER. The EIIβNOTF primer was designed to introduce a Not I restriction site and a translation initiation site at the beginning of the amplified fragment. The EIIβSPER primer was designed to introduce an Spe I restriction site at the end of the amplified fragment and to contain an altered translational stop codon to allow for in-frame translation of the FLAG epitope. The PCR mix contained the following: 1× Expand PCR buffer, 100 ng *M. elsdenii* genomic DNA, 0.2 µM of each primer, 0.2 mM each dNTP, and 5.25 units of Expand DNA Polymerase in a final volume of 100 µL. The PCR reaction was performed in an MJ Research PTC100 under the following conditions: an initial denaturation at 94° C. for 1 minute; 8 cycles of 94° C. for 30 seconds, 55° C. for 45 seconds, and 72° C. for 3 minutes; 24 cycles of 94° C. for 30 seconds, 62° C. for 45 seconds, and 72° C. for 3 minutes; and a final extension for 7 minutes at 72° C. The amplification product was separated by gel electrophoresis using a 1% TAE-agarose gel, and a 1.1 Kb fragment was excised and purified. The purified fragment was digested with Spe I restriction enzyme, purified with a QIAquick PCR Purification Column, digested with Not I restriction enzyme, purified again with a QIAquick PCR Purification Column, and quantified on a minigel.

38 ng of the digested PCR product containing the nucleic acid encoding the *M. elsdenii* E2β polypeptide and 50 ng of the prepared pESC-Leu/EIIα vector were ligated using T4 DNA ligase at 16° C. for 16 hours. One µL of the ligation reaction was used to electroporate 40 µL of *E. coli* Electromax™ DH10B™ cells. The electroporated cells were plated onto LBC plates. Individual colonies were screened using colony PCR with the EIIβNOTF and EIIβSPER primers. Individual colonies were suspended in about 25 µL of 10 mM Tris, and 2 µL of the suspension was plated on LBC media. The remnant suspension was heated for 10 minutes at 95° C. to break open the bacterial cells, and 2 µL of the heated cells was used in a 25 µL PCR reaction. The PCR mix contained the following: 1×Taq buffer, 0.2 µM each primer, 0.2 mM each dNTP, and 1 unit of Taq DNA polymerase per reaction. The PCR program used was the same as described above for amplification of the gene from genomic DNA.

Plasmid DNA was isolated from cultures of colonies having the desired insert and was sequenced to confirm the lack of nucleotide errors from PCR. A pESC-Leu/EIIα/EIIβ construct with a confirmed sequence was co-transformed along with the pESC-Trp/OS19/EI vector into *S. cerevisiae* strain YPH500 using a Frozen-EZ Yeast Transformation II™ Kit (Zymo Research, Orange, Calif.). Transformation reactions were plated on SC-Trp-Leu media. Individual yeast colonies were screened for the presence of the OS19, E1, E2α, and E2β nucleic acid by colony PCR. Colonies were suspended in 20 µL of Y-Lysis Buffer (Zymo Research) containing 5 units of zymolase and heated at 37° C. for 10 minutes. Three µL of this suspension was then used in a 25 µL PCR reaction using the PCR reaction mixtures and programs described for the colony screens of the *E. coli* transformants. The pESC-Trp/OS19 and pESC-Leu vectors were also co-transformed into YPH500 for use as a lactyl-CoA dehydratase assay control.

These transformants were colony screened using the GAL1 and GAL10 primers (Instruction manual, pESC Yeast Epitope Tagging Vectors, Stratagene).

D. Construction of the pESC-His/D-LDH/PCT Vector

Three µg of DNA of the vector pESC-His was digested with the restriction enzyme Xho I, and the digest was purified using a QIAquick PCR Purification Column. The vector DNA was then digested with the restriction enzyme Apa I and gel purified from a 1% TAE-agarose gel. The double-digested vector DNA was dephosphorylated with shrimp alkaline phosphatase (Roche) and purified using a QIAquick PCR Purification Column.

The *E. coli* D-LDH gene was amplified from genomic DNA of strain DH10B using the PCR primer pair LDHAPAF and LDHXHOR. LDHAPAF was designed to introduce an Apa I restriction site and a translation initiation site at the beginning of the amplified fragment. The LDHXHOR primer was designed to introduce an Xho I restriction site at the end of the amplified fragment and to contain the translational stop codon for the D-LDH gene. The PCR mix contained the following: 1× Expand PCR buffer, 100 ng *E. coli* genomic DNA, 0.2 µM of each primer, 0.2 mM each dNTP, and 5.25 units of Expand DNA Polymerase in a final volume of 100 µL. The PCR reaction was performed in an MJ Research PTC100 under the following conditions: an initial denaturation at 94° C. for 1 minute; 8 cycles of 94° C. for 30 seconds, 59° C. for 45 seconds, and 72° C. for 2 minutes; 24 cycles of 94° C. for 30 seconds, 64° C. for 45 seconds, and 72° C. for 2 minutes; and a final extension for 7 minutes at 72° C. The amplification product was separated by gel electrophoresis using a 1% TAE-agarose gel, and a 1.0 Kb fragment was excised and purified. The purified fragment was digested with Apa I restriction enzyme, purified with a QIAquick PCR Purification Column, digested with Xho I restriction enzyme, purified again with a QIAquick PCR Purification Column, and quantified on a minigel.

80 ng of the digested PCR product containing the *E. coli* D-LDH gene and 80 ng of the prepared pESC-His vector were ligated using T4 DNA ligase at 16° C. for 16 hours. One µL of the ligation reaction was used to electroporate 40 µL of *E. coli* Electromax™ DH10B™ cells. The electroporated cells were plated onto LBC media. Individual colonies were screened using colony PCR with the LDHAPAF and LDHXHOR primers. Individual colonies were suspended in about 25 µL of 10 mM Tris, and 2 µL of the suspension was plated on LBC media. The remnant suspension was heated for 10 minutes at 95° C. to break open the bacterial cells, and 2 µL of the heated cells used in a 25 µL PCR reaction. The PCR mix contained the following: 1×Taq buffer, 0.2 µM each primer, 0.2 mM each dNTP, and 1 unit of Taq DNA polymerase per reaction. The PCR program used was the same as described above for amplification of the gene from genomic DNA. Plasmid DNA was isolated from cultures of colonies having the desired insert and was sequenced to confirm the lack of nucleotide errors from PCR.

Plasmid DNA of a pESC-His/D-LDH construct with a confirmed sequence was used for insertion of the nucleic acid encoding the *M. elsdenii* PCT polypeptide. Three µg of plasmid DNA was digested with the restriction enzyme Pac I, and the digest was purified using a QIAquick PCR Purification Column. The vector DNA was then digested with the restriction enzyme Spe I and gel purified from a 1% TAE-agarose gel. The double-digested vector DNA was dephosphorylated with shrimp alkaline phosphatase (Roche) and purified with a QIAquick PCR Purification Column.

The nucleic acid encoding the *M. elsdenii* PCT polypeptide was amplified from genomic DNA using the PCR primer pair PCTSPEF and PCTPACR. PCTSPEF was designed to introduce an Spe I restriction site and a translation initiation site at the beginning of the amplified fragment. The PCTPACR primer was designed to introduce a Pac I restriction site at the end of the amplified fragment and to contain the translational stop codon for the PCT gene. The PCR mix contained the following: 1×Expand PCR buffer, 100 ng *M. elsdenii* genomic DNA, 0.2 µM of each primer, 0.2 mM each dNTP, and 5.25 units of Expand DNA Polymerase in a final volume of 100 µL. The PCR reaction was performed in an MJ Research PTC100 under the following conditions: an initial denaturation at 94° C. for 1 minute; 8 cycles of 94° C. for 30 seconds, 56° C. for 45 seconds, and 72° C. for 2.5 minutes; 24 cycles of 94° C. for 30 seconds, 64° C. for 45 seconds, and 72° C. for 2.5 minutes; and a final extension for 7 minutes at 72° C. The amplification product was separated by gel electrophoresis using a 1% TAE-agarose gel, and a 1.55 Kb fragment was excised and purified. The purified fragment was digested with Pac I restriction enzyme, purified with a QIAquick PCR Purification Column, digested with Spe I restriction enzyme, purified again with a QIAquick PCR Purification Column, and quantified on a minigel.

95 ng of the digested PCR product containing the nucleic acid encoding the *M. elsdenii* PCT polypeptide and 75 ng of the prepared pESC-His/D-LDH vector were ligated using T4 DNA ligase at 16° C. for 16 hours. One µL of the ligation reaction was used to electroporate 40 µL of *E. coli* Electromax™ DH10B™ cells. The electroporated cells were plated onto LBC plates. Individual colonies were screened using colony PCR with the PCTSPEF and PCTPACR primers. Individual colonies were suspended in about 25 µL of 10 mM Tris, and 2 µL of the suspension was plated on LBC media. The remnant suspension was heated for 10 minutes at 95° C. to break open the bacterial cells, and 2 µL of the heated cells used in a 25 µL PCR reaction. The PCR mix contained the following: 1×Taq buffer, 0.2 µM each primer, 0.2 mM each dNTP, and 1 unit of Taq DNA polymerase per reaction. The PCR program used was the same as described above for amplification of the gene from genomic DNA.

Plasmid DNA was isolated from cultures of colonies having the desired insert and was sequenced to confirm the lack of nucleotide errors from PCR. A construct with a confirmed sequence was transformed into *S. cerevisiae* strain YPH500 using a Frozen-EZ Yeast Transformation II™ Kit (Zymo Research, Orange, Calif.). Transformation reactions were plated on SC-His media. Individual yeast colonies were screened for the presence of the D-LDH and PCT genes by colony PCR. Colonies were suspended in 20 µL of Y-Lysis Buffer (Zymo Research) containing 5 units of zymolase and heated at 37° C. for 10 minutes. Three µL of this suspension was then used in a 25 µL PCR reaction using the PCR reaction mixture and program described for the colony screen of the *E. coli* transformants. The pESC-His vector was also transformed into YPH500 for use as an assay control, and transformants were screened by PCR using GAL1 and GAL10 primers.

Example 13

Expression of Enzymes in *S. cerevisiae*

A. Hydratase Activity in Transformed Yeast

Individual colonies carrying the pESC-Trp/OS19 construct or the pESC-Trp vector (negative control) were used to inoculate 5 mL cultures of SC-Trp media containing 2% glucose. These cultures were grown for 16 hours at 30° C. and used to inoculate 35 mL of the same media. The subcultures were grown for 7 hours at 30° C., and their $OD_{600}$s were determined. A volume of cells giving an OD×volume equal to 40 was pelleted, washed with SC-Trp media with no carbon source, and repelleted. The cells were suspended in 5 mL of SC-Trp media containing 2% galactose and used to inoculate a total volume of 100 mL of this media. Cultures were grown for 17.5 hours at 30° C. and 250 rpm. Cells were then pelleted, rinsed in 0.85% NaCl, and repelleted. Cell pellets (70 mg) were suspended in 140 µL of 50 mM Tris HCl, pH 7.5, and an equal volume (pellet plus buffer) of pre-rinsed glass beads (Sigma, 150-212 microns) was added. This mixture was vortexed for 30 seconds and placed on ice for 1 minute, and the vortexing/cooling cycle was repeated 8 additional times. The cells were then centrifuged for 6 minutes at 5,000 g, and the supernatant was removed to a fresh tube. The beads/pellet were washed twice with 250 µL of buffer, centrifuged, and the supernatants joined with the first supernatant.

An *E. coli* strain carrying the pETBlue-1/OS19 construct, described previously, was used as a positive control for hydratase assays. A culture of this strain was grown to saturation overnight and diluted 1:20 the following morning in fresh LBC media. The culture was grown at 37° C. and 250 rpm to an $OD_{600}$ of 0.6, at which point it was induced with IPTG at a final concentration of 1 mM. The culture was incubated for an additional two hours at 37° C. and 250 rpm. Cells were pelleted, washed with 0.85% NaCl, and repelleted. Cells were disrupted using BugBuster™ Protein Extraction Reagent and Benzonase® (Novagen) as per manufacturer's instructions with a 20 minute incubation at room temperature. After centrifugation at 16,000 g and 4° C., the supernatant was transferred to a new tube and used in the activity assay.

Total protein content of cell extracts from *S. cerevisiae* described above were quantified using a microplate Bio-Rad Protein Assay (Bio-Rad, Hercules, Calif.). The OS19 constructs (both Apa I-Sal I and Apa I-Kpn I sites) in YPH500, the pESC-Trp negative control in YPH500, and the pETBlue-1/OS19 construct in *E. coli* were tested for their ability to convert acrylyl-CoA to 3-hydroxypropionyl-CoA. The assay was conducted as previously described for the pETBlue-1/OS19 constructs in the *E. coli* Tuner strain. When cell extract of the negative control strain was added to the reaction mixture containing acrylyl-CoA, one dominant peak of MW 823 was exhibited. This peak corresponds to acrylyl-CoA and indicates that acrylyl-CoA was not converted to any other product. When cell extract of the strain carrying a pESC-Trp/OS19 construct (either Apa I-Sal I or Apa I-Kpn I sites) was added to the reaction mix, the dominant peak shifted to MW 841, which corresponds to 3-hydroxypropionyl-CoA. The reaction mix from the *E. coli* control also showed the MW 841 peak. A time course study was conducted for the pESC-Trp/OS19(Apa I-Sal I) construct, which measured the appearance of the MW 841 and MW 823 peaks after 0, 1, 3, 7, 15, 30, and 60 minutes of reaction time. An increase in the 3-hydroxypropionyl-CoA peak was seen over time with the cell extracts from both this construct and the *E. coli* control, whereas cell extract from the YPH500 strain with vector only showed a dominant acrylyl-CoA peak.

B. Propionyl CoA-Transferase Activity in Transformed Yeast

Individual colonies of *S. cerevisiae* strain YPH500 carrying the pESC-His/D-LDH or pESC-His/D-LDH/PCT construct or the pESC-His vector with no insert (negative control) were used to inoculate 5 mL cultures of SC-His media containing 2% glucose. These cultures were grown for 16 hours at 30° C. and 250 rpm and were then used to inoculate 35 mL of the same media. The subcultures were grown for 7 hours at 30° C., and their $OD_{600}$s were determined. For each strain, a volume of cells giving an OD×volume equal to 40 was pelleted, washed with SC-His media with no carbon source, and repelleted. The cells were suspended in 5 mL of SC-His media containing 2% galactose and used to inoculate a total volume of 100 mL of this media. Cultures were grown for 16.75 hours at 30° C. and 250 rpm. Cells were then pelleted, rinsed in 0.85% NaCl, and repelleted. Cell pellets (70 mg) were suspended in 140 µL of 100 mM potassium phosphate buffer, pH 7.5, and an equal volume (pellet plus buffer) of pre-rinsed glass beads (Sigma, 150-212 microns) was added. This mixture was vortexed for 30 seconds and placed on ice for 1 minute, and the vortexing/cooling cycle was repeated 8 additional times. The cells were then centrifuged for 6 minutes at 5,000 g, and the supernatant was removed to a fresh tube. The beads/pellet were washed twice with 250 µL of buffer and centrifuged, and the supernatants joined with the first supernatant.

An E. coli strain carrying the pETBlue-1/PCT construct, described previously, was used as a positive control for propionyl CoA transferase assays. A culture of this strain was grown to saturation overnight and diluted 1:20 the following morning in fresh LB media containing 100 µg/mL of carbenicillin. The culture was grown at 37° C. and 250 rpm to an $OD_{600}$ of 0.6, at which point it was induced with IPTG at a final concentration of 1 mM. The culture was incubated for an additional two hours at 37° C. and 250 rpm. Cells were pelleted, washed with 0.85% NaCl, and repelleted. Cells were disrupted using BugBuster™ Protein Extraction Reagent and Benzonase® (Novagen) as per manufacturer's instructions with a 20 minute incubation at room temperature. After centrifugation at 16,000 g and 4° C., the supernatant was transferred to a new tube and used in the activity assay.

Total protein content of cell extracts was quantified using a microplate Bio-Rad Protein Assay (Bio-Rad, Hercules, Calif.). The D-LDH and D-LDH/PCT constructs in S. cerevisiae strain YPH500, the pESC-His negative control in YPH500, and the pETBlue-1/PCT construct in E. coli were tested for their ability to catalyze the conversion of propionyl-CoA and acetate to acetyl-CoA and propionate. The assay mixture used was that previously described for the pETBlue-1/PCT constructs in the E. coli Tuner strain.

When 1 µg of total cell extract protein of the negative control strain or the YPH500/pESC-His/D-LDH strain was added to the reaction mixture, no increase in absorbance (0.00 to 0.00) was seen over 11 minutes. Increases in absorbance from 0.00 to 0.04 and from 0.00 to 0.06 were seen, respectively, with 1 µg of cell extract protein from the YPH500/pESC-His/D-LDH/PCT strain and the E. coli/PCT strain. With 2 mg of total cell extract protein, the negative control strain and the YPH500/pESC-His/D-LDH strain showed an increase in absorbance from 0.00 to 0.01 over 11 minutes, whereas increases from 0.00 to 0.10 and 0.00 to 0.08 were seen, respectively, with the YPH500/pESC-His/D-LDH/PCT strain and the E. coli/PCT strain.

C. Lactyl-CoA Dehydratase Activity in Transformed Yeast

Individual colonies of S. cerevisiae strain YPH500 carrying the pESC-His/D-LDH or pESC-His/D-LDH/PCT construct or the pESC-His vector with no insert (negative control) were used to inoculate 5 mL cultures of SC-His media containing 4% glucose. These cultures were grown for 23 hours at 30° C. and used to inoculate 35 mL of SC-His media containing 2% raffinose. The subcultures were grown for 8 hours at 30° C., and their $OD_{600}$s were determined. For each strain, a volume of cells giving an ODxvolume equal to 40 was pelleted, resuspended in 10 mL of SC-His media containing 2% galactose, and used to inoculate a total volume of 100 mL of this media. Cultures were grown for 17 hours at 30° C. and 250 rpm. Cells were then pelleted, rinsed in 0.85% NaCl, and repelleted. Cell pellets (190 mg) were suspended in 380 µL of 100 mM potassium phosphate buffer, pH 7.5, and an equal volume (pellet plus buffer) of pre-rinsed glass beads (Sigma, 150-212 microns) was added. This mixture was vortexed for 30 seconds and placed on ice for 1 minute, and the vortexing/cooling cycle was repeated 7 additional times. The cells were then centrifuged for 6 minutes at 5,000 g and the supernatant was removed to a fresh tube. The beads/pellet were washed twice with 300 µL of buffer and centrifuged, and the supernatants joined with the first supernatant.

An anaerobically-grown culture of E. coli strain DH10B was used as a positive control for D-LDH assays. A culture of this strain was grown to saturation overnight and diluted 1:20 the following morning in fresh LB media. The culture was grown anaerobically at 37° C. for 7.5 hours. Cells were pelleted, washed with 0.85% NaCl, and repelleted. Cells were disrupted using BugBuster™ Protein Extraction Reagent and Benzonase® (Novagen) as per manufacturer's instructions with a 20-minute incubation at room temperature. After centrifugation at 16,000 g and 4° C., the supernatant was transferred to a new tube and used in the activity assay.

Total protein content of cell extracts was quantified using a microplate Bio-Rad Protein Assay (Bio-Rad, Hercules, Calif.). The D-LDH and D-LDH/PCT constructs in YPH500, the pESC-His negative control in YPH500, and the anaerobically-grown E. coli strain were tested for their ability to catalyze the conversion of pyruvate to lactate by assaying the concurrent oxidation of NADH to NAD. The assay mixture contained 100 mM potassium phosphate buffer, pH 7.5, 0.2 mM NADH, and 0.5-1.0 µg of cell extract. The reaction was started by the addition of sodium pyruvate to a final concentration of 5 mM, and the decrease in absorbance at 340 nm was measured over 10 minutes. When 0.5 µg of total cell extract protein of the negative control strain was added to the reaction mixture, a decrease in absorbance from −0.01 to −0.02 was seen over 200 seconds. A decrease in absorbance from −0.21 to −0.47 and −0.20 to −0.47 over 200 seconds was seen, respectively, for cell extract from the YPH500/pESC-His/D-LDH or YPH500/pESC-His/D-LDH/PCT strains. 0.5 µL (7.85 µg) of cell extract from the anaerobically-grown E. coli strain showed a decrease in absorbance very similar to that for 1 µg of cell extract of the YPH500/pESC-His/D-LDH/PCT strain. When 4 µg of cell extract was used, the YPH500/pESC-His/D-LDH/PCT strain showed a decrease in absorbance from −0.18 to −0.60 over 10 minutes, whereas the negative control strain showed no decrease in absorbance (−0.08 to −0.08).

D. Demonstration of 3-HP Production in S. cerevisiae

The pESC-Trp/OS19/EI, pESC-Leu/EIIa/EIIB, and pESC-His/D-LDH/PCT constructs were transformed into a single strain of S. cerevisiae YPH500 using a Frozen-EZ Yeast Transformation II™ Kit (Zymo Research, Orange, Calif.). A negative control strain was also developed by transformation of the pESC-Trp, pESC-Leu, and pESC-His vectors into a single YPH500 strain. Transformation reactions were plated on SC-Trp-Leu-His media. Individual yeast colonies were screened by colony PCR for the presence or absence of nucleic acid corresponding to each construct.

The strain carrying all six genes and the negative control strain were grown in 5 mL of SC-Trp-Leu-His media containing 2% glucose. These cultures were grown for 31 hours at 30° C., and 2 mL was used to inoculate 50 mL of the same media. The subcultures were grown for 19 hours at 30° C., and their OD600s were determined. For each strain, a volume of cells giving an ODxvolume equal to 100 was pelleted, washed with SC-Trp-Leu-His media with no carbon source, and repelleted. The cells were suspended in 10 mL of SC-Trp- Leu-His media containing 2% galactose and 2% raffinose and used to inoculate a total volume of 250 mL of this media. The cultures were grown in bottles at 30° C. with no shaking, and samples were taken at 0, 4.5, 20, 28.5, 45, and 70 hours. Samples were spun down to remove cells and the supernatant was filtered using 0.45 micron Acrodisc Syrige Filters (Pall Gelman Laboratory, Ann Arbor, Mich.).

100 microliters of the filtered broth was used to derive CoA esters of any lactate or 3-HP in the broth using 6 micrograms of purified propionyl-CoA transferase, 50 mM potassium phosphate buffer (pH 7.0), and 1 mM acetyl-CoA. The reaction was allowed to proceed at room temperature for 15 minutes and was stopped by adding 1 volume 10% trifluoroacetic acid. The reaction mixtures were purified using Sep Pak C18 columns as previously described and analyzed by LC/MS.

Example 14

Constructing a Biosynthetic Pathway that Produces Organic Acids from β-alanine

One possible pathway to 3-HP from β-alanine involves the use of a polypeptide having CoA transferase activity (e.g., an enzyme from a class of enzymes that transfers a CoA group from one metabolite to the other). As shown in FIG. 54, β-alanine can be converted to β-alanyl-CoA using a polypeptide having CoA transferase activity and CoA donors such as acetyl-CoA or propionyl-CoA. Alternatively, β-alanyl-CoA can be generated by the action of a polypeptide having CoA synthetase activity. The β-alanyl-CoA can be deaminated to form acrylyl-CoA by a polypeptide having β-alanyl-CoA ammonia lyase activity. The hydration of acrylyl-CoA at the β position to yield 3-HP-CoA can be carried out by a polypeptide having 3-HP-CoA dehydratase activity. The 3-HP-CoA can act as a CoA donor for β-alanine, a reaction that can be catalyzed a polypeptide having CoA transferase activity, thus yielding 3-HP as a product. Alternatively, 3-HP-CoA can be hydrolyzed to yield 3-HP by a polypeptide having specific CoA hydrolase activity.

Methods for isolating, sequencing, expressing, and testing the activity of a polypeptide having CoA transferase activity are described herein.
A. Isolation of a Polypeptide Having D-alanyl-CoA Ammonia Lyase Activity Polypeptides having β-alanyl-CoA ammonia lyase activity can catalyze the conversion of β-alanyl-CoA into acrylyl-CoA. The activity of such polypeptides has been described by Vagelos et al. (*J. Biol. Chem.*, 234:490-497 (1959)) in *Clostridum propionicum*. This polypeptide can be used as part of the acrylate pathway in *Clostridum propionicum* to produce propionic acid.

*C. propionicum* was grown at 37° C. in an anoxic medium containing 0.2% yeast extract, 0.2% trypticase peptone, 0.05% cysteine, 0.5% b-alanine, 0.4% VRB-salts, 5 mM potassium phosphate, pH 7.0. The cells were harvested after 12 hours and washed twice with 50 mM potassium phosphate (Kpi), pH 7.0. About 2 g of wet packed cells were re-suspended in 40 mL of Kpi, pH 7.0, 1 mM $MgCl_2$, 1 mM EDTA, and 1 mM DTT (Buffer A), and homogenized by sonication at about 85-100 W power using a 3 mm tip (Branson sonifier 250). Cell debris was removed by centrifugation at 100,000 g for 45 minutes in a Centricon T-1080 Ultra centrifuge, and the cell free extract (~110 U/mg activity) was subjected to anion exchange chromatography on Source-15Q-material. The Source-15Q column was loaded with 32 mL of cell free extract. The column was developed by a linear gradient of 0 M to 0.5 M NaCl within 10 column volumes. The polypeptide eluted between 70-110 mM NaCl.

The solution was adjusted to a final concentration of 1 M $(NH_4)_2SO_4$ and applied onto a Resource-Phe column equilibrated with 1 M $(NH_4)_2SO_4$ in buffer A. The polypeptide did not bind to this column.

The final preparation was obtained after concentration in an Amicon chamber (filter cut-off 30 kDa). The functional polypeptide is composed of four polypeptide sub-units, each having a molecular mass of 16 kDa. The polypeptide had a final specific activity of 1033 U/mg in the standard assay (see below).

The polypeptide sample after every purification step was separated on a 15% SDS-PAGE gel. The gel was stained with 0.1% Coomassie R 250, and the destaining was achieved by using 7.1% acetic acid/5% ethanol solution.

The polypeptide was desalted by RP-HPLC and subjected to N-terminal sequencing by gas phase Edman degradation. The results of this analysis yielded a 35 amino acid N-terminal sequence of the polypeptide. The sequence was as follows:

(SEQ ID NO: 177)
MV-GKKVVHHLMMSAKDAHYTGNLVNGARIVNQWGD.

B. Amplification of a Gene Fragment

The 35 amino acid sequence of the polypeptide having β-alanine-CoA ammonia lyase activity was used to design primers with which to amplify the corresponding DNA from genome of *C. propionicium*. Genomic DNA from *C. propionicum* was isolated using the Gentra Genomic DNA isolation Kit (Gentra Systems, Minneapolis) following the genomic DNA protocol for gram-positive bacteria. A codon usage table for *Clostridium propionicum* was used to back translate the seven amino acids on either end of the amino acid sequence to obtain 20-nucleotide degenerate primers:

ACLF: 5'-ATGGTWGGYAARAARGTWGT-3' (SEQ ID NO: 178)

ACLR: 5'-TCRCCCCAYTGRTTWACRAT-3' (SEQ ID NO: 179)

The primers were used in a 50 μL PCR reaction containing 1×Taq PCR buffer, 0.6 μM each primer, 0.2 mM each dNTP, 2 units of Taq DNA polymerase (Roche Molecular Biochemicals, Indianapolis, Ind.), 2.5% (v/v) DMSO, and 100 ng of genomic DNA. PCR was conducted using a touchdown PCR program with 4 cycles at an annealing temperature of 58° C., 4 cycles at 56° C., 4 cycles at 54° C., and 24 cycles at 52° C. Each cycle used an initial 30 second denaturing step at 94° C. and a 1.25 minute extension at 72° C., and the program had an initial denaturation step at 94° C. for 2 minutes and final extension at 72° C. for 5 minutes. The amounts of PCR primer used in the reaction were increased three-fold above typical PCR amounts due to the amount of degeneracy in the 3' end of the primer. In addition, separate PCR reactions containing each individual primer were made to identify PCR product resulting from single degenerate primers. Twenty μL of each PCR product was separated on a 2.0% TAE (Tris-acetate-EDTA)-agarose gel.

A band of about 100 bp was produced by the reaction containing both the forward and reverse primers, but was not present in the individual forward and reverse primer control reactions. This fragment was excised and purified using a QIAquick Gel Extraction Kit (Qiagen, Valencia, Calif.). Four microliters of the purified band was ligated into pCRII-TOPO vector and transformed by a heat-shock method into TOP10

E. coli cells using a TOPO cloning procedure (Invitrogen, Carlsbad, Calif.). Transformations were plated on LB media containing 50 μg/mL of kanamycin and 50 μg/mL of 5-Bromo-4-Chloro-3-Indolyl-B-D-Galactopyranoside (X-gal). Individual, white colonies were resuspended in 25 μL of 10 mM Tris and heated for 10 minutes at 95° C. to break open the bacterial cells. Two microliters of the heated cells were used in a 25 μL PCR reaction using M13R and M13F universal primers homologous to the pCRII-TOPO vector. The PCR mix contained the following: 1×Taq PCR buffer, 0.2 μM each primer, 0.2 mM each dNTP, and 1 unit of Taq DNA polymerase per reaction. The PCR reaction was performed in a MJ Research PTC 100 under the following conditions: an initial denaturation at 94° C. for 2 minutes; 30 cycles of 94° C. for 30 seconds, 52° C. for 1 minute, and 72° C. for 1.25 minutes; and a final extension for 7 minutes at 72° C. Plasmid DNA was obtained (QIAprep Spin Miniprep Kit, Qiagen) from cultures of colonies showing the desired insert and was used for DNA sequencing with M13R universal primer. The following nucleic acid sequence was internal to the degenerate primers and corresponds to a portion of the 35 amino acid residue sequence:

```
                                            (SEQ ID NO: 180)
5'-ACATCATTTAATGATGA-GCGCAAAAGATGCTCACTATACTGGAAAC

TTAGTAAACGGCGCTAGA-3'.
```

C. Genome Walking to Obtain the Complete Coding Sequence

Primers for conducting genome walking in both upstream and downstream directions were designed using the portion of the nucleic acid sequence that was internal to the degenerate primers. The primer sequences were as follows:

```
                                            (SEQ ID NO: 181)
ACLGSP1F:   5'-GTACATCATTTAATGATGAGCGCAAAAGATG-3'

(SEQ ID NO: 182)
ACLGSP2F:   5'-GATGCTCACTATACTGGAAACTTAGTAAAC-3'

(SEQ ID NO: 183)
ACLGSP1R:   5'-ATTCTAGCGCCGTTTACTAAGTTTCCAG-3'

(SEQ ID NO: 184)
ACLGSP2R:   5'-CCAGTATAGTGAGCATCTTTTGCGCTCATC-3'
```

GSP1F and GSP2F are primers facing downstream, GSP1R and GSP2R are primers facing upstream, and GSP2F and GSP2R are primers nested inside GSP1F and GSP1R, respectively. Genome walking libraries were constructed according to the manual for CLONTECH's Universal Genome Walking Kit (CLONTECH Laboratories, Palo Alto, Calif.), with the exception that the restriction enzymes Ssp I and Hinc II were used in addition to Dra I, EcoR V, and Pvu II. PCR was conducted in a Perkin Elmer 9700 Thermocycler using the following reaction mix: 1×XL Buffer II, 0.2 mM each dNTP, 1.25 mM Mg(OAc)$_2$, 0.2 μM each primer, 2 units of rTth DNA polymerase XL (Applied Biosystems, Foster City, Calif.), and 1 μL of library per 50 μL reaction. First round PCR used an initial denaturation at 94° C. for 5 seconds; 7 cycles consisting of 2 sec at 94° C. and 3 min at 70° C.; 32 cycles consisting of 2 sec at 94° C. and 3 min at 64° C.; and a final extension at 64° C. for 4 min. Second round PCR used an initial denaturation at 94° C. for 15 seconds; 5 cycles consisting of 5 sec at 94° C. and 3 min at 70° C.; 26 cycles consisting of 5 sec at 94° C. and 3 min at 64° C.; and a final extension at 66° C. for 7 min. Twenty μL of each first and second round product was run on a 1.0% TAE-agarose gel. In the second round PCR for the forward reactions, a 1.4 Kb band was obtained for Dra I, a 1.5 Kb band for Hinc II, a 4.0 Kb band for Pvu II, and 2.0 and 2.6 Kb bands were obtained for Ssp I. In the second round PCR for the reverse reactions, a 1.5 Kb band was obtained for Dra I, a 0.8 Kb band for EcoR V, a 2.0 Kb band for Hinc II, a 2.9 Kb band for Pvu II, and a 1.5 Kb band was obtained for Ssp I. Several of these fragments were gel purified, cloned, and sequenced.

The coding sequence of the polypeptide having β-alanyl-CoA ammonia lyase activity is set forth in SEQ ID NO:162. This coding sequence encodes the amino acid sequence set forth in SEQ ID NO:160. The coding sequence was cloned and expressed in bacterial cells. A polypeptide with the expected size was isolated and tested for enzymatic activity.

The isolation of a nucleic acid molecule encoding a polypeptide having 3-HP-CoA dehydratase activity (e.g., the seventh enzymatic activity in FIG. 54, which can be accomplished with a polypeptide having the amino acid sequence set forth in SEQ ID NO:41) is described herein. This polypeptide in combination with a polypeptide having CoA transferase activity (e.g., a polypeptide having the amino acid sequence set forth in SEQ ID NO:2) and a polypeptide having β-alanyl-CoA ammonia lyase activity (e.g., a polypeptide having the amino acid sequence set forth in SEQ ID NO: 160) provides one method of making 3-HP from β-alanine.

Example 15

Constructing a Biosynthetic Pathway that Produces Organic Acids from β-alanine

In another pathway, β-alanine generated from aspartate can be deaminated by a polypeptide having 4,4-aminobutyrate aminotransferase activity (FIG. 55). This reaction also can regenerate glutamate that is consumed in the formation of aspartate. The deamination of β-alanine can yield malonate semialdehyde, which can be further reduced to 3-HP by a polypeptide having 3-hydroxypropionate dehydrogenase activity or a polypeptide having 3-hydroxyisobutyrate dehydrogenase activity. Such polypeptides can be obtained as follows.

A. Cloning gabT (4-aminobutyrate aminotransferase) from *C. acetobutycilicum*

The following PCR primers were designed based on a published sequence for a gabT gene from *Clostridium acetobutycilicum* (GenBank# AE007654):

```
Cac aba nco sen:
5'-GAGCCATGGAAGAAATAAATGCTAAAG-3'    (SEQ ID NO: 185)

Cac aba bam anti:
5'-AGAGGATGGCTTTTTAAATCGCTATTC-3'    (SEQ ID NO: 186)
```

The primers introduced a NcoI site at the 5' end and a BamH I site at the 3' end. A PCR reaction was set up using chromosomal DNA from *C. acetobutylicum* as the template.

| | | |
|---|---|---|
| H2O | 80.75 μL | PCR Program |
| Taq Plus Long 10× Buffer | 10 μL | 94° C. 5 minutes |
| dNTP mix (10 mM) | 3 μL | 25 cycles of: |
| Cac aba nco sen (20 mM) | 2 μL | 94° C. 30 seconds |
| Cac aba bam anti (20 mM) | 2 μL | 50° C. 30 seconds |
| *C. acetobutylicum* DNA (~100 ng) | 1 μL | 72° C. 80 seconds + 2 seconds/cycle |
| Taq Plus Long (5 U/mL) | 1 μL | |

| | | |
|---|---|---|
| Pfu (2.5 U/mL) | 0.25 µL | 1 cycle of: 68° C. 7 minutes<br>4° C. until use |

Upon agarose gel analysis a single band was observed of ~1.3 Kb in size. This fragment was purified using QIAquick PCR purification kit (Qiagen, Valencia, Calif.) and cloned into pCRII TOPO using the TOPO Zero Blunt PCR cloning kit (Invitrogen, Carlsbad, Calif.). 1 µL of the pCRII TOPO ligation mix was used to transform chemically competent TOP10 *E. coli* cells. The cells were for 1 hour in SOC media, and the transformants were selected on LB/kanamycin (50 µg/mL) plates. Single colonies of the transformant grown overnight in LB/kanamycin media, and the plasmid DNA was extracted using a Mini prep kit (Qiagen, Valencia, Calif.). The super-coiled plasmid DNA was separated on a 1% agarose gel digested, and the colonies with insert were selected. The insert was sequenced to confirm the sequence and its quality.

The plasmid having the correct insert was digested with restriction enzyme Nco I and BamH I. The digested insert was gel isolated and ligated to pET28b expression vector that was also restricted with Nco I and BamH I enzymes. 1 µl of ligation mix was used to transform chemically competent TOP10 *E. coli* cells. The cells were recovered for 1 hour in SOC media, and the transformants were selected on LB/kanamycin (50 µg/mL) plates. The super-coiled plasmid DNA was separated on a 1% agarose gel digested, and the colonies with insert were selected. The plasmid with the insert was isolated using a Mini prep kit (Qiagen, Valencia, Calif.), and 1 µL of this plasmid DNA was used to transform electrocompetent BL21(DE3) (Novagen, Madison, Wis.). These cells were used to check the expression of a polypeptide having 4-aminobutyrate aminotransferase activity.

B. Cloning mmsB (3-hydroxyisobutyrate dehydrogenase) from *P. aeruginosa*

The following PCR primers was designed based on a published sequence for a mmsB gene from *Pseudomona aeruginosa* (GenBank# M84911):

```
Ppu hid nde sen:
5'-ATACATATGACCGACCGACATCGCATT-3'    (SEQ ID NO: 186)

Ppu hid sal anti:
5'-ATAGTCGACGGGTCAGTCCTTGCCGCG-3'    (SEQ ID NO: 187)
```

The primers introduced a Nde I site at the 5' end and a BamH I site at the 3' end.

| | | |
|---|---|---|
| H₂O | 80.75 µL | PCR Program |
| Taq Plus Long 10× Buffer | 10 µL | 94° C. 5 minutes |
| dNTP mix (10 mM) | 3 µL | 25 cycles of:<br>94° C. 30 seconds<br>55° C. 30 seconds<br>72° C. 90 seconds + 2 seconds/cycle |
| Ppu hid nde sen (20 µM) | 2 µL | 68° C. 7 minutes |
| Ppu hid sal anti (20 µM) | 2 µL | 4° C. until use |
| *C. acetobutylicum* DNA (~100 ng) | 1 µl | |
| Taq Plus Long (Stratagene, La Jolla, CA) | 1 µL | |
| Pfu (Stratagene, La Jolla, CA) | 0.25 µL | |

A PCR reaction was set up using chromosomal DNA from *P. aeruginosa* as the template. Chromosomal DNA was obtained from ATCC (Manassas, Va.) *P. aeruginosa* 17933D.

Upon agarose gel analysis, a single band was observed of ~1.6 Kb in size. This fragment was purified using QIAquick PCR purification kit (Qiagen, Valencia, Calif.) and cloned into pCRII TOPO using the TOPO Zero Blunt PCR cloning kit (Invitrogen, Carlsbad, Calif.). 1 µL of the pCRII TOPO ligation mix was used to transform chemically competent TOP10 *E. coli* cells. The cells were recovered for 1 hour in SOC media, and the transformants were selected on LB/kanamycin (50 µg/mL) plates. Single colonies of the transformant grown overnight in LB/kanamycin media, and the plasmid DNA was extracted using a Mini prep kit (Qiagen, Valencia, Calif.). The super-coiled plasmid DNA was separated on a 1% agarose gel and digested, and the colonies with insert were selected. The insert was sequenced to confirm the sequence and its quality.

The plasmid having the correct insert was digested with restriction enzyme Nde I and BamHI. The digested insert was gel isolated and ligated to pET30a expression vector that was also restricted with Nde I and BamH I enzymes. 1 µL of ligation mix was used to transform chemically competent TOP10 *E. coli* cells. The cells were recovered for 1 hour in SOC media, and the transformants were selected on LB/kanamycin (50 µg/mL) plates. The super-coiled plasmid DNA was separated on a 1% agarose gel and digested, and the colonies with insert were selected. The plasmid with the insert was isolated using a Mini prep kit (Qiagen, Valencia, Calif.), and 1 µl of this plasmid DNA was used to transform electrocompetent BL21(DE3) (Novagen, Madison, Wis.). These cells were used to check the expression of a polypeptide having 3-hydroxyisobutyrate dehydrogenase activity.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. An isolated transformed cell comprising:
a nucleic acid molecule comprising at least 90% sequence identity to SEQ ID NO: 9, encoding an E1 activator of an enzyme having lactyl-CoA dehydratase activity;
a nucleic acid molecule comprising at least 90% sequence identity to SEQ ID NO: 17, encoding an E2 α subunit of an enzyme having lactyl-CoA dehydratase activity;
a nucleic acid molecule comprising at least 90% sequence identity to SEQ ID NO: 25, encoding an E2 β subunit of an enzyme having lactyl-CoA dehydratase activity;
a nucleic acid molecule comprising at least 90% sequence identity to SEQ ID NO: 40, encoding an enzyme having 3-hydroxypropionyl-CoA dehydratase activity; and
a nucleic acid molecule encoding an enzyme having poly hydroxyacid synthase activity.

2. The isolated transformed cell of claim 1, wherein said cell produces polymerized 3-HP.

3. The isolated transformed cell of claim 1, wherein said cell is prokaryotic.

4. The isolated transformed cell of claim 1, wherein said cell is selected from the group consisting of yeast, *Lactobacillus*, *Lactococcus*, *Bacillus*, and *Escherichia* cells.

5. The isolated transformed cell of claim 1, wherein said poly hydroxyacid synthase activity is encoded by a nucleic acid sequence comprising a sequence as set forth in SEQ ID NO: 189 or a sequence that hybridizes to SEQ ID NO: 189 under highly stringent hybridization conditions, wherein the highly stringent hybridization conditions comprise hybridization at about 42° C. in a hybridization solution comprising 25 mM KPO4 (pH 7.4), 5×SSC, 5×Denhart's solution, 50 μg/mL denatured, sonicated salmon sperm DNA, 50% formamide, 10% Dextran sulfate, and 1-15ng/mL SEQ ID NO: 189, washing at about 65° C. in a wash solution comprising 0.2×SSC and 0.1% sodium dodecyl sulfate.

6. The transformed isolated cell of claim 1, further comprising CoA synthetase activity.

7. The isolated transformed cell of claim 1, wherein the cell is a yeast cell.

8. The isolated transformed cell of claim 1, wherein:

the nucleic acid molecule encoding an E1 activator of an enzyme having lactyl-CoA dehydratase activity comprises at least 95% sequence identity to SEQ ID NO: 9;

the nucleic acid molecule encoding an E2 α subunit of an enzyme having lactyl-CoA dehydratase activity comprises at least 95% sequence identity to SEQ ID NO: 17;

the nucleic acid molecule encoding an E2 β subunit of an enzyme having lactyl-CoA dehydratase activity comprises at least 95% sequence identity to SEQ ID NO: 25;

the nucleic acid molecule encoding an enzyme having 3-hydroxypropionyl-CoA dehydratase activity comprises at least 95% sequence identity to SEQ ID NO: 40; and the nucleic acid molecule encoding an enzyme having poly hydroxyacid synthase activity comprises SEQ ID NO: 189 or a sequence that hybridizes to SEQ ID NO: 189 under highly stringent hybridization conditions, wherein the highly stringent hybridization conditions comprise hybridization at about 42° C. in a hybridization solution comprising 25 mM KPO4 (pH 7.4), 5×SSC, 5×Denhart's solution, 50 μg/mL denatured, sonicated salmon sperm DNA, 50% formamide, 10% Dextran sulfate, and 1-15 ng/mL SEQ ID NO: 189, washing at about 65° C. in a wash solution comprising 0.2×SSC and 0.1% sodium dodecyl sulfate.

9. The isolated transformed cell of claim 1, wherein:

the nucleic acid molecule encoding an E1 activator of an enzyme having lactyl-CoA dehydratase activity comprises at least 97% sequence identity to SEQ ID NO: 9;

the nucleic acid molecule encoding an E2 α subunit of an enzyme having lactyl-CoA dehydratase activity comprises at least 97% sequence identity to SEQ ID NO: 17;

the nucleic acid molecule encoding an E2 β subunit of an enzyme having lactyl-CoA dehydratase activity comprises at least 97% sequence identity to SEQ ID NO: 25;

the nucleic acid molecule encoding an enzyme having 3-hydroxypropionyl-CoA dehydratase activity comprises at least 97% sequence identity to SEQ ID NO: 40; and the nucleic acid molecule encoding an enzyme having poly hydroxyacid synthase activity comprises SEQ ID NO: 189 or a sequence that hybridizes to SEQ ID NO: 189 under highly stringent hybridization conditions, wherein the highly stringent hybridization conditions comprise hybridization at about 42° C. in a hybridization solution comprising 25 mM KPO4 (pH 7.4), 5×SSC, 5×Denhart's solution, 50 μg/mL denatured, sonicated salmon sperm DNA, 50% formamide, 10% Dextran sulfate, and 1-15 ng/mL SEQ ID NO: 189, washing at about 65° C. in a wash solution comprising 0.2×SSC and 0.1% sodium dodecyl sulfate.

10. The isolated transformed cell of claim 1, wherein:

the nucleic acid molecule encoding an E1 activator of an enzyme having lactyl-CoA dehydratase activity comprises at least 98% sequence identity to SEQ ID NO: 9;

the nucleic acid molecule encoding an E2 α subunit of an enzyme having lactyl-CoA dehydratase activity comprises at least 98% sequence identity to SEQ ID NO: 17;

the nucleic acid molecule encoding an E2 β subunit of an enzyme having lactyl-CoA dehydratase activity comprises at least 98% sequence identity to SEQ ID NO: 25;

the nucleic acid molecule encoding an enzyme having 3-hydroxypropionyl-CoA dehydratase activity comprises at least 98% sequence identity to SEQ ID NO: 40; and the nucleic acid molecule encoding an enzyme having poly hydroxyacid synthase activity comprises SEQ ID NO: 189 or a sequence that hybridizes to SEQ ID NO: 189 under highly stringent hybridization conditions, wherein the highly stringent hybridization conditions comprise hybridization at about 42° C. in a hybridization solution comprising 25 mM KPO4 (pH 7.4), 5×SSC, 5×Denhart's solution, 50μg/mL denatured, sonicated salmon sperm DNA, 50% formamide, 10% Dextran sulfate, and 1-15 ng/mL SEQ ID NO: 189, washing at about 65° C. in a wash solution comprising 0.2×SSC and 0.1% sodium dodecyl sulfate.

11. The isolated transformed cell of claim 1, wherein:

the nucleic acid molecule encoding an E1 activator of an enzyme having lactyl-CoA dehydratase activity comprises at least 99% sequence identity to SEQ ID NO: 9;

the nucleic acid molecule encoding an E2 α subunit of an enzyme having lactyl-CoA dehydratase activity comprises at least 99% sequence identity to SEQ ID NO: 17;

the nucleic acid molecule encoding an E2 β subunit of an enzyme having lactyl-CoA dehydratase activity comprises at least 99% sequence identity to SEQ ID NO: 25;

the nucleic acid molecule encoding an enzyme having 3-hydroxypropionyl-CoA dehydratase activity comprises at least 99% sequence identity to SEQ ID NO: 40; and the nucleic acid molecule encoding an enzyme having poly hydroxyacid synthase activity comprises SEQ ID NO: 189 or a sequence that hybridizes to SEQ ID NO: 189 under highly stringent hybridization conditions, wherein the highly stringent hybridization conditions comprise hybridization at about 42° C. in a hybridization solution comprising 25 mM KPO4 (pH 7.4), 5×SSC, 5×Denhart's solution, 50μg/mL denatured, sonicated salmon sperm DNA, 50% formamide, 10% Dextran sulfate, and 1-15 ng/mL SEQ ID NO: 189, washing at about 65° C. in a wash solution comprising 0.2×SSC and 0.1% sodium dodecyl sulfate.

* * * * *

UNITED STATES PATENT AND TRADEMARK OFFICE
CERTIFICATE OF CORRECTION

| | | |
|---|---|---|
| PATENT NO. | : 8,076,120 B2 | Page 1 of 5 |
| APPLICATION NO. | : 12/127700 | |
| DATED | : December 13, 2011 | |
| INVENTOR(S) | : Gokarn et al. | |

It is certified that error appears in the above-identified patent and that said Letters Patent is hereby corrected as shown below:

Column 3, line 56, "a nucleic sequences" should be --nucleic sequences--.

Column 4, line 1, "any the" should be --any of the--.

Column 10, line 48, "polypeptide" should be --polypeptides--.

Column 11, line 64, "(1990)" should be --(1990))--.

Column 13, line 60, "is" should be --are--.

Column 13, line 61, "is" should be --are--.

Column 16, line 20, "*cervisiae*" should be --*cerevisiae*--.

Column 22, line 9, "a amino" should be --an amino--.

Column 22, line 14, "that an" should be --that contain an--.

Column 23, line 42, "Spring, Harbor" should be --Spring Harbor--.

Column 23, line 63, "a standard DNA mutagenesis techniques" should be --standard DNA mutagenesis techniques--.

Column 26, line 8, "a similar nucleic acid molecules" should be --similar nucleic acid molecules--.

Column 27, line 36, "Examples biosynthetic" should be --Examples of biosynthetic--.

Column 29, line 5, "Stems" should be --Sterns--.

Column 29, line 30, "synthatase" should be --synthetase--.

Column 29, line 56, "polypeptides have" should be --polypeptides that have--.

Column 30, line 9, "used convert" should be --used to convert--.

Column 30, line 62, "is" should be --in--.

Column 31, line 3, "13-alanine" should be --β-alanine--.

Column 31, line 21, "lead" should be --led--.

Column 31, line 26, "synthatase" should be --synthetase--.

Column 31, line 33, "is yeast" should be --in yeast--.

Signed and Sealed this
Eighteenth Day of September, 2012

David J. Kappos
*Director of the United States Patent and Trademark Office*

CERTIFICATE OF CORRECTION (continued)
U.S. Pat. No. 8,076,120 B2

Column 31, lines 40-41, "*aurantacius*" should be --*aurantiacus*--.

Column 32, line 32, "1.1.1.159" should be --1.1.1.59--.

Column 32, line 50, "than" should be --then--.

Column 36, line 61, "E1R15'" should be --E1R1 5'--.

Column 36, line 62, "E1R25'" should be --E1R2 5'--.

Column 36, line 64, "E1R35'" should be --E1R3 5'--.

Column 36, line 65, "E1R45'" should be --E1R4 5'--.

Column 36, line 66, "E1R55'" should be --E1R5 5'--.

Column 37, line 47, "EIF2" should be --E1F2--.

Column 38, line 57, "containing" should be --contain--.

Column 40, line 39, "CRR15'" should be --CRR1 5'--.

Column 40, line 40, "CRR25'" should be --CRR2 5'--.

Column 40, line 41, "CRR35'" should be --CRR3 5'--.

Column 41, line 30, "OS17R15'" should be --OS17R1 5'--.

Column 41, line 32, "OS17R25'" should be --OS17R2 5'--.

Column 41, line 33, "OS17R35'" should be --OS17R3 5'--.

Column 41, line 66, "OS17R45'" should be --OS17R4 5'--.

Column 42, line 1, "OS17R55'" should be --OS17R5 5'--.

Column 42, line 10, "OS 17R5" should be --OS17R5--.

Column 42, line 12, "OS 17F5" should be --OS17F5--.

Column 42, line 23, "synthesases" should be --synthetases--.

Column 42, line 48, "synthesases" should be --synthetases--.

Column 44, line 20, "where" should be --were--.

Column 46, lines 21, "hydroxypropinyl" should be --hydroxypropionyl--.

Column 46, lines 61-62, "visa-versa" should be --vice versa--.

Column 47, line 28, "of by PCR" should be --by PCR--.

Column 47, line 51, "direction" should be --directions--.

Column 47, line 66, "inactive" should be --inactivate--.

Column 48, lines 32-33, "of by PCR" should be --by PCR--.

Column 48, line 33, "OSXNHF" should be --OSXNhF--.

Column 48, line 56, "direction" should be --directions--.

Column 49, line 3, "inactive" should be --inactivate--.

Column 50, line 26, "of by PCR" should be --by PCR--.

Column 50, line 46, "direction" should be --directions--.

Column 50, line 57, "with gel purified the CoA" should be --with gel purified CoA--.

CERTIFICATE OF CORRECTION (continued)
U.S. Pat. No. 8,076,120 B2

Column 50, line 61, "direction" should be --directions--.

Column 51, line 9, "inactive" should be --inactivate--.

Column 51, line 61, "of by PCR" should be --by PCR--.

Column 52, line 12, "direction" should be --directions--.

Column 52, line 23, "with gel purified the CoA" should be --with gel purified CoA--.

Column 52, line 27, "direction" should be --directions--.

Column 52, line 42, "inactive" should be --inactivate--.

Column 53, line 16, "enzymes, XbaI" should be --enzymes. XbaI--.

Column 53, line 17, "Quagen" should be --Qiagen--.

Column 53, line 18, "Bacillu" should be --Bacillus--.

Column 53, lines 51-52, "of by PCR" should be --by PCR--.

Column 54, line 4, "direction" should be --directions--.

Column 54, line 19, "inactive" should be --inactivate--.

Column 55, line 23, "% DE3" should be --λ DE3--.

Column 55, line 24, "manufacture's" should be --manufacturer's--.

Column 58, line 7, " GCGGCCGC" should be -- *GCGGCCGC* --.

Column 58, line 8, " ATGAGCGAAGAAAGCTTATT C" should be -- *ATGAGCGAAGAAAGCTTATT C* --.

Column 58, line 11, "CTCGAG" should be -- *CTCGAG* --.

Column 58, lines 11-12, " TAG-CTAAATTAAATTACATCAATAGTA" should be -- *TAG- CTAAATTAAATTACATCAATAGTA* --.

Column 58, lines 37-38, "carbencillin" should be --carbenicillin--.

Column 58, line 43, "carbencillin" should be --carbenicillin--.

Column 58, line 64, "*auarantiacus*" should be --*aurantiacus*--.

Column 58, line 67, "*auarantiacus*" should be --*aurantiacus*--.

Column 59, line 1, "obtained" should be --obtain--.

Column 59, line 53, "chromotography" should be --chromatography--.

Column 60, line 25, "a Microcon YM-10 columns" should be --a Microcon YM-10 column--.

Column 60, line 26, "manufacture's" should be --manufacturer's--.

Column 60, line 35, "manufacture's" should be --manufacturer's--.

Column 60, line 43, "Mm" should be --mM--.

Column 61, line 41, "BASLTX" should be --BLASTX--.

Column 62, lines 13-14, " 5'-ATGGCGACGGGCGAGTCCATGAG-3'" should be -- *5'-ATGGCGACGGGCGAGTCCATGAG-3'* --.

Column 62, line 20, "change" should be --changed--.

CERTIFICATE OF CORRECTION (continued)
U.S. Pat. No. 8,076,120 B2

Column 63, line 4, "2.5 U/μL)" should be --(2.5 U/μL)--.

Column 63, line 41, "manufacture's" should be --manufacturer's--.

Column 63, line 43, "manufacture's" should be --manufacturer's--.

Column 64, line 9, "clone" should be --clones--.

Column 64, lines 12-13, "manufacture's" should be --manufacturer's--.

Column 65, line 20, "quandrupole" should be --quadrupole--.

Column 65, lines 53-54, "carbencillin" should be --carbenicillin--.

Column 66, line 4, "dissolve" should be --dissolved--.

Column 66, line 9, "carbencillin" should be --carbenicillin--.

Column 66, line 11, "reached" should be --reaches--.

Column 66, line 19, "with of 50" should be --with 50--.

Column 66, line 25, "pisg" should be --psig--.

Column 66, line 27, "demonstrated" should be --demonstrate--.

Column 66, line 43, "quadropole" should be --quadrupole--.

Column 67, line 16, "*Escherishia*" should be --*Escherichia*--.

Column 70, line 24, "EIIaαSALR" should be --EIIαSALR--.

Column 75, line 54, "Dehvdratase" should be --Dehydratase--.

Column 76, line 64, "OD600s" should be --$OD_{600}$s--.

Column 77, line 6, "Syrige" should be --Syringe--.

Column 77, line 37, "catalyzed a" should be --catalyzed by a--.

Column 77, line 44, "D-alanyl" should be --β-alanyl--.

Column 77, line 47, "acryly" should be --acrylyl--.

Column 77, lines 49-50, "Clostridum" should be --Clostridium--.

Column 77, line 51, "Clostridum" should be --Clostridium--.

Column 78, line 31, "*propionicium*" should be --*propionicum*--.

Column 80, line 44, "*acetobutycilicum*" should be --*acetobutylicum*--.

Column 80, lines 46-47, "*acetobutycilicum*" should be --*acetobutylicum*--.

Column 81, lines 17-18, "gel digested" should be --gel and digested--.

Column 81, line 28, "gel digested" should be --gel and digested--.

Column 81, line 37, "was" should be --were--.

In the Claims:

Column 268, line 58, claim 5, "KPO4" should be --$KPO_4$--.

Column 269, line 21, claim 8, "KPO4" should be --$KPO_4$--.

Column 269, line 48, claim 9, "KPO4" should be --$KPO_4$--.

CERTIFICATE OF CORRECTION (continued)
U.S. Pat. No. 8,076,120 B2

Column 270, line 20, claim 10, "KPO4" should be --$KPO_4$--.

Column 270, line 46, claim 11, "KPO4" should be --$KPO_4$--.

SEQUENCE LISTING

```
<160> NUMBER OF SEQ ID NOS: 189

<210> SEQ ID NO 1
<211> LENGTH: 1554
<212> TYPE: DNA
<213> ORGANISM: Megasphaera elsdenii
<220> FEATURE:
<221> NAME/KEY: CDS
<222> LOCATION: (1)..(1551)
```

<400> SEQUENCE: 1

```
atg aga aaa gta gaa atc att aca gct gaa caa gca gct cag ctc gta      48
Met Arg Lys Val Glu Ile Ile Thr Ala Glu Gln Ala Ala Gln Leu Val
1               5                   10                  15 aaa gac aac gac acg att acg tct atc ggc ttt gtc agc agc gcc cat      96
Lys Asp Asn Asp Thr Ile Thr Ser Ile Gly Phe Val Ser Ser Ala His
            20                  25                  30 ccg gaa gca ctg acc aaa gct ttg gaa aaa cgg ttc ctg gac acg aac     144
Pro Glu Ala Leu Thr Lys Ala Leu Glu Lys Arg Phe Leu Asp Thr Asn
        35                  40                  45 acc ccg cag aac ttg acc tac atc tat gca ggc tct cag ggc aaa cgc     192
Thr Pro Gln Asn Leu Thr Tyr Ile Tyr Ala Gly Ser Gln Gly Lys Arg
    50                  55                  60 gat ggc cgt gcc gct gaa cat ctg gca cac aca ggc ctt ttg aaa cgc     240
Asp Gly Arg Ala Ala Glu His Leu Ala His Thr Gly Leu Leu Lys Arg
65                  70                  75                  80 gcc atc atc ggt cac tgg cag act gta ccg gct atc ggt aaa ctg gct     288
Ala Ile Ile Gly His Trp Gln Thr Val Pro Ala Ile Gly Lys Leu Ala
                85                  90                  95 gtc gaa aac aag att gaa gct tac aac ttc tcg cag ggc acg ttg gtc     336
Val Glu Asn Lys Ile Glu Ala Tyr Asn Phe Ser Gln Gly Thr Leu Val
            100                 105                 110 cac tgg ttc cgc gcc ttg gca ggt cat aag ctc ggc gtc ttc acc gac     384
His Trp Phe Arg Ala Leu Ala Gly His Lys Leu Gly Val Phe Thr Asp
        115                 120                 125 atc ggt ctg gaa act ttc ctc gat ccc cgt cag ctc ggc ggc aag ctc     432
Ile Gly Leu Glu Thr Phe Leu Asp Pro Arg Gln Leu Gly Gly Lys Leu
    130                 135                 140 aat gac gta acc aaa gaa gac ctc gtc aaa ctg atc gaa gtc gat ggt     480
Asn Asp Val Thr Lys Glu Asp Leu Val Lys Leu Ile Glu Val Asp Gly
145                 150                 155                 160 cat gaa cag ctt ttc tac ccg acc ttc ccg gtc aac gta gct ttc ctc     528
His Glu Gln Leu Phe Tyr Pro Thr Phe Pro Val Asn Val Ala Phe Leu
                165                 170                 175 cgc ggt acg tat gct gat gaa tcc ggc aat atc acc atg gac gaa gaa     576
Arg Gly Thr Tyr Ala Asp Glu Ser Gly Asn Ile Thr Met Asp Glu Glu
            180                 185                 190 atc ggg cct ttc gaa agc act tcc gta gcc cag gcc gtt cac aac tgt     624
Ile Gly Pro Phe Glu Ser Thr Ser Val Ala Gln Ala Val His Asn Cys
        195                 200                 205 ggc ggt aaa gtc gtc gtc cag gtc aaa gac gtc gtc gct cac ggc agc     672
Gly Gly Lys Val Val Val Gln Val Lys Asp Val Val Ala His Gly Ser
    210                 215                 220 ctc gac ccg cgc atg gtc aag atc cct ggc atc tat gtc gac tac gtc     720
Leu Asp Pro Arg Met Val Lys Ile Pro Gly Ile Tyr Val Asp Tyr Val
225                 230                 235                 240 gtc gta gca gct ccg gaa gac cat cag cag acg tat gac tgc gaa tac     768
Val Val Ala Ala Pro Glu Asp His Gln Gln Thr Tyr Asp Cys Glu Tyr
                245                 250                 255 gat ccg tcc ctc agc ggt gaa cat cgt gct cct gaa ggc gct acc gat     816
Asp Pro Ser Leu Ser Gly Glu His Arg Ala Pro Glu Gly Ala Thr Asp
            260                 265                 270 gca gct ctc ccc atg agc gct aag aaa atc atc ggc cgc cgc ggc gct     864
Ala Ala Leu Pro Met Ser Ala Lys Lys Ile Ile Gly Arg Arg Gly Ala
        275                 280                 285 ttg gaa ttg act gaa aac gct gtc gtc aac ctc ggc gtc ggt gct ccg     912
Leu Glu Leu Thr Glu Asn Ala Val Val Asn Leu Gly Val Gly Ala Pro
    290                 295                 300 gaa tac gtt gct tct gtt gcc ggt gaa gaa ggt atc gcc gat acc att     960
Glu Tyr Val Ala Ser Val Ala Gly Glu Glu Gly Ile Ala Asp Thr Ile
```

```
              305                 310                 315                 320
acc ctg acc gtc gaa ggt ggc gcc atc ggt ggc gta ccg cag ggc ggt        1008
Thr Leu Thr Val Glu Gly Gly Ala Ile Gly Gly Val Pro Gln Gly Gly
                325                 330                 335 gcc cgc ttc ggt tcg tcc cgc aat gcc gat gcc atc atc gac cac acc        1056
Ala Arg Phe Gly Ser Ser Arg Asn Ala Asp Ala Ile Ile Asp His Thr
                340                 345                 350 tat cag ttc gac ttc tac gat ggc ggt ctg gac atc gct tac ctc            1104
Tyr Gln Phe Asp Phe Tyr Asp Gly Gly Leu Asp Ile Ala Tyr Leu
            355                 360                 365 ggc ctg gcc cag tgc gat ggc tcg ggc aac atc aac gtc agc aag ttc        1152
Gly Leu Ala Gln Cys Asp Gly Ser Gly Asn Ile Asn Val Ser Lys Phe
            370                 375                 380 ggt act aac gtt gcc ggc tgc ggc ggt ttc ccc aac att tcc cag cag        1200
Gly Thr Asn Val Ala Gly Cys Gly Gly Phe Pro Asn Ile Ser Gln Gln
385                 390                 395                 400 aca ccg aat gtt tac ttc tgc ggc acc ttc acg gct ggc ggc ttg aaa        1248
Thr Pro Asn Val Tyr Phe Cys Gly Thr Phe Thr Ala Gly Gly Leu Lys
                405                 410                 415 atc gct gtc gaa gac ggc aaa gtc aag atc ctc cag gaa ggc aaa gcc        1296
Ile Ala Val Glu Asp Gly Lys Val Lys Ile Leu Gln Glu Gly Lys Ala
                420                 425                 430 aag aag ttc atc aaa gct gtc gac cag atc act ttc aac ggt tcc tat        1344
Lys Lys Phe Ile Lys Ala Val Asp Gln Ile Thr Phe Asn Gly Ser Tyr
                435                 440                 445 gca gcc cgc aac ggc aaa cac gtt ctc tac atc aca gaa cgc tgc gta        1392
Ala Ala Arg Asn Gly Lys His Val Leu Tyr Ile Thr Glu Arg Cys Val
                450                 455                 460 ttt gaa ctg acc aaa gaa ggc ttg aaa ctc atc gaa gtc gca ccg ggc        1440
Phe Glu Leu Thr Lys Glu Gly Leu Lys Leu Ile Glu Val Ala Pro Gly
465                 470                 475                 480 atc gat att gaa aaa gat atc ctc gct cac atg gac ttc aag ccg atc        1488
Ile Asp Ile Glu Lys Asp Ile Leu Ala His Met Asp Phe Lys Pro Ile
                485                 490                 495 att gat aat ccg aaa ctc atg gat gcc cgc ctc ttc cag gac ggt ccc        1536
Ile Asp Asn Pro Lys Leu Met Asp Ala Arg Leu Phe Gln Asp Gly Pro
                500                 505                 510 atg gga ctg aaa aaa taa                                                1554
Met Gly Leu Lys Lys
            515

<210> SEQ ID NO 2
<211> LENGTH: 517
<212> TYPE: PRT
<213> ORGANISM: Megasphaera elsdenii

<400> SEQUENCE: 2

Met Arg Lys Val Glu Ile Ile Thr Ala Glu Gln Ala Ala Gln Leu Val
1               5                   10                  15

Lys Asp Asn Asp Thr Ile Thr Ser Ile Gly Phe Val Ser Ser Ala His
                20                  25                  30

Pro Glu Ala Leu Thr Lys Ala Leu Glu Lys Arg Phe Leu Asp Thr Asn
            35                  40                  45

Thr Pro Gln Asn Leu Thr Tyr Ile Tyr Ala Gly Ser Gln Gly Lys Arg
        50                  55                  60

Asp Gly Arg Ala Ala Glu His Leu Ala His Thr Gly Leu Leu Lys Arg
65                  70                  75                  80

Ala Ile Ile Gly His Trp Gln Thr Val Pro Ala Ile Gly Lys Leu Ala
                85                  90                  95
```

```
Val Glu Asn Lys Ile Glu Ala Tyr Asn Phe Ser Gln Gly Thr Leu Val
            100                 105                 110

His Trp Phe Arg Ala Leu Ala Gly His Lys Leu Gly Val Phe Thr Asp
            115                 120                 125

Ile Gly Leu Glu Thr Phe Leu Asp Pro Arg Gln Leu Gly Gly Lys Leu
            130                 135                 140

Asn Asp Val Thr Lys Glu Asp Leu Val Lys Leu Ile Glu Val Asp Gly
145                 150                 155                 160

His Glu Gln Leu Phe Tyr Pro Thr Phe Pro Val Asn Val Ala Phe Leu
                165                 170                 175

Arg Gly Thr Tyr Ala Asp Glu Ser Gly Asn Ile Thr Met Asp Glu Glu
            180                 185                 190

Ile Gly Pro Phe Glu Ser Thr Ser Val Ala Gln Ala Val His Asn Cys
            195                 200                 205

Gly Gly Lys Val Val Gln Val Lys Asp Val Val Ala His Gly Ser
            210                 215                 220

Leu Asp Pro Arg Met Val Lys Ile Pro Gly Ile Tyr Val Asp Tyr Val
225                 230                 235                 240

Val Val Ala Ala Pro Glu Asp His Gln Gln Thr Tyr Asp Cys Glu Tyr
                245                 250                 255

Asp Pro Ser Leu Ser Gly Glu His Arg Ala Pro Glu Gly Ala Thr Asp
            260                 265                 270

Ala Ala Leu Pro Met Ser Ala Lys Lys Ile Ile Gly Arg Arg Gly Ala
            275                 280                 285

Leu Glu Leu Thr Glu Asn Ala Val Val Asn Leu Gly Val Gly Ala Pro
            290                 295                 300

Glu Tyr Val Ala Ser Val Ala Gly Glu Glu Gly Ile Ala Asp Thr Ile
305                 310                 315                 320

Thr Leu Thr Val Glu Gly Gly Ala Ile Gly Gly Val Pro Gln Gly Gly
            325                 330                 335

Ala Arg Phe Gly Ser Ser Arg Asn Ala Asp Ala Ile Ile Asp His Thr
            340                 345                 350

Tyr Gln Phe Asp Phe Tyr Asp Gly Gly Gly Leu Asp Ile Ala Tyr Leu
            355                 360                 365

Gly Leu Ala Gln Cys Asp Gly Ser Gly Asn Ile Asn Val Ser Lys Phe
            370                 375                 380

Gly Thr Asn Val Ala Gly Cys Gly Gly Phe Pro Asn Ile Ser Gln Gln
385                 390                 395                 400

Thr Pro Asn Val Tyr Phe Cys Gly Thr Phe Thr Ala Gly Gly Leu Lys
                405                 410                 415

Ile Ala Val Glu Asp Gly Lys Val Lys Ile Leu Gln Glu Gly Lys Ala
            420                 425                 430

Lys Lys Phe Ile Lys Ala Val Asp Gln Ile Thr Phe Asn Gly Ser Tyr
            435                 440                 445

Ala Ala Arg Asn Gly Lys His Val Leu Tyr Ile Thr Glu Arg Cys Val
            450                 455                 460

Phe Glu Leu Thr Lys Glu Gly Leu Lys Leu Ile Glu Val Ala Pro Gly
465                 470                 475                 480

Ile Asp Ile Glu Lys Asp Ile Leu Ala His Met Asp Phe Lys Pro Ile
                485                 490                 495

Ile Asp Asn Pro Lys Leu Met Asp Ala Arg Leu Phe Gln Asp Gly Pro
            500                 505                 510

Met Gly Leu Lys Lys
            515
```

<210> SEQ ID NO 3
<211> LENGTH: 1560
<212> TYPE: DNA
<213> ORGANISM: Escherichia coli

<400> SEQUENCE: 3

```
gtgccggtcc tgtcggcaca ggaagcggtg aattatattc ccgacgaagc aacactttgt      60
gtgttaggcg ctggcggcgg tattctggaa gccaccacgt taattactgc tcttgctgat     120
aaatataaac agactcaaac accacgtaat ttatcgatta ttagtccaac agggcttggc     180
gatcgcgccg accgtggtat tagtcctctg gcgcaagaag gtctggtgaa atgggcatta     240
tgtggtcact ggggacaatc gccgcgtatt tctgaactcg cagaacaaaa taaaattatt     300
gcttataact acccacaagg tgtacttaca caaaccttac gcgccgccgc agcccaccag     360
cctggtatta ttagtgatat tggcatcggg acatttgtcg atccacgcca gcaaggcggc     420
aaactgaatg aagtcactaa agaagacctg attaaactgg tcgagtttga taacaaagaa     480
tatctctatt acaaagcgat tgcgccagat attgccttca ttcgcgctac cacctgcgac     540
agtgaaggct acgccacttt tgaagatgag gtgatgtatc tcgacgcatt ggttattgcc     600
caggcggtgc acaataacgg cggtattgtg atgatgcagg tgcagaaaat ggttaagaaa     660
gccacgctgc atcctaaatc tgtccgtatt ccggttatc tggtggatat tgtggtggtc     720
gatccggatc aaacccaact gtatggcggt gcaccggtta accgctttat ttctggtgac     780
ttcacccttg atgacagtac caaacttagc ctgcccctaa accaacgtaa attagttgcg     840
cggcgcgcat tattcgaaat gcgtaaaggc gcggtgggga atgtcggcgt cggtattgct     900
gacggcattg gcctggtcgc ccgagaagaa ggttgtgctg atgactttat tctgacggta     960
gaaacaggtc cgattggcgg aattacttca caggggatcg cctttggcgc gaacgtgaat    1020
acccgtgcca ttctggatat gacgtcccag tttgattttt atcacggtgg cggtctggat    1080
gttttgttatt tgagttttgc tgaagtcgac cagcacggta acgtcggcgt gcataaattc    1140
aatggtaaaa tcatgggcac cggtggattt attgatatca gtgccacttc gaagaaaatc    1200
attttctgcg gcacattaac tgcgggcagt ttaaaaacag aaattaccga cggcaaatta    1260
aatatcgtcc aggaaggacg ggtgaagaaa tttattcggg aactaccgga aattactttc    1320
agcggaaaaa tcgctctcga gcgagggctg gatgttcgtt atatcactga gcgcgcagta    1380
ttcacgctga agaagacgg cctgcattta atcgaaatcg cccctggcgt cgatttacaa    1440
aaagatattc tcgacaaaat ggatttcacc ccagtgattt cgccagaact caaactgatg    1500
gacgaaagat tatttatcga tgcggcgatg ggttttgtcc tgcctgaagc ggctcattaa    1560
```

<210> SEQ ID NO 4
<211> LENGTH: 1566
<212> TYPE: DNA
<213> ORGANISM: Caenorhabditis elegans

<400> SEQUENCE: 4

```
atgccgattc tctcaaaaat atgggcggct ccagcagctg gaatcttgag aaaaactccg      60
agaaatgctc atcaaatgag gctaatctca atgacatcct cgatgaaagc aaaagtcttt     120
aactctgccg aagaagccgt gaaggatatt ccagataatg caaagctttt agttggcggc     180
ttcggactat gcggaatccc agaaaatctc atccaagcta tcacaaaaac tggtcaaaaa     240
ggtcttacat gtgtatcaaa caatgcggga gttgataatt ggggacttgg cttgctcctt     300
caaactcgac aaatcaagaa aatgatctca tcgtacgtcg gtgaaaacgg agaatttgct     360
```

```
cgacaatatc ttagcggaga gctcgagttg gaattcacac cacaaggaac actcgccgaa    420
cgaattcgtg cagctggtgc cggtgttccc gcattctaca caccaacagg atacggtacc    480
cagattcaag aaggaggtgc tccgattaag tacagtaaaa ctgaaaaagg aaagattgaa    540
gttgcaagta aagcgaaaga aacacgacaa ttcaatggaa ttaattatgt aatggaagag    600
gctatttggg gagattttgc attgatcaag gcgtggagag cagatactct tggaaatatt    660
caattcagac atgctgctgg aaatttcaat aatccaatgt gcaaagcctc taaatgcacc    720
atcgtcgaag tagaggaaat cgtcgaaccg ggagtaattg ctccaaacga tgtgcacatt    780
ccatcaatct attgtcatcg tctagttttg ggaaagaact acaaaaaacc aatcgaacgg    840
ccaatgttcg cacacgaagg accaataaaa ccatctacat cggctgctgg aaaatcgaga    900
gaaatcattg cagcacgtgc agctttggag ttcacagatg gaatgtacgc caatttgggt    960
atcgggattc cgactttggc gccaaattat ataccaaatg gatttactgt tcatttgcaa   1020
agtgagaatg gtattattgg agtgggacca tatccaagaa aaggaacaga agacgccgat   1080
ctcattaatg ctggaaaaga gccaattact cttctcaaag gagcttcaat tgttggttct   1140
gatgaatcat tcgcaatgat tcgtggttct catatggata ttactgtgct cggtgcactt   1200
cagtgctcac agtttggaga tttagcgaat tggatgattc cgggaaaatt ggtgaaagga   1260
atgggcggtg caatggatct tgtctctgct cccggagccc gtgtgatcgt tgtaatggag   1320
catgtatcga agaacggaga gccaaaaatt ctagagcact gcgaacttcc tctgaccggc   1380
aaaggagtaa tttcccgaat cattactgat atggcagttt tcgacgtgga cacaaagaac   1440
ggattgacat tgatcgaagt caggaaggat cttactgtag atgatatcaa gaaactcacc   1500
gcttgcaaat tcgaaatttc cgaaaatctg aagccaatgg acaggctccc tcttaatcaa   1560
ggataa                                                              1566

<210> SEQ ID NO 5
<211> LENGTH: 672
<212> TYPE: DNA
<213> ORGANISM: Haemophilus influenzae

<400> SEQUENCE: 5
atgaatgcaa agaattaat cgctcgccga attgcgatgg aattacatga tggagatatt     60
gttaatctcg gtattggttt accaacacag gttgttaatt atttacctga taatgtcaat    120
attacacttc aatcagaaaa tggctttctt ggtttaactg catttgaccc agaaaatgct    180
aattcaaact tagtaaatgc tggtggtcag ccttgtggaa ttaaaaaagg cggctctact    240
tttgatagtg ctttttcttt cgctttaatt cgtggcggtc atgttgatgc ctgtgtgcta    300
ggtggacttg aagttgatca agaagcaaat ctcgctaact ggatggtgcc tggcaaaatg    360
gtaccaggaa tgggcggagc aatggactta gtgactggtg caaaaaaagt gattattggc    420
atggaacatt gtgccaagtc aggttcctca aaaattctaa agaaatgtac attaccgctc    480
acagcaagta aaaagttgc catggtggtt accgaattgg cagtatttaa cttcattgaa    540
ggcagattag ttctaaaaga acatgctcct catgtgaatt tagaaacaat taagccaaa    600 acagaagccg atttcattgt tgccgatgat ttcaagaaaa tgcaaatcag ccagaaagga    660
cttgaattat ga                                                      672

<210> SEQ ID NO 6
<211> LENGTH: 519
<212> TYPE: PRT
<213> ORGANISM: Escherichia coli
```

<400> SEQUENCE: 6

```
Met Pro Val Leu Ser Ala Gln Glu Ala Val Asn Tyr Ile Pro Asp Glu
1               5                   10                  15

Ala Thr Leu Cys Val Leu Gly Ala Gly Gly Ile Leu Glu Ala Thr
            20                  25                  30

Thr Leu Ile Thr Ala Leu Ala Asp Lys Tyr Lys Gln Thr Gln Thr Pro
        35                  40                  45

Arg Asn Leu Ser Ile Ile Ser Pro Thr Gly Leu Gly Asp Arg Ala Asp
        50                  55                  60

Arg Gly Ile Ser Pro Leu Ala Gln Glu Gly Leu Val Lys Trp Ala Leu
65                  70                  75                  80

Cys Gly His Trp Gly Gln Ser Pro Arg Ile Ser Glu Leu Ala Glu Gln
                85                  90                  95

Asn Lys Ile Ile Ala Tyr Asn Tyr Pro Gln Gly Val Leu Thr Gln Thr
            100                 105                 110

Leu Arg Ala Ala Ala His Gln Pro Gly Ile Ile Ser Asp Ile Gly
        115                 120                 125

Ile Gly Thr Phe Val Asp Pro Arg Gln Gln Gly Lys Leu Asn Glu
130                 135                 140

Val Thr Lys Glu Asp Leu Ile Lys Leu Val Glu Phe Asp Asn Lys Glu
145                 150                 155                 160

Tyr Leu Tyr Tyr Lys Ala Ile Ala Pro Asp Ile Ala Phe Ile Arg Ala
                165                 170                 175

Thr Thr Cys Asp Ser Glu Gly Tyr Ala Thr Phe Glu Asp Glu Val Met
            180                 185                 190

Tyr Leu Asp Ala Leu Val Ile Ala Gln Ala Val His Asn Asn Gly Gly
        195                 200                 205

Ile Val Met Met Gln Val Gln Lys Met Val Lys Lys Ala Thr Leu His
210                 215                 220

Pro Lys Ser Val Arg Ile Pro Gly Tyr Leu Val Asp Ile Val Val Val
225                 230                 235                 240

Asp Pro Asp Gln Thr Gln Leu Tyr Gly Gly Ala Pro Val Asn Arg Phe
                245                 250                 255

Ile Ser Gly Asp Phe Thr Leu Asp Asp Ser Thr Lys Leu Ser Leu Pro
            260                 265                 270

Leu Asn Gln Arg Lys Leu Val Ala Arg Arg Ala Leu Phe Glu Met Arg
        275                 280                 285

Lys Gly Ala Val Gly Asn Val Gly Val Gly Ile Ala Asp Gly Ile Gly
290                 295                 300

Leu Val Ala Arg Glu Glu Gly Cys Ala Asp Asp Phe Ile Leu Thr Val
305                 310                 315                 320

Glu Thr Gly Pro Ile Gly Gly Ile Thr Ser Gln Gly Ile Ala Phe Gly
                325                 330                 335

Ala Asn Val Asn Thr Arg Ala Ile Leu Asp Met Thr Ser Gln Phe Asp
            340                 345                 350

Phe Tyr His Gly Gly Gly Leu Asp Val Cys Tyr Leu Ser Phe Ala Glu
        355                 360                 365

Val Asp Gln His Gly Asn Val Gly Val His Lys Phe Asn Gly Lys Ile
370                 375                 380

Met Gly Thr Gly Gly Phe Ile Asp Ile Ser Ala Thr Ser Lys Lys Ile
385                 390                 395                 400

Ile Phe Cys Gly Thr Leu Thr Ala Gly Ser Leu Lys Thr Glu Ile Thr
                405                 410                 415
```

```
Asp Gly Lys Leu Asn Ile Val Gln Glu Gly Arg Val Lys Lys Phe Ile
            420                 425                 430

Arg Glu Leu Pro Glu Ile Thr Phe Ser Gly Lys Ile Ala Leu Glu Arg
        435                 440                 445

Gly Leu Asp Val Arg Tyr Ile Thr Glu Arg Ala Val Phe Thr Leu Lys
    450                 455                 460

Glu Asp Gly Leu His Leu Ile Glu Ile Ala Pro Gly Val Asp Leu Gln
465                 470                 475                 480

Lys Asp Ile Leu Asp Lys Met Asp Phe Thr Pro Val Ile Ser Pro Glu
                485                 490                 495

Leu Lys Leu Met Asp Glu Arg Leu Phe Ile Asp Ala Ala Met Gly Phe
            500                 505                 510

Val Leu Pro Glu Ala Ala His
        515

<210> SEQ ID NO 7
<211> LENGTH: 521
<212> TYPE: PRT
<213> ORGANISM: Caenorhabditis elegans

<400> SEQUENCE: 7

Met Pro Ile Leu Ser Lys Ile Trp Ala Ala Pro Ala Ala Gly Ile Leu
1               5                   10                  15

Arg Lys Thr Pro Arg Asn Ala His Gln Met Arg Leu Ile Ser Met Thr
            20                  25                  30

Ser Ser Met Lys Ala Lys Val Phe Asn Ser Ala Glu Gly Ala Val Lys
        35                  40                  45

Asp Ile Pro Asp Asn Ala Lys Leu Leu Val Gly Gly Phe Gly Leu Cys
    50                  55                  60

Gly Ile Pro Glu Asn Leu Ile Gln Ala Ile Thr Lys Thr Gly Gln Lys
65                  70                  75                  80

Gly Leu Thr Cys Val Ser Asn Asn Ala Gly Val Asp Asn Trp Gly Leu
                85                  90                  95

Gly Leu Leu Leu Gln Thr Arg Gln Ile Lys Lys Met Ile Ser Ser Tyr
            100                 105                 110

Val Gly Glu Asn Gly Glu Phe Ala Arg Gln Tyr Leu Ser Gly Glu Leu
        115                 120                 125

Glu Leu Glu Phe Thr Pro Gln Gly Thr Leu Ala Glu Arg Ile Arg Ala
    130                 135                 140

Ala Gly Ala Gly Val Pro Ala Phe Tyr Thr Pro Thr Gly Tyr Gly Thr
145                 150                 155                 160

Gln Ile Gln Glu Gly Gly Ala Pro Ile Lys Tyr Ser Lys Thr Glu Lys
                165                 170                 175

Gly Lys Ile Glu Val Ala Ser Lys Ala Lys Glu Thr Arg Gln Phe Asn
            180                 185                 190

Gly Ile Asn Tyr Val Met Glu Glu Ala Ile Trp Gly Asp Phe Ala Leu
        195                 200                 205

Ile Lys Ala Trp Arg Ala Asp Thr Leu Gly Asn Ile Gln Phe Arg His
    210                 215                 220

Ala Ala Gly Asn Phe Asn Asn Pro Met Cys Lys Ala Ser Lys Cys Thr
225                 230                 235                 240

Ile Val Glu Val Glu Glu Ile Val Glu Pro Gly Val Ile Ala Pro Asn
                245                 250                 255

Asp Val His Ile Pro Ser Ile Tyr Cys His Arg Leu Val Leu Gly Lys
            260                 265                 270
```

Asn Tyr Lys Lys Pro Ile Glu Arg Pro Met Phe Ala His Glu Gly Pro
            275                 280                 285

Ile Lys Pro Ser Thr Ser Ala Gly Lys Ser Arg Glu Ile Ile Ala
    290                 295                 300

Ala Arg Ala Ala Leu Glu Phe Thr Asp Gly Met Tyr Ala Asn Leu Gly
305                 310                 315                 320

Ile Gly Ile Pro Thr Leu Ala Pro Asn Tyr Ile Pro Asn Gly Phe Thr
                325                 330                 335

Val His Leu Gln Ser Glu Asn Gly Ile Ile Gly Val Gly Pro Tyr Pro
            340                 345                 350

Arg Lys Gly Thr Glu Asp Ala Asp Leu Ile Asn Ala Gly Lys Glu Pro
        355                 360                 365

Ile Thr Leu Leu Lys Gly Ala Ser Ile Val Gly Ser Asp Glu Ser Phe
    370                 375                 380

Ala Met Ile Arg Gly Ser His Met Asp Ile Thr Val Leu Gly Ala Leu
385                 390                 395                 400

Gln Cys Ser Gln Phe Gly Asp Leu Ala Asn Trp Met Ile Pro Gly Lys
                405                 410                 415

Leu Val Lys Gly Met Gly Gly Ala Met Asp Leu Val Ser Ala Pro Gly
            420                 425                 430

Ala Arg Val Ile Val Met Glu His Val Ser Lys Asn Gly Glu Pro
        435                 440                 445

Lys Ile Leu Glu His Cys Glu Leu Pro Leu Thr Gly Lys Gly Val Ile
    450                 455                 460

Ser Arg Ile Ile Thr Asp Met Ala Val Phe Asp Val Asp Thr Lys Asn
465                 470                 475                 480

Gly Leu Thr Leu Ile Glu Val Arg Lys Asp Leu Thr Val Asp Asp Ile
                485                 490                 495

Lys Lys Leu Thr Ala Cys Lys Phe Glu Ile Ser Glu Asn Leu Lys Pro
            500                 505                 510

Met Gly Gln Ala Pro Leu Asn Gln Gly
        515                 520

<210> SEQ ID NO 8
<211> LENGTH: 223
<212> TYPE: PRT
<213> ORGANISM: Haemophilus influenzae

<400> SEQUENCE: 8

Met Asn Ala Lys Glu Leu Ile Ala Arg Arg Ile Ala Met Glu Leu His
1               5                   10                  15

Asp Gly Asp Ile Val Asn Leu Gly Ile Gly Leu Pro Thr Gln Val Val
                20                  25                  30

Asn Tyr Leu Pro Asp Asn Val Asn Ile Thr Leu Gln Ser Glu Asn Gly
            35                  40                  45

Phe Leu Gly Leu Thr Ala Phe Asp Pro Glu Asn Ala Asn Ser Asn Leu
        50                  55                  60

Val Asn Ala Gly Gly Gln Pro Cys Gly Ile Lys Lys Gly Gly Ser Thr
65                  70                  75                  80

Phe Asp Ser Ala Phe Ser Phe Ala Leu Ile Arg Gly Gly His Val Asp
                85                  90                  95

Ala Cys Val Leu Gly Gly Leu Glu Val Asp Gln Glu Ala Asn Leu Ala
            100                 105                 110

Asn Trp Met Val Pro Gly Lys Met Val Pro Gly Met Gly Gly Ala Met
        115                 120                 125

```
Asp Leu Val Thr Gly Ala Lys Lys Val Ile Ile Gly Met Glu His Cys
    130                 135                 140

Ala Lys Ser Gly Ser Ser Lys Ile Leu Lys Lys Cys Thr Leu Pro Leu
145                 150                 155                 160

Thr Ala Ser Lys Lys Val Ala Met Val Val Thr Glu Leu Ala Val Phe
                165                 170                 175

Asn Phe Ile Glu Gly Arg Leu Val Leu Lys Glu His Ala Pro His Val
            180                 185                 190

Asp Leu Glu Thr Ile Lys Ala Lys Thr Glu Ala Asp Phe Ile Val Ala
        195                 200                 205

Asp Asp Phe Lys Glu Met Gln Ile Ser Gln Lys Gly Leu Glu Leu
    210                 215                 220

<210> SEQ ID NO 9
<211> LENGTH: 786
<212> TYPE: DNA
<213> ORGANISM: Megasphaera elsdenii
<220> FEATURE:
<221> NAME/KEY: CDS
<222> LOCATION: (1)..(783)

<400> SEQUENCE: 9 gtg aaa act gtg tat act ctc gga atc gac gtt ggt tct tct tct tcc    48
Val Lys Thr Val Tyr Thr Leu Gly Ile Asp Val Gly Ser Ser Ser Ser
1               5                   10                  15 aag gca gtc atc ctg gaa gat ggc aag aag atc gtc gcc cat gcc gtc    96
Lys Ala Val Ile Leu Glu Asp Gly Lys Lys Ile Val Ala His Ala Val
                20                  25                  30 gtt gaa atc ggc acc ggt tcg acc ggt ccg gaa cgc gtc ctg gac gaa   144
Val Glu Ile Gly Thr Gly Ser Thr Gly Pro Glu Arg Val Leu Asp Glu
            35                  40                  45 gtc ttc aaa gat acc aac tta aaa att gaa gac atg gcg aac atc atc   192
Val Phe Lys Asp Thr Asn Leu Lys Ile Glu Asp Met Ala Asn Ile Ile
        50                  55                  60 gcc aca ggc tat ggc cgt ttc aat gtc gac tgc gcc aaa ggc gaa gtc   240
Ala Thr Gly Tyr Gly Arg Phe Asn Val Asp Cys Ala Lys Gly Glu Val
65                  70                  75                  80 agc gaa atc acg tgc cat gcc aaa ggg gcc ctc ttt gaa tgc ccc ggt   288
Ser Glu Ile Thr Cys His Ala Lys Gly Ala Leu Phe Glu Cys Pro Gly
                85                  90                  95 acg acg acc atc ctc gat atc ggc ggt cag gac gtc aag tcc atc aaa   336
Thr Thr Thr Ile Leu Asp Ile Gly Gly Gln Asp Val Lys Ser Ile Lys
                100                 105                 110 ttg aat ggc cag ggc ctg gtc atg cag ttt gcc atg aac gac aaa tgc   384
Leu Asn Gly Gln Gly Leu Val Met Gln Phe Ala Met Asn Asp Lys Cys
            115                 120                 125 gcc gct ggt acg ggc cgt ttc ctc gac gtc atg tcg aag gta ctg gaa   432
Ala Ala Gly Thr Gly Arg Phe Leu Asp Val Met Ser Lys Val Leu Glu
        130                 135                 140 atc ccc atg tct gaa atg ggg gac tgg tac ttc aaa tcg aag cat ccc   480
Ile Pro Met Ser Glu Met Gly Asp Trp Tyr Phe Lys Ser Lys His Pro
145                 150                 155                 160 gct gcc gtc agc agt acc tgc acg gtt ttt gct gaa tcg gaa gtc att   528
Ala Ala Val Ser Ser Thr Cys Thr Val Phe Ala Glu Ser Glu Val Ile
                165                 170                 175 tcc ctt ctt tcc aag aat gtc ccg aaa gaa gat atc gta gcc ggt gtc   576
Ser Leu Leu Ser Lys Asn Val Pro Lys Glu Asp Ile Val Ala Gly Val
                180                 185                 190 cat cag tcc atc gcc gcc aaa gcc tgc gct ctc gtg cgc cgc gtc ggt   624
His Gln Ser Ile Ala Ala Lys Ala Cys Ala Leu Val Arg Arg Val Gly
        195                 200                 205
```

```
              195                 200                 205
gtc ggt gaa gac ctg acc atg acc ggc ggt ggc tcc cgc gat ccc ggc      672
Val Gly Glu Asp Leu Thr Met Thr Gly Gly Gly Ser Arg Asp Pro Gly
    210                 215                 220 gtc gtc gat gcc gta tcg aaa gaa tta ggt att cct gtc aga gtc gct      720
Val Val Asp Ala Val Ser Lys Glu Leu Gly Ile Pro Val Arg Val Ala
225                 230                 235                 240 ctg cat ccc caa gcg gtg ggt gct ctc gga gct gct ttg att gct tat      768
Leu His Pro Gln Ala Val Gly Ala Leu Gly Ala Ala Leu Ile Ala Tyr
                245                 250                 255 gat aaa atc aag aaa taa                                              786
Asp Lys Ile Lys Lys
            260

<210> SEQ ID NO 10
<211> LENGTH: 261
<212> TYPE: PRT
<213> ORGANISM: Megasphaera elsdenii

<400> SEQUENCE: 10

Val Lys Thr Val Tyr Thr Leu Gly Ile Asp Val Gly Ser Ser Ser
1               5                   10                  15

Lys Ala Val Ile Leu Glu Asp Gly Lys Lys Ile Val Ala His Ala Val
                20                  25                  30

Val Glu Ile Gly Thr Gly Ser Thr Gly Pro Glu Arg Val Leu Asp Glu
            35                  40                  45

Val Phe Lys Asp Thr Asn Leu Lys Ile Glu Asp Met Ala Asn Ile Ile
        50                  55                  60

Ala Thr Gly Tyr Gly Arg Phe Asn Val Asp Cys Ala Lys Gly Glu Val
65                  70                  75                  80

Ser Glu Ile Thr Cys His Ala Lys Gly Ala Leu Phe Glu Cys Pro Gly
                85                  90                  95

Thr Thr Thr Ile Leu Asp Ile Gly Gly Gln Asp Val Lys Ser Ile Lys
            100                 105                 110

Leu Asn Gly Gln Gly Leu Val Met Gln Phe Ala Met Asn Asp Lys Cys
        115                 120                 125

Ala Ala Gly Thr Gly Arg Phe Leu Asp Val Met Ser Lys Val Leu Glu
130                 135                 140

Ile Pro Met Ser Glu Met Gly Asp Trp Tyr Phe Lys Ser Lys His Pro
145                 150                 155                 160

Ala Ala Val Ser Ser Thr Cys Thr Val Phe Ala Glu Ser Glu Val Ile
                165                 170                 175

Ser Leu Leu Ser Lys Asn Val Pro Lys Glu Asp Ile Val Ala Gly Val
            180                 185                 190

His Gln Ser Ile Ala Ala Lys Ala Cys Ala Leu Val Arg Arg Val Gly
        195                 200                 205

Val Gly Glu Asp Leu Thr Met Thr Gly Gly Gly Ser Arg Asp Pro Gly
210                 215                 220

Val Val Asp Ala Val Ser Lys Glu Leu Gly Ile Pro Val Arg Val Ala
225                 230                 235                 240

Leu His Pro Gln Ala Val Gly Ala Leu Gly Ala Ala Leu Ile Ala Tyr
                245                 250                 255

Asp Lys Ile Lys Lys
            260

<210> SEQ ID NO 11
<211> LENGTH: 783
```

```
<212> TYPE: DNA
<213> ORGANISM: Acidaminococcus fermentans

<400> SEQUENCE: 11
atgagtatct ataccttggg aatcgatgtt ggatctactg catccaagtg cattatcctg      60
aaagatggaa aagaaatcgt ggcgaaatcc ctggtagccg tggggaccgg aacttccggt     120
cccgcacggt ctatttcgga agtcctggaa aatgcccaca tgaaaaaaga agacatggcc     180
tttaccctgg ctaccggcta cggacgcaat tcgctggaag gcattgccga caagcagatg     240
agcgaactga gctgccatgc catgggcgcc agctttatct ggcccaacgt ccataccgtc     300
atcgatatcg gcgggcagga tgtgaaggtc atccatgtgg aaaacgggac catgaccaat     360
ttccagatga atgataaatg cgctgccggg actggccgtt cctggatgt tatgccaat      420
atcctggaag tgaaggtttc cgacctggct gagctgggag ccaaatccac caaacgggtg     480
gctatcagct ccacctgtac tgtgtttgca gaaagtgaag tcatcagcca gctgtccaaa     540
ggaaccgaca agatcgacat cattgccggg atccatcgtt ctgtagccag ccgggtcatt     600
ggtcttgcca atcgggtggg gattgtgaaa gacgtggtca tgaccggcgg tgtagcccag     660
aactatggcg tgagaggagc cctggaagaa ggccttggcg tggaaatcaa gacgtctccc     720
ctggctcagt acaacggtgc cctgggtgcc gctctgtatg cgtataaaaa agcagccaaa     780
taa                                                                   783

<210> SEQ ID NO 12
<211> LENGTH: 774
<212> TYPE: DNA
<213> ORGANISM: Escherichia coli

<400> SEQUENCE: 12
gtggcagtgg catattcgat tggcattgat tccggctcaa ccgccaccaa agggatctta      60
ctggcagacg gcgtgattac gcgccgtttc ctcgttccaa ccccctttcg cccggcaaca     120
gcaattactg aagcctggga aactctgcgc gaagggttag agacaacgcc gtttctgacg     180
ctcaccggct acgggcggca actggtggat tttgccgata acaggtaac ggaaatctcc      240
tgtcacgggc tgggcgcacg gtttcttgcg ccagcaacgc gcgcggtaat cgacatcggt     300
ggtcaggaca gcaaagtgat tcagcttgat gatgacggta acctgtgcga tttcctgatg     360
aatgacaaat gcgcggcggg caccgggcgt ttcctggagg tgatctcgcg cacgcttggc     420
accagcgtcg agcaactcga cagcattacc gaaaatgtca cgccgcacgc catcacgagt     480
atgtgcacag tgtttgctga atcagaagcg atcagcctgc gctcagcggg cgtcgcgcca     540
gaagcgattc tcgcaggagt gattaacgcg atggcgcgga ggagtgccaa tttcattgct     600
cgtctctcct gtgaagcgcc gattctgttt actggtggcg ttagtcattg ccagaagttt     660
gcccggatgc tggaatctca cctgcgaatg ccggtaaata cccatcctga tgcgcaattt     720
gctggcgcaa ttggcgcggc ggtaattggt caacgagtga ggacacgccg atga          774

<210> SEQ ID NO 13
<211> LENGTH: 732
<212> TYPE: DNA
<213> ORGANISM: Methanocaldococcus jannaschii

<400> SEQUENCE: 13
atgattttag ggatagatgt tggatctaca acaacgaaga tggttctaat ggaagatagc      60
aagataattt ggtataagat agaggatatt ggagttgtta tgagaagaa tattttatta      120
aaaatggtta aggagattga acaaaaatat ccaatagata aaatcgttgc aactggatat     180
```

```
ggaaggcata aggttagttt tgcagataag atagttccag aagttattgc attgggaaaa      240
ggagctaact atttctttaa cgaggcagat ggagttatag acattggagg gcaagataca      300
aaggtcttaa agattgataa aaacggaaaa gttgttgatt ttatcctatc agataaatgt      360
gccgctggaa ctggaaaatt cttagaaaag gcattagata ttttaaaaat tgataaaaat      420
gagataaata aatacaaatc agataatatc gctaaaatat cttcaatgtg tgctgtcttt      480
gctgaaagtg agataataag cttactatca aaaaagttc caaggaagg cattttaatg       540 ggcgtctatg agagtataat aaatagggtt atcccaatga ccaataggct taaaattcaa      600
aacatagtgt ttagtggagg agttgctaaa ataaggtttt ggttgagat gtttgagaaa       660 aaattgaata aaaaactact aattccaaaa gaaccacaga ttgtttgctg tgttggagct      720
atattggttt aa                                                          732

<210> SEQ ID NO 14
<211> LENGTH: 260
<212> TYPE: PRT
<213> ORGANISM: Acidaminococcus fermentans

<400> SEQUENCE: 14

Met Ser Ile Tyr Thr Leu Gly Ile Asp Val Gly Ser Thr Ala Ser Lys
1               5                   10                  15

Cys Ile Ile Leu Lys Asp Gly Lys Glu Ile Val Ala Lys Ser Leu Val
            20                  25                  30

Ala Val Gly Thr Gly Thr Ser Gly Pro Ala Arg Ser Ile Ser Glu Val
        35                  40                  45

Leu Glu Asn Ala His Met Lys Lys Glu Asp Met Ala Phe Thr Leu Ala
    50                  55                  60

Thr Gly Tyr Gly Arg Asn Ser Leu Glu Gly Ile Ala Asp Lys Gln Met
65                  70                  75                  80

Ser Glu Leu Ser Cys His Ala Met Gly Ala Ser Phe Ile Trp Pro Asn
                85                  90                  95

Val His Thr Val Ile Asp Ile Gly Gly Gln Asp Val Lys Val Ile His
            100                 105                 110

Val Glu Asn Gly Thr Met Thr Asn Phe Gln Met Asn Asp Lys Cys Ala
        115                 120                 125

Ala Gly Thr Gly Arg Phe Leu Asp Val Met Ala Asn Ile Leu Glu Val
    130                 135                 140

Lys Val Ser Asp Leu Ala Glu Leu Gly Ala Lys Ser Thr Lys Arg Val
145                 150                 155                 160

Ala Ile Ser Ser Thr Cys Thr Val Phe Ala Glu Ser Glu Val Ile Ser
                165                 170                 175

Gln Leu Ser Lys Gly Thr Asp Lys Ile Asp Ile Ile Ala Gly Ile His
            180                 185                 190

Arg Ser Val Ala Ser Arg Val Ile Gly Leu Ala Asn Arg Val Gly Ile
        195                 200                 205

Val Lys Asp Val Val Met Thr Gly Gly Val Ala Gln Asn Tyr Gly Val
    210                 215                 220

Arg Gly Ala Leu Glu Glu Gly Leu Gly Val Glu Ile Lys Thr Ser Pro
225                 230                 235                 240

Leu Ala Gln Tyr Asn Gly Ala Leu Gly Ala Leu Tyr Ala Tyr Lys
                245                 250                 255

Lys Ala Ala Lys
            260
```

<210> SEQ ID NO 15
<211> LENGTH: 257
<212> TYPE: PRT
<213> ORGANISM: Escherichia coli

<400> SEQUENCE: 15

Met Ala Val Ala Tyr Ser Ile Gly Ile Asp Ser Gly Ser Thr Ala Thr
1               5                   10                  15

Lys Gly Ile Leu Leu Ala Asp Gly Val Ile Thr Arg Arg Phe Leu Val
            20                  25                  30

Pro Thr Pro Phe Arg Pro Ala Thr Ala Ile Thr Glu Ala Trp Glu Thr
        35                  40                  45

Leu Arg Glu Gly Leu Glu Thr Thr Pro Phe Leu Thr Leu Thr Gly Tyr
    50                  55                  60

Gly Arg Gln Leu Val Asp Phe Ala Asp Lys Gln Val Thr Glu Ile Ser
65                  70                  75                  80

Cys His Gly Leu Gly Ala Arg Phe Leu Ala Pro Ala Thr Arg Ala Val
                85                  90                  95

Ile Asp Ile Gly Gly Gln Asp Ser Lys Val Ile Gln Leu Asp Asp Asp
            100                 105                 110

Gly Asn Leu Cys Asp Phe Leu Met Asn Asp Lys Cys Ala Ala Gly Thr
        115                 120                 125

Gly Arg Phe Leu Glu Val Ile Ser Arg Thr Leu Gly Thr Ser Val Glu
    130                 135                 140

Gln Leu Asp Ser Ile Thr Glu Asn Val Thr Pro His Ala Ile Thr Ser
145                 150                 155                 160

Met Cys Thr Val Phe Ala Glu Ser Glu Ala Ile Ser Leu Arg Ser Ala
                165                 170                 175

Gly Val Ala Pro Glu Ala Ile Leu Ala Gly Val Ile Asn Ala Met Ala
            180                 185                 190

Arg Arg Ser Ala Asn Phe Ile Ala Arg Leu Ser Cys Gly Ala Pro Ile
        195                 200                 205

Leu Phe Thr Gly Gly Val Ser His Cys Gln Lys Phe Ala Arg Met Leu
    210                 215                 220

Glu Ser His Leu Arg Met Pro Val Asn Thr His Pro Asp Ala Gln Phe
225                 230                 235                 240

Ala Gly Ala Ile Gly Ala Ala Val Ile Gly Gln Arg Val Arg Thr Arg
                245                 250                 255

Arg

<210> SEQ ID NO 16
<211> LENGTH: 243
<212> TYPE: PRT
<213> ORGANISM: Methanocaldococcus jannaschii

<400> SEQUENCE: 16

Met Ile Leu Gly Ile Asp Val Gly Ser Thr Thr Thr Lys Met Val Leu
1               5                   10                  15

Met Glu Asp Ser Lys Ile Ile Trp Tyr Lys Glu Asp Ile Gly Val
            20                  25                  30

Val Ile Glu Glu Asp Ile Leu Leu Lys Met Val Lys Glu Ile Glu Gln
        35                  40                  45

Lys Tyr Pro Ile Asp Lys Ile Val Ala Thr Gly Tyr Gly Arg His Lys
    50                  55                  60

Val Ser Phe Ala Asp Lys Ile Val Pro Glu Val Ile Ala Leu Gly Lys
65                  70                  75                  80

```
Gly Ala Asn Tyr Phe Phe Asn Glu Ala Asp Gly Val Ile Asp Ile Gly
                85                  90                  95

Gly Gln Asp Thr Lys Val Leu Lys Ile Asp Lys Asn Gly Lys Val Val
            100                 105                 110

Asp Phe Ile Leu Ser Asp Lys Cys Ala Ala Gly Thr Gly Lys Phe Leu
            115                 120                 125

Glu Lys Ala Leu Asp Ile Leu Lys Ile Asp Lys Asn Glu Ile Asn Lys
130                 135                 140

Tyr Lys Ser Asp Asn Ile Ala Lys Ile Ser Ser Met Cys Ala Val Phe
145                 150                 155                 160

Ala Glu Ser Glu Ile Ile Ser Leu Leu Ser Lys Lys Val Pro Lys Glu
                165                 170                 175

Gly Ile Leu Met Gly Val Tyr Glu Ser Ile Ile Asn Arg Val Ile Pro
            180                 185                 190

Met Thr Asn Arg Leu Lys Ile Gln Asn Ile Val Phe Ser Gly Gly Val
            195                 200                 205

Ala Lys Asn Lys Val Leu Val Glu Met Phe Glu Lys Lys Leu Asn Lys
            210                 215                 220

Lys Leu Leu Ile Pro Lys Glu Pro Gln Ile Val Cys Cys Val Gly Ala
225                 230                 235                 240

Ile Leu Val

<210> SEQ ID NO 17
<211> LENGTH: 1287
<212> TYPE: DNA
<213> ORGANISM: Megasphaera elsdenii
<220> FEATURE:
<221> NAME/KEY: CDS
<222> LOCATION: (1)..(1284)

<400> SEQUENCE: 17 atg agt gaa gaa aaa aca gta gat att gaa agc atg agc tcc aag gaa      48
Met Ser Glu Glu Lys Thr Val Asp Ile Glu Ser Met Ser Ser Lys Glu
1               5                   10                  15 gcc ctt ggt tac ttc ttg ccg aaa gtc gat gaa gac gca cgt aaa gcg      96
Ala Leu Gly Tyr Phe Leu Pro Lys Val Asp Glu Asp Ala Arg Lys Ala
            20                  25                  30 aaa aaa gaa ggc cgc ctc gtt tgc tgg tcc gct tct gtc gct cct ccg     144
Lys Lys Glu Gly Arg Leu Val Cys Trp Ser Ala Ser Val Ala Pro Pro
        35                  40                  45 gaa ttc tgc acg gct atg gac atc gcc atc gtc tat ccg gaa act cac     192
Glu Phe Cys Thr Ala Met Asp Ile Ala Ile Val Tyr Pro Glu Thr His
50                  55                  60 gca gct ggt atc ggt gcc cgt cac ggt gct ccg gcc atg ctc gaa gtt     240
Ala Ala Gly Ile Gly Ala Arg His Gly Ala Pro Ala Met Leu Glu Val
65                  70                  75                  80 gct gaa aac aaa ggt tac aac cag gac atc tgt tcc tac tgc cgc gtc     288
Ala Glu Asn Lys Gly Tyr Asn Gln Asp Ile Cys Ser Tyr Cys Arg Val
            85                  90                  95 aac atg ggc tac atg gaa ctc ctc aaa cag cag gct ctg aca ggc gaa     336
Asn Met Gly Tyr Met Glu Leu Leu Lys Gln Gln Ala Leu Thr Gly Glu
            100                 105                 110 acg ccg gaa gtc ctc aaa aac tcc ccg gct tct ccg att ccc ctt ccg     384
Thr Pro Glu Val Leu Lys Asn Ser Pro Ala Ser Pro Ile Pro Leu Pro
        115                 120                 125 gat gtt gtc ctc act tgc aac aac atc tgc aat acc ttg ctc aaa tgg     432
Asp Val Val Leu Thr Cys Asn Asn Ile Cys Asn Thr Leu Leu Lys Trp
130                 135                 140
```

```
tat gaa aac ttg gct aaa gaa ttg aac gta cct ctc atc aac atc gac      480
Tyr Glu Asn Leu Ala Lys Glu Leu Asn Val Pro Leu Ile Asn Ile Asp
145                 150                 155                 160 gta ccg ttc aac cat gaa ttc cct gtt acg aaa cac gct aaa cag tac      528
Val Pro Phe Asn His Glu Phe Pro Val Thr Lys His Ala Lys Gln Tyr
                165                 170                 175 atc gtc ggc gaa ttc aaa cat gct atc aaa cag ctc gaa gac ctt tgc      576
Ile Val Gly Glu Phe Lys His Ala Ile Lys Gln Leu Glu Asp Leu Cys
            180                 185                 190 ggc cgt ccc ttc gac tat gac aaa ttc ttc gaa gta cag aaa cag aca      624
Gly Arg Pro Phe Asp Tyr Asp Lys Phe Phe Glu Val Gln Lys Gln Thr
        195                 200                 205 cag cgc tcc atc gct gcc tgg aac aaa atc gct acg tac ttc cag tac      672
Gln Arg Ser Ile Ala Ala Trp Asn Lys Ile Ala Thr Tyr Phe Gln Tyr
    210                 215                 220 aaa ccg tcg ccg ctc aac ggc ttc gac ctc ttc aac tac atg ggc ctc      720
Lys Pro Ser Pro Leu Asn Gly Phe Asp Leu Phe Asn Tyr Met Gly Leu
225                 230                 235                 240 gcc gtt gct gcc cgc tcc ttg aac tac tcg gaa atc acg ttc aac aaa      768
Ala Val Ala Ala Arg Ser Leu Asn Tyr Ser Glu Ile Thr Phe Asn Lys
                245                 250                 255 ttc ctc aaa gaa ttg gac gaa aaa gta gct aat aag aaa tgg gct ttc      816
Phe Leu Lys Glu Leu Asp Glu Lys Val Ala Asn Lys Lys Trp Ala Phe
            260                 265                 270 ggt gaa aac gaa aaa tcc cgt gtt act tgg gaa ggt atc gct gtc tgg      864
Gly Glu Asn Glu Lys Ser Arg Val Thr Trp Glu Gly Ile Ala Val Trp
        275                 280                 285 atc gct ctc ggc cac acc ttc aaa gaa ctc aaa ggt cag ggc gct ctc      912
Ile Ala Leu Gly His Thr Phe Lys Glu Leu Lys Gly Gln Gly Ala Leu
    290                 295                 300 atg act ggt tcc gct tat cct ggc atg tgg gac gtt tcc tac gaa ccg      960
Met Thr Gly Ser Ala Tyr Pro Gly Met Trp Asp Val Ser Tyr Glu Pro
305                 310                 315                 320 ggc gac ctc gaa tcc atg gca gaa gct tat tcc cgt aca tac atc aac     1008
Gly Asp Leu Glu Ser Met Ala Glu Ala Tyr Ser Arg Thr Tyr Ile Asn
                325                 330                 335 tgc tgc ctc gaa cag cgc ggt gct gtt ctt gaa aaa gtt gtc cgc gat     1056
Cys Cys Leu Glu Gln Arg Gly Ala Val Leu Glu Lys Val Val Arg Asp
            340                 345                 350 ggc aaa tgc gac ggc ttg atc atg cac cag aac cgt tcc tgc aag aac     1104
Gly Lys Cys Asp Gly Leu Ile Met His Gln Asn Arg Ser Cys Lys Asn
        355                 360                 365 atg agc ctc ctc aac aac gaa ggc ggc cag cgc atc cag aag aac ctc     1152
Met Ser Leu Leu Asn Asn Glu Gly Gly Gln Arg Ile Gln Lys Asn Leu
    370                 375                 380 ggc gta ccg tac gtc atc ttc gac ggc gac cag acc gat gct cgt aac     1200
Gly Val Pro Tyr Val Ile Phe Asp Gly Asp Gln Thr Asp Ala Arg Asn
385                 390                 395                 400 ttc tcg gaa gca cag ttc gat acc cgc gta gaa gct ttg gca gaa atg     1248
Phe Ser Glu Ala Gln Phe Asp Thr Arg Val Glu Ala Leu Ala Glu Met
                405                 410                 415 atg gca gac aaa aaa gcc aat gaa gga gga aac cac taa                 1287
Met Ala Asp Lys Lys Ala Asn Glu Gly Gly Asn His
            420                 425

<210> SEQ ID NO 18
<211> LENGTH: 428
<212> TYPE: PRT
<213> ORGANISM: Megasphaera elsdenii

<400> SEQUENCE: 18
```

```
Met Ser Glu Glu Lys Thr Val Asp Ile Glu Ser Met Ser Lys Glu
1               5                   10                  15

Ala Leu Gly Tyr Phe Leu Pro Lys Val Asp Glu Asp Ala Arg Lys Ala
                20                  25                  30

Lys Lys Glu Gly Arg Leu Val Cys Trp Ser Ala Ser Val Ala Pro Pro
            35                  40                  45

Glu Phe Cys Thr Ala Met Asp Ile Ala Ile Val Tyr Pro Glu Thr His
    50                  55                  60

Ala Ala Gly Ile Gly Ala Arg His Gly Ala Pro Ala Met Leu Glu Val
65                  70                  75                  80

Ala Glu Asn Lys Gly Tyr Asn Gln Asp Ile Cys Ser Tyr Cys Arg Val
                85                  90                  95

Asn Met Gly Tyr Met Glu Leu Leu Lys Gln Gln Ala Leu Thr Gly Glu
                100                 105                 110

Thr Pro Glu Val Leu Lys Asn Ser Pro Ala Ser Pro Ile Pro Leu Pro
            115                 120                 125

Asp Val Val Leu Thr Cys Asn Asn Ile Cys Asn Thr Leu Leu Lys Trp
    130                 135                 140

Tyr Glu Asn Leu Ala Lys Glu Leu Asn Val Pro Leu Ile Asn Ile Asp
145                 150                 155                 160

Val Pro Phe Asn His Glu Phe Pro Val Thr Lys His Ala Lys Gln Tyr
                165                 170                 175

Ile Val Gly Glu Phe Lys His Ala Ile Lys Gln Leu Glu Asp Leu Cys
                180                 185                 190

Gly Arg Pro Phe Asp Tyr Asp Lys Phe Glu Val Gln Lys Gln Thr
            195                 200                 205

Gln Arg Ser Ile Ala Ala Trp Asn Lys Ile Ala Thr Tyr Phe Gln Tyr
    210                 215                 220

Lys Pro Ser Pro Leu Asn Gly Phe Asp Leu Phe Asn Tyr Met Gly Leu
225                 230                 235                 240

Ala Val Ala Ala Arg Ser Leu Asn Tyr Ser Glu Ile Thr Phe Asn Lys
                245                 250                 255

Phe Leu Lys Glu Leu Asp Glu Lys Val Ala Asn Lys Lys Trp Ala Phe
            260                 265                 270

Gly Glu Asn Glu Lys Ser Arg Val Thr Trp Glu Gly Ile Ala Val Trp
            275                 280                 285

Ile Ala Leu Gly His Thr Phe Lys Glu Leu Lys Gly Gln Gly Ala Leu
        290                 295                 300

Met Thr Gly Ser Ala Tyr Pro Gly Met Trp Asp Val Ser Tyr Glu Pro
305                 310                 315                 320

Gly Asp Leu Glu Ser Met Ala Glu Ala Tyr Ser Arg Thr Tyr Ile Asn
            325                 330                 335

Cys Cys Leu Glu Gln Arg Gly Ala Val Leu Glu Lys Val Val Arg Asp
            340                 345                 350

Gly Lys Cys Asp Gly Leu Ile Met His Gln Asn Arg Ser Cys Lys Asn
            355                 360                 365

Met Ser Leu Leu Asn Asn Glu Gly Gly Gln Arg Ile Gln Lys Asn Leu
    370                 375                 380

Gly Val Pro Tyr Val Ile Phe Asp Gly Asp Gln Thr Asp Ala Arg Asn
385                 390                 395                 400

Phe Ser Glu Ala Gln Phe Asp Thr Arg Val Glu Ala Leu Ala Glu Met
            405                 410                 415

Met Ala Asp Lys Lys Ala Asn Glu Gly Gly Asn His
            420                 425
```

<210> SEQ ID NO 19
<211> LENGTH: 1434
<212> TYPE: DNA
<213> ORGANISM: Acidaminococcus fermentans

<400> SEQUENCE: 19

```
atgccaaaga cagtaagccc tggcgttcag gcattgagag atgtagttga aaaggtttac    60
agagaactgc gggaaccgaa agaaagagga gaaaaagtag gctggtcctc ttccaagttc   120
ccctgcgaac tggctgaatc ttttcggctg catgttgggt atccggaaaa ccaggctgct   180
ggtatcgctg ccaaccgtga cggcgaagtg atgtgccagg ctgcagaaga tatcggttat   240
gacaacgata tctgcggcta tgcccgtatt tccctggctt atgctgccgg gttccggggt   300
gccaacaaaa tggacaaaga tggcaactat gtcatcaacc cccacagcgg caaacagatg   360
aaagatgcca atggcaaaaa ggtattcgac gcagatggca aacccgtaat cgatcccaag   420
accctgaaac cctttgccac caccgacaac atctatgaaa tcgctgctct gccggaaggg   480
gaagaaaaga cccgccgcca gaatgccctg cacaaatatc gtcagatgac catgcccatg   540
ccggacttcg tgctgtgctg caacaacatc tgcaactgca tgaccaaatg gtatgaagac   600
attgcccgtc ggcacaacat tcctttgatc atgatcgacg ttccttacaa cgaattcgac   660
catgtcaacg aagccaacgt gaaatacatc cggtcccagc tggatacggc catccgtcaa   720
atggaagaaa tcaccggcaa gaagttcgat gaagacaaat tcgaacagtg ctgccagaac   780
gccaaccgta ctgccaaagc atggctgaag gtttgcgact acctgcagta caaaccggct   840
ccgttcaacg ggttcgacct gttcaaccat atggctgacg tggttaccgc ccgtggccgt   900
gtggaagctg ctgaagcttt cgaactgctg gccaaggaac tggaacagca tgtgaaggaa   960
ggcaccacca ccgctccctt caaagaacag catcgtatca tgttcgaagg gatcccctgc  1020
tggccgaaac tgccgaacct gttcaaaccg ctgaaagcca acggcctgaa catcaccggc  1080
gttgtatatg ctcctgcttt cgggttcgtg tacaacaacc tggacgaatt ggtcaaagcc  1140
tactgcaaag ccccgaactc cgtcagcatc gaacagggtg ttgcctggcg tgaaggcctg  1200
atccgcgaca acaaggttga cggcgtactg gttcactaca ccggtcctg caaaccctgg  1260
agcggctaca tgcctgaaat gcagcgtcgt ttcaccaaag acatgggtat ccccactgct  1320
ggattcgacg gtgaccaggc tgacccgaga aacttcaacg cggctcagta tgagacccgt  1380
gttcagggct tggtcgaagc catggaagca aatgatgaaa agaagggaa ataa          1434
```

<210> SEQ ID NO 20
<211> LENGTH: 1122
<212> TYPE: DNA
<213> ORGANISM: Methanocaldococcus jannaschii

<400> SEQUENCE: 20

```
atgatgaaat taaaggcaat tgaaaagttg atgcaaaaat cgccagtag aaaagaacag    60
ctatataagc aaaaagaaga aggtagaaaa gttttttggaa tgttctgtgc ctatgttcca   120
atagaaataa ttttagcagc aaatgcaatc ccagttggtt tgtgtggagg taaaaatgac   180
acaatcccaa tagcagagga ggatttgcca agaaacctat gcccattaat aaaatcatcc   240
tatggttta agaggcaaa aacctgccct tactttgaag catctgatat agttattgga   300
gaaactacct gtgaaggaaa gaagaagatg tttgagttga tggagagatt ggtgccaatg   360
catataatgc acctcccaca catgaaagat gaagattctt tgaaaatctg gattaaagaa   420
gttgaaaagc taaagaatt ggttgagaaa gagactggaa ataaaataac agaggaaaag   480
```

-continued

```
ttaaaagaga cagttgataa agtaaataaa gttagggagt tgtttttataa actctatgaa      540 ttgaggaaga ataaaccagc tccaattaag ggtttagatg ttttaaaatt attccagttt      600
gcctatttat tggatattga tgacacaata gggattttag aggatttaat tgaggagtta      660
gaggagagag ttaaaaaagg agaaggttat gaaggaaaga gaattttaat aactggctgt      720
ccaatggttg ctggaaacaa taagattgtt gaaattattg aggaagttgg aggagtagtt      780
gttggtgaag aaagctgcac tggaacaaga ttctttgaaa actttgttga gggctatagc      840
gtagaggaca ttgcaaaaag atactttaaa atcccatgtg cttgtagatt taaaaacgat      900
gagagagttg aaaatataaa gagattggtt aaagagttgg acgtcgatgg agttgtttat      960
tacactttgc agtattgcca tacatttaac atagagggag ctaaggtaga ggaggcatta     1020
aaagaggagg gcattccaat tataagaatt gaaactgact attctgaaag tgatagagag     1080
cagttaaaaa caaggttgga ggcatttatt gagatgattt aa                        1122
```

<210> SEQ ID NO 21
<211> LENGTH: 1152
<212> TYPE: DNA
<213> ORGANISM: Escherichia coli

<400> SEQUENCE: 21

```
atgtcacttg tcaccgatct acccgccatt ttcgatcagt tctctgaagc tcgccagaca       60
ggctttctca ccgtcatgga tctcaaggag cgcggcattc cgctggttgg cacttactgc      120
acctttatgc cgcaagagat cccgatggca gccggtgcgg ttgtggtttc gctctgttcc      180
acctctgatg aaaccattga agaagcggag aaagatctgc cgcgcaacct ctgcccgctg      240
attaaaagca gctacggctt cggcaaaacc gataaatgcc cctacttcta cttttcggat      300
ctggtggtcg gtgaaaccac ctgcgacggc aaaaagaaaa tgtatgaata catggcggag      360
tttaagcctg ttcatgtgat gcaattgccc aacagcgtta aggacgatgc ctcgcgtgcg      420
ttatggaaag ccgagatgct gcgcttgcaa aaaacggtag aagaacgttt tgggcacgag      480
attagcgaag atgctctgcg cgatgccatt gcgctgaaaa accgcgaacg tcgcgcactg      540 gctaatttt atcatcttgg gcagttaaat cctccggcgc ttagcggcag cgacattctg      600
aaagtggttt acgcgcaac cttccggttc gataaagagg cgttgatcaa tgaactggat      660
gcaatgaccg cccgcgttcg tcagcagtgg gaagaaggcc agcgactgga cccgcgtccg      720
cgcattttaa tcaccggctg cccgattggc ggcgcagcag aaaagtggt gcgcgcgatt      780 gaagagaatg gcggctgggt tgtcggttat gaaaactgca ccggggcgaa agcgaccgag      840
caatgcgtgg cagaaacggg cgatgtctac gacgcgctgg cggataaata tctggcgatt      900
ggctgctcct gtgtttcgcc gaacgatcag cgcctgaaaa tgctcagcca gatggtggag      960
gaatatcagg tcgatggcgt agttgatgtg attttgcagg cgtgccatac ctacgcggtg     1020
gaatcgctgg cgattaaacg tcatgtgcgc cagcagcaca acattcctta tcgctatt      1080 gaaacagact actccacctc ggatgtcggg cagctcagta cccgtgtcgc ggcctttatt     1140
gagatgctgt aa                                                          1152
```

<210> SEQ ID NO 22
<211> LENGTH: 477
<212> TYPE: PRT
<213> ORGANISM: Acidaminococcus fermentans

<400> SEQUENCE: 22

Met Pro Lys Thr Val Ser Pro Gly Val Gln Ala Leu Arg Asp Val Val

-continued

```
1               5               10              15
Glu Lys Val Tyr Arg Glu Leu Arg Glu Pro Lys Glu Arg Gly Glu Lys
                20              25              30

Val Gly Trp Ser Ser Ser Lys Phe Pro Cys Glu Leu Ala Glu Ser Phe
            35              40              45

Arg Leu His Val Gly Tyr Pro Glu Asn Gln Ala Ala Gly Ile Ala Ala
        50              55              60

Asn Arg Asp Gly Glu Val Met Cys Gln Ala Ala Glu Asp Ile Gly Tyr
65              70              75              80

Asp Asn Asp Ile Cys Gly Tyr Ala Arg Ile Ser Leu Ala Tyr Ala Ala
                85              90              95

Gly Phe Arg Gly Ala Asn Lys Met Asp Lys Asp Gly Asn Tyr Val Ile
                100             105             110

Asn Pro His Ser Gly Lys Gln Met Lys Asp Ala Asn Gly Lys Lys Val
            115             120             125

Phe Asp Ala Asp Gly Lys Pro Val Ile Asp Pro Lys Thr Leu Lys Pro
        130             135             140

Phe Ala Thr Thr Asp Asn Ile Tyr Glu Ile Ala Ala Leu Pro Glu Gly
145             150             155             160

Glu Glu Lys Thr Arg Arg Gln Asn Ala Leu His Lys Tyr Arg Gln Met
                165             170             175

Thr Met Pro Met Pro Asp Phe Val Leu Cys Cys Asn Asn Ile Cys Asn
            180             185             190

Cys Met Thr Lys Trp Tyr Glu Asp Ile Ala Arg Arg His Asn Ile Pro
            195             200             205

Leu Ile Met Ile Asp Val Pro Tyr Asn Glu Phe Asp His Val Asn Glu
        210             215             220

Ala Asn Val Lys Tyr Ile Arg Ser Gln Leu Asp Thr Ala Ile Arg Gln
225             230             235             240

Met Glu Glu Ile Thr Gly Lys Lys Phe Asp Asp Lys Phe Glu Gln
                245             250             255

Cys Cys Gln Asn Ala Asn Arg Thr Ala Lys Ala Trp Leu Lys Val Cys
            260             265             270

Asp Tyr Leu Gln Tyr Lys Pro Ala Pro Phe Asn Gly Phe Asp Leu Phe
        275             280             285

Asn His Met Ala Asp Val Val Thr Ala Arg Gly Arg Val Glu Ala Ala
        290             295             300

Glu Ala Phe Glu Leu Leu Ala Lys Glu Leu Glu Gln His Val Lys Glu
305             310             315             320

Gly Thr Thr Thr Ala Pro Phe Lys Glu Gln His Arg Ile Met Phe Glu
                325             330             335

Gly Ile Pro Cys Trp Pro Lys Leu Pro Asn Leu Phe Lys Pro Leu Lys
                340             345             350

Ala Asn Gly Leu Asn Ile Thr Gly Val Val Tyr Ala Pro Ala Phe Gly
            355             360             365

Phe Val Tyr Asn Asn Leu Asp Glu Leu Val Lys Ala Tyr Cys Lys Ala
        370             375             380

Pro Asn Ser Val Ser Ile Glu Gln Gly Val Ala Trp Arg Glu Gly Leu
385             390             395             400

Ile Arg Asp Asn Lys Val Asp Gly Val Leu Val His Tyr Asn Arg Ser
                405             410             415

Cys Lys Pro Trp Ser Gly Tyr Met Pro Glu Met Gln Arg Arg Phe Thr
            420             425             430
```

```
Lys Asp Met Gly Ile Pro Thr Ala Gly Phe Asp Gly Asp Gln Ala Asp
            435                 440                 445

Pro Arg Asn Phe Asn Ala Ala Gln Tyr Glu Thr Arg Val Gln Gly Leu
        450                 455                 460

Val Glu Ala Met Glu Ala Asn Asp Glu Lys Lys Gly Lys
465                 470                 475
```

<210> SEQ ID NO 23
<211> LENGTH: 373
<212> TYPE: PRT
<213> ORGANISM: Methanocaldococcus jannaschii

<400> SEQUENCE: 23

```
Met Met Lys Leu Lys Ala Ile Glu Lys Leu Met Gln Lys Phe Ala Ser
1               5                  10                   15

Arg Lys Glu Gln Leu Tyr Lys Gln Lys Glu Glu Gly Arg Lys Val Phe
            20                  25                  30

Gly Met Phe Cys Ala Tyr Val Pro Ile Glu Ile Ile Leu Ala Ala Asn
        35                  40                  45

Ala Ile Pro Val Gly Leu Cys Gly Gly Lys Asn Asp Thr Ile Pro Ile
50                  55                  60

Ala Glu Glu Asp Leu Pro Arg Asn Leu Cys Pro Leu Ile Lys Ser Ser
65                  70                  75                  80

Tyr Gly Phe Lys Lys Ala Lys Thr Cys Pro Tyr Phe Glu Ala Ser Asp
            85                  90                  95

Ile Val Ile Gly Glu Thr Thr Cys Glu Gly Lys Lys Lys Met Phe Glu
        100                 105                 110

Leu Met Glu Arg Leu Val Pro Met His Ile Met His Leu Pro His Met
        115                 120                 125

Lys Asp Glu Asp Ser Leu Lys Ile Trp Ile Lys Glu Val Glu Lys Leu
130                 135                 140

Lys Glu Leu Val Glu Lys Glu Thr Gly Asn Lys Ile Thr Glu Glu Lys
145                 150                 155                 160

Leu Lys Glu Thr Val Asp Lys Val Asn Lys Val Arg Glu Leu Phe Tyr
            165                 170                 175

Lys Leu Tyr Glu Leu Arg Lys Asn Lys Pro Ala Pro Ile Lys Gly Leu
        180                 185                 190

Asp Val Leu Lys Leu Phe Gln Phe Ala Tyr Leu Leu Asp Ile Asp Asp
        195                 200                 205

Thr Ile Gly Ile Leu Glu Asp Leu Ile Glu Glu Leu Glu Glu Arg Val
210                 215                 220

Lys Lys Gly Glu Gly Tyr Glu Gly Lys Arg Ile Leu Ile Thr Gly Cys
225                 230                 235                 240

Pro Met Val Ala Gly Asn Asn Lys Ile Val Glu Ile Ile Glu Glu Val
            245                 250                 255

Gly Gly Val Val Val Gly Glu Glu Ser Cys Thr Gly Thr Arg Phe Phe
        260                 265                 270

Glu Asn Phe Val Glu Gly Tyr Ser Val Glu Asp Ile Ala Lys Arg Tyr
        275                 280                 285

Phe Lys Ile Pro Cys Ala Cys Arg Phe Lys Asn Asp Glu Arg Val Glu
290                 295                 300

Asn Ile Lys Arg Leu Val Lys Glu Leu Asp Val Asp Gly Val Val Tyr
305                 310                 315                 320

Tyr Thr Leu Gln Tyr Cys His Thr Phe Asn Ile Glu Gly Ala Lys Val
            325                 330                 335
```

Glu Glu Ala Leu Lys Glu Gly Ile Pro Ile Ile Arg Ile Glu Thr
              340                 345                 350

Asp Tyr Ser Glu Ser Asp Arg Glu Gln Leu Lys Thr Arg Leu Glu Ala
            355                 360                 365

Phe Ile Glu Met Ile
    370

<210> SEQ ID NO 24
<211> LENGTH: 383
<212> TYPE: PRT
<213> ORGANISM: Methanocaldococcus jannaschii

<400> SEQUENCE: 24

Met Ser Leu Val Thr Asp Leu Pro Ala Ile Phe Asp Gln Phe Ser Glu
1               5                   10                  15

Ala Arg Gln Thr Gly Phe Leu Thr Val Met Asp Leu Lys Glu Arg Gly
            20                  25                  30

Ile Pro Leu Val Gly Thr Tyr Cys Thr Phe Met Pro Gln Glu Ile Pro
        35                  40                  45

Met Ala Ala Gly Ala Val Val Val Ser Leu Cys Ser Thr Ser Asp Glu
    50                  55                  60

Thr Ile Glu Glu Ala Glu Lys Asp Leu Pro Arg Asn Leu Cys Pro Leu
65                  70                  75                  80

Ile Lys Ser Ser Tyr Gly Phe Gly Lys Thr Asp Lys Cys Pro Tyr Phe
                85                  90                  95

Tyr Phe Ser Asp Leu Val Val Gly Glu Thr Thr Cys Asp Gly Lys Lys
            100                 105                 110

Lys Met Tyr Glu Tyr Met Ala Glu Phe Lys Pro Val His Val Met Gln
        115                 120                 125

Leu Pro Asn Ser Val Lys Asp Asp Ala Ser Arg Ala Leu Trp Lys Ala
    130                 135                 140

Glu Met Leu Arg Leu Gln Lys Thr Val Glu Arg Phe Gly His Glu
145                 150                 155                 160

Ile Ser Glu Asp Ala Leu Arg Asp Ala Ile Ala Leu Lys Asn Arg Glu
                165                 170                 175

Arg Arg Ala Leu Ala Asn Phe Tyr His Leu Gly Gln Leu Asn Pro Pro
            180                 185                 190

Ala Leu Ser Gly Ser Asp Ile Leu Lys Val Val Tyr Gly Ala Thr Phe
        195                 200                 205

Arg Phe Asp Lys Glu Ala Leu Ile Asn Glu Leu Asp Ala Met Thr Ala
    210                 215                 220

Arg Val Arg Gln Gln Trp Glu Glu Gly Gln Arg Leu Asp Pro Arg Pro
225                 230                 235                 240

Arg Ile Leu Ile Thr Gly Cys Pro Ile Gly Gly Ala Ala Glu Lys Val
                245                 250                 255

Val Arg Ala Ile Glu Glu Asn Gly Gly Trp Val Val Gly Tyr Glu Asn
            260                 265                 270

Cys Thr Gly Ala Lys Ala Thr Glu Gln Cys Val Ala Glu Thr Gly Asp
        275                 280                 285

Val Tyr Asp Ala Leu Ala Asp Lys Tyr Leu Ala Ile Gly Cys Ser Cys
    290                 295                 300

Val Ser Pro Asn Asp Gln Arg Leu Lys Met Leu Ser Gln Met Val Glu
305                 310                 315                 320

Glu Tyr Gln Val Asp Gly Val Asp Val Ile Leu Gln Ala Cys His
                325                 330                 335

```
              Thr Tyr Ala Val Glu Ser Leu Ala Ile Lys Arg His Val Arg Gln Gln
                      340                 345                 350

His Asn Ile Pro Tyr Ile Ala Ile Glu Thr Asp Tyr Ser Thr Ser Asp
                      355                 360                 365

Val Gly Gln Leu Ser Thr Arg Val Ala Ala Phe Ile Glu Met Leu
                      370                 375                 380

<210> SEQ ID NO 25
<211> LENGTH: 1119
<212> TYPE: DNA
<213> ORGANISM: Megasphaera elsdenii
<220> FEATURE:
<221> NAME/KEY: CDS
<222> LOCATION: (1)..(1116)

<400> SEQUENCE: 25 atg agt cag atc gac gaa ctt atc agc aaa tta cag gaa gta tcc aac        48
Met Ser Gln Ile Asp Glu Leu Ile Ser Lys Leu Gln Glu Val Ser Asn
1               5                   10                  15 cat ccc cag aag acg gtt ttg aat tat aaa aaa cag ggt aaa ggc ctc        96
His Pro Gln Lys Thr Val Leu Asn Tyr Lys Lys Gln Gly Lys Gly Leu
                20                  25                  30 gta ggc atg atg ccc tac tac gct ccg gaa gaa atc gta tat gct gca       144
Val Gly Met Met Pro Tyr Tyr Ala Pro Glu Glu Ile Val Tyr Ala Ala
            35                  40                  45 ggc tac ctc ccg gta ggc atg ttc ggt tcc cag aac ccg cag atc tcc       192
Gly Tyr Leu Pro Val Gly Met Phe Gly Ser Gln Asn Pro Gln Ile Ser
        50                  55                  60 gca gct cgt acg tac ctt cct ccg ttc gct tgc tcc ttg atg cag gct       240
Ala Ala Arg Thr Tyr Leu Pro Pro Phe Ala Cys Ser Leu Met Gln Ala
65                  70                  75                  80 gac atg gaa ctc cag ctc aac ggc acc tat gac tgc ctc gac gct gtt       288
Asp Met Glu Leu Gln Leu Asn Gly Thr Tyr Asp Cys Leu Asp Ala Val
                85                  90                  95 atc ttc tcc gtt cct tgc gac act ctc cgc tgc atg agc cag aaa tgg       336
Ile Phe Ser Val Pro Cys Asp Thr Leu Arg Cys Met Ser Gln Lys Trp
                100                 105                 110 cac ggc aaa gct ccg gtc atc gtc ttc aca cag ccg cag aac cgt aag       384
His Gly Lys Ala Pro Val Ile Val Phe Thr Gln Pro Gln Asn Arg Lys
            115                 120                 125 atc cgc ccg gct gtc gat ttc ctc aaa gct gaa tac gaa cat gtc cgt       432
Ile Arg Pro Ala Val Asp Phe Leu Lys Ala Glu Tyr Glu His Val Arg
        130                 135                 140 acg gaa ttg gga cgt atc ctc aac gta aaa atc tcc gac ctg gct atc       480
Thr Glu Leu Gly Arg Ile Leu Asn Val Lys Ile Ser Asp Leu Ala Ile
145                 150                 155                 160 cag gaa gct atc aaa gta tat aac gaa aac cgt cag gtt atg cgt gaa       528
Gln Glu Ala Ile Lys Val Tyr Asn Glu Asn Arg Gln Val Met Arg Glu
                165                 170                 175 ttc tgc gac gta gct gct cag tac ccg cag atc ttc act ccg ata aaa       576
Phe Cys Asp Val Ala Ala Gln Tyr Pro Gln Ile Phe Thr Pro Ile Lys
                180                 185                 190 cgt cat gac gtc atc aaa gcc cgc tgg ttc atg gac aaa gct gaa cac       624
Arg His Asp Val Ile Lys Ala Arg Trp Phe Met Asp Lys Ala Glu His
            195                 200                 205 acc gct ttg gtc cgc gaa ctc atc gac gct gtc aag aaa gaa ccg gta       672
Thr Ala Leu Val Arg Glu Leu Ile Asp Ala Val Lys Lys Glu Pro Val
        210                 215                 220 cag ccg tgg aat ggc aaa aaa gtc atc ctc tcc ggt atc atg gca gaa       720
Gln Pro Trp Asn Gly Lys Lys Val Ile Leu Ser Gly Ile Met Ala Glu
225                 230                 235                 240
```

```
ccg gat gaa ttc ctc gat atc ttc agc gaa ttc aac atc gct gtc gtc    768
Pro Asp Glu Phe Leu Asp Ile Phe Ser Glu Phe Asn Ile Ala Val Val
            245                 250                 255 gct gac gac ctc gct cag gaa tcc cgc cag ttc cgt aca gac gta ccg    816
Ala Asp Asp Leu Ala Gln Glu Ser Arg Gln Phe Arg Thr Asp Val Pro
            260                 265                 270 tcc ggc atc gat ccc ctc gaa cag ctc gct cag cag tgg cag gac ttc    864
Ser Gly Ile Asp Pro Leu Glu Gln Leu Ala Gln Gln Trp Gln Asp Phe
        275                 280                 285 gat ggc tgc ccg ctc gct ttg aac gaa gac aaa ccg cgt ggc cag atg    912
Asp Gly Cys Pro Leu Ala Leu Asn Glu Asp Lys Pro Arg Gly Gln Met
    290                 295                 300 ctc atc gac atg act aag aaa tac aat gct gac gcc gtc gtc atc tgc    960
Leu Ile Asp Met Thr Lys Lys Tyr Asn Ala Asp Ala Val Val Ile Cys
305                 310                 315                 320 atg atg cgt ttc tgc gat cct gaa gaa ttc gac tat ccg att tac aaa   1008
Met Met Arg Phe Cys Asp Pro Glu Glu Phe Asp Tyr Pro Ile Tyr Lys
                325                 330                 335 ccg gaa ttt gaa gct gct ggc gtt cgt tac acg gtc ctc gac ctc gac   1056
Pro Glu Phe Glu Ala Ala Gly Val Arg Tyr Thr Val Leu Asp Leu Asp
            340                 345                 350 atc gaa tct ccg tcc ctc gaa cag ctc cgc acc cgt atc cag gct ttc   1104
Ile Glu Ser Pro Ser Leu Glu Gln Leu Arg Thr Arg Ile Gln Ala Phe
        355                 360                 365 tcg gaa atc ctc taa                                               1119
Ser Glu Ile Leu
    370

<210> SEQ ID NO 26
<211> LENGTH: 372
<212> TYPE: PRT
<213> ORGANISM: Megasphaera elsdenii

<400> SEQUENCE: 26

Met Ser Gln Ile Asp Glu Leu Ile Ser Lys Leu Gln Glu Val Ser Asn
1               5                   10                  15

His Pro Gln Lys Thr Val Leu Asn Tyr Lys Lys Gln Gly Lys Gly Leu
            20                  25                  30

Val Gly Met Met Pro Tyr Tyr Ala Pro Glu Glu Ile Val Tyr Ala Ala
        35                  40                  45

Gly Tyr Leu Pro Val Gly Met Phe Gly Ser Gln Asn Pro Gln Ile Ser
    50                  55                  60

Ala Ala Arg Thr Tyr Leu Pro Pro Phe Ala Cys Ser Leu Met Gln Ala
65                  70                  75                  80

Asp Met Glu Leu Gln Leu Asn Gly Thr Tyr Asp Cys Leu Asp Ala Val
                85                  90                  95

Ile Phe Ser Val Pro Cys Asp Thr Leu Arg Cys Met Ser Gln Lys Trp
            100                 105                 110

His Gly Lys Ala Pro Val Ile Val Phe Thr Gln Pro Gln Asn Arg Lys
        115                 120                 125

Ile Arg Pro Ala Val Asp Phe Leu Lys Ala Glu Tyr Glu His Val Arg
    130                 135                 140

Thr Glu Leu Gly Arg Ile Leu Asn Val Lys Ile Ser Asp Leu Ala Ile
145                 150                 155                 160

Gln Glu Ala Ile Lys Val Tyr Asn Glu Asn Arg Gln Val Met Arg Glu
                165                 170                 175

Phe Cys Asp Val Ala Ala Gln Tyr Pro Gln Ile Phe Thr Pro Ile Lys
            180                 185                 190
```

```
Arg His Asp Val Ile Lys Ala Arg Trp Phe Met Asp Lys Ala Glu His
        195                 200                 205
Thr Ala Leu Val Arg Glu Leu Ile Asp Ala Val Lys Lys Glu Pro Val
    210                 215                 220
Gln Pro Trp Asn Gly Lys Lys Val Ile Leu Ser Gly Ile Met Ala Glu
225                 230                 235                 240
Pro Asp Glu Phe Leu Asp Ile Phe Ser Glu Phe Asn Ile Ala Val Val
                245                 250                 255
Ala Asp Asp Leu Ala Gln Glu Ser Arg Gln Phe Arg Thr Asp Val Pro
                260                 265                 270
Ser Gly Ile Asp Pro Leu Glu Gln Leu Ala Gln Trp Gln Asp Phe
        275                 280                 285
Asp Gly Cys Pro Leu Ala Leu Asn Glu Asp Lys Pro Arg Gly Gln Met
    290                 295                 300
Leu Ile Asp Met Thr Lys Lys Tyr Asn Ala Asp Ala Val Val Ile Cys
305                 310                 315                 320
Met Met Arg Phe Cys Asp Pro Glu Glu Phe Asp Tyr Pro Ile Tyr Lys
                325                 330                 335
Pro Glu Phe Glu Ala Ala Gly Val Arg Tyr Thr Val Leu Asp Leu Asp
                340                 345                 350
Ile Glu Ser Pro Ser Leu Glu Gln Leu Arg Thr Arg Ile Gln Ala Phe
        355                 360                 365
Ser Glu Ile Leu
    370

<210> SEQ ID NO 27
<211> LENGTH: 1140
<212> TYPE: DNA
<213> ORGANISM: Acidaminococcus fermentans

<400> SEQUENCE: 27
atggctatca gtgcacttat tgaagagttc caaaaagtat ctgccagccc gaagaccatg      60
ctggccaaat ataaagccca gggcaaaaaa gccatcggct gcctgccgta ctatgttccg     120
gaagaactgg tctatgctgc aggcatggtt cccatggggt tatggggctg caatggcaaa     180
caggaagtcc gttccaagga atactgtgct tccttctact gcaccattgc ccagcagtct     240
ctggaaatgc tgctgacgg gaccctggat gggttgacg ggatcatcac tccggtactg     300
tgtgataccc tgcgtcccat gagccagaac ttcaaagtgg ccatgaaaga caagatgccg     360
gttattttcc tggctcatcc ccaggtccgt cagaatgccg ccggcaagca gttcacctat     420
gatgcctaca gcgaagtgaa aggccatctg aagaaatct gcggccatga atcaccaat     480 gatgccatcc tggatgccat caaagtgtac aacaagagcc gtgctgcccg ccgcgaattc     540
tgcaaactgg ccaacgaaca tcctgatctg atcccggctt ccgtacgggc caccgtactg     600
cgtgccgctt acttcatgct gaaggatgaa tacaccgaaa agctggaaga actgaacaag     660
gaactggcag ctgctcctgc cggcaagttc gacggccaca agtggttgt ttccggcatc     720 atctacaaca cgcccggcat cctgaaagcc atggatgaca caaactggc cattgctgct     780 gatgactgcg cttatgaaag ccgcagcttt gccgtggatg ctccggaaga tctggacaac     840
ggactgcatg ctctggctgt acagttctcc aaacagaaga acgatgttct gctgtacgat     900
cctgaatttg ccaagaatac ccgttctgaa cacgttggca atctggtaaa agaaagcggc     960
gcagaaggac tgatcgtgtt catgatgcag ttctgcgatc cggaagaaat ggaatatcct    1020
gatctgaaga aggctctgga tgcccaccac attcctcatg tgaagattgg tgtggaccag    1080
```

```
atgacccggg actttggtca ggcccagacc gctctggaag ctttcgcaga aagcctgtaa    1140
```

<210> SEQ ID NO 28
<211> LENGTH: 1122
<212> TYPE: DNA
<213> ORGANISM: Methanocaldococcus jannaschii

<400> SEQUENCE: 28

```
atgatgaaat taaaggcaat tgaaaagttg atgcaaaaat tcgccagtag aaaagaacag      60
ctatataagc aaaaagaaga aggtagaaaa gttttttggaa tgttctgtgc ctatgttcca    120
atagaaataa ttttagcagc aaatgcaatc ccagttggtt tgtgtggagg taaaaatgac    180
acaatcccaa tagcagagga ggatttgcca agaaacctat gcccattaat aaaatcatcc    240
tatggtttta agaaggcaaa aacctgccct tactttgaag catctgatat agttattgga    300
gaaactacct gtgaaggaaa gaagaagatg tttgagttga tggagagatt ggtgccaatg    360
catataatgc acctcccaca catgaaagat gaagattctt tgaaaatctg gattaaagaa    420
gttgaaaagc taaagaatt ggttgagaaa gagactggaa ataaaataac agaggaaaag    480
ttaaaagaga cagttgataa agtaaataaa gttagggagt tgttttataa actctatgaa    540
ttgaggaaga ataaaccagc tccaattaag ggtttagatg ttttaaaatt attccagttt    600
gcctatttat tggatattga tgcacaata gggattttag aggatttaat tgaggagtta    660
gaggagagag ttaaaaaagg agaaggttat gaaggaaaga gaatttttaat aactggctgt    720
ccaatggttg ctggaaacaa taagattgtt gaaattattg aggaagttgg aggagtagtt    780
gttggtgaag aaagctgcac tggaacaaga ttctttgaaa actttgttga gggctatagc    840
gtagaggaca ttgcaaaaag atactttaaa atcccatgtg cttgtagatt taaaaacgat    900
gagagagttg aaaatataaa agattggtt aaagagttgg acgtcgatgg agttgtttat    960
tacactttgc agtattgcca tacatttaac atagagggag ctaaggtaga ggaggcatta   1020
aaagaggagg gcattccaat tataagaatt gaaactgact attctgaaag tgatagagag   1080
cagttaaaaa caaggttgga ggcatttatt gagatgattt aa                      1122
```

<210> SEQ ID NO 29
<211> LENGTH: 1152
<212> TYPE: DNA
<213> ORGANISM: Escherichia coli

<400> SEQUENCE: 29

```
atgtcacttg tcaccgatct acccgccatt ttcgatcagt tctctgaagc tcgccagaca     60
ggctttctca ccgtcatgga tctcaaggag cgcggcattc cgctggttgg cacttactgc    120
acctttatgc cgcaagagat cccgatggca gccggtgcgg ttgtggtttc gctctgttcc    180
acctctgatg aaaccattga agaagcggag aaagatctgc cgcgcaacct ctgcccgctg    240
attaaaagca gctacggctt cggcaaaacc gataaatgcc cctacttcta cttttcggat    300
ctggtggtcg gtgaaaccac ctgcgacggc aaaaagaaaa tgtatgaata catggcggag    360
tttaagcctg ttcatgtgat gcaattgccc aacagcgtta aggacgatgc ctcgcgtgcg    420
ttatggaaag ccgagatgct gcgcttgcaa aaaacggtag aagaacgttt tgggcacgag    480
attagcgaag atgctctgcg cgatgccatt gcgctgaaaa accgcgaacg tcgcgcactg    540
gctaattttt atcatcttgg gcagttaaat cctccggcgc ttagcggcag cgacattctg    600
aaagtggttt acggcgcaac cttccggttc gataaagagg cgttgatcaa tgaactggat    660
gcaatgaccg cccgcgttcg tcagcagtgg gaagaaggcc agcgactgga cccgcgtccg    720
```

```
cgcattttaa tcaccggctg cccgattggc ggcgcagcag aaaaagtggt gcgcgcgatt      780
gaagagaatg gcggctgggt tgtcggttat gaaaactgca ccggggcgaa agcgaccgag      840
caatgcgtgg cagaaacggg cgatgtctac gacgcgctgg cggataaata tctggcgatt      900
ggctgctcct gtgtttcgcc gaacgatcag cgcctgaaaa tgctcagcca gatggtggag      960
gaatatcagg tcgatggcgt agttgatgtg attttgcagg cgtgccatac ctacgcggtg     1020
gaatcgctgg cgattaaacg tcatgtgcgc cagcagcaca acattcctta tatcgctatt     1080
gaaacagact actccacctc ggatgtcggg cagctcagta cccgtgtcgc ggcctttatt     1140
gagatgctgt aa                                                         1152

<210> SEQ ID NO 30
<211> LENGTH: 379
<212> TYPE: PRT
<213> ORGANISM: Acidaminococcus fermentans

<400> SEQUENCE: 30

Met Ala Ile Ser Ala Leu Ile Glu Glu Phe Gln Lys Val Ser Ala Ser
  1               5                  10                  15

Pro Lys Thr Met Leu Ala Lys Tyr Lys Ala Gln Gly Lys Lys Ala Ile
                 20                  25                  30

Gly Cys Leu Pro Tyr Tyr Val Pro Glu Glu Leu Val Tyr Ala Ala Gly
             35                  40                  45

Met Val Pro Met Gly Val Trp Gly Cys Asn Gly Lys Gln Glu Val Arg
         50                  55                  60

Ser Lys Glu Tyr Cys Ala Ser Phe Tyr Cys Thr Ile Ala Gln Gln Ser
 65                  70                  75                  80

Leu Glu Met Leu Leu Asp Gly Thr Leu Asp Gly Leu Asp Gly Ile Ile
                 85                  90                  95

Thr Pro Val Leu Cys Asp Thr Leu Arg Pro Met Ser Gln Asn Phe Lys
            100                 105                 110

Val Ala Met Lys Asp Lys Met Pro Val Ile Phe Leu Ala His Pro Gln
        115                 120                 125

Val Arg Gln Asn Ala Ala Gly Lys Gln Phe Thr Tyr Asp Ala Tyr Ser
    130                 135                 140

Glu Val Lys Gly His Leu Glu Glu Ile Cys Gly His Glu Ile Thr Asn
145                 150                 155                 160

Asp Ala Ile Leu Asp Ala Ile Lys Val Tyr Asn Lys Ser Arg Ala Ala
                165                 170                 175

Arg Arg Glu Phe Cys Lys Leu Ala Asn Glu His Pro Asp Leu Ile Pro
            180                 185                 190

Ala Ser Val Arg Ala Thr Val Leu Arg Ala Ala Tyr Phe Met Leu Lys
        195                 200                 205

Asp Glu Tyr Thr Glu Lys Leu Glu Glu Leu Asn Lys Glu Leu Ala Ala
    210                 215                 220

Ala Pro Ala Gly Lys Phe Asp Gly His Lys Val Val Ser Gly Ile
225                 230                 235                 240

Ile Tyr Asn Thr Pro Gly Ile Leu Lys Ala Met Asp Asp Asn Lys Leu
                245                 250                 255

Ala Ile Ala Ala Asp Asp Cys Ala Tyr Glu Ser Arg Ser Phe Ala Val
            260                 265                 270

Asp Ala Pro Glu Asp Leu Asp Asn Gly Leu His Ala Leu Ala Val Gln
        275                 280                 285

Phe Ser Lys Gln Lys Asn Asp Val Leu Leu Tyr Asp Pro Glu Phe Ala
    290                 295                 300
```

Lys Asn Thr Arg Ser Glu His Val Gly Asn Leu Val Lys Glu Ser Gly
305                 310                 315                 320

Ala Glu Gly Leu Ile Val Phe Met Met Gln Phe Cys Asp Pro Glu Glu
            325                 330                 335

Met Glu Tyr Pro Asp Leu Lys Lys Ala Leu Asp Ala His His Ile Pro
            340                 345                 350

His Val Lys Ile Gly Val Asp Gln Met Thr Arg Asp Phe Gly Gln Ala
        355                 360                 365

Gln Thr Ala Leu Glu Ala Phe Ala Glu Ser Leu
    370                 375

<210> SEQ ID NO 31
<211> LENGTH: 373
<212> TYPE: PRT
<213> ORGANISM: Methanocaldococcus jannaschii

<400> SEQUENCE: 31

Met Met Lys Leu Lys Ala Ile Glu Lys Leu Met Gln Lys Phe Ala Ser
1               5                   10                  15

Arg Lys Glu Gln Leu Tyr Lys Gln Lys Glu Glu Gly Arg Lys Val Phe
            20                  25                  30

Gly Met Phe Cys Ala Tyr Val Pro Ile Glu Ile Ile Leu Ala Ala Asn
        35                  40                  45

Ala Ile Pro Val Gly Leu Cys Gly Gly Lys Asn Asp Thr Ile Pro Ile
    50                  55                  60

Ala Glu Glu Asp Leu Pro Arg Asn Leu Cys Pro Leu Ile Lys Ser Ser
65                  70                  75                  80

Tyr Gly Phe Lys Lys Ala Lys Thr Cys Pro Tyr Phe Glu Ala Ser Asp
                85                  90                  95

Ile Val Ile Gly Glu Thr Thr Cys Glu Gly Lys Lys Lys Met Phe Glu
            100                 105                 110

Leu Met Glu Arg Leu Val Pro Met His Ile Met His Leu Pro His Met
        115                 120                 125

Lys Asp Glu Asp Ser Leu Lys Ile Trp Ile Lys Glu Val Glu Lys Leu
    130                 135                 140

Lys Glu Leu Val Glu Lys Glu Thr Gly Asn Lys Ile Thr Glu Lys
145                 150                 155                 160

Leu Lys Glu Thr Val Asp Lys Val Asn Lys Val Arg Glu Leu Phe Tyr
                165                 170                 175

Lys Leu Tyr Glu Leu Arg Lys Asn Lys Pro Ala Pro Ile Lys Gly Leu
            180                 185                 190

Asp Val Leu Lys Leu Phe Gln Phe Ala Tyr Leu Leu Asp Ile Asp Asp
        195                 200                 205

Thr Ile Gly Ile Leu Glu Asp Leu Ile Glu Glu Leu Glu Glu Arg Val
    210                 215                 220

Lys Lys Gly Glu Gly Tyr Glu Gly Lys Arg Ile Leu Ile Thr Gly Cys
225                 230                 235                 240

Pro Met Val Ala Gly Asn Asn Lys Ile Val Glu Ile Ile Glu Glu Val
                245                 250                 255

Gly Gly Val Val Val Gly Glu Glu Ser Cys Thr Gly Thr Arg Phe Phe
            260                 265                 270

Glu Asn Phe Val Glu Gly Tyr Ser Val Glu Asp Ile Ala Lys Arg Tyr
        275                 280                 285

Phe Lys Ile Pro Cys Ala Cys Arg Phe Lys Asn Asp Glu Arg Val Glu
    290                 295                 300

Asn Ile Lys Arg Leu Val Lys Glu Leu Asp Val Asp Gly Val Val Tyr
305                 310                 315                 320

Tyr Thr Leu Gln Tyr Cys His Thr Phe Asn Ile Glu Gly Ala Lys Val
            325                 330                 335

Glu Glu Ala Leu Lys Glu Glu Gly Ile Pro Ile Ile Arg Ile Glu Thr
            340                 345                 350

Asp Tyr Ser Glu Ser Asp Arg Glu Gln Leu Lys Thr Arg Leu Glu Ala
        355                 360                 365

Phe Ile Glu Met Ile
    370

<210> SEQ ID NO 32
<211> LENGTH: 383
<212> TYPE: PRT
<213> ORGANISM: Methanocaldococcus jannaschii

<400> SEQUENCE: 32

Met Ser Leu Val Thr Asp Leu Pro Ala Ile Phe Asp Gln Phe Ser Glu
1               5                   10                  15

Ala Arg Gln Thr Gly Phe Leu Thr Val Met Asp Leu Lys Glu Arg Gly
            20                  25                  30

Ile Pro Leu Val Gly Thr Tyr Cys Thr Phe Met Pro Gln Glu Ile Pro
        35                  40                  45

Met Ala Ala Gly Ala Val Val Val Ser Leu Cys Ser Thr Ser Asp Glu
    50                  55                  60

Thr Ile Glu Glu Ala Lys Asp Leu Pro Arg Asn Leu Cys Pro Leu
65                  70                  75                  80

Ile Lys Ser Ser Tyr Gly Phe Gly Lys Thr Asp Lys Cys Pro Tyr Phe
                85                  90                  95

Tyr Phe Ser Asp Leu Val Val Gly Glu Thr Thr Cys Asp Gly Lys Lys
            100                 105                 110

Lys Met Tyr Glu Tyr Met Ala Glu Phe Lys Pro Val His Val Met Gln
        115                 120                 125

Leu Pro Asn Ser Val Lys Asp Asp Ala Ser Arg Ala Leu Trp Lys Ala
    130                 135                 140

Glu Met Leu Arg Leu Gln Lys Thr Val Glu Glu Arg Phe Gly His Glu
145                 150                 155                 160

Ile Ser Glu Asp Ala Leu Arg Asp Ala Ile Ala Leu Lys Asn Arg Glu
                165                 170                 175

Arg Arg Ala Leu Ala Asn Phe Tyr His Leu Gly Gln Leu Asn Pro Pro
            180                 185                 190

Ala Leu Ser Gly Ser Asp Ile Leu Lys Val Val Tyr Gly Ala Thr Phe
        195                 200                 205

Arg Phe Asp Lys Glu Ala Leu Ile Asn Glu Leu Asp Ala Met Thr Ala
    210                 215                 220

Arg Val Arg Gln Gln Trp Glu Glu Gly Gln Arg Leu Asp Pro Arg Pro
225                 230                 235                 240

Arg Ile Leu Ile Thr Gly Cys Pro Ile Gly Gly Ala Ala Glu Lys Val
                245                 250                 255

Val Arg Ala Ile Glu Glu Asn Gly Gly Trp Val Val Gly Tyr Glu Asn
            260                 265                 270

Cys Thr Gly Ala Lys Ala Thr Glu Gln Cys Val Ala Glu Thr Gly Asp
        275                 280                 285

Val Tyr Asp Ala Leu Ala Asp Lys Tyr Leu Ala Ile Gly Cys Ser Cys
    290                 295                 300

| | | | | | | | | | | | |
|---|---|---|---|---|---|---|---|---|---|---|---|
|Val|Ser|Pro|Asn|Asp|Gln|Arg|Leu|Lys|Met|Leu|Ser Gln Met Val Glu|
| |305| | | |310| | | |315| |320|

Glu Tyr Gln Val Asp Gly Val Val Asp Val Ile Leu Gln Ala Cys His
                325                 330                 335

Thr Tyr Ala Val Glu Ser Leu Ala Ile Lys Arg His Val Arg Gln Gln
            340                 345                 350

His Asn Ile Pro Tyr Ile Ala Ile Glu Thr Asp Tyr Ser Thr Ser Asp
        355                 360                 365

Val Gly Gln Leu Ser Thr Arg Val Ala Ala Phe Ile Glu Met Leu
    370                 375                 380

<210> SEQ ID NO 33
<211> LENGTH: 6295
<212> TYPE: DNA
<213> ORGANISM: Megasphaera elsdenii

<400> SEQUENCE: 33

```
cgacggcccg ggctggtatc attctagtca gtaattcacc tttggaaaat tttcacaaag     60
gcagtacgac agaagcgtcg atacattcca tttagcagga ggaagttacg gtaatgagaa    120
aagtagaaat cattacagct gaacaagcag ctcagctcgt aaaagacaac gacacgatta    180
cgtctatcgg ctttgtcagc agcgcccatc cggaagcact gaccaaagct ttggaaaaac    240
ggttcctgga cacgaacacc ccgcagaact tgacctacat ctatgcaggc tctcagggca    300
aacgcgatgg ccgtgccgct gaacatctgg cacacacagg ccttttgaaa cgcgccatca    360
tcggtcactg gcagactgta ccggctatcg gtaaactggc tgtcgaaaac aagattgaag    420
cttacaactt ctcgcagggc acgttggtcc actggttccg cgccttggca ggtcataagc    480
tcggcgtctt caccgacatc ggtctggaaa cttttcctcga tccccgtcag ctcggcggca    540
agctcaatga cgtaaccaaa gaagacctcg tcaaactgat cgaagtcgat ggtcatgaac    600
agcttttcta cccgaccttc ccggtcaacg tagctttcct ccgcggtacg tatgctgatg    660
aatccggcaa tatcaccatg gacgaagaaa tcgggccttt cgaaagcact tccgtagccc    720
aggccgttca caactgtggc ggtaaagtcg tcgtccaggt caaagacgtc gtcgctcacg    780
gcagcctcga cccgcgcatg gtcaagatcc ctggcatcta tgtcgactac gtcgtcgtag    840
cagctccgga agaccatcag cagacgtatg actgcgaata cgatccgtcc ctcagcggtg    900
aacatcgtgc tcctgaaggc gctaccgatg cagctctccc catgagcgct aagaaaatca    960
tcggccgccg cggcgctttg gaattgactg aaaacgctgt cgtcaacctc ggcgtcggtg   1020
ctccggaata cgttgcttct gttgccggtg aagaaggtat cgccgatacc attaccctga   1080
ccgtcgaagg tggcgccatc ggtggcgtac cgcagggcgg tgcccgcttc ggttcgtccc   1140
gcaatgccga tgccatcatc gaccacacct atcagttcga cttctacgat ggcggcggtc   1200
tggacatcgc ttacctcggc ctggcccagt gcgatggctc gggcaacatc aacgtcagca   1260
agttcggtac taacgttgcc ggctgcggcg gtttccccaa catttcccag cagacaccga   1320
atgtttactt ctgcggcacc ttcacggctg cggcttgaa atcgctgtc gaagacggca   1380
aagtcaagat cctccaggaa ggcaaagcca agaagttcat caaagctgtc gaccagatca   1440
ctttcaacgg ttcctatgca gcccgcaacg gcaaacacgt tctctacatc acagaacgct   1500
gcgtatttga actgaccaaa gaaggcttga aactcatcga agtcgcaccg ggcatcgata   1560
ttgaaaaaga tatcctcgct cacatggact tcaagccgat cattgataat ccgaaactca   1620
tggatgcccg cctcttccag gacggtccca tgggactgaa aaaataaatc tctgctgtaa   1680
```

-continued

```
aggagacttt actatgaaac caatgagact acatcacgta ggcattgtcc tgccgacctt   1740
agaaaaagcc catgaattca tgcagaataa tggacttgaa atcgactatg ccggctatgt   1800
cgatgcttac caggctgatc tcattttcac taagtttggt gaatttgcca gcccgattga   1860
aatgattatc ccgcactccg gtgtgcttac ccaattcaat ggtggccgcg cggcattgc    1920
ccacatcgcc ttcgaagtgg acgatgtcga agctgtccgc caggaaatgg aagcagattg   1980
tccgggatgc atgttagaaa agaaagctgt ccagggtacg gacgcacatta tcgtcaactt  2040
ccgccgcccg acaaccaacc agggtatcct cgttgaatat gttcagacga cagcacctat   2100
caccggccgc ggcgaaaatc ctttcgttaa gaatctcggc ccggaaaaag ggaagctcaa    2160
cgaaacatgg catcccatgc gcctgcacca tatcggcatc gtcttgccga ccttggaaaa   2220
ggcccatgaa ttcatcaaga ccaatggtct ggaagtggaa tattccggtt tcgtcgacgc   2280
ctaccatgcg gatctcattt tcactaaaaa aggtgaaaac agtacgccta tcgaattcat   2340
tattccccgt gaaggggtcc tcaaagattt caatcatggc aggggaggta tcgctcatat   2400
cgcctttgaa gtggatgatg tcgaaaaggt acgtcagatt atggaaagcc agaagcctgg   2460
ttgcatgctc gaaaagaaag ccgtccgggg aacggacgac atcatcgtca acttccgccg   2520
tcccagcacg gacgccggca tcctcgtcga atatgtccag accgtagctc ccatcaatcg   2580
cagcaatccc aaccctttta atgattgatt tttataaag aaaggtgaaa actgtgtata    2640
ctctcggaat cgacgttggt tcttcttctt ccaaggcagt catcctggaa gatggcaaga   2700
agatcgtcgc ccatgccgtc gttgaaatcg gcaccggttc gaccggtccg gaacgcgtcc   2760
tggacgaagt cttcaaagat accaacttaa aaattgaaga catggcgaac atcatcgcca   2820
caggctatgg ccgtttcaat gtcgactgcg ccaaaggcga agtcagcgaa atcacgtgcc   2880
atgccaaagg ggccctcttt gaatgccccg gtacgacgac catcctcgat atcggcggtc   2940
aggacgtcaa gtccatcaaa ttgaatggcc agggcctggt catgcagttt gccatgaacg   3000
acaaatgcgc cgctggtacg ggccgtttcc tcgacgtcat gtcgaaggta ctggaaatcc   3060
ccatgtctga atgggggac tggtacttca aatcgaagca tcccgctgcc gtcagcagta    3120
cctgcacggt ttttgctgaa tcggaagtca tttcccttct ttccaagaat gtcccgaaag   3180
aagatatcgt agccggtgtc catcagtcca tcgccgccaa agcctgcgct ctcgtgcgcc   3240
gcgtcggtgt cggtgaagac ctgaccatga ccggcgtgg ctcccgcgat cccggcgtcg    3300
tcgatgccgt atcgaaagaa ttaggtattc ctgtcagagt cgctctgcat ccccaagcgg   3360
tgggtgctct cggagctgct ttgattgctt atgataaaat caagaaataa gtcaaaggag   3420
agaacaaaat catgagtgaa gaaaaaacag tagatattga aagcatgagc tccaaggaag   3480
cccttggtta cttcttgccg aaagtcgatg aagacgcacg taaagcgaaa aaagaaggcc   3540
gcctcgtttg ctggtccgct tctgtcgctc ctccggaatt ctgcacggct atggacatcg   3600
ccatcgtcta tccggaaact cacgcagctg gtatcggtgc ccgtcacggt gctccggcca   3660
tgctcgaagt tgctgaaaac aaaggttaca accaggacat ctgttcctac tgccgcgtca   3720
acatgggcta catggaactc ctcaaacagc aggctctgac aggcgaaacg ccggaagtcc   3780
tcaaaaactc cccggcttct ccgattcccc ttccggatgt tgtcctcact tgcaacaaca   3840
tctgcaatac cttgctcaaa tggtatgaaa acttggctaa agaattgaac gtacctctca   3900
tcaacatcga cgtaccgttc aaccatgaat ccctgttac gaaacacgct aaacagtaca    3960
tcgtcggcga attcaaacat gctatcaaac agctcgaaga cctttgcggc cgtcccttcg   4020
actatgacaa attcttcgaa gtacagaaac agacacagcg ctccatcgct gcctggaaca   4080
```

```
aaatcgctac gtacttccag tacaaaccgt cgccgctcaa cggcttcgac ctcttcaact    4140
acatgggcct cgccgttgct gcccgctcct tgaactactc ggaaatcacg ttcaacaaat    4200
tcctcaaaga attggacgaa aaagtagcta ataagaaatg gctttcggt gaaaacgaaa     4260
aatcccgtgt tacttgggaa ggtatcgctg tctggatcgc tctcggccac accttcaaag   4320
aactcaaagg tcagggcgct ctcatgactg gttccgctta tcctggcatg tgggacgttt   4380
cctacgaacc gggcgacctc gaatccatgg cagaagctta ttcccgtaca tacatcaact   4440
gctgcctcga acagcgcggt gctgttcttg aaaaagttgt ccgcgatggc aaatgcgacg   4500
gcttgatcat gcaccagaac cgttcctgca agaacatgag cctcctcaac aacgaaggcg   4560
gccagcgcat ccagaagaac ctcggcgtac cgtacgtcat cttcgacggc gaccagaccg   4620
atgctcgtaa cttctcggaa gcacagttcg atacccgcgt agaagctttg gcagaaatga   4680
tggcagacaa aaaagccaat gaaggaggaa accactaatg agtcagatcg acgaacttat   4740
cagcaaatta caggaagtat ccaaccatcc ccagaagacg gttttgaatt ataaaaaaca   4800
gggtaaaggc ctcgtaggca tgatgcccta ctacgctccg gaagaaatcg tatatgctgc   4860
aggctacctc ccggtaggca tgttcggttc ccagaacccg cagatctccg cagctcgtac   4920
gtaccttcct ccgttcgctt gctccttgat gcaggctgac atggaactcc agctcaacgg   4980
cacctatgac tgcctcgacg ctgttatctt ctccgttcct tgcgacactc tccgctgcat   5040
gagccagaaa tggcacggca agctccggt catcgtcttc acacagccgc agaaccgtaa   5100
gatccgcccg gctgtcgatt tcctcaaagc tgaatacgaa catgtccgta cggaattggg   5160
acgtatcctc aacgtaaaaa tctccgacct ggctatccag gaagctatca agtatataa    5220
cgaaaaccgt caggttatgc gtgaattctg cgacgtagct gctcagtacc cgcagatctt    5280
cactccgata aaacgtcatg acgtcatcaa agcccgctgg ttcatggaca aagctgaaca    5340
caccgctttg gtccgcgaac tcatcgacgc tgtcaagaaa gaaccggtac agccgtggaa    5400
tggcaaaaaa gtcatcctct ccggtatcat ggcagaaccg gatgaattcc tcgatatctt    5460
cagcgaattc aacatcgctg tcgtcgctga cgacctcgct caggaatccc gccagttccg    5520
tacagacgta ccgtccggca tcgatcccct cgaacagctc gctcagcagt ggcaggactt    5580
cgatggctgc ccgctcgctt tgaacgaaga caaaccgcgt ggccagatgc tcatcgacat    5640
gactaagaaa tacaatgctg acgccgtcgt catctgcatg atgcgtttct gcgatcctga    5700
agaattcgac tatccgattt acaaaccgga atttgaagct gctggcgttc gttacacggt    5760
cctcgacctc gacatcgaat ctccgtccct cgaacagctc cgcacccgta tccaggcttt    5820
ctcggaaatc ctctaagaat cgcctgaatc atcaaacatc tgggcgggac tccgaaggt    5880
gcctgctaca tgatacattg cctgttttca ggcagacaga tttgcagctt gcggccccca    5940
ttgtacgggc tgcaagctgt caatgatgct ttaaagacgg ctctgccgtt tttaaataaa    6000
aacataaaac catatataat ctattaggag gaaactcaat catggaattc aaactttctg    6060
aattacagca agatatcgca aatctcgcaa aagatttcgc agaaaaaaaa ttagctccca    6120
ctgtcaaaga gcgtgacgaa aaagaagttt tcgatcgtgc tatccttgac gaagtgggta    6180
ctctcggcct tctcggtatt ccctgggaag aagaaacgg cggcgtaggc gctgacttcc    6240
tcagcctcgc agttgcttgc gaagaagtag ctaaagttac cagcccgggc cgtcg         6295
```

<210> SEQ ID NO 34
<211> LENGTH: 915
<212> TYPE: DNA
<213> ORGANISM: Megasphaera elsdenii

<400> SEQUENCE: 34

```
atgaaaccaa tgagactaca tcacgtaggc attgtcctgc cgaccttaga aaaagcccat      60
gaattcatgc agaataatgg acttgaaatc gactatgccg gctatgtcga tgcttaccag     120
gctgatctca ttttcactaa gtttggtgaa tttgccagcc cgattgaaat gattatcccg     180
cactccggtg tgcttaccca attcaatggt ggccgcggcg gcattgccca tcgccttc      240
gaagtggacg atgtcgaagc tgtccgccag gaaatggaag cagattgtcc gggatgcatg     300
ttagaaaaga aagctgtcca gggtacggac gacattatcg tcaacttccg ccgcccgaca     360
accaaccagg gtatcctcgt tgaatatgtt cagacgacag cacctatcac cggccgcggc     420
gaaaatcctt tcgttaagaa tctcggcccg gaaaagggga agctcaacga aacatggcat     480
cccatgcgcc tgcaccatat cggcatcgtc ttgccgacct tggaaaaggc ccatgaattc     540
atcaagacca atggtctgga agtggattat tccggtttcg tcgacgccta ccatgcggat     600
ctcattttca ctaaaaaagg tgaaaacagt acgcctatcg aattcattat tccccgtgaa     660
ggggtcctca agatttcaa tcatggcagg ggaggtatcg ctcatatcgc ctttgaagtg     720
gatgatgtcg aaaaggtacg tcagattatg gaaagccaga agcctggttg catgctcgaa     780
aagaaagccg tccggggaac ggacgatatc atcgtcaact tccgccgtcc cagcacggac     840
gccggcatcc tcgtcgaata tgtccagacc gtagctccca tcaatcgcag caatcccaac     900
cctttaatg attga                                                       915
```

<210> SEQ ID NO 35
<211> LENGTH: 304
<212> TYPE: PRT
<213> ORGANISM: Megasphaera elsdenii

<400> SEQUENCE: 35

```
Met Lys Pro Met Arg Leu His His Val Gly Ile Val Leu Pro Thr Leu
1               5                   10                  15

Glu Lys Ala His Glu Phe Met Gln Asn Asn Gly Leu Glu Ile Asp Tyr
            20                  25                  30

Ala Gly Tyr Val Asp Ala Tyr Gln Ala Asp Leu Ile Phe Thr Lys Phe
        35                  40                  45

Gly Glu Phe Ala Ser Pro Ile Glu Met Ile Ile Pro His Ser Gly Val
    50                  55                  60

Leu Thr Gln Phe Asn Gly Gly Arg Gly Gly Ile Ala His Ile Ala Phe
65                  70                  75                  80

Glu Val Asp Asp Val Glu Ala Val Arg Gln Glu Met Glu Ala Asp Cys
                85                  90                  95

Pro Gly Cys Met Leu Glu Lys Lys Ala Val Gln Gly Thr Asp Asp Ile
            100                 105                 110

Ile Val Asn Phe Arg Arg Pro Thr Thr Asn Gln Gly Ile Leu Val Glu
        115                 120                 125

Tyr Val Gln Thr Thr Ala Pro Ile Thr Gly Arg Gly Glu Asn Pro Phe
    130                 135                 140

Val Lys Asn Leu Gly Pro Glu Lys Gly Lys Leu Asn Glu Thr Trp His
145                 150                 155                 160

Pro Met Arg Leu His His Ile Gly Ile Val Leu Pro Thr Leu Glu Lys
                165                 170                 175

Ala His Glu Phe Ile Lys Thr Asn Gly Leu Glu Val Asp Tyr Ser Gly
            180                 185                 190

Phe Val Asp Ala Tyr His Ala Asp Leu Ile Phe Thr Lys Lys Gly Glu
        195                 200                 205
```

Asn Ser Thr Pro Ile Glu Phe Ile Ile Pro Arg Glu Gly Val Leu Lys
    210                 215                 220

Asp Phe Asn His Gly Arg Gly Gly Ile Ala His Ile Ala Phe Glu Val
225                 230                 235                 240

Asp Asp Val Glu Lys Val Arg Gln Ile Met Glu Ser Gln Lys Pro Gly
                245                 250                 255

Cys Met Leu Glu Lys Lys Ala Val Arg Gly Thr Asp Ile Ile Val
                260                 265                 270

Asn Phe Arg Arg Pro Ser Thr Asp Ala Gly Ile Leu Val Glu Tyr Val
            275                 280                 285

Gln Thr Val Ala Pro Ile Asn Arg Ser Asn Pro Asn Pro Phe Asn Asp
    290                 295                 300

<210> SEQ ID NO 36
<211> LENGTH: 254
<212> TYPE: DNA
<213> ORGANISM: Megasphaera elsdenii

<400> SEQUENCE: 36
atggaattca aactttctga attacagcaa gatatcgcaa atctcgcaaa agatttcgca      60 gaaaaaaat tagctcccac tgtcaaagag cgtgacgaaa agaagttttt cgatcgtgct     120
atccttgacg aagtgggtac tctcggcctt ctcggtattc cctgggaaga gaaaacggc    180 ggcgtaggcg ctgacttcct cagcctcgca gttgcttgcg aagaagtagc taaagttacc   240
agcccgggcc gtcg                                                      254

<210> SEQ ID NO 37
<211> LENGTH: 84
<212> TYPE: PRT
<213> ORGANISM: Megasphaera elsdenii

<400> SEQUENCE: 37

Met Glu Phe Lys Leu Ser Glu Leu Gln Gln Asp Ile Ala Asn Leu Ala
1               5                   10                  15

Lys Asp Phe Ala Glu Lys Lys Leu Ala Pro Thr Val Lys Glu Arg Asp
                20                  25                  30

Glu Lys Glu Val Phe Asp Arg Ala Ile Leu Asp Glu Val Gly Thr Leu
            35                  40                  45

Gly Leu Leu Gly Ile Pro Trp Glu Glu Glu Asn Gly Gly Val Gly Ala
        50                  55                  60

Asp Phe Leu Ser Leu Ala Val Ala Cys Glu Glu Val Ala Lys Val Thr
65                  70                  75                  80

Ser Pro Gly Arg

<210> SEQ ID NO 38
<211> LENGTH: 6141
<212> TYPE: DNA
<213> ORGANISM: Chloroflexus aurantiacus
<220> FEATURE:
<221> NAME/KEY: CDS
<222> LOCATION: (480)..(5945)

<400> SEQUENCE: 38
gtgagcacac acttgatagc tgatgccgtc aatgatcagt tgttcgtcta tagcaggctg      60
aaaggacatg ggtttggtca cagtctgagc agttgcaggc agtcaaacac gttcgtaact     120
acgctgtaga tgatataagc agtataccat cttgctacgc tctcgttgat caggttgaat    180
gctttgagga aggtcaggcg aatagccatg cctcttgttt ccagaacatg gcatggggat    240

-continued

```
ggatcgacgg taccctgtcg gatgcatgct atgcgtggca ttcatatcat caaccagaat    300
ttgatcttga actacacagc aattctgcgc gttatgcaag tgtcttcggt cagatggtga    360
acaattctca attgttgagg tcttgacgaa ttgcgttata cactgtaggc tatagtatgc    420
accccttgtt atctatatca caaccggtct attagcattt gcgtcaagga ggatggtcg     479
```

```
atg atc gac act gcg ccc ctt gcc cca cca cgg gcg ccc cgc tct aat      527
Met Ile Asp Thr Ala Pro Leu Ala Pro Pro Arg Ala Pro Arg Ser Asn
1               5                   10                  15 ccg att cgg gat cga gtt gat tgg gaa gct cag cgc gct gct gcg ctg      575
Pro Ile Arg Asp Arg Val Asp Trp Glu Ala Gln Arg Ala Ala Ala Leu
            20                  25                  30 gca gat ccc ggt gcc ttt cat ggc gcg att gcc cgg aca gtt atc cac      623
Ala Asp Pro Gly Ala Phe His Gly Ala Ile Ala Arg Thr Val Ile His
        35                  40                  45 tgg tac gac cca caa cac cat tgc tgg att cgc ttc aac gag tct agt      671
Trp Tyr Asp Pro Gln His His Cys Trp Ile Arg Phe Asn Glu Ser Ser
    50                  55                  60 cag cgt tgg gaa ggg ctg gat gcc gct acc ggt gcc cct gta acg gta      719
Gln Arg Trp Glu Gly Leu Asp Ala Ala Thr Gly Ala Pro Val Thr Val
65              70                  75                  80 gac tat ccc gcc gat tat cag ccc tgg caa cag gcg ttt gat gat agt      767
Asp Tyr Pro Ala Asp Tyr Gln Pro Trp Gln Gln Ala Phe Asp Asp Ser
                85                  90                  95 gaa gcg ccg ttt tac cgc tgg ttt agt ggt ggg ttg aca aat gcc tgc      815
Glu Ala Pro Phe Tyr Arg Trp Phe Ser Gly Gly Leu Thr Asn Ala Cys
            100                 105                 110 ttt aat gaa gta gac cgg cat gtc atg atg ggc tat ggc gac gag gtg      863
Phe Asn Glu Val Asp Arg His Val Met Met Gly Tyr Gly Asp Glu Val
        115                 120                 125 gcc tac tac ttt gaa ggt gac cgc tgg gat aac tcg ctc aac aat ggt      911
Ala Tyr Tyr Phe Glu Gly Asp Arg Trp Asp Asn Ser Leu Asn Asn Gly
    130                 135                 140 cgt ggt ggt ccg gtt gtc cag gag aca atc acg cgg cgg cgc ctg ttg      959
Arg Gly Gly Pro Val Val Gln Glu Thr Ile Thr Arg Arg Arg Leu Leu
145                 150                 155                 160 gtg gag gtg gtg aag gct gcg cag gtg ttg cgt gat ctg ggc ctg aag      1007
Val Glu Val Val Lys Ala Ala Gln Val Leu Arg Asp Leu Gly Leu Lys
                165                 170                 175 aag ggt gat cgg att gct ctg aat atg ccg aat att atg ccg cag att      1055
Lys Gly Asp Arg Ile Ala Leu Asn Met Pro Asn Ile Met Pro Gln Ile
            180                 185                 190 tat tat acg gaa gcg gca aaa cga ctg ggt att ctg tac acg ccg gtc      1103
Tyr Tyr Thr Glu Ala Ala Lys Arg Leu Gly Ile Leu Tyr Thr Pro Val
        195                 200                 205 ttc ggt ggc ttc tcg gac aag act ctt tcc gac cgt att cac aat gcc      1151
Phe Gly Gly Phe Ser Asp Lys Thr Leu Ser Asp Arg Ile His Asn Ala
    210                 215                 220 ggt gca cga gtg gtg att acc tct gat ggt gcg tac cgc aac gcg cag      1199
Gly Ala Arg Val Val Ile Thr Ser Asp Gly Ala Tyr Arg Asn Ala Gln
225                 230                 235                 240 gtg gtg ccc tac aaa gaa gcg tat acc gat cag gcg ctc gat aag tat      1247
Val Val Pro Tyr Lys Glu Ala Tyr Thr Asp Gln Ala Leu Asp Lys Tyr
                245                 250                 255 att ccg gtt gag acg gcg cag gcg att gtt gcg cag acc ctg gcc acc      1295
Ile Pro Val Glu Thr Ala Gln Ala Ile Val Ala Gln Thr Leu Ala Thr
            260                 265                 270 ttg ccc ctg act gag tcg cag cgc cag acg atc atc acc gaa gtg gag      1343
Leu Pro Leu Thr Glu Ser Gln Arg Gln Thr Ile Ile Thr Glu Val Glu
        275                 280                 285
```

```
gcc gca ctg gcc ggt gag att acg gtt gag cgc tcg gac gtg atg cgt    1391
Ala Ala Leu Ala Gly Glu Ile Thr Val Glu Arg Ser Asp Val Met Arg
290             295                 300 ggg gtt ggt tct gcc ctc gca aag ctc cgc gat ctt gat gca agc gtg    1439
Gly Val Gly Ser Ala Leu Ala Lys Leu Arg Asp Leu Asp Ala Ser Val
305                 310                 315                 320 cag gca aag gtg cgt aca gta ctg gcg cag gcg ctg gtc gag tcg ccg    1487
Gln Ala Lys Val Arg Thr Val Leu Ala Gln Ala Leu Val Glu Ser Pro
        325                 330                 335 ccg cgg gtt gaa gct gtg gtg gtt gtg cgt cat acc ggt cag gag att    1535
Pro Arg Val Glu Ala Val Val Val Val Arg His Thr Gly Gln Glu Ile
    340                 345                 350 ttg tgg aac gag ggg cga gat cgc tgg agt cac gac ttg ctg gat gct    1583
Leu Trp Asn Glu Gly Arg Asp Arg Trp Ser His Asp Leu Leu Asp Ala
355                 360                 365 gcg ctg gcg aag att ctg gcc aat gcg cgt gct gcc ggc ttt gat gtg    1631
Ala Leu Ala Lys Ile Leu Ala Asn Ala Arg Ala Ala Gly Phe Asp Val
370                 375                 380 cac agt gag aat gat ctg ctc aat ctc ccc gat gac cag ctt atc cgt    1679
His Ser Glu Asn Asp Leu Leu Asn Leu Pro Asp Asp Gln Leu Ile Arg
385                 390                 395                 400 gcg ctc tac gcc agt att ccc tgt gaa ccg gtt gat gct gaa tat ccg    1727
Ala Leu Tyr Ala Ser Ile Pro Cys Glu Pro Val Asp Ala Glu Tyr Pro
                405                 410                 415 atg ttt atc att tac aca tcg ggt agc acc ggt aag ccc aag ggt gtg    1775
Met Phe Ile Ile Tyr Thr Ser Gly Ser Thr Gly Lys Pro Lys Gly Val
        420                 425                 430 atc cac gtt cac ggc ggt tat gtc gcc ggt gtg gtg cac acc ttg cgg    1823
Ile His Val His Gly Gly Tyr Val Ala Gly Val Val His Thr Leu Arg
    435                 440                 445 gtc agt ttt gac gcc gag ccg ggt gat acg ata tat gtg atc gcc gat    1871
Val Ser Phe Asp Ala Glu Pro Gly Asp Thr Ile Tyr Val Ile Ala Asp
450                 455                 460 ccg ggc tgg atc acc ggt cag agc tat atg ctc aca gcc aca atg gcc    1919
Pro Gly Trp Ile Thr Gly Gln Ser Tyr Met Leu Thr Ala Thr Met Ala
465                 470                 475                 480 ggt cgg ctg acc ggg gtg att gcc gag gga tca ccg ctc ttc ccc tca    1967
Gly Arg Leu Thr Gly Val Ile Ala Glu Gly Ser Pro Leu Phe Pro Ser
                485                 490                 495 gcc ggg cgt tat gcc agc atc atc gag cgc tat ggg gtg cag atc ttt    2015
Ala Gly Arg Tyr Ala Ser Ile Ile Glu Arg Tyr Gly Val Gln Ile Phe
        500                 505                 510 aag gcg ggt gtg acc ttc ctc aag aca gtg atg tcc aat ccg cag aat    2063
Lys Ala Gly Val Thr Phe Leu Lys Thr Val Met Ser Asn Pro Gln Asn
    515                 520                 525 gtt gaa gat gtg cga ctc tat gat atg cac tcg ctg cgg gtt gca acc    2111
Val Glu Asp Val Arg Leu Tyr Asp Met His Ser Leu Arg Val Ala Thr
530                 535                 540 ttc tgc gcc gag ccg gtc agt ccg gcg gtg cag cag ttt ggt atg cag    2159
Phe Cys Ala Glu Pro Val Ser Pro Ala Val Gln Gln Phe Gly Met Gln
545                 550                 555                 560 atc atg acc ccg cag tat atc aat tcg tac tgg gcg acc gag cac ggt    2207
Ile Met Thr Pro Gln Tyr Ile Asn Ser Tyr Trp Ala Thr Glu His Gly
                565                 570                 575 gga att gtc tgg acg cat ttc tac ggt aat cag gac ttc ccg ctt cgt    2255
Gly Ile Val Trp Thr His Phe Tyr Gly Asn Gln Asp Phe Pro Leu Arg
        580                 585                 590 ccc gat gcc cat acc tat ccc ttg ccc tgg gtg atg ggt gat gtc tgg    2303
Pro Asp Ala His Thr Tyr Pro Leu Pro Trp Val Met Gly Asp Val Trp
    595                 600                 605
```

| | | |
|---|---|---|
| gtg gcc gaa act gat gag agc ggg acg acg cgc tat cgg gtc gct gat<br>Val Ala Glu Thr Asp Glu Ser Gly Thr Thr Arg Tyr Arg Val Ala Asp<br>610                     615                             620 | 2351 |
| ttc gat gag aag ggc gag att gtg att acc gcc ccg tat ccc tac ctg<br>Phe Asp Glu Lys Gly Glu Ile Val Ile Thr Ala Pro Tyr Pro Tyr Leu<br>625                   630                     635                   640 | 2399 |
| acc cgc aca ctc tgg ggt gat gtg ccc ggt ttc gag gcg tac ctg cgc<br>Thr Arg Thr Leu Trp Gly Asp Val Pro Gly Phe Glu Ala Tyr Leu Arg<br>                   645                     650                   655 | 2447 |
| ggt gag att ccg ctg cgg gcc tgg aag ggt gat gcc gag cgt ttc gtc<br>Gly Glu Ile Pro Leu Arg Ala Trp Lys Gly Asp Ala Glu Arg Phe Val<br>660                     665                          670 | 2495 |
| aag acc tac tgg cga cgt ggg cca aac ggt gaa tgg ggc tat atc cag<br>Lys Thr Tyr Trp Arg Arg Gly Pro Asn Gly Glu Trp Gly Tyr Ile Gln<br>               675                     680                   685 | 2543 |
| ggt gat ttt gcc atc aag tac ccc gat ggt agc ttc acg ctc cac gga<br>Gly Asp Phe Ala Ile Lys Tyr Pro Asp Gly Ser Phe Thr Leu His Gly<br>690                     695                     700 | 2591 |
| cgc cct gac gat gtg atc aat gtg tcg ggc cac cgt atg ggc acc gag<br>Arg Pro Asp Asp Val Ile Asn Val Ser Gly His Arg Met Gly Thr Glu<br>705                     710                     715                   720 | 2639 |
| gag att gag ggt gcc att ttg cgt gac cgc cag atc acg ccc gac tcg<br>Glu Ile Glu Gly Ala Ile Leu Arg Asp Arg Gln Ile Thr Pro Asp Ser<br>                   725                     730                   735 | 2687 |
| ccc gtc ggt aat tgt att gtg gtc ggt gcg ccg cac cgt gag aag ggt<br>Pro Val Gly Asn Cys Ile Val Val Gly Ala Pro His Arg Glu Lys Gly<br>               740                     745                   750 | 2735 |
| ctg acc ccg gtt gcc ttc att caa cct gcg cct ggc cgt cat ctg acc<br>Leu Thr Pro Val Ala Phe Ile Gln Pro Ala Pro Gly Arg His Leu Thr<br>755                     760                          765 | 2783 |
| ggc gcc gac cgg cgc cgt ctc gat gag ctg gtg cgt acc gag aag ggg<br>Gly Ala Asp Arg Arg Arg Leu Asp Glu Leu Val Arg Thr Glu Lys Gly<br>770                     775                     780 | 2831 |
| gcg gtc agt gtc cca gag gat tac atc gag gtc agt gcc ttt ccc gaa<br>Ala Val Ser Val Pro Glu Asp Tyr Ile Glu Val Ser Ala Phe Pro Glu<br>785                     790                     795                   800 | 2879 |
| acc cgc agc ggg aag tat atg cgg cgc ttt ttg cgc aat atg atg ctc<br>Thr Arg Ser Gly Lys Tyr Met Arg Arg Phe Leu Arg Asn Met Met Leu<br>                   805                     810                   815 | 2927 |
| gat gaa cca ctg ggt gat acg acg ttg cgc aat cct gaa gtg ctc<br>Asp Glu Pro Leu Gly Asp Thr Thr Thr Leu Arg Asn Pro Glu Val Leu<br>820                     825                     830 | 2975 |
| gaa gag att gca gcc aag atc gct gag tgg aaa cgc gtc cag cgt atg<br>Glu Glu Ile Ala Ala Lys Ile Ala Glu Trp Lys Arg Val Gln Arg Met<br>835                     840                     845 | 3023 |
| gcc gaa gag cag cag atc atc gaa cgc tat cgc tac ttc cgg atc gag<br>Ala Glu Glu Gln Gln Ile Ile Glu Arg Tyr Arg Tyr Phe Arg Ile Glu<br>850                     855                     860 | 3071 |
| tat cac cca cca acg gcc agt gcg ggt aaa ctc gcg gta gtg acg gtg<br>Tyr His Pro Pro Thr Ala Ser Ala Gly Lys Leu Ala Val Val Thr Val<br>865                     870                     875                   880 | 3119 |
| aca aat ccg ccg gtg aac gca ctg aat gag cgt gcg ctc gat gag ttg<br>Thr Asn Pro Pro Val Asn Ala Leu Asn Glu Arg Ala Leu Asp Glu Leu<br>                     885                     890                   895 | 3167 |
| aac aca att gtt gac cac ctg gcc cgt cgt cag gat gtt gcc gca att<br>Asn Thr Ile Val Asp His Leu Ala Arg Arg Gln Asp Val Ala Ala Ile<br>                     900                     905                   910 | 3215 |
| gtc ttc acc gga cag ggc gcc agg agt ttt gtc gcc ggc gct gat att<br>Val Phe Thr Gly Gln Gly Ala Arg Ser Phe Val Ala Gly Ala Asp Ile<br>               915                     920                   925 | 3263 |

```
cgc cag ttg ctc gaa gag att cat acg gtt gaa gag gca atg gcc ctg      3311
Arg Gln Leu Leu Glu Glu Ile His Thr Val Glu Glu Ala Met Ala Leu
        930                 935                 940 ccg aat aac gcc cat ctt gct ttc cgc aag att gag cgt atg aat aag      3359
Pro Asn Asn Ala His Leu Ala Phe Arg Lys Ile Glu Arg Met Asn Lys
945                 950                 955                 960 ccg tgt atc gcg gcg atc aac ggt gtg gcg ctc ggt ggt ggt ctg gaa      3407
Pro Cys Ile Ala Ala Ile Asn Gly Val Ala Leu Gly Gly Gly Leu Glu
                965                 970                 975 ttc gcc atg gcc tgc cat tac cgg gtt gcc gat gtc tat gcc gaa ttc      3455
Phe Ala Met Ala Cys His Tyr Arg Val Ala Asp Val Tyr Ala Glu Phe
            980                 985                 990 ggt cag cca gag att aat ctg cgc ttg cta cct ggt tat ggt ggc acg      3503
Gly Gln Pro Glu Ile Asn Leu Arg Leu Leu Pro Gly Tyr Gly Gly Thr
        995                 1000                1005 cag cgc ttg ccg cgc ctg ttg tac aag cgc aac aac ggc acc ggt          3548
Gln Arg Leu Pro Arg Leu Leu Tyr Lys Arg Asn Asn Gly Thr Gly
    1010                1015                1020 ctg ctc cga gcg ctg gag atg att ctg ggt ggg cgt agc gta ccg          3593
Leu Leu Arg Ala Leu Glu Met Ile Leu Gly Gly Arg Ser Val Pro
    1025                1030                1035 gct gat gag gcg ctg aag ctg ggt ctg atc gat gcc att gct acc          3638
Ala Asp Glu Ala Leu Lys Leu Gly Leu Ile Asp Ala Ile Ala Thr
    1040                1045                1050 ggc gat cag gac tca ctg tcg ctg gca tgc gcg tta gcc cgt gcc          3683
Gly Asp Gln Asp Ser Leu Ser Leu Ala Cys Ala Leu Ala Arg Ala
    1055                1060                1065 gca atc ggc gcc gat ggt cag ttg atc gag tcg gct gcg gtg acc          3728
Ala Ile Gly Ala Asp Gly Gln Leu Ile Glu Ser Ala Ala Val Thr
    1070                1075                1080 cag gct ttc cgc cat cgc cac gag cag ctt gac gag tgg cgc aaa          3773
Gln Ala Phe Arg His Arg His Glu Gln Leu Asp Glu Trp Arg Lys
    1085                1090                1095 cca gac ccg cgc ttt gcc gat gac gaa ctg cgc tcg att atc gcc          3818
Pro Asp Pro Arg Phe Ala Asp Asp Glu Leu Arg Ser Ile Ile Ala
    1100                1105                1110 cat cca cgt atc gag cgg att atc cgg cag gcc cat acc gtt ggg          3863
His Pro Arg Ile Glu Arg Ile Ile Arg Gln Ala His Thr Val Gly
    1115                1120                1125 cgc gat gcg gca gtg cat cgg gca ctg gat gca atc cgc tat ggc          3908
Arg Asp Ala Ala Val His Arg Ala Leu Asp Ala Ile Arg Tyr Gly
    1130                1135                1140 att atc cac ggc ttc gag gcc ggt ctg gag cac gag gcg aag ctc          3953
Ile Ile His Gly Phe Glu Ala Gly Leu Glu His Glu Ala Lys Leu
    1145                1150                1155 ttt gcc gag gca gtg gtt gac ccg aac ggt ggc aag cgt ggt att          3998
Phe Ala Glu Ala Val Val Asp Pro Asn Gly Gly Lys Arg Gly Ile
    1160                1165                1170 cgc gag ttc ctc gac cgc cag agt gcg ccg ttg cca acc cgc cga          4043
Arg Glu Phe Leu Asp Arg Gln Ser Ala Pro Leu Pro Thr Arg Arg
    1175                1180                1185 cca ttg att aca cct gaa cag gag caa ctc ttg cgc gat cag aaa          4088
Pro Leu Ile Thr Pro Glu Gln Glu Gln Leu Leu Arg Asp Gln Lys
    1190                1195                1200 gaa ctg ttg ccg gtt ggt tca ccc ttc ttc ccc ggt gtt gac cgg          4133
Glu Leu Leu Pro Val Gly Ser Pro Phe Phe Pro Gly Val Asp Arg
    1205                1210                1215 att ccg aag tgg cag tac gcg cag gcg gtt att cgt gat ccg gac          4178
Ile Pro Lys Trp Gln Tyr Ala Gln Ala Val Ile Arg Asp Pro Asp
    1220                1225                1230
```

```
acc ggt gcg gcg gct cac ggc gat ccc atc gtg gct gaa aag cag    4223
Thr Gly Ala Ala Ala His Gly Asp Pro Ile Val Ala Glu Lys Gln
    1235                1240                1245 att att gtg ccg gtg gaa cgc ccc cgc gcc aat cag gcg ctg atc    4268
Ile Ile Val Pro Val Glu Arg Pro Arg Ala Asn Gln Ala Leu Ile
    1250                1255                1260 tat gtt ctg gcc tcg gag gtg aac ttc aac gat atc tgg gcg att    4313
Tyr Val Leu Ala Ser Glu Val Asn Phe Asn Asp Ile Trp Ala Ile
    1265                1270                1275 acc ggt att ccg gtg tca cgg ttt gat gag cac gac cgc gac tgg    4358
Thr Gly Ile Pro Val Ser Arg Phe Asp Glu His Asp Arg Asp Trp
    1280                1285                1290 cac gtt acc ggt tca ggt ggc atc ggc ctg atc gtt gcg ctg ggt    4403
His Val Thr Gly Ser Gly Gly Ile Gly Leu Ile Val Ala Leu Gly
    1295                1300                1305 gaa gag gcg cga cgc gaa ggc cgg ctg aag gtg ggt gat ctg gtg    4448
Glu Glu Ala Arg Arg Glu Gly Arg Leu Lys Val Gly Asp Leu Val
    1310                1315                1320 gcg atc tac tcc ggg cag tcg gat ctg ctc tca ccg ctg atg ggc    4493
Ala Ile Tyr Ser Gly Gln Ser Asp Leu Leu Ser Pro Leu Met Gly
    1325                1330                1335 ctt gat ccg atg gcc gcc gat ttc gtc atc cag ggg aac gac acg    4538
Leu Asp Pro Met Ala Ala Asp Phe Val Ile Gln Gly Asn Asp Thr
    1340                1345                1350 cca gat gga tcg cat cag caa ttt atg ctg gcc cag gcc ccg cag    4583
Pro Asp Gly Ser His Gln Gln Phe Met Leu Ala Gln Ala Pro Gln
    1355                1360                1365 tgt ctg ccc atc cca acc gat atg tct atc gag gca gcc ggc agc    4628
Cys Leu Pro Ile Pro Thr Asp Met Ser Ile Glu Ala Ala Gly Ser
    1370                1375                1380 tac atc ctc aat ctc ggt acg atc tat cgc gcc ctc ttt acg acg    4673
Tyr Ile Leu Asn Leu Gly Thr Ile Tyr Arg Ala Leu Phe Thr Thr
    1385                1390                1395 ttg caa atc aag gcc gga cgc acc atc ttt atc gag ggt gcg gcg    4718
Leu Gln Ile Lys Ala Gly Arg Thr Ile Phe Ile Glu Gly Ala Ala
    1400                1405                1410 acc ggt acc ggt ctg gac gca gcg cgc tcg gcg gcc cgg aat ggt    4763
Thr Gly Thr Gly Leu Asp Ala Ala Arg Ser Ala Ala Arg Asn Gly
    1415                1420                1425 ctg cgc gta att gga atg gtc agt tcg tcg tca cgt gcg tct acg    4808
Leu Arg Val Ile Gly Met Val Ser Ser Ser Ser Arg Ala Ser Thr
    1430                1435                1440 ctg ctg gct gcg ggt gcc cac ggt gcg att aac cgt aaa gac ccg    4853
Leu Leu Ala Ala Gly Ala His Gly Ala Ile Asn Arg Lys Asp Pro
    1445                1450                1455 gag gtt gcc gat tgt ttc acg cgc gtg ccc gaa gat cca tca gcc    4898
Glu Val Ala Asp Cys Phe Thr Arg Val Pro Glu Asp Pro Ser Ala
    1460                1465                1470 tgg gca gcc tgg gaa gcc gcc ggt cag ccg ttg ctg gcg atg ttc    4943
Trp Ala Ala Trp Glu Ala Ala Gly Gln Pro Leu Leu Ala Met Phe
    1475                1480                1485 cgg gcg cag aac gac ggg cga ctg gcc gat tat gtg gtc tcg cac    4988
Arg Ala Gln Asn Asp Gly Arg Leu Ala Asp Tyr Val Val Ser His
    1490                1495                1500 gcg ggc gag acg gcc ttc ccg cgc agt ttc cag ctt ctc ggc gag    5033
Ala Gly Glu Thr Ala Phe Pro Arg Ser Phe Gln Leu Leu Gly Glu
    1505                1510                1515 cca cgc gat ggt cac att ccg acg ctc aca ttc tac ggt gcc acc    5078
Pro Arg Asp Gly His Ile Pro Thr Leu Thr Phe Tyr Gly Ala Thr
    1520                1525                1530
```

| | | | | | | | | | | | | |
|---|---|---|---|---|---|---|---|---|---|---|---|---|
| agt | ggc | tac | cac | ttc | acc | ttc | ctg | ggt | aag | cca | ggg | tca gct tcg | 5123 |
| Ser | Gly | Tyr | His | Phe | Thr | Phe | Leu | Gly | Lys | Pro | Gly | Ser Ala Ser |
| | 1535 | | | | 1540 | | | | 1545 | | | |
| ccg | acc | gag | atg | ctg | cgg | cgg | gcc | aat | ctc | cgc | gcc | ggt gag gcg | 5168 |
| Pro | Thr | Glu | Met | Leu | Arg | Arg | Ala | Asn | Leu | Arg | Ala | Gly Glu Ala |
| | 1550 | | | | 1555 | | | | 1560 | | | |
| gtg | ttg | atc | tac | tac | ggg | gtt | ggg | agc | gat | gac | ctg | gta gat acc | 5213 |
| Val | Leu | Ile | Tyr | Tyr | Gly | Val | Gly | Ser | Asp | Asp | Leu | Val Asp Thr |
| | 1565 | | | | 1570 | | | | 1575 | | | |
| ggc | ggt | ctg | gag | gct | atc | gag | gcg | gcg | cgg | caa | atg | gga gcg cgg | 5258 |
| Gly | Gly | Leu | Glu | Ala | Ile | Glu | Ala | Ala | Arg | Gln | Met | Gly Ala Arg |
| | 1580 | | | | 1585 | | | | 1590 | | | |
| atc | gtc | gtc | gtt | acc | gtc | agc | gat | gcg | caa | cgc | gag | ttt gtc ctc | 5303 |
| Ile | Val | Val | Val | Thr | Val | Ser | Asp | Ala | Gln | Arg | Glu | Phe Val Leu |
| | 1595 | | | | 1600 | | | | 1605 | | | |
| tcg | ttg | ggc | ttc | ggg | gct | gcc | cta | cgt | ggt | gtc | gtc | agc ctg gcg | 5348 |
| Ser | Leu | Gly | Phe | Gly | Ala | Ala | Leu | Arg | Gly | Val | Val | Ser Leu Ala |
| | 1610 | | | | 1615 | | | | 1620 | | | |
| gaa | ctc | aaa | cgg | cgc | ttc | ggc | gat | gag | ttt | gag | tgg | ccg cgc acg | 5393 |
| Glu | Leu | Lys | Arg | Arg | Phe | Gly | Asp | Glu | Phe | Glu | Trp | Pro Arg Thr |
| | 1625 | | | | 1630 | | | | 1635 | | | |
| atg | ccg | ccg | ttg | ccg | aac | gcc | cgc | cag | gac | ccg | cag | ggt ctg aaa | 5438 |
| Met | Pro | Pro | Leu | Pro | Asn | Ala | Arg | Gln | Asp | Pro | Gln | Gly Leu Lys |
| | 1640 | | | | 1645 | | | | 1650 | | | |
| gag | gct | gtc | cgc | cgc | ttc | aac | gat | ctg | gtc | ttc | aag | ccg cta gga | 5483 |
| Glu | Ala | Val | Arg | Arg | Phe | Asn | Asp | Leu | Val | Phe | Lys | Pro Leu Gly |
| | 1655 | | | | 1660 | | | | 1665 | | | |
| agc | gcg | gtc | ggt | gtc | ttc | ttg | cgg | agt | gcc | gac | aat | ccg cgt ggc | 5528 |
| Ser | Ala | Val | Gly | Val | Phe | Leu | Arg | Ser | Ala | Asp | Asn | Pro Arg Gly |
| | 1670 | | | | 1675 | | | | 1680 | | | |
| tac | ccc | gat | ctg | atc | atc | gag | cgg | gct | gcc | cac | gat | gca ctg gcg | 5573 |
| Tyr | Pro | Asp | Leu | Ile | Ile | Glu | Arg | Ala | Ala | His | Asp | Ala Leu Ala |
| | 1685 | | | | 1690 | | | | 1695 | | | |
| gtg | agc | gcg | atg | ctg | atc | aag | ccc | ttc | acc | gga | cgg | att gtc tac | 5618 |
| Val | Ser | Ala | Met | Leu | Ile | Lys | Pro | Phe | Thr | Gly | Arg | Ile Val Tyr |
| | 1700 | | | | 1705 | | | | 1710 | | | |
| ttc | gag | gac | att | ggt | ggg | cgg | cgt | tac | tcc | ttc | ttc | gca ccg caa | 5663 |
| Phe | Glu | Asp | Ile | Gly | Gly | Arg | Arg | Tyr | Ser | Phe | Phe | Ala Pro Gln |
| | 1715 | | | | 1720 | | | | 1725 | | | |
| atc | tgg | gtg | cgc | cag | cgc | cgc | atc | tac | atg | ccg | acg | gca cag atc | 5708 |
| Ile | Trp | Val | Arg | Gln | Arg | Arg | Ile | Tyr | Met | Pro | Thr | Ala Gln Ile |
| | 1730 | | | | 1735 | | | | 1740 | | | |
| ttt | ggt | acg | cac | ctc | tca | aat | gcg | tat | gaa | att | ctg | cgt ctg aat | 5753 |
| Phe | Gly | Thr | His | Leu | Ser | Asn | Ala | Tyr | Glu | Ile | Leu | Arg Leu Asn |
| | 1745 | | | | 1750 | | | | 1755 | | | |
| gat | gag | atc | agc | gcc | ggt | ctg | ctg | acg | att | acc | gag | ccg gca gtg | 5798 |
| Asp | Glu | Ile | Ser | Ala | Gly | Leu | Leu | Thr | Ile | Thr | Glu | Pro Ala Val |
| | 1760 | | | | 1765 | | | | 1770 | | | |
| gtg | ccg | tgg | gat | gaa | cta | ccc | gaa | gca | cat | cag | gcg | atg tgg gaa | 5843 |
| Val | Pro | Trp | Asp | Glu | Leu | Pro | Glu | Ala | His | Gln | Ala | Met Trp Glu |
| | 1775 | | | | 1780 | | | | 1785 | | | |
| aat | cgc | cac | acg | gcg | gcc | act | tat | gtg | gtg | aat | cat | gcc tta cca | 5888 |
| Asn | Arg | His | Thr | Ala | Ala | Thr | Tyr | Val | Val | Asn | His | Ala Leu Pro |
| | 1790 | | | | 1795 | | | | 1800 | | | |
| cgt | ctc | ggc | cta | aag | aac | agg | gac | gag | ctg | tac | gag | gcg tgg acg | 5933 |
| Arg | Leu | Gly | Leu | Lys | Asn | Arg | Asp | Glu | Leu | Tyr | Glu | Ala Trp Thr |
| | 1805 | | | | 1810 | | | | 1815 | | | |
| gcc | ggc | gag | cgg | tagcgcggat | gggtattgaa | caggtaacgg | acggaagatc | | | | | | 5985 |
| Ala | Gly | Glu | Arg | | | | | | | | | |
| | 1820 | | | | | | | | | | | |

```
gaaccttccg tccgttatct tttggccgtc gaagcgtgct gagccgatta tcgttgccgt    6045
ggttgtcccg atgggcagac gcgctcgaac cagatgatac caccgacggc tatcgtcacc    6105
aaaccggcga agaccaggta agcctctgaa ggacgc                              6141
```

<210> SEQ ID NO 39
<211> LENGTH: 1822
<212> TYPE: PRT
<213> ORGANISM: Chloroflexus aurantiacus

<400> SEQUENCE: 39

```
Met Ile Asp Thr Ala Pro Leu Ala Pro Arg Ala Pro Arg Ser Asn
1               5                   10                  15

Pro Ile Arg Asp Arg Val Asp Trp Glu Ala Gln Arg Ala Ala Leu
            20                  25                  30

Ala Asp Pro Gly Ala Phe His Gly Ala Ile Ala Arg Thr Val Ile His
        35                  40                  45

Trp Tyr Asp Pro Gln His His Cys Trp Ile Arg Phe Asn Glu Ser Ser
    50                  55                  60

Gln Arg Trp Glu Gly Leu Asp Ala Ala Thr Gly Ala Pro Val Thr Val
65                  70                  75                  80

Asp Tyr Pro Ala Asp Tyr Gln Pro Trp Gln Gln Ala Phe Asp Ser
            85                  90                  95

Glu Ala Pro Phe Tyr Arg Trp Phe Ser Gly Gly Leu Thr Asn Ala Cys
        100                 105                 110

Phe Asn Glu Val Asp Arg His Val Met Met Gly Tyr Gly Asp Glu Val
    115                 120                 125

Ala Tyr Tyr Phe Glu Gly Asp Arg Trp Asp Asn Ser Leu Asn Asn Gly
130                 135                 140

Arg Gly Gly Pro Val Val Gln Glu Thr Ile Thr Arg Arg Leu Leu
145                 150                 155                 160

Val Glu Val Val Lys Ala Ala Gln Val Leu Arg Asp Leu Gly Leu Lys
            165                 170                 175

Lys Gly Asp Arg Ile Ala Leu Asn Met Pro Asn Ile Met Pro Gln Ile
        180                 185                 190

Tyr Tyr Thr Glu Ala Ala Lys Arg Leu Gly Ile Leu Tyr Thr Pro Val
    195                 200                 205

Phe Gly Gly Phe Ser Asp Lys Thr Leu Ser Asp Arg Ile His Asn Ala
210                 215                 220

Gly Ala Arg Val Val Ile Thr Ser Asp Gly Ala Tyr Arg Asn Ala Gln
225                 230                 235                 240

Val Val Pro Tyr Lys Glu Ala Tyr Thr Asp Gln Ala Leu Asp Lys Tyr
            245                 250                 255

Ile Pro Val Glu Thr Ala Gln Ala Ile Val Ala Gln Thr Leu Ala Thr
        260                 265                 270

Leu Pro Leu Thr Glu Ser Gln Arg Gln Thr Ile Ile Thr Glu Val Glu
    275                 280                 285

Ala Ala Leu Ala Gly Glu Ile Thr Val Glu Arg Ser Asp Val Met Arg
290                 295                 300

Gly Val Gly Ser Ala Leu Ala Lys Leu Arg Asp Leu Asp Ala Ser Val
305                 310                 315                 320

Gln Ala Lys Val Arg Thr Val Leu Ala Gln Ala Leu Val Glu Ser Pro
            325                 330                 335

Pro Arg Val Glu Ala Val Val Val Arg His Thr Gly Gln Glu Ile
        340                 345                 350
```

-continued

Leu Trp Asn Glu Gly Arg Asp Arg Trp Ser His Asp Leu Leu Asp Ala
            355                 360                 365

Ala Leu Ala Lys Ile Leu Ala Asn Ala Arg Ala Ala Gly Phe Asp Val
        370                 375                 380

His Ser Glu Asn Asp Leu Leu Asn Leu Pro Asp Asp Gln Leu Ile Arg
385                 390                 395                 400

Ala Leu Tyr Ala Ser Ile Pro Cys Glu Pro Val Asp Ala Glu Tyr Pro
                405                 410                 415

Met Phe Ile Ile Tyr Thr Ser Gly Ser Thr Gly Lys Pro Lys Gly Val
            420                 425                 430

Ile His Val His Gly Gly Tyr Val Ala Gly Val Val His Thr Leu Arg
        435                 440                 445

Val Ser Phe Asp Ala Glu Pro Gly Asp Thr Ile Tyr Val Ile Ala Asp
    450                 455                 460

Pro Gly Trp Ile Thr Gly Gln Ser Tyr Met Leu Thr Ala Thr Met Ala
465                 470                 475                 480

Gly Arg Leu Thr Gly Val Ile Ala Glu Gly Ser Pro Leu Phe Pro Ser
                485                 490                 495

Ala Gly Arg Tyr Ala Ser Ile Ile Glu Arg Tyr Gly Val Gln Ile Phe
            500                 505                 510

Lys Ala Gly Val Thr Phe Leu Lys Thr Val Met Ser Asn Pro Gln Asn
        515                 520                 525

Val Glu Asp Val Arg Leu Tyr Asp Met His Ser Leu Arg Val Ala Thr
    530                 535                 540

Phe Cys Ala Glu Pro Val Ser Pro Ala Val Gln Gln Phe Gly Met Gln
545                 550                 555                 560

Ile Met Thr Pro Gln Tyr Ile Asn Ser Tyr Trp Ala Thr Glu His Gly
                565                 570                 575

Gly Ile Val Trp Thr His Phe Tyr Gly Asn Gln Asp Phe Pro Leu Arg
            580                 585                 590

Pro Asp Ala His Thr Tyr Pro Leu Pro Trp Val Met Gly Asp Val Trp
        595                 600                 605

Val Ala Glu Thr Asp Glu Ser Gly Thr Thr Arg Tyr Arg Val Ala Asp
    610                 615                 620

Phe Asp Glu Lys Gly Glu Ile Val Ile Thr Ala Pro Tyr Pro Tyr Leu
625                 630                 635                 640

Thr Arg Thr Leu Trp Gly Asp Val Pro Gly Phe Glu Ala Tyr Leu Arg
                645                 650                 655

Gly Glu Ile Pro Leu Arg Ala Trp Lys Gly Asp Ala Glu Arg Phe Val
            660                 665                 670

Lys Thr Tyr Trp Arg Arg Gly Pro Asn Gly Glu Trp Gly Tyr Ile Gln
        675                 680                 685

Gly Asp Phe Ala Ile Lys Tyr Pro Asp Gly Ser Phe Thr Leu His Gly
    690                 695                 700

Arg Pro Asp Asp Val Ile Asn Val Ser Gly His Arg Met Gly Thr Glu
705                 710                 715                 720

Glu Ile Glu Gly Ala Ile Leu Arg Asp Arg Gln Ile Thr Pro Asp Ser
                725                 730                 735

Pro Val Gly Asn Cys Ile Val Val Gly Ala Pro His Arg Glu Lys Gly
            740                 745                 750

Leu Thr Pro Val Ala Phe Ile Gln Pro Ala Pro Gly Arg His Leu Thr
        755                 760                 765

Gly Ala Asp Arg Arg Arg Leu Asp Glu Leu Val Arg Thr Glu Lys Gly

```
                    770             775             780
Ala Val Ser Val Pro Glu Asp Tyr Ile Glu Val Ser Ala Phe Pro Glu
785                 790                 795                 800

Thr Arg Ser Gly Lys Tyr Met Arg Arg Phe Leu Arg Asn Met Met Leu
                    805                 810                 815

Asp Glu Pro Leu Gly Asp Thr Thr Thr Leu Arg Asn Pro Glu Val Leu
                    820                 825                 830

Glu Glu Ile Ala Ala Lys Ile Ala Glu Trp Lys Arg Arg Gln Arg Met
                835                 840                 845

Ala Glu Glu Gln Gln Ile Ile Glu Arg Tyr Arg Tyr Phe Arg Ile Glu
850                 855                 860

Tyr His Pro Pro Thr Ala Ser Ala Gly Lys Leu Ala Val Val Thr Val
865                 870                 875                 880

Thr Asn Pro Pro Val Asn Ala Leu Asn Glu Arg Ala Leu Asp Glu Leu
                    885                 890                 895

Asn Thr Ile Val Asp His Leu Ala Arg Arg Gln Asp Val Ala Ala Ile
                900                 905                 910

Val Phe Thr Gly Gln Gly Ala Arg Ser Phe Val Ala Gly Ala Asp Ile
                915                 920                 925

Arg Gln Leu Leu Glu Glu Ile His Thr Val Glu Glu Ala Met Ala Leu
930                 935                 940

Pro Asn Asn Ala His Leu Ala Phe Arg Lys Ile Glu Arg Met Asn Lys
945                 950                 955                 960

Pro Cys Ile Ala Ala Ile Asn Gly Val Ala Leu Gly Gly Gly Leu Glu
                965                 970                 975

Phe Ala Met Ala Cys His Tyr Arg Val Ala Asp Val Tyr Ala Glu Phe
                980                 985                 990

Gly Gln Pro Glu Ile Asn Leu Arg Leu Leu Pro Gly Tyr Gly Gly Thr
                995                 1000                1005

Gln Arg Leu Pro Arg Leu Leu Tyr Lys Arg Asn Asn Gly Thr Gly
    1010            1015                1020

Leu Leu Arg Ala Leu Glu Met Ile Leu Gly Gly Arg Ser Val Pro
    1025            1030                1035

Ala Asp Glu Ala Leu Lys Leu Gly Leu Ile Asp Ala Ile Ala Thr
    1040            1045                1050

Gly Asp Gln Asp Ser Leu Ser Leu Ala Cys Ala Leu Ala Arg Ala
    1055            1060                1065

Ala Ile Gly Ala Asp Gly Gln Leu Ile Glu Ser Ala Ala Val Thr
    1070            1075                1080

Gln Ala Phe Arg His Arg His Glu Gln Leu Asp Glu Trp Arg Lys
    1085            1090                1095

Pro Asp Pro Arg Phe Ala Asp Asp Glu Leu Arg Ser Ile Ile Ala
    1100            1105                1110

His Pro Arg Ile Glu Arg Ile Ile Arg Gln Ala His Thr Val Gly
    1115            1120                1125

Arg Asp Ala Ala Val His Arg Ala Leu Asp Ala Ile Arg Tyr Gly
    1130            1135                1140

Ile Ile His Gly Phe Glu Ala Gly Leu Glu His Glu Ala Lys Leu
    1145            1150                1155

Phe Ala Glu Ala Val Val Asp Pro Asn Gly Gly Lys Arg Gly Ile
    1160            1165                1170

Arg Glu Phe Leu Asp Arg Gln Ser Ala Pro Leu Pro Thr Arg Arg
    1175            1180                1185
```

```
Pro Leu Ile Thr Pro Glu Gln Glu Gln Leu Leu Arg Asp Gln Lys
1190                1195                1200

Glu Leu Leu Pro Val Gly Ser Pro Phe Phe Pro Gly Val Asp Arg
1205                1210                1215

Ile Pro Lys Trp Gln Tyr Ala Gln Ala Val Ile Arg Asp Pro Asp
1220                1225                1230

Thr Gly Ala Ala Ala His Gly Asp Pro Ile Val Ala Glu Lys Gln
1235                1240                1245

Ile Ile Val Pro Val Glu Arg Pro Arg Ala Asn Gln Ala Leu Ile
1250                1255                1260

Tyr Val Leu Ala Ser Glu Val Asn Phe Asn Asp Ile Trp Ala Ile
1265                1270                1275

Thr Gly Ile Pro Val Ser Arg Phe Asp Glu His Asp Arg Asp Trp
1280                1285                1290

His Val Thr Gly Ser Gly Gly Ile Gly Leu Ile Val Ala Leu Gly
1295                1300                1305

Glu Glu Ala Arg Arg Glu Gly Arg Leu Lys Val Gly Asp Leu Val
1310                1315                1320

Ala Ile Tyr Ser Gly Gln Ser Asp Leu Leu Ser Pro Leu Met Gly
1325                1330                1335

Leu Asp Pro Met Ala Ala Asp Phe Val Ile Gln Gly Asn Asp Thr
1340                1345                1350

Pro Asp Gly Ser His Gln Gln Phe Met Leu Ala Gln Ala Pro Gln
1355                1360                1365

Cys Leu Pro Ile Pro Thr Asp Met Ser Ile Glu Ala Ala Gly Ser
1370                1375                1380

Tyr Ile Leu Asn Leu Gly Thr Ile Tyr Arg Ala Leu Phe Thr Thr
1385                1390                1395

Leu Gln Ile Lys Ala Gly Arg Thr Ile Phe Ile Glu Gly Ala Ala
1400                1405                1410

Thr Gly Thr Gly Leu Asp Ala Ala Arg Ser Ala Ala Arg Asn Gly
1415                1420                1425

Leu Arg Val Ile Gly Met Val Ser Ser Ser Ser Arg Ala Ser Thr
1430                1435                1440

Leu Leu Ala Ala Gly Ala His Gly Ala Ile Asn Arg Lys Asp Pro
1445                1450                1455

Glu Val Ala Asp Cys Phe Thr Arg Val Pro Glu Asp Pro Ser Ala
1460                1465                1470

Trp Ala Ala Trp Glu Ala Ala Gly Gln Pro Leu Leu Ala Met Phe
1475                1480                1485

Arg Ala Gln Asn Asp Gly Arg Leu Ala Asp Tyr Val Val Ser His
1490                1495                1500

Ala Gly Glu Thr Ala Phe Pro Arg Ser Phe Gln Leu Leu Gly Glu
1505                1510                1515

Pro Arg Asp Gly His Ile Pro Thr Leu Thr Phe Tyr Gly Ala Thr
1520                1525                1530

Ser Gly Tyr His Phe Thr Phe Leu Gly Lys Pro Gly Ser Ala Ser
1535                1540                1545

Pro Thr Glu Met Leu Arg Arg Ala Asn Leu Arg Ala Gly Glu Ala
1550                1555                1560

Val Leu Ile Tyr Tyr Gly Val Gly Ser Asp Asp Leu Val Asp Thr
1565                1570                1575

Gly Gly Leu Glu Ala Ile Glu Ala Ala Arg Gln Met Gly Ala Arg
1580                1585                1590
```

```
Ile Val Val Val Thr Val Ser Asp Ala Gln Arg Glu Phe Val Leu
    1595                1600                1605

Ser Leu Gly Phe Gly Ala Ala Leu Arg Gly Val Val Ser Leu Ala
    1610                1615                1620

Glu Leu Lys Arg Arg Phe Gly Asp Glu Phe Glu Trp Pro Arg Thr
    1625                1630                1635

Met Pro Pro Leu Pro Asn Ala Arg Gln Asp Pro Gln Gly Leu Lys
    1640                1645                1650

Glu Ala Val Arg Arg Phe Asn Asp Leu Val Phe Lys Pro Leu Gly
    1655                1660                1665

Ser Ala Val Gly Val Phe Leu Arg Ser Ala Asp Asn Pro Arg Gly
    1670                1675                1680

Tyr Pro Asp Leu Ile Ile Glu Arg Ala Ala His Asp Ala Leu Ala
    1685                1690                1695

Val Ser Ala Met Leu Ile Lys Pro Phe Thr Gly Arg Ile Val Tyr
    1700                1705                1710

Phe Glu Asp Ile Gly Gly Arg Arg Tyr Ser Phe Phe Ala Pro Gln
    1715                1720                1725

Ile Trp Val Arg Gln Arg Arg Ile Tyr Met Pro Thr Ala Gln Ile
    1730                1735                1740

Phe Gly Thr His Leu Ser Asn Ala Tyr Glu Ile Leu Arg Leu Asn
    1745                1750                1755

Asp Glu Ile Ser Ala Gly Leu Leu Thr Ile Thr Glu Pro Ala Val
    1760                1765                1770

Val Pro Trp Asp Glu Leu Pro Glu Ala His Gln Ala Met Trp Glu
    1775                1780                1785

Asn Arg His Thr Ala Ala Thr Tyr Val Val Asn His Ala Leu Pro
    1790                1795                1800

Arg Leu Gly Leu Lys Asn Arg Asp Glu Leu Tyr Glu Ala Trp Thr
    1805                1810                1815

Ala Gly Glu Arg
    1820

<210> SEQ ID NO 40
<211> LENGTH: 777
<212> TYPE: DNA
<213> ORGANISM: Chloroflexus aurantiacus
<220> FEATURE:
<221> NAME/KEY: CDS
<222> LOCATION: (1)..(774)

<400> SEQUENCE: 40 atg agt gaa gag tct ctg gtt ctc agc aca att gaa ggc ccc atc gcc    48
Met Ser Glu Glu Ser Leu Val Leu Ser Thr Ile Glu Gly Pro Ile Ala
1               5                   10                  15 atc ctc acc ctc aat cgc ccc cag gcc ctc aat gcg ctc agt ccg gcc    96
Ile Leu Thr Leu Asn Arg Pro Gln Ala Leu Asn Ala Leu Ser Pro Ala
            20                  25                  30 ttg att gat gac ctc att cgc cat tta gaa gcc tgc gat gcc gat gac   144
Leu Ile Asp Asp Leu Ile Arg His Leu Glu Ala Cys Asp Ala Asp Asp
        35                  40                  45 aca atc cgc gtg atc att atc acc ggc gcc gga cgg gca ttt gct gcc   192
Thr Ile Arg Val Ile Ile Ile Thr Gly Ala Gly Arg Ala Phe Ala Ala
    50                  55                  60 ggc gct gat atc aaa gcg atg gcc aat gcc acg cct att gat atg ctc   240
Gly Ala Asp Ile Lys Ala Met Ala Asn Ala Thr Pro Ile Asp Met Leu
65                  70                  75                  80
```

```
acc agt ggc atg att gcg cgc tgg gca cgc atc gcc gcg gtg cgc aaa      288
Thr Ser Gly Met Ile Ala Arg Trp Ala Arg Ile Ala Ala Val Arg Lys
            85                  90                  95 ccg gtg att gct gcc gtg aat ggg tat gcg ctc ggt ggt ggt tgt gaa      336
Pro Val Ile Ala Ala Val Asn Gly Tyr Ala Leu Gly Gly Gly Cys Glu
        100                 105                 110 ttg gca atg atg tgc gac atc atc atc gcc agt gaa aac gcg cag ttc      384
Leu Ala Met Met Cys Asp Ile Ile Ile Ala Ser Glu Asn Ala Gln Phe
        115                 120                 125 gga caa ccg gaa atc aat ctg ggc atc att ccc ggt gct ggt ggc acc      432
Gly Gln Pro Glu Ile Asn Leu Gly Ile Ile Pro Gly Ala Gly Gly Thr
130                 135                 140 caa cgg ctg acc cgc gcc ctt ggc ccg tat cgc gca atg gaa ttg atc      480
Gln Arg Leu Thr Arg Ala Leu Gly Pro Tyr Arg Ala Met Glu Leu Ile
145                 150                 155                 160 ctg acc ggc gcg acc atc agt gct cag gaa gct ctc gcc cac ggc ctg      528
Leu Thr Gly Ala Thr Ile Ser Ala Gln Glu Ala Leu Ala His Gly Leu
                165                 170                 175 gtg tgc cgg gtc tgc ccg cct gaa agc ctg ctc gat gaa gcc cgt cgg      576
Val Cys Arg Val Cys Pro Pro Glu Ser Leu Leu Asp Glu Ala Arg Arg
            180                 185                 190 atc gcg caa acc att gcc acc aaa tca cca ctg gct gta cag ttg gcg      624
Ile Ala Gln Thr Ile Ala Thr Lys Ser Pro Leu Ala Val Gln Leu Ala
        195                 200                 205 aaa gag gca gtc cgt atg gcc gcc gaa acc act gtg cgc gag ggg ttg      672
Lys Glu Ala Val Arg Met Ala Ala Glu Thr Thr Val Arg Glu Gly Leu
        210                 215                 220 gct atc gag ctg cgt aac ttc tat ctg ctg ttt gcc agt gct gac caa      720
Ala Ile Glu Leu Arg Asn Phe Tyr Leu Leu Phe Ala Ser Ala Asp Gln
225                 230                 235                 240 aaa gag ggg atg cag gca ttt atc gag aaa cgc gct ccc aac ttc agt      768
Lys Glu Gly Met Gln Ala Phe Ile Glu Lys Arg Ala Pro Asn Phe Ser
                245                 250                 255 ggt cgt tga                                                          777
Gly Arg <210> SEQ ID NO 41
<211> LENGTH: 258
<212> TYPE: PRT
<213> ORGANISM: Chloroflexus aurantiacus

<400> SEQUENCE: 41

Met Ser Glu Glu Ser Leu Val Leu Ser Thr Ile Glu Gly Pro Ile Ala
1               5                   10                  15

Ile Leu Thr Leu Asn Arg Pro Gln Ala Leu Asn Ala Leu Ser Pro Ala
            20                  25                  30

Leu Ile Asp Asp Leu Ile Arg His Leu Glu Ala Cys Asp Ala Asp Asp
        35                  40                  45

Thr Ile Arg Val Ile Ile Thr Gly Ala Gly Arg Ala Phe Ala Ala
    50                  55                  60

Gly Ala Asp Ile Lys Ala Met Ala Asn Ala Thr Pro Ile Asp Met Leu
65                  70                  75                  80

Thr Ser Gly Met Ile Ala Arg Trp Ala Arg Ile Ala Ala Val Arg Lys
                85                  90                  95

Pro Val Ile Ala Ala Val Asn Gly Tyr Ala Leu Gly Gly Gly Cys Glu
            100                 105                 110

Leu Ala Met Met Cys Asp Ile Ile Ile Ala Ser Glu Asn Ala Gln Phe
        115                 120                 125

Gly Gln Pro Glu Ile Asn Leu Gly Ile Ile Pro Gly Ala Gly Gly Thr
```

```
                130                135                140
Gln Arg Leu Thr Arg Ala Leu Gly Pro Tyr Arg Ala Met Glu Leu Ile
145                150                155                160

Leu Thr Gly Ala Thr Ile Ser Ala Gln Glu Ala Leu Ala His Gly Leu
                165                170                175

Val Cys Arg Val Cys Pro Pro Glu Ser Leu Leu Asp Glu Ala Arg Arg
            180                185                190

Ile Ala Gln Thr Ile Ala Thr Lys Ser Pro Leu Ala Val Gln Leu Ala
        195                200                205

Lys Glu Ala Val Arg Met Ala Ala Glu Thr Thr Val Arg Glu Gly Leu
    210                215                220

Ala Ile Glu Leu Arg Asn Phe Tyr Leu Leu Phe Ala Ser Ala Asp Gln
225                230                235                240

Lys Glu Gly Met Gln Ala Phe Ile Glu Lys Arg Ala Pro Asn Phe Ser
                245                250                255

Gly Arg

<210> SEQ ID NO 42
<211> LENGTH: 1220
<212> TYPE: DNA
<213> ORGANISM: Chloroflexus aurantiacus

<400> SEQUENCE: 42
ggcgtaatcc gaccggcagg ttagggtctt ctactggggt caaggcgcgt ctccttttgg      60
tggcgcgagc aacccggctt ttcctggctt caatgtacca tagagcggtt acttcgtgca     120
acgggcgtgg tacaatcgag agcaaccttt cgcaaaagct atccaatcct gcacacgtgc     180
atctgttaca gggtattatt gtcggcaaac gacagtcctg tcgtttatgt acaaggagat     240
caacgtatga gtgaagagtc tctggttctc agcacaattg aaggccccat cgccatcctc     300
accctcaatc gccccaggc cctcaatgcg ctcagtccgg ccttgattga tgacctcatt     360 cgccattag aagcctgcga tgccgatgac acaatccgcg tgatcattat caccggcgcc     420
ggacgggcat ttgctgccgg cgctgatatc aaagcgatgg ccaatgccac gcctattgat     480
atgctcacca gtggcatgat tgcgcgctgg gcacgcatcg ccgcggtgcg caaaccggtg     540
attgctgccg tgaatgggta tgcgctcggt ggtggttgtg aattggcaat gatgtgcgac     600
atcatcatcg ccagtgaaaa cgcgcagttc ggacaaccgg aaatcaatct gggcatcatt     660
cccggtgctg gtggcaccca acggctgacc cgcgcccttg gccgtatcg cgcaatggaa     720 ttgatcctga ccggcgcgac catcagtgct caggaagctc tcgcccacgg cctggtgtgc     780
cgggtctgcc cgcctgaaag cctgctcgat gaagcccgtc ggatcgcgca aaccattgcc     840
accaaatcac cactggctgt acagttggcg aaagaggcag tccgtatggc cgccgaaacc     900
actgtgcgcg aggggttggc tatcgagctg cgtaacttct atctgctgtt tgccagtgct     960
gaccaaaaag aggggatgca ggcatttatc gagaaacgcg ctcccaactt cagtggtcgt    1020
tgatcacgcg cagaacatgg cagcaggggc aatacctgca cgtactgcct cctgccgcca    1080
tactaccaga tgatcgagca gtaaagggta atactctat caatctggcc agataagcgg    1140
ttgggtaaca acgcaatgct ccaaaggaga cgatcatgga catacacgag cgattgcgat    1200
ctctcgaacg cgaaaatgct                                                1220

<210> SEQ ID NO 43
<211> LENGTH: 774
<212> TYPE: DNA
<213> ORGANISM: Mycobacterium tuberculosis
```

<400> SEQUENCE: 43

| | | | | | |
|---|---|---|---|---|---|
| atgacgtacg | aaaccatcct | ggtcgagcgc | gatcagcgag | ttggcattat | cacgctgaac | 60 |
| cgtccccagg | cactgaacgc | gctcaacagc | caggtgatga | acgaggtcac | cagcgctgca | 120 |
| accgaactgg | acgatgaccc | ggacattggg | gcgatcatca | tcaccggttc | ggccaaagcg | 180 |
| tttgccgccg | gagccgacat | caaagaaatg | gccgacctga | cgttcgccga | cgcgttcacc | 240 |
| gccgacttct | tcgccacctg | gggcaagctg | gccgccgtgc | gcaccccgac | gatcgccgcg | 300 |
| gtggcgggat | acgcgctcgg | cggtggctgc | gagctggcga | tgatgtgcga | cgtgctgatc | 360 |
| gccgccgaca | ccgcgaagtt | cggacagccc | gagataaagc | tgggcgtgct | gccaggcatg | 420 |
| ggcggctccc | agcggctgac | ccgggctatc | ggcaaggcta | aggcgatgga | cctcatcctg | 480 |
| accgggcgca | ccatggacgc | cgccgaggcc | gagcgcagcg | gtctggtttc | acgggtggtg | 540 |
| ccggccgacg | acttgctgac | cgaagccagg | gccactgcca | cgaccatttc | gcagatgtcg | 600 |
| gcctcggcgg | cccggatggc | caaggaggcc | gtcaaccggg | ctttcgaatc | cagtttgtcc | 660 |
| gaggggctgc | tctacgaacg | ccggcttttc | cattcggctt | tcgcgaccga | agaccaatcc | 720 |
| gaaggtatgg | cagcgttcat | cgagaaacgc | gctccccagt | tcacccaccg | atga | 774 |

<210> SEQ ID NO 44
<211> LENGTH: 873
<212> TYPE: DNA
<213> ORGANISM: Homo sapiens

<400> SEQUENCE: 44

| | | | | | |
|---|---|---|---|---|---|
| atggccgccc | tgcgtgtcct | gctgtcctgc | gcccgcggcc | cgctgaggcc | cccggttcgc | 60 |
| tgtcccgcct | ggcgtcccct | cgcctcgggt | gctaactttg | agtacatcat | cgcagaaaaa | 120 |
| agagggaaga | ataacaccgt | ggggttgatc | caactgaacc | gccccaaggc | cctcaatgca | 180 |
| ctttgcgatg | gcctgattga | cgagctcaac | caggccctga | gatcttcga | ggaggacccg | 240 |
| gccgttgggg | gcattgtcct | caccggcggg | gataaggcct | ttgcagctgg | agctgatatc | 300 |
| aaggaaatgc | agaacctgag | tttccaggac | tgttactcca | gcaagttctt | gaagcactgg | 360 |
| ggccacctca | cccaggtcaa | gaagccagtc | atcgctgctg | tcaatggcta | tccgtttggc | 420 |
| gggggctgtg | agcttgccat | gatgtgtgat | atcatctatg | ccggtgagaa | ggcccagttt | 480 |
| gcacagccgg | agatcttaat | aggaaccatc | ccaggtgcag | gcggcaccca | gagactcacc | 540 |
| cgtgctgttg | ggaagtcgct | ggagctggag | atggtcctca | ccggtgacgc | gatctcagcc | 600 |
| caggacgcca | gcaagcagg | tcttgtcagc | aagatttgtc | ctgttgagac | actggtggaa | 660 |
| gaagccatcc | agtgtgcaga | aaaaattgcc | agcaattcta | aaattgtagt | agcgatggcc | 720 |
| aaagaatcag | tgaatgcagc | ttttgaaatg | acattaacag | aaggaagtaa | gttggagaag | 780 |
| aaactctttt | attcaacctt | tgccactgat | gaccggaaag | aagggatgac | cgcgtttgtg | 840 |
| gaaaagagaa | aggccaactt | caaagaccag | tga | | | 873 |

<210> SEQ ID NO 45
<211> LENGTH: 873
<212> TYPE: DNA
<213> ORGANISM: Rattus norvegicus

<400> SEQUENCE: 45

| | | | | | |
|---|---|---|---|---|---|
| atggcggccc | tgcgtgctct | gctgcccaga | gcctgcaact | cgctgttgtc | cccagttcgc | 60 |
| tgcccagaat | tccggcgctt | cgcctcgggt | gctaactttc | agtacatcat | cacggaaaag | 120 |
| aaaggaaaga | atagcagcgt | ggggctgatc | cagttgaacc | gtcccaaagc | actcaatgca | 180 |

```
ctttgcaatg gactgattga ggagctcaac caagcactgg agacctttga ggaagatccc    240
gctgtgggcg ccattgtgct cactggtggg gagaaggcct ttgcagccgg agctgacatc    300
aaggaaatgc agaaccggac atttcaggac tgttactcag gcaagttcct gagccactgg    360
gaccatatca cccggatcaa gaaaccggtc atcgcggctg tcaatggcta tgctcttggt    420
gggggctgtg aacttgccat gatgtgcgat atcatctatg ctggtgagaa agcccagttt    480
ggacagccag aaatcctcct ggggaccatc ccaggtgcag ggggcactca gagactcacc    540
cgagcagtcg gcaaatcact agcaatggag atggtcctca ctggtgaccg aatttcagca    600
caggatgcca agcaagcagg tcttgtaagc aagattttc ccgttgaaac actggttgaa     660
gaggccatcc aatgtgcaga aaagatcgcc aacaattcca agatcatagt agccatggcg    720
aaagaatctg tgaatgcagc ctttgaaatg acgttaacag aaggaaataa gctggagaag    780
aagctcttct attccacctt tgccactgat gaccggagag aagggatgtc tgcctttgtg    840
gagaaaagga aggccaactt caaagaccac tga                                 873

<210> SEQ ID NO 46
<211> LENGTH: 257
<212> TYPE: PRT
<213> ORGANISM: Mycobacterium tuberculosis

<400> SEQUENCE: 46

Met Thr Tyr Glu Thr Ile Leu Val Glu Arg Asp Gln Arg Val Gly Ile
1               5                   10                  15

Ile Thr Leu Asn Arg Pro Gln Ala Leu Asn Ala Leu Asn Ser Gln Val
            20                  25                  30

Met Asn Glu Val Thr Ser Ala Ala Thr Glu Leu Asp Asp Asp Pro Asp
        35                  40                  45

Ile Gly Ala Ile Ile Ile Thr Gly Ser Ala Lys Ala Phe Ala Ala Gly
    50                  55                  60

Ala Asp Ile Lys Glu Met Ala Asp Leu Thr Phe Ala Asp Ala Phe Thr
65                  70                  75                  80

Ala Asp Phe Phe Ala Thr Trp Gly Lys Leu Ala Ala Val Arg Thr Pro
                85                  90                  95

Thr Ile Ala Ala Val Ala Gly Tyr Ala Leu Gly Gly Gly Cys Glu Leu
            100                 105                 110

Ala Met Met Cys Asp Val Leu Ile Ala Ala Asp Thr Ala Lys Phe Gly
        115                 120                 125

Gln Pro Glu Ile Lys Leu Gly Val Leu Pro Gly Met Gly Gly Ser Gln
    130                 135                 140

Arg Leu Thr Arg Ala Ile Gly Lys Ala Lys Ala Met Asp Leu Ile Leu
145                 150                 155                 160

Thr Gly Arg Thr Met Asp Ala Ala Glu Ala Glu Arg Ser Gly Leu Val
                165                 170                 175

Ser Arg Val Val Pro Ala Asp Asp Leu Leu Thr Glu Ala Arg Ala Thr
            180                 185                 190

Ala Thr Thr Ile Ser Gln Met Ser Ala Ser Ala Ala Arg Met Ala Lys
        195                 200                 205

Glu Ala Val Asn Arg Ala Phe Glu Ser Ser Leu Ser Glu Gly Leu Leu
    210                 215                 220

Tyr Glu Arg Arg Leu Phe His Ser Ala Phe Ala Thr Glu Asp Gln Ser
225                 230                 235                 240

Glu Gly Met Ala Ala Phe Ile Glu Lys Arg Ala Pro Gln Phe Thr His
                245                 250                 255
```

Arg

<210> SEQ ID NO 47
<211> LENGTH: 290
<212> TYPE: PRT
<213> ORGANISM: Homo sapiens

<400> SEQUENCE: 47

Met Ala Ala Leu Arg Val Leu Leu Ser Cys Ala Arg Gly Pro Leu Arg
1               5                   10                  15

Pro Pro Val Arg Cys Pro Ala Trp Arg Pro Phe Ala Ser Gly Ala Asn
            20                  25                  30

Phe Glu Tyr Ile Ile Ala Glu Lys Arg Gly Lys Asn Asn Thr Val Gly
        35                  40                  45

Leu Ile Gln Leu Asn Arg Pro Lys Ala Leu Asn Ala Leu Cys Asp Gly
    50                  55                  60

Leu Ile Asp Glu Leu Asn Gln Ala Leu Lys Ile Phe Glu Glu Asp Pro
65                  70                  75                  80

Ala Val Gly Ala Ile Val Leu Thr Gly Gly Asp Lys Ala Phe Ala Ala
                85                  90                  95

Gly Ala Asp Ile Lys Glu Met Gln Asn Leu Ser Phe Gln Asp Cys Tyr
            100                 105                 110

Ser Ser Lys Phe Leu Lys His Trp Asp His Leu Thr Gln Val Lys Lys
        115                 120                 125

Pro Val Ile Ala Ala Val Asn Gly Tyr Ala Phe Gly Gly Gly Cys Glu
    130                 135                 140

Leu Ala Met Met Cys Asp Ile Ile Tyr Ala Gly Glu Lys Ala Gln Phe
145                 150                 155                 160

Ala Gln Pro Glu Ile Leu Ile Gly Thr Ile Pro Gly Ala Gly Gly Thr
                165                 170                 175

Gln Arg Leu Thr Arg Ala Val Gly Lys Ser Leu Ala Met Glu Met Val
            180                 185                 190

Leu Thr Gly Asp Arg Ile Ser Ala Gln Asp Ala Lys Gln Ala Gly Leu
        195                 200                 205

Val Ser Lys Ile Cys Pro Val Glu Thr Leu Val Glu Glu Ala Ile Gln
    210                 215                 220

Cys Ala Glu Lys Ile Ala Ser Asn Ser Lys Ile Val Val Ala Met Ala
225                 230                 235                 240

Lys Glu Ser Val Asn Ala Ala Phe Glu Met Thr Leu Thr Glu Gly Ser
                245                 250                 255

Lys Leu Glu Lys Lys Leu Phe Tyr Ser Thr Phe Ala Thr Asp Asp Arg
            260                 265                 270

Lys Glu Gly Met Thr Ala Phe Val Glu Lys Arg Lys Ala Asn Phe Lys
        275                 280                 285

Asp Gln
    290

<210> SEQ ID NO 48
<211> LENGTH: 290
<212> TYPE: PRT
<213> ORGANISM: Rattus norvegicus

<400> SEQUENCE: 48

Met Ala Ala Leu Arg Ala Leu Leu Pro Arg Ala Cys Asn Ser Leu Leu
1               5                   10                  15

Ser Pro Val Arg Cys Pro Glu Phe Arg Arg Phe Ala Ser Gly Ala Asn

```
                20                  25                  30
Phe Gln Tyr Ile Ile Thr Glu Lys Lys Gly Lys Asn Ser Ser Val Gly
         35                  40                  45

Leu Ile Gln Leu Asn Arg Pro Lys Ala Leu Asn Ala Leu Cys Asn Gly
 50                  55                  60

Leu Ile Glu Glu Leu Asn Gln Ala Leu Glu Thr Phe Glu Glu Asp Pro
65                  70                  75                  80

Ala Val Gly Ala Ile Val Leu Thr Gly Gly Lys Ala Phe Ala Ala
                 85                  90                  95

Gly Ala Asp Ile Lys Glu Met Gln Asn Arg Thr Phe Gln Asp Cys Tyr
                100                 105                 110

Ser Gly Lys Phe Leu Ser His Trp Asp His Ile Thr Arg Ile Lys Lys
            115                 120                 125

Pro Val Ile Ala Ala Val Asn Gly Tyr Ala Leu Gly Gly Gly Cys Glu
        130                 135                 140

Leu Ala Met Met Cys Asp Ile Ile Tyr Ala Gly Glu Lys Ala Gln Phe
145                 150                 155                 160

Gly Gln Pro Glu Ile Leu Leu Gly Thr Ile Pro Gly Ala Gly Gly Thr
                165                 170                 175

Gln Arg Leu Thr Arg Ala Val Gly Lys Ser Leu Ala Met Glu Met Val
            180                 185                 190

Leu Thr Gly Asp Arg Ile Ser Ala Gln Asp Ala Lys Gln Ala Gly Leu
        195                 200                 205

Val Ser Lys Ile Phe Pro Val Glu Thr Leu Val Glu Glu Ala Ile Gln
    210                 215                 220

Cys Ala Glu Lys Ile Ala Asn Asn Ser Lys Ile Ile Val Ala Met Ala
225                 230                 235                 240

Lys Glu Ser Val Asn Ala Ala Phe Glu Met Thr Leu Thr Glu Gly Asn
                245                 250                 255

Lys Leu Glu Lys Lys Leu Phe Tyr Ser Thr Phe Ala Thr Asp Asp Arg
            260                 265                 270

Arg Glu Gly Met Ser Ala Phe Val Glu Lys Arg Lys Ala Asn Phe Lys
        275                 280                 285

Asp His
    290

<210> SEQ ID NO 49
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: n is any nucleotide; w is a or t; y is t or c;
      s is g or c

<400> SEQUENCE: 49
gaawscggys cnatyggygg                                                   20

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
```
ttytgyggyr sbttyacbgc wgg                                                    23

<210> SEQ ID NO 51
<211> LENGTH: 23
<212> TYPE: DNA
<213> ORGANISM: Artificial Sequence
<220> FEATURE:
<223> OTHER INFORMATION: Primer

<400> SEQUENCE: 51
ccwgcvgtra avsyrccrca raa                                                    23

<210> SEQ ID NO 52
<211> LENGTH: 23
<212> TYPE: DNA
<213> ORGANISM: Artificial Sequence
<220> FEATURE:
<223> OTHER INFORMATION: Primer

<400> SEQUENCE: 52
aaracdsmrc gttcvgtrat rta                                                    23

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
tcrayrccsg gwgcrayttc                                                        20

<210> SEQ ID NO 54
<211> LENGTH: 27
<212> TYPE: DNA
<213> ORGANISM: Artificial Sequence
<220> FEATURE:
<223> OTHER INFORMATION: Primer

<400> SEQUENCE: 54
gaatgtttac ttctgcggca ccttcac                                                27

<210> SEQ ID NO 55
<211> LENGTH: 28
<212> TYPE: DNA
<213> ORGANISM: Artificial Sequence
<220> FEATURE:
<223> OTHER INFORMATION: Primer

<400> SEQUENCE: 55
gaccagatca ctttcaacgg ttcctatg                                               28

<210> SEQ ID NO 56
<211> LENGTH: 27
<212> TYPE: DNA
<213> ORGANISM: Artificial Sequence
<220> FEATURE:
<223> OTHER INFORMATION: Primer

<400> SEQUENCE: 56
gcataggaac cgttgaaagt gatctgg                                                27

<210> SEQ ID NO 57
<211> LENGTH: 28
<212> TYPE: DNA
<213> ORGANISM: Artificial Sequence
<220> FEATURE:

<223> OTHER INFORMATION: Primer

<400> SEQUENCE: 57
gttagtaccg aacttgctga cgttgatg                    28

<210> SEQ ID NO 58
<211> LENGTH: 23
<212> TYPE: DNA
<213> ORGANISM: Artificial Sequence
<220> FEATURE:
<223> OTHER INFORMATION: Primer

<400> SEQUENCE: 58
atgagaaaag tagaaatcat tac                         23

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
ggcggaagtt gacgataatg                             20

<210> SEQ ID NO 60
<211> LENGTH: 17
<212> TYPE: DNA
<213> ORGANISM: Artificial Sequence
<220> FEATURE:
<223> OTHER INFORMATION: Primer

<400> SEQUENCE: 60
gcwacbggyt ayggycg                                17

<210> SEQ ID NO 61
<211> LENGTH: 23
<212> TYPE: DNA
<213> ORGANISM: Artificial Sequence
<220> FEATURE:
<223> OTHER INFORMATION: Primer

<400> SEQUENCE: 61
gtyrtygayr tyggyggyca gga                         23

<210> SEQ ID NO 62
<211> LENGTH: 23
<212> TYPE: DNA
<213> ORGANISM: Artificial Sequence
<220> FEATURE:
<223> OTHER INFORMATION: Primer

<400> SEQUENCE: 62
atgaacgaya artgygcwgc wgg                         23

<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
tgygcwgcwg gyacbggycg ytt                         23

<210> SEQ ID NO 64

```
<211> LENGTH: 23
<212> TYPE: DNA
<213> ORGANISM: Artificial Sequence
<220> FEATURE:
<223> OTHER INFORMATION: Primer

<400> SEQUENCE: 64
tcctgrccrc crayrtcray rac                                              23

<210> SEQ ID NO 65
<211> LENGTH: 23
<212> TYPE: DNA
<213> ORGANISM: Artificial Sequence
<220> FEATURE:
<223> OTHER INFORMATION: Primer

<400> SEQUENCE: 65
ccwgcwgcrc ayttrtcgtt cat                                              23

<210> SEQ ID NO 66
<211> LENGTH: 23
<212> TYPE: DNA
<213> ORGANISM: Artificial Sequence
<220> FEATURE:
<223> OTHER INFORMATION: Primer

<400> SEQUENCE: 66
aarcgrccvg trccwgcwgc rca                                              23

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
gcttcgswtt cracratgsw                                                  20

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
gswratract tcgcwttcwg craa                                             24

<210> SEQ ID NO 69
<211> LENGTH: 27
<212> TYPE: DNA
<213> ORGANISM: Artificial Sequence
<220> FEATURE:
<223> OTHER INFORMATION: Primer

<400> SEQUENCE: 69
acgtcatgtc gaaggtactg gaaatcc                                          27

<210> SEQ ID NO 70
<211> LENGTH: 27
<212> TYPE: DNA
<213> ORGANISM: Artificial Sequence
<220> FEATURE:
<223> OTHER INFORMATION: Primer

<400> SEQUENCE: 70
```
gggactggta cttcaaatcg aagcatc                                          27

<210> SEQ ID NO 71
<211> LENGTH: 27
<212> TYPE: DNA
<213> ORGANISM: Artificial Sequence
<220> FEATURE:
<223> OTHER INFORMATION: Primer

<400> SEQUENCE: 71
tgacggcagc gggatgcttc gatttga                                          27

<210> SEQ ID NO 72
<211> LENGTH: 27
<212> TYPE: DNA
<213> ORGANISM: Artificial Sequence
<220> FEATURE:
<223> OTHER INFORMATION: Primer

<400> SEQUENCE: 72
tcagacatgg ggatttccag taccttc                                          27

<210> SEQ ID NO 73
<211> LENGTH: 30
<212> TYPE: DNA
<213> ORGANISM: Artificial Sequence
<220> FEATURE:
<223> OTHER INFORMATION: Primer

<400> SEQUENCE: 73
ccgtgttact tgggaaggta tcgctgtctg                                       30

<210> SEQ ID NO 74
<211> LENGTH: 30
<212> TYPE: DNA
<213> ORGANISM: Artificial Sequence
<220> FEATURE:
<223> OTHER INFORMATION: Primer

<400> SEQUENCE: 74
gccaatgaag gaggaaacca ctaatgagtc                                       30

<210> SEQ ID NO 75
<211> LENGTH: 32
<212> TYPE: DNA
<213> ORGANISM: Artificial Sequence
<220> FEATURE:
<223> OTHER INFORMATION: Primer

<400> SEQUENCE: 75
gggaattcca tatgaaaact gtgtatactc tc                                    32

<210> SEQ ID NO 76
<211> LENGTH: 31
<212> TYPE: DNA
<213> ORGANISM: Artificial Sequence
<220> FEATURE:
<223> OTHER INFORMATION: Primer

<400> SEQUENCE: 76
cgacggatcc ttagaggatt tccgagaaag c                                     31

<210> SEQ ID NO 77
<211> LENGTH: 23
<212> TYPE: DNA
<213> ORGANISM: Artificial Sequence
<220> FEATURE:

```
<223> OTHER INFORMATION: Primer
<220> FEATURE:
<221> NAME/KEY: misc_feature
<222> LOCATION: (1)..(23)
<223> OTHER INFORMATION: n is any nucleotide; y is t or c; b is g, c or
      t; v is a, g, or c; s is g or c

<400> SEQUENCE: 77
aaycgbccva argcnctsaa ygc                                              23

<210> SEQ ID NO 78
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: n is any nucleotide; y is t or c; b is c, g, or
      t

<400> SEQUENCE: 78
ttygtbgcng gygcngayat                                                  20

<210> SEQ ID NO 79
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: n is any nucleotide; r is g or a; v is a, g, or
      c.

<400> SEQUENCE: 79
atrtcngcrc cngcvacraa                                                  20

<210> SEQ ID NO 80
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(23)
<223> OTHER INFORMATION: n is any nucleotide; r is g or a; s is g or c;
      w is a or t.

<400> SEQUENCE: 80
ccrccrccsa gngcrwarcc rtt                                              23

<210> SEQ ID NO 81
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(21)
<223> OTHER INFORMATION: n is any nucleotide; r is g or a; s is g or c;
      w is a or t; v is a, g or c.

<400> SEQUENCE: 81
sswngcratv cgratrtcra c                                                21
```

```
<210> SEQ ID NO 82
<211> LENGTH: 26
<212> TYPE: DNA
<213> ORGANISM: Artificial Sequence
<220> FEATURE:
<223> OTHER INFORMATION: Primer

<400> SEQUENCE: 82
cgctgatatt cgccagttgc tcgaag                                  26

<210> SEQ ID NO 83
<211> LENGTH: 27
<212> TYPE: DNA
<213> ORGANISM: Artificial Sequence
<220> FEATURE:
<223> OTHER INFORMATION: Primer

<400> SEQUENCE: 83
cccatcttgc tttccgcaag attgagc                                 27

<210> SEQ ID NO 84
<211> LENGTH: 28
<212> TYPE: DNA
<213> ORGANISM: Artificial Sequence
<220> FEATURE:
<223> OTHER INFORMATION: Primer

<400> SEQUENCE: 84
caatggccct gccgaataac gcccatct                                28

<210> SEQ ID NO 85
<211> LENGTH: 26
<212> TYPE: DNA
<213> ORGANISM: Artificial Sequence
<220> FEATURE:
<223> OTHER INFORMATION: Primer

<400> SEQUENCE: 85
cttcgagcaa ctggcgaata tcagcg                                  26

<210> SEQ ID NO 86
<211> LENGTH: 27
<212> TYPE: DNA
<213> ORGANISM: Artificial Sequence
<220> FEATURE:
<223> OTHER INFORMATION: Primer

<400> SEQUENCE: 86
gctcaatctt gcggaaagca agatggg                                 27

<210> SEQ ID NO 87
<211> LENGTH: 28
<212> TYPE: DNA
<213> ORGANISM: Artificial Sequence
<220> FEATURE:
<223> OTHER INFORMATION: Primer

<400> SEQUENCE: 87
agatgggcgt tattcggcag ggccattg                                28

<210> SEQ ID NO 88
<211> LENGTH: 30
<212> TYPE: DNA
<213> ORGANISM: Artificial Sequence
<220> FEATURE:
<223> OTHER INFORMATION: Primer

<400> SEQUENCE: 88
```
aagctgggtc tgatcgatgc cattgctacc                                              30

<210> SEQ ID NO 89
<211> LENGTH: 28
<212> TYPE: DNA
<213> ORGANISM: Artificial Sequence
<220> FEATURE:
<223> OTHER INFORMATION: Primer

<400> SEQUENCE: 89
ctcgattatc gcccatccac gtatcgag                                                28

<210> SEQ ID NO 90
<211> LENGTH: 30
<212> TYPE: DNA
<213> ORGANISM: Artificial Sequence
<220> FEATURE:
<223> OTHER INFORMATION: Primer

<400> SEQUENCE: 90
tggatgcaat ccgctatggc attatccacg                                              30

<210> SEQ ID NO 91
<211> LENGTH: 30
<212> TYPE: DNA
<213> ORGANISM: Artificial Sequence
<220> FEATURE:
<223> OTHER INFORMATION: Primer

<400> SEQUENCE: 91
tcattcagtg cgttcaccgg cggatttgtc                                              30

<210> SEQ ID NO 92
<211> LENGTH: 30
<212> TYPE: DNA
<213> ORGANISM: Artificial Sequence
<220> FEATURE:
<223> OTHER INFORMATION: Primer

<400> SEQUENCE: 92
tcgatccgga agtagcgata gcgttcgatg                                              30

<210> SEQ ID NO 93
<211> LENGTH: 30
<212> TYPE: DNA
<213> ORGANISM: Artificial Sequence
<220> FEATURE:
<223> OTHER INFORMATION: Primer

<400> SEQUENCE: 93
cttggctgca atctcttcga gcacttcagg                                              30

<210> SEQ ID NO 94
<211> LENGTH: 26
<212> TYPE: DNA
<213> ORGANISM: Artificial Sequence
<220> FEATURE:
<223> OTHER INFORMATION: Primer

<400> SEQUENCE: 94
catcagaggt aatcaccact cgtgca                                                  26

<210> SEQ ID NO 95
<211> LENGTH: 26
<212> TYPE: DNA
<213> ORGANISM: Artificial Sequence

```
<220> FEATURE:
<223> OTHER INFORMATION: Primer

<400> SEQUENCE: 95
aagtagtagg ccacctcgtc gccata                                         26

<210> SEQ ID NO 96
<211> LENGTH: 26
<212> TYPE: DNA
<213> ORGANISM: Artificial Sequence
<220> FEATURE:
<223> OTHER INFORMATION: Primer

<400> SEQUENCE: 96
gccaatcagg cgctgatcta tgttct                                         26

<210> SEQ ID NO 97
<211> LENGTH: 26
<212> TYPE: DNA
<213> ORGANISM: Artificial Sequence
<220> FEATURE:
<223> OTHER INFORMATION: Primer

<400> SEQUENCE: 97
ctgatctatg ttctggcctc ggaggt                                         26

<210> SEQ ID NO 98
<211> LENGTH: 27
<212> TYPE: DNA
<213> ORGANISM: Artificial Sequence
<220> FEATURE:
<223> OTHER INFORMATION: Primer

<400> SEQUENCE: 98
ggctgatatc aaagcgatgg ccaatgc                                        27

<210> SEQ ID NO 99
<211> LENGTH: 27
<212> TYPE: DNA
<213> ORGANISM: Artificial Sequence
<220> FEATURE:
<223> OTHER INFORMATION: Primer

<400> SEQUENCE: 99
ccacgcctat tgatatgctc accagtg                                        27

<210> SEQ ID NO 100
<211> LENGTH: 28
<212> TYPE: DNA
<213> ORGANISM: Artificial Sequence
<220> FEATURE:
<223> OTHER INFORMATION: Primer

<400> SEQUENCE: 100
gcaaaccggt gattgctgcc gtgaatgg                                       28

<210> SEQ ID NO 101
<211> LENGTH: 27
<212> TYPE: DNA
<213> ORGANISM: Artificial Sequence
<220> FEATURE:
<223> OTHER INFORMATION: Primer

<400> SEQUENCE: 101
gcattggcca tcgctttgat atcagcc                                        27
```

```
<210> SEQ ID NO 102
<211> LENGTH: 27
<212> TYPE: DNA
<213> ORGANISM: Artificial Sequence
<220> FEATURE:
<223> OTHER INFORMATION: Primer

<400> SEQUENCE: 102
cactggtgag catatcaata ggcgtgg                                27

<210> SEQ ID NO 103
<211> LENGTH: 28
<212> TYPE: DNA
<213> ORGANISM: Artificial Sequence
<220> FEATURE:
<223> OTHER INFORMATION: Primer

<400> SEQUENCE: 103
ccattcacgg cagcaatcac cggtttgc                               28

<210> SEQ ID NO 104
<211> LENGTH: 30
<212> TYPE: DNA
<213> ORGANISM: Artificial Sequence
<220> FEATURE:
<223> OTHER INFORMATION: Primer

<400> SEQUENCE: 104
tcatcatcgc cagtgaaaac gcgcagttcg                             30

<210> SEQ ID NO 105
<211> LENGTH: 30
<212> TYPE: DNA
<213> ORGANISM: Artificial Sequence
<220> FEATURE:
<223> OTHER INFORMATION: Primer

<400> SEQUENCE: 105
ggatcgcgca aaccattgcc accaaatcac                             30

<210> SEQ ID NO 106
<211> LENGTH: 27
<212> TYPE: DNA
<213> ORGANISM: Artificial Sequence
<220> FEATURE:
<223> OTHER INFORMATION: Primer

<400> SEQUENCE: 106
atgagtgaag agtctctggt tctcagc                                27

<210> SEQ ID NO 107
<211> LENGTH: 24
<212> TYPE: DNA
<213> ORGANISM: Artificial Sequence
<220> FEATURE:
<223> OTHER INFORMATION: Primer

<400> SEQUENCE: 107
agatcgcaat cgctcgtgta tgtc                                   24

<210> SEQ ID NO 108
<211> LENGTH: 39
<212> TYPE: DNA
<213> ORGANISM: Artificial Sequence
<220> FEATURE:
<223> OTHER INFORMATION: Primer

<400> SEQUENCE: 108
```

```
gggaattcca tatgagaaaa gtagaaatca ttacagctg                                 39

<210> SEQ ID NO 109
<211> LENGTH: 39
<212> TYPE: DNA
<213> ORGANISM: Artificial Sequence
<220> FEATURE:
<223> OTHER INFORMATION: Primer

<400> SEQUENCE: 109
gagagtatac acagttttca cctcctttac agcagagat                                 39

<210> SEQ ID NO 110
<211> LENGTH: 39
<212> TYPE: DNA
<213> ORGANISM: Artificial Sequence
<220> FEATURE:
<223> OTHER INFORMATION: Primer

<400> SEQUENCE: 110
atctctgctg taaaggaggt gaaaactgtg tatactctc                                 39

<210> SEQ ID NO 111
<211> LENGTH: 40
<212> TYPE: DNA
<213> ORGANISM: Artificial Sequence
<220> FEATURE:
<223> OTHER INFORMATION: Primer

<400> SEQUENCE: 111
acgttgatct ccttgtacat tagaggattt ccgagaaagc                                40

<210> SEQ ID NO 112
<211> LENGTH: 40
<212> TYPE: DNA
<213> ORGANISM: Artificial Sequence
<220> FEATURE:
<223> OTHER INFORMATION: Primer

<400> SEQUENCE: 112
gctttctcgg aaatcctcta atgtacaagg agatcaacgt                                40

<210> SEQ ID NO 113
<211> LENGTH: 30
<212> TYPE: DNA
<213> ORGANISM: Artificial Sequence
<220> FEATURE:
<223> OTHER INFORMATION: Primer

<400> SEQUENCE: 113
cgacggatcc tcaacgacca ctgaagttgg                                           30

<210> SEQ ID NO 114
<211> LENGTH: 31
<212> TYPE: DNA
<213> ORGANISM: Artificial Sequence
<220> FEATURE:
<223> OTHER INFORMATION: Primer

<400> SEQUENCE: 114
cgacggatcc ttagaggatt tccgagaaag c                                         31

<210> SEQ ID NO 115
<211> LENGTH: 38
<212> TYPE: DNA
<213> ORGANISM: Artificial Sequence
```

```
<220> FEATURE:
<223> OTHER INFORMATION: Primer

<400> SEQUENCE: 115
ggtgtctaga gacagtcctg tcgtttatgt agaaggag                        38

<210> SEQ ID NO 116
<211> LENGTH: 52
<212> TYPE: DNA
<213> ORGANISM: Artificial Sequence
<220> FEATURE:
<223> OTHER INFORMATION: Primer

<400> SEQUENCE: 116
gggaattcca tatgcgtaac ttcctcctgc tatcaacgac cactgaagtt gg        52

<210> SEQ ID NO 117
<211> LENGTH: 38
<212> TYPE: DNA
<213> ORGANISM: Artificial Sequence
<220> FEATURE:
<223> OTHER INFORMATION: Primer

<400> SEQUENCE: 117
acgttgatct ccttctacat tatttttca gtcccatg                         38

<210> SEQ ID NO 118
<211> LENGTH: 38
<212> TYPE: DNA
<213> ORGANISM: Artificial Sequence
<220> FEATURE:
<223> OTHER INFORMATION: Primer

<400> SEQUENCE: 118
ggtgtctaga gtcaaaggag agaacaaaat catgagtg                        38

<210> SEQ ID NO 119
<211> LENGTH: 53
<212> TYPE: DNA
<213> ORGANISM: Artificial Sequence
<220> FEATURE:
<223> OTHER INFORMATION: Primer

<400> SEQUENCE: 119
gggaattcca tatgcgtaac ttcctcctgc tattagagga tttccgagaa agc       53

<210> SEQ ID NO 120
<211> LENGTH: 52
<212> TYPE: DNA
<213> ORGANISM: Artificial Sequence
<220> FEATURE:
<223> OTHER INFORMATION: Primer

<400> SEQUENCE: 120
tcagtggtcg ttgatcacgc tataaagaaa ggtgaaaact gtgtatactc tc        52

<210> SEQ ID NO 121
<211> LENGTH: 32
<212> TYPE: DNA
<213> ORGANISM: Artificial Sequence
<220> FEATURE:
<223> OTHER INFORMATION: Primer

<400> SEQUENCE: 121
cgacggatcc cttccttgga gctcatgctt tc                              32
```

```
<210> SEQ ID NO 122
<211> LENGTH: 38
<212> TYPE: DNA
<213> ORGANISM: Artificial Sequence
<220> FEATURE:
<223> OTHER INFORMATION: Primer

<400> SEQUENCE: 122
catgggactg aaaaaataat gtagaaggag atcaacgt                              38

<210> SEQ ID NO 123
<211> LENGTH: 52
<212> TYPE: DNA
<213> ORGANISM: Artificial Sequence
<220> FEATURE:
<223> OTHER INFORMATION: Primer

<400> SEQUENCE: 123
gagagtatac acagttttca cctttcttta tagcgtgatc aacgaccact ga             52

<210> SEQ ID NO 124
<211> LENGTH: 40
<212> TYPE: DNA
<213> ORGANISM: Artificial Sequence
<220> FEATURE:
<223> OTHER INFORMATION: Primer

<400> SEQUENCE: 124
ccaacttcag tggtcgttag tgaaaactgt gtatactctc                           40

<210> SEQ ID NO 125
<211> LENGTH: 40
<212> TYPE: DNA
<213> ORGANISM: Artificial Sequence
<220> FEATURE:
<223> OTHER INFORMATION: Primer

<400> SEQUENCE: 125
gagagtatac acagttttca ctaacgacca ctgaagttgg                           40

<210> SEQ ID NO 126
<211> LENGTH: 35
<212> TYPE: DNA
<213> ORGANISM: Artificial Sequence
<220> FEATURE:
<223> OTHER INFORMATION: Primer

<400> SEQUENCE: 126
gtcgcagaat tcccatcaat cgcagcaatc ccaac                                35

<210> SEQ ID NO 127
<211> LENGTH: 35
<212> TYPE: DNA
<213> ORGANISM: Artificial Sequence
<220> FEATURE:
<223> OTHER INFORMATION: Primer

<400> SEQUENCE: 127
taacatggta ccgacagaag cggaccagca aacga                                35

<210> SEQ ID NO 128
<211> LENGTH: 30
<212> TYPE: DNA
<213> ORGANISM: Artificial Sequence
<220> FEATURE:
<223> OTHER INFORMATION: Primer

<400> SEQUENCE: 128
```
cgacggatcc tcaacgacca ctgaagttgg         30

<210> SEQ ID NO 129
<211> LENGTH: 5469
<212> TYPE: DNA
<213> ORGANISM: Chloroflexus aurantiacus

<400> SEQUENCE: 129

| | |
|---|---|
| atgatcgaca ctgcgcccct tgccccacca cgggcgcccc gctctaatcc gattcgggat | 60 |
| cgagttgatt gggaagctca gcgcgctgct gcgctggcag atcccggtgc ctttcatggc | 120 |
| gcgattgccc ggacagttat ccactggtac gacccacaac accattgctg gattcgcttc | 180 |
| aacgagtcta gtcagcgttg gaagggctg gatgccgcta ccgtgcccc tgtaacggta | 240 |
| gactatcccg ccgattatca gccctggcaa caggcgtttg atgatagtga agcgccgttt | 300 |
| taccgctggt ttagtggtgg gttgacaaat gcctgcttta tgaagtaga ccggcatgtc | 360 |
| atgatgggct atggcgacga ggtggcctac tactttgaag gtgaccgctg ggataactcg | 420 |
| ctcaacaatg gtcgtggtgg tccggttgtc caggagacaa tcacgcggcg cgcctgttg | 480 |
| gtggaggtgg tgaaggctgc gcaggtgttg cgtgatctgg gcctgaagaa gggtgatcgg | 540 |
| attgctctga atatgccgaa tattatgccg cagatttatt atacggaagc ggcaaaacga | 600 |
| ctgggtattc tgtacacgcc ggtcttcggt ggcttctcgg acaagactct ttccgaccgt | 660 |
| attcacaatg ccggtgcacg agtggtgatt acctctgatg gtgcgtaccg caacgcgcag | 720 |
| gtggtgccct acaaagaagc gtataccgat caggcgctcg ataagtatat tccggttgag | 780 |
| acggcgcagg cgattgttgc gcagaccctg gccaccttgc cctgactga gtcgcagcgc | 840 |
| cagacgatca tcaccgaagt ggaggccgca ctggccggtg agattacggt tgagcgctcg | 900 |
| gacgtgatgc gtggggttgg ttctgccctc gcaaagctcc gcgatcttga tgcaagcgtg | 960 |
| caggcaaagg tgcgtacagt actgcgcag gcgctggtcg agtcgccgcc gcgggttgaa | 1020 |
| gctgtggtgg ttgtgcgtca taccggtcag gagattttgt ggaacgaggg gcgagatcgc | 1080 |
| tggagtcacg acttgctgga tgctgcgctg gcgaagattc tggccaatgc gcgtgctgcc | 1140 |
| ggctttgatg tgcacagtga gaatgatctg ctcaatctcc ccgatgacca gcttatccgt | 1200 |
| gcgctctacg ccagtattcc ctgtgaaccg gttgatgctg aatatccgat gtttatcatt | 1260 |
| tacacatcgg gtagcaccgg taagcccaag ggtgtgatcc acgttcacgg cggttatgtc | 1320 |
| gccggtgtgg tgcacacctt gcgggtcagt tttgacgccg agccgggtga tacgatatat | 1380 |
| gtgatcgccg atccgggctg gatcaccggt cagagctata tgctcacagc cacaatggcc | 1440 |
| ggtcggctga ccggggtgat tgccgaggga tcaccgctct cccctcagc cgggcgttat | 1500 |
| gccagcatca tcgagcgcta tgggtgcag atctttaagg cgggtgtgac cttcctcaag | 1560 |
| acagtgatgt ccaatccgca gaatgttgaa gatgtgcgac tctatgatat gcactcgctg | 1620 |
| cgggttgcaa ccttctgcgc cgagccggtc agtccggcgg tgcagcagtt tggtatgcag | 1680 |
| atcatgaccc cgcagtatat caattcgtac tgggcgaccg agcacggtgg aattgtctgg | 1740 |
| acgcatttct acggtaatca ggacttcccg cttcgtcccg atgcccatac ctatcccttg | 1800 |
| ccctgggtga tgggtgatgt ctgggtggcc gaaactgatg agagcgggac gacgcgctat | 1860 |
| cgggtcgctg atttcgatga agggcgag attgtgatta ccgccccgta tccctacctg | 1920 |
| acccgcacac tctgggtga tgtgcccggt ttcgaggcgt acctgcgcgg tgagattccg | 1980 |
| ctgcggggcct ggaagggtga tgccgagcgt ttcgtcaaga cctactggcg acgtgggcca | 2040 |
| aacggtgaat ggggctatat ccagggtgat tttgccatca agtaccccga tggtagcttc | 2100 |

```
acgctccacg gacgccctga cgatgtgatc aatgtgtcgg gccaccgtat gggcaccgag    2160
gagattgagg gtgccatttt gcgtgaccgc cagatcacgc ccgactcgcc cgtcggtaat    2220
tgtattgtgg tcggtgcgcc gcaccgtgag aagggtctga ccccggttgc cttcattcaa    2280
cctgcgcctg gccgtcatct gaccggcgcc gaccggcgcc gtctcgatga gctggtgcgt    2340
accgagaagg gggcggtcag tgtcccagag gattacatcg aggtcagtgc ctttcccgaa    2400
acccgcagcg ggaagtatat gcggcgcttt ttgcgcaata tgatgctcga tgaaccactg    2460
ggtgatacga cgacgttgcg caatcctgaa gtgctcgaag agattgcagc caagatcgct    2520
gagtggaaac gccgtcagcg tatggccgaa gagcagcaga tcatcgaacg ctatcgctac    2580
ttccggatcg agtatcaccc accaacggcc agtgcgggta aactcgcggt agtgacggtg    2640
acaaatccgc cggtgaacgc actgaatgag cgtgcgctcg atgagttgaa cacaattgtt    2700
gaccacctgg cccgtcgtca ggatgttgcc gcaattgtct tcaccggaca gggcgccagg    2760
agttttgtcg ccggcgctga tattcgccag ttgctcgaag agattcatac ggttgaagag    2820
gcaatggccc tgccgaataa cgcccatctt gctttccgca agattgagcg tatgaataag    2880
ccgtgtatcg cggcgatcaa cggtgtggcg ctcggtggtg gtctggaatt cgccatggcc    2940
tgccattacc gggttgccga tgtctatgcc gaattcggtc agccagagat taatctgcgc    3000
ttgctacctg gttatggtgg cacgcagcgc ttgccgcgcc tgttgtacaa gcgcaacaac    3060
ggcaccggtc tgctccgagc gctggagatg attctgggtg ggcgtagcgt accggctgat    3120
gaggcgctga gctgggtct gatcgatgcc attgctaccg gcgatcagga ctcactgtcg    3180
ctggcatgcg cgttagcccg tgccgcaatc ggcgccgatg gtcagttgat cgagtcggct    3240
gcggtgaccc aggcttttccg ccatcgccac gagcagcttg acgagtggcg caaaccagac    3300
ccgcgctttg ccgatgacga actgcgctcg attatcgccc atccacgtat cgagcggatt    3360
atccggcagg cccataccgt tgggcgcgat cggcagtgc atcgggcact ggatgcaatc    3420
cgctatggca ttatccacgg cttcgaggcc ggtctggagc acgaggcgaa gctcttttgcc    3480 gaggcagtgg ttgaccccgaa cggtggcaag cgtggtattc gcgagttcct cgaccgccag    3540
agtgcgccgt tgccaacccg ccgaccattg attacacctg aacaggagca actcttgcgc    3600
gatcagaaag aactgttgcc ggttggttca cccttcttcc ccggtgttga ccggattccg    3660
aagtggcagt acgcgcaggc ggttattcgt gatccggaca ccggtgcggc ggctcacggc    3720
gatcccatcg tggctgaaaa gcagattatt gtgccggtgg aacgcccccg cgccaatcag    3780
gcgctgatct atgttctggc ctcggaggtg aacttcaacg atatctgggc gattaccggt    3840
attccggtgt cacggtttga tgagcacgac cgcgactggc acgttaccgg ttcaggtggc    3900
atcggcctga tcgttgcgct gggtgaagag gcgcgacgcg aaggccggct gaaggtgggt    3960
gatctggtgg cgatctactc cgggcagtcg gatctgctct caccgctgat gggccttgat    4020
ccgatggccg ccgatttcgt catccagggg aacgacacgc cagatggatc gcatcagcaa    4080
tttatgctgg cccaggcccc gcagtgtctg cccatcccaa ccgatatgtc tatcgaggca    4140
gccggcagct acatcctcaa tctcggtacg atctatcgcg ccctctttac gacgttgcaa    4200
atcaaggccg gacgcaccat ctttatcgag ggtgcggcga ccggtaccgg tctggacgca    4260
gcgcgctcgg cggcccggaa tggtctgcgc gtaattggaa tggtcagttc gtcgtcacgt    4320
gcgtctacgc tgctggctgc gggtgccac ggtgcgatta accgtaaaga cccggaggtt    4380
gccgattgtt tcacgcgcgt gcccgaagat ccatcagcct gggcagcctg ggaagccgcc    4440
ggtcagccgt tgctggcgat gttccgggcg cagaacgacg ggcgactggc cgattatgtg    4500
```

```
gtctcgcacg cgggcgagac ggccttcccg cgcagtttcc agcttctcgg cgagccacgc   4560
gatggtcaca ttccgacgct cacattctac ggtgccacca gtggctacca cttcaccttc   4620
ctgggtaagc cagggtcagc ttcgccgacc gagatgctgc ggcgggccaa tctccgcgcc   4680
ggtgaggcgg tgttgatcta ctacggggtt gggagcgatg acctggtaga taccggcggt   4740
ctggaggcta tcgaggcggc gcggcaaatg ggagcgcgga tcgtcgtcgt taccgtcagc   4800
gatgcgcaac gcgagtttgt cctctcgttg ggcttcgggg ctgccctacg tggtgtcgtc   4860
agcctggcgg aactcaaacg cgcgcttcgg cgatgagtttg agtggccgcg cacgatgccg   4920
ccgttgccga acgcccgcca ggacccgcag ggtctgaaag aggctgtccg ccgcttcaac   4980
gatctggtct tcaagccgct aggaagcgcg gtcggtgtct tcttgcggag tgccgacaat   5040
ccgcgtggct accccgatct gatcatcgag cgggctgccc acgatgcact ggcggtgagc   5100
gcgatgctga tcaagccctt caccggacgg attgtctact tcgaggacat tggtgggcgg   5160
cgttactcct tcttcgcacc gcaaatctgg gtgcgccagc gccgcatcta catgccgacg   5220
gcacagatct ttggtacgca cctctcaaat gcgtatgaaa ttctgcgtct gaatgatgag   5280
atcagcgccg gtctgctgac gattaccgag ccggcagtgg tgccgtggga tgaactaccc   5340
gaagcacatc aggcgatgtg ggaaaatcgc cacacggcgg ccacttatgt ggtgaatcat   5400
gccttaccac gtctcggcct aaagaacagg gacgagctgt acgaggcgtg gacggccggc   5460
gagcggtag                                                            5469
```

<210> SEQ ID NO 130
<211> LENGTH: 701
<212> TYPE: PRT
<213> ORGANISM: Homo sapiens

<400> SEQUENCE: 130

```
Met Gly Leu Pro Glu Glu Arg Val Arg Ser Gly Ser Gly Ser Arg Gly
1               5                   10                  15

Gln Glu Glu Ala Gly Ala Gly Gly Arg Ala Arg Ser Trp Ser Pro Pro
            20                  25                  30

Pro Glu Val Ser Arg Ser Ala His Val Pro Ser Leu Gln Arg Tyr Arg
        35                  40                  45

Glu Leu His Arg Arg Ser Val Glu Glu Pro Arg Glu Phe Trp Gly Asp
    50                  55                  60

Ile Ala Lys Glu Phe Tyr Trp Lys Thr Pro Cys Pro Gly Pro Phe Leu
65                  70                  75                  80

Arg Tyr Asn Phe Asp Val Thr Lys Gly Lys Ile Phe Ile Glu Trp Met
                85                  90                  95

Lys Gly Ala Thr Thr Asn Ile Cys Tyr Asn Val Leu Asp Arg Asn Val
            100                 105                 110

His Glu Lys Lys Leu Gly Asp Lys Val Ala Phe Tyr Trp Glu Gly Asn
        115                 120                 125

Glu Pro Gly Glu Thr Thr Gln Ile Thr Tyr His Gln Leu Leu Val Gln
    130                 135                 140

Val Cys Gln Phe Ser Asn Val Leu Arg Lys Gln Gly Ile Gln Lys Gly
145                 150                 155                 160

Asp Arg Val Ala Ile Tyr Met Pro Met Ile Pro Glu Leu Val Val Ala
                165                 170                 175

Met Leu Ala Cys Ala Arg Ile Gly Ala Leu His Ser Ile Val Phe Ala
            180                 185                 190

Gly Phe Ser Ser Glu Ser Leu Cys Glu Arg Ile Leu Asp Ser Ser Cys
```

```
            195                 200                 205
Ser Leu Leu Ile Thr Thr Asp Ala Phe Tyr Arg Gly Glu Lys Leu Val
    210                 215                 220

Asn Leu Lys Glu Leu Ala Asp Glu Ala Leu Gln Lys Cys Gln Glu Lys
225                 230                 235                 240

Gly Phe Pro Val Arg Cys Cys Ile Val Val Lys His Leu Gly Arg Ala
                245                 250                 255

Glu Leu Gly Met Gly Asp Ser Thr Ser Gln Ser Pro Ile Lys Arg
                260                 265                 270

Ser Cys Pro Asp Val Gln Ile Ser Trp Asn Gln Gly Ile Asp Leu Trp
            275                 280                 285

Trp His Glu Leu Met Gln Glu Ala Gly Asp Glu Cys Glu Pro Glu Trp
        290                 295                 300

Cys Asp Ala Glu Asp Pro Leu Phe Ile Leu Tyr Thr Ser Gly Ser Thr
305                 310                 315                 320

Gly Lys Pro Lys Gly Val Val His Thr Val Gly Gly Tyr Met Leu Tyr
                325                 330                 335

Val Ala Thr Thr Phe Lys Tyr Val Phe Asp Phe His Ala Glu Asp Val
                340                 345                 350

Phe Trp Cys Thr Ala Asp Ile Gly Trp Ile Thr Gly His Ser Tyr Val
        355                 360                 365

Thr Tyr Gly Pro Leu Ala Asn Gly Ala Thr Ser Val Leu Phe Glu Gly
        370                 375                 380

Ile Pro Thr Tyr Pro Asp Val Asn Arg Leu Trp Ser Ile Val Asp Lys
385                 390                 395                 400

Tyr Lys Val Thr Lys Phe Tyr Thr Ala Pro Thr Ala Ile Arg Leu Leu
                405                 410                 415

Met Lys Phe Gly Asp Glu Pro Val Thr Lys His Ser Arg Ala Ser Leu
                420                 425                 430

Gln Val Leu Gly Thr Val Gly Glu Pro Ile Asn Pro Glu Ala Trp Leu
            435                 440                 445

Trp Tyr His Arg Val Val Gly Ala Gln Arg Cys Pro Ile Val Asp Thr
        450                 455                 460

Phe Trp Gln Thr Glu Thr Gly Gly His Met Leu Thr Pro Leu Pro Gly
465                 470                 475                 480

Ala Thr Pro Met Lys Pro Gly Ser Ala Thr Phe Pro Phe Phe Gly Val
                485                 490                 495

Ala Pro Ala Ile Leu Asn Glu Ser Gly Glu Glu Leu Glu Gly Glu Ala
            500                 505                 510

Glu Gly Tyr Leu Val Phe Lys Gln Pro Trp Pro Gly Ile Met Arg Thr
        515                 520                 525

Val Tyr Gly Asn His Glu Arg Phe Glu Thr Thr Tyr Phe Lys Lys Phe
        530                 535                 540

Pro Gly Tyr Tyr Val Thr Gly Asp Gly Cys Arg Asp Gln Asp Gly
545                 550                 555                 560

Tyr Tyr Trp Ile Thr Gly Arg Ile Asp Asp Met Leu Asn Val Ser Gly
                565                 570                 575

His Leu Leu Ser Thr Ala Glu Val Glu Ser Ala Leu Val Glu His Glu
            580                 585                 590

Ala Val Ala Glu Ala Ala Val Val Gly His Pro His Pro Val Lys Gly
        595                 600                 605

Glu Cys Leu Tyr Cys Phe Val Thr Leu Cys Asp Gly His Thr Phe Ser
610                 615                 620
```

```
Pro Lys Leu Thr Glu Glu Leu Lys Lys Gln Ile Arg Glu Lys Ile Gly
625                 630                 635                 640

Pro Ile Ala Thr Pro Asp Tyr Ile Gln Asn Ala Pro Gly Leu Pro Lys
            645                 650                 655

Thr Arg Ser Gly Lys Ile Met Arg Arg Val Leu Arg Lys Ile Ala Gln
        660                 665                 670

Asn Asp His Asp Leu Gly Asp Met Ser Thr Val Ala Asp Pro Ser Val
    675                 680                 685

Ile Ser His Leu Phe Ser His Arg Cys Leu Thr Ile Gln
    690                 695                 700

<210> SEQ ID NO 131
<211> LENGTH: 670
<212> TYPE: PRT
<213> ORGANISM: Pyrobaculum aerophilum

<400> SEQUENCE: 131

Met Ser Leu Glu Leu Lys Glu Lys Glu Ser Glu Leu Pro Phe Asp Glu
1               5                   10                  15

Gln Ile Ile Asn Asp Lys Trp Arg Ser Lys Tyr Thr Pro Ile Asp Ala
                20                  25                  30

Tyr Phe Lys Phe His Arg Gln Thr Val Glu Asn Leu Glu Ser Phe Trp
            35                  40                  45

Glu Ser Val Ala Lys Glu Leu Glu Trp Phe Lys Pro Trp Asp Lys Val
50                  55                  60

Leu Asp Ala Ser Asn Pro Pro Phe Tyr Lys Trp Phe Val Gly Gly Arg
65                  70                  75                  80

Leu Asn Leu Ser Tyr Leu Ala Val Asp Arg His Val Lys Thr Trp Arg
                85                  90                  95

Lys Asn Lys Leu Ala Ile Glu Trp Glu Gly Pro Val Asp Glu Asn
            100                 105                 110

Gly Tyr Pro Thr Asp Arg Arg Lys Leu Thr Tyr Tyr Asp Leu Tyr Arg
        115                 120                 125

Glu Val Asn Arg Val Ala Tyr Met Leu Lys Gln Asn Phe Gly Val Lys
130                 135                 140

Lys Gly Asp Lys Ile Thr Leu Tyr Leu Pro Met Val Pro Glu Leu Pro
145                 150                 155                 160

Ile Thr Met Leu Ala Ala Trp Arg Ile Gly Ala Ile Thr Ser Val Val
                165                 170                 175

Phe Ser Gly Phe Ser Ala Asp Ala Leu Ala Glu Arg Ile Asn Asp Ser
            180                 185                 190

Gln Ser Arg Ile Val Ile Thr Ala Asp Gly Phe Trp Arg Arg Gly Arg
        195                 200                 205

Val Val Arg Leu Lys Glu Val Asp Ala Ala Leu Glu Lys Ala Thr
210                 215                 220

Gly Val Glu Ser Val Ile Val Leu Pro Arg Leu Gly Leu Lys Asp Val
225                 230                 235                 240

Pro Met Thr Glu Gly Arg Asp Tyr Trp Trp Asn Lys Leu Met Gln Gly
                245                 250                 255

Ile Pro Pro Asn Ala Tyr Ile Glu Pro Glu Pro Val Glu Ser Glu His
            260                 265                 270

Pro Ser Phe Ile Leu Tyr Thr Ser Gly Thr Thr Gly Lys Pro Lys Gly
        275                 280                 285

Ile Val His Asp Thr Gly Gly Trp Ala Val His Val Tyr Ala Thr Met
290                 295                 300
```

-continued

```
Lys Trp Val Phe Asp Ile Arg Asp Asp Ile Phe Trp Cys Thr Ala
305                 310                 315                 320

Asp Ile Gly Trp Thr Gly His Ser Tyr Val Val Leu Gly Pro Leu
                325                 330                 335

Leu Met Gly Ala Thr Glu Val Ile Tyr Glu Gly Ala Pro Asp Tyr Pro
                340                 345                 350

Gln Pro Asp Arg Trp Ser Ile Ile Glu Arg Tyr Gly Val Thr Ile
                355                 360                 365

Phe Tyr Thr Ser Pro Thr Ala Ile Arg Met Phe Met Arg Tyr Gly Glu
    370                 375                 380

Glu Trp Pro Arg Lys His Asp Leu Ser Thr Leu Arg Ile Ile His Ser
385                 390                 395                 400

Val Gly Glu Pro Ile Asn Pro Glu Ala Trp Arg Trp Ala Tyr Arg Val
                405                 410                 415

Leu Gly Asn Glu Lys Val Ala Phe Gly Ser Thr Trp Trp Met Thr Glu
                420                 425                 430

Thr Gly Gly Ile Val Ile Ser His Ala Pro Gly Leu Tyr Leu Val Pro
                435                 440                 445

Met Lys Pro Gly Thr Asn Gly Pro Pro Leu Pro Gly Phe Glu Val Asp
    450                 455                 460

Val Val Asp Glu Asn Gly Asn Pro Ala Pro Gly Val Lys Gly Tyr
465                 470                 475                 480

Leu Val Ile Lys Lys Pro Trp Pro Gly Met Leu His Gly Ile Trp Gly
                485                 490                 495

Asp Pro Glu Arg Tyr Ile Lys Thr Tyr Trp Ser Arg Phe Pro Gly Met
                500                 505                 510

Phe Tyr Ala Gly Asp Tyr Ala Ile Lys Asp Lys Asp Gly Tyr Ile Trp
    515                 520                 525

Val Leu Gly Arg Ala Asp Glu Val Ile Lys Val Ala Gly His Arg Leu
530                 535                 540

Gly Thr Tyr Glu Leu Glu Ser Ala Leu Ile Ser His Pro Ala Val Ala
545                 550                 555                 560

Glu Ser Ala Val Val Gly Val Pro Asp Ala Ile Lys Gly Glu Val Pro
                565                 570                 575

Ile Ala Phe Val Val Leu Lys Gln Gly Val Ala Pro Ser Asp Glu Leu
                580                 585                 590

Arg Lys Glu Leu Arg Glu His Val Arg Arg Thr Ile Gly Pro Ile Ala
    595                 600                 605

Glu Pro Ala Gln Ile Phe Phe Val Thr Lys Leu Pro Lys Thr Arg Ser
    610                 615                 620

Gly Lys Ile Met Arg Arg Leu Leu Lys Ala Val Ala Thr Gly Ala Pro
625                 630                 635                 640

Leu Gly Asp Val Thr Thr Leu Glu Asp Glu Thr Ser Val Glu Glu Ala
                645                 650                 655

Lys Arg Ala Tyr Glu Glu Ile Lys Ala Glu Met Ala Arg Thr
    660                 665                 670

<210> SEQ ID NO 132
<211> LENGTH: 261
<212> TYPE: PRT
<213> ORGANISM: Clostridium acetobutylicum

<400> SEQUENCE: 132

Met Glu Leu Asn Asn Val Ile Leu Glu Lys Glu Gly Lys Val Ala Val
1               5                   10                  15
```

```
Val Thr Ile Asn Arg Pro Lys Ala Leu Asn Ala Leu Asn Ser Asp Thr
         20                  25                  30

Leu Lys Glu Met Asp Tyr Val Ile Gly Glu Ile Glu Asn Asp Ser Glu
             35                  40                  45

Val Leu Ala Val Ile Leu Thr Gly Ala Gly Lys Ser Phe Val Ala
 50                  55                  60

Gly Ala Asp Ile Ser Glu Met Lys Glu Met Asn Thr Ile Glu Gly Arg
 65                  70                  75                  80

Lys Phe Gly Ile Leu Gly Asn Lys Val Phe Arg Arg Leu Glu Leu Leu
                 85                  90                  95

Glu Lys Pro Val Ile Ala Ala Val Asn Gly Phe Ala Leu Gly Gly Gly
             100                 105                 110

Cys Glu Ile Ala Met Ser Cys Asp Ile Arg Ile Ala Ser Ser Asn Ala
             115                 120                 125

Arg Phe Gly Gln Pro Glu Val Gly Leu Gly Ile Thr Pro Gly Phe Gly
130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
            195                 200                 205

Leu Ser Lys Gln Ala Ile Asn Arg Gly Met Gln Cys Asp Ile Asp Thr
210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260

<210> SEQ ID NO 133
<211> LENGTH: 259
<212> TYPE: PRT
<213> ORGANISM: Thermoanaerobacterium thermosaccharolyticum

<400> SEQUENCE: 133

Met Asp Phe Asn Asn Val Leu Leu Asn Lys Asp Asp Gly Ile Ala Leu
1               5                   10                  15

Ile Ile Ile Asn Arg Pro Lys Ala Leu Asn Ala Leu Asn Tyr Glu Thr
            20                  25                  30

Leu Lys Glu Leu Asp Ser Val Leu Asp Ile Val Glu Asn Asp Lys Glu
            35                  40                  45

Ile Lys Val Leu Ile Ile Thr Gly Ser Gly Glu Lys Thr Phe Val Ala
         50                  55                  60

Gly Ala Asp Ile Ala Glu Met Ser Asn Met Thr Pro Leu Glu Ala Lys
65                  70                  75                  80

Lys Phe Ser Leu Tyr Gly Gln Lys Val Phe Arg Lys Ile Glu Met Leu
                85                  90                  95

Ser Lys Pro Val Ile Ala Ala Val Asn Gly Phe Ala Leu Gly Gly Gly
            100                 105                 110

Cys Glu Leu Ser Met Ala Cys Asp Ile Arg Ile Ala Ser Lys Asn Ala
            115                 120                 125
```

```
Lys Phe Gly Gln Pro Glu Val Gly Leu Gly Ile Ile Pro Gly Phe Ser
        130                 135                 140

Gly Thr Gln Arg Leu Pro Arg Leu Ile Gly Thr Ser Lys Ala Lys Glu
145                 150                 155                 160

Leu Ile Phe Thr Gly Asp Met Ile Asn Ser Asp Glu Ala Tyr Lys Ile
                165                 170                 175

Gly Leu Ile Ser Lys Val Val Glu Leu Ser Asp Leu Ile Glu Glu Ala
                180                 185                 190

Lys Lys Leu Ala Lys Lys Met Met Ser Lys Ser Gln Ile Ala Ile Ser
                195                 200                 205

Leu Ala Lys Glu Ala Ile Asn Lys Gly Met Glu Thr Asp Leu Asp Thr
                210                 215                 220

Gly Asn Thr Ile Glu Ala Glu Lys Phe Ser Leu Cys Phe Thr Thr Asp
225                 230                 235                 240

Asp Gln Lys Glu Gly Met Ile Ala Phe Ser Glu Lys Arg Ala Pro Lys
                        245                 250                 255

Phe Gly Lys

<210> SEQ ID NO 134
<211> LENGTH: 432
<212> TYPE: PRT
<213> ORGANISM: Methylobacterium extorquens

<400> SEQUENCE: 134

Met Ala Ala Ser Ala Ala Pro Ala Trp Thr Gly Gln Thr Ala Glu Ala
1               5                   10                  15

Lys Asp Leu Tyr Glu Leu Gly Glu Ile Pro Pro Leu Gly His Val Pro
                20                  25                  30

Ala Lys Met Tyr Ala Trp Ala Ile Arg Arg Glu Arg His Gly Pro Pro
            35                  40                  45

Glu Gln Ser His Gln Leu Glu Val Leu Pro Val Trp Glu Ile Gly Asp
        50                  55                  60

Asp Glu Val Leu Val Tyr Val Met Ala Gly Val Asn Tyr Asn Gly
65                  70                  75                  80

Val Trp Ala Gly Leu Gly Gly Pro Ile Ser Pro Phe Asp Val His Lys
                85                  90                  95

Gly Glu Tyr His Ile Ala Gly Ser Asp Ala Ser Gly Ile Val Trp Lys
            100                 105                 110

Val Gly Ala Lys Val Lys Arg Trp Lys Val Gly Asp Glu Val Ile Val
        115                 120                 125

His Cys Asn Gln Asp Asp Gly Asp Glu Glu Cys Asn Gly Gly Asp
    130                 135                 140

Pro Met Phe Ser Pro Thr Gln Arg Ile Trp Gly Tyr Glu Thr Gly Asp
145                 150                 155                 160

Gly Ser Phe Ala Gln Phe Cys Arg Val Gln Ser Arg Gln Leu Met Ala
                165                 170                 175

Arg Pro Lys His Leu Thr Trp Glu Glu Ala Ala Cys Tyr Thr Leu Thr
                180                 185                 190

Leu Ala Thr Ala Tyr Arg Met Leu Phe Gly His Ala Pro His Thr Val
            195                 200                 205

Arg Pro Gly Gln Asn Val Leu Ile Trp Gly Ala Ser Gly Gly Leu Gly
        210                 215                 220

Val Phe Gly Val Gln Leu Cys Ala Ala Ser Gly Ala Asn Ala Ile Ala
225                 230                 235                 240

Val Ile Ser Asp Glu Ser Lys Arg Asp Tyr Val Met Ser Leu Gly Ala
```

```
                  245                 250                 255
Lys Gly Val Ile Asn Arg Lys Asp Phe Asp Cys Trp Gly Gln Leu Pro
            260                 265                 270

Thr Val Asn Ser Pro Glu Tyr Asn Thr Trp Leu Lys Glu Ala Arg Lys
            275                 280                 285

Phe Gly Lys Ala Ile Trp Asp Ile Thr Gly Lys Gly Asn Asp Val Asp
            290                 295                 300

Ile Val Phe Glu His Pro Gly Glu Ala Thr Phe Pro Val Ser Thr Leu
305                 310                 315                 320

Val Ala Lys Arg Gly Gly Met Ile Val Phe Cys Ala Gly Thr Thr Gly
                325                 330                 335

Phe Asn Ile Thr Phe Asp Ala Arg Tyr Val Trp Met Arg Gln Lys Arg
                340                 345                 350

Ile Gln Gly Ser His Phe Ala His Leu Lys Gln Ala Ser Ala Ala Asn
                355                 360                 365

Gln Phe Val Met Asp Arg Arg Val Asp Pro Cys Met Ser Glu Val Phe
            370                 375                 380

Pro Trp Asp Lys Ile Pro Ala Ala His Thr Lys Met Trp Lys Asn Gln
385                 390                 395                 400

His Pro Pro Gly Asn Met Ala Val Leu Val Asn Ser Thr Arg Ala Gly
                405                 410                 415

Leu Arg Thr Val Glu Asp Val Ile Glu Ala Gly Pro Leu Lys Ala Met
                420                 425                 430

<210> SEQ ID NO 135
<211> LENGTH: 424
<212> TYPE: PRT
<213> ORGANISM: Caulobacter crescentus

<400> SEQUENCE: 135

Met Thr Ile Gln Thr Leu Glu Thr Thr Ala Leu Lys Asp Leu Tyr Glu
1               5                   10                  15

Ile Gly Glu Ile Pro Pro Ala Phe His Val Pro Lys Thr Met Tyr Ala
            20                  25                  30

Trp Ser Ile Arg Lys Glu Arg His Gly Lys Pro Thr Gln Ala Met Gln
        35                  40                  45

Val Glu Val Val Pro Thr Trp Glu Ile Gly Asp Glu Val Leu Val
    50                  55                  60

Leu Val Met Ala Ala Gly Val Asn Tyr Asn Gly Val Trp Ala Ala Leu
65                  70                  75                  80

Gly Glu Pro Ile Ser Pro Leu Asp Gly His Lys Gln Pro Phe His Ile
                85                  90                  95

Ala Gly Ser Asp Ala Ser Gly Ile Val Trp Lys Val Gly Ala Lys Val
            100                 105                 110

Lys Arg Trp Lys Leu Gly Asp Glu Val Val Ile His Cys Asn Gln Asp
        115                 120                 125

Asp Gly Asp Asp Glu Glu Cys Asn Gly Gly Asp Pro Met Phe Ser Ser
    130                 135                 140

Ser Gln Arg Ile Trp Gly Tyr Glu Thr Pro Asp Gly Ser Phe Ala Gln
145                 150                 155                 160

Phe Cys Arg Val Gln Ser Arg Gln Leu Leu Pro Arg Pro Lys His Leu
                165                 170                 175

Thr Trp Glu Glu Ser Ala Cys Tyr Thr Leu Thr Leu Ala Thr Ala Tyr
            180                 185                 190

Arg Met Leu Phe Gly His Lys Pro His Glu Leu Lys Pro Gly Gln Asn
```

```
                195                 200                 205
Val Leu Val Trp Gly Ala Ser Gly Gly Leu Gly Val Phe Ala Thr Gln
210                 215                 220

Leu Ala Val Ala Gly Ala Asn Ala Ile Gly Val Val Ser Ser Glu
225                 230                 235                 240

Asp Lys Arg Glu Phe Val Leu Ser Met Gly Ala Lys Ala Val Leu Asn
                245                 250                 255

Arg Gly Glu Phe Asn Cys Trp Gly Gln Leu Pro Lys Val Asn Gly Pro
                260                 265                 270

Glu Phe Asn Asp Tyr Met Lys Glu Ser Arg Lys Phe Gly Lys Ala Ile
                275                 280                 285

Trp Gln Ile Thr Gly Asn Lys Asp Val Asp Met Val Phe Glu His Pro
290                 295                 300

Gly Glu Gln Thr Phe Pro Val Ser Val Phe Leu Val Lys Arg Gly Gly
305                 310                 315                 320

Met Val Val Ile Cys Ala Gly Thr Thr Gly Phe Asn Leu Thr Met Asp
                325                 330                 335

Ala Arg Phe Leu Trp Met Arg Gln Lys Arg Val Gln Gly Ser His Phe
                340                 345                 350

Ala Asn Leu Met Gln Ala Ser Ala Ala Asn Gln Leu Val Ile Asp Arg
                355                 360                 365

Arg Val Asp Pro Cys Leu Ser Glu Val Phe Pro Trp Asp Gln Ile Pro
                370                 375                 380

Ala Ala His Glu Lys Met Leu Ala Asn Gln His Leu Pro Gly Asn Met
385                 390                 395                 400

Ala Val Leu Val Cys Ala Gln Arg Pro Gly Leu Arg Thr Phe Glu Glu
                405                 410                 415

Val Gln Glu Leu Ser Gly Ala Pro
                420

<210> SEQ ID NO 136
<211> LENGTH: 26
<212> TYPE: DNA
<213> ORGANISM: Artificial Sequence
<220> FEATURE:
<223> OTHER INFORMATION: Primer

<400> SEQUENCE: 136
gggaattcca tatgatcgac actgcg                                           26

<210> SEQ ID NO 137
<211> LENGTH: 30
<212> TYPE: DNA
<213> ORGANISM: Artificial Sequence
<220> FEATURE:
<223> OTHER INFORMATION: Primer

<400> SEQUENCE: 137
cgaaggatcc aacgataatc ggctcagcac                                       30

<210> SEQ ID NO 138
<211> LENGTH: 44
<212> TYPE: DNA
<213> ORGANISM: Artificial Sequence
<220> FEATURE:
<223> OTHER INFORMATION: Primer

<400> SEQUENCE: 138
ataggcggcc gcaggaatgc tgtatgagcg aagaaagctt attc                        44
```

<210> SEQ ID NO 139
<211> LENGTH: 43
<212> TYPE: DNA
<213> ORGANISM: Artificial Sequence
<220> FEATURE:
<223> OTHER INFORMATION: Primer

<400> SEQUENCE: 139
atgctcgcat ctcgagtagc taaattaaat tacatcaata gta                43

<210> SEQ ID NO 140
<211> LENGTH: 3678
<212> TYPE: DNA
<213> ORGANISM: Chloroflexus aurantiacus
<220> FEATURE:
<221> NAME/KEY: CDS
<222> LOCATION: (1)..(3675)

<400> SEQUENCE: 140

| atg | gcg | acg | ggg | gag | tcc | atg | agc | gga | aca | gga | cga | ctg | gca | gga | aag | 48 |
|-----|-----|-----|-----|-----|-----|-----|-----|-----|-----|-----|-----|-----|-----|-----|-----|-----|
| Met | Ala | Thr | Gly | Glu | Ser | Met | Ser | Gly | Thr | Gly | Arg | Leu | Ala | Gly | Lys |    |
| 1   |     |     |     | 5   |     |     |     |     | 10  |     |     |     |     | 15  |     |    |

| att | gcg | tta | att | acc | ggt | ggc | gcc | ggc | aat | atc | ggc | agt | gaa | ttg | aca | 96 |
| Ile | Ala | Leu | Ile | Thr | Gly | Gly | Ala | Gly | Asn | Ile | Gly | Ser | Glu | Leu | Thr |    |
|     |     |     | 20  |     |     |     |     | 25  |     |     |     |     | 30  |     |     |    |

| cgt | cgc | ttt | ctc | gca | gag | gga | gcg | acg | gtc | att | att | agt | gga | cgg | aat | 144 |
| Arg | Arg | Phe | Leu | Ala | Glu | Gly | Ala | Thr | Val | Ile | Ile | Ser | Gly | Arg | Asn |     |
| 35  |     |     |     |     | 40  |     |     |     |     | 45  |     |     |     |     |     |     |

| cgg | gcg | aag | ttg | acc | gca | ctg | gcc | gaa | cgg | atg | cag | gca | gag | gca | gga | 192 |
| Arg | Ala | Lys | Leu | Thr | Ala | Leu | Ala | Glu | Arg | Met | Gln | Ala | Glu | Ala | Gly |     |
| 50  |     |     |     |     | 55  |     |     |     |     | 60  |     |     |     |     |     |     |

| gtg | ccg | gca | aag | cgc | atc | gat | ctc | gaa | gtc | atg | gat | ggg | agt | gat | ccg | 240 |
| Val | Pro | Ala | Lys | Arg | Ile | Asp | Leu | Glu | Val | Met | Asp | Gly | Ser | Asp | Pro |     |
| 65  |     |     |     | 70  |     |     |     |     | 75  |     |     |     |     | 80  |     |     |

| gtc | gcg | gta | cgt | gcc | ggt | atc | gaa | gcg | att | gtg | gcc | cgt | cac | ggc | cag | 288 |
| Val | Ala | Val | Arg | Ala | Gly | Ile | Glu | Ala | Ile | Val | Ala | Arg | His | Gly | Gln |     |
|     |     |     | 85  |     |     |     |     | 90  |     |     |     |     | 95  |     |     |     |

| atc | gac | att | ctg | gtc | aac | aat | gca | gga | agt | gcc | ggt | gcc | cag | cgt | cgt | 336 |
| Ile | Asp | Ile | Leu | Val | Asn | Asn | Ala | Gly | Ser | Ala | Gly | Ala | Gln | Arg | Arg |     |
|     |     |     | 100 |     |     |     |     | 105 |     |     |     |     | 110 |     |     |     |

| ctg | gcc | gag | att | cca | ctc | act | gaa | gct | gaa | tta | ggc | cct | ggc | gcc | gaa | 384 |
| Leu | Ala | Glu | Ile | Pro | Leu | Thr | Glu | Ala | Glu | Leu | Gly | Pro | Gly | Ala | Glu |     |
|     | 115 |     |     |     |     | 120 |     |     |     |     | 125 |     |     |     |     |     |

| gag | acg | ctt | cat | gcc | agc | atc | gcc | aat | tta | ctt | ggt | atg | gga | tgg | cat | 432 |
| Glu | Thr | Leu | His | Ala | Ser | Ile | Ala | Asn | Leu | Leu | Gly | Met | Gly | Trp | His |     |
|     | 130 |     |     |     |     | 135 |     |     |     |     | 140 |     |     |     |     |     |

| ctg | atg | cgt | att | gcg | gca | cct | cat | atg | ccg | gta | gga | agt | gcg | gtc | atc | 480 |
| Leu | Met | Arg | Ile | Ala | Ala | Pro | His | Met | Pro | Val | Gly | Ser | Ala | Val | Ile |     |
| 145 |     |     |     |     | 150 |     |     |     |     | 155 |     |     |     |     | 160 |     |

| aat | gtc | tcg | acc | atc | ttt | tca | cgg | gct | gag | tac | tac | ggg | cgg | att | ccg | 528 |
| Asn | Val | Ser | Thr | Ile | Phe | Ser | Arg | Ala | Glu | Tyr | Tyr | Gly | Arg | Ile | Pro |     |
|     |     |     |     | 165 |     |     |     |     | 170 |     |     |     |     | 175 |     |     |

| tat | gtc | acc | cct | aaa | gct | gct | ctt | aat | gct | cta | tct | caa | ctt | gct | gcg | 576 |
| Tyr | Val | Thr | Pro | Lys | Ala | Ala | Leu | Asn | Ala | Leu | Ser | Gln | Leu | Ala | Ala |     |
|     |     |     | 180 |     |     |     |     | 185 |     |     |     |     | 190 |     |     |     |

| cgt | gag | tta | ggt | gca | cgt | ggc | atc | cgc | gtt | aat | acg | atc | ttt | ccc | ggc | 624 |
| Arg | Glu | Leu | Gly | Ala | Arg | Gly | Ile | Arg | Val | Asn | Thr | Ile | Phe | Pro | Gly |     |
|     |     | 195 |     |     |     |     | 200 |     |     |     |     | 205 |     |     |     |     |

| ccg | att | gaa | agt | gat | cgc | atc | cgt | aca | gtg | ttc | cag | cgt | atg | gat | cag | 672 |
| Pro | Ile | Glu | Ser | Asp | Arg | Ile | Arg | Thr | Val | Phe | Gln | Arg | Met | Asp | Gln |     |
|     | 210 |     |     |     |     | 215 |     |     |     |     | 220 |     |     |     |     |     |

| ctc | aag | ggg | cgg | ccc | gaa | ggc | gac | aca | gcg | cac | cat | ttt | ttg | aac | acc | 720 |

```
Leu Lys Gly Arg Pro Glu Gly Asp Thr Ala His His Phe Leu Asn Thr
225                 230                 235                 240 atg cga ttg tgt cgt gcc aac gac cag ggc gcg ctt gaa cgt cgg ttc        768
Met Arg Leu Cys Arg Ala Asn Asp Gln Gly Ala Leu Glu Arg Arg Phe
                245                 250                 255 ccc tcc gtc ggt gat gtg gca gac gcc gct gtc ttt ctg gcc agt gcc        816
Pro Ser Val Gly Asp Val Ala Asp Ala Ala Val Phe Leu Ala Ser Ala
                260                 265                 270 gaa tcc gcc gct ctc tcc ggt gag acg att gag gtt acg cac gga atg        864
Glu Ser Ala Ala Leu Ser Gly Glu Thr Ile Glu Val Thr His Gly Met
            275                 280                 285 gag ttg ccg gcc tgc agt gag acc agc ctg ctg gcc cgt act gat ctg        912
Glu Leu Pro Ala Cys Ser Glu Thr Ser Leu Leu Ala Arg Thr Asp Leu
        290                 295                 300 cgc acg att gat gcc agt ggc cgc acg acg ctc atc tgc gcc ggc gac        960
Arg Thr Ile Asp Ala Ser Gly Arg Thr Thr Leu Ile Cys Ala Gly Asp
305                 310                 315                 320 cag att gaa gag gtg atg gcg ctc acc ggt atg ttg cgt acc tgt ggg       1008
Gln Ile Glu Glu Val Met Ala Leu Thr Gly Met Leu Arg Thr Cys Gly
                325                 330                 335 agt gaa gtg atc atc ggc ttc cgt tcg gct gcg gcg ctg gcc cag ttc       1056
Ser Glu Val Ile Ile Gly Phe Arg Ser Ala Ala Ala Leu Ala Gln Phe
                340                 345                 350 gag cag gca gtc aat gag agt cgg cgg ctg gcc ggc gca gac ttt acg       1104
Glu Gln Ala Val Asn Glu Ser Arg Arg Leu Ala Gly Ala Asp Phe Thr
            355                 360                 365 cct ccc att gcc ttg cca ctc gat cca cgc gat ccg gca aca att gac       1152
Pro Pro Ile Ala Leu Pro Leu Asp Pro Arg Asp Pro Ala Thr Ile Asp
        370                 375                 380 gct gtc ttc gat tgg gcc ggc gag aat acc ggc ggg att cat gca gcg       1200
Ala Val Phe Asp Trp Ala Gly Glu Asn Thr Gly Gly Ile His Ala Ala
385                 390                 395                 400 gtg att ctg cct gct acc agt cac gaa ccg gca ccg tgc gtg att gag       1248
Val Ile Leu Pro Ala Thr Ser His Glu Pro Ala Pro Cys Val Ile Glu
                405                 410                 415 gtt gat gat gag cgg gtg ctg aat ttt ctg gcc gat gaa atc acc ggg       1296
Val Asp Asp Glu Arg Val Leu Asn Phe Leu Ala Asp Glu Ile Thr Gly
                420                 425                 430 aca att gtg att gcc agt cgc ctg gcc cgt tac tgg cag tcg caa cgg       1344
Thr Ile Val Ile Ala Ser Arg Leu Ala Arg Tyr Trp Gln Ser Gln Arg
            435                 440                 445 ctt acc ccc ggc gca cgt gcg cgt ggg ccg cgt gtc att ttt ctc tcg       1392
Leu Thr Pro Gly Ala Arg Ala Arg Gly Pro Arg Val Ile Phe Leu Ser
        450                 455                 460 aac ggt gcc gat caa aat ggg aat gtt tac gga cgc att caa agt gcc       1440
Asn Gly Ala Asp Gln Asn Gly Asn Val Tyr Gly Arg Ile Gln Ser Ala
465                 470                 475                 480 gct atc ggt cag ctc att cgt gtg tgg cgt cac gag gct gaa ctt gac       1488
Ala Ile Gly Gln Leu Ile Arg Val Trp Arg His Glu Ala Glu Leu Asp
                485                 490                 495 tat cag cgt gcc agc gcc gcc ggt gat cat gtg ctg ccg ccg gta tgg       1536
Tyr Gln Arg Ala Ser Ala Ala Gly Asp His Val Leu Pro Pro Val Trp
                500                 505                 510 gcc aat cag att gtg cgc ttc gct aac cgc agc ctt gaa ggg tta gaa       1584
Ala Asn Gln Ile Val Arg Phe Ala Asn Arg Ser Leu Glu Gly Leu Glu
            515                 520                 525 ttt gcc tgt gcc tgg aca gct caa ttg ctc cat agt caa cgc cat atc       1632
Phe Ala Cys Ala Trp Thr Ala Gln Leu Leu His Ser Gln Arg His Ile
        530                 535                 540 aat gag att acc ctc aac atc cct gcc aac att agc gcc acc acc ggc       1680
```

```
Asn Glu Ile Thr Leu Asn Ile Pro Ala Asn Ile Ser Ala Thr Thr Gly
545                 550                 555                 560 gca cgc agt gca tcg gtc gga tgg gcg gaa agc ctg atc ggg ttg cat      1728
Ala Arg Ser Ala Ser Val Gly Trp Ala Glu Ser Leu Ile Gly Leu His
                565                 570                 575 ttg ggg aaa gtt gcc ttg att acc ggt ggc agc gcc ggt att ggt ggg      1776
Leu Gly Lys Val Ala Leu Ile Thr Gly Gly Ser Ala Gly Ile Gly Gly
                580                 585                 590 cag atc ggg cgc ctc ctg gct ttg agt ggc gcg cgc gtg atg ctg gca      1824
Gln Ile Gly Arg Leu Leu Ala Leu Ser Gly Ala Arg Val Met Leu Ala
                595                 600                 605 gcc cgt gat cgg cat aag ctc gaa cag atg cag gcg atg atc caa tct      1872
Ala Arg Asp Arg His Lys Leu Glu Gln Met Gln Ala Met Ile Gln Ser
610                 615                 620 gag ctg gct gag gtg ggg tat acc gat gtc gaa gat cgc gtc cac att      1920
Glu Leu Ala Glu Val Gly Tyr Thr Asp Val Glu Asp Arg Val His Ile
625                 630                 635                 640 gca ccg ggc tgc gat gtg agt agc gaa gcg cag ctt gcg gat ctt gtt      1968
Ala Pro Gly Cys Asp Val Ser Ser Glu Ala Gln Leu Ala Asp Leu Val
                645                 650                 655 gaa cgt acc ctg tca gct ttt ggc acc gtc gat tat ctg atc aac aac      2016
Glu Arg Thr Leu Ser Ala Phe Gly Thr Val Asp Tyr Leu Ile Asn Asn
                660                 665                 670 gcc ggg atc gcc ggt gtc gaa gag atg gtt atc gat atg cca gtt gag      2064
Ala Gly Ile Ala Gly Val Glu Glu Met Val Ile Asp Met Pro Val Glu
                675                 680                 685 gga tgg cgc cat acc ctc ttc gcc aat ctg atc agc aac tac tcg ttg      2112
Gly Trp Arg His Thr Leu Phe Ala Asn Leu Ile Ser Asn Tyr Ser Leu
                690                 695                 700 atg cgc aaa ctg gcg ccg ttg atg aaa aaa cag ggt agc ggt tac atc      2160
Met Arg Lys Leu Ala Pro Leu Met Lys Lys Gln Gly Ser Gly Tyr Ile
705                 710                 715                 720 ctt aac gtc tca tca tac ttt ggc ggt gaa aaa gat gcg gcc att ccc      2208
Leu Asn Val Ser Ser Tyr Phe Gly Gly Glu Lys Asp Ala Ala Ile Pro
                725                 730                 735 tac ccc aac cgt gcc gat tac gcc gtc tcg aag gct ggt cag cgg gca      2256
Tyr Pro Asn Arg Ala Asp Tyr Ala Val Ser Lys Ala Gly Gln Arg Ala
                740                 745                 750 atg gcc gaa gtc ttt gcg cgc ttc ctt ggc ccg gag ata cag atc aat      2304
Met Ala Glu Val Phe Ala Arg Phe Leu Gly Pro Glu Ile Gln Ile Asn
                755                 760                 765 gcc att gcg ccg ggt ccg gtc gaa ggt gat cgc ttg cgc ggt acc ggt      2352
Ala Ile Ala Pro Gly Pro Val Glu Gly Asp Arg Leu Arg Gly Thr Gly
                770                 775                 780 gaa cgt ccc ggc ctc ttt gcc cgt cgg gcg cgg ctg att ttg gag aac      2400
Glu Arg Pro Gly Leu Phe Ala Arg Arg Ala Arg Leu Ile Leu Glu Asn
785                 790                 795                 800 aag cgg ctg aat gag ctt cac gct gct ctt atc gcg gct gcg cgc acc      2448
Lys Arg Leu Asn Glu Leu His Ala Ala Leu Ile Ala Ala Ala Arg Thr
                805                 810                 815 gat gag cga tct atg cac gaa ctg gtt gaa ctg ctc tta ccc aat gat      2496
Asp Glu Arg Ser Met His Glu Leu Val Glu Leu Leu Leu Pro Asn Asp
                820                 825                 830 gtg gcc gca cta gag cag aat ccc gca gca cct acc gcg ttg cgt gaa      2544
Val Ala Ala Leu Glu Gln Asn Pro Ala Ala Pro Thr Ala Leu Arg Glu
                835                 840                 845 ctg gca cga cgt ttt cgc agc gaa ggc gat ccg gcg gca tca tca agc      2592
Leu Ala Arg Arg Phe Arg Ser Glu Gly Asp Pro Ala Ala Ser Ser Ser
850                 855                 860 agt gcg ctg ctg aac cgt tca att gcc gct aaa ttg ctg gct cgt ttg      2640
```

-continued

```
Ser Ala Leu Leu Asn Arg Ser Ile Ala Ala Lys Leu Leu Ala Arg Leu
865                 870                 875                 880 cat aat ggt ggc tat gtg ttg cct gcc gac atc ttt gca aac ctg cca      2688
His Asn Gly Gly Tyr Val Leu Pro Ala Asp Ile Phe Ala Asn Leu Pro
                    885                 890                 895 aac ccg ccc gat ccc ttc ttc acc cga gcc cag att gat cgc gag gct      2736
Asn Pro Pro Asp Pro Phe Phe Thr Arg Ala Gln Ile Asp Arg Glu Ala
                900                 905                 910 cgc aag gtt cgt gac ggc atc atg ggg atg ctc tac ctg caa cgg atg      2784
Arg Lys Val Arg Asp Gly Ile Met Gly Met Leu Tyr Leu Gln Arg Met
            915                 920                 925 ccg act gag ttt gat gtc gca atg gcc acc gtc tat tac ctt gcc gac      2832
Pro Thr Glu Phe Asp Val Ala Met Ala Thr Val Tyr Tyr Leu Ala Asp
        930                 935                 940 cgc aat gtc agt ggt gag aca ttc cac cca tca ggt ggt ttg cgt tac      2880
Arg Asn Val Ser Gly Glu Thr Phe His Pro Ser Gly Gly Leu Arg Tyr
945                 950                 955                 960 gaa cgc acc cct acc ggt ggc gaa ctc ttc ggc ttg ccc tca ccg gaa      2928
Glu Arg Thr Pro Thr Gly Gly Glu Leu Phe Gly Leu Pro Ser Pro Glu
                965                 970                 975 cgg ctg gcg gag ctg gtc gga agc acg gtc tat ctg ata ggt gaa cat      2976
Arg Leu Ala Glu Leu Val Gly Ser Thr Val Tyr Leu Ile Gly Glu His
                980                 985                 990 ctg act gaa cac ctt aac ctg ctt  gcc cgt gcg tac ctc  gaa cgt tac    3024
Leu Thr Glu His Leu Asn Leu Leu  Ala Arg Ala Tyr Leu  Glu Arg Tyr
            995                 1000                1005 ggg gca cgt cag gta gtg atg  att gtt gag aca gaa  acc ggg gca        3069
Gly Ala Arg Gln Val Val Met  Ile Val Glu Thr Glu  Thr Gly Ala
        1010                1015                1020 gag aca atg cgt cgc ttg ctc  cac gat cac gtc gag  gct ggt cgg        3114
Glu Thr Met Arg Arg Leu Leu  His Asp His Val Glu  Ala Gly Arg
        1025                1030                1035 ctg atg act att gtg gcc ggt  gat cag atc gaa gcc  gct atc gac        3159
Leu Met Thr Ile Val Ala Gly  Asp Gln Ile Glu Ala  Ala Ile Asp
        1040                1045                1050 cag gct atc act cgc tac ggt  cgc cca ggg ccg gtc  gtc tgt acc        3204
Gln Ala Ile Thr Arg Tyr Gly  Arg Pro Gly Pro Val  Val Cys Thr
        1055                1060                1065 ccc ttc cgg cca ctg ccg acg  gta cca ctg gtc ggg  cgt aaa gac        3249
Pro Phe Arg Pro Leu Pro Thr  Val Pro Leu Val Gly  Arg Lys Asp
        1070                1075                1080 agt gac tgg agc aca gtg ttg  agt gag gct gaa ttt  gcc gag ttg        3294
Ser Asp Trp Ser Thr Val Leu  Ser Glu Ala Glu Phe  Ala Glu Leu
        1085                1090                1095 tgc gaa cac cag ctc acc cac  cat ttc cgg gta gcg  cgc aag att        3339
Cys Glu His Gln Leu Thr His  His Phe Arg Val Ala  Arg Lys Ile
        1100                1105                1110 gcc ctg agt gat ggt gcc agt  ctc gcg ctg gtc act  ccc gaa act        3384
Ala Leu Ser Asp Gly Ala Ser  Leu Ala Leu Val Thr  Pro Glu Thr
        1115                1120                1125 acg gct acc tca act acc gag  caa ttt gct ctg gct  aac ttc atc        3429
Thr Ala Thr Ser Thr Thr Glu  Gln Phe Ala Leu Ala  Asn Phe Ile
        1130                1135                1140 aaa acg acc ctt cac gct ttt  acg gct acg att ggt  gtc gag agc        3474
Lys Thr Thr Leu His Ala Phe  Thr Ala Thr Ile Gly  Val Glu Ser
        1145                1150                1155 gaa aga act gct cag cgc att  ctg atc aat caa gtc  gat ctg acc        3519
Glu Arg Thr Ala Gln Arg Ile  Leu Ile Asn Gln Val  Asp Leu Thr
        1160                1165                1170 cgg cgt gcg cgt gcc gaa gag  ccg cgt gat ccg cac  gag cgt caa        3564
```

```
Arg Arg Ala Arg Ala Glu Glu Pro Arg Asp Pro His Glu Arg Gln
    1175                1180                1185 caa gaa ctg gaa cgt ttt atc gag gca gtc ttg ctg gtc act gca       3609
Gln Glu Leu Glu Arg Phe Ile Glu Ala Val Leu Leu Val Thr Ala
    1190                1195                1200 cca ctc ccg cct gaa gcc gat acc cgt tac gcc ggg cgg att cat       3654
Pro Leu Pro Pro Glu Ala Asp Thr Arg Tyr Ala Gly Arg Ile His
    1205                1210                1215 cgc gga cgg gcg att acc gtg taa                                    3678
Arg Gly Arg Ala Ile Thr Val
    1220            1225

<210> SEQ ID NO 141
<211> LENGTH: 1225
<212> TYPE: PRT
<213> ORGANISM: Chloroflexus aurantiacus

<400> SEQUENCE: 141

Met Ala Thr Gly Glu Ser Met Ser Gly Thr Gly Arg Leu Ala Gly Lys
1               5                   10                  15

Ile Ala Leu Ile Thr Gly Gly Ala Gly Asn Ile Gly Ser Glu Leu Thr
            20                  25                  30

Arg Arg Phe Leu Ala Glu Gly Ala Thr Val Ile Ile Ser Gly Arg Asn
        35                  40                  45

Arg Ala Lys Leu Thr Ala Leu Ala Glu Arg Met Gln Ala Glu Ala Gly
    50                  55                  60

Val Pro Ala Lys Arg Ile Asp Leu Glu Val Met Asp Gly Ser Asp Pro
65                  70                  75                  80

Val Ala Val Arg Ala Gly Ile Glu Ala Ile Val Ala Arg His Gly Gln
                85                  90                  95

Ile Asp Ile Leu Val Asn Asn Ala Gly Ser Ala Gly Ala Gln Arg Arg
            100                 105                 110

Leu Ala Glu Ile Pro Leu Thr Glu Ala Glu Leu Gly Pro Gly Ala Glu
        115                 120                 125

Glu Thr Leu His Ala Ser Ile Ala Asn Leu Leu Gly Met Gly Trp His
    130                 135                 140

Leu Met Arg Ile Ala Ala Pro His Met Pro Val Gly Ser Ala Val Ile
145                 150                 155                 160

Asn Val Ser Thr Ile Phe Ser Arg Ala Glu Tyr Tyr Gly Arg Ile Pro
                165                 170                 175

Tyr Val Thr Pro Lys Ala Ala Leu Asn Ala Leu Ser Gln Leu Ala Ala
            180                 185                 190

Arg Glu Leu Gly Ala Arg Gly Ile Arg Val Asn Thr Ile Phe Pro Gly
        195                 200                 205

Pro Ile Glu Ser Asp Arg Ile Arg Thr Val Phe Gln Arg Met Asp Gln
    210                 215                 220

Leu Lys Gly Arg Pro Glu Gly Asp Thr Ala His Phe Leu Asn Thr
225                 230                 235                 240

Met Arg Leu Cys Arg Ala Asn Asp Gln Gly Ala Leu Glu Arg Arg Phe
                245                 250                 255

Pro Ser Val Gly Asp Val Ala Asp Ala Ala Val Phe Leu Ala Ser Ala
            260                 265                 270

Glu Ser Ala Ala Leu Ser Gly Glu Thr Ile Glu Val Thr His Gly Met
        275                 280                 285

Glu Leu Pro Ala Cys Ser Glu Thr Ser Leu Leu Ala Arg Thr Asp Leu
    290                 295                 300
```

-continued

```
Arg Thr Ile Asp Ala Ser Gly Arg Thr Thr Leu Ile Cys Ala Gly Asp
305                 310                 315                 320

Gln Ile Glu Glu Val Met Ala Leu Thr Gly Met Leu Arg Thr Cys Gly
            325                 330                 335

Ser Glu Val Ile Ile Gly Phe Arg Ser Ala Ala Leu Ala Gln Phe
        340                 345                 350

Glu Gln Ala Val Asn Glu Ser Arg Arg Leu Ala Gly Ala Asp Phe Thr
        355                 360                 365

Pro Pro Ile Ala Leu Pro Leu Asp Pro Arg Asp Pro Ala Thr Ile Asp
370                 375                 380

Ala Val Phe Asp Trp Ala Gly Glu Asn Thr Gly Gly Ile His Ala Ala
385                 390                 395                 400

Val Ile Leu Pro Ala Thr Ser His Glu Pro Ala Pro Cys Val Ile Glu
                405                 410                 415

Val Asp Asp Glu Arg Val Leu Asn Phe Leu Ala Asp Glu Ile Thr Gly
            420                 425                 430

Thr Ile Val Ile Ala Ser Arg Leu Ala Arg Tyr Trp Gln Ser Gln Arg
        435                 440                 445

Leu Thr Pro Gly Ala Arg Ala Arg Gly Pro Arg Val Ile Phe Leu Ser
    450                 455                 460

Asn Gly Ala Asp Gln Asn Gly Asn Val Tyr Gly Arg Ile Gln Ser Ala
465                 470                 475                 480

Ala Ile Gly Gln Leu Ile Arg Val Trp Arg His Glu Ala Glu Leu Asp
                485                 490                 495

Tyr Gln Arg Ala Ser Ala Ala Gly Asp His Val Leu Pro Pro Val Trp
            500                 505                 510

Ala Asn Gln Ile Val Arg Phe Ala Asn Arg Ser Leu Glu Gly Leu Glu
        515                 520                 525

Phe Ala Cys Ala Trp Thr Ala Gln Leu Leu His Ser Gln Arg His Ile
    530                 535                 540

Asn Glu Ile Thr Leu Asn Ile Pro Ala Asn Ile Ser Ala Thr Thr Gly
545                 550                 555                 560

Ala Arg Ser Ala Ser Val Gly Trp Ala Glu Ser Leu Ile Gly Leu His
                565                 570                 575

Leu Gly Lys Val Ala Leu Ile Thr Gly Gly Ser Ala Gly Ile Gly Gly
            580                 585                 590

Gln Ile Gly Arg Leu Leu Ala Leu Ser Gly Ala Arg Val Met Leu Ala
        595                 600                 605

Ala Arg Asp Arg His Lys Leu Glu Gln Met Gln Ala Met Ile Gln Ser
    610                 615                 620

Glu Leu Ala Glu Val Gly Tyr Thr Asp Val Glu Asp Arg Val His Ile
625                 630                 635                 640

Ala Pro Gly Cys Asp Val Ser Ser Glu Ala Gln Leu Ala Asp Leu Val
                645                 650                 655

Glu Arg Thr Leu Ser Ala Phe Gly Thr Val Asp Tyr Leu Ile Asn Asn
            660                 665                 670

Ala Gly Ile Ala Gly Val Glu Glu Met Val Ile Asp Met Pro Val Glu
        675                 680                 685

Gly Trp Arg His Thr Leu Phe Ala Asn Leu Ile Ser Asn Tyr Ser Leu
    690                 695                 700

Met Arg Lys Leu Ala Pro Leu Met Lys Lys Gln Gly Ser Gly Tyr Ile
705                 710                 715                 720

Leu Asn Val Ser Ser Tyr Phe Gly Gly Glu Lys Asp Ala Ala Ile Pro
                725                 730                 735
```

```
Tyr Pro Asn Arg Ala Asp Tyr Ala Val Ser Lys Ala Gly Gln Arg Ala
            740                 745                 750

Met Ala Glu Val Phe Ala Arg Phe Leu Gly Pro Glu Ile Gln Ile Asn
            755                 760                 765

Ala Ile Ala Pro Gly Pro Val Glu Gly Asp Arg Leu Arg Gly Thr Gly
        770                 775                 780

Glu Arg Pro Gly Leu Phe Ala Arg Arg Ala Arg Leu Ile Leu Glu Asn
785                 790                 795                 800

Lys Arg Leu Asn Glu Leu His Ala Ala Leu Ile Ala Ala Ala Arg Thr
                805                 810                 815

Asp Glu Arg Ser Met His Glu Leu Val Glu Leu Leu Leu Pro Asn Asp
                820                 825                 830

Val Ala Ala Leu Glu Gln Asn Pro Ala Ala Pro Thr Ala Leu Arg Glu
                835                 840                 845

Leu Ala Arg Arg Phe Arg Ser Glu Gly Asp Pro Ala Ala Ser Ser Ser
850                 855                 860

Ser Ala Leu Leu Asn Arg Ser Ile Ala Ala Lys Leu Leu Ala Arg Leu
865                 870                 875                 880

His Asn Gly Gly Tyr Val Leu Pro Ala Asp Ile Phe Ala Asn Leu Pro
                885                 890                 895

Asn Pro Pro Asp Pro Phe Phe Thr Arg Ala Gln Ile Asp Arg Glu Ala
                900                 905                 910

Arg Lys Val Arg Asp Gly Ile Met Gly Met Leu Tyr Leu Gln Arg Met
                915                 920                 925

Pro Thr Glu Phe Asp Val Ala Met Ala Thr Val Tyr Tyr Leu Ala Asp
                930                 935                 940

Arg Asn Val Ser Gly Glu Thr Phe His Pro Ser Gly Gly Leu Arg Tyr
945                 950                 955                 960

Glu Arg Thr Pro Thr Gly Gly Glu Leu Phe Gly Leu Pro Ser Pro Glu
                965                 970                 975

Arg Leu Ala Glu Leu Val Gly Ser Thr Val Tyr Leu Ile Gly Glu His
                980                 985                 990

Leu Thr Glu His Leu Asn Leu Leu Ala Arg Ala Tyr Leu Glu Arg Tyr
            995                 1000                1005

Gly Ala Arg Gln Val Val Met Ile Val Glu Thr Glu Thr Gly Ala
        1010                1015                1020

Glu Thr Met Arg Arg Leu Leu His Asp His Val Glu Ala Gly Arg
    1025                1030                1035

Leu Met Thr Ile Val Ala Gly Asp Gln Ile Glu Ala Ala Ile Asp
    1040                1045                1050

Gln Ala Ile Thr Arg Tyr Gly Arg Pro Gly Pro Val Val Cys Thr
    1055                1060                1065

Pro Phe Arg Pro Leu Pro Thr Val Pro Leu Val Gly Arg Lys Asp
    1070                1075                1080

Ser Asp Trp Ser Thr Val Leu Ser Glu Ala Glu Phe Ala Glu Leu
    1085                1090                1095

Cys Glu His Gln Leu Thr His His Phe Arg Val Ala Arg Lys Ile
    1100                1105                1110

Ala Leu Ser Asp Gly Ala Ser Leu Ala Leu Val Thr Pro Glu Thr
    1115                1120                1125

Thr Ala Thr Ser Thr Thr Glu Gln Phe Ala Leu Ala Asn Phe Ile
    1130                1135                1140

Lys Thr Thr Leu His Ala Phe Thr Ala Thr Ile Gly Val Glu Ser
```

```
                1145                1150                1155
Glu Arg Thr Ala Gln Arg Ile Leu Ile Asn Gln Val Asp Leu Thr
        1160                1165                1170

Arg Arg Ala Arg Ala Glu Glu Pro Arg Asp Pro His Glu Arg Gln
    1175                1180                1185

Gln Glu Leu Glu Arg Phe Ile Glu Ala Val Leu Leu Val Thr Ala
    1190                1195                1200

Pro Leu Pro Pro Glu Ala Asp Thr Arg Tyr Ala Gly Arg Ile His
    1205                1210                1215

Arg Gly Arg Ala Ile Thr Val
    1220                1225

<210> SEQ ID NO 142
<211> LENGTH: 336
<212> TYPE: DNA
<213> ORGANISM: Chloroflexus aurantiacus

<400> SEQUENCE: 142
tctttctggc cagtgccgaa tccgccgctc tctccggtga gacgattgag gttacgcacg      60
gaatggagtt gccggcctgc agtgagacca gcctgctggc ccgtactgat ctgcgcacga     120
ttgatgccag tggccgcacg acgctcatct gcgccggcga ccagattgaa gaggtgatgg     180
cgctcaccgg tatgttgcgt acctgtggga gtgaagtgat catcggcttc cgttcggctg     240
cggcgctggc ccagttcgag caggcagtca atgagagtcg gcggctggcc ggcgcagact     300
ttacgcctcc cattgccttg ccactcgatc cacgcg                              336

<210> SEQ ID NO 143
<211> LENGTH: 249
<212> TYPE: PRT
<213> ORGANISM: Spodoptera littoralis

<400> SEQUENCE: 143

Met Phe Ala Asn Lys Val Val Leu Val Thr Gly Gly Ser Ser Gly Ile
1               5                   10                  15

Gly Ala Ala Thr Val Glu Ala Phe Val Lys Glu Gly Ala Ser Val Ala
            20                  25                  30

Phe Val Gly Arg Asn Gln Ala Lys Leu Lys Glu Val Glu Ser Arg Cys
        35                  40                  45

Gln Gln His Gly Ala Asn Ile Leu Ala Ile Lys Ala Asp Val Ser Lys
    50                  55                  60

Asp Glu Glu Ala Lys Ile Ile Val Gln Gln Thr Val Asp Lys Phe Gly
65                  70                  75                  80

Lys Leu Asp Val Leu Val Asn Asn Ala Gly Ile Leu Arg Phe Ala Ser
                85                  90                  95

Val Leu Glu Pro Thr Leu Ile Gln Thr Phe Asp Glu Thr Met Asn Thr
            100                 105                 110

Asn Leu Arg Pro Val Val Leu Ile Thr Ser Leu Ala Ile Pro His Leu
        115                 120                 125

Ile Ala Thr Lys Gly Ser Ile Val Asn Val Ser Ser Ile Leu Ser Thr
    130                 135                 140

Ile Val Arg Ile Pro Gly Ile Met Ser Tyr Ser Val Ser Lys Ala Ala
145                 150                 155                 160

Met Asp His Phe Thr Lys Leu Ala Ala Leu Glu Leu Ala Pro Ser Gly
                165                 170                 175

Val Arg Val Asn Ser Val Asn Pro Gly Pro Val Leu Thr Asp Ile Ala
            180                 185                 190
```

```
Ala Gly Ser Gly Phe Ser Pro Asp Leu Leu Glu Asp Thr Gly Ala His
            195                 200                 205

Thr Pro Leu Gly Lys Ala Ala Gln Ser Glu Glu Ile Ala Asp Met Ile
    210                 215                 220

Val Tyr Leu Ala Ser Asp Lys Ala Lys Ser Val Thr Gly Ser Cys Tyr
225                 230                 235                 240

Ile Met Asp Asn Gly Leu Ala Leu Gln
                245
```

<210> SEQ ID NO 144
<211> LENGTH: 246
<212> TYPE: PRT
<213> ORGANISM: Thermotoga maritima

<400> SEQUENCE: 144

```
Met Arg Leu Glu Gly Lys Val Cys Leu Ile Thr Gly Ala Ala Ser Gly
1               5                   10                  15

Ile Gly Lys Ala Thr Thr Leu Leu Phe Ala Gln Glu Gly Ala Thr Val
            20                  25                  30

Ile Ala Gly Asp Ile Ser Lys Glu Asn Leu Asp Ser Leu Val Lys Glu
        35                  40                  45

Ala Glu Gly Leu Pro Gly Lys Val Asp Pro Tyr Val Leu Asn Val Thr
    50                  55                  60

Asp Arg Asp Gln Ile Lys Glu Val Val Glu Lys Val Val Gln Lys Tyr
65                  70                  75                  80

Gly Arg Ile Asp Val Leu Val Asn Asn Ala Gly Ile Thr Arg Asp Ala
                85                  90                  95

Leu Leu Val Arg Met Lys Glu Glu Asp Trp Asp Ala Val Ile Asn Val
            100                 105                 110

Asn Leu Lys Gly Val Phe Asn Val Thr Gln Met Val Val Pro Tyr Met
        115                 120                 125

Ile Lys Gln Arg Asn Gly Ser Ile Val Asn Val Ser Ser Val Val Gly
    130                 135                 140

Ile Tyr Gly Asn Pro Gly Gln Thr Asn Tyr Ala Ala Ser Lys Ala Gly
145                 150                 155                 160

Val Ile Gly Met Thr Lys Thr Trp Ala Lys Glu Leu Ala Gly Arg Asn
                165                 170                 175

Ile Arg Val Asn Ala Val Ala Pro Gly Phe Ile Glu Thr Pro Met Thr
            180                 185                 190

Glu Lys Leu Pro Glu Lys Ala Arg Glu Thr Ala Leu Ser Arg Ile Pro
        195                 200                 205

Leu Gly Arg Phe Gly Lys Pro Glu Glu Val Ala Gln Val Ile Leu Phe
    210                 215                 220

Leu Ala Ser Asp Glu Ser Ser Tyr Val Thr Gly Gln Val Ile Gly Ile
225                 230                 235                 240

Asp Gly Gly Leu Val Ile
                245
```

<210> SEQ ID NO 145
<211> LENGTH: 289
<212> TYPE: PRT
<213> ORGANISM: Bacillus subtilis

<400> SEQUENCE: 145

```
Met Asn Pro Met Asp Arg Gln Thr Glu Gly Gln Glu Pro Gln His Gln
1               5                   10                  15
```

-continued

Asp Arg Gln Pro Gly Ile Glu Ser Lys Met Asn Pro Leu Pro Leu Ser
             20                  25                  30

Glu Asp Glu Asp Tyr Arg Gly Ser Gly Lys Leu Lys Gly Lys Val Ala
         35                  40                  45

Ile Ile Thr Gly Gly Asp Ser Gly Ile Gly Arg Ala Ala Ile Ala
 50                  55                  60

Phe Ala Lys Glu Gly Ala Asp Ile Ser Ile Leu Tyr Leu Asp Glu His
 65                  70                  75                  80

Ser Asp Ala Glu Glu Thr Arg Lys Arg Ile Glu Lys Glu Asn Val Arg
                 85                  90                  95

Cys Leu Leu Ile Pro Gly Asp Val Gly Asp Glu Asn His Cys Glu Gln
            100                 105                 110

Ala Val Gln Gln Thr Val Asp His Phe Gly Lys Leu Asp Ile Leu Val
        115                 120                 125

Asn Asn Ala Ala Glu Gln His Pro Gln Asp Ser Ile Leu Asn Ile Ser
130                 135                 140

Thr Glu Gln Leu Glu Lys Thr Phe Arg Thr Asn Ile Phe Ser Met Phe
145                 150                 155                 160

His Met Thr Lys Lys Ala Leu Pro His Leu Gln Glu Gly Cys Ala Ile
                165                 170                 175

Ile Asn Thr Thr Ser Ile Thr Ala Tyr Glu Gly Asp Thr Ala Leu Ile
            180                 185                 190

Asp Tyr Ser Ser Thr Lys Gly Ala Ile Val Ser Phe Thr Arg Ser Met
        195                 200                 205

Ala Lys Ser Leu Ala Asp Lys Gly Ile Arg Val Asn Ala Val Ala Pro
210                 215                 220

Gly Pro Ile Trp Thr Pro Leu Ile Pro Ala Thr Phe Pro Glu Glu Lys
225                 230                 235                 240

Val Lys Gln His Gly Leu Asp Thr Pro Met Gly Arg Pro Gly Gln Pro
                245                 250                 255

Val Glu His Ala Gly Ala Tyr Val Leu Leu Ala Ser Asp Glu Ser Ser
            260                 265                 270

Tyr Met Thr Gly Gln Thr Ile His Val Asn Gly Gly Arg Phe Ile Ser
        275                 280                 285

Thr

<210> SEQ ID NO 146
<211> LENGTH: 285
<212> TYPE: PRT
<213> ORGANISM: Sinorhizobium meliloti

<400> SEQUENCE: 146

Met Glu Lys Phe Pro His Pro Pro Phe Pro Arg Gln Thr Gln Glu Met
1               5                   10                  15

Pro Gly Thr Thr Asp Arg Met Gln Pro Leu Pro Asp His Gly Glu Asn
             20                  25                  30

Ser Tyr Gln Gly Ser Gly Arg Leu Lys Asp Lys Arg Ala Ile Ile Thr
         35                  40                  45

Gly Gly Asp Ser Gly Ile Gly Arg Ala Val Ala Ile Ala Tyr Ala Arg
 50                  55                  60

Glu Gly Ala Asp Val Leu Ile Ser Tyr Leu Ser Glu His Asp Asp Ala
 65                  70                  75                  80

Met Ala Thr Lys Ala Leu Val Glu Glu Ala Gly Arg Lys Ala Val Leu
                 85                  90                  95

Ala Ala Gly Asp Ile Gln Ser Ser Asp His Cys Arg Arg Ile Val Glu

```
                   100                 105                 110
Thr Ala Val Arg Glu Leu Gly Gly Ile Asp Ile Leu Val Asn Asn Ala
                115                 120                 125

Ala His Gln Ala Thr Phe Lys Asn Ile Glu Asp Ile Ser Asp Glu Glu
    130                 135                 140

Trp Glu Leu Thr Phe Arg Val Asn Met His Ala Met Phe Tyr Leu Thr
145                 150                 155                 160

Lys Ala Ala Val Pro His Met Lys Lys Gly Ser Ala Ile Ile Asn Thr
                165                 170                 175

Ala Ser Ile Asn Ala Asp Val Pro Asn Pro Ile Leu Ala Tyr Ala
        180                 185                 190

Thr Thr Lys Gly Ala Ile His Asn Phe Ser Ala Gly Leu Ala Gln Met
        195                 200                 205

Leu Ala Glu Arg Gly Ile Arg Val Asn Val Val Ala Pro Gly Pro Ile
    210                 215                 220

Trp Thr Pro Leu Ile Pro Ser Thr Met Pro Glu Asp Thr Val Ala Asp
225                 230                 235                 240

Phe Gly Lys Gln Val Pro Met Lys Arg Pro Gly Gln Pro Val Glu Leu
                245                 250                 255

Ala Ser Ala Tyr Val Met Leu Ala Asp Pro Met Ser Ser Tyr Val Ser
            260                 265                 270

Gly Ala Thr Ile Ala Val Thr Gly Gly Lys Pro Phe Leu
            275                 280                 285

<210> SEQ ID NO 147
<211> LENGTH: 257
<212> TYPE: PRT
<213> ORGANISM: Mesorhizobium loti

<400> SEQUENCE: 147

Met Arg Leu Leu His Lys Arg Thr Leu Val Thr Gly Gly Ser Asp Gly
1               5                   10                  15

Ile Gly Leu Ala Ile Ala Glu Ala Phe Leu Ser Glu Gly Ala Asp Val
                20                  25                  30

Leu Ile Val Gly Arg Asp Ala Ala Lys Leu Glu Ala Ala Arg Gln Lys
            35                  40                  45

Leu Ala Leu Gly Gln Ala Gly Ala Val Glu Thr Ser Ser Ala Asp
    50                  55                  60

Leu Ala Thr Ser Leu Gly Val Ala Thr Val Val Glu Gln Val Lys Glu
65                  70                  75                  80

Thr Gly Arg Pro Leu Asp Ile Pro Ile Asn Asn Ala Gly Val Ala Asp
                85                  90                  95

Leu Val Pro Phe Glu Ser Val Ser Glu Ala Gln Phe Gln His Ser Phe
                100                 105                 110

Ala Leu Asn Val Ala Ala Phe Phe Leu Thr Gln Gly Leu Leu Pro
            115                 120                 125

His Phe Gly Ala Gly Ala Ser Ile Ile Asn Ile Ser Ser Tyr Phe Ala
    130                 135                 140

Arg Lys Met Ile Pro Lys Arg Pro Ser Ser Val Tyr Ser Leu Ser Lys
145                 150                 155                 160

Gly Ala Leu Asn Ser Leu Thr Arg Ser Leu Ala Phe Glu Leu Gly Pro
                165                 170                 175

Arg Gly Ile Arg Val Asn Ala Ile Ala Pro Gly Thr Val Asp Thr Ala
            180                 185                 190

Met Arg Arg Lys Thr Val Asp Asn Leu Pro Ala Glu Ala Lys Ala Glu
```

```
                 195                 200                 205
Leu Lys Ala Tyr Val Glu Arg Ser Tyr Pro Leu Gly Arg Ile Gly Arg
            210                 215                 220

Pro Asp Asp Leu Ala Gly Met Ala Val Tyr Leu Ala Ser Asp Glu Ala
225                 230                 235                 240

Ala Trp Thr Ser Gly Gly Ile Phe Ala Val Asp Gly Gly Tyr Thr Ala
                245                 250                 255

Gly

<210> SEQ ID NO 148
<211> LENGTH: 774
<212> TYPE: DNA
<213> ORGANISM: Mesorhizobium loti

<400> SEQUENCE: 148
atgagacttc tgcacaagcg cacgctggtg accggcggct cggacggtat cggcctggca      60
atcgccgagg cgttcctgag cgagggcgcc gatgtcctga tcgtcggccg tgacgccgcc     120
aagctcgaag ccgcgcgcca gaagctggcg gctcttggcc aggccggcgc ggtggagacg     180
tcgtccgccg atcttgccac cagcctcggt gtcgcaaccg tcgtcgagca ggtgaaagag     240
accggccggc cgctcgacat tcctatcaac aatgccggtg tcgccgacct cgtgccgttc     300
gagagcgtca gcgaggcgca gttccagcac tccttcgcgc tcaatgtggc ggcggcgttc     360
ttcctcaccc aggggctgct gccgcatttc ggcgccggtg catcgatcat caacatctct     420
tcctatttcg cccgcaagat gatcccgaag cggccatcca gcgtctactc cctgtccaag     480
ggcgcgttga actcgttgac cagatcgctg gccttcgagc tcggcccgcg cggcatccgc     540
gtcaacgcca tcgcgcccgg cacggtcgac accgccatgc ggcgcaagac cgtcgacaac     600
ctgccggccg aggccaaggc cgaactgaag gcctatgtcg aacgcagcta tccgctgggc     660
cgcatcggcc gtccggacga cctcgccggc atggcggttt atctagccag cgacgaggcg     720
gcctggacga gcggtgggat ctttgccgtg gatggtggct acacggccgg atga          774

<210> SEQ ID NO 149
<211> LENGTH: 750
<212> TYPE: DNA
<213> ORGANISM: Spodoptera littoralis

<400> SEQUENCE: 149
atgttcgcaa ataaagtggt actagtaaca ggtggtagct ccggtatcgg cgcagctact      60
gtggaagcat tcgttaagga aggcgcttct gtagccttcg tgggaagaaa ccaagccaag     120
cttaaggaag tagagagccg ctgccagcag catggagcca acatcctggc tatcaaagca     180
gatgtctcca agacgagga agcgaaaatc atcgtacaac aaactgtcga caagttcggg     240
aagcttgatg tgcttgttaa caacgctggg attctacggt tcgcgagtgt tctggagccg     300
actttaatac aaacttttga tgaaactatg aacacgaatt tacgtccagt tgtcctcatc     360
actagcctgg ctatccctca tttgattgct acaaaaggga gcatagttaa cgtatccagt     420
atactgtcta caatagtaag aataccaggg attatgtcat acagtgtgtc aaaggctgct     480
atggatcact tcacaaaatt ggcagcgttg gagctggctc cttctggcgt gcgagtgaac     540
tcagtcaacc ctggaccagt tcttactgat atcgcagctg ttctggcctt ttctcctgat     600
ctgcttgaag atacaggggc tcatacaccg ttggggaaag ctgcgcagtc tgaggagatt     660
gctgatatga ttgtgtatct ggctagtgat aaagctaaga gtgttacggg gtcctgttat     720
atcatggaca atgggactcg cctgcagtaa                                     750
```

<210> SEQ ID NO 150
<211> LENGTH: 741
<212> TYPE: DNA
<213> ORGANISM: Thermotoga maritima

<400> SEQUENCE: 150

```
atgaggcttg aagggaaagt gtgtctgatc acaggggctg caagcgggat agggaaagcc     60
accacgcttc ttttcgcaca ggaaggagct acggtgatcg ctggcgatat ctcgaaagaa    120
aatctcgact ctcttgtgaa agaggcagaa ggacttccgg ggaaggttga tccctacgtt    180
ttgaacgtga ccgacaggga tcagataaag gaagttgtgg aaaaagtcgt tcaaaagtac    240
ggtcgaatcg atgttctggt gaacaacgcg gaataacaa gggatgcgct tcttgtgagg     300
atgaaagaag aagactggga tgcggtaata acgtgaatc tgaagggtgt tttcaacgtg     360
actcagatgg tggtgcccta catgatcaaa cagaggaacg gttcgatcgt gaacgtctcc    420
tctgtcgttg aatatacgg gaatcctggt cagacgaatt acgcggcgtc gaaggcggga    480
gtcataggaa tgaccaagac gtgggcgaag gaactcgctg aagaaacat cagggtgaac     540
gctgtggcac ccggattcat agaaaccccc atgaccgaaa acttccaga aaagcccgt      600
gaaacggccc tttccagaat accgctggga aggtttggga agccagaaga ggtggcgcag    660
gttatactct cctcgcatc ggacgagtcg agttacgtca ccggacaggt gataggaata    720
gatgggggcc tcgtgatctg a                                              741
```

<210> SEQ ID NO 151
<211> LENGTH: 858
<212> TYPE: DNA
<213> ORGANISM: Sinorhizobium meliloti

<400> SEQUENCE: 151

```
atggaaaaat ttccgcaccc tcccttcc cgccaaaccc aggaaatgcc cggcactacc       60
gatcggatgc agccgctgcc cgatcacggg gaaaactcct accagggttc cggacgcctg    120
aaggacaaga gagccatcat caccggcggg gacagcggca tcggcagggc cgtggcgatc    180
gcctatgcgc gcgagggagc ggacgtcctt atcagctatc tgagcgagca tgacgacgcg    240
atggccacca aggctctggt ggaggaagca ggtcgcaagg ccgtgcttgc cgccggcgac    300
atccagtcgt ccgaccattg ccgcaggatc gtcgaaacgg ccgttcggga actcggcggc    360
atcgacattc tcgtcaacaa tgcagcccat caggcgacct tcaagaacat cgaagacatc    420
agcgacgagg agtgggagct gacattccgc gtcaacatgc acgccatgtt ctacctgacc    480
aaggcagcgg tgccgcacat gaagaagggc agcgcgatca tcaacaccgc ttccatcaat    540
gccgacgttc ccaatccgat cctactcgcc tatgcgacca caagggcgc gatccacaat    600
ttcagcgccg gtctcgcgca gatgctggcc gaacgcggga taagagtgaa tgtcgtggcc    660
ccgggcccga tctggacgcc gctgatcccc tccaccatgc ccgaggatac cgtcgccgat    720
ttcggcaaac aggtgcctat gaagcgaccg ggccagcccg tggaactcgc ctcggcctat    780
gtcatgctgg cggatccgat gtcgagctac gtgtcaggcg caacgattgc cgtgaccggc    840
ggcaagcctt ccttttga                                                  858
```

<210> SEQ ID NO 152
<211> LENGTH: 870
<212> TYPE: DNA
<213> ORGANISM: Bacillus subtilis

<400> SEQUENCE: 152

```
gtgaacccaa tggacagaca aacagaagga caagaaccgc agcatcagga cagacagccg      60
ggcattgagt caaaaatgaa tccgctgccg ctgtcagagg acgaggatta tcgaggaagc     120
ggaaaactga aggaaaagt tgcgatcatt actggaggcg acagcggaat agggagagca      180
gcagctattg cctttgctaa agaggggct gatatctcca ttctatactt agacgagcat      240
tcggacgcag aggaaacacg caaacggatc gaaaaggaga atgtccgctg cctgcttatc      300
ccgggagatg ttggggacga gaaccattgt gaacaagctg tgcagcaaac agtggaccat     360
tttggtaaac tcgatatctt agtgaacaac gccgctgaac agcatcccca ggacagcatt     420
ctcaatattt caacagaaca gctggaaaaa acctttcgca caaatatttt ttccatgttt     480
catatgacga agaaagcttt gcctcacctg caagagggt gtgccattat taatacgaca       540
tcgattaccg cttatgaagg ggatacggcg ttaattgatt attccagcac aaagggtgcg     600
attgtttcct ttacgcgttc catggcgaag tcgcttgcag ataaaggcat cagagtgaat     660
gcggtggcgc ccggtccgat ttggacaccg cttattccgg cgacattccc tgaggaaaaa      720
gtgaaacagc acggcttgga taccccaatg ggaagaccgg acagccggt tgagcatgca      780 ggcgcctatg ttctgctggc gtctgacgaa tcttcctata tgacagggca gaccattcat      840
gtgaatggcg gccgttttat ttcaacgtaa                                      870
```

<210> SEQ ID NO 153
<211> LENGTH: 23
<212> TYPE: DNA
<213> ORGANISM: Artificial Sequence
<220> FEATURE:
<223> OTHER INFORMATION: Primer

<400> SEQUENCE: 153
atggcgacgg gcgagtccat gag         23

<210> SEQ ID NO 154
<211> LENGTH: 23
<212> TYPE: DNA
<213> ORGANISM: Artificial Sequence
<220> FEATURE:
<223> OTHER INFORMATION: Primer

<400> SEQUENCE: 154
ggacacgaag aacagggcga cac         23

<210> SEQ ID NO 155
<211> LENGTH: 23
<212> TYPE: DNA
<213> ORGANISM: Artificial Sequence
<220> FEATURE:
<223> OTHER INFORMATION: Primer

<400> SEQUENCE: 155
gaactgtctg gagtaaggct gtc         23

<210> SEQ ID NO 156
<211> LENGTH: 20
<212> TYPE: DNA
<213> ORGANISM: Artificial Sequence
<220> FEATURE:
<223> OTHER INFORMATION: Primer

<400> SEQUENCE: 156
gattccgtat gtcacccta         20

```
<210> SEQ ID NO 157
<211> LENGTH: 20
<212> TYPE: DNA
<213> ORGANISM: Artificial Sequence
<220> FEATURE:
<223> OTHER INFORMATION: Primer

<400> SEQUENCE: 157
caggcgactg gcaatcacaa                                               20

<210> SEQ ID NO 158
<211> LENGTH: 23
<212> TYPE: DNA
<213> ORGANISM: Artificial Sequence
<220> FEATURE:
<223> OTHER INFORMATION: Primer

<400> SEQUENCE: 158
gagaccacaa cggtttccct cta                                           23

<210> SEQ ID NO 159
<211> LENGTH: 23
<212> TYPE: DNA
<213> ORGANISM: Artificial Sequence
<220> FEATURE:
<223> OTHER INFORMATION: Primer

<400> SEQUENCE: 159
ggacacgaag aacagggcga cac                                           23

<210> SEQ ID NO 160
<211> LENGTH: 145
<212> TYPE: PRT
<213> ORGANISM: Clostridium propionicum

<400> SEQUENCE: 160
```

Met Val Gly Lys Lys Val Val His His Leu Met Met Ser Ala Lys Asp
1               5                   10                  15

Ala His Tyr Thr Gly Asn Leu Val Asn Gly Ala Arg Ile Val Asn Gln
                20                  25                  30

Trp Gly Asp Val Gly Thr Glu Leu Met Val Tyr Val Asp Gly Asp Ile
            35                  40                  45

Ser Leu Phe Leu Gly Tyr Lys Asp Ile Glu Phe Thr Ala Pro Val Tyr
        50                  55                  60

Val Gly Asp Phe Met Glu Tyr His Gly Trp Ile Glu Lys Val Gly Asn
65                  70                  75                  80

Gln Ser Tyr Thr Cys Lys Phe Glu Ala Trp Lys Val Ala Thr Met Val
                85                  90                  95

Asp Ile Thr Asn Pro Gln Asp Thr Arg Ala Thr Ala Cys Glu Pro Pro
            100                 105                 110

Val Leu Cys Gly Arg Ala Thr Gly Ser Leu Phe Ile Ala Lys Lys Asp
        115                 120                 125

Gln Arg Gly Pro Gln Glu Ser Ser Phe Lys Arg Lys His Pro Gly
    130                 135                 140

Glu
145

```
<210> SEQ ID NO 161
<211> LENGTH: 144
<212> TYPE: PRT
<213> ORGANISM: Clostridium propionicum

<400> SEQUENCE: 161
```

```
Met Val Gly Lys Lys Val Val His His Leu Met Met Ser Ala Lys Asp
1               5                   10                  15

Ala His Tyr Thr Gly Asn Leu Val Asn Gly Ala Arg Ile Val Asn Gln
            20                  25                  30

Trp Gly Asp Val Gly Thr Glu Leu Met Val Tyr Val Asp Gly Asp Ile
            35                  40                  45

Ser Leu Phe Leu Gly Tyr Lys Asp Ile Glu Phe Thr Ala Pro Val Tyr
    50                  55                  60

Val Gly Asp Phe Met Glu Tyr His Gly Trp Ile Glu Lys Val Gly Asn
65              70                  75                  80

Gln Ser Tyr Thr Cys Lys Phe Glu Ala Trp Lys Val Ala Lys Met Val
                85                  90                  95

Asp Ile Thr Asn Pro Gln Asp Thr Arg Ala Thr Ala Cys Glu Pro Pro
                100                 105                 110

Val Leu Cys Gly Thr Ala Thr Gly Ser Leu Phe Ile Ala Lys Asp Asn
            115                 120                 125

Gln Arg Gly Pro Gln Glu Ser Ser Phe Lys Asp Ala Lys His Pro Gln
130                 135                 140
```

<210> SEQ ID NO 162
<211> LENGTH: 438
<212> TYPE: DNA
<213> ORGANISM: Clostridium propionicum

<400> SEQUENCE: 162

```
atggtaggta aaaggttgt  acatcattta  atgatgagcg  caaaagatgc  tcactatact    60
ggaaacttag taaacggcgc tagaattgtg aatcagtggg gcgacgttgg tacagaatta    120
atggtttatg ttgatggtga cataagctta ttccttgggct acaaagatat cgaattcaca    180
gctcctgtat atgttggtga ctttatggaa taccacggct ggattgaaaa agttggtaac    240
cagtcctata catgtaaatt tgaagcatgg aaagttgcaa aatggttga  atcacaaat     300
cctcaggata cacgcgcaac agcttgtgag cctccggtat tgtgcggaag agcaacgggt    360
agtttgttca tcgcaaaaaa agatcagaga ggccctcagg aatcctcttt taagagaga    420
aagcaccccg gtgaatga                                                  438
```

<210> SEQ ID NO 163
<211> LENGTH: 435
<212> TYPE: DNA
<213> ORGANISM: Clostridium propionicum

<400> SEQUENCE: 163

```
atggtaggta aaaggttgt  acatcattta  atgatgagcg  caaaagatgc  tcactatact    60
ggaaacttag taaacggcgc tagaattgtg aatcagtggg gcgacgtagg tacagaatta    120
atggtttatg ttgatggtga catcagctta ttccttgggct acaaagatat cgaattcaca    180
gctcctgtat atgttggtga ttttatggaa taccacggct ggattgaaaa agttggcaac    240
cagtcctata catgtaaatt tgaagcatgg aaagtagcaa agatggttga atcacaaat     300
ccacaggata cacgtgcaac agcttgtgaa cctccggtac tttgtggtac tgcaacaggc    360
agccttttca tcgcaaagga taatcagaga ggtcctcagg aatcttcctt caaggatgca    420
aagcaccctc aataa                                                     435
```

<210> SEQ ID NO 164
<211> LENGTH: 44
<212> TYPE: DNA

```
<213> ORGANISM: Artificial Sequence
<220> FEATURE:
<223> OTHER INFORMATION: Primer

<400> SEQUENCE: 164
atagggccca ggagatcaaa ccatgggtga agagtctctg gttc          44

<210> SEQ ID NO 165
<211> LENGTH: 40
<212> TYPE: DNA
<213> ORGANISM: Artificial Sequence
<220> FEATURE:
<223> OTHER INFORMATION: Primer

<400> SEQUENCE: 165
cctctgctac agtcgacaca acgaccactg aagttgggag              40

<210> SEQ ID NO 166
<211> LENGTH: 40
<212> TYPE: DNA
<213> ORGANISM: Artificial Sequence
<220> FEATURE:
<223> OTHER INFORMATION: Primer

<400> SEQUENCE: 166
agtctgctat cggtacctca acgaccactg aagttgggag              40

<210> SEQ ID NO 167
<211> LENGTH: 40
<212> TYPE: DNA
<213> ORGANISM: Artificial Sequence
<220> FEATURE:
<223> OTHER INFORMATION: Primer

<400> SEQUENCE: 167
atagcggccg cataatggat actctcggaa tcgacgttgg              40

<210> SEQ ID NO 168
<211> LENGTH: 40
<212> TYPE: DNA
<213> ORGANISM: Artificial Sequence
<220> FEATURE:
<223> OTHER INFORMATION: Primer

<400> SEQUENCE: 168
ccccatcgat acatatttct tgattttatc ataagcaatc              40

<210> SEQ ID NO 169
<211> LENGTH: 40
<212> TYPE: DNA
<213> ORGANISM: Artificial Sequence
<220> FEATURE:
<223> OTHER INFORMATION: Primer

<400> SEQUENCE: 169
ccagggccca taatgggtga agaaaaaaca gtagatattg              40

<210> SEQ ID NO 170
<211> LENGTH: 38
<212> TYPE: DNA
<213> ORGANISM: Artificial Sequence
<220> FEATURE:
<223> OTHER INFORMATION: Primer

<400> SEQUENCE: 170
ggtagacttg tcgacgtagt ggtttcctcc ttcattgg                38
```

```
<210> SEQ ID NO 171
<211> LENGTH: 40
<212> TYPE: DNA
<213> ORGANISM: Artificial Sequence
<220> FEATURE:
<223> OTHER INFORMATION: Primer

<400> SEQUENCE: 171
atagcggccg cataatgggt cagatcgacg aacttatcag                40

<210> SEQ ID NO 172
<211> LENGTH: 39
<212> TYPE: DNA
<213> ORGANISM: Artificial Sequence
<220> FEATURE:
<223> OTHER INFORMATION: Primer

<400> SEQUENCE: 172
aggttcaact agttcgtaga ggatttccga gaaagcctg                 39

<210> SEQ ID NO 173
<211> LENGTH: 35
<212> TYPE: DNA
<213> ORGANISM: Artificial Sequence
<220> FEATURE:
<223> OTHER INFORMATION: Primer

<400> SEQUENCE: 173
ctagggccca taatggaact cgccgtttat agcac                     35

<210> SEQ ID NO 174
<211> LENGTH: 34
<212> TYPE: DNA
<213> ORGANISM: Artificial Sequence
<220> FEATURE:
<223> OTHER INFORMATION: Primer

<400> SEQUENCE: 174
acttctcgag ttaaaccagt tcgttcgggc aggt                      34

<210> SEQ ID NO 175
<211> LENGTH: 37
<212> TYPE: DNA
<213> ORGANISM: Artificial Sequence
<220> FEATURE:
<223> OTHER INFORMATION: Primer

<400> SEQUENCE: 175
gggactagta taatgggaaa agtagaaatc attacag                   37

<210> SEQ ID NO 176
<211> LENGTH: 37
<212> TYPE: DNA
<213> ORGANISM: Artificial Sequence
<220> FEATURE:
<223> OTHER INFORMATION: Primer

<400> SEQUENCE: 176
cggcttaatt aacagcagag atttattttt tcagtcc                   37

<210> SEQ ID NO 177
<211> LENGTH: 35
<212> TYPE: PRT
<213> ORGANISM: Clostridium propionicum

<400> SEQUENCE: 177
```

```
Met Val Gly Lys Lys Val Val His His Leu Met Met Ser Ala Lys Asp
1               5                   10                  15

Ala His Tyr Thr Gly Asn Leu Val Asn Gly Ala Arg Ile Val Asn Gln
            20                  25                  30

Trp Gly Asp
        35
```

<210> SEQ ID NO 178
<211> LENGTH: 20
<212> TYPE: DNA
<213> ORGANISM: Artificial Sequence
<220> FEATURE:
<223> OTHER INFORMATION: Primer

<400> SEQUENCE: 178
atggtwggya araargtwgt     20

<210> SEQ ID NO 179
<211> LENGTH: 20
<212> TYPE: DNA
<213> ORGANISM: Artificial Sequence
<220> FEATURE:
<223> OTHER INFORMATION: Primer

<400> SEQUENCE: 179
tcrccccayt grttwacrat     20

<210> SEQ ID NO 180
<211> LENGTH: 64
<212> TYPE: DNA
<213> ORGANISM: Artificial Sequence
<220> FEATURE:
<223> OTHER INFORMATION: Primer

<400> SEQUENCE: 180
acatcattta atgatgagcg caaaagatgc tcactatact ggaaacttag taaacggcgc     60
taga     64

<210> SEQ ID NO 181
<211> LENGTH: 31
<212> TYPE: DNA
<213> ORGANISM: Artificial Sequence
<220> FEATURE:
<223> OTHER INFORMATION: Primer

<400> SEQUENCE: 181
gtacatcatt taatgatgag cgcaaaagat g     31

<210> SEQ ID NO 182
<211> LENGTH: 30
<212> TYPE: DNA
<213> ORGANISM: Artificial Sequence
<220> FEATURE:
<223> OTHER INFORMATION: Primer

<400> SEQUENCE: 182
gatgctcact atactggaaa cttagtaaac     30

<210> SEQ ID NO 183
<211> LENGTH: 28
<212> TYPE: DNA
<213> ORGANISM: Artificial Sequence
<220> FEATURE:
<223> OTHER INFORMATION: Primer

<400> SEQUENCE: 183

```
attctagcgc cgtttactaa gtttccag                                           28

<210> SEQ ID NO 184
<211> LENGTH: 30
<212> TYPE: DNA
<213> ORGANISM: Artificial Sequence
<220> FEATURE:
<223> OTHER INFORMATION: Primer

<400> SEQUENCE: 184
ccagtatagt gagcatcttt tgcgctcatc                                         30

<210> SEQ ID NO 185
<211> LENGTH: 27
<212> TYPE: DNA
<213> ORGANISM: Artificial Sequence
<220> FEATURE:
<223> OTHER INFORMATION: Primer

<400> SEQUENCE: 185
gagccatgga agaaataaat gctaaag                                            27

<210> SEQ ID NO 186
<211> LENGTH: 27
<212> TYPE: DNA
<213> ORGANISM: Artificial Sequence
<220> FEATURE:
<223> OTHER INFORMATION: Primer

<400> SEQUENCE: 186
agaggatggc ttttaaatc gctattc                                             27

<210> SEQ ID NO 187
<211> LENGTH: 27
<212> TYPE: DNA
<213> ORGANISM: Artificial Sequence
<220> FEATURE:
<223> OTHER INFORMATION: Primer

<400> SEQUENCE: 187
atacatatga ccgaccgaca tcgcatt                                            27

<210> SEQ ID NO 188
<211> LENGTH: 27
<212> TYPE: DNA
<213> ORGANISM: Artificial Sequence
<220> FEATURE:
<223> OTHER INFORMATION: Primer

<400> SEQUENCE: 188
atagtcgacg ggtcagtcct tgccgcg                                            27

<210> SEQ ID NO 189
<211> LENGTH: 1830
<212> TYPE: DNA
<213> ORGANISM: Rhodobacter sphaeroides

<400> SEQUENCE: 189
atggcaaccg aagagcagtc tccgggttcc ggccgtgacg ctcagttcga gcgtctgaac        60
gcgaatctca cccgcatcga cgagctgtcg aaacggctga cggccgctct cacgaagcgc       120
aaactgtccg accccgcgtt gcacgggccc tcgagcgacg tcttcctgaa ggcgatgacg       180
gcctacatgg ccgagatgat gcagaacccg gccaagatcc tcgagcatca gatcagtttc       240
tggggcaaga gcctgaaaca ttacgttgag gcgcagcatc agctggtgaa gggcgagctg       300
```

-continued

```
aagccgccgc cggacgtgac gccgaaggac cgccgcttct cgaacccgct ctggcagacg      360
catccgttct tcaactatct caagcagcag tatctgatga acgccgaggc ggttaatcag      420
gccgtcgagg cgctggagca tatcgagcct tccgacaaga agcgggtcga gtatttctcg      480
cgccagatcg tcgatctttt ctcgcccacc aacttcttcg gcaccaatcc cgacgcgctc      540
gagcgcgcca ttgccaccga tggcgagagc ctcgtgcagg ggctggagaa tctcgtgcgc      600
gacatcgagg ccaacaaggg cgatctgctc gtcacgctgg ccgatcccga ggccttccag      660
gtgggccaga acctcgccac caccgaaggg tcggtcgtct accgcaaccg catgttcgag      720
ctgatccagt acaagcccac gaccgagacg gtccacgaga cgccgctcct gatctttccg      780
ccctggatca acaagttcta cattctcgat ctcaagccgc agaactccct gctgaagtgg      840
ctggtggatc agggcttcac ggtcttcgtc gtctcctggg tgaaccccga caagagctat      900
gccggcatcg gcatggacga ctacatccgc gatggctaca tgcgcgccat ggccgaggtg      960
cgcgcgatca cccggcagaa gcagatcaac gcggtgggct actgcatcgc gggcaccacg     1020
ctgacgctga cgctggccca cctgcagaag gcgggcgatc cgtccgtccg ctcggccacc     1080
ttcttcacca cgctcaccga cttctcggat ccgggcgagg tggggtgtt cctcaacgac      1140
gatttcgtcg acggtatcga gcggcaggtg gcggtggacg ggatcctcga caagaccttc     1200
atgtcgcgca ccttcagcta cctgcgctcg aacgacctga tctatcagcc cgccatcaag     1260
agctacatga tgggagaggc gccccccgcc ttcgatctgc tctactggaa cggagacggc     1320
accaacctgc cggcgcagat ggcggtcgaa tatctgcgcg gcctctgcca gcaggaccgg     1380
ctggcgggcg gcaccttccc ggtgctgggc tcgcccgtgg gcctgaagga tgtgacgctg     1440
ccggtctgcg ccatcgcctg cgagaccgac catatcgcgc cgtggaaaag cagcttcaac     1500
ggcttccgcc agttcggctc gaccgacaag accttcattc tttcggaatc gggccatgtg     1560
gcggcatcg tgaacccgcc cagccgcaac aaatacggcc attacaccaa cgagggtcct     1620
ctcgacacac ccgccgcgtt ccgcgagggg gccgagttcc acgcaggctc ctggtggccg     1680
cgctggggcg cctggctggc cgagcggtcg ggcaagcagg tcccggcgcg ccagccgggc     1740
gattcgaaac atcccgagct cgcgccggcg ccgggatcct atgtggcggc accgggcggg     1800
gcggaagtcg ccaagcctgc cgcgaggtaa                                     1830
```